US009045248B2

(12) United States Patent
Cusack et al.

(10) Patent No.: US 9,045,248 B2
(45) Date of Patent: Jun. 2, 2015

(54) **SOLUBLE FRAGMENTS OF INFLUENZA VIRUS PB2 PROTEIN CAPABLE OF BINDING RNA-CA

(56) References Cited

OTHER PUBLICATIONS

Honda, A., Two Separate Sequences of PB2 Subunit Constitute the RNA Cap-Binding Site of Influenza Virus RNA Polymerase, Genes to Cells, vol. 4, 1999, pp. 473-485, whole document.
Fechter, P., Two Aromatic Residues in the PB2 Subunit of Influenza A RNA Polymerase are Crucial for Cap Binding, J. Biol. Chem, vol. 278, No. 22, May 30, 2003, pp. 20381-20388, whole document.
Li, M., The Active Sties of the Influenza Cap-Dependent Endonuclease are on Different Polymerase Subunits, EMBO J., vol. 20, No. 8, 2001, pp. 2078-2086, whole document.
Guilligay, D., The Structural Basis for Cap Binding by influenza Virus Polymerase Subunit PB2, Nature Struct., Mol. Biol., vol. 15, No. 5, May 2008, pp. 500-506, whole document.
Tarendeau F. et al.: "Structure and nuclear import function of the C-terminal domain of influenza virus polymerase PB2 domain" Nature Struct. Mol. Biol., vol. 14, No. 3, Mar. 2007.
Area E. et al.: "3D structure of the influenza virus polymerase complex: localization of subunit domains." PNAS, vol. 101, 2004, pp. 308-313.
Eric Martz: 'Atomic coordinate file', [Online] May 26, 2010, Proteopedia, Life in 3D; ISPC, Weizman Institute of Science Retrieved from the Internet: [retrieved on Aug. 30, 2011].

* cited by examiner

Figure 4

Influenza polymerase PB2 subunit
cap-binding domain (native protein)
BM14

Figure 18 -1

```
HEADER    ----                                            XX-XXX-XX   xxxx
COMPND    --REMARK    3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.30
REMARK   3   RESOLUTION RANGE LOW  (ANGSTROMS) :  29.53
REMARK   3   DATA CUTOFF            (SIGMA(F)) : NONE
REMARK   3   COMPLETENESS FOR RANGE        (%) :  99.65
REMARK   3   NUMBER OF REFLECTIONS             :  40781
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.18859
REMARK   3   R VALUE             (WORKING SET) : 0.18611
REMARK   3   FREE R VALUE                      : 0.23465
REMARK   3   FREE R VALUE TEST SET SIZE   (%) :  5.0
REMARK   3   FREE R VALUE TEST SET COUNT      :  2165
REMARK   3
REMARK   3  FIT IN THE HIGHEST RESOLUTION BIN.
REMARK   3   TOTAL NUMBER OF BINS USED            :      20
REMARK   3   BIN RESOLUTION RANGE HIGH            :   2.300
REMARK   3   BIN RESOLUTION RANGE LOW             :   2.360
REMARK   3   REFLECTION IN BIN     (WORKING SET) :    2984
REMARK   3   BIN COMPLETENESS (WORKING+TEST) (%) :   98.55
REMARK   3   BIN R VALUE           (WORKING SET) :   0.250
REMARK   3   BIN FREE R VALUE SET COUNT           :     148
REMARK   3   BIN FREE R VALUE                     :   0.312
REMARK   3
REMARK   3  NUMBER OF NON-HYDROGEN ATOMS USED IN REFINEMENT.
REMARK   3   ALL ATOMS          :       6926
REMARK   3
REMARK   3  B VALUES.
REMARK   3   FROM WILSON PLOT           (A**2) : NULL
REMARK   3   MEAN B VALUE      (OVERALL, A**2) :  32.465
REMARK   3   OVERALL ANISOTROPIC B VALUE.
REMARK   3    B11 (A**2) :     0.44
REMARK   3    B22 (A**2) :     0.68
REMARK   3    B33 (A**2) :    -1.12
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                        (A):   0.317
REMARK   3   ESU BASED ON FREE R VALUE                   (A):   0.227
REMARK   3   ESU BASED ON MAXIMUM LIKELIHOOD             (A):   0.160
REMARK   3   ESU FOR B VALUES BASED ON MAXIMUM LIKELIHOOD (A**2):  13.245
REMARK   3
REMARK   3 CORRELATION COEFFICIENTS.
REMARK   3   CORRELATION COEFFICIENT FO-FC      :  0.946
REMARK   3   CORRELATION COEFFICIENT FO-FC FREE :  0.920
REMARK   3
REMARK   3  RMS DEVIATIONS FROM IDEAL VALUES        COUNT    RMS    WEIGHT
REMARK   3   BOND LENGTHS REFINED ATOMS       (A): 6764 ; 0.013 ; 0.022
REMARK   3   BOND ANGLES REFINED ATOMS   (DEGREES): 9116 ; 1.519 ; 1.987
REMARK   3   TORSION ANGLES, PERIOD 1    (DEGREES):  823 ; 6.267 ; 5.000
REMARK   3   TORSION ANGLES, PERIOD 2    (DEGREES):  297 ;35.379 ;23.199
REMARK   3   TORSION ANGLES, PERIOD 3    (DEGREES): 1291 ;16.121 ;15.000
REMARK   3   TORSION ANGLES, PERIOD 4    (DEGREES):   62 ;18.647 ;15.000
REMARK   3   CHIRAL-CENTER RESTRAINTS       (A**3): 1027 ; 0.093 ; 0.200
REMARK   3   GENERAL PLANES REFINED ATOMS     (A): 4923 ; 0.005 ; 0.020
```

FIGURE 18-2

```
REMARK   3    NON-BONDED CONTACTS REFINED ATOMS   (A):   2631 ; 0.200 ; 0.200
REMARK   3    NON-BONDED TORSION REFINED ATOMS    (A):   4496 ; 0.292 ; 0.200
REMARK   3    H-BOND (X...Y) REFINED ATOMS        (A):    321 ; 0.173 ; 0.200
REMARK   3    SYMMETRY VDW REFINED ATOMS          (A):    124 ; 0.333 ; 0.200
REMARK   3    SYMMETRY H-BOND REFINED ATOMS       (A):     17 ; 0.205 ; 0.200
REMARK   3
REMARK   3   ISOTROPIC THERMAL FACTOR RESTRAINTS.      COUNT    RMS      WEIGHT
REMARK   3    MAIN-CHAIN BOND REFINED ATOMS     (A**2):  4221 ; 0.728 ; 1.500
REMARK   3    MAIN-CHAIN ANGLE REFINED ATOMS    (A**2):  6577 ; 1.124 ; 2.000
REMARK   3    SIDE-CHAIN BOND REFINED ATOMS     (A**2):  2920 ; 2.095 ; 3.000
REMARK   3    SIDE-CHAIN ANGLE REFINED ATOMS    (A**2):  2539 ; 3.232 ; 4.500
REMARK   3
REMARK   3   NCS RESTRAINTS STATISTICS
REMARK   3    NUMBER OF DIFFERENT NCS GROUPS :    1
REMARK   3
REMARK   3   NCS GROUP NUMBER                   :    1
REMARK   3      CHAIN NAMES                     :  B D E A
REMARK   3      NUMBER OF COMPONENTS NCS GROUP  :    9
REMARK   3        COMPONENT C  SSSEQI  TO  C   SSSEQI   CODE
REMARK   3            1      B    323       B    330      1
REMARK   3            1      D    323       D    330      1
REMARK   3            1      E    323       E    330      1
REMARK   3            1      A    323       A    330      1
REMARK   3            2      B    333       B    340      1
REMARK   3            2      D    333       D    340      1
REMARK   3            2      E    333       E    340      1
REMARK   3            2      A    333       A    340      1
REMARK   3            3      B    350       B    368      1
REMARK   3            3      D    350       D    368      1
REMARK   3            3      E    350       E    368      1
REMARK   3            3      A    350       A    368      1
REMARK   3            4      B    370       B    389      1
REMARK   3            4      D    370       D    389      1
REMARK   3            4      E    370       E    389      1
REMARK   3            4      A    370       A    389      1
REMARK   3            5      B    393       B    407      1
REMARK   3            5      D    393       D    407      1
REMARK   3            5      E    393       E    407      1
REMARK   3            5      A    393       A    407      1
REMARK   3            6      B    411       B    420      1
REMARK   3            6      D    411       D    420      1
REMARK   3            6      E    411       E    420      1
REMARK   3            6      A    411       A    420      1
REMARK   3            7      B    428       B    434      1
REMARK   3            7      D    428       D    434      1
REMARK   3            7      E    428       E    434      1
REMARK   3            7      A    428       A    434      1
REMARK   3            8      B    443       B    451      1
REMARK   3            8      D    443       D    451      1
REMARK   3            8      E    443       E    451      1
REMARK   3            8      A    443       A    451      1
REMARK   3            9      B    455       B    482      1
REMARK   3            9      D    455       D    482      1
REMARK   3            9      E    455       E    482      1
REMARK   3            9      A    455       A    482      1
REMARK   3                  GROUP CHAIN         COUNT    RMS      WEIGHT
REMARK   3    TIGHT POSITIONAL     1     B    (A):    965 ; 0.05 ; 0.05
REMARK   3    TIGHT POSITIONAL     1     D    (A):    965 ; 0.04 ; 0.05
REMARK   3    TIGHT POSITIONAL     1     E    (A):    965 ; 0.05 ; 0.05
REMARK   3    TIGHT POSITIONAL     1     A    (A):    965 ; 0.06 ; 0.05
REMARK   3    TIGHT THERMAL        1     B  (A**2):   965 ; 1.46 ; 5.00
REMARK   3    TIGHT THERMAL        1     D  (A**2):   965 ; 1.42 ; 5.00
REMARK   3    TIGHT THERMAL        1     E  (A**2):   965 ; 1.17 ; 5.00
REMARK   3    TIGHT THERMAL        1     A  (A**2):   965 ; 1.46 ; 5.00
REMARK   3
REMARK   3
REMARK   3   TLS DETAILS
REMARK   3    NUMBER OF TLS GROUPS  :    5
REMARK   3    ATOM RECORD CONTAINS SUM OF TLS AND RESIDUAL B FACTORS
REMARK   3    ANISOU RECORD CONTAINS SUM OF TLS AND RESIDUAL U FACTORS
REMARK   3
```

FIGURE 18-3

```
REMARK   3    TLS GROUP :      1
REMARK   3     NUMBER OF COMPONENTS GROUP :     2
REMARK   3     COMPONENTS        C SSSEQI    TO   C SSSEQI
REMARK   3     RESIDUE RANGE :   A    320         A    483
REMARK   3     RESIDUE RANGE :   A      1         A      1
REMARK   3     ORIGIN FOR THE GROUP (A):   35.1410   19.8550  -23.4970
REMARK   3     T TENSOR
REMARK   3       T11:  -0.1550 T22:   -0.1929
REMARK   3       T33:  -0.1067 T12:    0.0176
REMARK   3       T13:  -0.0298 T23:    0.0184
REMARK   3     L TENSOR
REMARK   3       L11:   2.3533 L22:    1.7075
REMARK   3       L33:   2.2571 L12:    0.0348
REMARK   3       L13:  -0.0773 L23:    0.5035
REMARK   3     S TENSOR
REMARK   3       S11:   0.0055 S12:    0.1725 S13:    0.1938
REMARK   3       S21:  -0.0821 S22:    0.0154 S23:   -0.0549
REMARK   3       S31:   0.0216 S32:    0.1221 S33:   -0.0208
REMARK   3
REMARK   3    TLS GROUP :      2
REMARK   3     NUMBER OF COMPONENTS GROUP :     2
REMARK   3     COMPONENTS        C SSSEQI    TO   C SSSEQI
REMARK   3     RESIDUE RANGE :   B    320         B    483
REMARK   3     RESIDUE RANGE :   B      1         B      1
REMARK   3     ORIGIN FOR THE GROUP (A):   12.4750   -3.5580  -19.4120
REMARK   3     T TENSOR
REMARK   3       T11:  -0.1896 T22:   -0.1182
REMARK   3       T33:  -0.0978 T12:   -0.0381
REMARK   3       T13:  -0.0171 T23:   -0.0637
REMARK   3     L TENSOR
REMARK   3       L11:   1.9172 L22:    2.6126
REMARK   3       L33:   3.6260 L12:    0.0348
REMARK   3       L13:  -0.2423 L23:   -0.1860
REMARK   3     S TENSOR
REMARK   3       S11:  -0.0729 S12:    0.1999 S13:   -0.0806
REMARK   3       S21:  -0.0771 S22:    0.0269 S23:    0.2153
REMARK   3       S31:   0.1325 S32:   -0.3438 S33:    0.0460
REMARK   3
REMARK   3    TLS GROUP :      3
REMARK   3     NUMBER OF COMPONENTS GROUP :     2
REMARK   3     COMPONENTS        C SSSEQI    TO   C SSSEQI
REMARK   3     RESIDUE RANGE :   D    319         D    483
REMARK   3     RESIDUE RANGE :   D      1         D      1
REMARK   3     ORIGIN FOR THE GROUP (A):   58.8840   -3.4260  -19.4800
REMARK   3     T TENSOR
REMARK   3       T11:  -0.2007 T22:   -0.1084
REMARK   3       T33:  -0.1629 T12:    0.0008
REMARK   3       T13:   0.0350 T23:   -0.0105
REMARK   3     L TENSOR
REMARK   3       L11:   2.5312 L22:    3.5830
REMARK   3       L33:   2.7686 L12:   -0.2516
REMARK   3       L13:  -0.0723 L23:    0.1658
REMARK   3     S TENSOR
REMARK   3       S11:   0.0281 S12:    0.3485 S13:   -0.0276
REMARK   3       S21:  -0.3438 S22:   -0.1013 S23:   -0.1815
REMARK   3       S31:   0.0548 S32:   -0.1509 S33:    0.0732
REMARK   3
REMARK   3    TLS GROUP :      4
REMARK   3     NUMBER OF COMPONENTS GROUP :     2
REMARK   3     COMPONENTS        C SSSEQI    TO   C SSSEQI
REMARK   3     RESIDUE RANGE :   E    320         E    483
REMARK   3     RESIDUE RANGE :   E      1         E      1
REMARK   3     ORIGIN FOR THE GROUP (A):   35.6570  -25.9320  -15.2800
REMARK   3     T TENSOR
REMARK   3       T11:  -0.0768 T22:   -0.2139
REMARK   3       T33:  -0.0804 T12:   -0.0233
REMARK   3       T13:   0.0636 T23:   -0.0476
REMARK   3     L TENSOR
REMARK   3       L11:   3.7194 L22:    2.4929
REMARK   3       L33:   2.9822 L12:    0.6274
REMARK   3       L13:   0.2948 L23:    1.0025
```

FIGURE 18-4

```
REMARK   3     S TENSOR
REMARK   3        S11:   -0.0484 S12:    0.3196 S13:   -0.2371
REMARK   3        S21:   -0.1986 S22:    0.0864 S23:   -0.0561
REMARK   3        S31:    0.1208 S32:    0.1243 S33:   -0.0380
REMARK   3
REMARK   3    TLS GROUP :     5
REMARK   3     NUMBER OF COMPONENTS GROUP :    2
REMARK   3     COMPONENTS        C SSSEQI    TO   C SSSEQI
REMARK   3     RESIDUE RANGE :   F   322         F   483
REMARK   3     RESIDUE RANGE :   F     1         F     1
REMARK   3     ORIGIN FOR THE GROUP (A):  29.6550  -7.6170 -50.4960
REMARK   3     T TENSOR
REMARK   3        T11:    0.0277 T22:    0.2406
REMARK   3        T33:   -0.1217 T12:    0.0164
REMARK   3        T13:   -0.0146 T23:   -0.0766
REMARK   3     L TENSOR
REMARK   3        L11:    2.4339 L22:    4.7601
REMARK   3        L33:    4.8718 L12:    0.4947
REMARK   3        L13:   -0.0699 L23:    1.5231
REMARK   3     S TENSOR
REMARK   3        S11:   -0.0489 S12:    0.5805 S13:   -0.1649
REMARK   3        S21:   -0.2269 S22:    0.0375 S23:   -0.0293
REMARK   3        S31:    0.2872 S32:    0.3181 S33:    0.0114
REMARK   3
REMARK   3
REMARK   3   BULK SOLVENT MODELLING.
REMARK   3    METHOD USED : MASK
REMARK   3    PARAMETERS FOR MASK CALCULATION
REMARK   3    VDW PROBE RADIUS    :   1.40
REMARK   3    ION PROBE RADIUS    :   0.80
REMARK   3    SHRINKAGE RADIUS    :   0.80
REMARK   3
REMARK   3   OTHER REFINEMENT REMARKS:
REMARK   3   HYDROGENS HAVE BEEN ADDED IN THE RIDING POSITIONS
REMARK   3
LINK              VAL B 421                 ALA B 424                gap
LINK              ASN E 422                 ARG E 427                gap
LINK              ASN F 422                 ASN F 425                gap
CRYST1   92.200   94.440  220.400  90.00  90.00  90.00 C 2 2 21
SCALE1      0.010846  0.000000  0.000000        0.00000
SCALE2      0.000000  0.010589  0.000000        0.00000
SCALE3      0.000000  0.000000  0.004537        0.00000
ATOM      1  N   SER A 320      54.724  26.969 -16.114  1.00 49.27           N
ANISOU    1  N   SER A 320     4119   7020   7581   -643   -576   -957       N
ATOM      2  CA  SER A 320      53.387  26.747 -16.772  1.00 47.48           C
ANISOU    2  CA  SER A 320     4127   6616   7296   -583   -499   -811       C
ATOM      3  CB  SER A 320      52.263  27.451 -15.989  1.00 46.88           C
ANISOU    3  CB  SER A 320     4227   6364   7221   -625   -539   -825       C
ATOM      4  OG  SER A 320      51.912  26.737 -14.806  1.00 47.95           O
ANISOU    4  OG  SER A 320     4428   6550   7242   -485   -673   -881       O
ATOM      5  C   SER A 320      53.375  27.229 -18.230  1.00 47.12           C
ANISOU    5  C   SER A 320     4085   6503   7314   -693   -330   -697       C
ATOM      6  O   SER A 320      54.163  28.116 -18.614  1.00 48.38           O
ANISOU    6  O   SER A 320     4111   6684   7588   -870   -256   -724       O
ATOM      7  N   SER A 321      52.500  26.617 -19.034  1.00 44.78           N
ANISOU    7  N   SER A 321     3940   6137   6937   -592   -270   -571       N
ATOM      8  CA  SER A 321      52.188  27.123 -20.378  1.00 43.99           C
ANISOU    8  CA  SER A 321     3899   5951   6864   -686   -122   -442       C
ATOM      9  CB  SER A 321      52.645  26.139 -21.481  1.00 44.33           C
ANISOU    9  CB  SER A 321     3883   6132   6831   -594    -42   -388       C
ATOM     10  OG  SER A 321      51.642  25.165 -21.790  1.00 44.54           O
ANISOU   10  OG  SER A 321     4074   6110   6740   -434    -58   -318       O
ATOM     11  C   SER A 321      50.674  27.446 -20.489  1.00 41.02           C
ANISOU   11  C   SER A 321     3753   5371   6461   -667   -116   -344       C
ATOM     12  O   SER A 321      49.828  26.667 -20.050  1.00 38.76           O
ANISOU   12  O   SER A 321     3585   5058   6085   -525   -186   -338       O
ATOM     13  N   SER A 322      50.365  28.608 -21.063  1.00 39.94           N
ANISOU   13  N   SER A 322     3672   5093   6409   -814    -31   -267       N
ATOM     14  CA  SER A 322      48.990  29.066 -21.192  1.00 37.50           C
ANISOU   14  CA  SER A 322     3558   4592   6098   -798    -28   -177       C
ATOM     15  CB  SER A 322      48.780  30.408 -20.502  1.00 38.36           C
```

FIGURE 18-5

```
ANISOU   15  CB   SER A 322     3699   4533   6342   -928    -45   -227       C
ATOM     16  OG   SER A 322     48.807  30.236 -19.105  1.00 41.26           O
ANISOU   16  OG   SER A 322     4040   4932   6704   -882   -161   -379      O
ATOM     17  C    SER A 322     48.540  29.176 -22.627  1.00 35.90           C
ANISOU   17  C    SER A 322     3439   4343   5858   -813     81    -11      C
ATOM     18  O    SER A 322     49.323  29.452 -23.543  1.00 36.92           O
ANISOU   18  O    SER A 322     3488   4535   6006   -912    183     47      O
ATOM     19  N    PHE A 323     47.261  28.915 -22.811  1.00 32.90           N
ANISOU   19  N    PHE A 323     3216   3870   5414   -714     56     62      N
ATOM     20  CA   PHE A 323     46.611  29.195 -24.077  1.00 31.70           C
ANISOU   20  CA   PHE A 323     3167   3652   5224   -726    134    223      C
ATOM     21  CB   PHE A 323     46.730  28.032 -25.092  1.00 30.07           C
ANISOU   21  CB   PHE A 323     2953   3600   4872   -634    177    274      C
ATOM     22  CG   PHE A 323     46.322  26.714 -24.552  1.00 27.72           C
ANISOU   22  CG   PHE A 323     2678   3371   4481   -474     93    196      C
ATOM     23  CD1  PHE A 323     45.030  26.271 -24.707  1.00 25.75           C
ANISOU   23  CD1  PHE A 323     2566   3057   4162   -378     53    245      C
ATOM     24  CE1  PHE A 323     44.642  25.070 -24.196  1.00 24.05           C
ANISOU   24  CE1  PHE A 323     2380   2888   3871   -251    -15    180      C
ATOM     25  CZ   PHE A 323     45.541  24.275 -23.524  1.00 24.93           C
ANISOU   25  CZ   PHE A 323     2397   3105   3969   -195    -52     76      C
ATOM     26  CE2  PHE A 323     46.840  24.686 -23.357  1.00 25.71           C
ANISOU   26  CE2  PHE A 323     2350   3285   4133   -269    -26     23      C
ATOM     27  CD2  PHE A 323     47.234  25.908 -23.874  1.00 28.00           C
ANISOU   27  CD2  PHE A 323     2597   3536   4504   -418     51     77      C
ATOM     28  C    PHE A 323     45.163  29.568 -23.830  1.00 29.89           C
ANISOU   28  C    PHE A 323     3093   3256   5008   -667     82    270      C
ATOM     29  O    PHE A 323     44.616  29.366 -22.743  1.00 29.10           O
ANISOU   29  O    PHE A 323     3023   3117   4917   -600     -3    175      O
ATOM     30  N    SER A 324     44.553  30.095 -24.867  1.00 29.85           N
ANISOU   30  N    SER A 324     3182   3167   4994   -688    135    420      N
ATOM     31  CA   SER A 324     43.159  30.471 -24.844  1.00 30.29           C
ANISOU   31  CA   SER A 324     3369   3076   5062   -621     90    481      C
ATOM     32  CB   SER A 324     43.035  31.897 -25.367  1.00 32.34           C
ANISOU   32  CB   SER A 324     3691   3160   5436   -725    143    602      C
ATOM     33  OG   SER A 324     41.869  32.520 -24.855  1.00 36.69           O
ANISOU   33  OG   SER A 324     4337   3538   6064   -667     84    602      O
ATOM     34  C    SER A 324     42.357  29.507 -25.724  1.00 28.87           C
ANISOU   34  C    SER A 324     3257   2982   4731   -505     81    560      C
ATOM     35  O    SER A 324     42.760  29.221 -26.855  1.00 29.40           O
ANISOU   35  O    SER A 324     3315   3147   4709   -524    146    648      O
ATOM     36  N    PHE A 325     41.252  28.971 -25.199  1.00 26.88           N
ANISOU   36  N    PHE A 325     3064   2706   4445   -394      5    517      N
ATOM     37  CA   PHE A 325     40.371  28.148 -25.992  1.00 25.57           C
ANISOU   37  CA   PHE A 325     2960   2603   4153   -299    -13    580      C
ATOM     38  CB   PHE A 325     40.776  26.659 -25.905  1.00 24.87           C
ANISOU   38  CB   PHE A 325     2828   2671   3952   -233    -24    493      C
ATOM     39  CG   PHE A 325     39.944  25.733 -26.769  1.00 23.25           C
ANISOU   39  CG   PHE A 325     2684   2533   3617   -152    -40    535      C
ATOM     40  CD1  PHE A 325     40.003  25.815 -28.165  1.00 25.46           C
ANISOU   40  CD1  PHE A 325     2990   2876   3809   -171     12    645      C
ATOM     41  CE1  PHE A 325     39.243  24.954 -28.976  1.00 23.62           C
ANISOU   41  CE1  PHE A 325     2810   2717   3447   -102    -11    664      C
ATOM     42  CZ   PHE A 325     38.430  23.990 -28.377  1.00 23.09           C
ANISOU   42  CZ   PHE A 325     2768   2648   3358    -24    -79    576      C
ATOM     43  CE2  PHE A 325     38.359  23.916 -26.980  1.00 19.84           C
ANISOU   43  CE2  PHE A 325     2336   2168   3036     -9   -119    485      C
ATOM     44  CD2  PHE A 325     39.118  24.773 -26.195  1.00 20.21           C
ANISOU   44  CD2  PHE A 325     2332   2156   3190    -67   -102    463      C
ATOM     45  C    PHE A 325     38.945  28.342 -25.493  1.00 25.59           C
ANISOU   45  C    PHE A 325     3035   2502   4189   -224    -81    574      C
ATOM     46  O    PHE A 325     38.673  28.189 -24.307  1.00 24.95           O
ANISOU   46  O    PHE A 325     2941   2388   4150   -195   -126    462      O
ATOM     47  N    GLY A 326     38.032  28.646 -26.416  1.00 25.94           N
ANISOU   47  N    GLY A 326     3147   2510   4200   -188    -90    693      N
ATOM     48  CA   GLY A 326     36.612  28.725 -26.111  1.00 25.17           C
ANISOU   48  CA   GLY A 326     3096   2344   4125   -103   -155    690      C
ATOM     49  C    GLY A 326     36.229  29.790 -25.105  1.00 26.10           C
ANISOU   49  C    GLY A 326     3221   2299   4397   -108   -174    641      C
ATOM     50  O    GLY A 326     35.223  29.646 -24.422  1.00 25.44           O
ANISOU   50  O    GLY A 326     3144   2187   4334    -38   -220    574      O
```

FIGURE 18-6

```
ATOM     51  N   GLY A 327      37.027  30.862 -25.017  1.00 27.43           N
ANISOU   51  N   GLY A 327     3385   2361   4675   -198   -132    664       N
ATOM     52  CA  GLY A 327      36.814  31.912 -24.021  1.00 27.22           C
ANISOU   52  CA  GLY A 327     3367   2168   4806   -214   -145    590       C
ATOM     53  C   GLY A 327      37.405  31.621 -22.645  1.00 26.92           C
ANISOU   53  C   GLY A 327     3269   2165   4793   -247   -155    409       C
ATOM     54  O   GLY A 327      37.162  32.382 -21.694  1.00 27.56           O
ANISOU   54  O   GLY A 327     3357   2128   4986   -254   -170    314       O
ATOM     55  N   PHE A 328      38.164  30.521 -22.524  1.00 25.21           N
ANISOU   55  N   PHE A 328     2998   2113   4470   -258   -153    357       N
ATOM     56  CA  PHE A 328      38.854  30.196 -21.271  1.00 24.27           C
ANISOU   56  CA  PHE A 328     2818   2049   4354   -284   -175    202       C
ATOM     57  CB  PHE A 328      38.420  28.823 -20.748  1.00 21.36           C
ANISOU   57  CB  PHE A 328     2450   1807   3859   -193   -216    141       C
ATOM     58  CG  PHE A 328      37.002  28.783 -20.278  1.00 21.75           C
ANISOU   58  CG  PHE A 328     2552   1805   3906   -115   -245    118       C
ATOM     59  CD1 PHE A 328      36.703  28.945 -18.927  1.00 20.12           C
ANISOU   59  CD1 PHE A 328     2344   1576   3724   -103   -269    -11       C
ATOM     60  CE1 PHE A 328      35.409  28.928 -18.474  1.00 18.66           C
ANISOU   60  CE1 PHE A 328     2192   1359   3539    -36   -280    -42       C
ATOM     61  CZ  PHE A 328      34.350  28.706 -19.370  1.00 19.24           C
ANISOU   61  CZ  PHE A 328     2291   1424   3594     24   -280     54       C
ATOM     62  CE2 PHE A 328      34.621  28.534 -20.739  1.00 19.65           C
ANISOU   62  CE2 PHE A 328     2351   1500   3614     16   -271    184       C
ATOM     63  CD2 PHE A 328      35.943  28.578 -21.186  1.00 20.82           C
ANISOU   63  CD2 PHE A 328     2476   1679   3755    -53   -247    216       C
ATOM     64  C   PHE A 328      40.359  30.228 -21.450  1.00 24.86           C
ANISOU   64  C   PHE A 328     2812   2194   4438   -383   -140    189       C
ATOM     65  O   PHE A 328      40.866  29.801 -22.489  1.00 25.40           O
ANISOU   65  O   PHE A 328     2860   2349   4442   -398    -98    278       O
ATOM     66  N   THR A 329      41.061  30.721 -20.433  1.00 25.87           N
ANISOU   66  N   THR A 329     2885   2302   4643   -451   -157     64       N
ATOM     67  CA  THR A 329      42.516  30.587 -20.320  1.00 26.02           C
ANISOU   67  CA  THR A 329     2793   2427   4668   -537   -143      9       C
ATOM     68  CB  THR A 329      43.119  31.743 -19.510  1.00 27.28           C
ANISOU   68  CB  THR A 329     2908   2490   4967   -657   -149   -100       C
ATOM     69  OG1 THR A 329      42.778  32.984 -20.135  1.00 28.71           O
ANISOU   69  OG1 THR A 329     3154   2479   5276   -731    -95     -9       O
ATOM     70  CG2 THR A 329      44.634  31.634 -19.423  1.00 28.51           C
ANISOU   70  CG2 THR A 329     2923   2773   5137   -755   -139   -164       C
ATOM     71  C   THR A 329      42.803  29.250 -19.623  1.00 25.30           C
ANISOU   71  C   THR A 329     2656   2504   4453   -448   -202    -77       C
ATOM     72  O   THR A 329      42.381  29.020 -18.481  1.00 24.62           O
ANISOU   72  O   THR A 329     2591   2422   4339   -397   -263   -177       O
ATOM     73  N   PHE A 330      43.508  28.370 -20.328  1.00 25.13           N
ANISOU   73  N   PHE A 330     2578   2617   4353   -425   -178    -34       N
ATOM     74  CA  PHE A 330      44.004  27.109 -19.781  1.00 23.76           C
ANISOU   74  CA  PHE A 330     2354   2594   4080   -338   -231   -105       C
ATOM     75  CB  PHE A 330      44.025  26.057 -20.885  1.00 22.27           C
ANISOU   75  CB  PHE A 330     2176   2492   3794   -266   -193    -21       C
ATOM     76  CG  PHE A 330      42.680  25.488 -21.239  1.00 20.53           C
ANISOU   76  CG  PHE A 330     2078   2221   3502   -181   -200     43       C
ATOM     77  CD1 PHE A 330      42.392  24.145 -20.983  1.00 19.04           C
ANISOU   77  CD1 PHE A 330     1924   2097   3213    -73   -240     19       C
ATOM     78  CE1 PHE A 330      41.140  23.599 -21.356  1.00 18.69           C
ANISOU   78  CE1 PHE A 330     1982   2010   3110    -15   -244     70       C
ATOM     79  CZ  PHE A 330      40.183  24.409 -21.969  1.00 16.45           C
ANISOU   79  CZ  PHE A 330     1753   1636   2861    -47   -219    144       C
ATOM     80  CE2 PHE A 330      40.483  25.735 -22.229  1.00 17.52           C
ANISOU   80  CE2 PHE A 330     1861   1702   3092   -134   -185    180       C
ATOM     81  CD2 PHE A 330      41.712  26.267 -21.870  1.00 18.89           C
ANISOU   81  CD2 PHE A 330     1947   1901   3330   -209   -170    131       C
ATOM     82  C   PHE A 330      45.442  27.334 -19.342  1.00 25.60           C
ANISOU   82  C   PHE A 330     2443   2923   4362   -411   -244   -196       C
ATOM     83  O   PHE A 330      46.220  27.886 -20.103  1.00 26.69           O
ANISOU   83  O   PHE A 330     2504   3075   4562   -509   -176   -160       O
ATOM     84  N   LYS A 331      45.798  26.952 -18.116  1.00 26.58           N
ANISOU   84  N   LYS A 331     2524   3119   4455   -370   -331   -311       N
ATOM     85  CA  LYS A 331      47.198  26.814 -17.729  1.00 28.34           C
ANISOU   85  CA  LYS A 331     2589   3483   4695   -400   -366   -401       C
ATOM     86  CB  LYS A 331      47.576  27.791 -16.597  1.00 29.96           C
```

FIGURE 18-7

```
ANISOU   86  CB   LYS A 331     2740   3665   4978    -499   -424   -533          C
ATOM     87  CG   LYS A 331      46.950  29.141 -16.805  1.00 33.02              C
ANISOU   87  CG   LYS A 331     3199   3864   5484    -618   -366   -514          C
ATOM     88  CD   LYS A 331      47.691  30.310 -16.166  1.00 36.96              C
ANISOU   88  CD   LYS A 331     3609   4328   6108    -772   -384   -641          C
ATOM     89  CE   LYS A 331      46.932  31.614 -16.487  1.00 38.10              C
ANISOU   89  CE   LYS A 331     3856   4240   6381    -869   -318   -602          C
ATOM     90  NZ   LYS A 331      45.453  31.490 -16.098  1.00 35.18              N
ANISOU   90  NZ   LYS A 331     3643   3766   5958    -754   -340   -582          N
ATOM     91  C    LYS A 331      47.426  25.382 -17.285  1.00 27.41              C
ANISOU   91  C    LYS A 331     2461   3496   4457    -247   -438   -423          C
ATOM     92  O    LYS A 331      46.686  24.886 -16.436  1.00 26.89              O
ANISOU   92  O    LYS A 331     2493   3409   4316    -163   -502   -440          O
ATOM     93  N    ARG A 332      48.430  24.719 -17.857  1.00 27.61              N
ANISOU   93  N    ARG A 332     2371   3651   4467    -207   -422   -419          N
ATOM     94  CA   ARG A 332      48.758  23.355 -17.455  1.00 27.40              C
ANISOU   94  CA   ARG A 332     2331   3735   4345     -47   -494   -440          C
ATOM     95  CB   ARG A 332      49.602  22.651 -18.535  1.00 28.32              C
ANISOU   95  CB   ARG A 332     2347   3958   4456       6   -433   -413          C
ATOM     96  CG   ARG A 332      49.838  21.151 -18.250  1.00 27.07              C
ANISOU   96  CG   ARG A 332     2199   3876   4209     196   -503   -424          C
ATOM     97  CD   ARG A 332      50.442  20.434 -19.426  1.00 28.72              C
ANISOU   97  CD   ARG A 332     2338   4163   4411     261   -425   -404          C
ATOM     98  NE   ARG A 332      51.692  21.044 -19.875  1.00 33.91              N
ANISOU   98  NE   ARG A 332     2788   4950   5147     174   -371   -457          N
ATOM     99  CZ   ARG A 332      52.274  20.789 -21.043  1.00 34.89              C
ANISOU   99  CZ   ARG A 332     2824   5156   5276     178   -265   -445          C
ATOM    100  NH1  ARG A 332      51.722  19.917 -21.900  1.00 36.69              N
ANISOU  100  NH1  ARG A 332     3162   5348   5430     273   -212   -393          N
ATOM    101  NH2  ARG A 332      53.401  21.404 -21.362  1.00 33.49              N
ANISOU  101  NH2  ARG A 332     2447   5104   5173      80   -208   -495          N
ATOM    102  C    ARG A 332      49.478  23.325 -16.100  1.00 28.09              C
ANISOU  102  C    ARG A 332     2332   3923   4419     -22   -617   -552          C
ATOM    103  O    ARG A 332      50.525  23.979 -15.940  1.00 29.61              O
ANISOU  103  O    ARG A 332     2361   4203   4686    -112   -631   -634          O
ATOM    104  N    THR A 333      48.919  22.570 -15.143  1.00 26.95              N
ANISOU  104  N    THR A 333     2293   3774   4172      91   -705   -554          N
ATOM    105  CA   THR A 333      49.474  22.450 -13.787  1.00 27.54              C
ANISOU  105  CA   THR A 333     2315   3954   4195     133   -836   -647          C
ATOM    106  CB   THR A 333      48.388  22.724 -12.718  1.00 27.54              C
ANISOU  106  CB   THR A 333     2466   3874   4125     122   -877   -663          C
ATOM    107  OG1  THR A 333      47.269  21.862 -12.950  1.00 25.80              O
ANISOU  107  OG1  THR A 333     2413   3561   3829     209   -841   -558          O
ATOM    108  CG2  THR A 333      47.898  24.155 -12.811  1.00 27.45              C
ANISOU  108  CG2  THR A 333     2468   3750   4212     -40   -814   -706          C
ATOM    109  C    THR A 333      50.166  21.106 -13.487  1.00 28.06              C
ANISOU  109  C    THR A 333     2339   4142   4179     311   -925   -636          C
ATOM    110  O    THR A 333      50.964  21.028 -12.549  1.00 29.37              O
ANISOU  110  O    THR A 333     2410   4438   4313     352  -1042   -713          O
ATOM    111  N    SER A 334      49.860  20.070 -14.277  1.00 27.10              N
ANISOU  111  N    SER A 334     2292   3978   4028     420   -875   -547          N
ATOM    112  CA   SER A 334      50.480  18.728 -14.162  1.00 27.68              C
ANISOU  112  CA   SER A 334     2343   4130   4045     606   -945   -529          C
ATOM    113  CB   SER A 334      49.626  17.789 -13.327  1.00 26.96              C
ANISOU  113  CB   SER A 334     2442   3966   3835     718  -1011   -462          C
ATOM    114  OG   SER A 334      50.099  17.727 -12.010  1.00 30.72              O
ANISOU  114  OG   SER A 334     2890   4542   4239     772  -1148   -505          O
ATOM    115  C    SER A 334      50.552  18.102 -15.525  1.00 26.76              C
ANISOU  115  C    SER A 334     2220   3985   3963     656   -843   -480          C
ATOM    116  O    SER A 334      49.729  18.424 -16.392  1.00 25.27              O
ANISOU  116  O    SER A 334     2118   3691   3794     573   -735   -429          O
ATOM    117  N    GLY A 335      51.514  17.201 -15.702  1.00 27.29              N
ANISOU  117  N    GLY A 335     2187   4150   4033     801   -881   -502          N
ATOM    118  CA   GLY A 335      51.543  16.328 -16.851  1.00 27.54              C
ANISOU  118  CA   GLY A 335     2237   4152   4073     890   -798   -470          C
ATOM    119  C    GLY A 335      52.108  16.996 -18.081  1.00 28.17              C
ANISOU  119  C    GLY A 335     2172   4300   4230     785   -672   -502          C
ATOM    120  O    GLY A 335      52.658  18.070 -18.002  1.00 28.84              O
ANISOU  120  O    GLY A 335     2118   4461   4377     651   -657   -549          O
ATOM    121  N    SER A 336      51.966  16.334 -19.225  1.00 29.01              N
ANISOU  121  N    SER A 336     2317   4378   4327     841   -577   -478          N
```

FIGURE 18-8

```
ATOM    122  CA  SER A 336      52.594  16.734 -20.488  1.00 29.82           C
ANISOU  122  CA  SER A 336    2284   4572   4476    770   -446   -503        C
ATOM    123  CB  SER A 336      54.095  16.434 -20.467  1.00 31.95           C
ANISOU  123  CB  SER A 336    2316   5026   4798    861   -468   -597        C
ATOM    124  OG  SER A 336      54.337  15.074 -20.142  1.00 33.68           O
ANISOU  124  OG  SER A 336    2566   5243   4988   1088   -549   -616        O
ATOM    125  C   SER A 336      51.901  15.920 -21.579  1.00 29.25           C
ANISOU  125  C   SER A 336    2348   4417   4348    830   -360   -463        C
ATOM    126  O   SER A 336      51.086  15.038 -21.269  1.00 29.76           O
ANISOU  126  O   SER A 336    2585   4361   4362    927   -411   -428        O
ATOM    127  N   SER A 337      52.166  16.233 -22.844  1.00 28.72           N
ANISOU  127  N   SER A 337    2213   4414   4284    760   -226   -467        N
ATOM    128  CA  SER A 337      51.555  15.491 -23.941  1.00 27.37           C
ANISOU  128  CA  SER A 337    2163   4189   4047    811   -146   -447        C
ATOM    129  CB  SER A 337      50.107  15.923 -24.208  1.00 25.82           C
ANISOU  129  CB  SER A 337    2159   3849   3801    703   -126   -356        C
ATOM    130  OG  SER A 337      49.993  17.233 -24.736  1.00 25.02           O
ANISOU  130  OG  SER A 337    2022   3769   3717    524    -47   -301        O
ATOM    131  C   SER A 337      52.380  15.600 -25.197  1.00 28.77           C
ANISOU  131  C   SER A 337    2201   4511   4219    786     -9   -489        C
ATOM    132  O   SER A 337      53.165  16.538 -25.354  1.00 29.57           O
ANISOU  132  O   SER A 337    2138   4728   4370    669     48   -499        O
ATOM    133  N   ILE A 338      52.232  14.601 -26.062  1.00 28.60           N
ANISOU  133  N   ILE A 338    2243   4486   4138    894     46   -524        N
ATOM    134  CA  ILE A 338      52.744  14.661 -27.433  1.00 29.37           C
ANISOU  134  CA  ILE A 338    2253   4715   4191    862    197   -558        C
ATOM    135  CB  ILE A 338      53.684  13.470 -27.745  1.00 30.62           C
ANISOU  135  CB  ILE A 338    2306   4969   4358   1060    220   -684        C
ATOM    136  CG1 ILE A 338      52.951  12.126 -27.567  1.00 28.62           C
ANISOU  136  CG1 ILE A 338    2242   4558   4076   1227    144   -711        C
ATOM    137  CD1 ILE A 338      53.801  10.890 -27.901  1.00 31.84           C
ANISOU  137  CD1 ILE A 338    2573   5023   4504   1443    164   -841        C
ATOM    138  CG2 ILE A 338      54.936  13.557 -26.869  1.00 29.51           C
ANISOU  138  CG2 ILE A 338    1946   4947   4320   1128    157   -748        C
ATOM    139  C   ILE A 338      51.544  14.715 -28.383  1.00 29.43           C
ANISOU  139  C   ILE A 338    2448   4638   4097    787    257   -490        C
ATOM    140  O   ILE A 338      50.421  14.456 -27.965  1.00 27.50           O
ANISOU  140  O   ILE A 338    2379   4237   3831    796    177   -443        O
ATOM    141  N   LYS A 339      51.768  15.077 -29.643  1.00 32.18           N
ANISOU  141  N   LYS A 339    2753   5101   4374    708    395   -484        N
ATOM    142  CA  LYS A 339      50.659  15.264 -30.588  1.00 32.96           C
ANISOU  142  CA  LYS A 339    3017   5146   4361    628    443   -410        C
ATOM    143  CB  LYS A 339      50.689  16.636 -31.277  1.00 33.66           C
ANISOU  143  CB  LYS A 339    3068   5303   4417    436    542   -299        C
ATOM    144  CG  LYS A 339      50.626  17.879 -30.433  1.00 35.13           C
ANISOU  144  CG  LYS A 339    3225   5418   4704    302    495   -209        C
ATOM    145  CD  LYS A 339      50.839  19.070 -31.356  1.00 39.41           C
ANISOU  145  CD  LYS A 339    3730   6034   5211    126    622   -105        C
ATOM    146  CE  LYS A 339      51.214  20.330 -30.602  1.00 43.35           C
ANISOU  146  CE  LYS A 339    4145   6489   5837    -18    608    -49        C
ATOM    147  NZ  LYS A 339      51.747  21.354 -31.562  1.00 47.40           N
ANISOU  147  NZ  LYS A 339    4590   7093   6327   -188    758     41        N
ATOM    148  C   LYS A 339      50.829  14.249 -31.693  1.00 34.82           C
ANISOU  148  C   LYS A 339    3269   5464   4496    730    526   -506        C
ATOM    149  O   LYS A 339      51.942  13.867 -32.033  1.00 35.45           O
ANISOU  149  O   LYS A 339    3198   5686   4586    804    603   -605        O
ATOM    150  N   ARG A 340      49.708  13.859 -32.287  1.00 34.88           N
ANISOU  150  N   ARG A 340    3453   5392   4405    727    514   -488        N
ATOM    151  CA  ARG A 340      49.725  12.999 -33.446  1.00 37.31           C
ANISOU  151  CA  ARG A 340    3799   5779   4597    798    594   -585        C
ATOM    152  CB  ARG A 340      49.722  11.545 -32.981  1.00 37.81           C
ANISOU  152  CB  ARG A 340    3918   5738   4710    985    522   -715        C
ATOM    153  CG  ARG A 340      49.740  10.518 -34.090  1.00 41.11           C
ANISOU  153  CG  ARG A 340    4385   6209   5025   1077    596   -851        C
ATOM    154  CD  ARG A 340      49.106   9.264 -33.574  1.00 44.08           C
ANISOU  154  CD  ARG A 340    4906   6391   5449   1202    493   -927        C
ATOM    155  NE  ARG A 340      49.351   8.129 -34.448  1.00 49.69           N
ANISOU  155  NE  ARG A 340    5647   7130   6103   1325    557  -1096        N
ATOM    156  CZ  ARG A 340      48.735   6.956 -34.322  1.00 52.03           C
ANISOU  156  CZ  ARG A 340    6093   7254   6423   1418    492  -1183        C
ATOM    157  NH1 ARG A 340      47.836   6.774 -33.353  1.00 51.49           N
```

FIGURE 18-9

```
ANISOU  157  NH1  ARG A 340     6152   6986   6426   1395    368  -1102       N
ATOM    158  NH2  ARG A 340     49.013   5.967 -35.163  1.00 53.54            N
ANISOU  158  NH2  ARG A 340     6308   7469   6565   1528    558  -1356       N
ATOM    159  C    ARG A 340     48.494  13.280 -34.318  1.00 36.74            C
ANISOU  159  C    ARG A 340     3889   5680   4391    701    601   -510       C
ATOM    160  O    ARG A 340     47.381  13.418 -33.808  1.00 35.04            O
ANISOU  160  O    ARG A 340     3799   5317   4196    663    499   -439       O
ATOM    161  N    GLU A 341     48.689  13.298 -35.631  1.00 38.65            N
ANISOU  161  N    GLU A 341     4121   6076   4488    670    720   -537       N
ATOM    162  CA   GLU A 341     47.613  13.581 -36.585  1.00 38.96            C
ANISOU  162  CA   GLU A 341     4300   6129   4373    584    724   -467       C
ATOM    163  CB   GLU A 341     48.207  14.150 -37.884  1.00 41.11            C
ANISOU  163  CB   GLU A 341     4510   6619   4490    505    881   -436       C
ATOM    164  CG   GLU A 341     47.223  14.984 -38.717  1.00 44.93            C
ANISOU  164  CG   GLU A 341     5114   7131   4828    380    878   -285       C
ATOM    165  CD   GLU A 341     47.713  16.411 -38.966  1.00 50.98            C
ANISOU  165  CD   GLU A 341     5809   7976   5584    232    968   -111       C
ATOM    166  OE1  GLU A 341     48.843  16.587 -39.478  1.00 53.24            O
ANISOU  166  OE1  GLU A 341     5969   8430   5831    202   1115   -135       O
ATOM    167  OE2  GLU A 341     46.961  17.362 -38.638  1.00 52.85            O
ANISOU  167  OE2  GLU A 341     6117   8101   5863    142    896     49       O
ATOM    168  C    GLU A 341     46.793  12.331 -36.867  1.00 38.09            C
ANISOU  168  C    GLU A 341     4327   5941   4204    678    662   -589       C
ATOM    169  O    GLU A 341     47.339  11.310 -37.253  1.00 39.85            O
ANISOU  169  O    GLU A 341     4528   6213   4402    792    712   -749       O
ATOM    170  N    GLU A 342     45.486  12.415 -36.661  1.00 36.22            N
ANISOU  170  N    GLU A 342     4225   5579   3958    630    556   -523       N
ATOM    171  CA   GLU A 342     44.583  11.283 -36.867  1.00 35.81            C
ANISOU  171  CA   GLU A 342     4305   5437   3866    688    488   -634       C
ATOM    172  CB   GLU A 342     44.147  10.658 -35.531  1.00 34.01            C
ANISOU  172  CB   GLU A 342     4129   4994   3799    747    372   -653       C
ATOM    173  CG   GLU A 342     45.206   9.806 -34.803  1.00 36.13            C
ANISOU  173  CG   GLU A 342     4330   5210   4188    889    381   -758       C
ATOM    174  CD   GLU A 342     44.743   9.377 -33.407  1.00 35.59            C
ANISOU  174  CD   GLU A 342     4326   4936   4262    929    264   -729       C
ATOM    175  OE1  GLU A 342     45.588   9.256 -32.489  1.00 36.85            O
ANISOU  175  OE1  GLU A 342     4407   5063   4532   1012    245   -731       O
ATOM    176  OE2  GLU A 342     43.515   9.182 -33.211  1.00 38.13            O
ANISOU  176  OE2  GLU A 342     4771   5140   4578    874    190   -700       O
ATOM    177  C    GLU A 342     43.348  11.764 -37.613  1.00 34.67            C
ANISOU  177  C    GLU A 342     4264   5320   3589    586    446   -553       C
ATOM    178  O    GLU A 342     42.952  12.925 -37.477  1.00 33.00            O
ANISOU  178  O    GLU A 342     4047   5109   3382    490    423   -388       O
ATOM    179  N    GLU A 343     42.744  10.866 -38.396  1.00 34.97            N
ANISOU  179  N    GLU A 343     4394   5378   3515    612    430   -675       N
ATOM    180  CA   GLU A 343     41.458  11.149 -39.027  1.00 34.95            C
ANISOU  180  CA   GLU A 343     4487   5398   3393    529    359   -621       C
ATOM    181  CB   GLU A 343     41.400  10.673 -40.480  1.00 36.90            C
ANISOU  181  CB   GLU A 343     4778   5818   3423    531    413   -733       C
ATOM    182  CG   GLU A 343     42.297  11.448 -41.402  1.00 40.28            C
ANISOU  182  CG   GLU A 343     5137   6463   3706    499    544   -666       C
ATOM    183  CD   GLU A 343     42.120  11.051 -42.851  1.00 46.55            C
ANISOU  183  CD   GLU A 343     5988   7449   4252    492    592   -767       C
ATOM    184  OE1  GLU A 343     42.201   9.829 -43.156  1.00 49.23            O
ANISOU  184  OE1  GLU A 343     6363   7781   4562    569    603   -985       O
ATOM    185  OE2  GLU A 343     41.906  11.965 -43.686  1.00 47.82            O
ANISOU  185  OE2  GLU A 343     6164   7764   4241    412    616   -627       O
ATOM    186  C    GLU A 343     40.331  10.521 -38.238  1.00 33.33            C
ANISOU  186  C    GLU A 343     4367   5004   3293    529    234   -656       C
ATOM    187  O    GLU A 343     40.314   9.306 -37.987  1.00 33.83            O
ANISOU  187  O    GLU A 343     4478   4963   3412    597    215   -808       O
ATOM    188  N    VAL A 344     39.377  11.366 -37.868  1.00 31.66            N
ANISOU  188  N    VAL A 344     4174   4745   3110    451    153   -512       N
ATOM    189  CA   VAL A 344     38.220  10.946 -37.086  1.00 29.70            C
ANISOU  189  CA   VAL A 344     3988   4336   2960    430     43   -524       C
ATOM    190  CB   VAL A 344     38.219  11.619 -35.676  1.00 27.60            C
ANISOU  190  CB   VAL A 344     3682   3937   2866    420      8   -403       C
ATOM    191  CG1  VAL A 344     39.536  11.354 -34.968  1.00 27.04            C
ANISOU  191  CG1  VAL A 344     3551   3828   2895    497     68   -437       C
ATOM    192  CG2  VAL A 344     38.006  13.082 -35.781  1.00 26.27            C
ANISOU  192  CG2  VAL A 344     3472   3829   2680    354      3   -231       C
```

FIGURE 18-10

```
ATOM    193  C   VAL A 344      36.924  11.195 -37.880  1.00 29.93           C
ANISOU  193  C   VAL A 344    4067  4436  2869    358   -34  -498            C
ATOM    194  O   VAL A 344      36.926  11.910 -38.891  1.00 30.08           O
ANISOU  194  O   VAL A 344    4076  4615  2736    327   -12  -427            O
ATOM    195  N   LEU A 345      35.842  10.556 -37.454  1.00 29.10           N
ANISOU  195  N   LEU A 345    4013  4220  2824    331  -122  -559            N
ATOM    196  CA  LEU A 345      34.564  10.639 -38.170  1.00 29.46           C
ANISOU  196  CA  LEU A 345    4088  4339  2767    267  -210  -564            C
ATOM    197  CB  LEU A 345      34.148   9.271 -38.665  1.00 30.37           C
ANISOU  197  CB  LEU A 345    4269  4435  2834    260  -234  -769            C
ATOM    198  CG  LEU A 345      34.852   8.751 -39.913  1.00 33.75           C
ANISOU  198  CG  LEU A 345    4723  5011  3089    297  -167  -900            C
ATOM    199  CD1 LEU A 345      35.036   7.242 -39.784  1.00 35.77           C
ANISOU  199  CD1 LEU A 345    5045  5139  3408    333  -149 -1117            C
ATOM    200  CD2 LEU A 345      34.081   9.105 -41.171  1.00 33.10           C
ANISOU  200  CD2 LEU A 345    4653  5125  2797    243  -226  -900            C
ATOM    201  C   LEU A 345      33.486  11.170 -37.248  1.00 27.67           C
ANISOU  201  C   LEU A 345    3841  4009  2661    219  -296  -463            C
ATOM    202  O   LEU A 345      33.301  10.630 -36.166  1.00 27.33           O
ANISOU  202  O   LEU A 345    3812  3808  2766    218  -308  -498            O
ATOM    203  N   THR A 346      32.793  12.229 -37.663  1.00 27.06           N
ANISOU  203  N   THR A 346    3734  4024  2522    186  -351  -335            N
ATOM    204  CA  THR A 346      31.706  12.815 -36.857  1.00 25.51           C
ANISOU  204  CA  THR A 346    3504  3749  2440    153  -431  -248            C
ATOM    205  CB  THR A 346      31.306  14.244 -37.367  1.00 25.70           C
ANISOU  205  CB  THR A 346    3492  3871  2401    152  -474   -71            C
ATOM    206  OG1 THR A 346      30.535  14.151 -38.575  1.00 27.06           O
ANISOU  206  OG1 THR A 346    3676  4199  2405    136  -550   -97            O
ATOM    207  CG2 THR A 346      32.515  15.135 -37.609  1.00 24.02           C
ANISOU  207  CG2 THR A 346    3273  3699  2154    177  -384    49            C
ATOM    208  C   THR A 346      30.457  11.896 -36.816  1.00 26.38           C
ANISOU  208  C   THR A 346    3628  3829  2568    101  -515  -371            C
ATOM    209  O   THR A 346      30.402  10.882 -37.518  1.00 27.44           O
ANISOU  209  O   THR A 346    3805  4004  2616     84  -521  -521            O
ATOM    210  N   GLY A 347      29.450  12.255 -36.016  1.00 25.61           N
ANISOU  210  N   GLY A 347    3486  3661  2583     68  -575  -320            N
ATOM    211  CA  GLY A 347      28.142  11.586 -36.109  1.00 25.17           C
ANISOU  211  CA  GLY A 347    3414  3613  2535      0  -659  -421            C
ATOM    212  C   GLY A 347      27.442  11.653 -37.467  1.00 26.55           C
ANISOU  212  C   GLY A 347    3572  3975  2541    -19  -747  -458            C
ATOM    213  O   GLY A 347      26.559  10.833 -37.753  1.00 27.47           O
ANISOU  213  O   GLY A 347    3681  4117  2641    -85  -811  -591            O
ATOM    214  N   ASN A 348      27.812  12.630 -38.302  1.00 26.51           N
ANISOU  214  N   ASN A 348    3561  4103  2408     31  -754  -337            N
ATOM    215  CA  ASN A 348      27.340  12.690 -39.715  1.00 27.47           C
ANISOU  215  CA  ASN A 348    3685  4430  2323     26  -835  -360            C
ATOM    216  CB  ASN A 348      27.036  14.128 -40.155  1.00 27.65           C
ANISOU  216  CB  ASN A 348    3670  4556  2281     75  -894  -155            C
ATOM    217  CG  ASN A 348      25.936  14.197 -41.212  1.00 30.51           C
ANISOU  217  CG  ASN A 348    3999  5108  2487     66 -1036  -172            C
ATOM    218  OD1 ASN A 348      25.056  13.330 -41.277  1.00 32.90           O
ANISOU  218  OD1 ASN A 348    4267  5438  2795      8 -1112  -331            O
ATOM    219  ND2 ASN A 348      26.001  15.206 -42.070  1.00 30.49           N
ANISOU  219  ND2 ASN A 348    4008  5240  2337    120 -1076    -9            N
ATOM    220  C   ASN A 348      28.300  12.039 -40.715  1.00 28.41           C
ANISOU  220  C   ASN A 348    3879  4646  2270     37  -769  -462            C
ATOM    221  O   ASN A 348      28.092  12.120 -41.927  1.00 29.94           O
ANISOU  221  O   ASN A 348    4087  5027  2260     37  -821  -478            O
ATOM    222  N   LEU A 349      29.339  11.376 -40.203  1.00 27.99           N
ANISOU  222  N   LEU A 349    3869  4473  2293     53  -657  -538            N
ATOM    223  CA  LEU A 349      30.311  10.650 -41.043  1.00 29.00           C
ANISOU  223  CA  LEU A 349    4058  4676  2284     77  -577  -664            C
ATOM    224  CB  LEU A 349      29.602   9.567 -41.884  1.00 30.71           C
ANISOU  224  CB  LEU A 349    4309  4973  2386     27  -646  -875            C
ATOM    225  CG  LEU A 349      28.751   8.531 -41.136  1.00 30.08           C
ANISOU  225  CG  LEU A 349    4234  4731  2466    -42  -696 -1020            C
ATOM    226  CD1 LEU A 349      28.022   7.598 -42.085  1.00 30.19           C
ANISOU  226  CD1 LEU A 349    4274  4842  2357   -109  -773 -1229            C
ATOM    227  CD2 LEU A 349      29.637   7.731 -40.222  1.00 29.27           C
ANISOU  227  CD2 LEU A 349    4181  4417  2521    -10  -593 -1087            C
ATOM    228  C   LEU A 349      31.195  11.574 -41.914  1.00 29.53           C
```

FIGURE 18-11

```
ANISOU  228  C    LEU A 349    4130  4907  2185   121  -512  -535      C
ATOM    229  O    LEU A 349   31.589  11.202 -43.025  1.00 31.24       O
ANISOU  229  O    LEU A 349    4386  5279  2206   128  -480  -624      O
ATOM    230  N    GLN A 350   31.500  12.768 -41.395  1.00 28.82       N
ANISOU  230  N    GLN A 350    4003  4776  2171   141  -485  -330      N
ATOM    231  CA   GLN A 350   32.430  13.729 -42.020  1.00 30.27       C
ANISOU  231  CA   GLN A 350    4189  5072  2238   164  -402  -180      C
ATOM    232  CB   GLN A 350   31.967  15.164 -41.722  1.00 29.66       C
ANISOU  232  CB   GLN A 350    4082  4968  2219   164  -454    54      C
ATOM    233  CG   GLN A 350   32.811  16.292 -42.325  1.00 30.58       C
ANISOU  233  CG   GLN A 350    4211  5174  2234   167  -373   242      C
ATOM    234  CD   GLN A 350   32.356  17.682 -41.883  1.00 30.94       C
ANISOU  234  CD   GLN A 350    4238  5137  2382   172  -423   464      C
ATOM    235  OE1  GLN A 350   31.407  17.830 -41.095  1.00 28.70       O
ANISOU  235  OE1  GLN A 350    3920  4739  2246   182  -518   470      O
ATOM    236  NE2  GLN A 350   33.032  18.708 -42.394  1.00 31.65       N
ANISOU  236  NE2  GLN A 350    4350  5278  2397   161  -353   643      N
ATOM    237  C    GLN A 350   33.826  13.515 -41.457  1.00 29.30       C
ANISOU  237  C    GLN A 350    4053  4868  2210   193  -262  -209      C
ATOM    238  O    GLN A 350   33.975  13.375 -40.257  1.00 27.88       O
ANISOU  238  O    GLN A 350    3848  4515  2231   203  -253  -217      O
ATOM    239  N    THR A 351   34.832  13.499 -42.315  1.00 30.89       N
ANISOU  239  N    THR A 351    4265  5208  2262   207  -156  -226      N
ATOM    240  CA   THR A 351   36.226  13.364 -41.880  1.00 31.43       C
ANISOU  240  CA   THR A 351    4295  5233  2412   241   -21  -254      C
ATOM    241  CB   THR A 351   37.120  12.811 -43.019  1.00 33.11       C
ANISOU  241  CB   THR A 351    4522  5629  2431   264    91  -373      C
ATOM    242  OG1  THR A 351   36.598  11.543 -43.428  1.00 32.96       O
ANISOU  242  OG1  THR A 351    4555  5620  2346   282    42  -592      O
ATOM    243  CG2  THR A 351   38.567  12.622 -42.553  1.00 34.11       C
ANISOU  243  CG2  THR A 351    4582  5723  2657   309   229  -418      C
ATOM    244  C    THR A 351   36.792  14.669 -41.370  1.00 31.33       C
ANISOU  244  C    THR A 351    4233  5181  2492   220    30   -48      C
ATOM    245  O    THR A 351   36.719  15.702 -42.065  1.00 32.56       O
ANISOU  245  O    THR A 351    4400  5442  2531   184    38   119      O
ATOM    246  N    LEU A 352   37.338  14.623 -40.153  1.00 30.61       N
ANISOU  246  N    LEU A 352    4091  4933  2605   240    57   -57      N
ATOM    247  CA   LEU A 352   38.103  15.732 -39.588  1.00 30.88       C
ANISOU  247  CA   LEU A 352    4065  4923  2744   215   120    94      C
ATOM    248  CB   LEU A 352   37.467  16.248 -38.296  1.00 28.81       C
ANISOU  248  CB   LEU A 352    3790  4476  2680   205    35   169      C
ATOM    249  CG   LEU A 352   36.033  16.805 -38.295  1.00 28.66       C
ANISOU  249  CG   LEU A 352    3809  4417  2663   183   -86   262      C
ATOM    250  CD1  LEU A 352   35.625  17.143 -36.864  1.00 26.74       C
ANISOU  250  CD1  LEU A 352    3538  3992  2629   184  -138   291      C
ATOM    251  CD2  LEU A 352   35.847  18.027 -39.226  1.00 29.78       C
ANISOU  251  CD2  LEU A 352    3972  4656  2686   149   -86   449      C
ATOM    252  C    LEU A 352   39.550  15.297 -39.350  1.00 32.06       C
ANISOU  252  C    LEU A 352    4145  5094  2942   250   241     5      C
ATOM    253  O    LEU A 352   39.807  14.219 -38.805  1.00 31.91       O
ANISOU  253  O    LEU A 352    4119  5002  3003   313   237  -151      O
ATOM    254  N    LYS A 353   40.489  16.127 -39.790  1.00 33.85       N
ANISOU  254  N    LYS A 353    4320  5423  3120   208   350   105      N
ATOM    255  CA   LYS A 353   41.898  15.963 -39.470  1.00 34.96       C
ANISOU  255  CA   LYS A 353    4358  5594  3332   230   465    43      C
ATOM    256  CB   LYS A 353   42.735  16.484 -40.626  1.00 37.50       C
ANISOU  256  CB   LYS A 353    4644  6115  3488   179   606   104      C
ATOM    257  CG   LYS A 353   44.133  15.905 -40.717  1.00 41.91       C
ANISOU  257  CG   LYS A 353    5091  6777  4055   224   740   -29      C
ATOM    258  CD   LYS A 353   44.876  16.499 -41.917  1.00 48.11       C
ANISOU  258  CD   LYS A 353    5841  7780  4658   151   894    45      C
ATOM    259  CE   LYS A 353   45.805  15.477 -42.553  1.00 51.72       C
ANISOU  259  CE   LYS A 353    6232  8401  5018   228  1016  -154      C
ATOM    260  NZ   LYS A 353   46.301  15.930 -43.897  1.00 55.83       N
ANISOU  260  NZ   LYS A 353    6745  9164  5305   155  1168   -93      N
ATOM    261  C    LYS A 353   42.176  16.775 -38.212  1.00 33.47       C
ANISOU  261  C    LYS A 353    4107  5260  3349   199   442   138      C
ATOM    262  O    LYS A 353   42.115  18.008 -38.238  1.00 33.44       O
ANISOU  262  O    LYS A 353    4099  5242  3365   118   453   305      O
ATOM    263  N    ILE A 354   42.447  16.075 -37.110  1.00 32.36       N
ANISOU  263  N    ILE A 354    3930  5007  3360   266   404    30      N
```

FIGURE 18-12

```
ATOM    264  CA  ILE A 354      42.806  16.720 -35.842  1.00 31.37           C
ANISOU  264  CA  ILE A 354    3738   4762   3418    245    377     87        C
ATOM    265  CB  ILE A 354      41.737  16.490 -34.731  1.00 29.39           C
ANISOU  265  CB  ILE A 354    3552   4334   3280    270    247     81        C
ATOM    266  CG1 ILE A 354      41.620  15.001 -34.379  1.00 28.30           C
ANISOU  266  CG1 ILE A 354    3451   4143   3159    368    206    -78        C
ATOM    267  CD1 ILE A 354      40.879  14.705 -33.055  1.00 28.35           C
ANISOU  267  CD1 ILE A 354    3501   3978   3294    389    104    -86        C
ATOM    268  CG2 ILE A 354      40.373  17.085 -35.158  1.00 29.30           C
ANISOU  268  CG2 ILE A 354    3629   4293   3209    219    176    185        C
ATOM    269  C   ILE A 354      44.170  16.257 -35.328  1.00 31.76           C
ANISOU  269  C   ILE A 354    3668   4847   3552    301    442    -15        C
ATOM    270  O   ILE A 354      44.603  15.135 -35.611  1.00 32.13           O
ANISOU  270  O   ILE A 354    3703   4946   3559    394    471   -157        O
ATOM    271  N   ARG A 355      44.834  17.127 -34.571  1.00 31.99           N
ANISOU  271  N   ARG A 355    3606   4847   3703    249    457     49        N
ATOM    272  CA  ARG A 355      46.027  16.753 -33.847  1.00 32.46           C
ANISOU  272  CA  ARG A 355    3536   4929   3866    306    483    -44        C
ATOM    273  CB  ARG A 355      46.987  17.948 -33.720  1.00 34.26           C
ANISOU  273  CB  ARG A 355    3637   5219   4163    198    559     35        C
ATOM    274  CG  ARG A 355      47.656  18.288 -35.032  1.00 39.00           C
ANISOU  274  CG  ARG A 355    4181   5997   4639    132    708     67        C
ATOM    275  CD  ARG A 355      48.600  19.431 -34.872  1.00 45.77           C
ANISOU  275  CD  ARG A 355    4910   6902   5578      6    790    144        C
ATOM    276  NE  ARG A 355      48.574  20.333 -36.023  1.00 52.25           N
ANISOU  276  NE  ARG A 355    5764   7806   6284   -123    901    284        N
ATOM    277  CZ  ARG A 355      49.146  21.539 -36.057  1.00 56.14           C
ANISOU  277  CZ  ARG A 355    6188   8307   6837   -272    980    398        C
ATOM    278  NH1 ARG A 355      49.801  22.023 -34.996  1.00 55.45           N
ANISOU  278  NH1 ARG A 355    5982   8157   6928   -320    956    369        N
ATOM    279  NH2 ARG A 355      49.061  22.269 -37.166  1.00 58.73           N
ANISOU  279  NH2 ARG A 355    6571   8703   7040   -381   1083    542        N
ATOM    280  C   ARG A 355      45.608  16.213 -32.488  1.00 29.93           C
ANISOU  280  C   ARG A 355    3252   4453   3666    379    359    -91        C
ATOM    281  O   ARG A 355      45.187  16.959 -31.616  1.00 28.02           O
ANISOU  281  O   ARG A 355    3025   4108   3513    324    295    -17        O
ATOM    282  N   VAL A 356      45.705  14.897 -32.339  1.00 28.99           N
ANISOU  282  N   VAL A 356    3158   4313   3543    504    331   -216        N
ATOM    283  CA  VAL A 356      45.350  14.233 -31.098  1.00 27.31           C
ANISOU  283  CA  VAL A 356    2994   3955   3426    581    223   -254        C
ATOM    284  CB  VAL A 356      45.003  12.746 -31.341  1.00 27.54           C
ANISOU  284  CB  VAL A 356    3118   3930   3417    695    198   -368        C
ATOM    285  CG1 VAL A 356      44.842  11.989 -30.014  1.00 27.23           C
ANISOU  285  CG1 VAL A 356    3128   3741   3479    780     99   -394        C
ATOM    286  CG2 VAL A 356      43.732  12.634 -32.157  1.00 26.35           C
ANISOU  286  CG2 VAL A 356    3094   3753   3164    637    186   -350        C
ATOM    287  C   VAL A 356      46.460  14.367 -30.058  1.00 26.67           C
ANISOU  287  C   VAL A 356    2786   3889   3460    624    204   -279        C
ATOM    288  O   VAL A 356      47.604  14.038 -30.324  1.00 28.57           O
ANISOU  288  O   VAL A 356    2907   4239   3708    689    263   -354        O
ATOM    289  N   HIS A 357      46.128  14.879 -28.884  1.00 25.43           N
ANISOU  289  N   HIS A 357    2642   3635   3385    590    121   -224        N
ATOM    290  CA  HIS A 357      47.107  14.993 -27.808  1.00 25.05           C
ANISOU  290  CA  HIS A 357    2478   3607   3433    631     79   -254        C
ATOM    291  CB  HIS A 357      46.849  16.229 -26.954  1.00 23.90           C
ANISOU  291  CB  HIS A 357    2315   3412   3353    517     36   -177        C
ATOM    292  CG  HIS A 357      47.266  17.509 -27.615  1.00 24.64           C
ANISOU  292  CG  HIS A 357    2322   3585   3457    380    123   -117        C
ATOM    293  ND1 HIS A 357      48.390  18.216 -27.235  1.00 25.54           N
ANISOU  293  ND1 HIS A 357    2277   3779   3648    325    146   -136        N
ATOM    294  CE1 HIS A 357      48.507  19.290 -27.995  1.00 24.49           C
ANISOU  294  CE1 HIS A 357    2110   3684   3511    188    235    -62        C
ATOM    295  NE2 HIS A 357      47.505  19.300 -28.857  1.00 25.00           N
ANISOU  295  NE2 HIS A 357    2307   3703   3488    167    263      9        N
ATOM    296  CD2 HIS A 357      46.725  18.191 -28.652  1.00 22.30           C
ANISOU  296  CD2 HIS A 357    2077   3296   3100    282    192    -34        C
ATOM    297  C   HIS A 357      47.122  13.716 -26.984  1.00 25.08           C
ANISOU  297  C   HIS A 357    2536   3529   3463    781     -5   -319        C
ATOM    298  O   HIS A 357      46.079  13.215 -26.573  1.00 24.14           O
ANISOU  298  O   HIS A 357    2561   3280   3330    795    -66   -297        O
ATOM    299  N   GLU A 358      48.322  13.175 -26.778  1.00 25.97           N
```

FIGURE 18-13

```
ANISOU  299  N    GLU A 358    2530   3722   3616    895     -6   -397        N
ATOM    300  CA   GLU A 358     48.492   11.913  -26.065  1.00  25.43         C
ANISOU  300  CA   GLU A 358    2512   3575   3577   1062    -86   -451        C
ATOM    301  CB   GLU A 358     49.224   10.905  -26.939  1.00  26.70         C
ANISOU  301  CB   GLU A 358    2626   3796   3722   1198    -23   -558        C
ATOM    302  CG   GLU A 358     48.506   10.641  -28.264  1.00  26.20         C
ANISOU  302  CG   GLU A 358    2661   3726   3567   1151     64   -583        C
ATOM    303  CD   GLU A 358     49.340    9.852  -29.243  1.00  28.06         C
ANISOU  303  CD   GLU A 358    2826   4059   3777   1267    151   -709        C
ATOM    304  OE1  GLU A 358     50.595    9.994  -29.261  1.00  27.40         O
ANISOU  304  OE1  GLU A 358    2558   4117   3735   1329    192   -763        O
ATOM    305  OE2  GLU A 358     48.730    9.082  -30.014  1.00  28.42         O
ANISOU  305  OE2  GLU A 358    2993   4046   3760   1295    181   -767        O
ATOM    306  C    GLU A 358     49.233   12.107  -24.751  1.00  25.42         C
ANISOU  306  C    GLU A 358    2416   3596   3646   1113   -180   -446        C
ATOM    307  O    GLU A 358     50.317   12.638  -24.734  1.00  25.81         O
ANISOU  307  O    GLU A 358    2285   3785   3737   1107   -159   -481        O
ATOM    308  N    GLY A 359     48.608   11.697  -23.651  1.00  24.36         N
ANISOU  308  N    GLY A 359    2405   3335   3518   1152   -283   -403        N
ATOM    309  CA   GLY A 359     49.203   11.836  -22.335  1.00  23.73         C
ANISOU  309  CA   GLY A 359    2258   3280   3476   1204   -388   -394        C
ATOM    310  C    GLY A 359     48.271   12.445  -21.311  1.00  22.21         C
ANISOU  310  C    GLY A 359    2168   3005   3267   1103   -452   -318        C
ATOM    311  O    GLY A 359     47.324   13.163  -21.653  1.00  21.39         O
ANISOU  311  O    GLY A 359    2131   2854   3144    965   -404   -274        O
ATOM    312  N    TYR A 360     48.535   12.139  -20.049  1.00  22.42         N
ANISOU  312  N    TYR A 360    2206   3018   3293   1183   -562   -305        N
ATOM    313  CA   TYR A 360     47.836   12.761  -18.939  1.00  22.10         C
ANISOU  313  CA   TYR A 360    2238   2934   3226   1096   -623   -252        C
ATOM    314  CB   TYR A 360     48.072   11.966  -17.646  1.00  23.09         C
ANISOU  314  CB   TYR A 360    2423   3034   3318   1228   -745   -227        C
ATOM    315  CG   TYR A 360     47.620   12.724  -16.422  1.00  22.63         C
ANISOU  315  CG   TYR A 360    2399   2981   3217   1141   -809   -196        C
ATOM    316  CD1  TYR A 360     46.261   12.802  -16.094  1.00  21.89         C
ANISOU  316  CD1  TYR A 360    2469   2771   3076   1053   -784   -137        C
ATOM    317  CE1  TYR A 360     45.826   13.516  -14.980  1.00  22.60         C
ANISOU  317  CE1  TYR A 360    2589   2877   3121    976   -829   -125        C
ATOM    318  CZ   TYR A 360     46.759   14.181  -14.201  1.00  23.69         C
ANISOU  318  CZ   TYR A 360    2599   3145   3259    979   -908   -177        C
ATOM    319  OH   TYR A 360     46.326   14.889  -13.103  1.00  24.72         O
ANISOU  319  OH   TYR A 360    2764   3296   3335    903   -950   -184        O
ATOM    320  CE2  TYR A 360     48.122   14.118  -14.506  1.00  23.39         C
ANISOU  320  CE2  TYR A 360    2391   3226   3272   1057   -943   -234        C
ATOM    321  CD2  TYR A 360     48.543   13.397  -15.617  1.00  21.33         C
ANISOU  321  CD2  TYR A 360    2094   2952   3059   1140   -889   -241        C
ATOM    322  C    TYR A 360     48.232   14.229  -18.731  1.00  21.86         C
ANISOU  322  C    TYR A 360    2068   3007   3231    959   -615   -276        C
ATOM    323  O    TYR A 360     49.413   14.553  -18.673  1.00  23.34         O
ANISOU  323  O    TYR A 360    2082   3326   3462    981   -634   -333        O
ATOM    324  N    GLU A 361     47.237   15.100  -18.598  1.00  21.04         N
ANISOU  324  N    GLU A 361    2037   2837   3118    821   -587   -239        N
ATOM    325  CA   GLU A 361     47.450   16.524  -18.288  1.00  21.68         C
ANISOU  325  CA   GLU A 361    2021   2973   3244    684   -582   -262        C
ATOM    326  CB   GLU A 361     47.406   17.391  -19.552  1.00  20.98         C
ANISOU  326  CB   GLU A 361    1876   2893   3201    564   -469   -250        C
ATOM    327  CG   GLU A 361     48.599   17.217  -20.468  1.00  24.43         C
ANISOU  327  CG   GLU A 361    2161   3450   3670    596   -412   -291        C
ATOM    328  CD   GLU A 361     48.413   17.894  -21.813  1.00  22.96         C
ANISOU  328  CD   GLU A 361    1960   3269   3496    484   -289   -254        C
ATOM    329  OE1  GLU A 361     47.351   17.715  -22.440  1.00  20.90         O
ANISOU  329  OE1  GLU A 361    1833   2919   3188    469   -249   -198        O
ATOM    330  OE2  GLU A 361     49.338   18.607  -22.238  1.00  26.07         O
ANISOU  330  OE2  GLU A 361    2204   3762   3940    408   -232   -278        O
ATOM    331  C    GLU A 361     46.384   17.031  -17.332  1.00  20.41         C
ANISOU  331  C    GLU A 361    1975   2727   3053    614   -618   -235        C
ATOM    332  O    GLU A 361     45.240   16.587  -17.379  1.00  19.53         O
ANISOU  332  O    GLU A 361    2009   2512   2900    617   -599   -184        O
ATOM    333  N    GLU A 362     46.774   17.961  -16.476  1.00  21.16         N
ANISOU  333  N    GLU A 362    1994   2876   3172    547   -666   -282        N
ATOM    334  CA   GLU A 362     45.841   18.688  -15.628  1.00  22.46         C
ANISOU  334  CA   GLU A 362    2243   2974   3317    465   -683   -283        C
```

FIGURE 18-14

```
ATOM    335  CB  GLU A 362      46.105  18.430 -14.141  1.00 22.93           C
ANISOU  335  CB  GLU A 362    2317   3092   3304    522   -796   -319        C
ATOM    336  CG  GLU A 362      45.054  19.016 -13.191  1.00 23.73           C
ANISOU  336  CG  GLU A 362    2522   3135   3361    454   -803   -328        C
ATOM    337  CD  GLU A 362      45.445  18.797 -11.736  1.00 26.51           C
ANISOU  337  CD  GLU A 362    2881   3575   3616    507   -916   -369        C
ATOM    338  OE1 GLU A 362      44.878  17.909 -11.080  1.00 31.01           O
ANISOU  338  OE1 GLU A 362    3579   4121   4081    581   -946   -311        O
ATOM    339  OE2 GLU A 362      46.357  19.496 -11.254  1.00 32.87           O
ANISOU  339  OE2 GLU A 362    3562   4482   4446    471   -977   -458        O
ATOM    340  C   GLU A 362      45.923  20.184 -15.927  1.00 22.18           C
ANISOU  340  C   GLU A 362    2128   2929   3372    317   -633   -319        C
ATOM    341  O   GLU A 362      47.018  20.735 -16.087  1.00 23.04           O
ANISOU  341  O   GLU A 362    2089   3123   3544    271   -636   -371        O
ATOM    342  N   PHE A 363      44.759  20.825 -15.996  1.00 21.18           N
ANISOU  342  N   PHE A 363    2095   2693   3259    243   -588   -290        N
ATOM    343  CA  PHE A 363      44.646  22.260 -16.286  1.00 21.78           C
ANISOU  343  CA  PHE A 363    2129   2714   3431    111   -538   -309        C
ATOM    344  CB  PHE A 363      44.028  22.491 -17.691  1.00 20.64           C
ANISOU  344  CB  PHE A 363    2025   2495   3323     74   -443   -220        C
ATOM    345  CG  PHE A 363      44.832  21.911 -18.837  1.00 21.21           C
ANISOU  345  CG  PHE A 363    2029   2642   3388    104   -397   -186        C
ATOM    346  CD1 PHE A 363      45.831  22.663 -19.453  1.00 20.96           C
ANISOU  346  CD1 PHE A 363    1874   2663   3429     19   -346   -195        C
ATOM    347  CE1 PHE A 363      46.570  22.150 -20.514  1.00 21.38           C
ANISOU  347  CE1 PHE A 363    1855   2803   3465     45   -287   -172        C
ATOM    348  CZ  PHE A 363      46.313  20.885 -20.998  1.00 18.73           C
ANISOU  348  CZ  PHE A 363    1579   2489   3048    163   -284   -150        C
ATOM    349  CE2 PHE A 363      45.316  20.123 -20.407  1.00 20.47           C
ANISOU  349  CE2 PHE A 363    1932   2638   3209    242   -340   -139        C
ATOM    350  CD2 PHE A 363      44.570  20.637 -19.319  1.00 18.91           C
ANISOU  350  CD2 PHE A 363    1799   2365   3021    209   -392   -151        C
ATOM    351  C   PHE A 363      43.738  22.994 -15.315  1.00 21.72           C
ANISOU  351  C   PHE A 363    2196   2632   3426     65   -558   -349        C
ATOM    352  O   PHE A 363      42.737  22.439 -14.830  1.00 20.51           O
ANISOU  352  O   PHE A 363    2152   2441   3199    117   -569   -326        O
ATOM    353  N   THR A 364      44.060  24.266 -15.070  1.00 22.89           N
ANISOU  353  N   THR A 364    2282   2752   3664    -41   -553   -414        N
ATOM    354  CA  THR A 364      43.032  25.177 -14.615  1.00 23.63           C
ANISOU  354  CA  THR A 364    2449   2733   3796    -93   -534   -443        C
ATOM    355  CB  THR A 364      43.500  26.176 -13.539  1.00 25.43           C
ANISOU  355  CB  THR A 364    2624   2968   4069   -171   -580   -577        C
ATOM    356  OG1 THR A 364      44.450  27.087 -14.102  1.00 29.67           O
ANISOU  356  OG1 THR A 364    3054   3489   4730   -281   -554   -601        O
ATOM    357  CG2 THR A 364      44.117  25.466 -12.315  1.00 24.74           C
ANISOU  357  CG2 THR A 364    2509   3025   3866   -111   -682   -657        C
ATOM    358  C   THR A 364      42.480  25.903 -15.855  1.00 23.68           C
ANISOU  358  C   THR A 364    2479   2620   3896   -148   -448   -357        C
ATOM    359  O   THR A 364      43.224  26.192 -16.803  1.00 23.87           O
ANISOU  359  O   THR A 364    2436   2655   3980   -201   -406   -313        O
ATOM    360  N   MSE A 365      41.172  26.145 -15.860  1.00 22.96           N
ANISOU  360  N   MSE A 365    2483   2430   3811   -130   -423   -327        N
ATOM    361  CA  MSE A 365      40.493  26.940 -16.879  1.00 23.90           C
ANISOU  361  CA  MSE A 365    2637   2429   4017   -165   -361   -246        C
ATOM    362  CB  MSE A 365      39.333  26.162 -17.525  1.00 22.98           C
ANISOU  362  CB  MSE A 365    2597   2301   3833    -88   -343   -155        C
ATOM    363  CG  MSE A 365      39.696  24.837 -18.242  1.00 23.11           C
ANISOU  363  CG  MSE A 365    2611   2416   3753    -32   -341    -95        C
ATOM    364  SE  MSE A 365      38.160  23.718 -18.667  0.90 26.48           SE
ANISOU  364  SE  MSE A 365    3137   2833   4091     49   -336    -31        SE
ATOM    365  CE  MSE A 365      37.026  25.011 -19.510  1.00 21.85           C
ANISOU  365  CE  MSE A 365    2574   2128   3599     18   -301     38        C
ATOM    366  C   MSE A 365      39.916  28.149 -16.156  1.00 23.45           C
ANISOU  366  C   MSE A 365    2605   2254   4051   -209   -361   -322        C
ATOM    367  O   MSE A 365      39.223  27.994 -15.148  1.00 23.44           O
ANISOU  367  O   MSE A 365    2645   2258   4002   -167   -386   -396        O
ATOM    368  N   VAL A 366      40.215  29.346 -16.654  1.00 23.42           N
ANISOU  368  N   VAL A 366    2581   2139   4177   -293   -326   -306        N
ATOM    369  CA  VAL A 366      39.691  30.586 -16.090  1.00 23.54           C
ANISOU  369  CA  VAL A 366    2629   2009   4308   -331   -319   -382        C
ATOM    370  CB  VAL A 366      40.833  31.452 -15.443  1.00 25.39           C
```

FIGURE 18-15

```
ANISOU  370  CB   VAL A 366     2793  2224  4631   -448  -336  -505     C
ATOM    371  CG1  VAL A 366     40.312  32.803 -14.943  1.00 25.44      C
ANISOU  371  CG1  VAL A 366     2842  2047  4776   -492  -323  -594     C
ATOM    372  CG2  VAL A 366     41.533  30.678 -14.298  1.00 25.91      C
ANISOU  372  CG2  VAL A 366     2801  2461  4582   -433  -406  -628     C
ATOM    373  C    VAL A 366     38.916  31.393 -17.163  1.00 24.02      C
ANISOU  373  C    VAL A 366     2745  1911  4469   -329  -270  -260     C
ATOM    374  O    VAL A 366     39.498  31.895 -18.140  1.00 24.09      O
ANISOU  374  O    VAL A 366     2741  1868  4545   -398  -232  -164     O
ATOM    375  N    GLY A 367     37.609  31.524 -16.962  1.00 23.61      N
ANISOU  375  N    GLY A 367     2753  1792  4425   -248  -271  -262     N
ATOM    376  CA   GLY A 367     36.782  32.410 -17.779  1.00 25.53      C
ANISOU  376  CA   GLY A 367     3047  1876  4776   -223  -244  -164     C
ATOM    377  C    GLY A 367     36.277  33.660 -17.044  1.00 27.40      C
ANISOU  377  C    GLY A 367     3313  1940  5157   -225  -240  -269     C
ATOM    378  O    GLY A 367     36.620  33.896 -15.876  1.00 28.05      O
ANISOU  378  O    GLY A 367     3375  2032  5251   -261  -254  -435     O
ATOM    379  N    LYS A 368     35.459  34.461 -17.728  1.00 28.02      N
ANISOU  379  N    LYS A 368     3442  1863  5342   -177  -225  -178     N
ATOM    380  CA   LYS A 368     34.815  35.621 -17.111  1.00 30.01      C
ANISOU  380  CA   LYS A 368     3727  1931  5744   -146  -219  -276     C
ATOM    381  CB   LYS A 368     34.065  36.473 -18.152  1.00 31.76      C
ANISOU  381  CB   LYS A 368     4007  1974  6086    -83  -211  -125     C
ATOM    382  CG   LYS A 368     34.947  37.212 -19.147  1.00 36.76      C
ANISOU  382  CG   LYS A 368     4677  2481  6808   -185  -185    20     C
ATOM    383  CD   LYS A 368     34.052  37.959 -20.123  1.00 43.28      C
ANISOU  383  CD   LYS A 368     5574  3141  7729    -94  -190   186     C
ATOM    384  CE   LYS A 368     34.692  38.098 -21.504  1.00 48.10      C
ANISOU  384  CE   LYS A 368     6224  3733  8319   -165  -165   410     C
ATOM    385  NZ   LYS A 368     33.990  39.150 -22.301  1.00 50.85      N
ANISOU  385  NZ   LYS A 368     6662  3864  8792    -92  -174   569     N
ATOM    386  C    LYS A 368     33.837  35.243 -15.977  1.00 28.59      C
ANISOU  386  C    LYS A 368     3533  1823  5507    -54  -230  -427     C
ATOM    387  O    LYS A 368     33.803  35.912 -14.963  1.00 28.78      O
ANISOU  387  O    LYS A 368     3561  1774  5601    -66  -224  -594     O
ATOM    388  N    ARG A 369     33.047  34.184 -16.141  1.00 26.59      N
ANISOU  388  N    ARG A 369     3264  1712  5126     28  -239  -377     N
ATOM    389  CA   ARG A 369     32.032  33.851 -15.117  1.00 25.86      C
ANISOU  389  CA   ARG A 369     3155  1690  4982    105  -231  -507     C
ATOM    390  CB   ARG A 369     30.615  34.105 -15.636  1.00 26.07      C
ANISOU  390  CB   ARG A 369     3177  1657  5072    225  -227  -447     C
ATOM    391  CG   ARG A 369     30.370  35.495 -16.189  1.00 28.17      C
ANISOU  391  CG   ARG A 369     3477  1696  5532    264  -228  -403     C
ATOM    392  CD   ARG A 369     28.865  35.741 -16.363  1.00 30.60      C
ANISOU  392  CD   ARG A 369     3757  1968  5902    411  -232  -393     C
ATOM    393  NE   ARG A 369     28.465  36.887 -15.535  1.00 37.04      N
ANISOU  393  NE   ARG A 369     4580  2621  6871    463  -207  -550     N
ATOM    394  CZ   ARG A 369     27.527  36.892 -14.591  1.00 37.12      C
ANISOU  394  CZ   ARG A 369     4542  2678  6882    543  -176  -709     C
ATOM    395  NH1  ARG A 369     26.793  35.818 -14.317  1.00 34.10      N
ANISOU  395  NH1  ARG A 369     4097  2499  6360    575  -163  -727     N
ATOM    396  NH2  ARG A 369     27.296  38.024 -13.941  1.00 43.52      N
ANISOU  396  NH2  ARG A 369     5369  3322  7847    590  -151  -856     N
ATOM    397  C    ARG A 369     32.135  32.449 -14.526  1.00 23.85      C
ANISOU  397  C    ARG A 369     2878  1646  4537     96  -238  -539     C
ATOM    398  O    ARG A 369     31.300  32.046 -13.716  1.00 22.65      O
ANISOU  398  O    ARG A 369     2714  1571  4319    145  -220  -626     O
ATOM    399  N    ALA A 370     33.158  31.705 -14.934  1.00 23.31      N
ANISOU  399  N    ALA A 370     2805  1669  4383     35  -258  -466     N
ATOM    400  CA   ALA A 370     33.390  30.376 -14.395  1.00 22.66      C
ANISOU  400  CA   ALA A 370     2715  1763  4132     32  -271  -485     C
ATOM    401  CB   ALA A 370     32.551  29.299 -15.160  1.00 21.26      C
ANISOU  401  CB   ALA A 370     2543  1663  3872     89  -268  -369     C
ATOM    402  C    ALA A 370     34.875  30.034 -14.427  1.00 22.52      C
ANISOU  402  C    ALA A 370     2679  1811  4069    -42  -299  -476     C
ATOM    403  O    ALA A 370     35.619  30.550 -15.262  1.00 23.04      O
ANISOU  403  O    ALA A 370     2730  1812  4213    -93  -297  -408     O
ATOM    404  N    THR A 371     35.290  29.169 -13.503  1.00 22.37      N
ANISOU  404  N    THR A 371     2656  1925  3920    -44  -324  -542     N
ATOM    405  CA   THR A 371     36.622  28.573 -13.512  1.00 22.86      C
ANISOU  405  CA   THR A 371     2686  2083  3918    -84  -362  -529     C
```

FIGURE 18-16

```
ATOM    406  CB   THR A 371      37.577  29.196 -12.446  1.00 24.26           C
ANISOU  406  CB   THR A 371     2826   2283   4108   -147   -400   -676       C
ATOM    407  OG1  THR A 371      37.179  28.782 -11.144  1.00 27.06           O
ANISOU  407  OG1  THR A 371     3210   2727   4343   -114   -419   -776       O
ATOM    408  CG2  THR A 371      37.597  30.704 -12.518  1.00 22.87           C
ANISOU  408  CG2  THR A 371     2640   1949   4099   -210   -377   -743       C
ATOM    409  C    THR A 371      36.510  27.054 -13.335  1.00 21.90           C
ANISOU  409  C    THR A 371     2588   2092   3640    -29   -380   -480       C
ATOM    410  O    THR A 371      35.451  26.546 -12.967  1.00 22.77           O
ANISOU  410  O    THR A 371     2742   2223   3688     15   -360   -478       O
ATOM    411  N    ALA A 372      37.576  26.312 -13.616  1.00 21.17           N
ANISOU  411  N    ALA A 372     2467   2082   3493    -32   -413   -439       N
ATOM    412  CA   ALA A 372      37.495  24.865 -13.505  1.00 19.77           C
ANISOU  412  CA   ALA A 372     2327   1997   3186     28   -430   -386       C
ATOM    413  CB   ALA A 372      36.796  24.241 -14.737  1.00 18.33           C
ANISOU  413  CB   ALA A 372     2174   1784   3006     59   -394   -271       C
ATOM    414  C    ALA A 372      38.835  24.237 -13.308  1.00 19.97           C
ANISOU  414  C    ALA A 372     2310   2121   3156     39   -484   -393       C
ATOM    415  O    ALA A 372      39.853  24.849 -13.608  1.00 20.79           O
ANISOU  415  O    ALA A 372     2337   2231   3330     -8   -497   -419       O
ATOM    416  N    ILE A 373      38.816  23.010 -12.789  1.00 19.57           N
ANISOU  416  N    ILE A 373     2308   2144   2983    102   -514   -368       N
ATOM    417  CA   ILE A 373      39.963  22.112 -12.831  1.00 19.72           C
ANISOU  417  CA   ILE A 373     2295   2249   2948    151   -568   -345       C
ATOM    418  CB   ILE A 373      40.416  21.607 -11.444  1.00 20.88           C
ANISOU  418  CB   ILE A 373     2464   2493   2978    193   -643   -394       C
ATOM    419  CG1  ILE A 373      40.502  22.762 -10.432  1.00 22.57           C
ANISOU  419  CG1  ILE A 373     2645   2729   3201    130   -667   -517       C
ATOM    420  CD1  ILE A 373      40.936  22.348  -8.989  1.00 22.21           C
ANISOU  420  CD1  ILE A 373     2624   2805   3011    169   -752   -574       C
ATOM    421  CG2  ILE A 373      41.764  20.932 -11.585  1.00 18.66           C
ANISOU  421  CG2  ILE A 373     2115   2300   2676    252   -710   -381       C
ATOM    422  C    ILE A 373      39.645  20.919 -13.691  1.00 18.62           C
ANISOU  422  C    ILE A 373     2207   2092   2774    209   -544   -246       C
ATOM    423  O    ILE A 373      38.635  20.253 -13.476  1.00 18.19           O
ANISOU  423  O    ILE A 373     2241   2007   2662    231   -522   -209       O
ATOM    424  N    LEU A 374      40.530  20.643 -14.656  1.00 18.68           N
ANISOU  424  N    LEU A 374     2154   2125   2818    229   -542   -216       N
ATOM    425  CA   LEU A 374      40.328  19.586 -15.652  1.00 16.99           C
ANISOU  425  CA   LEU A 374     1981   1892   2582    281   -514   -144       C
ATOM    426  CB   LEU A 374      40.251  20.197 -17.064  1.00 15.29           C
ANISOU  426  CB   LEU A 374     1724   1644   2441    233   -453   -108       C
ATOM    427  CG   LEU A 374      40.219  19.251 -18.265  1.00 15.44           C
ANISOU  427  CG   LEU A 374     1766   1665   2434    277   -421    -57       C
ATOM    428  CD1  LEU A 374      38.992  18.305 -18.302  1.00 14.91           C
ANISOU  428  CD1  LEU A 374     1810   1543   2313    303   -413    -24       C
ATOM    429  CD2  LEU A 374      40.303  20.021 -19.573  1.00 16.74           C
ANISOU  429  CD2  LEU A 374     1884   1827   2651    222   -365    -20       C
ATOM    430  C    LEU A 374      41.486  18.592 -15.607  1.00 17.53           C
ANISOU  430  C    LEU A 374     2018   2033   2611    368   -562   -144       C
ATOM    431  O    LEU A 374      42.663  19.008 -15.663  1.00 18.31           O
ANISOU  431  O    LEU A 374     2004   2204   2748    365   -586   -185       O
ATOM    432  N    ARG A 375      41.161  17.302 -15.495  1.00 16.74           N
ANISOU  432  N    ARG A 375     2010   1906   2444    445   -575   -102       N
ATOM    433  CA   ARG A 375      42.128  16.231 -15.749  1.00 17.32           C
ANISOU  433  CA   ARG A 375     2066   2016   2497    550   -609    -93       C
ATOM    434  CB   ARG A 375      42.224  15.233 -14.612  1.00 17.75           C
ANISOU  434  CB   ARG A 375     2205   2070   2469    639   -680    -69       C
ATOM    435  CG   ARG A 375      43.006  15.772 -13.443  1.00 18.20           C
ANISOU  435  CG   ARG A 375     2196   2225   2493    651   -761   -113       C
ATOM    436  CD   ARG A 375      42.926  14.833 -12.281  1.00 20.67           C
ANISOU  436  CD   ARG A 375     2618   2538   2698    734   -831    -66       C
ATOM    437  NE   ARG A 375      43.721  15.319 -11.164  1.00 22.34           N
ANISOU  437  NE   ARG A 375     2762   2868   2856    753   -925   -115       N
ATOM    438  CZ   ARG A 375      43.603  14.892  -9.911  1.00 24.36           C
ANISOU  438  CZ   ARG A 375     3108   3157   2992    799   -993    -83       C
ATOM    439  NH1  ARG A 375      42.718  13.955  -9.595  1.00 26.04           N
ANISOU  439  NH1  ARG A 375     3486   3280   3130    822   -967     10       N
ATOM    440  NH2  ARG A 375      44.383  15.409  -8.971  1.00 27.64           N
ANISOU  440  NH2  ARG A 375     3448   3702   3353    812  -1089   -144       N
ATOM    441  C    ARG A 375      41.742  15.522 -17.009  1.00 17.19           C
```

FIGURE 18-17

| | | | | | | | | | | |
|---|---|---|---|---|---|---|---|---|---|---|
| ANISOU | 441 | C | ARG A 375 | 2092 | 1945 | 2495 | 569 | -551 | -62 | C |
| ATOM | 442 | O | ARG A 375 | 40.566 | 15.227 | -17.252 | 1.00 | 16.68 | | O |
| ANISOU | 442 | O | ARG A 375 | 2122 | 1802 | 2414 | 533 | -514 | -29 | O |
| ATOM | 443 | N | LYS A 376 | 42.743 | 15.264 | -17.830 | 1.00 | 17.94 | | N |
| ANISOU | 443 | N | LYS A 376 | 2106 | 2093 | 2619 | 621 | -540 | -83 | N |
| ATOM | 444 | CA | LYS A 376 | 42.484 | 14.748 | -19.154 | 1.00 | 18.80 | | C |
| ANISOU | 444 | CA | LYS A 376 | 2238 | 2172 | 2732 | 630 | -477 | -75 | C |
| ATOM | 445 | CB | LYS A 376 | 42.485 | 15.948 | -20.089 | 1.00 | 19.04 | | C |
| ANISOU | 445 | CB | LYS A 376 | 2186 | 2243 | 2804 | 530 | -415 | -73 | C |
| ATOM | 446 | CG | LYS A 376 | 42.472 | 15.657 | -21.514 | 1.00 | 22.12 | | C |
| ANISOU | 446 | CG | LYS A 376 | 2573 | 2649 | 3183 | 532 | -351 | -70 | C |
| ATOM | 447 | CD | LYS A 376 | 43.216 | 16.738 | -22.249 | 1.00 | 25.06 | | C |
| ANISOU | 447 | CD | LYS A 376 | 2826 | 3105 | 3592 | 464 | -298 | -68 | C |
| ATOM | 448 | CE | LYS A 376 | 43.015 | 16.490 | -23.721 | 1.00 | 26.93 | | C |
| ANISOU | 448 | CE | LYS A 376 | 3079 | 3367 | 3787 | 456 | -227 | -54 | C |
| ATOM | 449 | NZ | LYS A 376 | 43.691 | 15.264 | -24.120 | 1.00 | 27.50 | | N |
| ANISOU | 449 | NZ | LYS A 376 | 3143 | 3478 | 3828 | 566 | -218 | -111 | N |
| ATOM | 450 | C | LYS A 376 | 43.569 | 13.729 | -19.486 | 1.00 | 19.24 | | C |
| ANISOU | 450 | C | LYS A 376 | 2256 | 2266 | 2787 | 756 | -493 | -106 | C |
| ATOM | 451 | O | LYS A 376 | 44.650 | 13.770 | -18.915 | 1.00 | 20.06 | | O |
| ANISOU | 451 | O | LYS A 376 | 2269 | 2448 | 2907 | 818 | -543 | -135 | O |
| ATOM | 452 | N | ALA A 377 | 43.257 | 12.766 | -20.348 | 1.00 | 19.46 | | N |
| ANISOU | 452 | N | ALA A 377 | 2354 | 2239 | 2799 | 802 | -456 | -112 | N |
| ATOM | 453 | CA | ALA A 377 | 44.251 | 11.822 | -20.856 | 1.00 | 20.59 | | C |
| ANISOU | 453 | CA | ALA A 377 | 2459 | 2411 | 2953 | 930 | -454 | -160 | C |
| ATOM | 454 | CB | ALA A 377 | 44.120 | 10.473 | -20.155 | 1.00 | 20.90 | | C |
| ANISOU | 454 | CB | ALA A 377 | 2623 | 2340 | 2977 | 1047 | -512 | -144 | C |
| ATOM | 455 | C | ALA A 377 | 44.003 | 11.728 | -22.371 | 1.00 | 20.76 | | C |
| ANISOU | 455 | C | ALA A 377 | 2480 | 2447 | 2962 | 897 | -367 | -192 | C |
| ATOM | 456 | O | ALA A 377 | 43.249 | 12.533 | -22.902 | 1.00 | 20.64 | | O |
| ANISOU | 456 | O | ALA A 377 | 2473 | 2438 | 2933 | 780 | -325 | -163 | O |
| ATOM | 457 | N | THR A 378 | 44.622 | 10.780 | -23.061 | 1.00 | 22.11 | | N |
| ANISOU | 457 | N | THR A 378 | 2642 | 2627 | 3133 | 1005 | -342 | -253 | N |
| ATOM | 458 | CA | THR A 378 | 44.428 | 10.601 | -24.505 | 1.00 | 22.78 | | C |
| ANISOU | 458 | CA | THR A 378 | 2731 | 2741 | 3183 | 981 | -260 | -299 | C |
| ATOM | 459 | CB | THR A 378 | 45.231 | 9.415 | -25.017 | 1.00 | 23.45 | | C |
| ANISOU | 459 | CB | THR A 378 | 2808 | 2825 | 3277 | 1131 | -241 | -389 | C |
| ATOM | 460 | OG1 | THR A 378 | 46.575 | 9.539 | -24.551 | 1.00 | 23.66 | | O |
| ANISOU | 460 | OG1 | THR A 378 | 2689 | 2950 | 3349 | 1227 | -263 | -415 | O |
| ATOM | 461 | CG2 | THR A 378 | 45.203 | 9.355 | -26.561 | 1.00 | 23.42 | | C |
| ANISOU | 461 | CG2 | THR A 378 | 2787 | 2895 | 3216 | 1103 | -145 | -456 | C |
| ATOM | 462 | C | THR A 378 | 42.959 | 10.423 | -24.902 | 1.00 | 22.92 | | C |
| ANISOU | 462 | C | THR A 378 | 2886 | 2662 | 3160 | 891 | -249 | -274 | C |
| ATOM | 463 | O | THR A 378 | 42.361 | 9.373 | -24.664 | 1.00 | 23.13 | | O |
| ANISOU | 463 | O | THR A 378 | 3038 | 2563 | 3187 | 929 | -277 | -288 | O |
| ATOM | 464 | N | ARG A 379 | 42.395 | 11.464 | -25.505 | 1.00 | 23.07 | | N |
| ANISOU | 464 | N | ARG A 379 | 2878 | 2739 | 3150 | 770 | -213 | -235 | N |
| ATOM | 465 | CA | ARG A 379 | 41.001 | 11.461 | -25.957 | 1.00 | 23.17 | | C |
| ANISOU | 465 | CA | ARG A 379 | 2988 | 2693 | 3123 | 683 | -211 | -213 | C |
| ATOM | 466 | CB | ARG A 379 | 40.838 | 10.623 | -27.240 | 1.00 | 23.76 | | C |
| ANISOU | 466 | CB | ARG A 379 | 3108 | 2781 | 3137 | 707 | -169 | -291 | C |
| ATOM | 467 | CG | ARG A 379 | 41.771 | 11.029 | -28.390 | 1.00 | 23.77 | | C |
| ANISOU | 467 | CG | ARG A 379 | 3011 | 2933 | 3089 | 720 | -95 | -325 | C |
| ATOM | 468 | CD | ARG A 379 | 41.330 | 10.371 | -29.694 | 1.00 | 25.40 | | C |
| ANISOU | 468 | CD | ARG A 379 | 3277 | 3169 | 3207 | 718 | -57 | -401 | C |
| ATOM | 469 | NE | ARG A 379 | 40.022 | 10.902 | -30.106 | 1.00 | 24.50 | | N |
| ANISOU | 469 | NE | ARG A 379 | 3216 | 3051 | 3041 | 606 | -80 | -347 | N |
| ATOM | 470 | CZ | ARG A 379 | 39.252 | 10.392 | -31.059 | 1.00 | 24.10 | | C |
| ANISOU | 470 | CZ | ARG A 379 | 3232 | 3014 | 2911 | 577 | -79 | -404 | C |
| ATOM | 471 | NH1 | ARG A 379 | 39.641 | 9.323 | -31.758 | 1.00 | 25.54 | | N |
| ANISOU | 471 | NH1 | ARG A 379 | 3449 | 3204 | 3050 | 644 | -47 | -530 | N |
| ATOM | 472 | NH2 | ARG A 379 | 38.099 | 10.974 | -31.317 | 1.00 | 22.39 | | N |
| ANISOU | 472 | NH2 | ARG A 379 | 3041 | 2808 | 2658 | 485 | -115 | -345 | N |
| ATOM | 473 | C | ARG A 379 | 40.061 | 10.981 | -24.854 | 1.00 | 23.18 | | C |
| ANISOU | 473 | C | ARG A 379 | 3094 | 2563 | 3150 | 668 | -268 | -182 | C |
| ATOM | 474 | O | ARG A 379 | 39.189 | 10.137 | -25.092 | 1.00 | 24.70 | | O |
| ANISOU | 474 | O | ARG A 379 | 3388 | 2671 | 3327 | 652 | -272 | -208 | O |
| ATOM | 475 | N | ARG A 380 | 40.242 | 11.534 | -23.654 | 1.00 | 22.60 | | N |
| ANISOU | 475 | N | ARG A 380 | 2994 | 2481 | 3113 | 663 | -306 | -133 | N |
| ATOM | 476 | CA | ARG A 380 | 39.482 | 11.149 | -22.465 | 1.00 | 22.87 | | C |
| ANISOU | 476 | CA | ARG A 380 | 3120 | 2413 | 3156 | 648 | -350 | -96 | C |

FIGURE 18-18

```
ATOM    477  CB  ARG A 380      40.063   9.888 -21.829  1.00 23.67           C
ANISOU  477  CB  ARG A 380    3291   2436   3267    763   -386   -109        C
ATOM    478  CG  ARG A 380      39.313   9.349 -20.612  1.00 25.57           C
ANISOU  478  CG  ARG A 380    3648   2566   3499    747   -421    -54        C
ATOM    479  CD  ARG A 380      40.092   8.171 -20.021  1.00 30.01           C
ANISOU  479  CD  ARG A 380    4280   3051   4071    882   -464    -48        C
ATOM    480  NE  ARG A 380      39.887   8.025 -18.572  1.00 39.22           N
ANISOU  480  NE  ARG A 380    5520   4172   5211    888   -512     30        N
ATOM    481  CZ  ARG A 380      40.796   7.522 -17.733  1.00 40.49           C
ANISOU  481  CZ  ARG A 380    5699   4323   5363   1013   -577     62        C
ATOM    482  NH1 ARG A 380      41.968   7.110 -18.193  1.00 43.42           N
ANISOU  482  NH1 ARG A 380    6006   4723   5768   1149   -600     15        N
ATOM    483  NH2 ARG A 380      40.537   7.434 -16.435  1.00 42.81           N
ANISOU  483  NH2 ARG A 380    6069   4590   5607   1008   -619    141        N
ATOM    484  C   ARG A 380      39.490  12.279 -21.455  1.00 21.00           C
ANISOU  484  C   ARG A 380    2828   2214   2937    601   -375    -50        C
ATOM    485  O   ARG A 380      40.551  12.775 -21.067  1.00 20.79           O
ANISOU  485  O   ARG A 380    2713   2256   2929    638   -393    -57        O
ATOM    486  N   LEU A 381      38.288  12.705 -21.066  1.00 19.70           N
ANISOU  486  N   LEU A 381    2706   2009   2769    514   -373    -18        N
ATOM    487  CA  LEU A 381      38.090  13.567 -19.904  1.00 18.41           C
ANISOU  487  CA  LEU A 381    2522   1857   2616    475   -396      9        C
ATOM    488  CB  LEU A 381      36.745  14.289 -19.985  1.00 16.88           C
ANISOU  488  CB  LEU A 381    2337   1645   2433    380   -372     26        C
ATOM    489  CG  LEU A 381      36.469  15.343 -18.928  1.00 17.01           C
ANISOU  489  CG  LEU A 381    2323   1675   2467    338   -382     32        C
ATOM    490  CD1 LEU A 381      35.655  16.492 -19.499  1.00 12.78           C
ANISOU  490  CD1 LEU A 381    1738   1145   1973    273   -356     41        C
ATOM    491  CD2 LEU A 381      35.764  14.667 -17.749  1.00 15.08           C
ANISOU  491  CD2 LEU A 381    2164   1384   2181    330   -388     44        C
ATOM    492  C   LEU A 381      38.123  12.638 -18.694  1.00 18.24           C
ANISOU  492  C   LEU A 381    2589   1780   2564    525   -433     27        C
ATOM    493  O   LEU A 381      37.296  11.748 -18.564  1.00 17.60           O
ANISOU  493  O   LEU A 381    2610   1616   2464    509   -422     44        O
ATOM    494  N   VAL A 382      39.085  12.854 -17.814  1.00 18.87           N
ANISOU  494  N   VAL A 382    2628   1907   2635    580   -480     26        N
ATOM    495  CA  VAL A 382      39.212  12.031 -16.604  1.00 19.46           C
ANISOU  495  CA  VAL A 382    2791   1944   2660    640   -528     61        C
ATOM    496  CB  VAL A 382      40.671  11.956 -16.074  1.00 19.74           C
ANISOU  496  CB  VAL A 382    2760   2052   2688    749   -598     48        C
ATOM    497  CG1 VAL A 382      40.736  11.203 -14.743  1.00 20.37           C
ANISOU  497  CG1 VAL A 382    2942   2102   2697    814   -661    104        C
ATOM    498  CG2 VAL A 382      41.561  11.303 -17.093  1.00 19.70           C
ANISOU  498  CG2 VAL A 382    2711   2051   2723    843   -593     16        C
ATOM    499  C   VAL A 382      38.274  12.584 -15.548  1.00 19.47           C
ANISOU  499  C   VAL A 382    2832   1944   2622    558   -521     84        C
ATOM    500  O   VAL A 382      37.472  11.840 -14.971  1.00 19.89           O
ANISOU  500  O   VAL A 382    2999   1928   2631    538   -507    128        O
ATOM    501  N   GLN A 383      38.362  13.885 -15.307  1.00 18.92           N
ANISOU  501  N   GLN A 383    2671   1946   2571    507   -521     49        N
ATOM    502  CA  GLN A 383      37.483  14.517 -14.335  1.00 20.00           C
ANISOU  502  CA  GLN A 383    2833   2091   2675    436   -506     46        C
ATOM    503  CB  GLN A 383      37.874  14.122 -12.908  1.00 21.18           C
ANISOU  503  CB  GLN A 383    3042   2275   2732    481   -560     66        C
ATOM    504  CG  GLN A 383      36.899  14.605 -11.894  1.00 28.38           C
ANISOU  504  CG  GLN A 383    3993   3203   3587    409   -528     59        C
ATOM    505  CD  GLN A 383      36.981  13.887 -10.544  1.00 37.43           C
ANISOU  505  CD  GLN A 383    5244   4372   4605    445   -564    109        C
ATOM    506  OE1 GLN A 383      38.033  13.320 -10.146  1.00 36.64           O
ANISOU  506  OE1 GLN A 383    5163   4301   4457    540   -643    139        O
ATOM    507  NE2 GLN A 383      35.848  13.911  -9.823  1.00 39.52           N
ANISOU  507  NE2 GLN A 383    5575   4633   4808    372   -503    122        N
ATOM    508  C   GLN A 383      37.476  16.041 -14.523  1.00 18.54           C
ANISOU  508  C   GLN A 383    2542   1952   2551    374   -491     -8        C
ATOM    509  O   GLN A 383      38.482  16.611 -14.934  1.00 18.67           O
ANISOU  509  O   GLN A 383    2468   2013   2613    390   -513    -37        O
ATOM    510  N   LEU A 384      36.330  16.663 -14.252  1.00 16.78           N
ANISOU  510  N   LEU A 384    2330   1708   2337    305   -448    -21        N
ATOM    511  CA  LEU A 384      36.156  18.111 -14.349  1.00 16.11           C
ANISOU  511  CA  LEU A 384    2165   1634   2321    254   -431    -70        C
ATOM    512  CB  LEU A 384      35.379  18.478 -15.633  1.00 14.20           C
```

FIGURE 18-19

```
ANISOU  512  CB   LEU A 384    1897  1346  2153    221   -387    -47       C
ATOM    513  CG   LEU A 384    35.100  19.947 -15.893  1.00 15.78          C
ANISOU  513  CG   LEU A 384    2031  1526  2439    180   -369    -75       C
ATOM    514  CD1  LEU A 384    36.401  20.725 -16.207  1.00 10.81          C
ANISOU  514  CD1  LEU A 384    1330   915  1863    174   -391    -92       C
ATOM    515  CD2  LEU A 384    34.054  20.107 -16.999  1.00 14.91          C
ANISOU  515  CD2  LEU A 384    1914  1378  2373    164   -338    -36       C
ATOM    516  C    LEU A 384    35.367  18.584 -13.150  1.00 16.11          C
ANISOU  516  C    LEU A 384    2191  1646  2283    219   -413   -111       C
ATOM    517  O    LEU A 384    34.264  18.059 -12.911  1.00 16.54          O
ANISOU  517  O    LEU A 384    2303  1680  2301    197   -371    -89       O
ATOM    518  N    ILE A 385    35.903  19.575 -12.422  1.00 16.23          N
ANISOU  518  N    ILE A 385    2159  1700  2309    206   -439   -182       N
ATOM    519  CA   ILE A 385    35.136  20.337 -11.409  1.00 17.22          C
ANISOU  519  CA   ILE A 385    2291  1838  2415    170   -411   -252       C
ATOM    520  CB   ILE A 385    35.776  20.285  -9.974  1.00 19.18          C
ANISOU  520  CB   ILE A 385    2565  2173  2549    183   -460   -306       C
ATOM    521  CG1  ILE A 385    36.149  18.859  -9.636  1.00 21.06          C
ANISOU  521  CG1  ILE A 385    2884  2446  2673    236   -496   -222       C
ATOM    522  CD1  ILE A 385    37.060  18.725  -8.443  1.00 25.03          C
ANISOU  522  CD1  ILE A 385    3405  3048  3060    273   -575   -251       C
ATOM    523  CG2  ILE A 385    34.780  20.792  -8.871  1.00 18.63          C
ANISOU  523  CG2  ILE A 385    2525  2131  2421    148   -410   -379       C
ATOM    524  C    ILE A 385    35.022  21.812 -11.817  1.00 17.38          C
ANISOU  524  C    ILE A 385    2235  1809  2560    134   -392   -315       C
ATOM    525  O    ILE A 385    36.038  22.477 -12.052  1.00 16.35          O
ANISOU  525  O    ILE A 385    2047  1678  2489    122   -428   -346       O
ATOM    526  N    VAL A 386    33.788  22.308 -11.888  1.00 17.59          N
ANISOU  526  N    VAL A 386    2260  1791  2632    116   -336   -334       N
ATOM    527  CA   VAL A 386    33.497  23.673 -12.328  1.00 17.46          C
ANISOU  527  CA   VAL A 386    2187  1700  2747     99   -317   -379       C
ATOM    528  CB   VAL A 386    32.501  23.721 -13.521  1.00 17.32          C
ANISOU  528  CB   VAL A 386    2153  1623  2805    111   -285   -308       C
ATOM    529  CG1  VAL A 386    32.435  25.126 -14.121  1.00 14.48          C
ANISOU  529  CG1  VAL A 386    1746  1168  2586    108   -281   -322       C
ATOM    530  CG2  VAL A 386    32.875  22.722 -14.622  1.00 14.00          C
ANISOU  530  CG2  VAL A 386    1747  1216  2356    121   -303   -206       C
ATOM    531  C    VAL A 386    32.924  24.512 -11.181  1.00 19.48          C
ANISOU  531  C    VAL A 386    2439  1958  3003     89   -289   -498       C
ATOM    532  O    VAL A 386    32.052  24.065 -10.400  1.00 19.17          O
ANISOU  532  O    VAL A 386    2432  1971  2882     93   -248   -524       O
ATOM    533  N    SER A 387    33.434  25.741 -11.087  1.00 20.06          N
ANISOU  533  N    SER A 387    2475  1975  3174     69   -304   -576       N
ATOM    534  CA   SER A 387    32.894  26.762 -10.198  1.00 20.65          C
ANISOU  534  CA   SER A 387    2541  2021  3286     64   -273   -709       C
ATOM    535  CB   SER A 387    34.004  27.197  -9.236  1.00 21.25          C
ANISOU  535  CB   SER A 387    2612  2141  3321     26   -322   -822       C
ATOM    536  OG   SER A 387    33.536  28.081  -8.225  1.00 25.92          O
ANISOU  536  OG   SER A 387    3205  2723  3922     20   -293   -979       O
ATOM    537  C    SER A 387    32.403  27.938 -11.076  1.00 20.74          C
ANISOU  537  C    SER A 387    2515  1887  3478     75   -250   -705       C
ATOM    538  O    SER A 387    33.153  28.448 -11.920  1.00 20.93          O
ANISOU  538  O    SER A 387    2521  1834  3597     50   -277   -654       O
ATOM    539  N    GLY A 388    31.171  28.394 -10.876  1.00 20.37          N
ANISOU  539  N    GLY A 388    2457  1802  3480    115   -199   -755       N
ATOM    540  CA   GLY A 388    30.607  29.375 -11.771  1.00 20.03          C
ANISOU  540  CA   GLY A 388    2385  1621  3603    151   -188   -725       C
ATOM    541  C    GLY A 388    29.641  30.315 -11.094  1.00 21.29          C
ANISOU  541  C    GLY A 388    2524  1722  3843    198   -142   -856       C
ATOM    542  O    GLY A 388    29.139  30.030 -10.008  1.00 20.82          O
ANISOU  542  O    GLY A 388    2464  1757  3689    204   -100   -961       O
ATOM    543  N    LYS A 389    29.391  31.447 -11.743  1.00 22.34          N
ANISOU  543  N    LYS A 389    2643  1697  4149    235   -144   -847       N
ATOM    544  CA   LYS A 389    28.404  32.440 -11.252  1.00 23.74          C
ANISOU  544  CA   LYS A 389    2793  1788  4438    308   -101   -972       C
ATOM    545  CB   LYS A 389    28.635  33.761 -11.940  1.00 24.80          C
ANISOU  545  CB   LYS A 389    2942  1708  4771    330   -123   -951       C
ATOM    546  CG   LYS A 389    29.884  34.437 -11.447  1.00 28.40          C
ANISOU  546  CG   LYS A 389    3437  2087  5267    239   -141  -1042       C
ATOM    547  CD   LYS A 389    30.035  35.791 -12.096  1.00 35.05          C
ANISOU  547  CD   LYS A 389    4306  2688  6324    250   -150  -1019       C
```

FIGURE 18-20

```
ATOM    548  CE  LYS A 389      31.177  36.562 -11.441  1.00 41.60           C
ANISOU  548  CE  LYS A 389    5164   3432   7212    145   -160  -1153        C
ATOM    549  NZ  LYS A 389      31.822  37.562 -12.391  1.00 47.46           N
ANISOU  549  NZ  LYS A 389    5944   3955   8136     93   -174  -1054        N
ATOM    550  C   LYS A 389      26.964  32.018 -11.437  1.00 23.29           C
ANISOU  550  C   LYS A 389    2680   1796   4372    389    -64   -947        C
ATOM    551  O   LYS A 389      26.103  32.459 -10.703  1.00 24.56           O
ANISOU  551  O   LYS A 389    2804   1962   4567    446    -11  -1079        O
ATOM    552  N   ASP A 390      26.725  31.102 -12.371  1.00 22.47           N
ANISOU  552  N   ASP A 390    2563   1759   4214    388    -89   -794        N
ATOM    553  CA  ASP A 390      25.370  30.703 -12.704  1.00 23.07           C
ANISOU  553  CA  ASP A 390    2569   1900   4296    454    -66   -765        C
ATOM    554  CB  ASP A 390      24.663  31.853 -13.445  1.00 24.00           C
ANISOU  554  CB  ASP A 390    2644   1876   4601    562    -88   -743        C
ATOM    555  CG  ASP A 390      25.432  32.299 -14.704  1.00 24.13           C
ANISOU  555  CG  ASP A 390    2712   1766   4691    555   -157   -587        C
ATOM    556  OD1 ASP A 390      25.404  31.534 -15.677  1.00 25.37           O
ANISOU  556  OD1 ASP A 390    2865   1991   4783    541   -195   -449        O
ATOM    557  OD2 ASP A 390      26.078  33.378 -14.716  1.00 18.12           O
ANISOU  557  OD2 ASP A 390    1997    842   4045    553   -168   -605        O
ATOM    558  C   ASP A 390      25.431  29.453 -13.563  1.00 21.82           C
ANISOU  558  C   ASP A 390    2416   1838   4036    412    -98   -618        C
ATOM    559  O   ASP A 390      26.473  29.107 -14.095  1.00 21.61           O
ANISOU  559  O   ASP A 390    2445   1800   3967    359   -140   -529        O
ATOM    560  N   GLU A 391      24.289  28.816 -13.752  1.00 22.29           N
ANISOU  560  N   GLU A 391    2410   1991   4069    437    -77   -602        N
ATOM    561  CA  GLU A 391      24.220  27.543 -14.442  1.00 21.52           C
ANISOU  561  CA  GLU A 391    2317   1987   3871    387    -99   -494        C
ATOM    562  CB  GLU A 391      22.839  26.928 -14.190  1.00 22.15           C
ANISOU  562  CB  GLU A 391    2309   2181   3927    393    -50   -536        C
ATOM    563  CG  GLU A 391      22.286  26.000 -15.243  1.00 24.99           C
ANISOU  563  CG  GLU A 391    2632   2607   4255    372    -88   -439        C
ATOM    564  CD  GLU A 391      20.751  25.986 -15.206  1.00 33.67           C
ANISOU  564  CD  GLU A 391    3596   3789   5407    410    -56   -495        C
ATOM    565  OE1 GLU A 391      20.154  25.746 -14.111  1.00 34.20           O
ANISOU  565  OE1 GLU A 391    3622   3935   5438    379     35   -596        O
ATOM    566  OE2 GLU A 391      20.138  26.247 -16.270  1.00 38.52           O
ANISOU  566  OE2 GLU A 391    4139   4401   6095    472   -121   -439        O
ATOM    567  C   GLU A 391      24.611  27.602 -15.922  1.00 20.48           C
ANISOU  567  C   GLU A 391    2204   1800   3778    403   -176   -352        C
ATOM    568  O   GLU A 391      25.229  26.686 -16.401  1.00 19.95           O
ANISOU  568  O   GLU A 391    2183   1778   3619    346   -199   -277        O
ATOM    569  N   GLN A 392      24.288  28.689 -16.609  1.00 21.46           N
ANISOU  569  N   GLN A 392    2299   1824   4031    484   -212   -317        N
ATOM    570  CA  GLN A 392      24.666  28.910 -18.002  1.00 23.52           C
ANISOU  570  CA  GLN A 392    2587   2032   4318    502   -281   -172        C
ATOM    571  CB  GLN A 392      23.926  30.147 -18.557  1.00 24.65           C
ANISOU  571  CB  GLN A 392    2688   2067   4610    617   -317   -138        C
ATOM    572  CG  GLN A 392      24.537  30.860 -19.769  1.00 28.63           C
ANISOU  572  CG  GLN A 392    3252   2461   5164    639   -376     13        C
ATOM    573  CD  GLN A 392      24.305  32.416 -19.753  1.00 30.83           C
ANISOU  573  CD  GLN A 392    3540   2551   5624    735   -387     15        C
ATOM    574  OE1 GLN A 392      25.010  33.190 -19.035  1.00 34.80           O
ANISOU  574  OE1 GLN A 392    4092   2924   6205    705   -349    -58        O
ATOM    575  NE2 GLN A 392      23.321  32.867 -20.548  1.00 33.14           N
ANISOU  575  NE2 GLN A 392    3784   2821   5985    853   -447     94        N
ATOM    576  C   GLN A 392      26.188  29.017 -18.189  1.00 22.62           C
ANISOU  576  C   GLN A 392    2561   1858   4175    433   -289   -120        C
ATOM    577  O   GLN A 392      26.726  28.443 -19.125  1.00 21.91           O
ANISOU  577  O   GLN A 392    2503   1807   4016    398   -319    -17        O
ATOM    578  N   SER A 393      26.877  29.730 -17.295  1.00 22.81           N
ANISOU  578  N   SER A 393    2615   1801   4249    409   -260   -206        N
ATOM    579  CA  SER A 393      28.347  29.794 -17.315  1.00 21.99           C
ANISOU  579  CA  SER A 393    2570   1664   4121    331   -264   -183        C
ATOM    580  CB  SER A 393      28.857  30.874 -16.346  1.00 23.44           C
ANISOU  580  CB  SER A 393    2770   1738   4397    313   -242   -300        C
ATOM    581  OG  SER A 393      28.140  32.078 -16.569  1.00 25.29           O
ANISOU  581  OG  SER A 393    2992   1830   4786    390   -243   -305        O
ATOM    582  C   SER A 393      29.011  28.464 -16.993  1.00 20.66           C
ANISOU  582  C   SER A 393    2422   1626   3801    265   -259   -189        C
ATOM    583  O   SER A 393      30.049  28.132 -17.552  1.00 19.87           O
```

FIGURE 18-21

```
ANISOU   583  O    SER A 393     2350  1542  3659    219   -276   -122         O
ATOM     584  N    ILE A 394     28.422  27.713 -16.073  1.00 20.77            N
ANISOU   584  N    ILE A 394     2422  1732  3737    263   -230   -268         N
ATOM     585  CA   ILE A 394     28.889  26.369 -15.747  1.00 19.11            C
ANISOU   585  CA   ILE A 394     2244  1630  3386    214   -227   -260         C
ATOM     586  CB   ILE A 394     28.139  25.782 -14.497  1.00 19.85            C
ANISOU   586  CB   ILE A 394     2333  1806  3402    206   -179   -352         C
ATOM     587  CG1  ILE A 394     28.509  26.606 -13.259  1.00 20.43            C
ANISOU   587  CG1  ILE A 394     2415  1856  3490    201   -158   -477         C
ATOM     588  CD1  ILE A 394     27.499  26.518 -12.109  1.00 22.75            C
ANISOU   588  CD1  ILE A 394     2688  2218  3738    210    -93   -583         C
ATOM     589  CG2  ILE A 394     28.435  24.278 -14.274  1.00 15.59            C
ANISOU   589  CG2  ILE A 394     1843  1358  2723    163   -177   -313         C
ATOM     590  C    ILE A 394     28.784  25.474 -16.977  1.00 18.68            C
ANISOU   590  C    ILE A 394     2195  1619  3284    212   -254   -148         C
ATOM     591  O    ILE A 394     29.760  24.825 -17.311  1.00 17.57            O
ANISOU   591  O    ILE A 394     2090  1507  3080    182   -270   -104         O
ATOM     592  N    ALA A 395     27.630  25.500 -17.663  1.00 19.22            N
ANISOU   592  N    ALA A 395     2220  1695  3386    250   -262   -113         N
ATOM     593  CA   ALA A 395     27.401  24.738 -18.901  1.00 19.01            C
ANISOU   593  CA   ALA A 395     2194  1718  3313    248   -295    -23         C
ATOM     594  CB   ALA A 395     25.980  24.956 -19.419  1.00 18.56            C
ANISOU   594  CB   ALA A 395     2065  1683  3305    297   -314    -13         C
ATOM     595  C    ALA A 395     28.416  25.074 -19.990  1.00 19.20            C
ANISOU   595  C    ALA A 395     2250  1706  3340    245   -327     70         C
ATOM     596  O    ALA A 395     28.898  24.171 -20.671  1.00 18.93            O
ANISOU   596  O    ALA A 395     2244  1727  3223    220   -339    115         O
ATOM     597  N    GLU A 396     28.719  26.364 -20.157  1.00 20.22            N
ANISOU   597  N    GLU A 396     2377  1739  3567    267   -332     96         N
ATOM     598  CA   GLU A 396     29.710  26.818 -21.142  1.00 21.09            C
ANISOU   598  CA   GLU A 396     2517  1810  3684    247   -345    193         C
ATOM     599  CB   GLU A 396     29.807  28.341 -21.147  1.00 22.89            C
ANISOU   599  CB   GLU A 396     2749  1899  4047    266   -343    216         C
ATOM     600  CG   GLU A 396     28.607  29.009 -21.787  1.00 27.44            C
ANISOU   600  CG   GLU A 396     3306  2429  4693    349   -378    278         C
ATOM     601  CD   GLU A 396     28.571  30.513 -21.606  1.00 31.59            C
ANISOU   601  CD   GLU A 396     3844  2785  5373    385   -375    287         C
ATOM     602  OE1  GLU A 396     29.466  31.075 -20.945  1.00 37.15            O
ANISOU   602  OE1  GLU A 396     4573  3406  6136    328   -342    230         O
ATOM     603  OE2  GLU A 396     27.632  31.141 -22.145  1.00 34.90            O
ANISOU   603  OE2  GLU A 396     4250  3151  5862    473   -412    349         O
ATOM     604  C    GLU A 396     31.090  26.181 -20.894  1.00 19.62            C
ANISOU   604  C    GLU A 396     2357  1667  3430    186   -325    174         C
ATOM     605  O    GLU A 396     31.755  25.774 -21.820  1.00 19.19            O
ANISOU   605  O    GLU A 396     2317  1657  3319    166   -327    242         O
ATOM     606  N    ALA A 397     31.480  26.093 -19.631  1.00 18.63            N
ANISOU   606  N    ALA A 397     2231  1543  3306    164   -309     75         N
ATOM     607  CA   ALA A 397     32.722  25.456 -19.210  1.00 18.01            C
ANISOU   607  CA   ALA A 397     2163  1517  3164    125   -305     44         C
ATOM     608  CB   ALA A 397     32.994  25.795 -17.741  1.00 17.36            C
ANISOU   608  CB   ALA A 397     2076  1422  3099    108   -300    -69         C
ATOM     609  C    ALA A 397     32.768  23.936 -19.457  1.00 16.96            C
ANISOU   609  C    ALA A 397     2052  1477  2914    133   -311     60         C
ATOM     610  O    ALA A 397     33.775  23.398 -19.924  1.00 17.05            O
ANISOU   610  O    ALA A 397     2067  1532  2880    123   -313     85         O
ATOM     611  N    ILE A 398     31.668  23.250 -19.152  1.00 17.13            N
ANISOU   611  N    ILE A 398     2086  1526  2898    151   -309     38         N
ATOM     612  CA   ILE A 398     31.536  21.827 -19.422  1.00 15.91            C
ANISOU   612  CA   ILE A 398     1963  1430  2651    150   -312     51         C
ATOM     613  CB   ILE A 398     30.199  21.264 -18.834  1.00 17.18            C
ANISOU   613  CB   ILE A 398     2128  1608  2792    144   -297     15         C
ATOM     614  CG1  ILE A 398     30.119  21.527 -17.326  1.00 16.13            C
ANISOU   614  CG1  ILE A 398     2000  1471  2657    136   -271    -57         C
ATOM     615  CD1  ILE A 398     28.779  21.236 -16.716  1.00 16.58            C
ANISOU   615  CD1  ILE A 398     2043  1553  2705    121   -235    -95         C
ATOM     616  CG2  ILE A 398     30.022  19.747 -19.155  1.00 13.67            C
ANISOU   616  CG2  ILE A 398     1729  1199  2267    127   -297     27         C
ATOM     617  C    ILE A 398     31.671  21.562 -20.922  1.00 16.07            C
ANISOU   617  C    ILE A 398     1985  1475  2647    156   -326    121         C
ATOM     618  O    ILE A 398     32.434  20.686 -21.326  1.00 16.26            O
ANISOU   618  O    ILE A 398     2034  1535  2609    157   -326    128         O
```

FIGURE 18-22

```
ATOM    619  N   ILE A 399      30.963  22.335 -21.741  1.00 16.42           N
ANISOU  619  N   ILE A 399    2003  1502  2734   169  -339   169             N
ATOM    620  CA  ILE A 399      31.042  22.212 -23.210  1.00 16.68           C
ANISOU  620  CA  ILE A 399    2040  1574  2722   175  -356   243             C
ATOM    621  CB  ILE A 399      30.128  23.237 -23.951  1.00 17.23           C
ANISOU  621  CB  ILE A 399    2083  1621  2843   205  -385   310             C
ATOM    622  CG1 ILE A 399      28.652  22.926 -23.683  1.00 16.60           C
ANISOU  622  CG1 ILE A 399    1968  1565  2776   225  -410   268             C
ATOM    623  CD1 ILE A 399      27.669  24.079 -24.032  1.00 17.54           C
ANISOU  623  CD1 ILE A 399    2040  1648  2976   281  -446   315             C
ATOM    624  CG2 ILE A 399      30.379  23.228 -25.492  1.00 18.27           C
ANISOU  624  CG2 ILE A 399    2231  1807  2903   209  -404   401             C
ATOM    625  C   ILE A 399      32.467  22.321 -23.722  1.00 17.17           C
ANISOU  625  C   ILE A 399    2111  1650  2761   159  -335   277             C
ATOM    626  O   ILE A 399      32.926  21.437 -24.454  1.00 17.83           O
ANISOU  626  O   ILE A 399    2214  1798  2764   160  -329   282             O
ATOM    627  N   VAL A 400      33.152  23.398 -23.336  1.00 16.69           N
ANISOU  627  N   VAL A 400    2033  1534  2776   141  -318   289             N
ATOM    628  CA  VAL A 400      34.542  23.641 -23.732  1.00 16.70           C
ANISOU  628  CA  VAL A 400    2020  1553  2773   109  -288   316             C
ATOM    629  CB  VAL A 400      35.026  25.034 -23.221  1.00 16.70           C
ANISOU  629  CB  VAL A 400    1997  1463  2887    69  -273   321             C
ATOM    630  CG1 VAL A 400      36.523  25.234 -23.427  1.00 15.47           C
ANISOU  630  CG1 VAL A 400    1803  1337  2737    16  -236   327             C
ATOM    631  CG2 VAL A 400      34.216  26.116 -23.893  1.00 16.90           C
ANISOU  631  CG2 VAL A 400    2039  1410  2973    79  -281   410             C
ATOM    632  C   VAL A 400      35.510  22.529 -23.314  1.00 15.98           C
ANISOU  632  C   VAL A 400    1922  1527  2623   114  -279   252             C
ATOM    633  O   VAL A 400      36.327  22.104 -24.112  1.00 17.42           O
ANISOU  633  O   VAL A 400    2094  1773  2753   112  -256   272             O
ATOM    634  N   ALA A 401      35.406  22.061 -22.079  1.00 16.30           N
ANISOU  634  N   ALA A 401    1971  1556  2666   128  -297   178             N
ATOM    635  CA  ALA A 401      36.199  20.909 -21.593  1.00 16.28           C
ANISOU  635  CA  ALA A 401    1976  1604  2606   155  -305   128             C
ATOM    636  CB  ALA A 401      35.953  20.689 -20.091  1.00 14.87           C
ANISOU  636  CB  ALA A 401    1817  1404  2428   165  -328    68             C
ATOM    637  C   ALA A 401      35.896  19.628 -22.378  1.00 16.82           C
ANISOU  637  C   ALA A 401    2088  1709  2596   188  -304   136             C
ATOM    638  O   ALA A 401      36.802  18.869 -22.684  1.00 18.03           O
ANISOU  638  O   ALA A 401    2236  1907  2709   218  -296   118             O
ATOM    639  N   MSE A 402      34.624  19.373 -22.681  1.00 17.03           N
ANISOU  639  N   MSE A 402    2147  1717  2604   183  -313   147             N
ATOM    640  CA  MSE A 402      34.253  18.142 -23.412  1.00 17.44           C
ANISOU  640  CA  MSE A 402    2244  1796  2588   199  -316   135             C
ATOM    641  CB  MSE A 402      32.737  17.935 -23.431  1.00 16.42           C
ANISOU  641  CB  MSE A 402    2133  1649  2458   176  -333   130             C
ATOM    642  CG  MSE A 402      32.140  17.462 -22.125  1.00 16.29           C
ANISOU  642  CG  MSE A 402    2144  1590  2456   163  -332    92             C
ATOM    643  SE  MSE A 402      30.183  17.395 -22.251  0.90 20.12          SE
ANISOU  643  SE  MSE A 402    2609  2079  2958   119  -340    80            SE
ATOM    644  CE  MSE A 402      29.774  16.578 -20.532  1.00 14.21           C
ANISOU  644  CE  MSE A 402    1909  1287  2202    87  -307    39             C
ATOM    645  C   MSE A 402      34.797  18.137 -24.843  1.00 17.04           C
ANISOU  645  C   MSE A 402    2179  1807  2487   205  -298   163             C
ATOM    646  O   MSE A 402      35.297  17.114 -25.295  1.00 17.79           O
ANISOU  646  O   MSE A 402    2299  1933  2528   233  -288   126             O
ATOM    647  N   VAL A 403      34.697  19.277 -25.541  1.00 17.61           N
ANISOU  647  N   VAL A 403    2220  1894  2576   182  -292   230             N
ATOM    648  CA  VAL A 403      35.335  19.465 -26.866  1.00 17.49           C
ANISOU  648  CA  VAL A 403    2194  1951  2500   177  -261   275             C
ATOM    649  CB  VAL A 403      34.977  20.843 -27.538  1.00 18.05           C
ANISOU  649  CB  VAL A 403    2252  2014  2593   149  -261   380             C
ATOM    650  CG1 VAL A 403      35.759  21.042 -28.835  1.00 15.38           C
ANISOU  650  CG1 VAL A 403    1909  1761  2174   132  -215   441             C
ATOM    651  CG2 VAL A 403      33.475  20.963 -27.819  1.00 18.29           C
ANISOU  651  CG2 VAL A 403    2302  2033  2616   162  -316   405             C
ATOM    652  C   VAL A 403      36.880  19.322 -26.774  1.00 18.33           C
ANISOU  652  C   VAL A 403    2259  2096  2607   184  -216   250             C
ATOM    653  O   VAL A 403      37.496  18.607 -27.563  1.00 18.16           O
ANISOU  653  O   VAL A 403    2238  2149  2515   207  -185   224             O
ATOM    654  N   PHE A 404      37.482  20.014 -25.804  1.00 18.22           N
```

FIGURE 18-23

```
ANISOU  654  N    PHE A 404    2203  2042  2676    166  -213   246       N
ATOM    655  CA   PHE A 404    38.935  20.002 -25.606  1.00 18.45        C
ANISOU  655  CA   PHE A 404    2167  2120  2724    167  -180   215       C
ATOM    656  CB   PHE A 404    39.279  20.946 -24.451  1.00 18.40        C
ANISOU  656  CB   PHE A 404    2118  2060  2815    130  -197   203       C
ATOM    657  CG   PHE A 404    40.743  21.047 -24.167  1.00 16.27        C
ANISOU  657  CG   PHE A 404    1758  1850  2576    119  -176   163       C
ATOM    658  CD1  PHE A 404    41.538  21.926 -24.884  1.00 17.08        C
ANISOU  658  CD1  PHE A 404    1794  1990  2708     49  -116   207       C
ATOM    659  CE1  PHE A 404    42.921  22.016 -24.616  1.00 21.24        C
ANISOU  659  CE1  PHE A 404    2210  2589  3271     29   -94   157       C
ATOM    660  CZ   PHE A 404    43.501  21.222 -23.619  1.00 19.15        C
ANISOU  660  CZ   PHE A 404    1905  2364  3009     98  -148    68       C
ATOM    661  CE2  PHE A 404    42.718  20.351 -22.893  1.00 18.17        C
ANISOU  661  CE2  PHE A 404    1866  2192  2846    176  -211    40       C
ATOM    662  CD2  PHE A 404    41.325  20.260 -23.180  1.00 17.63        C
ANISOU  662  CD2  PHE A 404    1906  2047  2745    177  -217    86       C
ATOM    663  C    PHE A 404    39.518  18.593 -25.332  1.00 18.68        C
ANISOU  663  C    PHE A 404    2200  2187  2710    241  -190   135       C
ATOM    664  O    PHE A 404    40.673  18.296 -25.683  1.00 18.92        O
ANISOU  664  O    PHE A 404    2170  2292  2727    266  -154   105       O
ATOM    665  N    SER A 405    38.712  17.745 -24.692  1.00 18.21        N
ANISOU  665  N    SER A 405    2210  2070  2638    277  -233   102       N
ATOM    666  CA   SER A 405    39.091  16.363 -24.380  1.00 18.68        C
ANISOU  666  CA   SER A 405    2304  2127  2668    352  -249    41       C
ATOM    667  CB   SER A 405    38.012  15.723 -23.496  1.00 18.57        C
ANISOU  667  CB   SER A 405    2375  2027  2653    356  -290    32       C
ATOM    668  OG   SER A 405    36.849  15.381 -24.246  1.00 16.66        O
ANISOU  668  OG   SER A 405    2188  1765  2376    326  -287    37       O
ATOM    669  C    SER A 405    39.340  15.491 -25.619  1.00 20.09        C
ANISOU  669  C    SER A 405    2498  2356  2779    391  -214     8       C
ATOM    670  O    SER A 405    40.066  14.496 -25.533  1.00 21.25        O
ANISOU  670  O    SER A 405    2648  2509  2916    468  -213   -50       O
ATOM    671  N    GLN A 406    38.723  15.866 -26.758  1.00 20.26        N
ANISOU  671  N    GLN A 406    2533  2414  2751    345  -190    41       N
ATOM    672  CA   GLN A 406    38.832  15.162 -28.048  1.00 20.05        C
ANISOU  672  CA   GLN A 406    2527  2454  2636    368  -155     2       C
ATOM    673  CB   GLN A 406    40.290  15.095 -28.531  1.00 19.99        C
ANISOU  673  CB   GLN A 406    2441  2542  2612    409   -93   -31       C
ATOM    674  CG   GLN A 406    40.906  16.472 -28.726  1.00 20.76        C
ANISOU  674  CG   GLN A 406    2452  2702  2734    342   -49    46       C
ATOM    675  CD   GLN A 406    42.332  16.414 -29.196  1.00 20.39        C
ANISOU  675  CD   GLN A 406    2306  2766  2674    366    24     9       C
ATOM    676  OE1  GLN A 406    43.147  15.693 -28.645  1.00 19.25        O
ANISOU  676  OE1  GLN A 406    2117  2630  2566    444    17   -66       O
ATOM    677  NE2  GLN A 406    42.640  17.179 -30.233  1.00 22.01        N
ANISOU  677  NE2  GLN A 406    2474  3065  2824    301    97    68       N
ATOM    678  C    GLN A 406    38.164  13.777 -28.045  1.00 20.64        C
ANISOU  678  C    GLN A 406    2691  2466  2684    406  -184   -74       C
ATOM    679  O    GLN A 406    38.465  12.937 -28.887  1.00 22.16        O
ANISOU  679  O    GLN A 406    2906  2696  2817    445  -157  -144       O
ATOM    680  N    GLU A 407    37.248  13.554 -27.111  1.00 20.37        N
ANISOU  680  N    GLU A 407    2710  2337  2695    385  -231   -65       N
ATOM    681  CA   GLU A 407    36.556  12.268 -26.951  1.00 21.29        C
ANISOU  681  CA   GLU A 407    2916  2369  2805    396  -254  -125       C
ATOM    682  CB   GLU A 407    35.638  12.293 -25.718  1.00 19.97        C
ANISOU  682  CB   GLU A 407    2786  2110  2691    355  -289   -92       C
ATOM    683  CG   GLU A 407    36.371  12.188 -24.373  1.00 21.49        C
ANISOU  683  CG   GLU A 407    2982  2253  2931    404  -301   -73       C
ATOM    684  CD   GLU A 407    35.649  11.292 -23.352  1.00 21.16        C
ANISOU  684  CD   GLU A 407    3033  2101  2906    391  -321   -72       C
ATOM    685  OE1  GLU A 407    34.688  10.585 -23.711  1.00 21.26        O
ANISOU  685  OE1  GLU A 407    3107  2062  2909    342  -319  -101       O
ATOM    686  OE2  GLU A 407    36.071  11.267 -22.189  1.00 20.34        O
ANISOU  686  OE2  GLU A 407    2943  1965  2820    424  -339   -43       O
ATOM    687  C    GLU A 407    35.725  11.866 -28.158  1.00 22.08        C
ANISOU  687  C    GLU A 407    3052  2504  2835    357  -256  -169       C
ATOM    688  O    GLU A 407    35.066  12.694 -28.765  1.00 20.70        O
ANISOU  688  O    GLU A 407    2846  2394  2624    304  -267  -123       O
ATOM    689  N    ASP A 408    35.720  10.573 -28.461  1.00 23.34        N
ANISOU  689  N    ASP A 408    3280  2611  2976    386  -253  -261       N
```

FIGURE 18-24

```
ATOM    690  CA  ASP A 408      34.928  10.035 -29.544  1.00 24.61           C
ANISOU  690  CA  ASP A 408     3481   2801   3068    344   -263   -332       C
ATOM    691  CB  ASP A 408      35.160   8.530 -29.658  1.00 25.59           C
ANISOU  691  CB  ASP A 408     3692   2830   3202    388   -253   -449       C
ATOM    692  CG  ASP A 408      34.396   7.913 -30.801  1.00 27.72           C
ANISOU  692  CG  ASP A 408     4003   3131   3397    336   -265   -551       C
ATOM    693  OD1 ASP A 408      34.710   8.279 -31.958  1.00 31.59           O
ANISOU  693  OD1 ASP A 408     4457   3762   3786    347   -246   -579       O
ATOM    694  OD2 ASP A 408      33.492   7.066 -30.549  1.00 28.73           O
ANISOU  694  OD2 ASP A 408     4201   3151   3564    276   -293   -607       O
ATOM    695  C   ASP A 408      33.427  10.347 -29.389  1.00 24.65           C
ANISOU  695  C   ASP A 408     3488   2793   3084    249   -310   -301       C
ATOM    696  O   ASP A 408      32.784  10.796 -30.342  1.00 24.93           O
ANISOU  696  O   ASP A 408     3495   2927   3051    207   -333   -299       O
ATOM    697  N   ACYS A 409     32.869  10.126 -28.205  0.70 24.72           N
ANISOU  697  N   ACYS A 409    3524   2697   3172    218   -325   -276       N
ATOM    698  N   BCYS A 409     32.906  10.105 -28.182  0.30 24.11           N
ANISOU  698  N   BCYS A 409    3448   2617   3096    220   -324   -276       N
ATOM    699  CA  ACYS A 409     31.430  10.317 -28.021  0.70 25.22           C
ANISOU  699  CA  ACYS A 409    3572   2756   3254    128   -359   -264       C
ATOM    700  CA  BCYS A 409     31.506  10.359 -27.816  0.30 23.92           C
ANISOU  700  CA  BCYS A 409    3408   2580   3101    132   -355   -254       C
ATOM    701  CB  ACYS A 409     30.961   9.730 -26.681  0.70 25.40           C
ANISOU  701  CB  ACYS A 409    3644   2652   3353     91   -351   -253       C
ATOM    702  CB  BCYS A 409     31.313  10.176 -26.307  0.30 23.45           C
ANISOU  702  CB  BCYS A 409    3378   2413   3118    117   -345   -213       C
ATOM    703  SG  ACYS A 409     31.124  10.858 -25.325  0.70 28.09           S
ANISOU  703  SG  ACYS A 409    3936   2990   3746    108   -341   -150       S
ATOM    704  SG  BCYS A 409     31.533   8.502 -25.712  0.30 24.62           S
ANISOU  704  SG  BCYS A 409    3655   2400   3300    125   -326   -269       S
ATOM    705  C   ACYS A 409     31.016  11.792 -28.173  0.70 23.86           C
ANISOU  705  C   ACYS A 409    3310   2680   3076    114   -379   -177       C
ATOM    706  C   BCYS A 409     31.060  11.762 -28.191  0.30 23.24           C
ANISOU  706  C   BCYS A 409    3233   2600   2995    116   -378   -179       C
ATOM    707  O   ACYS A 409     29.841  12.089 -28.420  0.70 23.73           O
ANISOU  707  O   ACYS A 409    3255   2703   3058     58   -417   -174       O
ATOM    708  O   BCYS A 409     29.914  11.985 -28.591  0.30 23.42           O
ANISOU  708  O   BCYS A 409    3222   2670   3007     61   -417   -184       O
ATOM    709  N   MSE A 410      31.991  12.696 -28.033  1.00 22.71           N
ANISOU  709  N   MSE A 410     3128   2566   2936    166   -357   -110       N
ATOM    710  CA  MSE A 410      31.811  14.092 -28.382  1.00 21.64           C
ANISOU  710  CA  MSE A 410     2925   2503   2796    162   -370    -25       C
ATOM    711  CB  MSE A 410      32.941  14.929 -27.770  1.00 21.38           C
ANISOU  711  CB  MSE A 410     2860   2456   2807    198   -336     34       C
ATOM    712  CG  MSE A 410      32.895  16.431 -28.071  1.00 19.41           C
ANISOU  712  CG  MSE A 410     2554   2246   2573    190   -339    129       C
ATOM    713  SE  MSE A 410      33.826  17.055 -29.687  0.90 23.28          SE
ANISOU  713  SE  MSE A 410     3027   2856   2961    199   -303    190      SE
ATOM    714  CE  MSE A 410      35.627  16.334 -29.341  1.00 17.42           C
ANISOU  714  CE  MSE A 410     2275   2120   2226    242   -234    125       C
ATOM    715  C   MSE A 410      31.762  14.285 -29.903  1.00 22.99           C
ANISOU  715  C   MSE A 410     3085   2788   2861    162   -383    -21       C
ATOM    716  O   MSE A 410      30.839  14.974 -30.405  1.00 23.49           O
ANISOU  716  O   MSE A 410     3115   2908   2904    140   -429     26       O
ATOM    717  N   ILE A 411      32.750  13.711 -30.616  1.00 22.18           N
ANISOU  717  N   ILE A 411     3009   2728   2689    195   -345    -69       N
ATOM    718  CA  ILE A 411      32.822  13.744 -32.071  1.00 23.23           C
ANISOU  718  CA  ILE A 411     3145   2987   2693    196   -344    -80       C
ATOM    719  CB  ILE A 411      34.201  13.201 -32.577  1.00 24.59           C
ANISOU  719  CB  ILE A 411     3332   3203   2809    246   -273   -138       C
ATOM    720  CG1 ILE A 411      35.271  14.295 -32.388  1.00 26.32           C
ANISOU  720  CG1 ILE A 411     3493   3453   3056    263   -219    -38       C
ATOM    721  CD1 ILE A 411      36.666  13.790 -32.234  1.00 28.71           C
ANISOU  721  CD1 ILE A 411     3775   3761   3371    318   -151    -95       C
ATOM    722  CG2 ILE A 411      34.171  12.852 -34.050  1.00 25.93           C
ANISOU  722  CG2 ILE A 411     3524   3504   2824    243   -266   -195       C
ATOM    723  C   ILE A 411      31.610  13.049 -32.705  1.00 23.32           C
ANISOU  723  C   ILE A 411     3181   3033   2646    153   -406   -158       C
ATOM    724  O   ILE A 411      31.080  13.526 -33.698  1.00 23.80           O
ANISOU  724  O   ILE A 411     3225   3207   2611    139   -447   -126       O
ATOM    725  N   LYS A 412      31.150  11.948 -32.095  1.00 22.39           N
```

FIGURE 18-25

```
ANISOU  725  N    LYS A 412    3103  2816  2587   126  -417  -254      N
ATOM    726  CA   LYS A 412   30.008  11.189 -32.619  1.00 22.44       C
ANISOU  726  CA   LYS A 412    3126  2844  2557    64  -473  -349      C
ATOM    727  CB   LYS A 412   30.065   9.720 -32.145  1.00 22.70       C
ANISOU  727  CB   LYS A 412    3236  2744  2644    43  -450  -472      C
ATOM    728  CG   LYS A 412   31.201   8.920 -32.768  1.00 22.92       C
ANISOU  728  CG   LYS A 412    3324  2769  2614   105  -401  -564      C
ATOM    729  CD   LYS A 412   31.025   8.761 -34.293  1.00 21.99       C
ANISOU  729  CD   LYS A 412    3210  2800  2346    92  -424  -649      C
ATOM    730  CE   LYS A 412   32.028   7.811 -34.909  1.00 25.65       C
ANISOU  730  CE   LYS A 412    3734  3256  2754   152  -367  -778      C
ATOM    731  NZ   LYS A 412   33.428   8.304 -34.688  1.00 27.17       N
ANISOU  731  NZ   LYS A 412    3899  3468  2955   246  -293  -708      N
ATOM    732  C    LYS A 412   28.666  11.875 -32.299  1.00 21.94       C
ANISOU  732  C    LYS A 412    2995  2803  2540    14  -538  -292      C
ATOM    733  O    LYS A 412   27.630  11.557 -32.849  1.00 22.69       O
ANISOU  733  O    LYS A 412    3067  2958  2597   -40  -599  -352      O
ATOM    734  N    ALA A 413   28.709  12.869 -31.427  1.00 21.22       N
ANISOU  734  N    ALA A 413    2860  2671  2530    36  -525  -183      N
ATOM    735  CA   ALA A 413   27.536  13.650 -31.085  1.00 20.92       C
ANISOU  735  CA   ALA A 413    2747  2655  2548    13  -576  -129      C
ATOM    736  CB   ALA A 413   27.649  14.219 -29.668  1.00 18.88       C
ANISOU  736  CB   ALA A 413    2470  2294  2409    26  -537   -70      C
ATOM    737  C    ALA A 413   27.248  14.752 -32.097  1.00 21.86       C
ANISOU  737  C    ALA A 413    2818  2897  2593    49  -633   -41      C
ATOM    738  O    ALA A 413   26.187  15.379 -32.051  1.00 22.85       O
ANISOU  738  O    ALA A 413    2871  3058  2752    48  -693    -4      O
ATOM    739  N    VAL A 414   28.175  14.991 -33.014  1.00 22.39       N
ANISOU  739  N    VAL A 414    2922  3032  2556    85  -611    -4      N
ATOM    740  CA   VAL A 414   27.955  15.974 -34.070  1.00 23.35       C
ANISOU  740  CA   VAL A 414    3019  3272  2581   117  -662    98      C
ATOM    741  CB   VAL A 414   29.231  16.231 -34.885  1.00 23.82       C
ANISOU  741  CB   VAL A 414    3127  3392  2531   144  -600   150      C
ATOM    742  CG1  VAL A 414   28.916  17.030 -36.162  1.00 23.49       C
ANISOU  742  CG1  VAL A 414    3084  3492  2348   165  -656   255      C
ATOM    743  CG2  VAL A 414   30.269  16.960 -34.029  1.00 21.14       C
ANISOU  743  CG2  VAL A 414    2786  2952  2296   164  -520   231      C
ATOM    744  C    VAL A 414   26.807  15.533 -34.993  1.00 25.52       C
ANISOU  744  C    VAL A 414    3267  3670  2760    90  -761    34      C
ATOM    745  O    VAL A 414   26.724  14.372 -35.386  1.00 26.20       O
ANISOU  745  O    VAL A 414    3384  3785  2785    46  -766  -102      O
ATOM    746  N    ARG A 415   25.914  16.474 -35.297  1.00 26.58       N
ANISOU  746  N    ARG A 415    3339  3868  2891   121  -844   127      N
ATOM    747  CA   ARG A 415   24.812  16.243 -36.203  1.00 29.14       C
ANISOU  747  CA   ARG A 415    3617  4335  3118   109  -958    83      C
ATOM    748  CB   ARG A 415   23.449  16.436 -35.494  1.00 29.44       C
ANISOU  748  CB   ARG A 415    3545  4355  3286    99 -1027    62      C
ATOM    749  CG   ARG A 415   23.141  15.430 -34.381  1.00 29.25       C
ANISOU  749  CG   ARG A 415    3504  4222  3388    18  -974   -70      C
ATOM    750  CD   ARG A 415   23.007  14.000 -34.895  1.00 29.56       C
ANISOU  750  CD   ARG A 415    3579  4300  3352   -70  -985  -236      C
ATOM    751  NE   ARG A 415   22.856  13.082 -33.769  1.00 29.80       N
ANISOU  751  NE   ARG A 415    3621  4194  3510  -150  -917  -331      N
ATOM    752  CZ   ARG A 415   23.825  12.317 -33.266  1.00 28.42       C
ANISOU  752  CZ   ARG A 415    3546  3892  3360  -167  -824  -374      C
ATOM    753  NH1  ARG A 415   25.038  12.351 -33.797  1.00 29.21       N
ANISOU  753  NH1  ARG A 415    3727  3996  3374  -111  -782  -347      N
ATOM    754  NH2  ARG A 415   23.574  11.513 -32.230  1.00 25.27       N
ANISOU  754  NH2  ARG A 415    3164  3367  3070  -239  -772  -438      N
ATOM    755  C    ARG A 415   24.940  17.199 -37.386  1.00 30.32       C
ANISOU  755  C    ARG A 415    3784  4614  3121   172 -1013   223      C
ATOM    756  O    ARG A 415   25.119  18.400 -37.205  1.00 30.57       O
ANISOU  756  O    ARG A 415    3812  4599  3205   231 -1007   381      O
ATOM    757  N    GLY A 416   24.846  16.660 -38.592  1.00 31.60       N
ANISOU  757  N    GLY A 416    3973  4936  3096   156 -1066   164      N
ATOM    758  CA   GLY A 416   25.049  17.449 -39.795  1.00 32.75       C
ANISOU  758  CA   GLY A 416    4156  5224  3063   209 -1110   301      C
ATOM    759  C    GLY A 416   26.516  17.725 -40.084  1.00 32.51       C
ANISOU  759  C    GLY A 416    4216  5174  2960   216  -984   379      C
ATOM    760  O    GLY A 416   27.397  17.335 -39.318  1.00 30.64       O
ANISOU  760  O    GLY A 416    4002  4814  2824   191  -871   323      O
```

FIGURE 18-26

```
ATOM    761  N   ASP A 417      26.766  18.388 -41.211  1.00 34.28           N
ANISOU  761  N   ASP A 417     4487   5534   3002    249  -1005    511       N
ATOM    762  CA  ASP A 417      28.113  18.751 -41.645  1.00 35.22           C
ANISOU  762  CA  ASP A 417     4682   5669   3032    244   -879    601       C
ATOM    763  CB  ASP A 417      28.165  18.916 -43.173  1.00 37.33           C
ANISOU  763  CB  ASP A 417     5008   6157   3018    256   -915    671       C
ATOM    764  CG  ASP A 417      28.224  17.574 -43.905  1.00 40.79           C
ANISOU  764  CG  ASP A 417     5468   6743   3286    216   -916    453       C
ATOM    765  OD1 ASP A 417      28.476  16.530 -43.243  1.00 40.15           O
ANISOU  765  OD1 ASP A 417     5373   6567   3315    180   -861    264       O
ATOM    766  OD2 ASP A 417      28.023  17.556 -45.146  1.00 44.28           O
ANISOU  766  OD2 ASP A 417     5951   7394   3481    223   -973    470       O
ATOM    767  C   ASP A 417      28.588  20.023 -40.949  1.00 34.37           C
ANISOU  767  C   ASP A 417     4575   5408   3075    269   -821    788       C
ATOM    768  O   ASP A 417      27.782  20.865 -40.553  1.00 33.70           O
ANISOU  768  O   ASP A 417     4453   5250   3100    314   -901    893       O
ATOM    769  N   LEU A 418      29.902  20.142 -40.795  1.00 34.15           N
ANISOU  769  N   LEU A 418     4581   5331   3061    239   -680    814       N
ATOM    770  CA  LEU A 418      30.506  21.331 -40.188  1.00 34.32           C
ANISOU  770  CA  LEU A 418     4607   5210   3223    240   -613    976       C
ATOM    771  CB  LEU A 418      31.439  20.937 -39.032  1.00 32.56           C
ANISOU  771  CB  LEU A 418     4354   4852   3167    206   -504    872       C
ATOM    772  CG  LEU A 418      30.818  20.136 -37.877  1.00 32.15           C
ANISOU  772  CG  LEU A 418     4251   4695   3270    212   -546    713       C
ATOM    773  CD1 LEU A 418      31.869  19.758 -36.847  1.00 32.10           C
ANISOU  773  CD1 LEU A 418     4227   4578   3390    188   -444    632       C
ATOM    774  CD2 LEU A 418      29.674  20.910 -37.221  1.00 32.15           C
ANISOU  774  CD2 LEU A 418     4210   4598   3407    247   -640    782       C
ATOM    775  C   LEU A 418      31.217  22.207 -41.237  1.00 36.42           C
ANISOU  775  C   LEU A 418     4940   5563   3335    227   -553   1165       C
ATOM    776  O   LEU A 418      32.148  21.768 -41.919  1.00 36.22           O
ANISOU  776  O   LEU A 418     4945   5656   3162    188   -454   1130       O
ATOM    777  N   ASN A 419      30.740  23.444 -41.374  1.00 38.22           N
ANISOU  777  N   ASN A 419     5193   5731   3598    263   -611   1367       N
ATOM    778  CA  ASN A 419      31.215  24.360 -42.413  1.00 40.94           C
ANISOU  778  CA  ASN A 419     5619   6147   3791    250   -570   1584       C
ATOM    779  CB  ASN A 419      30.272  24.322 -43.627  1.00 42.84           C
ANISOU  779  CB  ASN A 419     5901   6577   3800    306   -702   1654       C
ATOM    780  CG  ASN A 419      30.365  23.011 -44.413  1.00 43.28           C
ANISOU  780  CG  ASN A 419     5958   6853   3634    281   -699   1469       C
ATOM    781  OD1 ASN A 419      31.429  22.652 -44.933  1.00 42.07           O
ANISOU  781  OD1 ASN A 419     5839   6798   3349    224   -567   1436       O
ATOM    782  ND2 ASN A 419      29.243  22.307 -44.522  1.00 41.71           N
ANISOU  782  ND2 ASN A 419     5716   6735   3396    320   -841   1339       N
ATOM    783  C   ASN A 419      31.355  25.811 -41.928  1.00 41.80           C
ANISOU  783  C   ASN A 419     5754   6059   4070    255   -549   1788       C
ATOM    784  O   ASN A 419      31.184  26.739 -42.727  1.00 43.13           O
ANISOU  784  O   ASN A 419     5997   6247   4142    277   -579   2006       O
ATOM    785  N   PHE A 420      31.654  25.990 -40.633  1.00 40.43           N
ANISOU  785  N   PHE A 420     5526   5694   4142    235   -501   1717       N
ATOM    786  CA  PHE A 420      31.813  27.317 -40.017  1.00 41.44           C
ANISOU  786  CA  PHE A 420     5674   5609   4463    231   -477   1867       C
ATOM    787  CB  PHE A 420      31.969  27.229 -38.484  1.00 38.75           C
ANISOU  787  CB  PHE A 420     5258   5093   4371    217   -448   1720       C
ATOM    788  CG  PHE A 420      30.717  26.787 -37.763  1.00 38.53           C
ANISOU  788  CG  PHE A 420     5167   5033   4438    296   -567   1596       C
ATOM    789  CD1 PHE A 420      30.638  25.508 -37.189  1.00 35.77           C
ANISOU  789  CD1 PHE A 420     4757   4741   4094    283   -566   1382       C
ATOM    790  CE1 PHE A 420      29.480  25.098 -36.517  1.00 35.30           C
ANISOU  790  CE1 PHE A 420     4636   4656   4121    336   -660   1273       C
ATOM    791  CZ  PHE A 420      28.390  25.961 -36.410  1.00 36.31           C
ANISOU  791  CZ  PHE A 420     4745   4716   4335    416   -759   1362       C
ATOM    792  CE2 PHE A 420      28.453  27.236 -36.976  1.00 37.91           C
ANISOU  792  CE2 PHE A 420     5009   4854   4542    452   -773   1570       C
ATOM    793  CD2 PHE A 420      29.615  27.647 -37.648  1.00 38.57           C
ANISOU  793  CD2 PHE A 420     5173   4948   4536    385   -676   1694       C
ATOM    794  C   PHE A 420      32.985  28.099 -40.621  1.00 43.58           C
ANISOU  794  C   PHE A 420     6013   5871   4673    144   -345   2038       C
ATOM    795  O   PHE A 420      34.016  27.544 -40.971  1.00 43.69           O
ANISOU  795  O   PHE A 420     6017   6000   4582     67   -227   1979       O
ATOM    796  N   VAL A 421      32.815  29.402 -40.734  1.00 46.01           N
```

FIGURE 18-27

```
ANISOU  796  N    VAL A 421     6388  6035  5060    155   -361   2250        N
ATOM    797  CA   VAL A 421     33.827  30.281 -41.275  1.00 48.42           C
ANISOU  797  CA   VAL A 421     6767  6301  5331     58   -235   2439        C
ATOM    798  CB   VAL A 421     33.415  30.657 -42.715  1.00 50.72           C
ANISOU  798  CB   VAL A 421     7168  6727  5375     95   -285   2662        C
ATOM    799  CG1  VAL A 421     33.405  32.139 -42.946  1.00 53.63           C
ANISOU  799  CG1  VAL A 421     7644  6908  5824     89   -278   2939        C
ATOM    800  CG2  VAL A 421     34.260  29.882 -43.738  1.00 50.83           C
ANISOU  800  CG2  VAL A 421     7196  6999  5117     16   -175   2634        C
ATOM    801  C    VAL A 421     33.969  31.474 -40.304  1.00 49.05           C
ANISOU  801  C    VAL A 421     6856  6092  5690     35   -213   2513        C
ATOM    802  O    VAL A 421     33.147  31.634 -39.405  1.00 48.40           O
ANISOU  802  O    VAL A 421     6734  5873  5784    117   -308   2435        O
ATOM    803  N    ASN A 422     35.019  32.281 -40.431  1.00 50.78           N
ANISOU  803  N    ASN A 422     7118  6220  5956    -86    -79   2641        N
ATOM    804  CA   ASN A 422     35.104  33.500 -39.619  1.00 51.41           C
ANISOU  804  CA   ASN A 422     7224  6012  6298   -114    -65   2718        C
ATOM    805  CB   ASN A 422     36.417  33.548 -38.825  1.00 50.54           C
ANISOU  805  CB   ASN A 422     7039  5832  6330   -263     80   2603        C
ATOM    806  CG   ASN A 422     37.651  33.599 -39.710  1.00 53.01           C
ANISOU  806  CG   ASN A 422     7370  6272  6500   -410    242   2706        C
ATOM    807  OD1  ASN A 422     38.708  33.120 -39.316  1.00 54.15           O
ANISOU  807  OD1  ASN A 422     7415  6486  6672   -510    351   2564        O
ATOM    808  ND2  ASN A 422     37.536  34.195 -40.891  1.00 54.93           N
ANISOU  808  ND2  ASN A 422     7734  6550  6586   -424    260   2956        N
ATOM    809  C    ASN A 422     34.855  34.791 -40.412  1.00 54.51           C
ANISOU  809  C    ASN A 422     7760  6272  6679   -107    -77   3020        C
ATOM    810  O    ASN A 422     34.565  34.742 -41.619  1.00 55.83           O
ANISOU  810  O    ASN A 422     8008  6590  6613    -71   -108   3185        O
ATOM    811  N    ARG A 423     34.971  35.936 -39.726  1.00 55.63           N
ANISOU  811  N    ARG A 423     7940  6128  7070   -139    -56   3090        N
ATOM    812  CA   ARG A 423     34.778  37.275 -40.329  1.00 58.60           C
ANISOU  812  CA   ARG A 423     8467  6310  7489   -134    -63   3384        C
ATOM    813  CB   ARG A 423     35.154  38.368 -39.309  1.00 59.00           C
ANISOU  813  CB   ARG A 423     8531  6029  7855   -205    -10   3374        C
ATOM    814  CG   ARG A 423     35.137  39.808 -39.824  1.00 63.01           C
ANISOU  814  CG   ARG A 423     9207  6282  8454   -228      9   3672        C
ATOM    815  CD   ARG A 423     35.119  40.813 -38.669  1.00 63.11           C
ANISOU  815  CD   ARG A 423     9229  5943  8808   -243     11   3608        C
ATOM    816  NE   ARG A 423     35.372  42.173 -39.147  1.00 69.55           N
ANISOU  816  NE   ARG A 423    10211  6488  9728   -310     65   3886        N
ATOM    817  CZ   ARG A 423     35.212  43.291 -38.432  1.00 71.04           C
ANISOU  817  CZ   ARG A 423    10463  6323 10208   -303     54   3903        C
ATOM    818  NH1  ARG A 423     34.780  43.251 -37.173  1.00 69.69           N
ANISOU  818  NH1  ARG A 423    10195  6035 10247   -226     -8   3649        N
ATOM    819  NH2  ARG A 423     35.491  44.463 -38.983  1.00 73.29           N
ANISOU  819  NH2  ARG A 423    10914  6362 10570   -377    112   4175        N
ATOM    820  C    ARG A 423     35.554  37.441 -41.644  1.00 60.66           C
ANISOU  820  C    ARG A 423     8824  6708  7516   -250     52   3610        C
ATOM    821  O    ARG A 423     34.991  37.878 -42.656  1.00 63.13           O
ANISOU  821  O    ARG A 423     9263  7049  7676   -176    -13   3852        O
ATOM    822  N    ALA A 424     36.833  37.059 -41.619  1.00 60.09           N
ANISOU  822  N    ALA A 424     8685  6740  7406   -424    220   3525        N
ATOM    823  CA   ALA A 424     37.733  37.087 -42.782  1.00 61.86           C
ANISOU  823  CA   ALA A 424     8968  7132  7403   -560    366   3695        C
ATOM    824  CB   ALA A 424     39.184  37.099 -42.313  1.00 61.84           C
ANISOU  824  CB   ALA A 424     8869  7119  7507   -766    558   3590        C
ATOM    825  C    ALA A 424     37.525  35.953 -43.803  1.00 61.47           C
ANISOU  825  C    ALA A 424     8907  7435  7014   -498    342   3661        C
ATOM    826  O    ALA A 424     38.302  35.834 -44.758  1.00 63.06           O
ANISOU  826  O    ALA A 424     9142  7818  7001   -608    476   3765        O
ATOM    827  N    ASN A 425     36.503  35.117 -43.583  1.00 59.19           N
ANISOU  827  N    ASN A 425     8565  7245  6681   -334    181   3501        N
ATOM    828  CA   ASN A 425     36.066  34.070 -44.533  1.00 58.70           C
ANISOU  828  CA   ASN A 425     8501  7493  6310   -257    119   3455        C
ATOM    829  CB   ASN A 425     35.834  34.650 -45.946  1.00 61.60           C
ANISOU  829  CB   ASN A 425     9027  7961  6417   -245    108   3760        C
ATOM    830  CG   ASN A 425     35.025  33.719 -46.851  1.00 61.89           C
ANISOU  830  CG   ASN A 425     9073  8290  6153   -127    -18   3714        C
ATOM    831  OD1  ASN A 425     34.099  33.032 -46.410  1.00 60.11           O
ANISOU  831  OD1  ASN A 425     8770  8100  5969     -2   -169   3531        O
```

FIGURE 18-28

```
ATOM    832  ND2 ASN A 425      35.377  33.700 -48.125  1.00 65.09           N
ANISOU  832  ND2 ASN A 425     9572   8911   6249   -176     49   3875       N
ATOM    833  C   ASN A 425      36.992  32.848 -44.543  1.00 56.85           C
ANISOU  833  C   ASN A 425     8150   7489   5962   -338    240   3221       C
ATOM    834  O   ASN A 425      37.088  32.101 -45.516  1.00 57.64           O
ANISOU  834  O   ASN A 425     8263   7855   5782   -333    263   3202       O
ATOM    835  N   GLN A 426      37.662  32.653 -43.424  1.00 54.65           N
ANISOU  835  N   GLN A 426     7757   7103   5906   -403    310   3033       N
ATOM    836  CA  GLN A 426      38.574  31.539 -43.259  1.00 52.90           C
ANISOU  836  CA  GLN A 426     7412   7061   5626   -461    416   2803       C
ATOM    837  CB  GLN A 426      39.823  31.999 -42.501  1.00 53.02           C
ANISOU  837  CB  GLN A 426     7345   6954   5845   -609    567   2761       C
ATOM    838  CG  GLN A 426      40.496  33.214 -43.170  1.00 57.14           C
ANISOU  838  CG  GLN A 426     7957   7403   6350   -755    700   3030       C
ATOM    839  CD  GLN A 426      41.953  33.340 -42.795  1.00 59.04           C
ANISOU  839  CD  GLN A 426     8085   7648   6699   -930    886   2958       C
ATOM    840  OE1 GLN A 426      42.294  33.478 -41.614  1.00 58.44           O
ANISOU  840  OE1 GLN A 426     7913   7417   6874   -964    882   2816       O
ATOM    841  NE2 GLN A 426      42.825  33.277 -43.793  1.00 60.49           N
ANISOU  841  NE2 GLN A 426     8269   8028   6687  -1044   1051   3047       N
ATOM    842  C   GLN A 426      37.859  30.413 -42.543  1.00 49.11           C
ANISOU  842  C   GLN A 426     6847   6621   5192   -339    290   2547       C
ATOM    843  O   GLN A 426      37.235  30.626 -41.508  1.00 47.36           O
ANISOU  843  O   GLN A 426     6597   6214   5183   -278    192   2479       O
ATOM    844  N   ARG A 427      37.920  29.226 -43.133  1.00 48.00           N
ANISOU  844  N   ARG A 427     6674   6721   4843   -307    298   2408       N
ATOM    845  CA  ARG A 427      37.341  28.025 -42.550  1.00 45.29           C
ANISOU  845  CA  ARG A 427     6256   6425   4525   -212    198   2160       C
ATOM    846  CB  ARG A 427      37.621  26.831 -43.471  1.00 45.82           C
ANISOU  846  CB  ARG A 427     6312   6763   4335   -202    242   2034       C
ATOM    847  CG  ARG A 427      37.173  25.507 -42.909  1.00 43.52           C
ANISOU  847  CG  ARG A 427     5952   6510   4074   -124    162   1771       C
ATOM    848  CD  ARG A 427      37.185  24.344 -43.919  1.00 44.50           C
ANISOU  848  CD  ARG A 427     6088   6884   3937    -97    174   1641       C
ATOM    849  NE  ARG A 427      36.589  23.168 -43.281  1.00 42.09           N
ANISOU  849  NE  ARG A 427     5732   6558   3701    -26     80   1406       N
ATOM    850  CZ  ARG A 427      35.305  22.813 -43.382  1.00 41.80           C
ANISOU  850  CZ  ARG A 427     5721   6535   3625     43    -78   1366       C
ATOM    851  NH1 ARG A 427      34.472  23.522 -44.138  1.00 40.53           N
ANISOU  851  NH1 ARG A 427     5630   6425   3343     70   -173   1541       N
ATOM    852  NH2 ARG A 427      34.859  21.734 -42.737  1.00 38.54           N
ANISOU  852  NH2 ARG A 427     5262   6088   3294     83   -141   1153       N
ATOM    853  C   ARG A 427      37.941  27.795 -41.156  1.00 42.92           C
ANISOU  853  C   ARG A 427     5846   5984   4476   -242    239   1985       C
ATOM    854  O   ARG A 427      39.158  27.682 -41.033  1.00 43.19           O
ANISOU  854  O   ARG A 427     5815   6060   4536   -330    378   1932       O
ATOM    855  N   LEU A 428      37.109  27.762 -40.111  1.00 40.68           N
ANISOU  855  N   LEU A 428     5537   5548   4373   -169    120   1900       N
ATOM    856  CA  LEU A 428      37.620  27.491 -38.771  1.00 38.47           C
ANISOU  856  CA  LEU A 428     5162   5153   4302   -189    146   1733       C
ATOM    857  CB  LEU A 428      36.507  27.485 -37.706  1.00 37.16           C
ANISOU  857  CB  LEU A 428     4983   4836   4300   -103     12   1656       C
ATOM    858  CG  LEU A 428      35.520  28.644 -37.563  1.00 38.47           C
ANISOU  858  CG  LEU A 428     5210   4834   4572    -57    -80   1807       C
ATOM    859  CD1 LEU A 428      34.640  28.465 -36.331  1.00 36.49           C
ANISOU  859  CD1 LEU A 428     4911   4461   4493     17   -177   1674       C
ATOM    860  CD2 LEU A 428      36.231  29.983 -37.520  1.00 40.33           C
ANISOU  860  CD2 LEU A 428     5484   4917   4922   -147      4   1968       C
ATOM    861  C   LEU A 428      38.327  26.130 -38.791  1.00 37.36           C
ANISOU  861  C   LEU A 428     4947   5175   4073   -187    206   1533       C
ATOM    862  O   LEU A 428      37.927  25.217 -39.528  1.00 37.44           O
ANISOU  862  O   LEU A 428     4980   5342   3905   -134    173   1466       O
ATOM    863  N   ASN A 429      39.393  26.000 -38.005  1.00 36.22           N
ANISOU  863  N   ASN A 429     4713   4996   4055   -240    291   1432       N
ATOM    864  CA  ASN A 429      40.027  24.699 -37.838  1.00 35.15           C
ANISOU  864  CA  ASN A 429     4501   4981   3874   -209    331   1232       C
ATOM    865  CB  ASN A 429      41.422  24.797 -37.154  1.00 35.29           C
ANISOU  865  CB  ASN A 429     4406   4986   4018   -278    438   1162       C
ATOM    866  CG  ASN A 429      41.376  25.137 -35.654  1.00 34.45           C
ANISOU  866  CG  ASN A 429     4253   4696   4142   -277    377   1100       C
ATOM    867  OD1 ASN A 429      40.351  25.025 -34.971  1.00 33.81           O
```

FIGURE 18-29

```
ANISOU  867 OD1 ASN A 429    4210  4506  4130  -211   263  1066       O
ATOM    868 ND2 ASN A 429    42.531  25.532 -35.132  1.00 32.90       N
ANISOU  868 ND2 ASN A 429    3961  4484  4057  -356   458  1073       N
ATOM    869 C   ASN A 429    39.062  23.680 -37.199  1.00 32.57       C
ANISOU  869 C   ASN A 429    4181  4618  3577  -107   207  1081       C
ATOM    870 O   ASN A 429    38.051  24.074 -36.619  1.00 31.85       O
ANISOU  870 O   ASN A 429    4121  4399  3582   -74   105  1113       O
ATOM    871 N   PRO A 430    39.325  22.378 -37.376  1.00 31.96       N
ANISOU  871 N   PRO A 430    4076  4654  3413   -60   223   919       N
ATOM    872 CA  PRO A 430    38.489  21.306 -36.827  1.00 30.42       C
ANISOU  872 CA  PRO A 430    3895  4422  3243    19   122   773       C
ATOM    873 CB  PRO A 430    39.374  20.073 -36.998  1.00 30.52       C
ANISOU  873 CB  PRO A 430    3865  4539  3194    51   191   608       C
ATOM    874 CG  PRO A 430    40.115  20.354 -38.256  1.00 32.63       C
ANISOU  874 CG  PRO A 430    4130  4972  3296     8   302   673       C
ATOM    875 CD  PRO A 430    40.439  21.822 -38.174  1.00 33.57       C
ANISOU  875 CD  PRO A 430    4239  5029  3487   -78   346   859       C
ATOM    876 C   PRO A 430    38.030  21.452 -35.362  1.00 28.84       C
ANISOU  876 C   PRO A 430    3672  4045  3243    38    48   733       C
ATOM    877 O   PRO A 430    36.844  21.250 -35.072  1.00 28.54       O
ANISOU  877 O   PRO A 430    3669  3949  3226    76   -51   715       O
ATOM    878 N   MSE A 431    38.938  21.798 -34.454  1.00 27.42       N
ANISOU  878 N   MSE A 431    3425  3793  3198     8    97   713       N
ATOM    879 CA  MSE A 431    38.573  21.963 -33.044  1.00 25.88       C
ANISOU  879 CA  MSE A 431    3213  3450  3172    23    33   670       C
ATOM    880 CB  MSE A 431    39.832  22.116 -32.159  1.00 25.62       C
ANISOU  880 CB  MSE A 431    3094  3390  3252    -8    89   615       C
ATOM    881 CG  MSE A 431    40.705  20.833 -32.079  1.00 26.44       C
ANISOU  881 CG  MSE A 431    3147  3586  3315    45   124   475       C
ATOM    882 SE  MSE A 431    39.842  19.246 -31.234  0.90 30.28      SE
ANISOU  882 SE  MSE A 431    3685  4010  3809   150    26   327      SE
ATOM    883 CE  MSE A 431    39.652  20.084 -29.473  1.00 25.02       C
ANISOU  883 CE  MSE A 431    2993  3190  3324   126   -33   340       C
ATOM    884 C   MSE A 431    37.575  23.100 -32.781  1.00 25.36       C
ANISOU  884 C   MSE A 431    3187  3264  3186     9   -30   783       C
ATOM    885 O   MSE A 431    36.673  22.960 -31.939  1.00 24.38       O
ANISOU  885 O   MSE A 431    3073  3052  3140    47  -107   735       O
ATOM    886 N   HIS A 432    37.743  24.212 -33.483  1.00 26.43       N
ANISOU  886 N   HIS A 432    3345  3391  3306   -42     7   933       N
ATOM    887 CA  HIS A 432    36.804  25.342 -33.406  1.00 27.85       C
ANISOU  887 CA  HIS A 432    3573  3450  3560   -37   -53  1055       C
ATOM    888 CB  HIS A 432    37.483  26.636 -33.864  1.00 29.15       C
ANISOU  888 CB  HIS A 432    3755  3560  3759  -119    20  1213       C
ATOM    889 CG  HIS A 432    38.458  27.164 -32.859  1.00 31.05       C
ANISOU  889 CG  HIS A 432    3933  3702  4163  -191    77  1164       C
ATOM    890 ND1 HIS A 432    39.711  26.614 -32.671  1.00 31.07       N
ANISOU  890 ND1 HIS A 432    3853  3795  4157  -238   156  1070       N
ATOM    891 CE1 HIS A 432    40.338  27.277 -31.714  1.00 33.02       C
ANISOU  891 CE1 HIS A 432    4046  3937  4562  -300   177  1035       C
ATOM    892 NE2 HIS A 432    39.529  28.221 -31.255  1.00 32.01       N
ANISOU  892 NE2 HIS A 432    3972  3642  4547  -295   121  1094       N
ATOM    893 CD2 HIS A 432    38.348  28.170 -31.956  1.00 32.70       C
ANISOU  893 CD2 HIS A 432    4141  3736  4548  -220    58  1179       C
ATOM    894 C   HIS A 432    35.510  25.078 -34.165  1.00 27.83       C
ANISOU  894 C   HIS A 432    3625  3502  3447    29  -143  1098       C
ATOM    895 O   HIS A 432    34.466  25.587 -33.800  1.00 28.93       O
ANISOU  895 O   HIS A 432    3780  3549  3665    73  -223  1134       O
ATOM    896 N   GLN A 433    35.608  24.283 -35.217  1.00 28.16       N
ANISOU  896 N   GLN A 433    3686  3705  3308    38  -128  1081       N
ATOM    897 CA  GLN A 433    34.467  23.712 -35.940  1.00 29.30       C
ANISOU  897 CA  GLN A 433    3866  3942  3324    95  -220  1070       C
ATOM    898 CB  GLN A 433    35.053  22.746 -36.985  1.00 30.36       C
ANISOU  898 CB  GLN A 433    4014  4260  3263    84  -165  1008       C
ATOM    899 CG  GLN A 433    34.400  22.595 -38.320  1.00 34.65       C
ANISOU  899 CG  GLN A 433    4611  4954  3599   106  -217  1065       C
ATOM    900 CD  GLN A 433    34.134  23.881 -39.054  1.00 37.03       C
ANISOU  900 CD  GLN A 433    4967  5253  3848   101  -235  1288       C
ATOM    901 OE1 GLN A 433    32.987  24.307 -39.137  1.00 38.30       O
ANISOU  901 OE1 GLN A 433    5148  5383  4022   154  -351  1359       O
ATOM    902 NE2 GLN A 433    35.176  24.486 -39.632  1.00 38.30       N
ANISOU  902 NE2 GLN A 433    5153  5454  3945    38  -121  1405       N
```

FIGURE 18-30

```
ATOM    903  C   GLN A 433      33.551  22.973 -34.938  1.00 27.21           C
ANISOU  903  C   GLN A 433     3569   3614   3155    140   -301    930       C
ATOM    904  O   GLN A 433      32.367  23.270 -34.843  1.00 26.79           O
ANISOU  904  O   GLN A 433     3518   3526   3136    182   -393    960       O
ATOM    905  N   LEU A 434      34.134  22.047 -34.166  1.00 25.47           N
ANISOU  905  N   LEU A 434     3317   3379   2983    132   -261    785       N
ATOM    906  CA  LEU A 434      33.444  21.324 -33.076  1.00 23.90           C
ANISOU  906  CA  LEU A 434     3095   3107   2877    157   -313    662       C
ATOM    907  CB  LEU A 434      34.364  20.255 -32.466  1.00 21.96           C
ANISOU  907  CB  LEU A 434     2834   2862   2649    154   -258    530       C
ATOM    908  CG  LEU A 434      34.764  19.139 -33.439  1.00 23.59           C
ANISOU  908  CG  LEU A 434     3064   3192   2709    164   -230    450       C
ATOM    909  CD1 LEU A 434      35.976  18.335 -32.918  1.00 20.60           C
ANISOU  909  CD1 LEU A 434     2659   2806   2361    179   -162    347       C
ATOM    910  CD2 LEU A 434      33.550  18.247 -33.779  1.00 19.71           C
ANISOU  910  CD2 LEU A 434     2602   2734   2153    179   -308    372       C
ATOM    911  C   LEU A 434      32.955  22.243 -31.952  1.00 23.68           C
ANISOU  911  C   LEU A 434     3044   2938   3017    164   -342    696       C
ATOM    912  O   LEU A 434      31.826  22.090 -31.488  1.00 22.82           O
ANISOU  912  O   LEU A 434     2922   2795   2954    191   -409    658       O
ATOM    913  N   LEU A 435      33.830  23.153 -31.512  1.00 23.88           N
ANISOU  913  N   LEU A 435     3056   2886   3130    132   -286    752       N
ATOM    914  CA  LEU A 435      33.499  24.163 -30.507  1.00 25.30           C
ANISOU  914  CA  LEU A 435     3221   2926   3468    134   -304    776       C
ATOM    915  CB  LEU A 435      34.675  25.123 -30.289  1.00 25.47           C
ANISOU  915  CB  LEU A 435     3231   2880   3567     76   -233    832       C
ATOM    916  CG  LEU A 435      34.639  26.078 -29.094  1.00 25.12           C
ANISOU  916  CG  LEU A 435     3169   2684   3693     62   -237    814       C
ATOM    917  CD1 LEU A 435      34.703  25.341 -27.754  1.00 24.17           C
ANISOU  917  CD1 LEU A 435     3012   2549   3622     73   -247    664       C
ATOM    918  CD2 LEU A 435      35.784  27.023 -29.203  1.00 25.51           C
ANISOU  918  CD2 LEU A 435     3211   2680   3803    -15   -167    880       C
ATOM    919  C   LEU A 435      32.245  24.976 -30.853  1.00 27.05           C
ANISOU  919  C   LEU A 435     3458   3104   3717    181   -377    868       C
ATOM    920  O   LEU A 435      31.290  25.013 -30.067  1.00 27.13           O
ANISOU  920  O   LEU A 435     3441   3056   3810    219   -426    813       O
ATOM    921  N   ARG A 436      32.256  25.645 -32.008  1.00 29.13           N
ANISOU  921  N   ARG A 436     3760   3400   3908    183   -382   1011       N
ATOM    922  CA  ARG A 436      31.117  26.464 -32.400  1.00 30.76           C
ANISOU  922  CA  ARG A 436     3982   3566   4140    248   -463   1117       C
ATOM    923  CB  ARG A 436      31.376  27.299 -33.659  1.00 33.08           C
ANISOU  923  CB  ARG A 436     4340   3883   4346    244   -457   1307       C
ATOM    924  CG  ARG A 436      32.474  28.404 -33.560  1.00 40.00           C
ANISOU  924  CG  ARG A 436     5252   4636   5311    174   -367   1413       C
ATOM    925  CD  ARG A 436      32.607  29.153 -32.189  1.00 47.23           C
ANISOU  925  CD  ARG A 436     6140   5358   6447    160   -347   1351       C
ATOM    926  NE  ARG A 436      34.019  29.442 -31.860  1.00 51.94           N
ANISOU  926  NE  ARG A 436     6729   5911   7097     53   -242   1339       N
ATOM    927  CZ  ARG A 436      34.460  30.070 -30.761  1.00 55.22           C
ANISOU  927  CZ  ARG A 436     7119   6181   7681     10   -211   1275       C
ATOM    928  NH1 ARG A 436      33.623  30.495 -29.823  1.00 56.84           N
ANISOU  928  NH1 ARG A 436     7313   6263   8019     70   -265   1212       N
ATOM    929  NH2 ARG A 436      35.766  30.280 -30.592  1.00 56.92           N
ANISOU  929  NH2 ARG A 436     7311   6387   7930    -96   -122   1262       N
ATOM    930  C   ARG A 436      29.860  25.608 -32.560  1.00 29.85           C
ANISOU  930  C   ARG A 436     3833   3546   3961    304   -554   1040       C
ATOM    931  O   ARG A 436      28.781  26.041 -32.179  1.00 29.79           O
ANISOU  931  O   ARG A 436     3791   3486   4041    365   -622   1042       O
ATOM    932  N   HIS A 437      30.000  24.397 -33.106  1.00 28.56           N
ANISOU  932  N   HIS A 437     3672   3522   3657    280   -551    961       N
ATOM    933  CA  HIS A 437      28.855  23.524 -33.256  1.00 27.62           C
ANISOU  933  CA  HIS A 437     3517   3491   3485    308   -633    872       C
ATOM    934  CB  HIS A 437      29.238  22.173 -33.872  1.00 26.97           C
ANISOU  934  CB  HIS A 437     3455   3538   3253    269   -613    771       C
ATOM    935  CG  HIS A 437      28.094  21.203 -33.939  1.00 24.96           C
ANISOU  935  CG  HIS A 437     3163   3358   2963    273   -691    657       C
ATOM    936  ND1 HIS A 437      27.096  21.289 -34.889  1.00 23.43           N
ANISOU  936  ND1 HIS A 437     2950   3277   2675    305   -793    694       N
ATOM    937  CE1 HIS A 437      26.222  20.315 -34.704  1.00 23.02           C
ANISOU  937  CE1 HIS A 437     2852   3273   2623    283   -843    560       C
ATOM    938  NE2 HIS A 437      26.611  19.602 -33.660  1.00 24.74           N
```

FIGURE 18-31

```
ANISOU   938  NE2 HIS A 437     3071  3399  2929    238   -771    453        N
ATOM     939  CD2 HIS A 437      27.787  20.134 -33.169  1.00 22.63           C
ANISOU   939  CD2 HIS A 437     2844  3039  2717    240   -683    510        C
ATOM     940  C   HIS A 437      28.175  23.327 -31.894  1.00 26.83           C
ANISOU   940  C   HIS A 437     3359  3302  3534    317   -643    763        C
ATOM     941  O   HIS A 437      26.971  23.545 -31.765  1.00 27.43           O
ANISOU   941  O   HIS A 437     3383  3382  3658    363   -717    757        O
ATOM     942  N   PHE A 438      28.958  22.972 -30.878  1.00 25.29           N
ANISOU   942  N   PHE A 438     3167  3035  3407    276   -569    682        N
ATOM     943  CA  PHE A 438      28.394  22.684 -29.559  1.00 24.57           C
ANISOU   943  CA  PHE A 438     3034  2877  3426    274   -566    579        C
ATOM     944  CB  PHE A 438      29.261  21.668 -28.812  1.00 22.50           C
ANISOU   944  CB  PHE A 438     2794  2601  3155    227   -502    477        C
ATOM     945  CG  PHE A 438      29.231  20.302 -29.427  1.00 20.80           C
ANISOU   945  CG  PHE A 438     2601  2477  2826    203   -510    405        C
ATOM     946  CD1 PHE A 438      28.021  19.574 -29.486  1.00 20.00           C
ANISOU   946  CD1 PHE A 438     2472  2420  2708    192   -562    337        C
ATOM     947  CE1 PHE A 438      27.970  18.314 -30.056  1.00 18.22           C
ANISOU   947  CE1 PHE A 438     2274  2260  2389    160   -571    256        C
ATOM     948  CZ  PHE A 438      29.155  17.745 -30.605  1.00 20.73           C
ANISOU   948  CZ  PHE A 438     2649  2605  2624    156   -525    238        C
ATOM     949  CE2 PHE A 438      30.357  18.468 -30.569  1.00 17.04           C
ANISOU   949  CE2 PHE A 438     2194  2113  2167    174   -469    308        C
ATOM     950  CD2 PHE A 438      30.383  19.739 -29.965  1.00 19.46           C
ANISOU   950  CD2 PHE A 438     2473  2349  2573    188   -464    392        C
ATOM     951  C   PHE A 438      28.046  23.929 -28.731  1.00 25.24           C
ANISOU   951  C   PHE A 438     3090  2842  3658    311   -567    615        C
ATOM     952  O   PHE A 438      27.189  23.875 -27.871  1.00 24.41           O
ANISOU   952  O   PHE A 438     2936  2710  3630    328   -580    543        O
ATOM     953  N   GLN A 439      28.691  25.057 -29.040  1.00 27.21           N
ANISOU   953  N   GLN A 439     3372  3021  3947    320   -548    723        N
ATOM     954  CA  GLN A 439      28.316  26.353 -28.476  1.00 28.57           C
ANISOU   954  CA  GLN A 439     3530  3062  4264    365   -557    766        C
ATOM     955  CB  GLN A 439      29.395  27.400 -28.724  1.00 29.66           C
ANISOU   955  CB  GLN A 439     3721  3102  4446    335   -509    870        C
ATOM     956  CG  GLN A 439      30.531  27.306 -27.690  1.00 30.49           C
ANISOU   956  CG  GLN A 439     3826  3151  4608    264   -433    781        C
ATOM     957  CD  GLN A 439      31.679  28.234 -27.997  1.00 34.96           C
ANISOU   957  CD  GLN A 439     4429  3638  5214    207   -379    871        C
ATOM     958  OE1 GLN A 439      31.762  28.782 -29.090  1.00 38.23           O
ANISOU   958  OE1 GLN A 439     4884  4053  5587    208   -383   1013        O
ATOM     959  NE2 GLN A 439      32.570  28.423 -27.029  1.00 35.77           N
ANISOU   959  NE2 GLN A 439     4515  3679  5395    149   -329    791        N
ATOM     960  C   GLN A 439      26.934  26.813 -28.925  1.00 29.99           C
ANISOU   960  C   GLN A 439     3669  3257  4470    454   -644    815        C
ATOM     961  O   GLN A 439      26.223  27.399 -28.120  1.00 30.12           O
ANISOU   961  O   GLN A 439     3639  3192  4612    505   -655    772        O
ATOM     962  N   LYS A 440      26.528  26.494 -30.162  1.00 31.18           N
ANISOU   962  N   LYS A 440     3825  3525  4496    477   -708    887        N
ATOM     963  CA  LYS A 440      25.142  26.739 -30.603  1.00 33.51           C
ANISOU   963  CA  LYS A 440     4058  3873  4799    568   -811    916        C
ATOM     964  CB  LYS A 440      24.983  26.655 -32.140  1.00 35.28           C
ANISOU   964  CB  LYS A 440     4316  4227  4864    593   -887   1034        C
ATOM     965  CG  LYS A 440      25.813  27.704 -32.903  1.00 37.77           C
ANISOU   965  CG  LYS A 440     4728  4471  5152    603   -867   1220        C
ATOM     966  CD  LYS A 440      25.401  27.909 -34.364  1.00 39.08           C
ANISOU   966  CD  LYS A 440     4927  4756  5164    659   -961   1367        C
ATOM     967  CE  LYS A 440      26.117  29.152 -34.913  1.00 43.76           C
ANISOU   967  CE  LYS A 440     5623  5235  5768    670   -931   1574        C
ATOM     968  NZ  LYS A 440      25.782  29.513 -36.329  1.00 47.40           N
ANISOU   968  NZ  LYS A 440     6140  5801  6067    730  -1019   1756        N
ATOM     969  C   LYS A 440      24.114  25.822 -29.905  1.00 32.70           C
ANISOU   969  C   LYS A 440     3858  3844  4721    562   -831    761        C
ATOM     970  O   LYS A 440      23.029  26.285 -29.495  1.00 33.55           O
ANISOU   970  O   LYS A 440     3882  3936  4931    635   -876    735        O
ATOM     971  N   ASP A 441      24.440  24.539 -29.780  1.00 30.72           N
ANISOU   971  N   ASP A 441     3617  3671  4384    475   -794    659        N
ATOM     972  CA  ASP A 441      23.533  23.580 -29.155  1.00 30.83           C
ANISOU   972  CA  ASP A 441     3554  3747  4415    443   -800    522        C
ATOM     973  CB  ASP A 441      22.400  23.160 -30.119  1.00 33.58           C
ANISOU   973  CB  ASP A 441     3830  4241  4688    466   -905    515        C
```

FIGURE 18-32

```
ATOM    974  CG  ASP A 441      21.496  22.044 -29.536  1.00 36.33           C
ANISOU  974  CG  ASP A 441    4094  4658  5053    398   -900   365           C
ATOM    975  OD1 ASP A 441      20.945  22.224 -28.422  1.00 37.04           O
ANISOU  975  OD1 ASP A 441    4116  4697  5259    402   -859   301           O
ATOM    976  OD2 ASP A 441      21.344  20.987 -30.206  1.00 39.15           O
ANISOU  976  OD2 ASP A 441    4455  5117  5303    335   -932   308           O
ATOM    977  C   ASP A 441      24.280  22.357 -28.620  1.00 28.33           C
ANISOU  977  C   ASP A 441    3285  3430  4047    345   -724   424           C
ATOM    978  O   ASP A 441      24.976  21.649 -29.360  1.00 27.35           O
ANISOU  978  O   ASP A 441    3222  3360  3809    305   -718   428           O
ATOM    979  N   ALA A 442      24.125  22.122 -27.320  1.00 26.96           N
ANISOU  979  N   ALA A 442    3088  3198  3956    316   -666   338           N
ATOM    980  CA  ALA A 442      24.818  21.037 -26.645  1.00 24.82           C
ANISOU  980  CA  ALA A 442    2872  2908  3650    240   -598   261           C
ATOM    981  CB  ALA A 442      25.668  21.599 -25.523  1.00 23.21           C
ANISOU  981  CB  ALA A 442    2703  2600  3517    243   -531   259           C
ATOM    982  C   ALA A 442      23.960  19.870 -26.145  1.00 24.67           C
ANISOU  982  C   ALA A 442    2817  2932  3624    175   -587   156           C
ATOM    983  O   ALA A 442      24.488  19.030 -25.378  1.00 25.14           O
ANISOU  983  O   ALA A 442    2932  2949  3670    120   -527   105           O
ATOM    984  N   LYS A 443      22.691  19.779 -26.585  1.00 24.95           N
ANISOU  984  N   LYS A 443    2761  3052  3668    177   -646   129           N
ATOM    985  CA  LYS A 443      21.742  18.689 -26.217  1.00 25.03           C
ANISOU  985  CA  LYS A 443    2718  3111  3680     93   -634    28           C
ATOM    986  CB  LYS A 443      20.371  18.874 -26.875  1.00 27.31           C
ANISOU  986  CB  LYS A 443    2874  3514  3986    110   -718     6           C
ATOM    987  CG  LYS A 443      19.531  19.967 -26.291  1.00 31.52           C
ANISOU  987  CG  LYS A 443    3294  4049  4632    188   -724    14           C
ATOM    988  CD  LYS A 443      18.276  20.175 -27.156  1.00 38.16           C
ANISOU  988  CD  LYS A 443    3995  5022  5481    230   -832     4           C
ATOM    989  CE  LYS A 443      17.658  21.570 -26.901  1.00 44.11           C
ANISOU  989  CE  LYS A 443    4650  5761  6348    365   -863    48           C
ATOM    990  NZ  LYS A 443      16.692  21.975 -27.987  1.00 44.43           N
ANISOU  990  NZ  LYS A 443    4575  5926  6381    450  -1000    80           N
ATOM    991  C   LYS A 443      22.191  17.276 -26.526  1.00 23.86           C
ANISOU  991  C   LYS A 443    2652  2965  3449      5   -617   -26           C
ATOM    992  O   LYS A 443      22.087  16.413 -25.659  1.00 22.54           O
ANISOU  992  O   LYS A 443    2510  2753  3301    -71   -554   -86           O
ATOM    993  N   VAL A 444      22.654  17.043 -27.761  1.00 23.85           N
ANISOU  993  N   VAL A 444    2695  3013  3353     17   -669    -5           N
ATOM    994  CA  VAL A 444      23.079  15.707 -28.183  1.00 23.44           C
ANISOU  994  CA  VAL A 444    2724  2958  3226    -53   -656   -74           C
ATOM    995  CB  VAL A 444      23.278  15.593 -29.728  1.00 24.08           C
ANISOU  995  CB  VAL A 444    2823  3139  3186    -33   -728   -69           C
ATOM    996  CG1 VAL A 444      23.640  14.169 -30.129  1.00 23.87           C
ANISOU  996  CG1 VAL A 444    2877  3100  3093   -104   -710  -171           C
ATOM    997  CG2 VAL A 444      22.026  16.031 -30.447  1.00 24.33           C
ANISOU  997  CG2 VAL A 444    2743  3297  3206    -20   -828   -70           C
ATOM    998  C   VAL A 444      24.327  15.306 -27.408  1.00 22.67           C
ANISOU  998  C   VAL A 444    2733  2748  3133    -54   -574   -66           C
ATOM    999  O   VAL A 444      24.445  14.151 -26.968  1.00 24.02           O
ANISOU  999  O   VAL A 444    2963  2860  3303   -117   -534  -131           O
ATOM   1000  N   LEU A 445      25.228  16.270 -27.203  1.00 20.80           N
ANISOU 1000  N   LEU A 445    2516  2477  2910     16   -553    14           N
ATOM   1001  CA  LEU A 445      26.470  16.029 -26.491  1.00 19.22           C
ANISOU 1001  CA  LEU A 445    2395  2194  2715     28   -491    22           C
ATOM   1002  CB  LEU A 445      27.355  17.284 -26.540  1.00 18.43           C
ANISOU 1002  CB  LEU A 445    2290  2081  2632     92   -482   107           C
ATOM   1003  CG  LEU A 445      28.698  17.335 -25.788  1.00 16.91           C
ANISOU 1003  CG  LEU A 445    2147  1823  2456    111   -430   119           C
ATOM   1004  CD1 LEU A 445      29.714  16.292 -26.272  1.00 15.64           C
ANISOU 1004  CD1 LEU A 445    2050  1668  2225    114   -410    86           C
ATOM   1005  CD2 LEU A 445      29.301  18.716 -25.861  1.00 17.13           C
ANISOU 1005  CD2 LEU A 445    2149  1839  2522    148   -425   195           C
ATOM   1006  C   LEU A 445      26.221  15.634 -25.038  1.00 19.21           C
ANISOU 1006  C   LEU A 445    2405  2118  2774    -10   -439   -11           C
ATOM   1007  O   LEU A 445      26.803  14.665 -24.554  1.00 20.41           O
ANISOU 1007  O   LEU A 445    2635  2211  2909    -32   -404   -39           O
ATOM   1008  N   PHE A 446      25.386  16.416 -24.350  1.00 18.58           N
ANISOU 1008  N   PHE A 446    2252  2045  2761     -8   -434    -3           N
ATOM   1009  CA  PHE A 446      25.072  16.215 -22.948  1.00 17.93           C
```

FIGURE 18-33

```
ANISOU 1009  CA  PHE A 446    2174  1919  2722    -43  -376   -31       C
ATOM   1010  CB  PHE A 446   24.302  17.424 -22.372  1.00 18.01          C
ANISOU 1010  CB  PHE A 446    2089  1949  2806    -10  -370   -27       C
ATOM   1011  CG  PHE A 446   25.186  18.610 -21.966  1.00 17.40          C
ANISOU 1011  CG  PHE A 446    2025  1826  2762     59  -363    15       C
ATOM   1012  CD1 PHE A 446   26.531  18.664 -22.307  1.00 16.25          C
ANISOU 1012  CD1 PHE A 446    1946  1647  2580     85  -369    55       C
ATOM   1013  CE1 PHE A 446   27.333  19.740 -21.958  1.00 16.45          C
ANISOU 1013  CE1 PHE A 446    1974  1630  2646    127  -361    84       C
ATOM   1014  CZ  PHE A 446   26.800  20.806 -21.285  1.00 17.43          C
ANISOU 1014  CZ  PHE A 446    2046  1728  2849    153  -350    69       C
ATOM   1015  CE2 PHE A 446   25.447  20.791 -20.941  1.00 21.09          C
ANISOU 1015  CE2 PHE A 446    2441  2224  3346    147  -342    25       C
ATOM   1016  CD2 PHE A 446   24.639  19.701 -21.302  1.00 18.75          C
ANISOU 1016  CD2 PHE A 446    2128  1987  3008     97  -348     2       C
ATOM   1017  C   PHE A 446   24.270  14.927 -22.727  1.00 18.39          C
ANISOU 1017  C   PHE A 446    2246  1974  2768   -139  -353   -89       C
ATOM   1018  O   PHE A 446   24.607  14.160 -21.843  1.00 18.65          O
ANISOU 1018  O   PHE A 446    2357  1942  2788   -177  -302   -95       O
ATOM   1019  N   GLN A 447   23.240  14.694 -23.545  1.00 18.81          N
ANISOU 1019  N   GLN A 447    2227  2095  2824   -180  -394  -128       N
ATOM   1020  CA  GLN A 447   22.379  13.508 -23.457  1.00 19.67          C
ANISOU 1020  CA  GLN A 447    2333  2203  2937   -294  -374  -195       C
ATOM   1021  CB  GLN A 447   21.108  13.676 -24.326  1.00 19.41          C
ANISOU 1021  CB  GLN A 447    2168  2284  2922   -326  -437  -243       C
ATOM   1022  CG  GLN A 447   20.183  14.825 -23.916  1.00 20.98          C
ANISOU 1022  CG  GLN A 447    2223  2556  3190   -282  -442  -234       C
ATOM   1023  CD  GLN A 447   19.493  14.638 -22.559  1.00 23.91          C
ANISOU 1023  CD  GLN A 447    2554  2915  3616   -353  -348  -267       C
ATOM   1024  OE1 GLN A 447   19.925  13.841 -21.725  1.00 20.75          O
ANISOU 1024  OE1 GLN A 447    2258  2433  3195   -418  -273  -264       O
ATOM   1025  NE2 GLN A 447   18.419  15.397 -22.335  1.00 26.39          N
ANISOU 1025  NE2 GLN A 447    2715  3316  3997   -331  -350  -295       N
ATOM   1026  C   GLN A 447   23.084  12.169 -23.771  1.00 20.15          C
ANISOU 1026  C   GLN A 447    2524  2184  2950   -339  -364  -221       C
ATOM   1027  O   GLN A 447   22.659  11.125 -23.307  1.00 21.51          O
ANISOU 1027  O   GLN A 447    2739  2297  3136   -437  -322  -259       O
ATOM   1028  N   ASN A 448   24.170  12.210 -24.531  1.00 20.43          N
ANISOU 1028  N   ASN A 448    2621  2207  2934   -265  -396  -202       N
ATOM   1029  CA  ASN A 448   24.872  11.006 -24.958  1.00 22.00          C
ANISOU 1029  CA  ASN A 448    2933  2333  3092   -282  -391  -242       C
ATOM   1030  CB  ASN A 448   25.032  10.974 -26.496  1.00 22.08          C
ANISOU 1030  CB  ASN A 448    2930  2422  3036   -256  -453  -284       C
ATOM   1031  CG  ASN A 448   23.720  10.673 -27.209  1.00 23.31          C
ANISOU 1031  CG  ASN A 448    3009  2660  3190   -343  -504  -359       C
ATOM   1032  OD1 ASN A 448   23.280   9.533 -27.269  1.00 24.47          O
ANISOU 1032  OD1 ASN A 448    3195  2755  3349   -439  -495  -443       O
ATOM   1033  ND2 ASN A 448   23.088  11.703 -27.735  1.00 23.68          N
ANISOU 1033  ND2 ASN A 448    2941  2828  3226   -310  -563  -330       N
ATOM   1034  C   ASN A 448   26.213  10.800 -24.295  1.00 21.90          C
ANISOU 1034  C   ASN A 448    3021  2230  3070   -213  -353  -198       C
ATOM   1035  O   ASN A 448   26.856   9.772 -24.513  1.00 23.82          O
ANISOU 1035  O   ASN A 448    3361  2395  3293   -206  -344  -230       O
ATOM   1036  N   TRP A 449   26.606  11.740 -23.448  1.00 22.09          N
ANISOU 1036  N   TRP A 449    3019  2260  3112   -160  -334  -133       N
ATOM   1037  CA  TRP A 449   27.908  11.699 -22.745  1.00 22.12          C
ANISOU 1037  CA  TRP A 449    3095  2205  3105    -89  -313   -92       C
ATOM   1038  CB  TRP A 449   28.184  13.060 -22.066  1.00 21.28          C
ANISOU 1038  CB  TRP A 449    2925  2138  3020    -41  -308   -42       C
ATOM   1039  CG  TRP A 449   29.534  13.158 -21.367  1.00 21.14          C
ANISOU 1039  CG  TRP A 449    2955  2087  2990     28  -301   -10       C
ATOM   1040  CD1 TRP A 449   29.786  12.971 -20.040  1.00 20.23          C
ANISOU 1040  CD1 TRP A 449    2886  1931  2868     31  -278    10       C
ATOM   1041  NE1 TRP A 449   31.129  13.124 -19.779  1.00 19.99          N
ANISOU 1041  NE1 TRP A 449    2874  1899  2823    107  -295    28       N
ATOM   1042  CE2 TRP A 449   31.780  13.406 -20.950  1.00 20.43          C
ANISOU 1042  CE2 TRP A 449    2892  1990  2881    146  -314    19       C
ATOM   1043  CD2 TRP A 449   30.800  13.453 -21.976  1.00 19.62          C
ANISOU 1043  CD2 TRP A 449    2757  1916  2781    100  -319     1       C
ATOM   1044  CE3 TRP A 449   31.205  13.729 -23.288  1.00 18.99          C
ANISOU 1044  CE3 TRP A 449    2646  1890  2681    125  -335    -3       C
```

FIGURE 18-34

```
ATOM   1045  CZ3 TRP A 449      32.565  13.992 -23.531  1.00 20.81           C
ANISOU 1045  CZ3 TRP A 449    2865   2143   2899    187   -331     10        C
ATOM   1046  CH2 TRP A 449      33.515  13.972 -22.478  1.00 18.26           C
ANISOU 1046  CH2 TRP A 449    2554   1793   2591    230   -327     19        C
ATOM   1047  CZ2 TRP A 449      33.141  13.677 -21.188  1.00 18.76           C
ANISOU 1047  CZ2 TRP A 449    2659   1805   2663    215   -327     25        C
ATOM   1048  C   TRP A 449      28.112  10.540 -21.757  1.00 22.76           C
ANISOU 1048  C   TRP A 449    3285   2175   3186   -114   -275    -87        C
ATOM   1049  O   TRP A 449      29.253  10.071 -21.571  1.00 24.65           O
ANISOU 1049  O   TRP A 449    3599   2358   3407    -44   -278    -71        O
ATOM   1050  N   GLY A 450      27.057  10.056 -21.115  1.00 22.54           N
ANISOU 1050  N   GLY A 450    3270   2117   3179   -211   -240    -94        N
ATOM   1051  CA  GLY A 450      27.269   9.021 -20.083  1.00 21.83           C
ANISOU 1051  CA  GLY A 450    3301   1913   3081   -237   -199    -61        C
ATOM   1052  C   GLY A 450      26.923   9.581 -18.715  1.00 21.43           C
ANISOU 1052  C   GLY A 450    3233   1890   3018   -259   -155    -11        C
ATOM   1053  O   GLY A 450      27.192  10.758 -18.436  1.00 20.21           O
ANISOU 1053  O   GLY A 450    3005   1815   2860   -202   -167      1        O
ATOM   1054  N   ILE A 451      26.284   8.751 -17.889  1.00 21.10           N
ANISOU 1054  N   ILE A 451    3262   1784   2970   -352    -98     14        N
ATOM   1055  CA  ILE A 451      25.818   9.147 -16.578  1.00 20.69           C
ANISOU 1055  CA  ILE A 451    3202   1772   2887   -392    -39     54        C
ATOM   1056  CB  ILE A 451      24.237   9.164 -16.503  1.00 21.84           C
ANISOU 1056  CB  ILE A 451    3255   1973   3069   -531     24     13        C
ATOM   1057  CG1 ILE A 451      23.720  10.086 -15.389  1.00 20.59           C
ANISOU 1057  CG1 ILE A 451    3025   1914   2885   -542     83     19        C
ATOM   1058  CD1 ILE A 451      23.706  11.556 -15.790  1.00 19.64           C
ANISOU 1058  CD1 ILE A 451    2765   1897   2800   -456     40    -28        C
ATOM   1059  CG2 ILE A 451      23.649   7.766 -16.361  1.00 22.44           C
ANISOU 1059  CG2 ILE A 451    3427   1942   3156   -663     78     26        C
ATOM   1060  C   ILE A 451      26.458   8.155 -15.621  1.00 22.07           C
ANISOU 1060  C   ILE A 451    3539   1838   3008   -382    -18    134        C
ATOM   1061  O   ILE A 451      26.781   7.044 -16.013  1.00 22.36           O
ANISOU 1061  O   ILE A 451    3682   1753   3060   -385    -30    146        O
ATOM   1062  N   GLU A 452      26.683   8.553 -14.378  1.00 22.05           N
ANISOU 1062  N   GLU A 452    3565   1877   2938   -359      8    187        N
ATOM   1063  CA  GLU A 452      27.397   7.691 -13.451  1.00 23.30           C
ANISOU 1063  CA  GLU A 452    3882   1946   3025   -326     10    280        C
ATOM   1064  CB  GLU A 452      28.909   8.005 -13.455  1.00 22.10           C
ANISOU 1064  CB  GLU A 452    3748   1802   2846   -164    -79    296        C
ATOM   1065  CG  GLU A 452      29.322   9.401 -12.931  1.00 21.20           C
ANISOU 1065  CG  GLU A 452    3532   1826   2696   -103   -103    268        C
ATOM   1066  CD  GLU A 452      30.841   9.593 -12.871  1.00 22.68           C
ANISOU 1066  CD  GLU A 452    3732   2026   2861     37   -190    281        C
ATOM   1067  OE1 GLU A 452      31.592   8.596 -12.982  1.00 27.30           O
ANISOU 1067  OE1 GLU A 452    4414   2519   3440    105   -229    328        O
ATOM   1068  OE2 GLU A 452      31.303  10.728 -12.689  1.00 23.21           O
ANISOU 1068  OE2 GLU A 452    3706   2189   2922     81   -220    240        O
ATOM   1069  C   GLU A 452      26.827   7.884 -12.057  1.00 24.23           C
ANISOU 1069  C   GLU A 452    4026   2124   3057   -392     85    331        C
ATOM   1070  O   GLU A 452      26.298   8.943 -11.755  1.00 22.41           O
ANISOU 1070  O   GLU A 452    3678   2018   2819    115    279               O
ATOM   1071  N   HIS A 453      26.937   6.859 -11.220  1.00 26.35           N
ANISOU 1071  N   HIS A 453    4453   2300   3257   -423    117    434        N
ATOM   1072  CA  HIS A 453      26.636   7.037  -9.814  1.00 29.05           C
ANISOU 1072  CA  HIS A 453    4843   2716   3480   -466    183    497        C
ATOM   1073  CB  HIS A 453      26.420   5.688  -9.121  1.00 31.54           C
ANISOU 1073  CB  HIS A 453    5346   2900   3737   -546    242    627        C
ATOM   1074  CG  HIS A 453      25.586   5.793  -7.881  1.00 37.83           C
ANISOU 1074  CG  HIS A 453    6167   3786   4420   -660    356    679        C
ATOM   1075  ND1 HIS A 453      26.069   5.479  -6.623  1.00 42.46           N
ANISOU 1075  ND1 HIS A 453    6901   4383   4849   -627    364    804        N
ATOM   1076  CE1 HIS A 453      25.122   5.697  -5.727  1.00 45.28           C
ANISOU 1076  CE1 HIS A 453    7243   4847   5115   -752    487    817        C
ATOM   1077  NE2 HIS A 453      24.054   6.168  -6.351  1.00 44.67           N
ANISOU 1077  NE2 HIS A 453    6999   4830   5145   -855    557    700        N
ATOM   1078  CD2 HIS A 453      24.320   6.241  -7.697  1.00 40.72           C
ANISOU 1078  CD2 HIS A 453    6418   4258   4796   -798    469    618        C
ATOM   1079  C   HIS A 453      27.767   7.838  -9.144  1.00 28.67           C
ANISOU 1079  C   HIS A 453    4790   2760   3345   -324    106    504        C
ATOM   1080  O   HIS A 453      28.940   7.782  -9.559  1.00 28.14           O
```

FIGURE 18-35

```
ANISOU 1080  O    HIS A 453     4741   2654   3297   -194      5    509           O
ATOM   1081  N    ILE A 454     27.423   8.618  -8.132  1.00 29.08                N
ANISOU 1081  N    ILE A 454     4802   2945   3304   -350    154    488           N
ATOM   1082  CA   ILE A 454     28.448   9.403  -7.440  1.00 28.83                C
ANISOU 1082  CA   ILE A 454     4760   3009   3183   -232     78    475           C
ATOM   1083  CB   ILE A 454     28.400  10.945  -7.822  1.00 27.51                C
ANISOU 1083  CB   ILE A 454     4412   2956   3086   -201     60    334           C
ATOM   1084  CG1  ILE A 454     27.220  11.666  -7.174  1.00 27.31                C
ANISOU 1084  CG1  ILE A 454     4309   3040   3029   -292    168    268           C
ATOM   1085  CD1  ILE A 454     27.215  13.162  -7.375  1.00 25.56                C
ANISOU 1085  CD1  ILE A 454     3937   2905   2872   -246    148    138           C
ATOM   1086  CG2  ILE A 454     28.360  11.131  -9.313  1.00 26.45                C
ANISOU 1086  CG2  ILE A 454     4180   2762   3106   -186     25    277           C
ATOM   1087  C    ILE A 454     28.381   9.208  -5.937  1.00 30.68                C
ANISOU 1087  C    ILE A 454     5104   3314   3238   -258    123    553           C
ATOM   1088  O    ILE A 454     27.341   8.876  -5.395  1.00 32.05                O
ANISOU 1088  O    ILE A 454     5312   3505   3359   -381    239    587           O
ATOM   1089  N    ASP A 455     29.506   9.410  -5.269  1.00 32.23                N
ANISOU 1089  N    ASP A 455     5348   3565   3333   -144     29    580           N
ATOM   1090  CA   ASP A 455     29.570   9.458  -3.811  1.00 34.84                C
ANISOU 1090  CA   ASP A 455     5769   4006   3465   -149     49    635           C
ATOM   1091  CB   ASP A 455     30.984   9.101  -3.357  1.00 36.54                C
ANISOU 1091  CB   ASP A 455     6075   4220   3587     -3    -92    712           C
ATOM   1092  CG   ASP A 455     31.449   7.732  -3.876  1.00 40.61                C
ANISOU 1092  CG   ASP A 455     6722   4552   4157     51   -140    845           C
ATOM   1093  OD1  ASP A 455     30.664   6.746  -3.860  1.00 45.61                O
ANISOU 1093  OD1  ASP A 455     7471   5067   4792    -46    -50    945           O
ATOM   1094  OD2  ASP A 455     32.617   7.641  -4.302  1.00 44.13                O
ANISOU 1094  OD2  ASP A 455     7150   4967   4651    190   -265    841           O
ATOM   1095  C    ASP A 455     29.193  10.845  -3.264  1.00 34.43                C
ANISOU 1095  C    ASP A 455     5588   4124   3368   -173     89    493           C
ATOM   1096  O    ASP A 455     29.396  11.863  -3.913  1.00 33.12                O
ANISOU 1096  O    ASP A 455     5280   3987   3318   -134     49    366           O
ATOM   1097  N    ASN A 456     28.616  10.872  -2.073  1.00 36.47                N
ANISOU 1097  N    ASN A 456     5907   4491   3459   -241    178    516           N
ATOM   1098  CA   ASN A 456     28.410  12.114  -1.357  1.00 36.78                C
ANISOU 1098  CA   ASN A 456     5852   4697   3426   -245    209    376           C
ATOM   1099  CB   ASN A 456     27.498  11.878  -0.155  1.00 38.76                C
ANISOU 1099  CB   ASN A 456     6179   5058   3489   -349    349    415           C
ATOM   1100  CG   ASN A 456     26.107  11.425  -0.555  1.00 39.81                C
ANISOU 1100  CG   ASN A 456     6277   5142   3709   -491    505    433           C
ATOM   1101  OD1  ASN A 456     25.486  11.995  -1.468  1.00 37.31                O
ANISOU 1101  OD1  ASN A 456     5803   4798   3573   -513    535    321           O
ATOM   1102  ND2  ASN A 456     25.598  10.397   0.136  1.00 39.68                N
ANISOU 1102  ND2  ASN A 456     6402   5117   3558   -591    604    578           N
ATOM   1103  C    ASN A 456     29.751  12.683  -0.903  1.00 36.67                C
ANISOU 1103  C    ASN A 456     5840   4760   3333   -121     63    333           C
ATOM   1104  O    ASN A 456     30.413  12.110  -0.036  1.00 37.97                O
ANISOU 1104  O    ASN A 456     6134   4970   3323    -74      2    435           O
ATOM   1105  N    VAL A 457     30.161  13.779  -1.535  1.00 35.06                N
ANISOU 1105  N    VAL A 457     5490   4565   3266    -71      2    190           N
ATOM   1106  CA   VAL A 457     31.320  14.556  -1.101  1.00 34.96                C
ANISOU 1106  CA   VAL A 457     5441   4642   3201     18   -121    106           C
ATOM   1107  CB   VAL A 457     32.418  14.572  -2.196  1.00 33.72                C
ANISOU 1107  CB   VAL A 457     5219   4392   3202    106   -247    107           C
ATOM   1108  CG1  VAL A 457     33.621  15.370  -1.740  1.00 33.63                C
ANISOU 1108  CG1  VAL A 457     5151   4481   3146    179   -372     14           C
ATOM   1109  CG2  VAL A 457     32.816  13.127  -2.554  1.00 35.71                C
ANISOU 1109  CG2  VAL A 457     5589   4533   3446    151   -290    281           C
ATOM   1110  C    VAL A 457     30.848  15.978  -0.779  1.00 34.15                C
ANISOU 1110  C    VAL A 457     5219   4633   3121    -16    -68    -85           C
ATOM   1111  O    VAL A 457     30.251  16.622  -1.639  1.00 32.78                O
ANISOU 1111  O    VAL A 457     4932   4395   3126    -42    -17   -167           O
ATOM   1112  N    MSE A 458     31.088  16.452   0.451  1.00 35.25                N
ANISOU 1112  N    MSE A 458     5390   4923   3079    -11    -81   -157           N
ATOM   1113  CA   MSE A 458     30.699  17.815   0.846  1.00 34.91                C
ANISOU 1113  CA   MSE A 458     5246   4964   3055    -34    -32   -361           C
ATOM   1114  CB   MSE A 458     30.871  18.047   2.353  1.00 37.58                C
ANISOU 1114  CB   MSE A 458     5655   5487   3136    -39    -33   -424           C
ATOM   1115  CG   MSE A 458     30.252  19.378   2.825  1.00 36.62                C
ANISOU 1115  CG   MSE A 458     5440   5445   3030    -71     49   -651           C
```

FIGURE 18-36

| | | | | | | | | | | |
|---|---|---|---|---|---|---|---|---|---|---|
| ATOM | 1116 | SE | MSE A 458 | 30.457 | 19.706 | 4.676 | 0.90 | 40.81 | | SE |
| ANISOU | 1116 | SE | MSE A 458 | 6058 | 6227 | 3221 | -80 | 51 | -762 | SE |
| ATOM | 1117 | CE | MSE A 458 | 29.473 | 21.279 | 4.926 | 1.00 | 43.27 | | C |
| ANISOU | 1117 | CE | MSE A 458 | 6238 | 6576 | 3626 | -113 | 185 | -1053 | C |
| ATOM | 1118 | C | MSE A 458 | 31.466 | 18.877 | 0.071 | 1.00 | 33.44 | | C |
| ANISOU | 1118 | C | MSE A 458 | 4933 | 4714 | 3057 | 13 | -127 | -485 | C |
| ATOM | 1119 | O | MSE A 458 | 32.657 | 18.724 | -0.155 | 1.00 | 34.08 | | O |
| ANISOU | 1119 | O | MSE A 458 | 5016 | 4783 | 3152 | 71 | -259 | -451 | O |
| ATOM | 1120 | N | GLY A 459 | 30.783 | 19.943 | -0.342 | 1.00 | 32.49 | | N |
| ANISOU | 1120 | N | GLY A 459 | 4703 | 4553 | 3090 | -12 | -57 | -623 | N |
| ATOM | 1121 | CA | GLY A 459 | 31.402 | 21.007 | -1.139 | 1.00 | 31.36 | | C |
| ANISOU | 1121 | CA | GLY A 459 | 4449 | 4324 | 3141 | 18 | -129 | -728 | C |
| ATOM | 1122 | C | GLY A 459 | 31.266 | 20.849 | -2.641 | 1.00 | 30.19 | | C |
| ANISOU | 1122 | C | GLY A 459 | 4243 | 4025 | 3204 | 28 | -132 | -646 | C |
| ATOM | 1123 | O | GLY A 459 | 31.810 | 21.635 | -3.395 | 1.00 | 28.91 | | O |
| ANISOU | 1123 | O | GLY A 459 | 4001 | 3786 | 3198 | 47 | -186 | -701 | O |
| ATOM | 1124 | N | MSE A 460 | 30.504 | 19.844 | -3.079 | 1.00 | 30.67 | | N |
| ANISOU | 1124 | N | MSE A 460 | 4344 | 4046 | 3265 | 4 | -68 | -519 | N |
| ATOM | 1125 | CA | MSE A 460 | 30.479 | 19.418 | -4.475 | 1.00 | 30.71 | | C |
| ANISOU | 1125 | CA | MSE A 460 | 4316 | 3927 | 3427 | 14 | -86 | -427 | C |
| ATOM | 1126 | CB | MSE A 460 | 31.612 | 18.422 | -4.661 | 1.00 | 30.18 | | C |
| ANISOU | 1126 | CB | MSE A 460 | 4321 | 3842 | 3305 | 58 | -185 | -308 | C |
| ATOM | 1127 | CG | MSE A 460 | 32.091 | 18.176 | -6.021 | 1.00 | 31.46 | | C |
| ANISOU | 1127 | CG | MSE A 460 | 4442 | 3899 | 3611 | 88 | -234 | -249 | C |
| ATOM | 1128 | SE | MSE A 460 | 33.476 | 16.771 | -5.852 | 0.90 | 37.35 | | SE |
| ANISOU | 1128 | SE | MSE A 460 | 5293 | 4649 | 4248 | 165 | -348 | -114 | SE |
| ATOM | 1129 | CE | MSE A 460 | 34.825 | 17.837 | -4.917 | 1.00 | 35.43 | | C |
| ANISOU | 1129 | CE | MSE A 460 | 4991 | 4531 | 3939 | 209 | -461 | -235 | C |
| ATOM | 1130 | C | MSE A 460 | 29.152 | 18.715 | -4.753 | 1.00 | 28.46 | | C |
| ANISOU | 1130 | C | MSE A 460 | 4042 | 3618 | 3154 | -41 | 24 | -362 | C |
| ATOM | 1131 | O | MSE A 460 | 28.575 | 18.079 | -3.850 | 1.00 | 28.50 | | O |
| ANISOU | 1131 | O | MSE A 460 | 4120 | 3694 | 3015 | -88 | 97 | -325 | O |
| ATOM | 1132 | N | VAL A 461 | 28.671 | 18.840 | -5.989 | 1.00 | 25.91 | | N |
| ANISOU | 1132 | N | VAL A 461 | 3643 | 3204 | 2995 | -44 | 34 | -348 | N |
| ATOM | 1133 | CA | VAL A 461 | 27.446 | 18.159 | -6.436 | 1.00 | 25.77 | | C |
| ANISOU | 1133 | CA | VAL A 461 | 3614 | 3165 | 3014 | -103 | 121 | -296 | C |
| ATOM | 1134 | CB | VAL A 461 | 26.129 | 19.057 | -6.389 | 1.00 | 26.21 | | C |
| ANISOU | 1134 | CB | VAL A 461 | 3552 | 3258 | 3149 | -125 | 217 | -406 | C |
| ATOM | 1135 | CG1 | VAL A 461 | 25.667 | 19.320 | -4.974 | 1.00 | 28.85 | | C |
| ANISOU | 1135 | CG1 | VAL A 461 | 3904 | 3710 | 3347 | -154 | 306 | -485 | C |
| ATOM | 1136 | CG2 | VAL A 461 | 26.293 | 20.405 | -7.139 | 1.00 | 25.60 | | C |
| ANISOU | 1136 | CG2 | VAL A 461 | 3368 | 3122 | 3236 | -60 | 167 | -496 | C |
| ATOM | 1137 | C | VAL A 461 | 27.621 | 17.605 | -7.849 | 1.00 | 24.27 | | C |
| ANISOU | 1137 | C | VAL A 461 | 3411 | 2873 | 2939 | -92 | 69 | -216 | C |
| ATOM | 1138 | O | VAL A 461 | 28.436 | 18.099 | -8.633 | 1.00 | 22.83 | | O |
| ANISOU | 1138 | O | VAL A 461 | 3191 | 2640 | 2843 | -37 | -10 | -224 | O |
| ATOM | 1139 | N | GLY A 462 | 26.837 | 16.583 | -8.174 | 1.00 | 23.87 | | N |
| ANISOU | 1139 | N | GLY A 462 | 3388 | 2795 | 2886 | -154 | 122 | -147 | N |
| ATOM | 1140 | CA | GLY A 462 | 26.661 | 16.169 | -9.564 | 1.00 | 21.99 | | C |
| ANISOU | 1140 | CA | GLY A 462 | 3116 | 2478 | 2763 | -158 | 90 | -107 | C |
| ATOM | 1141 | C | GLY A 462 | 25.731 | 17.096 | -10.366 | 1.00 | 21.21 | | C |
| ANISOU | 1141 | C | GLY A 462 | 2876 | 2387 | 2797 | -156 | 109 | -179 | C |
| ATOM | 1142 | O | GLY A 462 | 25.023 | 17.917 | -9.803 | 1.00 | 21.23 | | O |
| ANISOU | 1142 | O | GLY A 462 | 2805 | 2448 | 2813 | -158 | 166 | -260 | O |
| ATOM | 1143 | N | VAL A 463 | 25.746 | 16.937 | -11.686 | 1.00 | 19.62 | | N |
| ANISOU | 1143 | N | VAL A 463 | 2639 | 2130 | 2686 | -142 | 58 | -151 | N |
| ATOM | 1144 | CA | VAL A 463 | 24.947 | 17.731 | -12.581 | 1.00 | 19.75 | | C |
| ANISOU | 1144 | CA | VAL A 463 | 2533 | 2153 | 2820 | -125 | 52 | -195 | C |
| ATOM | 1145 | CB | VAL A 463 | 25.767 | 18.971 | -13.157 | 1.00 | 19.50 | | C |
| ANISOU | 1145 | CB | VAL A 463 | 2461 | 2085 | 2865 | -37 | -19 | -215 | C |
| ATOM | 1146 | CG1 | VAL A 463 | 26.906 | 18.526 | -14.079 | 1.00 | 18.45 | | C |
| ANISOU | 1146 | CG1 | VAL A 463 | 2382 | 1899 | 2729 | -11 | -93 | -148 | C |
| ATOM | 1147 | CG2 | VAL A 463 | 24.903 | 19.884 | -13.892 | 1.00 | 20.87 | | C |
| ANISOU | 1147 | CG2 | VAL A 463 | 2520 | 2259 | 3151 | -5 | -26 | -248 | C |
| ATOM | 1148 | C | VAL A 463 | 24.402 | 16.803 | -13.675 | 1.00 | 19.21 | | C |
| ANISOU | 1148 | C | VAL A 463 | 2454 | 2061 | 2785 | -173 | 38 | -153 | C |
| ATOM | 1149 | O | VAL A 463 | 25.117 | 15.975 | -14.245 | 1.00 | 17.34 | | O |
| ANISOU | 1149 | O | VAL A 463 | 2295 | 1770 | 2523 | -173 | -6 | -98 | O |
| ATOM | 1150 | N | LEU A 464 | 23.113 | 16.938 | -13.952 | 1.00 | 20.10 | | N |
| ANISOU | 1150 | N | LEU A 464 | 2460 | 2221 | 2955 | -211 | 75 | -193 | N |
| ATOM | 1151 | CA | LEU A 464 | 22.451 | 16.147 | -14.993 | 1.00 | 20.06 | | C |

FIGURE 18-37

```
ANISOU 1151  CA   LEU A 464     2423   2214   2986    -267     55   -179         C
ATOM   1152  CB   LEU A 464      20.978  15.896 -14.611  1.00 20.50              C
ANISOU 1152  CB   LEU A 464     2379   2345   3065    -356    136   -228         C
ATOM   1153  CG   LEU A 464      20.640  15.224 -13.271  1.00 20.46              C
ANISOU 1153  CG   LEU A 464     2432   2366   2978    -451    249   -224         C
ATOM   1154  CD1  LEU A 464      19.137  15.006 -13.119  1.00 21.72              C
ANISOU 1154  CD1  LEU A 464     2461   2614   3178    -551    334   -280         C
ATOM   1155  CD2  LEU A 464      21.359  13.932 -13.071  1.00 18.35              C
ANISOU 1155  CD2  LEU A 464     2330   2012   2629    -510    252   -143         C
ATOM   1156  C    LEU A 464      22.547  16.908 -16.326  1.00 19.95              C
ANISOU 1156  C    LEU A 464     2335   2196   3048    -190    -34   -178         C
ATOM   1157  O    LEU A 464      22.865  18.083 -16.323  1.00 19.98              O
ANISOU 1157  O    LEU A 464     2302   2195   3096    -107    -60   -189         O
ATOM   1158  N    PRO A 465      22.308  16.229 -17.470  1.00 20.59              N
ANISOU 1158  N    PRO A 465     2409   2275   3140    -222    -82   -163         N
ATOM   1159  CA   PRO A 465      22.309  16.897 -18.783  1.00 21.07              C
ANISOU 1159  CA   PRO A 465     2405   2352   3247    -154   -167   -151         C
ATOM   1160  CB   PRO A 465      21.839  15.803 -19.740  1.00 21.49              C
ANISOU 1160  CB   PRO A 465     2459   2425   3283    -226   -198   -161         C
ATOM   1161  CG   PRO A 465      22.268  14.552 -19.122  1.00 20.52              C
ANISOU 1161  CG   PRO A 465     2456   2236   3104    -304   -147   -152         C
ATOM   1162  CD   PRO A 465      22.139  14.772 -17.616  1.00 21.10              C
ANISOU 1162  CD   PRO A 465     2542   2310   3163    -323    -62   -154         C
ATOM   1163  C    PRO A 465      21.445  18.147 -18.919  1.00 22.58              C
ANISOU 1163  C    PRO A 465     2460   2598   3522     -89   -184   -180         C
ATOM   1164  O    PRO A 465      21.848  19.088 -19.645  1.00 22.93              O
ANISOU 1164  O    PRO A 465     2489   2623   3600      -1   -247   -143         O
ATOM   1165  N    ASP A 466      20.288  18.182 -18.246  1.00 23.41              N
ANISOU 1165  N    ASP A 466     2467   2765   3663    -127   -125   -240         N
ATOM   1166  CA   ASP A 466      19.484  19.423 -18.181  1.00 24.48              C
ANISOU 1166  CA   ASP A 466     2467   2944   3890     -41   -132   -280         C
ATOM   1167  CB   ASP A 466      17.987  19.137 -17.935  1.00 25.77              C
ANISOU 1167  CB   ASP A 466     2481   3214   4096     -97    -86   -353         C
ATOM   1168  CG   ASP A 466      17.711  18.432 -16.596  1.00 27.78              C
ANISOU 1168  CG   ASP A 466     2762   3494   4300    -205     43   -396         C
ATOM   1169  OD1  ASP A 466      18.616  18.350 -15.739  1.00 29.82              O
ANISOU 1169  OD1  ASP A 466     3148   3692   4490    -212     88   -374         O
ATOM   1170  OD2  ASP A 466      16.564  17.962 -16.383  1.00 29.01              O
ANISOU 1170  OD2  ASP A 466     2805   3739   4477    -288    100   -451         O
ATOM   1171  C    ASP A 466      20.026  20.476 -17.185  1.00 24.43              C
ANISOU 1171  C    ASP A 466     2490   2886   3906      30    -90   -302         C
ATOM   1172  O    ASP A 466      19.377  21.498 -16.948  1.00 24.93              O
ANISOU 1172  O    ASP A 466     2453   2967   4054     106    -80   -352         O
ATOM   1173  N    MSE A 467      21.206  20.210 -16.610  1.00 24.00              N
ANISOU 1173  N    MSE A 467     2568   2770   3780       9    -70   -275         N
ATOM   1174  CA   MSE A 467      21.905  21.152 -15.710  1.00 24.32              C
ANISOU 1174  CA   MSE A 467     2648   2764   3829      63    -45   -305         C
ATOM   1175  CB   MSE A 467      22.058  22.557 -16.331  1.00 24.10              C
ANISOU 1175  CB   MSE A 467     2574   2675   3907     171   -105   -297         C
ATOM   1176  CG   MSE A 467      23.071  22.602 -17.472  1.00 23.28              C
ANISOU 1176  CG   MSE A 467     2537   2512   3797     191   -185   -203         C
ATOM   1177  SE   MSE A 467      24.823  21.862 -16.977  0.90 26.00             SE
ANISOU 1177  SE   MSE A 467     3030   2817   4031     137   -179   -170        SE
ATOM   1178  CE   MSE A 467      25.294  23.125 -15.564  1.00 22.62              C
ANISOU 1178  CE   MSE A 467     2609   2344   3643     172   -138   -259         C
ATOM   1179  C    MSE A 467      21.320  21.226 -14.313  1.00 25.38              C
ANISOU 1179  C    MSE A 467     2754   2951   3936      34     55   -390         C
ATOM   1180  O    MSE A 467      21.736  22.059 -13.507  1.00 26.95              O
ANISOU 1180  O    MSE A 467     2972   3126   4141      78     79   -444         O
ATOM   1181  N    THR A 468      20.388  20.320 -14.021  1.00 25.59              N
ANISOU 1181  N    THR A 468     2740   3056   3927     -51    119   -408         N
ATOM   1182  CA   THR A 468      19.830  20.146 -12.684  1.00 25.97              C
ANISOU 1182  CA   THR A 468     2773   3176   3917    -106    235   -475         C
ATOM   1183  CB   THR A 468      18.559  19.255 -12.705  1.00 27.06              C
ANISOU 1183  CB   THR A 468     2822   3405   4054    -209    304   -491         C
ATOM   1184  OG1  THR A 468      17.500  19.937 -13.395  1.00 30.40              O
ANISOU 1184  OG1  THR A 468     3070   3880   4602    -149    278   -546         O
ATOM   1185  CG2  THR A 468      18.066  18.937 -11.284  1.00 30.00              C
ANISOU 1185  CG2  THR A 468     3200   3861   4340    -288    444   -541         C
ATOM   1186  C    THR A 468      20.882  19.520 -11.783  1.00 24.91              C
ANISOU 1186  C    THR A 468     2799   3016   3650    -153    260   -435         C
```

FIGURE 18-38

```
ATOM   1187  O   THR A 468      21.500  18.510 -12.160  1.00 23.50           O
ANISOU 1187  O   THR A 468     2721   2793   3415   -201    223   -351       O
ATOM   1188  N   PRO A 469      21.109  20.120 -10.592  1.00 25.19           N
ANISOU 1188  N   PRO A 469     2858   3082   3631   -131    315   -501       N
ATOM   1189  CA  PRO A 469      22.089  19.534  -9.669  1.00 24.77           C
ANISOU 1189  CA  PRO A 469     2952   3026   3434   -167    326   -461       C
ATOM   1190  CB  PRO A 469      22.210  20.588  -8.551  1.00 24.83           C
ANISOU 1190  CB  PRO A 469     2946   3078   3409   -120    369   -571       C
ATOM   1191  CG  PRO A 469      20.960  21.302  -8.583  1.00 26.70           C
ANISOU 1191  CG  PRO A 469     3035   3365   3743    -94    434   -668       C
ATOM   1192  CD  PRO A 469      20.505  21.340 -10.031  1.00 25.78           C
ANISOU 1192  CD  PRO A 469     2830   3197   3768    -64    364   -622       C
ATOM   1193  C   PRO A 469      21.549  18.221  -9.098  1.00 25.27           C
ANISOU 1193  C   PRO A 469     3071   3142   3390   -285    412   -407       C
ATOM   1194  O   PRO A 469      20.345  18.033  -8.949  1.00 25.16           O
ANISOU 1194  O   PRO A 469     2965   3199   3396   -348    501   -444       O
ATOM   1195  N   SER A 470      22.455  17.313  -8.793  1.00 24.98           N
ANISOU 1195  N   SER A 470     3182   3064   3245   -314    385   -316       N
ATOM   1196  CA  SER A 470      22.073  16.051  -8.215  1.00 25.82           C
ANISOU 1196  CA  SER A 470     3375   3189   3248   -425    463   -243       C
ATOM   1197  CB  SER A 470      21.885  14.999  -9.301  1.00 25.56           C
ANISOU 1197  CB  SER A 470     3359   3073   3278   -482    430   -169       C
ATOM   1198  OG  SER A 470      21.558  13.741  -8.711  1.00 26.57           O
ANISOU 1198  OG  SER A 470     3590   3189   3315   -600    509    -90       O
ATOM   1199  C   SER A 470      23.142  15.585  -7.255  1.00 25.97           C
ANISOU 1199  C   SER A 470     3556   3199   3112   -413    444   -175       C
ATOM   1200  O   SER A 470      24.333  15.726  -7.510  1.00 24.16           O
ANISOU 1200  O   SER A 470     3385   2915   2880   -333    339   -148       O
ATOM   1201  N   THR A 471      22.695  15.018  -6.149  1.00 27.91           N
ANISOU 1201  N   THR A 471     3869   3513   3224   -495    547   -143       N
ATOM   1202  CA  THR A 471      23.597  14.451  -5.161  1.00 29.38           C
ANISOU 1202  CA  THR A 471     4221   3704   3238   -487    529    -57       C
ATOM   1203  CB  THR A 471      23.171  14.821  -3.704  1.00 30.73           C
ANISOU 1203  CB  THR A 471     4408   4020   3246   -523    638   -106       C
ATOM   1204  OG1 THR A 471      21.791  14.497  -3.513  1.00 33.75           O
ANISOU 1204  OG1 THR A 471     4724   4465   3636   -644    787   -120       O
ATOM   1205  CG2 THR A 471      23.366  16.340  -3.446  1.00 32.23           C
ANISOU 1205  CG2 THR A 471     4493   4284   3469   -432    612   -268       C
ATOM   1206  C   THR A 471      23.718  12.925  -5.361  1.00 29.30           C
ANISOU 1206  C   THR A 471     4350   3591   3193   -555    530     94       C
ATOM   1207  O   THR A 471      24.416  12.246  -4.615  1.00 30.80           O
ANISOU 1207  O   THR A 471     4695   3763   3244   -545    509    197       O
ATOM   1208  N   GLU A 472      23.057  12.397  -6.388  1.00 28.16           N
ANISOU 1208  N   GLU A 472     4152   3371   3176   -619    544    105       N
ATOM   1209  CA  GLU A 472      22.982  10.945  -6.598  1.00 28.80           C
ANISOU 1209  CA  GLU A 472     4360   3336   3246   -706    563    226       C
ATOM   1210  CB  GLU A 472      21.524  10.456  -6.513  1.00 30.19           C
ANISOU 1210  CB  GLU A 472     4475   3546   3451   -873    704    218       C
ATOM   1211  CG  GLU A 472      20.831  10.674  -5.152  1.00 34.77           C
ANISOU 1211  CG  GLU A 472     5053   4266   3892   -953    848    212       C
ATOM   1212  CD  GLU A 472      19.477  11.392  -5.276  1.00 40.82           C
ANISOU 1212  CD  GLU A 472     5606   5160   4744  -1019    952     79       C
ATOM   1213  OE1 GLU A 472      18.438  10.760  -5.008  1.00 43.43           O
ANISOU 1213  OE1 GLU A 472     5909   5526   5067  -1176   1085     99       O
ATOM   1214  OE2 GLU A 472      19.441  12.599  -5.641  1.00 42.85           O
ANISOU 1214  OE2 GLU A 472     5717   5482   5083   -914    904    -45       O
ATOM   1215  C   GLU A 472      23.616  10.535  -7.934  1.00 26.87           C
ANISOU 1215  C   GLU A 472     4128   2959   3124   -647    448    242       C
ATOM   1216  O   GLU A 472      24.293   9.534  -8.021  1.00 26.79           O
ANISOU 1216  O   GLU A 472     4261   2832   3087   -633    404    339       O
ATOM   1217  N   MSE A 473      23.414  11.334  -8.971  1.00 25.30           N
ANISOU 1217  N   MSE A 473     3780   2780   3052   -603    399    145       N
ATOM   1218  CA  MSE A 473      23.895  10.993 -10.300  1.00 23.42           C
ANISOU 1218  CA  MSE A 473     3540   2442   2915   -559    305    147       C
ATOM   1219  CB  MSE A 473      22.729  10.564 -11.227  1.00 24.39           C
ANISOU 1219  CB  MSE A 473     3575   2550   3143   -667    341    105       C
ATOM   1220  CG  MSE A 473      21.879   9.393 -10.755  1.00 22.32           C
ANISOU 1220  CG  MSE A 473     3383   2245   2854   -828    445    157       C
ATOM   1221 SE   MSE A 473      22.758   7.582 -10.747  0.90 27.95          SE
ANISOU 1221 SE   MSE A 473     4356   2738   3528   -855    419    296      SE
ATOM   1222  CE  MSE A 473      23.101   7.399 -12.636  1.00 20.44           C
```

FIGURE 18-39

```
ANISOU 1222  CE   MSE A 473     3347  1704  2713   -798   301    216         C
ATOM   1223  C    MSE A 473    24.575  12.199 -10.916  1.00 22.43             C
ANISOU 1223  C    MSE A 473     3320  2354  2848   -433   214     81         C
ATOM   1224  O    MSE A 473    24.300  13.376 -10.550  1.00 22.03             O
ANISOU 1224  O    MSE A 473     3168  2395  2807   -401   232      9         O
ATOM   1225  N    SER A 474    25.430  11.929 -11.891  1.00 20.89             N
ANISOU 1225  N    SER A 474     3156  2083  2699   -366   125     99         N
ATOM   1226  CA   SER A 474    26.072  13.028 -12.627  1.00 19.23             C
ANISOU 1226  CA   SER A 474     2857  1900  2551   -266    47     49         C
ATOM   1227  CB   SER A 474    27.291  13.535 -11.840  1.00 18.96             C
ANISOU 1227  CB   SER A 474     2868  1886  2448   -177     2     61         C
ATOM   1228  OG   SER A 474    27.784  14.746 -12.377  1.00 16.50             O
ANISOU 1228  OG   SER A 474     2462  1603  2203   -107   -50      7         O
ATOM   1229  C    SER A 474    26.509  12.576 -14.024  1.00 18.90             C
ANISOU 1229  C    SER A 474     2818  1792  2572   -236   -19     56         C
ATOM   1230  O    SER A 474    26.803  11.396 -14.234  1.00 17.99             O
ANISOU 1230  O    SER A 474     2805  1592  2438   -253   -27     99         O
ATOM   1231  N    MSE A 475    26.581  13.518 -14.969  1.00 18.62             N
ANISOU 1231  N    MSE A 475     2681  1790  2605   -186   -65     13         N
ATOM   1232  CA   MSE A 475    27.294  13.281 -16.212  1.00 19.11             C
ANISOU 1232  CA   MSE A 475     2751  1815  2697   -138  -129     20         C
ATOM   1233  CB   MSE A 475    27.395  14.576 -17.035  1.00 19.24             C
ANISOU 1233  CB   MSE A 475     2658  1880  2771    -84  -169     -7         C
ATOM   1234  CG   MSE A 475    26.060  14.982 -17.637  1.00 19.93             C
ANISOU 1234  CG   MSE A 475     2644  2015  2915   -127  -159    -41         C
ATOM   1235  SE   MSE A 475    26.115  16.409 -18.957  0.90 21.44            SE
ANISOU 1235  SE   MSE A 475     2727  2246  3173    -52  -225    -41        SE
ATOM   1236  CE   MSE A 475    26.632  17.884 -17.856  1.00 18.53             C
ANISOU 1236  CE   MSE A 475     2330  1873  2838      6  -208    -53         C
ATOM   1237  C    MSE A 475    28.676  12.781 -15.867  1.00 18.97             C
ANISOU 1237  C    MSE A 475     2830  1750  2629    -68  -163     61         C
ATOM   1238  O    MSE A 475    29.338  13.335 -14.995  1.00 18.37             O
ANISOU 1238  O    MSE A 475     2759  1703  2518    -23  -174     68         O
ATOM   1239  N    ARG A 476    29.102  11.717 -16.541  1.00 19.82             N
ANISOU 1239  N    ARG A 476     3007  1787  2736    -55  -185     76         N
ATOM   1240  CA   ARG A 476    30.380  11.052 -16.273  1.00 20.30             C
ANISOU 1240  CA   ARG A 476     3158  1796  2760     27  -221    112         C
ATOM   1241  CB   ARG A 476    30.630  10.005 -17.344  1.00 20.86             C
ANISOU 1241  CB   ARG A 476     3281  1790  2855     42  -238     98         C
ATOM   1242  CG   ARG A 476    32.003   9.337 -17.254  1.00 24.78             C
ANISOU 1242  CG   ARG A 476     3849  2233  3333    153  -279    122         C
ATOM   1243  CD   ARG A 476    32.373   8.494 -18.498  1.00 24.21             C
ANISOU 1243  CD   ARG A 476     3807  2100  3292    190  -293     77         C
ATOM   1244  NE   ARG A 476    31.927   9.009 -19.813  1.00 28.63             N
ANISOU 1244  NE   ARG A 476     4278  2724  3877    152  -291     14         N
ATOM   1245  CZ   ARG A 476    32.680   9.734 -20.648  1.00 28.25             C
ANISOU 1245  CZ   ARG A 476     4147  2758  3829    211  -311    -11         C
ATOM   1246  NH1  ARG A 476    33.921  10.119 -20.292  1.00 26.44             N
ANISOU 1246  NH1  ARG A 476     3889  2565  3593    303  -333      8         N
ATOM   1247  NH2  ARG A 476    32.181  10.089 -21.830  1.00 24.34             N
ANISOU 1247  NH2  ARG A 476     3593  2320  3336    173  -310    -52         N
ATOM   1248  C    ARG A 476    31.621  11.984 -16.096  1.00 19.03             C
ANISOU 1248  C    ARG A 476     2942  1696  2591    121  -269    108         C
ATOM   1249  O    ARG A 476    32.010  12.709 -17.012  1.00 16.62             O
ANISOU 1249  O    ARG A 476     2556  1432  2328    149  -291     79         O
ATOM   1250  N    GLY A 477    32.221  11.942 -14.899  1.00 18.74             N
ANISOU 1250  N    GLY A 477     2952  1671  2495    159  -285    140         N
ATOM   1251  CA   GLY A 477    33.429  12.703 -14.578  1.00 17.97             C
ANISOU 1251  CA   GLY A 477     2803  1637  2389    236  -337    126         C
ATOM   1252  C    GLY A 477    33.226  14.205 -14.333  1.00 17.20             C
ANISOU 1252  C    GLY A 477     2603  1614  2317    207  -329     77         C
ATOM   1253  O    GLY A 477    34.210  14.931 -14.151  1.00 15.87             O
ANISOU 1253  O    GLY A 477     2380  1495  2157    250  -370     52         O
ATOM   1254  N    ILE A 478    31.964  14.675 -14.355  1.00 16.13             N
ANISOU 1254  N    ILE A 478     2436  1485  2208    135  -277     56         N
ATOM   1255  CA   ILE A 478    31.645  16.097 -14.197  1.00 15.15             C
ANISOU 1255  CA   ILE A 478     2221  1406  2129    118  -266      4         C
ATOM   1256  CB   ILE A 478    30.602  16.635 -15.259  1.00 15.06             C
ANISOU 1256  CB   ILE A 478     2137  1385  2200     83  -240    -12         C
ATOM   1257  CG1  ILE A 478    30.870  16.165 -16.718  1.00 12.67             C
ANISOU 1257  CG1  ILE A 478     1829  1058  1927     99  -266     15         C
```

FIGURE 18-40

```
ATOM   1258  CD1 ILE A 478      32.254  16.479 -17.326  1.00  8.92           C
ANISOU 1258  CD1 ILE A 478      1332     591   1465     154   -306     24    C
ATOM   1259  CG2 ILE A 478      30.433  18.171 -15.129  1.00 15.73           C
ANISOU 1259  CG2 ILE A 478      2137    1489   2350      90   -237    -59    C
ATOM   1260  C   ILE A 478      31.087  16.390 -12.800  1.00 16.26           C
ANISOU 1260  C   ILE A 478      2381    1587   2209      87   -228    -24    C
ATOM   1261  O   ILE A 478      30.163  15.703 -12.334  1.00 16.78           O
ANISOU 1261  O   ILE A 478      2496    1650   2231      35   -175     -4    O
ATOM   1262  N   ARG A 479      31.657  17.401 -12.128  1.00 16.30           N
ANISOU 1262  N   ARG A 479      2348    1635   2210     108   -251    -77    N
ATOM   1263  CA  ARG A 479      31.158  17.854 -10.825  1.00 16.29           C
ANISOU 1263  CA  ARG A 479      2357    1689   2145      82   -213   -129    C
ATOM   1264  CB  ARG A 479      32.041  17.347  -9.667  1.00 17.20           C
ANISOU 1264  CB  ARG A 479      2549    1855   2130     110   -254   -112    C
ATOM   1265  CG  ARG A 479      32.242  15.837  -9.578  1.00 17.87           C
ANISOU 1265  CG  ARG A 479      2744    1910   2135     125   -266     -8    C
ATOM   1266  CD  ARG A 479      30.940  15.106  -9.170  1.00 19.88           C
ANISOU 1266  CD  ARG A 479      3064    2151   2338      51   -176     33    C
ATOM   1267  NE  ARG A 479      31.198  13.695  -8.923  1.00 22.90           N
ANISOU 1267  NE  ARG A 479      3575    2483   2644      61   -187    138    N
ATOM   1268  CZ  ARG A 479      31.224  12.743  -9.866  1.00 24.84           C
ANISOU 1268  CZ  ARG A 479      3860    2631   2948      66   -195    193    C
ATOM   1269  NH1 ARG A 479      30.991  13.014 -11.161  1.00 21.80           N
ANISOU 1269  NH1 ARG A 479      3392    2208   2681      57   -195    153    N
ATOM   1270  NH2 ARG A 479      31.452  11.491  -9.507  1.00 27.04           N
ANISOU 1270  NH2 ARG A 479      4270    2843   3162      80   -203    287    N
ATOM   1271  C   ARG A 479      31.081  19.369 -10.792  1.00 16.55           C
ANISOU 1271  C   ARG A 479      2300    1729   2259      85   -209   -222    C
ATOM   1272  O   ARG A 479      31.858  20.053 -11.462  1.00 16.48           O
ANISOU 1272  O   ARG A 479      2240    1691   2330     108   -255   -234    O
ATOM   1273  N   VAL A 480      30.163  19.894  -9.992  1.00 17.45           N
ANISOU 1273  N   VAL A 480      2396    1878   2356      59   -149   -289    N
ATOM   1274  CA  VAL A 480      30.056  21.335  -9.776  1.00 17.94           C
ANISOU 1274  CA  VAL A 480      2387    1932   2497      69   -142   -394    C
ATOM   1275  CB  VAL A 480      28.637  21.841 -10.120  1.00 17.22           C
ANISOU 1275  CB  VAL A 480      2229    1821   2494      62    -74   -429    C
ATOM   1276  CG1 VAL A 480      28.491  23.277  -9.739  1.00 18.86           C
ANISOU 1276  CG1 VAL A 480      2378    2004   2783      87    -61   -546    C
ATOM   1277  CG2 VAL A 480      28.341  21.649 -11.590  1.00 16.12           C
ANISOU 1277  CG2 VAL A 480      2051    1622   2451      72    -96   -352    C
ATOM   1278  C   VAL A 480      30.431  21.686  -8.330  1.00 19.46           C
ANISOU 1278  C   VAL A 480      2611    2200   2583      64   -140   -483    C
ATOM   1279  O   VAL A 480      29.897  21.106  -7.379  1.00 20.11           O
ANISOU 1279  O   VAL A 480      2745    2355   2539      41    -90   -485    O
ATOM   1280  N   SER A 481      31.353  22.635  -8.168  1.00 20.47           N
ANISOU 1280  N   SER A 481      2707    2315   2754      77   -194   -558    N
ATOM   1281  CA  SER A 481      31.759  23.081  -6.858  1.00 22.30           C
ANISOU 1281  CA  SER A 481      2960    2626   2887      70   -207   -666    C
ATOM   1282  CB  SER A 481      33.078  23.835  -6.956  1.00 22.36           C
ANISOU 1282  CB  SER A 481      2929    2614   2953      72   -292   -723    C
ATOM   1283  OG  SER A 481      33.419  24.393  -5.699  1.00 24.36           O
ANISOU 1283  OG  SER A 481      3192    2948   3117      58   -312   -855    O
ATOM   1284  C   SER A 481      30.670  23.933  -6.189  1.00 24.56           C
ANISOU 1284  C   SER A 481      3218    2926   3189      60   -123   -791    C
ATOM   1285  O   SER A 481      30.019  24.767  -6.836  1.00 23.76           O
ANISOU 1285  O   SER A 481      3052    2737   3240      74    -89   -829    O
ATOM   1286  N   LYS A 482      30.448  23.692  -4.903  1.00 27.48           N
ANISOU 1286  N   LYS A 482      3637    3408   3395      45    -89   -850    N
ATOM   1287  CA  LYS A 482      29.583  24.554  -4.094  1.00 31.02           C
ANISOU 1287  CA  LYS A 482      4056    3893   3836      41     -6  -1002    C
ATOM   1288  CB  LYS A 482      28.838  23.725  -3.047  1.00 32.27           C
ANISOU 1288  CB  LYS A 482      4275    4186   3798      12     78   -988    C
ATOM   1289  CG  LYS A 482      27.735  22.854  -3.618  1.00 32.74           C
ANISOU 1289  CG  LYS A 482      4325    4232   3881     -11    159   -873    C
ATOM   1290  CD  LYS A 482      27.113  22.055  -2.499  1.00 40.38           C
ANISOU 1290  CD  LYS A 482      5361    5334   4646     -60    252   -853    C
ATOM   1291  CE  LYS A 482      25.586  22.137  -2.501  1.00 43.54           C
ANISOU 1291  CE  LYS A 482      5686    5766   5094     -88    391   -897    C
ATOM   1292  NZ  LYS A 482      25.001  21.133  -1.548  1.00 47.71           N
ANISOU 1292  NZ  LYS A 482      6289    6419   5421    -161    493   -835    N
ATOM   1293  C   LYS A 482      30.357  25.666  -3.391  1.00 33.07           C
```

FIGURE 18-41

```
ANISOU 1293  C   LYS A 482     4304  4164  4099    42   -55 -1167         C
ATOM   1294  O   LYS A 482    29.775  26.460  -2.686  1.00 34.72          O
ANISOU 1294  O   LYS A 482     4492  4396  4304    45     7 -1320         O
ATOM   1295  N   MSE A 483    31.670  25.718  -3.556  1.00 34.66          N
ANISOU 1295  N   MSE A 483     4509  4352  4306    37  -163 -1151         N
ATOM   1296  CA  MSE A 483    32.448  26.793  -2.918  1.00 37.65          C
ANISOU 1296  CA  MSE A 483     4866  4739  4700    19  -216 -1322         C
ATOM   1297  CB  MSE A 483    33.914  26.410  -2.812  1.00 37.80          C
ANISOU 1297  CB  MSE A 483     4893  4819  4650     7  -340 -1286         C
ATOM   1298  CG  MSE A 483    34.138  25.073  -2.119  1.00 39.83          C
ANISOU 1298  CG  MSE A 483     5231  5224  4679    26  -372 -1178         C
ATOM   1299  SE  MSE A 483    33.330  25.128  -0.344  0.90 47.98         SE
ANISOU 1299  SE  MSE A 483     6338  6432  5460    13  -299 -1311        SE
ATOM   1300  CE  MSE A 483    34.165  26.683   0.484  1.00 37.03          C
ANISOU 1300  CE  MSE A 483     4897  5079  4093   -21  -371 -1592         C
ATOM   1301  C   MSE A 483    32.325  28.052  -3.738  1.00 38.73          C
ANISOU 1301  C   MSE A 483     4933  4704  5077    19  -203 -1393         C
ATOM   1302  O   MSE A 483    32.588  27.979  -4.960  1.00 38.53          O
ANISOU 1302  O   MSE A 483     4879  4574  5187    23  -229 -1272         O
ATOM   1303  OXT MSE A 483    31.982  29.121  -3.192  1.00 40.68          O
ANISOU 1303  OXT MSE A 483     5163  4914  5380    17  -166 -1568         O
ATOM   1304  N   SER B 320     6.053  17.488 -14.523  1.00 52.35          N
ANISOU 1304  N   SER B 320     7545  5144  7203  2251   154  -336         N
ATOM   1305  CA  SER B 320     6.175  16.006 -14.678  1.00 50.09          C
ANISOU 1305  CA  SER B 320     6969  5155  6909  2037   116  -339         C
ATOM   1306  CB  SER B 320     5.622  15.284 -13.442  1.00 49.98          C
ANISOU 1306  CB  SER B 320     6809  5295  6886  2058   243  -458         C
ATOM   1307  OG  SER B 320     6.227  14.008 -13.284  1.00 47.08          O
ANISOU 1307  OG  SER B 320     6311  5089  6488  1786   217  -488         O
ATOM   1308  C   SER B 320     5.493  15.472 -15.958  1.00 50.02          C
ANISOU 1308  C   SER B 320     6692  5379  6934  2091    11  -208         C
ATOM   1309  O   SER B 320     4.593  16.118 -16.530  1.00 52.10          O
ANISOU 1309  O   SER B 320     6909  5650  7236  2351   -17  -120         O
ATOM   1310  N   SER B 321     5.933  14.292 -16.391  1.00 47.01          N
ANISOU 1310  N   SER B 321     6145  5184  6533  1852   -52  -200         N
ATOM   1311  CA  SER B 321     5.467  13.682 -17.637  1.00 46.52          C
ANISOU 1311  CA  SER B 321     5861  5338  6476  1841  -166   -97         C
ATOM   1312  CB  SER B 321     6.558  13.805 -18.715  1.00 45.54          C
ANISOU 1312  CB  SER B 321     5887  5120  6297  1664  -270   -17         C
ATOM   1313  OG  SER B 321     6.312  12.943 -19.816  1.00 45.99          O
ANISOU 1313  OG  SER B 321     5744  5402  6326  1586  -373    48         O
ATOM   1314  C   SER B 321     5.048  12.212 -17.426  1.00 44.12          C
ANISOU 1314  C   SER B 321     5267  5313  6185  1707  -153  -150         C
ATOM   1315  O   SER B 321     5.732  11.476 -16.721  1.00 42.89          O
ANISOU 1315  O   SER B 321     5134  5155  6007  1511  -100  -235         O
ATOM   1316  N   SER B 322     3.928  11.813 -18.037  1.00 43.82          N
ANISOU 1316  N   SER B 322     4963  5507  6179  1810  -209   -96         N
ATOM   1317  CA  SER B 322     3.371  10.454 -17.924  1.00 42.09          C
ANISOU 1317  CA  SER B 322     4461  5551  5981  1676  -201  -140         C
ATOM   1318  CB  SER B 322     2.114  10.463 -17.059  1.00 43.94          C
ANISOU 1318  CB  SER B 322     4489  5924  6284  1855   -88  -176         C
ATOM   1319  OG  SER B 322     2.445  10.678 -15.713  1.00 46.56          O
ANISOU 1319  OG  SER B 322     4969  6115  6605  1864    69  -271         O
ATOM   1320  C   SER B 322     2.996   9.800 -19.256  1.00 40.57          C
ANISOU 1320  C   SER B 322     4083  5563  5770  1602  -354   -68         C
ATOM   1321  O   SER B 322     2.599  10.477 -20.210  1.00 42.21          O
ANISOU 1321  O   SER B 322     4284  5791  5965  1754  -465    32         O
ATOM   1322  N   PHE B 323     3.081   8.475 -19.284  1.00 36.89          N
ANISOU 1322  N   PHE B 323     3479  5243  5295  1374  -362  -122         N
ATOM   1323  CA  PHE B 323     2.551   7.663 -20.374  1.00 36.10          C
ANISOU 1323  CA  PHE B 323     3178  5364  5176  1279  -495   -90         C
ATOM   1324  CB  PHE B 323     3.513   7.627 -21.574  1.00 34.59          C
ANISOU 1324  CB  PHE B 323     3153  5104  4888  1159  -613   -44         C
ATOM   1325  CG  PHE B 323     4.919   7.274 -21.200  1.00 30.95          C
ANISOU 1325  CG  PHE B 323     2900  4468  4391   973  -541  -102         C
ATOM   1326  CD1 PHE B 323     5.340   5.953 -21.231  1.00 26.79          C
ANISOU 1326  CD1 PHE B 323     2326  4009  3845   748  -533  -173         C
ATOM   1327  CE1 PHE B 323     6.630   5.629 -20.870  1.00 28.42          C
ANISOU 1327  CE1 PHE B 323     2700  4071  4027   608  -472  -218         C
ATOM   1328  CZ  PHE B 323     7.524   6.648 -20.464  1.00 28.42          C
ANISOU 1328  CZ  PHE B 323     2907  3870  4021   662  -426  -198         C
```

FIGURE 18-42

```
ATOM   1329  CE2 PHE B 323       7.088   7.988 -20.442  1.00 27.51           C
ANISOU 1329  CE2 PHE B 323    2862   3668   3922    862   -434   -134        C
ATOM   1330  CD2 PHE B 323       5.813   8.277 -20.801  1.00 27.06           C
ANISOU 1330  CD2 PHE B 323    2650   3742   3890   1028   -486    -86        C
ATOM   1331  C   PHE B 323       2.265   6.253 -19.873  1.00 35.08           C
ANISOU 1331  C   PHE B 323    2870   5383   5074   1071   -439   -175        C
ATOM   1332  O   PHE B 323       2.618   5.888 -18.744  1.00 33.74           O
ANISOU 1332  O   PHE B 323    2759   5134   4925    997   -303   -245        O
ATOM   1333  N   SER B 324       1.618   5.474 -20.725  1.00 35.51           N
ANISOU 1333  N   SER B 324    2724   5647   5120    971   -553   -167        N
ATOM   1334  CA  SER B 324       1.270   4.093 -20.446  1.00 35.61           C
ANISOU 1334  CA  SER B 324    2576   5797   5160    747   -521   -240        C
ATOM   1335  CB  SER B 324      -0.200   3.869 -20.791  1.00 38.02           C
ANISOU 1335  CB  SER B 324    2544   6381   5520    785   -594   -217        C
ATOM   1336  OG  SER B 324      -0.802   2.894 -19.960  1.00 41.46           O
ANISOU 1336  OG  SER B 324    2800   6931   6024    634   -483   -279        O
ATOM   1337  C   SER B 324       2.182   3.210 -21.320  1.00 33.97           C
ANISOU 1337  C   SER B 324    2498   5542   4866    521   -606   -273        C
ATOM   1338  O   SER B 324       2.389   3.498 -22.500  1.00 34.44           O
ANISOU 1338  O   SER B 324    2615   5622   4850    539   -742   -227        O
ATOM   1339  N   PHE B 325       2.760   2.167 -20.734  1.00 31.78           N
ANISOU 1339  N   PHE B 325    2289   5194   4592    327   -518   -348        N
ATOM   1340  CA  PHE B 325       3.513   1.176 -21.491  1.00 29.85           C
ANISOU 1340  CA  PHE B 325    2148   4915   4278    124   -577   -395        C
ATOM   1341  CB  PHE B 325       4.972   1.610 -21.693  1.00 28.12           C
ANISOU 1341  CB  PHE B 325    2192   4498   3995    143   -561   -383        C
ATOM   1342  CG  PHE B 325       5.770   0.673 -22.571  1.00 26.86           C
ANISOU 1342  CG  PHE B 325    2137   4311   3757    -27   -608   -429        C
ATOM   1343  CD1 PHE B 325       5.458   0.518 -23.931  1.00 28.72           C
ANISOU 1343  CD1 PHE B 325    2340   4663   3908    -68   -746   -422        C
ATOM   1344  CE1 PHE B 325       6.190  -0.356 -24.743  1.00 28.43           C
ANISOU 1344  CE1 PHE B 325    2420   4597   3784   -214   -772   -481        C
ATOM   1345  CZ  PHE B 325       7.263  -1.082 -24.196  1.00 26.96           C
ANISOU 1345  CZ  PHE B 325    2368   4261   3612   -302   -660   -539        C
ATOM   1346  CE2 PHE B 325       7.581  -0.933 -22.850  1.00 23.52           C
ANISOU 1346  CE2 PHE B 325    1951   3720   3265   -259   -543   -533        C
ATOM   1347  CD2 PHE B 325       6.831  -0.057 -22.045  1.00 25.04           C
ANISOU 1347  CD2 PHE B 325    2043   3944   3527   -131   -518   -483        C
ATOM   1348  C   PHE B 325       3.456  -0.162 -20.770  1.00 29.26           C
ANISOU 1348  C   PHE B 325    2036   4838   4242    -75   -486   -471        C
ATOM   1349  O   PHE B 325       3.759  -0.239 -19.586  1.00 27.73           O
ANISOU 1349  O   PHE B 325    1904   4545   4086    -67   -351   -485        O
ATOM   1350  N   GLY B 326       3.028  -1.202 -21.487  1.00 30.19           N
ANISOU 1350  N   GLY B 326    2067   5063   4339   -256   -565   -518        N
ATOM   1351  CA  GLY B 326       2.970  -2.562 -20.950  1.00 30.07           C
ANISOU 1351  CA  GLY B 326    2049   5020   4356   -471   -488   -587        C
ATOM   1352  C   GLY B 326       2.057  -2.782 -19.754  1.00 31.33           C
ANISOU 1352  C   GLY B 326    2041   5253   4609   -494   -364   -580        C
ATOM   1353  O   GLY B 326       2.288  -3.706 -18.964  1.00 30.80           O
ANISOU 1353  O   GLY B 326    2046   5095   4563   -632   -253   -612        O
ATOM   1354  N   GLY B 327       1.029  -1.938 -19.624  1.00 32.09           N
ANISOU 1354  N   GLY B 327    1922   5515   4756   -348   -374   -531        N
ATOM   1355  CA  GLY B 327       0.118  -1.987 -18.486  1.00 33.34           C
ANISOU 1355  CA  GLY B 327    1900   5769   4998   -337   -231   -519        C
ATOM   1356  C   GLY B 327       0.542  -1.183 -17.265  1.00 31.95           C
ANISOU 1356  C   GLY B 327    1846   5467   4829   -154    -76   -495        C
ATOM   1357  O   GLY B 327      -0.117  -1.257 -16.216  1.00 33.59           O
ANISOU 1357  O   GLY B 327    1940   5738   5083   -142     73   -490        O
ATOM   1358  N   PHE B 328       1.609  -0.399 -17.411  1.00 29.32           N
ANISOU 1358  N   PHE B 328    1738   4962   4439    -22   -107   -482        N
ATOM   1359  CA  PHE B 328       2.156   0.428 -16.338  1.00 28.13           C
ANISOU 1359  CA  PHE B 328    1744   4669   4277    135     12   -473        C
ATOM   1360  CB  PHE B 328       3.628   0.057 -16.050  1.00 25.60           C
ANISOU 1360  CB  PHE B 328    1698   4135   3894     50     27   -499        C
ATOM   1361  CG  PHE B 328       3.793  -1.258 -15.358  1.00 25.59           C
ANISOU 1361  CG  PHE B 328    1733   4099   3890   -141    113   -529        C
ATOM   1362  CD1 PHE B 328       3.840  -1.329 -13.968  1.00 25.50           C
ANISOU 1362  CD1 PHE B 328    1790   4033   3866   -125    261   -531        C
ATOM   1363  CE1 PHE B 328       3.965  -2.559 -13.319  1.00 24.09           C
ANISOU 1363  CE1 PHE B 328    1665   3812   3675   -297    342   -539        C
ATOM   1364  CZ  PHE B 328       4.054  -3.706 -14.047  1.00 24.40           C
```

FIGURE 18-43

```
ANISOU 1364  CZ   PHE B 328     1699  3843  3728   -482    279   -556        C
ATOM   1365  CE2  PHE B 328     4.005  -3.655 -15.450  1.00 25.53            C
ANISOU 1365  CE2  PHE B 328     1777  4043  3882   -505    132   -574        C
ATOM   1366  CD2  PHE B 328     3.876  -2.433 -16.092  1.00 24.35            C
ANISOU 1366  CD2  PHE B 328     1565  3954  3731   -335     49   -556        C
ATOM   1367  C    PHE B 328     2.093   1.894 -16.718  1.00 28.62            C
ANISOU 1367  C    PHE B 328     1826  4711  4336    382    -44   -429        C
ATOM   1368  O    PHE B 328     2.399   2.262 -17.854  1.00 28.17            O
ANISOU 1368  O    PHE B 328     1811  4646  4248    412   -185   -399        O
ATOM   1369  N    THR B 329     1.690   2.727 -15.760  1.00 29.74            N
ANISOU 1369  N    THR B 329     1959  4837  4502    563     74   -425        N
ATOM   1370  CA   THR B 329     1.801   4.169 -15.900  1.00 29.75            C
ANISOU 1370  CA   THR B 329     2059  4747  4498    808     49   -391        C
ATOM   1371  CB   THR B 329     0.751   4.914 -15.031  1.00 32.29            C
ANISOU 1371  CB   THR B 329     2253  5145  4871   1029    182   -390        C
ATOM   1372  OG1  THR B 329    -0.576   4.482 -15.374  1.00 31.53            O
ANISOU 1372  OG1  THR B 329     1818  5316  4846   1033    168   -364        O
ATOM   1373  CG2  THR B 329     0.846   6.411 -15.230  1.00 31.75            C
ANISOU 1373  CG2  THR B 329     2316  4948  4799   1297    153   -356        C
ATOM   1374  C    THR B 329     3.223   4.532 -15.485  1.00 28.41            C
ANISOU 1374  C    THR B 329     2200  4331  4263    781     67   -416        C
ATOM   1375  O    THR B 329     3.629   4.259 -14.350  1.00 29.14            O
ANISOU 1375  O    THR B 329     2399  4343  4330    729    183   -463        O
ATOM   1376  N    PHE B 330     3.995   5.073 -16.429  1.00 27.40            N
ANISOU 1376  N    PHE B 330     2210  4099  4102    796    -52   -380        N
ATOM   1377  CA   PHE B 330     5.301   5.664 -16.167  1.00 25.35            C
ANISOU 1377  CA   PHE B 330     2219  3620  3794    784    -48   -393        C
ATOM   1378  CB   PHE B 330     6.178   5.570 -17.410  1.00 24.18            C
ANISOU 1378  CB   PHE B 330     2153  3429  3605    684   -174   -355        C
ATOM   1379  CG   PHE B 330     6.737   4.194 -17.671  1.00 21.46            C
ANISOU 1379  CG   PHE B 330     1782  3132  3238    468   -193   -390        C
ATOM   1380  CD1  PHE B 330     8.110   3.963 -17.574  1.00 18.03            C
ANISOU 1380  CD1  PHE B 330     1514  2572  2767    358   -191   -410        C
ATOM   1381  CE1  PHE B 330     8.642   2.682 -17.836  1.00 18.22            C
ANISOU 1381  CE1  PHE B 330     1523  2625  2773    192   -201   -442        C
ATOM   1382  CZ   PHE B 330     7.787   1.630 -18.182  1.00 18.84            C
ANISOU 1382  CZ   PHE B 330     1451  2841  2869    110   -215   -462        C
ATOM   1383  CE2  PHE B 330     6.396   1.859 -18.267  1.00 18.39            C
ANISOU 1383  CE2  PHE B 330     1214  2923  2849    186   -226   -444        C
ATOM   1384  CD2  PHE B 330     5.895   3.134 -18.019  1.00 20.38            C
ANISOU 1384  CD2  PHE B 330     1457  3165  3123    377   -214   -404        C
ATOM   1385  C    PHE B 330     5.142   7.118 -15.831  1.00 27.08            C
ANISOU 1385  C    PHE B 330     2554  3714  4019   1002    -15   -376        C
ATOM   1386  O    PHE B 330     4.443   7.841 -16.532  1.00 28.76            O
ANISOU 1386  O    PHE B 330     2699  3969  4258   1167    -72   -316        O
ATOM   1387  N    LYS B 331     5.795   7.544 -14.756  1.00 27.03            N
ANISOU 1387  N    LYS B 331     2738  3549  3983   1008     70   -432        N
ATOM   1388  CA   LYS B 331     5.856   8.956 -14.420  1.00 29.58            C
ANISOU 1388  CA   LYS B 331     3242  3697  4301   1189    100   -435        C
ATOM   1389  CB   LYS B 331     5.064   9.247 -13.135  1.00 30.49            C
ANISOU 1389  CB   LYS B 331     3344  3823  4419   1336    253   -500        C
ATOM   1390  CG   LYS B 331     5.276  10.638 -12.593  1.00 34.42            C
ANISOU 1390  CG   LYS B 331     4088  4096  4893   1503    301   -536        C
ATOM   1391  CD   LYS B 331     4.335  10.970 -11.437  1.00 37.48            C
ANISOU 1391  CD   LYS B 331     4452  4511  5276   1692    469   -604        C
ATOM   1392  CE   LYS B 331     4.357  12.470 -11.157  1.00 44.58            C
ANISOU 1392  CE   LYS B 331     5601  5174  6164   1907    508   -635        C
ATOM   1393  NZ   LYS B 331     3.272  12.887 -10.223  1.00 50.24            N
ANISOU 1393  NZ   LYS B 331     6274  5932  6884   2152    684   -696        N
ATOM   1394  C    LYS B 331     7.324   9.355 -14.298  1.00 28.10            C
ANISOU 1394  C    LYS B 331     3311  3304  4062   1062     61   -456        C
ATOM   1395  O    LYS B 331     8.037   8.798 -13.466  1.00 27.89            O
ANISOU 1395  O    LYS B 331     3352  3249  3997    924     98   -517        O
ATOM   1396  N    ARG B 332     7.787  10.293 -15.132  1.00 28.13            N
ANISOU 1396  N    ARG B 332     3451  3172  4064   1099    -16   -397        N
ATOM   1397  CA   ARG B 332     9.184  10.755 -15.057  1.00 27.45            C
ANISOU 1397  CA   ARG B 332     3590  2899  3940    958    -50   -412        C
ATOM   1398  CB   ARG B 332     9.671  11.403 -16.367  1.00 27.67            C
ANISOU 1398  CB   ARG B 332     3703  2846  3966    939   -143   -313        C
ATOM   1399  CG   ARG B 332    11.213  11.679 -16.389  1.00 27.23            C
ANISOU 1399  CG   ARG B 332     3826  2642  3879    736   -173   -321        C
```

FIGURE 18-44

```
ATOM   1400  CD  ARG B 332      11.712  12.014 -17.789  1.00 28.39           C
ANISOU 1400  CD  ARG B 332     4015   2763   4011    677   -245   -212       C
ATOM   1401  NE  ARG B 332      11.084  13.243 -18.288  1.00 31.78           N
ANISOU 1401  NE  ARG B 332     4571   3058   4448    859   -260   -132       N
ATOM   1402  CZ  ARG B 332      11.095  13.644 -19.557  1.00 31.92           C
ANISOU 1402  CZ  ARG B 332     4626   3063   4438    881   -322    -10       C
ATOM   1403  NH1 ARG B 332      11.702  12.900 -20.497  1.00 29.06           N
ANISOU 1403  NH1 ARG B 332     4180   2829   4034    723   -365     33       N
ATOM   1404  NH2 ARG B 332      10.480  14.783 -19.881  1.00 27.89           N
ANISOU 1404  NH2 ARG B 332     4251   2412   3935   1075   -335     69       N
ATOM   1405  C   ARG B 332       9.449  11.702 -13.890  1.00 28.06           C
ANISOU 1405  C   ARG B 332     3890   2780   3993   1015     19   -492       C
ATOM   1406  O   ARG B 332       8.854  12.786 -13.811  1.00 29.26           O
ANISOU 1406  O   ARG B 332     4150   2809   4160   1208     53   -486       O
ATOM   1407  N   THR B 333      10.387  11.304 -13.020  1.00 26.57           N
ANISOU 1407  N   THR B 333     3782   2555   3757    850     30   -566       N
ATOM   1408  CA  THR B 333      10.701  12.072 -11.806  1.00 27.14           C
ANISOU 1408  CA  THR B 333     4076   2459   3779    868     83   -664       C
ATOM   1409  CB  THR B 333      10.605  11.185 -10.551  1.00 26.57           C
ANISOU 1409  CB  THR B 333     3954   2494   3648    824    153   -747       C
ATOM   1410  OG1 THR B 333      11.447  10.029 -10.706  1.00 26.24           O
ANISOU 1410  OG1 THR B 333     3808   2566   3597    626     88   -725       O
ATOM   1411  CG2 THR B 333       9.165  10.725 -10.341  1.00 27.09           C
ANISOU 1411  CG2 THR B 333     3835   2720   3738    992    259   -741       C
ATOM   1412  C   THR B 333      12.062  12.825 -11.844  1.00 26.96           C
ANISOU 1412  C   THR B 333     4273   2240   3731    703      8   -680       C
ATOM   1413  O   THR B 333      12.273  13.724 -11.056  1.00 27.63           O
ANISOU 1413  O   THR B 333     4577   2144   3775    722     33   -758       O
ATOM   1414  N   SER B 334      12.957  12.454 -12.768  1.00 25.38           N
ANISOU 1414  N   SER B 334     4008   2081   3552    536    -76   -610       N
ATOM   1415  CA  SER B 334      14.274  13.108 -12.964  1.00 25.51           C
ANISOU 1415  CA  SER B 334     4182   1950   3561    351   -143   -605       C
ATOM   1416  CB  SER B 334      15.373  12.428 -12.171  1.00 24.37           C
ANISOU 1416  CB  SER B 334     4014   1868   3377    157   -184   -671       C
ATOM   1417  OG  SER B 334      15.537  13.002 -10.926  1.00 29.53           O
ANISOU 1417  OG  SER B 334     4850   2400   3971    145   -173   -780       O
ATOM   1418  C   SER B 334      14.705  12.915 -14.375  1.00 24.24           C
ANISOU 1418  C   SER B 334     3928   1847   3436    271   -195   -492       C
ATOM   1419  O   SER B 334      14.323  11.934 -15.016  1.00 22.59           O
ANISOU 1419  O   SER B 334     3521   1822   3240    295   -199   -445       O
ATOM   1420  N   GLY B 335      15.562  13.811 -14.833  1.00 24.97           N
ANISOU 1420  N   GLY B 335     4172   1782   3533    151   -230   -453       N
ATOM   1421  CA  GLY B 335      16.223  13.648 -16.116  1.00 24.84           C
ANISOU 1421  CA  GLY B 335     4086   1821   3529     33   -264   -347       C
ATOM   1422  C   GLY B 335      15.352  14.058 -17.286  1.00 25.60           C
ANISOU 1422  C   GLY B 335     4192   1905   3631    188   -262   -234       C
ATOM   1423  O   GLY B 335      14.281  14.625 -17.106  1.00 27.00           O
ANISOU 1423  O   GLY B 335     4436   2007   3818    395   -241   -231       O
ATOM   1424  N   SER B 336      15.838  13.762 -18.487  1.00 25.43           N
ANISOU 1424  N   SER B 336     4099   1967   3594     95   -285   -138       N
ATOM   1425  CA  SER B 336      15.225  14.169 -19.749  1.00 26.34           C
ANISOU 1425  CA  SER B 336     4242   2078   3686    207   -303    -11       C
ATOM   1426  CB  SER B 336      15.484  15.656 -20.048  1.00 28.83           C
ANISOU 1426  CB  SER B 336     4827   2128   3998    202   -299     68       C
ATOM   1427  OG  SER B 336      16.856  16.025 -19.901  1.00 30.57           O
ANISOU 1427  OG  SER B 336     5147   2245   4224    -53   -286     57       O
ATOM   1428  C   SER B 336      15.816  13.280 -20.832  1.00 25.42           C
ANISOU 1428  C   SER B 336     3985   2145   3531     81   -316     46       C
ATOM   1429  O   SER B 336      16.779  12.541 -20.571  1.00 23.98           O
ANISOU 1429  O   SER B 336     3706   2050   3355    -85   -301     -9       O
ATOM   1430  N   SER B 337      15.231  13.301 -22.031  1.00 25.43           N
ANISOU 1430  N   SER B 337     3968   2213   3481    171   -346    151       N
ATOM   1431  CA  SER B 337      15.828  12.576 -23.140  1.00 24.60           C
ANISOU 1431  CA  SER B 337     3774   2261   3312     52   -346    201       C
ATOM   1432  CB  SER B 337      15.457  11.084 -23.140  1.00 23.13           C
ANISOU 1432  CB  SER B 337     3365   2304   3120     64   -359    122       C
ATOM   1433  OG  SER B 337      14.075  10.828 -23.373  1.00 25.51           O
ANISOU 1433  OG  SER B 337     3581   2702   3411    240   -413    131       O
ATOM   1434  C   SER B 337      15.505  13.216 -24.460  1.00 26.16           C
ANISOU 1434  C   SER B 337     4078   2434   3427    115   -376    348       C
ATOM   1435  O   SER B 337      14.583  14.017 -24.556  1.00 27.15           O
```

FIGURE 18-45

```
ANISOU 1435  O   SER B 337    4301  2463  3552   294  -417   413       O
ATOM   1436  N   ILE B 338    16.325  12.882 -25.455  1.00 26.35           N
ANISOU 1436  N   ILE B 338    4093  2544  3376   -27  -349   404       N
ATOM   1437  CA  ILE B 338    16.075  13.222 -26.849  1.00 27.55           C
ANISOU 1437  CA  ILE B 338    4332  2727  3410    14  -377   545       C
ATOM   1438  CB  ILE B 338    17.191  14.129 -27.454  1.00 28.81           C
ANISOU 1438  CB  ILE B 338    4678  2747  3523  -152  -306   660       C
ATOM   1439  CG1 ILE B 338    18.579  13.472 -27.383  1.00 26.68           C
ANISOU 1439  CG1 ILE B 338    4302  2568  3268  -384  -214   597       C
ATOM   1440  CD1 ILE B 338    19.665  14.286 -28.122  1.00 28.93           C
ANISOU 1440  CD1 ILE B 338    4733  2760  3499  -571  -128   723       C
ATOM   1441  CG2 ILE B 338    17.170  15.486 -26.777  1.00 29.60           C
ANISOU 1441  CG2 ILE B 338    4987  2564  3694  -128  -302   701       C
ATOM   1442  C   ILE B 338    15.884  11.899 -27.586  1.00 26.88           C
ANISOU 1442  C   ILE B 338    4074  2894  3245     3  -398   501       C
ATOM   1443  O   ILE B 338    16.186  10.856 -27.040  1.00 24.81           O
ANISOU 1443  O   ILE B 338    3658  2737  3031   -63  -370   378       O
ATOM   1444  N   LYS B 339    15.351  11.936 -28.800  1.00 29.34           N
ANISOU 1444  N   LYS B 339    4428  3294  3428    73  -455   600       N
ATOM   1445  CA  LYS B 339    15.109  10.715 -29.550  1.00 29.97           C
ANISOU 1445  CA  LYS B 339    4375  3601  3413    56  -486   546       C
ATOM   1446  CB  LYS B 339    13.657  10.595 -30.002  1.00 31.00           C
ANISOU 1446  CB  LYS B 339    4446  3844  3489   232  -625   574       C
ATOM   1447  CG  LYS B 339    12.575  10.731 -28.976  1.00 33.08           C
ANISOU 1447  CG  LYS B 339    4606  4083  3882   388  -683   524       C
ATOM   1448  CD  LYS B 339    11.246  10.804 -29.743  1.00 39.25           C
ANISOU 1448  CD  LYS B 339    5331  4998  4584   558  -828   596       C
ATOM   1449  CE  LYS B 339    10.060  11.092 -28.864  1.00 42.38           C
ANISOU 1449  CE  LYS B 339    5609  5391  5103   748  -881   574       C
ATOM   1450  NZ  LYS B 339     8.914  11.502 -29.728  1.00 47.09           N
ANISOU 1450  NZ  LYS B 339    6177  6097  5618   936 -1030   689       N
ATOM   1451  C   LYS B 339    15.927  10.747 -30.817  1.00 31.76           C
ANISOU 1451  C   LYS B 339    4705  3878  3485   -58  -431   632       C
ATOM   1452  O   LYS B 339    16.135  11.812 -31.422  1.00 33.75           O
ANISOU 1452  O   LYS B 339    5140  4018  3664   -59  -419   782       O
ATOM   1453  N   ARG B 340    16.350   9.566 -31.237  1.00 31.26           N
ANISOU 1453  N   ARG B 340    4539  3977  3361  -146  -389   540       N
ATOM   1454  CA  ARG B 340    16.998   9.401 -32.494  1.00 33.42           C
ANISOU 1454  CA  ARG B 340    4895  4340  3462  -234  -327   598       C
ATOM   1455  CB  ARG B 340    18.495   9.339 -32.275  1.00 33.24           C
ANISOU 1455  CB  ARG B 340    4857  4283  3488  -401  -164   576       C
ATOM   1456  CG  ARG B 340    19.324   9.305 -33.537  1.00 37.60           C
ANISOU 1456  CG  ARG B 340    5499  4922  3866  -502   -54   648       C
ATOM   1457  CD  ARG B 340    20.659   8.729 -33.170  1.00 40.36           C
ANISOU 1457  CD  ARG B 340    5728  5314  4294  -636   100   564       C
ATOM   1458  NE  ARG B 340    21.646   8.866 -34.226  1.00 47.19           N
ANISOU 1458  NE  ARG B 340    6660  6250  5019  -750   249   643       N
ATOM   1459  CZ  ARG B 340    22.821   8.236 -34.223  1.00 50.98           C
ANISOU 1459  CZ  ARG B 340    7018  6824  5528  -847   401   575       C
ATOM   1460  NH1 ARG B 340    23.142   7.436 -33.197  1.00 49.64           N
ANISOU 1460  NH1 ARG B 340    6666  6673  5521  -835   403   436       N
ATOM   1461  NH2 ARG B 340    23.677   8.409 -35.235  1.00 52.82           N
ANISOU 1461  NH2 ARG B 340    7309  7137  5623  -947   557   654       N
ATOM   1462  C   ARG B 340    16.484   8.111 -33.093  1.00 33.37           C
ANISOU 1462  C   ARG B 340    4794  4530  3355  -214  -380   492       C
ATOM   1463  O   ARG B 340    16.559   7.042 -32.483  1.00 31.57           O
ANISOU 1463  O   ARG B 340    4424  4358  3211  -242  -359   344       O
ATOM   1464  N   GLU B 341    15.934   8.230 -34.287  1.00 35.28           N
ANISOU 1464  N   GLU B 341    5133  4866  3405  -168  -458   572       N
ATOM   1465  CA  GLU B 341    15.436   7.081 -34.986  1.00 35.48           C
ANISOU 1465  CA  GLU B 341    5103  5074  3304  -171  -522   469       C
ATOM   1466  CB  GLU B 341    14.512   7.527 -36.105  1.00 37.67           C
ANISOU 1466  CB  GLU B 341    5486  5442  3384   -83  -672   584       C
ATOM   1467  CG  GLU B 341    14.003   6.403 -36.917  1.00 39.18           C
ANISOU 1467  CG  GLU B 341    5645  5825  3415  -110  -756   475       C
ATOM   1468  CD  GLU B 341    12.728   6.772 -37.589  1.00 43.97           C
ANISOU 1468  CD  GLU B 341    6272  6540  3896     5  -971   563       C
ATOM   1469  OE1 GLU B 341    12.775   7.040 -38.814  1.00 45.83           O
ANISOU 1469  OE1 GLU B 341    6670  6857  3888     4 -1010   659       O
ATOM   1470  OE2 GLU B 341    11.690   6.807 -36.876  1.00 44.98           O
ANISOU 1470  OE2 GLU B 341    6245  6681  4165   102 -1097   541       O
```

FIGURE 18-46

```
ATOM   1471  C   GLU B 341      16.615   6.290 -35.516  1.00 35.17           C
ANISOU 1471  C   GLU B 341    5086   5099   3177    -298    -363    393      C
ATOM   1472  O   GLU B 341      17.472   6.835 -36.209  1.00 37.32           O
ANISOU 1472  O   GLU B 341    5483   5357   3339    -362    -251    492      O
ATOM   1473  N   GLU B 342      16.644   5.013 -35.154  1.00 33.75           N
ANISOU 1473  N   GLU B 342    4787   4983   3052    -329    -342    219      N
ATOM   1474  CA  GLU B 342      17.705   4.076 -35.501  1.00 33.58           C
ANISOU 1474  CA  GLU B 342    4763   5018   2979    -412    -187    115      C
ATOM   1475  CB  GLU B 342      18.534   3.739 -34.259  1.00 32.29           C
ANISOU 1475  CB  GLU B 342    4466   4768   3036    -442     -80     40      C
ATOM   1476  CG  GLU B 342      19.606   4.754 -33.977  1.00 34.89           C
ANISOU 1476  CG  GLU B 342    4812   5012   3434    -500      36    153      C
ATOM   1477  CD  GLU B 342      20.496   4.362 -32.851  1.00 37.32           C
ANISOU 1477  CD  GLU B 342    4979   5269   3931    -536     124     77      C
ATOM   1478  OE1 GLU B 342      20.843   5.278 -32.069  1.00 41.51           O
ANISOU 1478  OE1 GLU B 342    5491   5694   4587    -569     129    148      O
ATOM   1479  OE2 GLU B 342      20.843   3.159 -32.724  1.00 37.32           O
ANISOU 1479  OE2 GLU B 342    4900   5327   3954    -527     180    -53      O
ATOM   1480  C   GLU B 342      17.091   2.790 -35.997  1.00 33.24           C
ANISOU 1480  C   GLU B 342    4709   5088   2833    -414    -253    -36      C
ATOM   1481  O   GLU B 342      15.936   2.497 -35.709  1.00 32.03           O
ANISOU 1481  O   GLU B 342    4490   4961   2718    -376    -409    -82      O
ATOM   1482  N   GLU B 343      17.874   2.026 -36.750  1.00 33.79           N
ANISOU 1482  N   GLU B 343    4844   5224   2771    -463    -125   -118      N
ATOM   1483  CA  GLU B 343      17.505   0.666 -37.091  1.00 33.29           C
ANISOU 1483  CA  GLU B 343    4790   5227   2632    -481    -154   -296      C
ATOM   1484  CB  GLU B 343      17.416   0.491 -38.604  1.00 36.07           C
ANISOU 1484  CB  GLU B 343    5318   5705   2683    -507    -163   -306      C
ATOM   1485  CG  GLU B 343      16.227   1.164 -39.223  1.00 38.05           C
ANISOU 1485  CG  GLU B 343    5629   6034   2792    -482    -375   -205      C
ATOM   1486  CD  GLU B 343      16.323   1.206 -40.720  1.00 44.38           C
ANISOU 1486  CD  GLU B 343    6631   6962   3270    -507    -371   -179      C
ATOM   1487  OE1 GLU B 343      17.386   1.640 -41.255  1.00 46.93           O
ANISOU 1487  OE1 GLU B 343    7056   7285   3489    -524    -186   -100      O
ATOM   1488  OE2 GLU B 343      15.327   0.808 -41.360  1.00 46.73           O
ANISOU 1488  OE2 GLU B 343    6979   7369   3409    -518    -553   -236      O
ATOM   1489  C   GLU B 343      18.493  -0.319 -36.484  1.00 31.64           C
ANISOU 1489  C   GLU B 343    4511   4962   2549    -492      10   -426      C
ATOM   1490  O   GLU B 343      19.706  -0.165 -36.609  1.00 31.47           O
ANISOU 1490  O   GLU B 343    4491   4938   2528    -499     188   -397      O
ATOM   1491  N   VAL B 344      17.937  -1.331 -35.831  1.00 30.29           N
ANISOU 1491  N   VAL B 344    4273   4751   2484    -492     -54   -560      N
ATOM   1492  CA  VAL B 344      18.689  -2.310 -35.054  1.00 28.25           C
ANISOU 1492  CA  VAL B 344    3947   4413   2372    -477      67   -673      C
ATOM   1493  CB  VAL B 344      18.436  -2.166 -33.514  1.00 26.46           C
ANISOU 1493  CB  VAL B 344    3570   4085   2396    -456      14   -647      C
ATOM   1494  CG1 VAL B 344      18.841  -0.786 -33.009  1.00 25.57           C
ANISOU 1494  CG1 VAL B 344    3398   3945   2372    -442      27   -489      C
ATOM   1495  CG2 VAL B 344      16.977  -2.489 -33.150  1.00 24.38           C
ANISOU 1495  CG2 VAL B 344    3272   3821   2170    -479    -160   -691      C
ATOM   1496  C   VAL B 344      18.313  -3.718 -35.484  1.00 28.72           C
ANISOU 1496  C   VAL B 344    4091   4473   2347    -501      54   -854      C
ATOM   1497  O   VAL B 344      17.259  -3.928 -36.106  1.00 29.90           O
ANISOU 1497  O   VAL B 344    4309   4683   2368    -553     -89   -899      O
ATOM   1498  N   LEU B 345      19.158  -4.685 -35.122  1.00 27.67           N
ANISOU 1498  N   LEU B 345    3954   4268   2292    -464     195   -959      N
ATOM   1499  CA  LEU B 345      19.009  -6.054 -35.598  1.00 28.06           C
ANISOU 1499  CA  LEU B 345    4127   4281   2253    -479     220  -1141      C
ATOM   1500  CB  LEU B 345      20.251  -6.481 -36.379  1.00 28.98           C
ANISOU 1500  CB  LEU B 345    4335   4421   2254    -413     431  -1204      C
ATOM   1501  CG  LEU B 345      20.407  -5.803 -37.751  1.00 30.75           C
ANISOU 1501  CG  LEU B 345    4677   4787   2220    -439     469  -1154      C
ATOM   1502  CD1 LEU B 345      21.733  -6.157 -38.415  1.00 30.52           C
ANISOU 1502  CD1 LEU B 345    4708   4796   2093    -363     717  -1205      C
ATOM   1503  CD2 LEU B 345      19.278  -6.215 -38.670  1.00 30.75           C
ANISOU 1503  CD2 LEU B 345    5033   5030   2199    -522     316  -1251      C
ATOM   1504  C   LEU B 345      18.720  -6.985 -34.436  1.00 27.04           C
ANISOU 1504  C   LEU B 345    3939   4015   2320    -476     193  -1220      C
ATOM   1505  O   LEU B 345      19.387  -6.910 -33.389  1.00 25.76           O
ANISOU 1505  O   LEU B 345    3661   3784   2342    -410     262  -1167      O
ATOM   1506  N   THR B 346      17.695  -7.823 -34.588  1.00 26.96           N
```

FIGURE 18-47

```
ANISOU 1506  N   THR B 346    4007  3970  2268   -562    81 -1336       N
ATOM   1507  CA  THR B 346   17.350  -8.749 -33.512  1.00 26.28         C
ANISOU 1507  CA  THR B 346    3888  3741  2355   -582    62 -1403       C
ATOM   1508  CB  THR B 346   15.887  -9.268 -33.635  1.00 26.91         C
ANISOU 1508  CB  THR B 346    4000  3826  2400   -731  -111 -1483       C
ATOM   1509  OG1 THR B 346   15.764 -10.147 -34.762  1.00 25.20         O
ANISOU 1509  OG1 THR B 346    3979  3603  1992   -799  -110 -1646       O
ATOM   1510  CG2 THR B 346   14.906  -8.098 -33.746  1.00 25.10         C
ANISOU 1510  CG2 THR B 346    3644  3748  2145   -775  -277 -1361       C
ATOM   1511  C   THR B 346   18.348  -9.919 -33.460  1.00 27.87         C
ANISOU 1511  C   THR B 346    4198  3808  2581   -499   229 -1520       C
ATOM   1512  O   THR B 346   19.239 -10.033 -34.325  1.00 29.40         O
ANISOU 1512  O   THR B 346    4483  4038  2650   -427   363 -1567       O
ATOM   1513  N   GLY B 347   18.192 -10.779 -32.459  1.00 27.20         N
ANISOU 1513  N   GLY B 347    4111  3571  2653   -499   231 -1563       N
ATOM   1514  CA  GLY B 347   18.936 -12.031 -32.387  1.00 29.00         C
ANISOU 1514  CA  GLY B 347    4473  3639  2908   -413   367 -1680       C
ATOM   1515  C   GLY B 347   18.678 -12.996 -33.546  1.00 32.22         C
ANISOU 1515  C   GLY B 347    5117  3994  3132   -473   388 -1868       C
ATOM   1516  O   GLY B 347   19.373 -14.017 -33.671  1.00 33.15         O
ANISOU 1516  O   GLY B 347    5381  3967  3245   -376   523 -1981       O
ATOM   1517  N   ASN B 348   17.675 -12.677 -34.381  1.00 32.97         N
ANISOU 1517  N   ASN B 348    5255  4201  3069   -499   248 -1904       N
ATOM   1518  CA  ASN B 348   17.405 -13.400 -35.631  1.00 35.54         C
ANISOU 1518  CA  ASN B 348    5814  4519  3172   -705   242 -2083       C
ATOM   1519  CB  ASN B 348   15.971 -13.938 -35.629  1.00 36.61         C
ANISOU 1519  CB  ASN B 348    5999  4622  3290   -925    51 -2171       C
ATOM   1520  CG  ASN B 348   15.795 -15.108 -36.571  1.00 39.61         C
ANISOU 1520  CG  ASN B 348    6662  4895  3493  -1018    63 -2399       C
ATOM   1521  OD1 ASN B 348   16.626 -16.016 -36.596  1.00 43.16         O
ANISOU 1521  OD1 ASN B 348    7285  5163  3950   -910   232 -2509       O
ATOM   1522  ND2 ASN B 348   14.725 -15.085 -37.373  1.00 40.71         N
ANISOU 1522  ND2 ASN B 348    6855  5147  3464  -1211  -120 -2476       N
ATOM   1523  C   ASN B 348   17.667 -12.572 -36.916  1.00 36.61         C
ANISOU 1523  C   ASN B 348    5990  4852  3067   -687   255 -2062       C
ATOM   1524  O   ASN B 348   17.122 -12.874 -37.983  1.00 38.05         O
ANISOU 1524  O   ASN B 348    6341  5088  3030   -793   181 -2183       O
ATOM   1525  N   LEU B 349   18.513 -11.541 -36.785  1.00 35.54         N
ANISOU 1525  N   LEU B 349    5710  4822  2971   -566   347 -1905       N
ATOM   1526  CA  LEU B 349   18.816 -10.526 -37.819  1.00 36.28         C
ANISOU 1526  CA  LEU B 349    5813  5105  2868   -550   371 -1824       C
ATOM   1527  CB  LEU B 349   19.731 -11.063 -38.920  1.00 38.60         C
ANISOU 1527  CB  LEU B 349    6300  5411  2954   -470   564 -1949       C
ATOM   1528  CG  LEU B 349   21.223 -11.340 -38.716  1.00 39.26         C
ANISOU 1528  CG  LEU B 349    6348  5448  3121   -285   826 -1953       C
ATOM   1529  CD1 LEU B 349   21.879 -11.427 -40.098  1.00 42.73         C
ANISOU 1529  CD1 LEU B 349    6964  5987  3283   -234   995 -2038       C
ATOM   1530  CD2 LEU B 349   21.941 -10.323 -37.866  1.00 36.33         C
ANISOU 1530  CD2 LEU B 349    5719  5139  2944   -211   877 -1751       C
ATOM   1531  C   LEU B 349   17.624  -9.803 -38.446  1.00 36.73         C
ANISOU 1531  C   LEU B 349    5872  5311  2775   -684   152 -1771       C
ATOM   1532  O   LEU B 349   17.698  -9.335 -39.579  1.00 38.72         O
ANISOU 1532  O   LEU B 349    6228  5696  2787   -694   154 -1759       O
ATOM   1533  N   GLN B 350   16.522  -9.716 -37.721  1.00 35.55         N
ANISOU 1533  N   GLN B 350    5604  5147  2756   -777   -33 -1735       N
ATOM   1534  CA  GLN B 350   15.386  -8.965 -38.230  1.00 36.17         C
ANISOU 1534  CA  GLN B 350    5639  5385  2719   -874  -250 -1664       C
ATOM   1535  CB  GLN B 350   14.078  -9.409 -37.570  1.00 35.38         C
ANISOU 1535  CB  GLN B 350    5441  5259  2744  -1005  -437 -1706       C
ATOM   1536  CG  GLN B 350   12.839  -8.730 -38.162  1.00 37.56         C
ANISOU 1536  CG  GLN B 350    5649  5725  2896  -1094  -678 -1646       C
ATOM   1537  CD  GLN B 350   11.541  -9.112 -37.450  1.00 37.75         C
ANISOU 1537  CD  GLN B 350    5522  5756  3067  -1225  -850 -1674       C
ATOM   1538  OE1 GLN B 350   11.541  -9.925 -36.534  1.00 37.89         O
ANISOU 1538  OE1 GLN B 350    5514  5620  3264  -1269  -784 -1742       O
ATOM   1539  NE2 GLN B 350   10.433  -8.514 -37.872  1.00 38.46         N
ANISOU 1539  NE2 GLN B 350    5505  6031  3077  -1284 -1067 -1612       N
ATOM   1540  C   GLN B 350   15.641  -7.495 -37.930  1.00 34.39         C
ANISOU 1540  C   GLN B 350    5259  5249  2560   -786  -250 -1441       C
ATOM   1541  O   GLN B 350   15.987  -7.132 -36.801  1.00 32.10         O
ANISOU 1541  O   GLN B 350    4817  4883  2495   -722  -194 -1348       O
```

FIGURE 18-48

```
ATOM   1542  N   THR B 351      15.480  -6.654 -38.937  1.00 35.51           N
ANISOU 1542  N   THR B 351     5460   5538   2492    -786   -314  -1357      N
ATOM   1543  CA  THR B 351      15.638  -5.218 -38.753  1.00 35.15           C
ANISOU 1543  CA  THR B 351     5308   5556   2491    -715   -325  -1141      C
ATOM   1544  CB  THR B 351      15.876  -4.493 -40.090  1.00 36.33           C
ANISOU 1544  CB  THR B 351     5605   5840   2357    -703   -319  -1061      C
ATOM   1545  OG1 THR B 351      17.037  -5.035 -40.720  1.00 36.38           O
ANISOU 1545  OG1 THR B 351     5755   5831   2237    -677    -97  -1150      O
ATOM   1546  CG2 THR B 351      16.109  -3.013 -39.855  1.00 35.19           C
ANISOU 1546  CG2 THR B 351     5379   5719   2273    -636   -312   -830      C
ATOM   1547  C   THR B 351      14.428  -4.602 -38.066  1.00 34.79           C
ANISOU 1547  C   THR B 351     5095   5543   2579    -732   -530  -1043      C
ATOM   1548  O   THR B 351      13.297  -4.781 -38.513  1.00 36.32           O
ANISOU 1548  O   THR B 351     5289   5835   2677    -804   -723  -1083      O
ATOM   1549  N   LEU B 352      14.669  -3.878 -36.979  1.00 33.75           N
ANISOU 1549  N   LEU B 352     4817   5341   2667    -663   -487   -922      N
ATOM   1550  CA  LEU B 352      13.622  -3.070 -36.344  1.00 34.12           C
ANISOU 1550  CA  LEU B 352     4710   5420   2832    -640   -648   -808      C
ATOM   1551  CB  LEU B 352      13.362  -3.513 -34.889  1.00 32.44           C
ANISOU 1551  CB  LEU B 352     4345   5100   2881    -645   -632   -847      C
ATOM   1552  CG  LEU B 352      12.886  -4.942 -34.597  1.00 32.96           C
ANISOU 1552  CG  LEU B 352     4408   5119   2994    -749   -654  -1020      C
ATOM   1553  CD1 LEU B 352      12.818  -5.103 -33.090  1.00 32.72           C
ANISOU 1553  CD1 LEU B 352     4242   4977   3214    -731   -607  -1006      C
ATOM   1554  CD2 LEU B 352      11.534  -5.282 -35.237  1.00 34.08           C
ANISOU 1554  CD2 LEU B 352     4529   5392   3028    -855   -857  -1081      C
ATOM   1555  C   LEU B 352      13.996  -1.589 -36.370  1.00 33.77           C
ANISOU 1555  C   LEU B 352     4660   5383   2790    -547   -626   -610      C
ATOM   1556  O   LEU B 352      15.095  -1.217 -35.983  1.00 33.03           O
ANISOU 1556  O   LEU B 352     4572   5204   2773    -512   -465   -558      O
ATOM   1557  N   LYS B 353      13.074  -0.753 -36.832  1.00 35.44           N
ANISOU 1557  N   LYS B 353     4859   5692   2916    -511   -793   -499      N
ATOM   1558  CA  LYS B 353      13.235   0.694 -36.758  1.00 35.60           C
ANISOU 1558  CA  LYS B 353     4887   5683   2957    -416   -792   -303      C
ATOM   1559  CB  LYS B 353      12.510   1.355 -37.917  1.00 37.98           C
ANISOU 1559  CB  LYS B 353     5277   6118   3036    -378   -955   -195      C
ATOM   1560  CG  LYS B 353      12.989   2.760 -38.252  1.00 40.38           C
ANISOU 1560  CG  LYS B 353     5690   6373   3280    -298   -911     12      C
ATOM   1561  CD  LYS B 353      12.251   3.271 -39.513  1.00 47.52           C
ANISOU 1561  CD  LYS B 353     6709   7420   3925    -254  -1086    121      C
ATOM   1562  CE  LYS B 353      13.174   4.063 -40.450  1.00 51.30           C
ANISOU 1562  CE  LYS B 353     7408   7878   4205    -253   -970    266      C
ATOM   1563  NZ  LYS B 353      12.550   4.327 -41.795  1.00 55.38           N
ANISOU 1563  NZ  LYS B 353     8074   8553   4416    -224  -1134    354      N
ATOM   1564  C   LYS B 353      12.636   1.177 -35.441  1.00 34.34           C
ANISOU 1564  C   LYS B 353     4557   5448   3042    -351   -841   -254      C
ATOM   1565  O   LYS B 353      11.425   1.077 -35.231  1.00 34.90           O
ANISOU 1565  O   LYS B 353     4510   5595   3155    -331   -997   -267      O
ATOM   1566  N   ILE B 354      13.478   1.693 -34.559  1.00 32.69           N
ANISOU 1566  N   ILE B 354     4329   5103   2987    -322   -706   -204      N
ATOM   1567  CA  ILE B 354      13.045   2.177 -33.262  1.00 31.87           C
ANISOU 1567  CA  ILE B 354     4097   4914   3098    -258   -726   -169      C
ATOM   1568  CB  ILE B 354      13.522   1.253 -32.057  1.00 29.83           C
ANISOU 1568  CB  ILE B 354     3748   4568   3018    -309   -619   -293      C
ATOM   1569  CG1 ILE B 354      15.045   1.231 -31.936  1.00 29.97           C
ANISOU 1569  CG1 ILE B 354     3830   4502   3055    -342   -447   -296      C
ATOM   1570  CD1 ILE B 354      15.560   0.674 -30.576  1.00 28.39           C
ANISOU 1570  CD1 ILE B 354     3540   4204   3043    -353   -362   -368      C
ATOM   1571  CG2 ILE B 354      12.948  -0.182 -32.167  1.00 28.73           C
ANISOU 1571  CG2 ILE B 354     3563   4495   2859    -389   -663   -447      C
ATOM   1572  C   ILE B 354      13.526   3.621 -33.042  1.00 32.17           C
ANISOU 1572  C   ILE B 354     4202   4845   3176    -186   -681    -10      C
ATOM   1573  O   ILE B 354      14.521   4.069 -33.643  1.00 32.57           O
ANISOU 1573  O   ILE B 354     4377   4863   3134    -221   -582     57      O
ATOM   1574  N   ARG B 355      12.815   4.352 -32.186  1.00 31.65           N
ANISOU 1574  N   ARG B 355     4061   4720   3243     -91   -742     48      N
ATOM   1575  CA  ARG B 355      13.288   5.641 -31.749  1.00 32.09           C
ANISOU 1575  CA  ARG B 355     4195   4629   3367     -34   -689    170      C
ATOM   1576  CB  ARG B 355      12.149   6.642 -31.605  1.00 34.12           C
ANISOU 1576  CB  ARG B 355     4439   4870   3656     122   -811    276      C
ATOM   1577  CG  ARG B 355      11.544   7.019 -32.964  1.00 40.68           C
```

FIGURE 18-49

```
ANISOU 1577  CG  ARG B 355    5351  5813  4294    184   -940    384        C
ATOM   1578  CD  ARG B 355   10.425   7.984 -32.784  1.00 49.99            C
ANISOU 1578  CD  ARG B 355    6500  6978  5518    372  -1063    495        C
ATOM   1579  NE  ARG B 355    9.347   7.782 -33.751  1.00 57.85            N
ANISOU 1579  NE  ARG B 355    7438  8169  6374    442  -1246    533        N
ATOM   1580  CZ  ARG B 355    8.140   8.351 -33.661  1.00 61.98            C
ANISOU 1580  CZ  ARG B 355    7861  8751  6936    624  -1388    610        C
ATOM   1581  NH1 ARG B 355    7.842   9.147 -32.628  1.00 61.47            N
ANISOU 1581  NH1 ARG B 355    7761  8550  7045    765  -1346    648        N
ATOM   1582  NH2 ARG B 355    7.220   8.116 -34.599  1.00 64.39            N
ANISOU 1582  NH2 ARG B 355    8099  9264  7103    672  -1573    644        N
ATOM   1583  C   ARG B 355   14.040   5.442 -30.452  1.00 29.39            C
ANISOU 1583  C   ARG B 355    3795  4172  3199    -82   -573     96        C
ATOM   1584  O   ARG B 355   13.448   5.166 -29.416  1.00 29.13            O
ANISOU 1584  O   ARG B 355    3651  4123  3296    -44   -595     33        O
ATOM   1585  N   VAL B 356   15.361   5.534 -30.531  1.00 27.06            N
ANISOU 1585  N   VAL B 356    3568  3818  2896   -173   -448    106        N
ATOM   1586  CA  VAL B 356   16.203   5.352 -29.374  1.00 24.71            C
ANISOU 1586  CA  VAL B 356    3213  3431  2745   -225   -354     44        C
ATOM   1587  CB  VAL B 356   17.660   4.989 -29.781  1.00 24.66            C
ANISOU 1587  CB  VAL B 356    3228  3443  2701   -334   -221     27        C
ATOM   1588  CG1 VAL B 356   18.584   4.978 -28.570  1.00 22.93            C
ANISOU 1588  CG1 VAL B 356    2938  3141  2632   -383   -149    -14        C
ATOM   1589  CG2 VAL B 356   17.691   3.637 -30.499  1.00 24.39            C
ANISOU 1589  CG2 VAL B 356    3163  3532  2572   -358   -198    -77        C
ATOM   1590  C   VAL B 356   16.195   6.627 -28.548  1.00 24.03            C
ANISOU 1590  C   VAL B 356    3178  3194  2758   -182   -360    122        C
ATOM   1591  O   VAL B 356   16.500   7.679 -29.070  1.00 25.01            O
ANISOU 1591  O   VAL B 356    3429  3245  2830   -189   -348    238        O
ATOM   1592  N   HIS B 357   15.853   6.512 -27.266  1.00 21.94            N
ANISOU 1592  N   HIS B 357    2836  2873  2626   -144   -371     56        N
ATOM   1593  CA  HIS B 357   15.871   7.643 -26.336  1.00 21.71            C
ANISOU 1593  CA  HIS B 357    2873  2687  2689   -106   -368     97        C
ATOM   1594  CB  HIS B 357   14.798   7.476 -25.251  1.00 20.79            C
ANISOU 1594  CB  HIS B 357    2672  2563  2663      2   -412     33        C
ATOM   1595  CG  HIS B 357   13.410   7.756 -25.737  1.00 21.75            C
ANISOU 1595  CG  HIS B 357    2767  2747  2751    144   -503     82        C
ATOM   1596  ND1 HIS B 357   12.706   8.884 -25.371  1.00 23.54            N
ANISOU 1596  ND1 HIS B 357    3056  2871  3017    287   -534    145        N
ATOM   1597  CE1 HIS B 357   11.530   8.882 -25.974  1.00 22.53            C
ANISOU 1597  CE1 HIS B 357    2858  2853  2849    411   -626    188        C
ATOM   1598  NE2 HIS B 357   11.450   7.797 -26.723  1.00 23.39            N
ANISOU 1598  NE2 HIS B 357    2873  3128  2886    329   -662    148        N
ATOM   1599  CD2 HIS B 357   12.613   7.077 -26.595  1.00 22.62            C
ANISOU 1599  CD2 HIS B 357    2792  3016  2786    170   -577     78        C
ATOM   1600  C   HIS B 357   17.247   7.801 -25.708  1.00 20.95            C
ANISOU 1600  C   HIS B 357    2796  2511  2655   -232   -283     74        C
ATOM   1601  O   HIS B 357   17.824   6.843 -25.188  1.00 18.76            O
ANISOU 1601  O   HIS B 357    2417  2290  2421   -290   -244    -15        O
ATOM   1602  N   GLU B 358   17.764   9.024 -25.773  1.00 21.60            N
ANISOU 1602  N   GLU B 358    3009  2459  2740   -276   -262    161        N
ATOM   1603  CA  GLU B 358   19.132   9.306 -25.328  1.00 21.12            C
ANISOU 1603  CA  GLU B 358    2957  2337  2730   -429   -192    153        C
ATOM   1604  CB  GLU B 358   19.907   9.942 -26.477  1.00 22.08            C
ANISOU 1604  CB  GLU B 358    3175  2446  2769   -535   -131    268        C
ATOM   1605  CG  GLU B 358   20.023   9.004 -27.665  1.00 22.15            C
ANISOU 1605  CG  GLU B 358    3121  2631  2664   -539    -93    272        C
ATOM   1606  CD  GLU B 358   20.615   9.629 -28.884  1.00 24.08            C
ANISOU 1606  CD  GLU B 358    3477  2879  2794   -626    -23    397        C
ATOM   1607  OE1 GLU B 358   20.524  10.875 -29.048  1.00 23.87            O
ANISOU 1607  OE1 GLU B 358    3613  2702  2753   -643    -34    513        O
ATOM   1608  OE2 GLU B 358   21.157   8.845 -29.705  1.00 25.65            O
ANISOU 1608  OE2 GLU B 358    3616  3224  2907   -671     52    379        O
ATOM   1609  C   GLU B 358   19.112  10.217 -24.111  1.00 21.14            C
ANISOU 1609  C   GLU B 358    3040  2167  2824   -430   -215    132        C
ATOM   1610  O   GLU B 358   18.544  11.303 -24.159  1.00 21.17            O
ANISOU 1610  O   GLU B 358    3194  2027  2822   -362   -242    198        O
ATOM   1611  N   GLY B 359   19.685   9.752 -23.008  1.00 20.16            N
ANISOU 1611  N   GLY B 359    2830  2055  2773   -490   -208     36        N
ATOM   1612  CA  GLY B 359   19.778  10.572 -21.819  1.00 20.57            C
ANISOU 1612  CA  GLY B 359    2974  1953  2890   -512   -231     -3        C
```

FIGURE 18-50

```
ATOM   1613  C   GLY B 359      19.326   9.821 -20.596  1.00 19.73           C
ANISOU 1613  C   GLY B 359     2783   1889   2826    -437    -258    -113    C
ATOM   1614  O   GLY B 359      18.499   8.922 -20.689  1.00 19.63           O
ANISOU 1614  O   GLY B 359     2676   1982   2800    -330    -265    -142    O
ATOM   1615  N   TYR B 360      19.863  10.218 -19.445  1.00 19.73           N
ANISOU 1615  N   TYR B 360     2828   1801   2865    -508    -274    -174    N
ATOM   1616  CA  TYR B 360      19.483   9.673 -18.153  1.00 18.62           C
ANISOU 1616  CA  TYR B 360     2650   1681   2744    -445    -296    -271    C
ATOM   1617  CB  TYR B 360      20.482  10.115 -17.053  1.00 19.15           C
ANISOU 1617  CB  TYR B 360     2770   1677   2830    -579    -329    -331    C
ATOM   1618  CG  TYR B 360      19.942   9.873 -15.646  1.00 18.18           C
ANISOU 1618  CG  TYR B 360     2679   1534   2694    -499    -350    -425    C
ATOM   1619  CD1 TYR B 360      19.945   8.585 -15.104  1.00 16.45           C
ANISOU 1619  CD1 TYR B 360     2326   1457   2469    -465    -354    -465    C
ATOM   1620  CE1 TYR B 360      19.438   8.342 -13.850  1.00 19.36           C
ANISOU 1620  CE1 TYR B 360     2735   1814   2805    -398    -359    -536    C
ATOM   1621  CZ  TYR B 360      18.885   9.395 -13.126  1.00 19.45           C
ANISOU 1621  CZ  TYR B 360     2920   1679   2790    -350    -353    -585    C
ATOM   1622  OH  TYR B 360      18.382   9.138 -11.873  1.00 18.88           O
ANISOU 1622  OH  TYR B 360     2897   1608   2666    -282    -339    -658    O
ATOM   1623  CE2 TYR B 360      18.840  10.677 -13.657  1.00 18.02           C
ANISOU 1623  CE2 TYR B 360     2881   1343   2625    -365    -349    -557    C
ATOM   1624  CD2 TYR B 360      19.353  10.902 -14.916  1.00 17.40           C
ANISOU 1624  CD2 TYR B 360     2762   1269   2579    -442    -351    -469    C
ATOM   1625  C   TYR B 360      18.049  10.089 -17.759  1.00 19.14           C
ANISOU 1625  C   TYR B 360     2798   1672   2803    -267    -294    -288    C
ATOM   1626  O   TYR B 360      17.680  11.247 -17.802  1.00 21.05           O
ANISOU 1626  O   TYR B 360     3194   1761   3044    -218    -294    -255    O
ATOM   1627  N   GLU B 361      17.263   9.137 -17.275  1.00 18.20           N
ANISOU 1627  N   GLU B 361     2574   1657   2683    -169    -284    -337    N
ATOM   1628  CA  GLU B 361      15.899   9.416 -16.844  1.00 19.16           C
ANISOU 1628  CA  GLU B 361     2724   1749   2806       0    -265    -357    C
ATOM   1629  CB  GLU B 361      14.901   9.154 -17.981  1.00 18.69           C
ANISOU 1629  CB  GLU B 361     2575   1784   2741     107    -272    -291    C
ATOM   1630  CG  GLU B 361      14.816  10.226 -19.056  1.00 20.04           C
ANISOU 1630  CG  GLU B 361     2852   1865   2895     146    -296    -193    C
ATOM   1631  CD  GLU B 361      13.917   9.795 -20.203  1.00 22.31           C
ANISOU 1631  CD  GLU B 361     3033   2288   3154     236    -330    -129    C
ATOM   1632  OE1 GLU B 361      14.066   8.623 -20.652  1.00 20.60           O
ANISOU 1632  OE1 GLU B 361     2685   2224   2919     163    -336    -149    O
ATOM   1633  OE2 GLU B 361      13.064  10.618 -20.659  1.00 23.98           O
ANISOU 1633  OE2 GLU B 361     3300   2452   3359     383    -357     -61    O
ATOM   1634  C   GLU B 361      15.557   8.512 -15.689  1.00 17.64           C
ANISOU 1634  C   GLU B 361     2458   1633   2612      27    -240    -437    C
ATOM   1635  O   GLU B 361      15.996   7.369 -15.651  1.00 17.76           O
ANISOU 1635  O   GLU B 361     2363   1760   2626     -43    -244    -451    O
ATOM   1636  N   GLU B 362      14.776   9.020 -14.758  1.00 18.34           N
ANISOU 1636  N   GLU B 362     2620   1655   2692     137    -205    -484    N
ATOM   1637  CA  GLU B 362      14.217   8.208 -13.690  1.00 18.97           C
ANISOU 1637  CA  GLU B 362     2638   1816   2755     180    -158    -546    C
ATOM   1638  CB  GLU B 362      14.698   8.683 -12.317  1.00 18.78           C
ANISOU 1638  CB  GLU B 362     2764   1691   2682     150    -150    -626    C
ATOM   1639  CG  GLU B 362      14.269   7.780 -11.129  1.00 19.81           C
ANISOU 1639  CG  GLU B 362     2854   1908   2765     175     -96    -679    C
ATOM   1640  CD  GLU B 362      14.658   8.416  -9.769  1.00 23.89           C
ANISOU 1640  CD  GLU B 362     3556   2321   3202     160     -92    -765    C
ATOM   1641  OE1 GLU B 362      15.700   8.061  -9.173  1.00 27.64           O
ANISOU 1641  OE1 GLU B 362     4065   2806   3630      38    -156    -790    O
ATOM   1642  OE2 GLU B 362      13.946   9.338  -9.332  1.00 31.97           O
ANISOU 1642  OE2 GLU B 362     4699   3247   4203     278     -32    -811    O
ATOM   1643  C   GLU B 362      12.692   8.261 -13.751  1.00 19.33           C
ANISOU 1643  C   GLU B 362     2608   1916   2818     350    -102    -537    C
ATOM   1644  O   GLU B 362      12.130   9.347 -13.924  1.00 21.05           O
ANISOU 1644  O   GLU B 362     2908   2040   3049     476     -89    -521    O
ATOM   1645  N   PHE B 363      12.053   7.096 -13.591  1.00 18.10           N
ANISOU 1645  N   PHE B 363     2298   1909   2669     352     -67    -544    N
ATOM   1646  CA  PHE B 363      10.603   6.935 -13.598  1.00 19.56           C
ANISOU 1646  CA  PHE B 363     2355   2196   2881     481     -10    -536    C
ATOM   1647  CB  PHE B 363      10.160   6.097 -14.830  1.00 18.76           C
ANISOU 1647  CB  PHE B 363     2078   2239   2813     443     -60    -483    C
ATOM   1648  CG  PHE B 363      10.538   6.710 -16.149  1.00 20.16           C
```

FIGURE 18-51

```
ANISOU 1648  CG  PHE B 363     2290  2378  2990    445  -145  -419       C
ATOM   1649  CD1 PHE B 363     9.671  7.585 -16.786  1.00 20.57          C
ANISOU 1649  CD1 PHE B 363     2324  2434  3060    595  -170  -365       C
ATOM   1650  CE1 PHE B 363    10.005  8.145 -17.991  1.00 22.34          C
ANISOU 1650  CE1 PHE B 363     2603  2620  3264    598  -247  -290       C
ATOM   1651  CZ  PHE B 363    11.229  7.855 -18.587  1.00 17.85          C
ANISOU 1651  CZ  PHE B 363     2100  2021  2662    440  -280  -275       C
ATOM   1652  CE2 PHE B 363    12.100  6.988 -17.975  1.00 18.88          C
ANISOU 1652  CE2 PHE B 363     2224  2160  2789    301  -251  -336       C
ATOM   1653  CD2 PHE B 363    11.761  6.407 -16.760  1.00 18.78          C
ANISOU 1653  CD2 PHE B 363     2166  2175  2793    306  -193  -403       C
ATOM   1654  C   PHE B 363    10.104  6.182 -12.366  1.00 19.99          C
ANISOU 1654  C   PHE B 363     2365  2319  2910    480    83  -588       C
ATOM   1655  O   PHE B 363    10.813  5.318 -11.820  1.00 19.21          O
ANISOU 1655  O   PHE B 363     2290  2232  2778    360    82  -608       O
ATOM   1656  N   THR B 364     8.874  6.490 -11.950  1.00 21.40          N
ANISOU 1656  N   THR B 364     2475  2551  3103    622   169  -600       N
ATOM   1657  CA  THR B 364     8.094  5.540 -11.194  1.00 22.37          C
ANISOU 1657  CA  THR B 364     2478  2803  3219    605   268  -619       C
ATOM   1658  CB  THR B 364     7.228  6.189 -10.082  1.00 24.65          C
ANISOU 1658  CB  THR B 364     2799  3088  3478    761   405  -666       C
ATOM   1659  OG1 THR B 364     6.244  7.069 -10.672  1.00 29.54          O
ANISOU 1659  OG1 THR B 364     3325  3737  4161    950   417  -641       O
ATOM   1660  CG2 THR B 364     8.077  6.917  -9.090  1.00 20.46          C
ANISOU 1660  CG2 THR B 364     2522  2392  2860    769   420  -732       C
ATOM   1661  C   THR B 364     7.200  4.826 -12.190  1.00 23.57          C
ANISOU 1661  C   THR B 364     2398  3119  3440    586   242  -570       C
ATOM   1662  O   THR B 364     6.734  5.447 -13.162  1.00 24.92          O
ANISOU 1662  O   THR B 364     2497  3317  3654    681   180  -530       O
ATOM   1663  N   MSE B 365     6.990  3.527 -11.962  1.00 23.51          N
ANISOU 1663  N   MSE B 365     2289  3210  3433    455   278  -570       N
ATOM   1664  CA  MSE B 365     6.070  2.707 -12.758  1.00 25.28          C
ANISOU 1664  CA  MSE B 365     2293  3596  3716    395   258  -541       C
ATOM   1665  CB  MSE B 365     6.777  1.479 -13.354  1.00 23.17          C
ANISOU 1665  CB  MSE B 365     2037  3323  3443    205   188  -537       C
ATOM   1666  CG  MSE B 365     7.959  1.767 -14.260  1.00 23.72          C
ANISOU 1666  CG  MSE B 365     2224  3295  3494    180    74  -527       C
ATOM   1667 SE   MSE B 365     9.006  0.180 -14.677  0.90 24.85         SE
ANISOU 1667 SE   MSE B 365     2418  3405  3619    -17    33  -540      SE
ATOM   1668  CE  MSE B 365     7.640 -1.058 -15.246  1.00 20.54          C
ANISOU 1668  CE  MSE B 365     1672  3014  3117   -135    41  -548       C
ATOM   1669  C   MSE B 365     4.961  2.217 -11.835  1.00 26.07          C
ANISOU 1669  C   MSE B 365     2259  3817  3829    397   400  -552       C
ATOM   1670  O   MSE B 365     5.252  1.610 -10.808  1.00 25.95          O
ANISOU 1670  O   MSE B 365     2332  3765  3763    319   488  -569       O
ATOM   1671  N   VAL B 366     3.699  2.486 -12.183  1.00 27.59          N
ANISOU 1671  N   VAL B 366     2234  4164  4084    489   424  -533       N
ATOM   1672  CA  VAL B 366     2.565  2.042 -11.348  1.00 29.18          C
ANISOU 1672  CA  VAL B 366     2265  4513  4308    484   578  -537       C
ATOM   1673  CB  VAL B 366     1.807  3.257 -10.708  1.00 31.18          C
ANISOU 1673  CB  VAL B 366     2482  4797  4568    737   692  -550       C
ATOM   1674  CG1 VAL B 366     0.547  2.816  -9.890  1.00 31.65          C
ANISOU 1674  CG1 VAL B 366     2322  5048  4655    741   877  -550       C
ATOM   1675  CG2 VAL B 366     2.757  4.071  -9.830  1.00 29.76          C
ANISOU 1675  CG2 VAL B 366     2601  4409  4296    827   734  -597       C
ATOM   1676  C   VAL B 366     1.630  1.113 -12.138  1.00 30.40          C
ANISOU 1676  C   VAL B 366     2151  4861  4538    349   536  -511       C
ATOM   1677  O   VAL B 366     1.042  1.529 -13.138  1.00 31.27          O
ANISOU 1677  O   VAL B 366     2097  5082  4703    424   432  -486       O
ATOM   1678  N   GLY B 367     1.533 -0.147 -11.709  1.00 30.76          N
ANISOU 1678  N   GLY B 367     2170  4939  4578    139   604  -513       N
ATOM   1679  CA  GLY B 367     0.588 -1.110 -12.303  1.00 32.91          C
ANISOU 1679  CA  GLY B 367     2196  5388  4921    -34   581  -500       C
ATOM   1680  C   GLY B 367    -0.498 -1.517 -11.325  1.00 35.94          C
ANISOU 1680  C   GLY B 367     2401  5920  5333    -85   771  -488       C
ATOM   1681  O   GLY B 367    -0.558 -0.986 -10.220  1.00 37.15          O
ANISOU 1681  O   GLY B 367     2625  6048  5442     44   925  -491       O
ATOM   1682  N   LYS B 368    -1.356 -2.458 -11.722  1.00 37.73          N
ANISOU 1682  N   LYS B 368     2403  6306  5626   -285   766  -478       N
ATOM   1683  CA  LYS B 368    -2.392 -2.977 -10.842  1.00 40.82          C
ANISOU 1683  CA  LYS B 368     2606  6852  6051   -385   959  -457       C
```

FIGURE 18-52

```
ATOM    1684  CB  LYS B 368      -3.379  -3.863 -11.614  1.00 43.14           C
ANISOU  1684  CB  LYS B 368     2608   7343   6439   -618    896   -451       C
ATOM    1685  CG  LYS B 368      -4.224  -3.164 -12.650  1.00 46.39           C
ANISOU  1685  CG  LYS B 368     2718   7976   6933   -496    753   -448       C
ATOM    1686  CD  LYS B 368      -5.098  -4.196 -13.325  1.00 53.87           C
ANISOU  1686  CD  LYS B 368     3403   9110   7957   -784    679   -454       C
ATOM    1687  CE  LYS B 368      -5.442  -3.835 -14.770  1.00 56.62           C
ANISOU  1687  CE  LYS B 368     3572   9602   8340   -740    427   -464       C
ATOM    1688  NZ  LYS B 368      -6.644  -4.642 -15.228  1.00 62.56           N
ANISOU  1688  NZ  LYS B 368     3968  10621   9180   -997    377   -470       N
ATOM    1689  C   LYS B 368      -1.811  -3.784  -9.679  1.00 40.22           C
ANISOU  1689  C   LYS B 368     2770   6621   5891   -521   1112   -444       C
ATOM    1690  O   LYS B 368      -2.325  -3.708  -8.559  1.00 41.54           O
ANISOU  1690  O   LYS B 368     2901   6854   6028   -488   1318   -424       O
ATOM    1691  N   ARG B 369      -0.739  -4.539  -9.950  1.00 38.40           N
ANISOU  1691  N   ARG B 369     2787   6190   5615   -656   1015   -452       N
ATOM    1692  CA  ARG B 369      -0.231  -5.556  -9.020  1.00 38.59           C
ANISOU  1692  CA  ARG B 369     3028   6068   5567   -815   1127   -423       C
ATOM    1693  CB  ARG B 369      -0.483  -6.952  -9.606  1.00 39.39           C
ANISOU  1693  CB  ARG B 369     3090   6155   5723  -1113   1085   -417       C
ATOM    1694  CG  ARG B 369      -1.889  -7.506  -9.367  1.00 43.61           C
ANISOU  1694  CG  ARG B 369     3344   6893   6331  -1301   1219   -390       C
ATOM    1695  CD  ARG B 369      -2.166  -8.798 -10.162  1.00 45.50           C
ANISOU  1695  CD  ARG B 369     3542   7112   6635  -1617   1138   -405       C
ATOM    1696  NE  ARG B 369      -2.734  -8.513 -11.485  1.00 50.50           N
ANISOU  1696  NE  ARG B 369     3925   7913   7351  -1634    956   -457       N
ATOM    1697  CZ  ARG B 369      -2.076  -8.625 -12.642  1.00 51.55           C
ANISOU  1697  CZ  ARG B 369     4162   7949   7474  -1642    750   -512       C
ATOM    1698  NH1 ARG B 369      -0.809  -9.053 -12.673  1.00 49.87           N
ANISOU  1698  NH1 ARG B 369     4281   7475   7191  -1634    707   -525       N
ATOM    1699  NH2 ARG B 369      -2.696  -8.327 -13.783  1.00 52.31           N
ANISOU  1699  NH2 ARG B 369     4025   8226   7624  -1654    588   -550       N
ATOM    1700  C   ARG B 369       1.251  -5.377  -8.622  1.00 35.98           C
ANISOU  1700  C   ARG B 369     3036   5502   5132   -717   1074   -428       C
ATOM    1701  O   ARG B 369       1.835  -6.216  -7.915  1.00 36.25           O
ANISOU  1701  O   ARG B 369     3277   5399   5097   -821   1132   -395       O
ATOM    1702  N   ALA B 370       1.852  -4.282  -9.083  1.00 33.63           N
ANISOU  1702  N   ALA B 370     2790   5164   4825   -519    958   -462       N
ATOM    1703  CA  ALA B 370       3.242  -3.951  -8.791  1.00 31.07           C
ANISOU  1703  CA  ALA B 370     2741   4650   4415   -426    890   -472       C
ATOM    1704  CB  ALA B 370       4.209  -4.861  -9.590  1.00 29.47           C
ANISOU  1704  CB  ALA B 370     2663   4314   4222   -553    754   -475       C
ATOM    1705  C   ALA B 370       3.536  -2.485  -9.087  1.00 30.13           C
ANISOU  1705  C   ALA B 370     2633   4522   4291   -205    816   -506       C
ATOM    1706  O   ALA B 370       2.837  -1.834  -9.869  1.00 30.45           O
ANISOU  1706  O   ALA B 370     2489   4676   4403   -120    767   -516       O
ATOM    1707  N   THR B 371       4.577  -1.968  -8.447  1.00 29.21           N
ANISOU  1707  N   THR B 371     2743   4267   4088   -115    802   -520       N
ATOM    1708  CA  THR B 371       5.070  -0.623  -8.712  1.00 28.42           C
ANISOU  1708  CA  THR B 371     2713   4108   3978     60    723   -553       C
ATOM    1709  CB  THR B 371       4.594   0.442  -7.657  1.00 29.87           C
ANISOU  1709  CB  THR B 371     2940   4307   4103    233    854   -584       C
ATOM    1710  OG1 THR B 371       5.182   0.139  -6.396  1.00 31.90           O
ANISOU  1710  OG1 THR B 371     3400   4485   4238    197    929   -590       O
ATOM    1711  CG2 THR B 371       3.077   0.486  -7.506  1.00 29.41           C
ANISOU  1711  CG2 THR B 371     2640   4434   4101    284    995   -575       C
ATOM    1712  C   THR B 371       6.587  -0.709  -8.730  1.00 26.74           C
ANISOU  1712  C   THR B 371     2715   3734   3710     26    611   -559       C
ATOM    1713  O   THR B 371       7.167  -1.696  -8.278  1.00 27.73           O
ANISOU  1713  O   THR B 371     2942   3802   3791    -84    618   -537       O
ATOM    1714  N   ALA B 372       7.245   0.306  -9.262  1.00 24.71           N
ANISOU  1714  N   ALA B 372     2524   3405   3458    120    509   -581       N
ATOM    1715  CA  ALA B 372       8.691   0.260  -9.366  1.00 22.74           C
ANISOU  1715  CA  ALA B 372     2435   3033   3172     78    402   -584       C
ATOM    1716  CB  ALA B 372       9.123  -0.612 -10.575  1.00 20.88           C
ANISOU  1716  CB  ALA B 372     2138   2802   2995    -29    305   -563       C
ATOM    1717  C   ALA B 372       9.313   1.651  -9.455  1.00 21.47           C
ANISOU  1717  C   ALA B 372     2381   2784   2993    183    338   -614       C
ATOM    1718  O   ALA B 372       8.644   2.637  -9.767  1.00 22.51           O
ANISOU  1718  O   ALA B 372     2465   2931   3157    299    353   -625       O
ATOM    1719  N   ILE B 373      10.596   1.712  -9.160  1.00 20.23           N
```

FIGURE 18-53

```
ATOM    1755  N   ALA B 377      19.344   5.004 -18.873  1.00 18.41           N
ANISOU  1755  N   ALA B 377     2158   2132   2704   -354   -244   -351       N
ATOM    1756  CA  ALA B 377      20.187   5.927 -19.633  1.00 19.30           C
ANISOU  1756  CA  ALA B 377     2313   2213   2809   -443   -234   -292       C
ATOM    1757  CB  ALA B 377      21.642   5.877 -19.139  1.00 18.88           C
ANISOU  1757  CB  ALA B 377     2200   2184   2791   -557   -236   -304       C
ATOM    1758  C   ALA B 377      20.043   5.447 -21.070  1.00 19.24           C
ANISOU  1758  C   ALA B 377     2269   2292   2751   -429   -199   -253       C
ATOM    1759  O   ALA B 377      19.145   4.641 -21.328  1.00 18.97           O
ANISOU  1759  O   ALA B 377     2199   2314   2694   -354   -205   -280       O
ATOM    1760  N   THR B 378      20.885   5.930 -21.991  1.00 19.58           N
ANISOU  1760  N   THR B 378     2326   2348   2766   -514   -160   -192       N
ATOM    1761  CA  THR B 378      20.812   5.546 -23.409  1.00 19.32           C
ANISOU  1761  CA  THR B 378     2285   2401   2653   -506   -118   -155       C
ATOM    1762  CB  THR B 378      21.861   6.284 -24.233  1.00 20.34           C
ANISOU  1762  CB  THR B 378     2444   2534   2751   -620    -56    -76       C
ATOM    1763  OG1 THR B 378      21.768   7.684 -23.973  1.00 20.74           O
ANISOU  1763  OG1 THR B 378     2618   2442   2819   -665    -85    -11       O
ATOM    1764  CG2 THR B 378      21.664   6.025 -25.717  1.00 20.00           C
ANISOU  1764  CG2 THR B 378     2433   2574   2591   -603    -11    -31       C
ATOM    1765  C   THR B 378      21.001   4.033 -23.613  1.00 19.30           C
ANISOU  1765  C   THR B 378     2178   2513   2641   -474    -84   -227       C
ATOM    1766  O   THR B 378      22.120   3.502 -23.476  1.00 19.32           O
ANISOU  1766  O   THR B 378     2096   2570   2676   -516    -33   -250       O
ATOM    1767  N   ARG B 379      19.914   3.359 -23.968  1.00 18.79           N
ANISOU  1767  N   ARG B 379     2122   2483   2535   -401   -113   -261       N
ATOM    1768  CA  ARG B 379      19.921   1.918 -24.208  1.00 19.22           C
ANISOU  1768  CA  ARG B 379     2121   2610   2572   -377    -84   -338       C
ATOM    1769  CB  ARG B 379      20.587   1.584 -25.568  1.00 20.01           C
ANISOU  1769  CB  ARG B 379     2232   2791   2579   -405    -10   -331       C
ATOM    1770  CG  ARG B 379      19.959   2.282 -26.762  1.00 21.05           C
ANISOU  1770  CG  ARG B 379     2454   2950   2595   -411    -34   -267       C
ATOM    1771  CD  ARG B 379      20.376   1.641 -28.060  1.00 20.86           C
ANISOU  1771  CD  ARG B 379     2459   3018   2448   -427     38   -291       C
ATOM    1772  NE  ARG B 379      19.805   0.291 -28.188  1.00 21.07           N
ANISOU  1772  NE  ARG B 379     2478   3077   2449   -392     21   -402       N
ATOM    1773  CZ  ARG B 379      20.169  -0.608 -29.110  1.00 21.75           C
ANISOU  1773  CZ  ARG B 379     2601   3225   2438   -392     91   -469       C
ATOM    1774  NH1 ARG B 379      21.092  -0.337 -30.021  1.00 20.29           N
ANISOU  1774  NH1 ARG B 379     2446   3100   2163   -415    195   -434       N
ATOM    1775  NH2 ARG B 379      19.594  -1.797 -29.126  1.00 22.67           N
ANISOU  1775  NH2 ARG B 379     2735   3336   2542   -377     67   -576       N
ATOM    1776  C   ARG B 379      20.589   1.159 -23.045  1.00 19.24           C
ANISOU  1776  C   ARG B 379     2052   2596   2663   -368    -69   -390       C
ATOM    1777  O   ARG B 379      21.432   0.291 -23.257  1.00 18.60           O
ANISOU  1777  O   ARG B 379     1921   2560   2586   -362    -11   -424       O
ATOM    1778  N   ARG B 380      20.187   1.503 -21.816  1.00 20.13           N
ANISOU  1778  N   ARG B 380     2170   2643   2835   -353   -120   -395       N
ATOM    1779  CA  ARG B 380      20.790   0.946 -20.598  1.00 20.31           C
ANISOU  1779  CA  ARG B 380     2146   2650   2921   -343   -125   -427       C
ATOM    1780  CB  ARG B 380      22.100   1.697 -20.262  1.00 21.34           C
ANISOU  1780  CB  ARG B 380     2237   2785   3086   -409   -126   -393       C
ATOM    1781  CG  ARG B 380      22.872   1.156 -19.087  1.00 24.13           C
ANISOU  1781  CG  ARG B 380     2528   3150   3490   -396   -155   -417       C
ATOM    1782  CD  ARG B 380      24.060   2.071 -18.796  1.00 33.52           C
ANISOU  1782  CD  ARG B 380     3664   4360   4713   -492   -179   -385       C
ATOM    1783  NE  ARG B 380      24.427   2.050 -17.376  1.00 40.26           N
ANISOU  1783  NE  ARG B 380     4504   5201   5593   -496   -257   -405       N
ATOM    1784  CZ  ARG B 380      25.066   3.030 -16.744  1.00 41.26           C
ANISOU  1784  CZ  ARG B 380     4631   5311   5736   -597   -318   -398       C
ATOM    1785  NH1 ARG B 380      25.427   4.118 -17.419  1.00 44.00           N
ANISOU  1785  NH1 ARG B 380     4992   5636   6088   -711   -298   -363       N
ATOM    1786  NH2 ARG B 380      25.345   2.919 -15.441  1.00 40.13           N
ANISOU  1786  NH2 ARG B 380     4489   5166   5591   -596   -403   -425       N
ATOM    1787  C   ARG B 380      19.822   1.058 -19.448  1.00 18.92           C
ANISOU  1787  C   ARG B 380     2007   2415   2767   -309   -171   -445       C
ATOM    1788  O   ARG B 380      19.320   2.129 -19.164  1.00 19.53           O
ANISOU  1788  O   ARG B 380     2136   2442   2844   -309   -199   -423       O
ATOM    1789  N   LEU B 381      19.535  -0.060 -18.802  1.00 19.03           N
ANISOU  1789  N   LEU B 381     2006   2427   2796   -274   -165   -485       N
ATOM    1790  CA  LEU B 381      18.844  -0.036 -17.509  1.00 18.96           C
```

FIGURE 18-54

```
ANISOU 1790  CA  LEU B 381     2029  2373  2800   -249  -186  -498       C
ATOM   1791  CB  LEU B 381    18.117  -1.356 -17.258  1.00 18.22         C
ANISOU 1791  CB  LEU B 381     1933  2281  2708   -229  -160  -529       C
ATOM   1792  CG  LEU B 381    17.277  -1.567 -16.000  1.00 18.70         C
ANISOU 1792  CG  LEU B 381     2025  2311  2770   -212  -152  -535       C
ATOM   1793  CD1 LEU B 381    16.073  -2.493 -16.303  1.00 16.19         C
ANISOU 1793  CD1 LEU B 381     1688  2009  2454   -232  -118  -558       C
ATOM   1794  CD2 LEU B 381    18.121  -2.129 -14.860  1.00 18.01         C
ANISOU 1794  CD2 LEU B 381     1969  2193  2680   -196  -161  -527       C
ATOM   1795  C   LEU B 381    19.942   0.175 -16.476  1.00 18.78         C
ANISOU 1795  C   LEU B 381     2006  2334  2794   -262  -216  -491       C
ATOM   1796  O   LEU B 381    20.876  -0.627 -16.374  1.00 18.28         O
ANISOU 1796  O   LEU B 381     1898  2301  2747   -252  -214  -491       O
ATOM   1797  N   VAL B 382    19.839   1.265 -15.730  1.00 19.29         N
ANISOU 1797  N   VAL B 382     2125  2353  2851   -279  -250  -489       N
ATOM   1798  CA  VAL B 382    20.836   1.563 -14.675  1.00 19.54         C
ANISOU 1798  CA  VAL B 382     2167  2377  2881   -314  -304  -493       C
ATOM   1799  CB  VAL B 382    20.934   3.093 -14.380  1.00 20.23         C
ANISOU 1799  CB  VAL B 382     2332  2395  2958   -372  -341  -498       C
ATOM   1800  CG1 VAL B 382    21.928   3.397 -13.238  1.00 19.44         C
ANISOU 1800  CG1 VAL B 382     2249  2295  2842   -433  -418  -518       C
ATOM   1801  CG2 VAL B 382    21.319   3.844 -15.652  1.00 20.85         C
ANISOU 1801  CG2 VAL B 382     2392  2472  3060   -431  -323  -459       C
ATOM   1802  C   VAL B 382    20.465   0.761 -13.431  1.00 19.16         C
ANISOU 1802  C   VAL B 382     2157  2320  2803   -264  -312  -511       C
ATOM   1803  O   VAL B 382    21.273   0.005 -12.911  1.00 20.08         O
ANISOU 1803  O   VAL B 382     2241  2469  2918   -251  -343  -500       O
ATOM   1804  N   GLN B 383    19.221   0.890 -12.992  1.00 18.96         N
ANISOU 1804  N   GLN B 383     2195  2258  2752   -228  -275  -528       N
ATOM   1805  CA  GLN B 383    18.755   0.178 -11.818  1.00 19.44         C
ANISOU 1805  CA  GLN B 383     2306  2311  2769   -193  -258  -534       C
ATOM   1806  CB  GLN B 383    19.339   0.796 -10.539  1.00 20.96         C
ANISOU 1806  CB  GLN B 383     2581  2483  2901   -208  -319  -552       C
ATOM   1807  CG  GLN B 383    18.988   0.003  -9.318  1.00 28.70         C
ANISOU 1807  CG  GLN B 383     3630  3464  3810   -172  -301  -545       C
ATOM   1808  CD  GLN B 383    19.917   0.256  -8.142  1.00 38.33         C
ANISOU 1808  CD  GLN B 383     4920  4691  4951   -190  -395  -552       C
ATOM   1809  OE1 GLN B 383    20.549   1.348  -8.009  1.00 37.76         O
ANISOU 1809  OE1 GLN B 383     4873  4607  4867   -246  -467  -588       O
ATOM   1810  NE2 GLN B 383    20.021  -0.768  -7.272  1.00 39.52         N
ANISOU 1810  NE2 GLN B 383     5116  4861  5041   -153  -403  -515       N
ATOM   1811  C   GLN B 383    17.247   0.146 -11.767  1.00 17.86         C
ANISOU 1811  C   GLN B 383     2121  2104  2562   -158  -184  -546       C
ATOM   1812  O   GLN B 383    16.598   1.075 -12.243  1.00 16.03         O
ANISOU 1812  O   GLN B 383     1886  1860  2344   -140  -169  -556       O
ATOM   1813  N   LEU B 384    16.709  -0.958 -11.236  1.00 17.13         N
ANISOU 1813  N   LEU B 384     2036  2020  2452   -149  -135  -536       N
ATOM   1814  CA  LEU B 384    15.291  -1.124 -11.035  1.00 17.71         C
ANISOU 1814  CA  LEU B 384     2096  2111  2521   -135   -54  -542       C
ATOM   1815  CB  LEU B 384    14.719  -2.032 -12.141  1.00 17.64         C
ANISOU 1815  CB  LEU B 384     2001  2134  2568   -172   -28  -537       C
ATOM   1816  CG  LEU B 384    13.218  -2.392 -12.135  1.00 17.32         C
ANISOU 1816  CG  LEU B 384     1897  2141  2542   -192    47  -541       C
ATOM   1817  CD1 LEU B 384    12.346  -1.239 -12.603  1.00 13.70         C
ANISOU 1817  CD1 LEU B 384     1367  1735  2105   -139    48  -553       C
ATOM   1818  CD2 LEU B 384    12.974  -3.626 -12.969  1.00 18.57         C
ANISOU 1818  CD2 LEU B 384     2013  2307  2737   -267    54  -544       C
ATOM   1819  C   LEU B 384    14.984  -1.751  -9.669  1.00 18.33         C
ANISOU 1819  C   LEU B 384     2251  2179  2533   -132    -1  -529       C
ATOM   1820  O   LEU B 384    15.530  -2.822  -9.331  1.00 18.89         O
ANISOU 1820  O   LEU B 384     2361  2229  2587   -149   -12  -496       O
ATOM   1821  N   ILE B 385    14.075  -1.135  -8.921  1.00 18.21         N
ANISOU 1821  N   ILE B 385     2267  2178  2475    -99    66  -548       N
ATOM   1822  CA  ILE B 385    13.525  -1.725  -7.689  1.00 19.18         C
ANISOU 1822  CA  ILE B 385     2460  2308  2520   -101   151  -530       C
ATOM   1823  CB  ILE B 385    13.787  -0.844  -6.427  1.00 20.69         C
ANISOU 1823  CB  ILE B 385     2787  2478  2597    -54   150  -561       C
ATOM   1824  CG1 ILE B 385    15.258  -0.466  -6.346  1.00 21.44         C
ANISOU 1824  CG1 ILE B 385     2946  2535  2668    -67    10  -570       C
ATOM   1825  CD1 ILE B 385    15.488   0.659  -5.362  1.00 26.55         C
ANISOU 1825  CD1 ILE B 385     3726  3152  3211    -43   -15  -628       C
```

FIGURE 18-55

```
ATOM   1826  CG2 ILE B 385      13.366  -1.580  -5.128  1.00 19.88           C
ANISOU 1826  CG2 ILE B 385     2782  2389  2383   -62    240   -529          C
ATOM   1827  C   ILE B 385      12.005  -1.915  -7.850  1.00 19.64           C
ANISOU 1827  C   ILE B 385     2419  2430  2616  -108    271   -529          C
ATOM   1828  O   ILE B 385      11.281  -0.951  -8.157  1.00 18.63           O
ANISOU 1828  O   ILE B 385     2224  2339  2517   -49    299   -561          O
ATOM   1829  N   VAL B 386      11.540  -3.146  -7.645  1.00 20.36           N
ANISOU 1829  N   VAL B 386     2497  2531  2708  -181    338   -489          N
ATOM   1830  CA  VAL B 386      10.150  -3.524  -7.836  1.00 21.66           C
ANISOU 1830  CA  VAL B 386     2538  2772  2919  -229    446   -483          C
ATOM   1831  CB  VAL B 386       9.994  -4.733  -8.805  1.00 21.60           C
ANISOU 1831  CB  VAL B 386     2463  2755  2991  -344    426   -466          C
ATOM   1832  CG1 VAL B 386       8.493  -5.016  -9.111  1.00 20.69           C
ANISOU 1832  CG1 VAL B 386     2180  2746  2934  -422    516   -468          C
ATOM   1833  CG2 VAL B 386      10.748  -4.499 -10.055  1.00 20.40           C
ANISOU 1833  CG2 VAL B 386     2279  2580  2894  -326    304   -494          C
ATOM   1834  C   VAL B 386       9.522  -3.950  -6.522  1.00 24.28           C
ANISOU 1834  C   VAL B 386     2935  3125  3166  -253    584   -450          C
ATOM   1835  O   VAL B 386      10.124  -4.709  -5.755  1.00 24.69           O
ANISOU 1835  O   VAL B 386     3130  3109  3141  -286    588   -403          O
ATOM   1836  N   SER B 387       8.292  -3.476  -6.306  1.00 26.04           N
ANISOU 1836  N   SER B 387     3043  3448  3401  -229    700   -466          N
ATOM   1837  CA  SER B 387       7.460  -3.856  -5.191  1.00 28.34           C
ANISOU 1837  CA  SER B 387     3353  3793  3620  -262    868   -434          C
ATOM   1838  CB  SER B 387       7.142  -2.619  -4.362  1.00 28.84           C
ANISOU 1838  CB  SER B 387     3457  3899  3602  -119    947   -482          C
ATOM   1839  OG  SER B 387       6.509  -2.975  -3.165  1.00 32.36           O
ANISOU 1839  OG  SER B 387     3957  4394  3942  -143   1122   -451          O
ATOM   1840  C   SER B 387       6.204  -4.454  -5.815  1.00 30.08           C
ANISOU 1840  C   SER B 387     3358  4122  3947  -367    949   -418          C
ATOM   1841  O   SER B 387       5.597  -3.846  -6.691  1.00 30.62           O
ANISOU 1841  O   SER B 387     3245  4280  4109  -323    915   -454          O
ATOM   1842  N   GLY B 388       5.827  -5.658  -5.406  1.00 31.67           N
ANISOU 1842  N   GLY B 388     3582  4316  4136  -517   1043   -359          N
ATOM   1843  CA  GLY B 388       4.716  -6.338  -6.053  1.00 33.63           C
ANISOU 1843  CA  GLY B 388     3625  4660  4491  -666   1099   -348          C
ATOM   1844  C   GLY B 388       3.996  -7.304  -5.157  1.00 36.39           C
ANISOU 1844  C   GLY B 388     3994  5032  4800  -818   1277   -279          C
ATOM   1845  O   GLY B 388       4.534  -7.712  -4.131  1.00 36.83           O
ANISOU 1845  O   GLY B 388     4267  4991  4736  -821   1336   -224          O
ATOM   1846  N   LYS B 389       2.775  -7.660  -5.557  1.00 39.31           N
ANISOU 1846  N   LYS B 389     4131  5538  5266  -952   1358   -276          N
ATOM   1847  CA  LYS B 389       1.905  -8.546  -4.799  1.00 42.59           C
ANISOU 1847  CA  LYS B 389     4517  6004  5664 -1134   1549   -207          C
ATOM   1848  CB  LYS B 389       0.455  -8.392  -5.270  1.00 45.19           C
ANISOU 1848  CB  LYS B 389     4495  6563  6111 -1219   1629   -227          C
ATOM   1849  CG  LYS B 389      -0.202  -7.040  -4.873  1.00 47.63           C
ANISOU 1849  CG  LYS B 389     4629  7059  6410  -998   1722   -262          C
ATOM   1850  CD  LYS B 389      -1.671  -6.960  -5.309  1.00 49.06           C
ANISOU 1850  CD  LYS B 389     4426  7496  6718 -1071   1803   -268          C
ATOM   1851  CE  LYS B 389      -2.366  -5.751  -4.683  1.00 52.41           C
ANISOU 1851  CE  LYS B 389     4699  8096  7120  -834   1950   -290          C
ATOM   1852  NZ  LYS B 389      -3.530  -5.319  -5.518  1.00 55.24           N
ANISOU 1852  NZ  LYS B 389     4659  8702  7629  -803   1926   -313          N
ATOM   1853  C   LYS B 389       2.346 -10.017  -4.832  1.00 42.90           C
ANISOU 1853  C   LYS B 389     4742  5859  5697 -1341   1534   -147          C
ATOM   1854  O   LYS B 389       2.093 -10.748  -3.870  1.00 44.63           O
ANISOU 1854  O   LYS B 389     5079  6036  5842 -1458   1691    -62          O
ATOM   1855  N   ASP B 390       3.002 -10.448  -5.926  1.00 41.86           N
ANISOU 1855  N   ASP B 390     4658  5610  5637 -1378   1356   -187          N
ATOM   1856  CA  ASP B 390       3.552 -11.836  -6.076  1.00 42.33           C
ANISOU 1856  CA  ASP B 390     4930  5455  5698 -1538   1326   -145          C
ATOM   1857  CB  ASP B 390       2.436 -12.859  -6.342  1.00 44.76           C
ANISOU 1857  CB  ASP B 390     5124  5793  6090 -1829   1420   -127          C
ATOM   1858  CG  ASP B 390       1.592 -12.508  -7.561  1.00 44.57           C
ANISOU 1858  CG  ASP B 390     4794  5948  6194 -1903   1333   -218          C
ATOM   1859  OD1 ASP B 390       2.129 -11.946  -8.525  1.00 43.20           O
ANISOU 1859  OD1 ASP B 390     4586  5778  6050 -1774   1162   -293          O
ATOM   1860  OD2 ASP B 390       0.384 -12.797  -7.556  1.00 46.53           O
ANISOU 1860  OD2 ASP B 390     4828  6344  6507 -2095   1432   -208          O
ATOM   1861  C   ASP B 390       4.666 -11.971  -7.140  1.00 40.43           C
```

FIGURE 18-56

```
ANISOU 1861  C    ASP B 390    4791   5075   5495  -1464   1126   -205        C
ATOM   1862  O    ASP B 390       4.998 -10.988  -7.788  1.00 39.18           O
ANISOU 1862  O    ASP B 390    4534   4994   5360  -1312   1011   -272        O
ATOM   1863  N    GLU B 391       5.221 -13.178  -7.325  1.00 40.63           N
ANISOU 1863  N    GLU B 391    5020   4893   5525  -1566   1099   -179        N
ATOM   1864  CA   GLU B 391       6.313 -13.425  -8.304  1.00 39.14           C
ANISOU 1864  CA   GLU B 391    4939   4566   5365  -1487    939   -236        C
ATOM   1865  CB   GLU B 391       6.913 -14.847  -8.174  1.00 40.09           C
ANISOU 1865  CB   GLU B 391    5332   4428   5474  -1569    953   -186        C
ATOM   1866  CG   GLU B 391       8.099 -14.930  -7.176  1.00 40.49           C
ANISOU 1866  CG   GLU B 391    5615   4348   5420  -1384    945    -95        C
ATOM   1867  CD   GLU B 391       8.475 -16.353  -6.733  1.00 43.04           C
ANISOU 1867  CD   GLU B 391    6221   4416   5717  -1454    995     -5        C
ATOM   1868  OE1  GLU B 391       8.222 -17.326  -7.492  1.00 45.74           O
ANISOU 1868  OE1  GLU B 391    6626   4619   6135  -1610    998    -44        O
ATOM   1869  OE2  GLU B 391       9.052 -16.495  -5.615  1.00 44.91           O
ANISOU 1869  OE2  GLU B 391    6636   4581   5848  -1347   1025    106        O
ATOM   1870  C    GLU B 391       5.964 -13.106  -9.762  1.00 38.03           C
ANISOU 1870  C    GLU B 391    4609   4525   5316  -1529    824   -347        C
ATOM   1871  O    GLU B 391       6.794 -12.544 -10.477  1.00 36.08           O
ANISOU 1871  O    GLU B 391    4365   4273   5069  -1380    701   -400        O
ATOM   1872  N    GLN B 392       4.750 -13.463 -10.192  1.00 39.60           N
ANISOU 1872  N    GLN B 392    4640   4822   5583  -1740    863   -375        N
ATOM   1873  CA   GLN B 392       4.252 -13.121 -11.535  1.00 38.76           C
ANISOU 1873  CA   GLN B 392    4333   4849   5544  -1791    743   -474        C
ATOM   1874  CB   GLN B 392       2.892 -13.797 -11.814  1.00 42.01           C
ANISOU 1874  CB   GLN B 392    4577   5357   6027  -2076    791   -493        C
ATOM   1875  CG   GLN B 392       2.290 -13.588 -13.235  1.00 44.80           C
ANISOU 1875  CG   GLN B 392    4722   5861   6437  -2162    643   -595        C
ATOM   1876  CD   GLN B 392       3.258 -13.942 -14.391  1.00 51.20           C
ANISOU 1876  CD   GLN B 392    5712   6521   7222  -2125    497   -682        C
ATOM   1877  OE1  GLN B 392       4.031 -14.910 -14.311  1.00 53.93           O
ANISOU 1877  OE1  GLN B 392    6326   6621   7545  -2163    520   -686        O
ATOM   1878  NE2  GLN B 392       3.209 -13.147 -15.476  1.00 51.38           N
ANISOU 1878  NE2  GLN B 392    5589   6692   7241  -2037    355   -747        N
ATOM   1879  C    GLN B 392       4.181 -11.602 -11.782  1.00 36.21           C
ANISOU 1879  C    GLN B 392    3816   4724   5219  -1585    678   -496        C
ATOM   1880  O    GLN B 392       4.634 -11.118 -12.828  1.00 34.96           O
ANISOU 1880  O    GLN B 392    3629   4588   5067  -1495    542   -558        O
ATOM   1881  N    SER B 393       3.649 -10.860 -10.813  1.00 34.95           N
ANISOU 1881  N    SER B 393    3549   4690   5041  -1504    785   -445        N
ATOM   1882  CA   SER B 393       3.519  -9.411 -10.941  1.00 33.17           C
ANISOU 1882  CA   SER B 393    3168   4622   4815  -1299    742   -464        C
ATOM   1883  CB   SER B 393       2.667  -8.847  -9.825  1.00 34.13           C
ANISOU 1883  CB   SER B 393    3167   4880   4919  -1250    901   -417        C
ATOM   1884  OG   SER B 393       1.467  -9.579  -9.745  1.00 38.87           O
ANISOU 1884  OG   SER B 393    3599   5590   5579  -1467    999   -399        O
ATOM   1885  C    SER B 393       4.865  -8.711 -10.949  1.00 30.03           C
ANISOU 1885  C    SER B 393    2939   4115   4358  -1091    657   -471        C
ATOM   1886  O    SER B 393       5.056  -7.742 -11.689  1.00 28.60           O
ANISOU 1886  O    SER B 393    2679   3999   4189   -962    554   -508        O
ATOM   1887  N    ILE B 394       5.786  -9.209 -10.124  1.00 28.74           N
ANISOU 1887  N    ILE B 394    3005   3789   4128  -1066    696   -428        N
ATOM   1888  CA   ILE B 394       7.140  -8.694 -10.082  1.00 26.95           C
ANISOU 1888  CA   ILE B 394    2927   3464   3849   -898    609   -432        C
ATOM   1889  CB   ILE B 394       7.945  -9.231  -8.866  1.00 27.07           C
ANISOU 1889  CB   ILE B 394    3165   3341   3778   -867    665   -365        C
ATOM   1890  CG1  ILE B 394       7.375  -8.668  -7.560  1.00 27.49           C
ANISOU 1890  CG1  ILE B 394    3213   3475   3757   -823    791   -323        C
ATOM   1891  CD1  ILE B 394       7.721  -9.498  -6.320  1.00 30.31           C
ANISOU 1891  CD1  ILE B 394    3780   3722   4015   -857    877   -236        C
ATOM   1892  CG2  ILE B 394       9.424  -8.817  -8.994  1.00 25.51           C
ANISOU 1892  CG2  ILE B 394    3088   3060   3545   -716    547   -374        C
ATOM   1893  C    ILE B 394       7.863  -8.944 -11.412  1.00 25.54           C
ANISOU 1893  C    ILE B 394    2774   3223   3709   -900    476   -486        C
ATOM   1894  O    ILE B 394       8.505  -8.056 -11.939  1.00 24.61           O
ANISOU 1894  O    ILE B 394    2639   3128   3585   -774    387   -513        O
ATOM   1895  N    ALA B 395       7.737 -10.156 -11.945  1.00 26.28           N
ANISOU 1895  N    ALA B 395    2921   3231   3834  -1051    474   -504        N
ATOM   1896  CA   ALA B 395       8.278 -10.524 -13.247  1.00 25.51           C
ANISOU 1896  CA   ALA B 395    2857   3077   3758  -1069    369   -571        C
```

FIGURE 18-57

```
ATOM   1897  CB  ALA B 395       8.021 -12.026 -13.536  1.00 26.45           C
ANISOU 1897  CB  ALA B 395    3085   3062   3901  -1258    400   -593        C
ATOM   1898  C   ALA B 395       7.733  -9.662 -14.399  1.00 24.95           C
ANISOU 1898  C   ALA B 395    2600   3169   3712  -1056    277   -628        C
ATOM   1899  O   ALA B 395       8.500  -9.203 -15.243  1.00 22.82           O
ANISOU 1899  O   ALA B 395    2354   2893   3424   -962    190   -660        O
ATOM   1900  N   GLU B 396       6.413  -9.463 -14.442  1.00 26.63           N
ANISOU 1900  N   GLU B 396    2622   3534   3962  -1148    299   -631        N
ATOM   1901  CA  GLU B 396       5.790  -8.559 -15.438  1.00 27.37           C
ANISOU 1901  CA  GLU B 396    2521   3803   4073  -1108    201   -664        C
ATOM   1902  CB  GLU B 396       4.277  -8.475 -15.213  1.00 29.22           C
ANISOU 1902  CB  GLU B 396    2520   4221   4361  -1205    245   -652        C
ATOM   1903  CG  GLU B 396       3.527  -9.794 -15.523  1.00 32.18           C
ANISOU 1903  CG  GLU B 396    2860   4592   4773  -1475    256   -688        C
ATOM   1904  CD  GLU B 396       2.066  -9.807 -15.029  1.00 35.39           C
ANISOU 1904  CD  GLU B 396    3014   5189   5242  -1595    335   -660        C
ATOM   1905  OE1 GLU B 396       1.642  -8.836 -14.337  1.00 37.14           O
ANISOU 1905  OE1 GLU B 396    3100   5536   5475  -1443    406   -611        O
ATOM   1906  OE2 GLU B 396       1.350 -10.800 -15.323  1.00 36.33           O
ANISOU 1906  OE2 GLU B 396    3073   5331   5402  -1846    335   -690        O
ATOM   1907  C   GLU B 396       6.422  -7.145 -15.460  1.00 25.68           C
ANISOU 1907  C   GLU B 396    2306   3621   3832   -885    157   -642        C
ATOM   1908  O   GLU B 396       6.720  -6.591 -16.526  1.00 25.72           O
ANISOU 1908  O   GLU B 396    2290   3663   3819   -824     51   -666        O
ATOM   1909  N   ALA B 397       6.661  -6.577 -14.284  1.00 24.70           N
ANISOU 1909  N   ALA B 397    2225   3468   3690   -776    239   -596        N
ATOM   1910  CA  ALA B 397       7.333  -5.290 -14.153  1.00 22.65           C
ANISOU 1910  CA  ALA B 397    2004   3200   3402   -591    205   -582        C
ATOM   1911  CB  ALA B 397       7.298  -4.867 -12.714  1.00 23.05           C
ANISOU 1911  CB  ALA B 397    2103   3231   3422   -516    311   -548        C
ATOM   1912  C   ALA B 397       8.789  -5.313 -14.662  1.00 21.56           C
ANISOU 1912  C   ALA B 397    2019   2943   3231   -547    131   -594        C
ATOM   1913  O   ALA B 397       9.232  -4.375 -15.328  1.00 21.06           O
ANISOU 1913  O   ALA B 397    1949   2897   3156   -455     60   -597        O
ATOM   1914  N   ILE B 398       9.536  -6.365 -14.321  1.00 20.90           N
ANISOU 1914  N   ILE B 398    2071   2737   3132   -604    158   -592        N
ATOM   1915  CA  ILE B 398      10.913  -6.523 -14.788  1.00 20.40           C
ANISOU 1915  CA  ILE B 398    2124   2579   3048   -554    103   -603        C
ATOM   1916  CB  ILE B 398      11.619  -7.735 -14.116  1.00 20.53           C
ANISOU 1916  CB  ILE B 398    2288   2459   3053   -583    148   -585        C
ATOM   1917  CG1 ILE B 398      11.713  -7.536 -12.597  1.00 20.53           C
ANISOU 1917  CG1 ILE B 398    2348   2434   3017   -534    206   -527        C
ATOM   1918  CD1 ILE B 398      12.047  -8.805 -11.842  1.00 22.94           C
ANISOU 1918  CD1 ILE B 398    2798   2613   3304   -574    257   -485        C
ATOM   1919  CG2 ILE B 398      13.040  -7.930 -14.677  1.00 20.38           C
ANISOU 1919  CG2 ILE B 398    2352   2365   3024   -509     97   -598        C
ATOM   1920  C   ILE B 398      10.967  -6.589 -16.325  1.00 20.24           C
ANISOU 1920  C   ILE B 398    2065   2595   3029   -586     28   -652        C
ATOM   1921  O   ILE B 398      11.740  -5.886 -16.951  1.00 20.94           O
ANISOU 1921  O   ILE B 398    2167   2693   3098   -509    -23   -654        O
ATOM   1922  N   ILE B 399      10.109  -7.406 -16.920  1.00 21.51           N
ANISOU 1922  N   ILE B 399    2184   2784   3204   -714     22   -692        N
ATOM   1923  CA  ILE B 399      10.015  -7.555 -18.364  1.00 20.76           C
ANISOU 1923  CA  ILE B 399    2067   2736   3085   -764    -55   -750        C
ATOM   1924  CB  ILE B 399       8.910  -8.566 -18.768  1.00 21.63           C
ANISOU 1924  CB  ILE B 399    2131   2876   3211   -946    -65   -802        C
ATOM   1925  CG1 ILE B 399       9.288  -9.984 -18.311  1.00 22.66           C
ANISOU 1925  CG1 ILE B 399    2424   2832   3354  -1040      7   -825        C
ATOM   1926  CD1 ILE B 399       8.135 -11.012 -18.342  1.00 22.92           C
ANISOU 1926  CD1 ILE B 399    2427   2865   3418  -1259     24   -864        C
ATOM   1927  CG2 ILE B 399       8.658  -8.506 -20.279  1.00 19.65           C
ANISOU 1927  CG2 ILE B 399    1844   2714   2910   -995   -171   -865        C
ATOM   1928  C   ILE B 399       9.770  -6.221 -19.068  1.00 21.46           C
ANISOU 1928  C   ILE B 399    2050   2953   3152   -676   -131   -730        C
ATOM   1929  O   ILE B 399      10.477  -5.901 -20.019  1.00 21.12           O
ANISOU 1929  O   ILE B 399    2054   2908   3061   -632   -180   -743        O
ATOM   1930  N   VAL B 400       8.760  -5.470 -18.605  1.00 22.28           N
ANISOU 1930  N   VAL B 400    2017   3161   3287   -643   -129   -693        N
ATOM   1931  CA  VAL B 400       8.423  -4.134 -19.122  1.00 21.58           C
ANISOU 1931  CA  VAL B 400    1838   3175   3186   -529   -194   -658        C
ATOM   1932  CB  VAL B 400       7.122  -3.570 -18.448  1.00 22.39           C
```

FIGURE 18-58

```
ANISOU 1932  CB  VAL B 400    1773  3394  3339  -487  -166  -626           C
ATOM   1933  CG1 VAL B 400       6.830  -2.142 -18.873  1.00 21.87         C
ANISOU 1933  CG1 VAL B 400    1642  3400  3267  -328  -226  -580           C
ATOM   1934  CG2 VAL B 400       5.918  -4.465 -18.794  1.00 22.46         C
ANISOU 1934  CG2 VAL B 400    1633  3525  3378  -639  -188  -659           C
ATOM   1935  C   VAL B 400       9.588  -3.144 -19.029  1.00 20.81         C
ANISOU 1935  C   VAL B 400    1846  2997  3063  -403  -194  -622           C
ATOM   1936  O   VAL B 400       9.846  -2.400 -19.974  1.00 21.60         O
ANISOU 1936  O   VAL B 400    1956  3127  3125  -349  -261  -603           O
ATOM   1937  N   ALA B 401      10.301  -3.154 -17.909  1.00 20.61         N
ANISOU 1937  N   ALA B 401    1904  2873  3052  -370  -125  -610           N
ATOM   1938  CA  ALA B 401      11.458  -2.262 -17.687  1.00 19.84         C
ANISOU 1938  CA  ALA B 401    1899  2702  2937  -283  -131  -583           C
ATOM   1939  CB  ALA B 401      11.879  -2.301 -16.225  1.00 19.17         C
ANISOU 1939  CB  ALA B 401    1879  2544  2860  -259   -68  -573           C
ATOM   1940  C   ALA B 401      12.637  -2.629 -18.608  1.00 19.90         C
ANISOU 1940  C   ALA B 401    1979  2670  2913  -310  -158  -597           C
ATOM   1941  O   ALA B 401      13.278  -1.758 -19.177  1.00 18.35         O
ANISOU 1941  O   ALA B 401    1809  2471  2693  -267  -189  -571           O
ATOM   1942  N   MSE B 402      12.894  -3.931 -18.781  1.00 20.40         N
ANISOU 1942  N   MSE B 402    2079  2699  2974  -381  -136  -638           N
ATOM   1943  CA  MSE B 402      13.954  -4.385 -19.707  1.00 20.55         C
ANISOU 1943  CA  MSE B 402    2161  2687  2958  -388  -140  -664           C
ATOM   1944  CB  MSE B 402      14.214  -5.888 -19.546  1.00 21.32         C
ANISOU 1944  CB  MSE B 402    2329  2705  3066  -438   -96  -712           C
ATOM   1945  CG  MSE B 402      14.859  -6.269 -18.205  1.00 19.84         C
ANISOU 1945  CG  MSE B 402    2193  2430  2916  -395   -51  -679           C
ATOM   1946  SE  MSE B 402      15.005  -8.198 -18.086  0.90 23.84        SE
ANISOU 1946  SE  MSE B 402    2821  2801  3435  -446     4  -723          SE
ATOM   1947  CE  MSE B 402      16.111  -8.378 -16.488  1.00 20.10         C
ANISOU 1947  CE  MSE B 402    2411  2243  2983  -338    29  -648           C
ATOM   1948  C   MSE B 402      13.680  -4.012 -21.179  1.00 20.87         C
ANISOU 1948  C   MSE B 402    2183  2810  2939  -405  -194  -677           C
ATOM   1949  O   MSE B 402      14.567  -3.492 -21.882  1.00 21.13         O
ANISOU 1949  O   MSE B 402    2248  2848  2930  -371  -196  -660           O
ATOM   1950  N   VAL B 403      12.449  -4.240 -21.642  1.00 20.78         N
ANISOU 1950  N   VAL B 403    2109  2873  2913  -463  -241  -701           N
ATOM   1951  CA  VAL B 403      12.053  -3.857 -22.988  1.00 19.97         C
ANISOU 1951  CA  VAL B 403    1987  2866  2733  -475  -317  -705           C
ATOM   1952  CB  VAL B 403      10.621  -4.369 -23.365  1.00 21.28         C
ANISOU 1952  CB  VAL B 403    2060  3133  2892  -566  -386  -744           C
ATOM   1953  CG1 VAL B 403      10.175  -3.778 -24.723  1.00 21.74         C
ANISOU 1953  CG1 VAL B 403    2093  3315  2853  -556  -494  -730           C
ATOM   1954  CG2 VAL B 403      10.574  -5.860 -23.429  1.00 19.64         C
ANISOU 1954  CG2 VAL B 403    1912  2867  2684  -694  -358  -835           C
ATOM   1955  C   VAL B 403      12.131  -2.338 -23.143  1.00 19.26         C
ANISOU 1955  C   VAL B 403    1877  2811  2630  -375  -351  -621           C
ATOM   1956  O   VAL B 403      12.691  -1.835 -24.114  1.00 18.91         O
ANISOU 1956  O   VAL B 403    1888  2786  2512  -354  -371  -595           O
ATOM   1957  N   PHE B 404      11.588  -1.610 -22.163  1.00 18.84         N
ANISOU 1957  N   PHE B 404    1763  2752  2642  -312  -343  -577           N
ATOM   1958  CA  PHE B 404      11.582  -0.161 -22.194  1.00 18.40         C
ANISOU 1958  CA  PHE B 404    1716  2693  2584  -208  -369  -502           C
ATOM   1959  CB  PHE B 404      10.817   0.351 -20.968  1.00 18.31         C
ANISOU 1959  CB  PHE B 404    1642  2669  2645  -138  -339  -486           C
ATOM   1960  CG  PHE B 404      10.743   1.833 -20.875  1.00 18.13         C
ANISOU 1960  CG  PHE B 404    1654  2608  2627   -16  -355  -420           C
ATOM   1961  CD1 PHE B 404       9.712   2.526 -21.510  1.00 21.57         C
ANISOU 1961  CD1 PHE B 404    2019  3125  3050    75  -424  -372           C
ATOM   1962  CE1 PHE B 404       9.623   3.911 -21.415  1.00 19.89         C
ANISOU 1962  CE1 PHE B 404    1867  2845  2845   209  -433  -306           C
ATOM   1963  CZ  PHE B 404      10.559   4.622 -20.695  1.00 19.02         C
ANISOU 1963  CZ  PHE B 404    1892  2583  2751   222  -377  -301           C
ATOM   1964  CE2 PHE B 404      11.600   3.964 -20.055  1.00 17.62         C
ANISOU 1964  CE2 PHE B 404    1765  2349  2583   115  -323  -353           C
ATOM   1965  CD2 PHE B 404      11.686   2.554 -20.149  1.00 18.96         C
ANISOU 1965  CD2 PHE B 404    1868  2590  2748    11  -311  -406           C
ATOM   1966  C   PHE B 404      13.000   0.452 -22.282  1.00 17.86         C
ANISOU 1966  C   PHE B 404    1756  2534  2495  -193  -334  -470           C
ATOM   1967  O   PHE B 404      13.187   1.520 -22.880  1.00 18.45         O
ANISOU 1967  O   PHE B 404    1877  2601  2533  -147  -362  -406           O
```

FIGURE 18-59

```
ATOM   1968  N   SER B 405      13.981  -0.215 -21.670  1.00 17.56           N
ANISOU 1968  N   SER B 405     1754   2433   2485    -234    -273    -506    N
ATOM   1969  CA  SER B 405      15.373   0.264 -21.614  1.00 17.50           C
ANISOU 1969  CA  SER B 405     1807   2365   2476    -236    -240    -480    C
ATOM   1970  CB  SER B 405      16.229  -0.605 -20.689  1.00 17.20           C
ANISOU 1970  CB  SER B 405     1772   2280   2483    -256    -192    -518    C
ATOM   1971  OG  SER B 405      16.462  -1.911 -21.262  1.00 20.67           O
ANISOU 1971  OG  SER B 405     2216   2738   2901    -289    -164    -571    O
ATOM   1972  C   SER B 405      16.025   0.316 -22.998  1.00 17.94           C
ANISOU 1972  C   SER B 405     1898   2462   2456    -265    -235    -464    C
ATOM   1973  O   SER B 405      16.989   1.044 -23.203  1.00 18.90           O
ANISOU 1973  O   SER B 405     2055   2558   2568    -275    -210    -418    O
ATOM   1974  N   GLN B 406      15.494  -0.461 -23.935  1.00 18.28           N
ANISOU 1974  N   GLN B 406     1937   2573   2437    -291    -256    -504    N
ATOM   1975  CA  GLN B 406      16.000  -0.549 -25.304  1.00 19.28           C
ANISOU 1975  CA  GLN B 406     2116   2752   2458    -318    -243    -503    C
ATOM   1976  CB  GLN B 406      15.955   0.817 -25.999  1.00 19.35           C
ANISOU 1976  CB  GLN B 406     2167   2777   2406    -291    -278    -404    C
ATOM   1977  CG  GLN B 406      14.532   1.352 -26.113  1.00 20.49           C
ANISOU 1977  CG  GLN B 406     2281   2965   2539    -240    -379    -367    C
ATOM   1978  CD  GLN B 406      14.456   2.710 -26.785  1.00 22.34           C
ANISOU 1978  CD  GLN B 406     2584   3192   2713    -188    -418    -254    C
ATOM   1979  OE1 GLN B 406      15.224   3.623 -26.471  1.00 20.91           O
ANISOU 1979  OE1 GLN B 406     2462   2918   2562    -184    -372    -193    O
ATOM   1980  NE2 GLN B 406      13.519   2.849 -27.714  1.00 20.46           N
ANISOU 1980  NE2 GLN B 406     2345   3047   2383    -154    -512    -221    N
ATOM   1981  C   GLN B 406      17.374  -1.207 -25.426  1.00 19.38           C
ANISOU 1981  C   GLN B 406     2150   2743   2469    -335    -149    -539    C
ATOM   1982  O   GLN B 406      18.039  -1.028 -26.432  1.00 21.03           O
ANISOU 1982  O   GLN B 406     2400   2994   2595    -348    -107    -522    O
ATOM   1983  N   GLU B 407      17.781  -1.976 -24.415  1.00 18.80           N
ANISOU 1983  N   GLU B 407     2049   2614   2481    -325    -113    -581    N
ATOM   1984  CA  GLU B 407      19.109  -2.576 -24.370  1.00 19.09           C
ANISOU 1984  CA  GLU B 407     2080   2636   2537    -307     -30    -605    C
ATOM   1985  CB  GLU B 407      19.365  -3.321 -23.048  1.00 18.52           C
ANISOU 1985  CB  GLU B 407     1981   2495   2561    -275     -21    -629    C
ATOM   1986  CG  GLU B 407      19.622  -2.433 -21.859  1.00 18.23           C
ANISOU 1986  CG  GLU B 407     1904   2432   2593    -268     -55    -571    C
ATOM   1987  CD  GLU B 407      20.657  -2.959 -20.879  1.00 20.08           C
ANISOU 1987  CD  GLU B 407     2101   2638   2890    -228     -36    -571    C
ATOM   1988  OE1 GLU B 407      21.347  -3.968 -21.157  1.00 24.36           O
ANISOU 1988  OE1 GLU B 407     2638   3181   3437    -183      17    -605    O
ATOM   1989  OE2 GLU B 407      20.803  -2.340 -19.816  1.00 15.98           O
ANISOU 1989  OE2 GLU B 407     1565   2098   2410    -232     -77    -538    O
ATOM   1990  C   GLU B 407      19.347  -3.519 -25.533  1.00 20.61           C
ANISOU 1990  C   GLU B 407     2328   2862   2643    -309      25    -675    C
ATOM   1991  O   GLU B 407      18.464  -4.263 -25.933  1.00 20.40           O
ANISOU 1991  O   GLU B 407     2351   2831   2570    -338      -7    -741    O
ATOM   1992  N   ASP B 408      20.557  -3.455 -26.078  1.00 21.85           N
ANISOU 1992  N   ASP B 408     2473   3056   2773    -287     113    -666    N
ATOM   1993  CA  ASP B 408      20.990  -4.385 -27.121  1.00 23.75           C
ANISOU 1993  CA  ASP B 408     2775   3323   2925    -264     199    -744    C
ATOM   1994  CB  ASP B 408      22.417  -4.035 -27.600  1.00 24.31           C
ANISOU 1994  CB  ASP B 408     2792   3464   2982    -234     316    -708    C
ATOM   1995  CG  ASP B 408      22.868  -4.897 -28.750  1.00 28.24           C
ANISOU 1995  CG  ASP B 408     3363   3999   3369    -193     429    -792    C
ATOM   1996  OD1 ASP B 408      22.218  -4.835 -29.818  1.00 30.42           O
ANISOU 1996  OD1 ASP B 408     3745   4314   3501    -240     412    -821    O
ATOM   1997  OD2 ASP B 408      23.858  -5.658 -28.585  1.00 29.98           O
ANISOU 1997  OD2 ASP B 408     3540   4212   3639    -103     531    -834    O
ATOM   1998  C   ASP B 408      20.919  -5.851 -26.691  1.00 23.93           C
ANISOU 1998  C   ASP B 408     2843   3258   2993    -219     222    -841    C
ATOM   1999  O   ASP B 408      20.644  -6.717 -27.523  1.00 26.33           O
ANISOU 1999  O   ASP B 408     3249   3545   3209    -226     252    -934    O
ATOM   2000  N   ACYS B 409     21.157  -6.152 -25.422  0.50 23.03           N
ANISOU 2000  N   ACYS B 409    2677   3074   2999    -178     208    -820    N
ATOM   2001  N   BCYS B 409     21.192  -6.118 -25.410  0.50 23.70           N
ANISOU 2001  N   BCYS B 409    2758   3161   3085    -177     209    -817    N
ATOM   2002  CA  ACYS B 409     21.117  -7.552 -25.013  0.50 23.05           C
ANISOU 2002  CA  ACYS B 409    2751   2969   3040    -130     237    -894    C
ATOM   2003  CA  BCYS B 409     21.114  -7.471 -24.832  0.50 24.45           C
```

FIGURE 18-60

```
ANISOU 2003  CA  BCYS B 409    2916  3144  3231   -129   228  -883       C
ATOM   2004  CB  ACYS B 409   21.870  -7.779 -23.708  0.50 22.54         C
ANISOU 2004  CB  ACYS B 409    2619  2853  3090   -46    240  -844       C
ATOM   2005  CB  BCYS B 409   21.537  -7.471 -23.355  0.50 23.66         C
ANISOU 2005  CB  BCYS B 409    2747  2996  3247   -76    201  -820       C
ATOM   2006  SG  ACYS B 409   20.881  -7.846 -22.247  0.50 20.66         S
ANISOU 2006  SG  ACYS B 409    2393  2533  2922   -91    150  -805       S
ATOM   2007  SG  BCYS B 409   23.267  -7.970 -23.032  0.50 30.51         S
ANISOU 2007  SG  BCYS B 409    3537  3875  4180    76    284  -802       S
ATOM   2008  C   ACYS B 409   19.678  -8.084 -24.950  0.50 23.04         C
ANISOU 2008  C   ACYS B 409    2832  2904  3018  -222    165  -946       C
ATOM   2009  C   BCYS B 409   19.704  -8.048 -24.956  0.50 23.79         C
ANISOU 2009  C   BCYS B 409    2924  3003  3114  -220    166  -944       C
ATOM   2010  O   ACYS B 409   19.462  -9.292 -25.088  0.50 23.63         O
ANISOU 2010  O   ACYS B 409    3015  2881  3084  -225    195 -1031       O
ATOM   2011  O   BCYS B 409   19.535  -9.243 -25.224  0.50 24.43         O
ANISOU 2011  O   BCYS B 409    3115  2992  3174  -221    200 -1033       O
ATOM   2012  N   MSE  B 410   18.715  -7.174 -24.763  1.00 22.13         N
ANISOU 2012  N   MSE  B 410    2663  2845  2900  -296     77  -895       N
ATOM   2013  CA  MSE  B 410   17.291  -7.506 -24.815  1.00 22.65         C
ANISOU 2013  CA  MSE  B 410    2756  2901  2947  -395      4  -935       C
ATOM   2014  CB  MSE  B 410   16.469  -6.363 -24.180  1.00 22.12         C
ANISOU 2014  CB  MSE  B 410    2589  2896  2920  -418    -73  -851       C
ATOM   2015  CG  MSE  B 410   14.919  -6.489 -24.305  1.00 23.37         C
ANISOU 2015  CG  MSE  B 410    2717  3098  3064  -513   -154  -876       C
ATOM   2016  SE  MSE  B 410   14.089  -5.800 -25.963  0.90 26.60        SE
ANISOU 2016  SE  MSE  B 410    3114  3662  3331  -562   -257  -885       SE
ATOM   2017  CE  MSE  B 410   14.915  -4.026 -25.917  1.00 18.43         C
ANISOU 2017  CE  MSE  B 410    2040  2665  2297  -451   -245  -752       C
ATOM   2018  C   MSE  B 410   16.832  -7.795 -26.261  1.00 24.21         C
ANISOU 2018  C   MSE  B 410    3030  3154  3015  -459    -18 -1015       C
ATOM   2019  O   MSE  B 410   16.097  -8.758 -26.507  1.00 26.05         O
ANISOU 2019  O   MSE  B 410    3337  3340  3223  -543    -42 -1103       O
ATOM   2020  N   ILE  B 411   17.279  -6.966 -27.209  1.00 23.73         N
ANISOU 2020  N   ILE  B 411    2964  3190  2862  -434    -10  -984       N
ATOM   2021  CA  ILE  B 411   16.968  -7.127 -28.621  1.00 24.58         C
ANISOU 2021  CA  ILE  B 411    3159  3368  2813  -484    -31 -1049       C
ATOM   2022  CB  ILE  B 411   17.364  -5.833 -29.388  1.00 25.91         C
ANISOU 2022  CB  ILE  B 411    3303  3651  2892  -455    -32  -956       C
ATOM   2023  CG1 ILE  B 411   16.275  -4.775 -29.197  1.00 25.08         C
ANISOU 2023  CG1 ILE  B 411    3119  3612  2799  -483   -161  -866       C
ATOM   2024  CD1 ILE  B 411   16.743  -3.369 -29.342  1.00 27.19         C
ANISOU 2024  CD1 ILE  B 411    3355  3923  3051  -438   -154  -740       C
ATOM   2025  CG2 ILE  B 411   17.488  -6.094 -30.859  1.00 27.26         C
ANISOU 2025  CG2 ILE  B 411    3593  3891  2874  -479     -9 -1022       C
ATOM   2026  C   ILE  B 411   17.630  -8.389 -29.207  1.00 25.31         C
ANISOU 2026  C   ILE  B 411    3387  3383  2845  -464     69 -1174       C
ATOM   2027  O   ILE  B 411   17.036  -9.078 -30.020  1.00 25.74         O
ANISOU 2027  O   ILE  B 411    3553  3436  2793  -541     34 -1280       O
ATOM   2028  N   LYS  B 412   18.851  -8.695 -28.771  1.00 24.46         N
ANISOU 2028  N   LYS  B 412    3273  3215  2808  -354    188 -1167       N
ATOM   2029  CA  LYS  B 412   19.531  -9.938 -29.166  1.00 25.83         C
ANISOU 2029  CA  LYS  B 412    3574  3291  2950  -290    300 -1283       C
ATOM   2030  CB  LYS  B 412   21.037  -9.850 -28.886  1.00 25.21         C
ANISOU 2030  CB  LYS  B 412    3423  3220  2935  -138    430 -1237       C
ATOM   2031  CG  LYS  B 412   21.773  -8.806 -29.742  1.00 23.92         C
ANISOU 2031  CG  LYS  B 412    3193  3213  2684  -119    493 -1176       C
ATOM   2032  CD  LYS  B 412   21.678  -9.165 -31.220  1.00 22.65         C
ANISOU 2032  CD  LYS  B 412    3183  3097  2327  -142    550 -1280       C
ATOM   2033  CE  LYS  B 412   22.511  -8.236 -32.094  1.00 20.84         C
ANISOU 2033  CE  LYS  B 412    2906  3018  1995  -121    647 -1213       C
ATOM   2034  NZ  LYS  B 412   21.948  -6.857 -32.071  1.00 20.43         N
ANISOU 2034  NZ  LYS  B 412    2781  3055  1928  -215    534 -1081       N
ATOM   2035  C   LYS  B 412   18.949 -11.213 -28.536  1.00 26.84         C
ANISOU 2035  C   LYS  B 412    3802  3249  3147  -329    281 -1365       C
ATOM   2036  O   LYS  B 412   19.226 -12.299 -29.012  1.00 28.99         O
ANISOU 2036  O   LYS  B 412    4229  3413  3371  -300    355 -1482       O
ATOM   2037  N   ALA  B 413   18.131 -11.068 -27.497  1.00 26.02         N
ANISOU 2037  N   ALA  B 413    3625  3115  3145  -398    193 -1304       N
ATOM   2038  CA  ALA  B 413   17.459 -12.202 -26.858  1.00 27.44         C
ANISOU 2038  CA  ALA  B 413    3899  3138  3389  -471    177 -1361       C
```

FIGURE 18-61

```
ATOM   2039  CB  ALA B 413      17.107 -11.851 -25.376  1.00 25.11           C
ANISOU 2039  CB  ALA B 413     3488   2823   3229   -476    137  -1246       C
ATOM   2040  C   ALA B 413      16.215 -12.670 -27.635  1.00 29.24           C
ANISOU 2040  C   ALA B 413     4212   3372   3526   -653     93  -1466       C
ATOM   2041  O   ALA B 413      15.635 -13.725 -27.336  1.00 30.83           O
ANISOU 2041  O   ALA B 413     4521   3433   3761   -753     87  -1536       O
ATOM   2042  N   VAL B 414      15.801 -11.893 -28.634  1.00 30.33           N
ANISOU 2042  N   VAL B 414     4307   3674   3544   -707     19  -1472       N
ATOM   2043  CA  VAL B 414      14.651 -12.269 -29.456  1.00 31.87           C
ANISOU 2043  CA  VAL B 414     4563   3912   3634   -882    -88  -1572       C
ATOM   2044  CB  VAL B 414      14.201 -11.126 -30.389  1.00 31.88           C
ANISOU 2044  CB  VAL B 414     4477   4127   3508   -905   -194  -1526       C
ATOM   2045  CG1 VAL B 414      13.206 -11.626 -31.408  1.00 31.91           C
ANISOU 2045  CG1 VAL B 414     4563   4190   3369  -1074   -313  -1646       C
ATOM   2046  CG2 VAL B 414      13.590 -10.006 -29.588  1.00 28.46           C
ANISOU 2046  CG2 VAL B 414     3837   3799   3177   -893   -273  -1380       C
ATOM   2047  C   VAL B 414      14.958 -13.532 -30.257  1.00 35.11           C
ANISOU 2047  C   VAL B 414     5209   4187   3946   -914    -25  -1742       C
ATOM   2048  O   VAL B 414      16.029 -13.670 -30.835  1.00 35.73           O
ANISOU 2048  O   VAL B 414     5385   4238   3952   -784     89  -1784       O
ATOM   2049  N   ARG B 415      14.009 -14.465 -30.261  1.00 37.91           N
ANISOU 2049  N   ARG B 415     5655   4449   4300  -1095    -89  -1844       N
ATOM   2050  CA  ARG B 415      14.141 -15.699 -31.006  1.00 40.89           C
ANISOU 2050  CA  ARG B 415     6289   4669   4580  -1157    -43  -2026       C
ATOM   2051  CB  ARG B 415      14.084 -16.913 -30.063  1.00 42.00           C
ANISOU 2051  CB  ARG B 415     6555   4547   4856  -1201     23  -2063       C
ATOM   2052  CG  ARG B 415      15.271 -17.043 -29.108  1.00 41.66           C
ANISOU 2052  CG  ARG B 415     6513   4373   4942   -969    167  -1969       C
ATOM   2053  CD  ARG B 415      16.615 -17.211 -29.848  1.00 43.44           C
ANISOU 2053  CD  ARG B 415     6857   4564   5085   -754    304  -2032       C
ATOM   2054  NE  ARG B 415      17.736 -17.257 -28.906  1.00 44.27           N
ANISOU 2054  NE  ARG B 415     6911   4587   5323   -528    418  -1927       N
ATOM   2055  CZ  ARG B 415      18.535 -16.226 -28.622  1.00 44.39           C
ANISOU 2055  CZ  ARG B 415     6727   4761   5378   -377    446  -1798       C
ATOM   2056  NH1 ARG B 415      18.363 -15.052 -29.226  1.00 42.41           N
ANISOU 2056  NH1 ARG B 415     6333   4736   5045   -419    386  -1752       N
ATOM   2057  NH2 ARG B 415      19.524 -16.371 -27.736  1.00 42.84           N
ANISOU 2057  NH2 ARG B 415     6481   4495   5301   -187    528  -1712       N
ATOM   2058  C   ARG B 415      13.024 -15.753 -32.047  1.00 42.87           C
ANISOU 2058  C   ARG B 415     6576   5039   4676  -1373   -200  -2134       C
ATOM   2059  O   ARG B 415      11.836 -15.538 -31.722  1.00 43.41           O
ANISOU 2059  O   ARG B 415     6496   5203   4795  -1543   -339  -2096       O
ATOM   2060  N   GLY B 416      13.414 -16.003 -33.295  1.00 43.58           N
ANISOU 2060  N   GLY B 416     6847   5143   4569  -1359   -179  -2265       N
ATOM   2061  CA  GLY B 416      12.471 -16.015 -34.399  1.00 44.83           C
ANISOU 2061  CA  GLY B 416     7057   5437   4540  -1552   -342  -2373       C
ATOM   2062  C   GLY B 416      12.035 -14.620 -34.801  1.00 43.68           C
ANISOU 2062  C   GLY B 416     6698   5579   4320  -1531   -474  -2238       C
ATOM   2063  O   GLY B 416      12.426 -13.636 -34.182  1.00 40.62           O
ANISOU 2063  O   GLY B 416     6131   5266   4039  -1383   -433  -2066       O
ATOM   2064  N   ASP B 417      11.220 -14.550 -35.849  1.00 45.98           N
ANISOU 2064  N   ASP B 417     7025   6022   4422  -1682   -641  -2318       N
ATOM   2065  CA  ASP B 417      10.713 -13.285 -36.381  1.00 46.13           C
ANISOU 2065  CA  ASP B 417     6873   6313   4341  -1660   -791  -2193       C
ATOM   2066  CB  ASP B 417      10.301 -13.462 -37.856  1.00 49.03           C
ANISOU 2066  CB  ASP B 417     7403   6811   4417  -1778   -927  -2325       C
ATOM   2067  CG  ASP B 417      11.490 -13.487 -38.803  1.00 49.91           C
ANISOU 2067  CG  ASP B 417     7750   6890   4322  -1638   -771  -2389       C
ATOM   2068  OD1 ASP B 417      12.611 -13.144 -38.380  1.00 49.40           O
ANISOU 2068  OD1 ASP B 417     7671   6752   4348  -1440   -575  -2299       O
ATOM   2069  OD2 ASP B 417      11.303 -13.843 -39.981  1.00 54.40           O
ANISOU 2069  OD2 ASP B 417     8515   7522   4632  -1731   -844  -2530       O
ATOM   2070  C   ASP B 417       9.534 -12.731 -35.573  1.00 45.38           C
ANISOU 2070  C   ASP B 417     6492   6343   4409  -1743   -943  -2070       C
ATOM   2071  O   ASP B 417       8.746 -13.487 -34.982  1.00 46.51           O
ANISOU 2071  O   ASP B 417     6586   6417   4670  -1916   -994  -2131       O
ATOM   2072  N   LEU B 418       9.403 -11.409 -35.575  1.00 44.04           N
ANISOU 2072  N   LEU B 418     6141   6353   4239  -1621  -1007  -1897       N
ATOM   2073  CA  LEU B 418       8.293 -10.755 -34.905  1.00 43.53           C
ANISOU 2073  CA  LEU B 418     5799   6428   4311  -1656  -1143  -1777       C
ATOM   2074  CB  LEU B 418       8.810  -9.653 -33.980  1.00 40.59           C
```

FIGURE 18-62

```
ANISOU 2074  CB  LEU B 418    5283   6046   4093  -1450  -1042  -1589          C
ATOM   2075  CG  LEU B 418     9.808 -10.051 -32.878  1.00 38.75               C
ANISOU 2075  CG  LEU B 418    5100   5593   4029  -1362   -833  -1577          C
ATOM   2076  CD1 LEU B 418    10.306  -8.834 -32.112  1.00 35.47               C
ANISOU 2076  CD1 LEU B 418    4554   5196   3728  -1178   -766  -1401          C
ATOM   2077  CD2 LEU B 418     9.250 -11.068 -31.915  1.00 39.40               C
ANISOU 2077  CD2 LEU B 418    5149   5552   4270  -1500   -811  -1642          C
ATOM   2078  C   LEU B 418     7.241 -10.235 -35.898  1.00 45.84               C
ANISOU 2078  C   LEU B 418    6001   6978   4439  -1735  -1384  -1763          C
ATOM   2079  O   LEU B 418     7.535  -9.394 -36.757  1.00 46.01               O
ANISOU 2079  O   LEU B 418    6071   7120   4290  -1621  -1431  -1691          O
ATOM   2080  N   ASN B 419     6.020 -10.759 -35.773  1.00 47.64               N
ANISOU 2080  N   ASN B 419    6094   7293   4714  -1936  -1539  -1827          N
ATOM   2081  CA  ASN B 419     4.923 -10.448 -36.687  1.00 50.61               C
ANISOU 2081  CA  ASN B 419    6358   7932   4940  -2038  -1799  -1833          C
ATOM   2082  CB  ASN B 419     4.793 -11.549 -37.747  1.00 53.52               C
ANISOU 2082  CB  ASN B 419    6955   8284   5095  -2259  -1891  -2052          C
ATOM   2083  CG  ASN B 419     5.967 -11.586 -38.713  1.00 54.69               C
ANISOU 2083  CG  ASN B 419    7420   8348   5013  -2152  -1783  -2116          C
ATOM   2084  OD1 ASN B 419     6.257 -10.605 -39.409  1.00 55.78               O
ANISOU 2084  OD1 ASN B 419    7577   8623   4994  -1997  -1823  -2005          O
ATOM   2085  ND2 ASN B 419     6.645 -12.728 -38.767  1.00 55.63               N
ANISOU 2085  ND2 ASN B 419    7797   8235   5105  -2228  -1634  -2293          N
ATOM   2086  C   ASN B 419     3.565 -10.242 -35.997  1.00 51.57               C
ANISOU 2086  C   ASN B 419    6141   8219   5233  -2130  -1940  -1764          C
ATOM   2087  O   ASN B 419     2.515 -10.554 -36.574  1.00 54.24               O
ANISOU 2087  O   ASN B 419    6375   8743   5492  -2316  -2156  -1834          O
ATOM   2088  N   PHE B 420     3.590  -9.705 -34.776  1.00 49.62               N
ANISOU 2088  N   PHE B 420    5719   7922   5214  -1998  -1820  -1630          N
ATOM   2089  CA  PHE B 420     2.373  -9.504 -33.976  1.00 50.02               C
ANISOU 2089  CA  PHE B 420    5439   8121   5445  -2058  -1900  -1560          C
ATOM   2090  CB  PHE B 420     2.712  -9.101 -32.538  1.00 47.52               C
ANISOU 2090  CB  PHE B 420    5026   7673   5357  -1910  -1701  -1445          C
ATOM   2091  CG  PHE B 420     3.276 -10.218 -31.721  1.00 47.20               C
ANISOU 2091  CG  PHE B 420    5137   7373   5425  -2025  -1514  -1537          C
ATOM   2092  CD1 PHE B 420     4.620 -10.241 -31.399  1.00 44.34               C
ANISOU 2092  CD1 PHE B 420    4992   6786   5070  -1880  -1326  -1527          C
ATOM   2093  CE1 PHE B 420     5.152 -11.271 -30.647  1.00 43.10               C
ANISOU 2093  CE1 PHE B 420    4980   6389   5008  -1957  -1165  -1597          C
ATOM   2094  CZ  PHE B 420     4.344 -12.302 -30.207  1.00 45.97               C
ANISOU 2094  CZ  PHE B 420    5299   6709   5458  -2199  -1177  -1678          C
ATOM   2095  CE2 PHE B 420     2.993 -12.306 -30.516  1.00 48.22               C
ANISOU 2095  CE2 PHE B 420    5362   7217   5743  -2379  -1352  -1696          C
ATOM   2096  CD2 PHE B 420     2.461 -11.261 -31.273  1.00 49.98               C
ANISOU 2096  CD2 PHE B 420    5411   7705   5873  -2283  -1527  -1627          C
ATOM   2097  C   PHE B 420     1.406  -8.507 -34.584  1.00 51.27               C
ANISOU 2097  C   PHE B 420    5363   8585   5534  -1978  -2129  -1452          C
ATOM   2098  O   PHE B 420     1.809  -7.486 -35.147  1.00 50.92               O
ANISOU 2098  O   PHE B 420    5373   8599   5374  -1767  -2166  -1341          O
ATOM   2099  N   VAL B 421     0.124  -8.817 -34.417  1.00 53.07               N
ANISOU 2099  N   VAL B 421    5320   9003   5842  -2148  -2275  -1475          N
ATOM   2100  CA  VAL B 421    -0.949  -8.217 -35.197  1.00 55.35               C
ANISOU 2100  CA  VAL B 421    5378   9617   6037  -2138  -2546  -1417          C
ATOM   2101  CB  VAL B 421    -1.320  -9.170 -36.362  1.00 58.38               C
ANISOU 2101  CB  VAL B 421    5876  10095   6212  -2420  -2749  -1597          C
ATOM   2102  CG1 VAL B 421    -2.801  -9.548 -36.346  1.00 62.13               C
ANISOU 2102  CG1 VAL B 421    6005  10842   6760  -2651  -2962  -1635          C
ATOM   2103  CG2 VAL B 421    -0.857  -8.594 -37.696  1.00 59.48               C
ANISOU 2103  CG2 VAL B 421    6222  10317   6062  -2293  -2882  -1575          C
ATOM   2104  C   VAL B 421    -2.181  -7.818 -34.375  1.00 55.75               C
ANISOU 2104  C   VAL B 421    5010   9876   6297  -2121  -2603  -1318          C
ATOM   2105  O   VAL B 421    -2.233  -7.998 -33.161  1.00 53.74               O
ANISOU 2105  O   VAL B 421    4650   9514   6255  -2128  -2419  -1295          O
ATOM   2106  N   ALA B 424    -8.330  -7.054 -34.316  1.00 83.41               N
ANISOU 2106  N   ALA B 424    6624  14886  10180  -2373  -3433  -1118          N
ATOM   2107  CA  ALA B 424    -8.109  -5.823 -35.078  1.00 83.39               C
ANISOU 2107  CA  ALA B 424    6684  14974  10028  -2016  -3575   -972          C
ATOM   2108  CB  ALA B 424    -7.502  -4.750 -34.179  1.00 80.03               C
ANISOU 2108  CB  ALA B 424    6321  14356   9729  -1638  -3328   -816          C
ATOM   2109  C   ALA B 424    -7.235  -6.044 -36.325  1.00 83.09               C
ANISOU 2109  C   ALA B 424    7065  14815   9689  -2072  -3692  -1054          C
```

FIGURE 18-63

```
ATOM   2110  O   ALA B 424      -7.422  -5.385 -37.357  1.00 84.69           O
ANISOU 2110  O   ALA B 424     7275  15205   9698  -1925  -3931   -976       O
ATOM   2111  N   ASN B 425      -6.283  -6.973 -36.206  1.00 81.03           N
ANISOU 2111  N   ASN B 425     7157  14244   9387  -2271  -3512  -1204       N
ATOM   2112  CA  ASN B 425      -5.300  -7.305 -37.262  1.00 80.26           C
ANISOU 2112  CA  ASN B 425     7495  13986   9016  -2326  -3549  -1305       C
ATOM   2113  CB  ASN B 425      -5.987  -7.797 -38.555  1.00 84.45           C
ANISOU 2113  CB  ASN B 425     8001  14775   9309  -2559  -3886  -1417       C
ATOM   2114  CG  ASN B 425      -5.041  -8.595 -39.454  1.00 84.90           C
ANISOU 2114  CG  ASN B 425     8524  14628   9108  -2728  -3870  -1597       C
ATOM   2115  OD1 ASN B 425      -4.463  -9.623 -39.028  1.00 84.50           O
ANISOU 2115  OD1 ASN B 425     8690  14300   9116  -2930  -3673  -1754       O
ATOM   2116  ND2 ASN B 425      -4.880  -8.118 -40.700  1.00 86.24           N
ANISOU 2116  ND2 ASN B 425     8858  14929   8980  -2630  -4069  -1569       N
ATOM   2117  C   ASN B 425      -4.251  -6.211 -37.547  1.00 77.13           C
ANISOU 2117  C   ASN B 425     7357  13442   8505  -1975  -3451  -1163       C
ATOM   2118  O   ASN B 425      -3.579  -6.224 -38.607  1.00 77.12           O
ANISOU 2118  O   ASN B 425     7668  13393   8242  -1971  -3519  -1205       O
ATOM   2119  N   GLN B 426      -4.098  -5.287 -36.579  1.00 74.28           N
ANISOU 2119  N   GLN B 426     6881  13003   8337  -1698  -3278  -1003       N
ATOM   2120  CA  GLN B 426      -3.150  -4.184 -36.730  1.00 71.77           C
ANISOU 2120  CA  GLN B 426     6789  12536   7944  -1383  -3177   -858       C
ATOM   2121  CB  GLN B 426      -3.642  -2.945 -35.979  1.00 71.41           C
ANISOU 2121  CB  GLN B 426     6489  12565   8078  -1069  -3143   -660       C
ATOM   2122  CG  GLN B 426      -4.259  -1.900 -36.902  1.00 75.93           C
ANISOU 2122  CG  GLN B 426     6956  13384   8510   -844  -3402   -501       C
ATOM   2123  CD  GLN B 426      -5.489  -1.238 -36.301  1.00 79.00           C
ANISOU 2123  CD  GLN B 426     6914  14008   9093   -664  -3487   -379       C
ATOM   2124  OE1 GLN B 426      -5.395  -0.480 -35.325  1.00 77.23           O
ANISOU 2124  OE1 GLN B 426     6622  13667   9055   -431  -3303   -275       O
ATOM   2125  NE2 GLN B 426      -6.657  -1.526 -36.882  1.00 82.04           N
ANISOU 2125  NE2 GLN B 426     7000  14737   9434   -772  -3766   -397       N
ATOM   2126  C   GLN B 426      -1.744  -4.552 -36.272  1.00 67.70           C
ANISOU 2126  C   GLN B 426     6612  11664   7446  -1398  -2889   -925       C
ATOM   2127  O   GLN B 426      -1.531  -4.823 -35.079  1.00 65.90           O
ANISOU 2127  O   GLN B 426     6334  11273   7433  -1414  -2675   -943       O
ATOM   2128  N   ARG B 427      -0.793  -4.546 -37.212  1.00 66.20           N
ANISOU 2128  N   ARG B 427     6756  11371   7026  -1382  -2882   -954       N
ATOM   2129  CA  ARG B 427       0.612  -4.844 -36.900  1.00 62.42           C
ANISOU 2129  CA  ARG B 427     6586  10583   6550  -1372  -2617  -1008       C
ATOM   2130  CB  ARG B 427       1.461  -4.982 -38.166  1.00 63.31           C
ANISOU 2130  CB  ARG B 427     7032  10653   6369  -1395  -2643  -1064       C
ATOM   2131  CG  ARG B 427       2.893  -5.323 -37.824  1.00 60.44           C
ANISOU 2131  CG  ARG B 427     6941   9997   6027  -1376  -2363  -1121       C
ATOM   2132  CD  ARG B 427       3.839  -5.274 -38.987  1.00 62.17           C
ANISOU 2132  CD  ARG B 427     7475  10176   5972  -1350  -2335  -1148       C
ATOM   2133  NE  ARG B 427       5.192  -5.498 -38.488  1.00 60.41           N
ANISOU 2133  NE  ARG B 427     7440   9693   5819  -1299  -2053  -1179       N
ATOM   2134  CZ  ARG B 427       5.789  -6.686 -38.435  1.00 61.00           C
ANISOU 2134  CZ  ARG B 427     7681   9608   5886  -1440  -1921  -1360       C
ATOM   2135  NH1 ARG B 427       5.165  -7.770 -38.880  1.00 62.69           N
ANISOU 2135  NH1 ARG B 427     7932   9872   6017  -1663  -2042  -1538       N
ATOM   2136  NH2 ARG B 427       7.015  -6.789 -37.940  1.00 59.05           N
ANISOU 2136  NH2 ARG B 427     7568   9150   5718  -1357  -1675  -1364       N
ATOM   2137  C   ARG B 427       1.276  -3.851 -35.925  1.00 58.46           C
ANISOU 2137  C   ARG B 427     6084   9911   6216  -1119  -2409   -857       C
ATOM   2138  O   ARG B 427       1.461  -2.673 -36.244  1.00 58.25           O
ANISOU 2138  O   ARG B 427     6093   9913   6128   -892  -2441   -697       O
ATOM   2139  N   LEU B 428       1.661  -4.365 -34.758  1.00 55.08           N
ANISOU 2139  N   LEU B 428     5646   9295   5987  -1171  -2200   -912       N
ATOM   2140  CA  LEU B 428       2.179  -3.563 -33.637  1.00 51.23           C
ANISOU 2140  CA  LEU B 428     5136   8653   5678   -972  -2010   -796       C
ATOM   2141  CB  LEU B 428       2.409  -4.453 -32.403  1.00 49.31           C
ANISOU 2141  CB  LEU B 428     4870   8241   5623  -1094  -1820   -888       C
ATOM   2142  CG  LEU B 428       1.337  -5.465 -31.970  1.00 49.76           C
ANISOU 2142  CG  LEU B 428     4722   8398   5786  -1320  -1873   -988       C
ATOM   2143  CD1 LEU B 428       1.713  -6.150 -30.667  1.00 44.96           C
ANISOU 2143  CD1 LEU B 428     4138   7589   5355  -1393  -1657  -1034       C
ATOM   2144  CD2 LEU B 428      -0.032  -4.799 -31.836  1.00 52.31           C
ANISOU 2144  CD2 LEU B 428     4701   8986   6189  -1248  -2023   -893       C
ATOM   2145  C   LEU B 428       3.472  -2.848 -33.998  1.00 48.96           C
```

FIGURE 18-64

```
ANISOU 2145  C   LEU B 428    5109  8206  5286   -819 -1897  -722          C
ATOM   2146  O   LEU B 428       4.238  -3.337 -34.840  1.00 49.40           O
ANISOU 2146  O   LEU B 428    5395  8205  5171   -902 -1877  -801          O
ATOM   2147  N   ASN B 429       3.711  -1.694 -33.375  1.00 46.41           N
ANISOU 2147  N   ASN B 429    4755  7813  5065   -605 -1817  -577          N
ATOM   2148  CA  ASN B 429       4.977  -1.001 -33.559  1.00 43.84           C
ANISOU 2148  CA  ASN B 429    4661  7322  4674   -490 -1689  -503          C
ATOM   2149  CB  ASN B 429       4.911   0.478 -33.085  1.00 43.47           C
ANISOU 2149  CB  ASN B 429    4569  7235  4712   -252 -1670  -326          C
ATOM   2150  CG  ASN B 429       4.794   0.641 -31.557  1.00 42.88           C
ANISOU 2150  CG  ASN B 429    4363  7053  4876   -193 -1534  -322          C
ATOM   2151  OD1 ASN B 429       4.994  -0.294 -30.774  1.00 42.00           O
ANISOU 2151  OD1 ASN B 429    4224  6868  4867   -321 -1425  -433          O
ATOM   2152  ND2 ASN B 429       4.489   1.865 -31.133  1.00 43.80           N
ANISOU 2152  ND2 ASN B 429    4425  7149  5068     13 -1537  -190          N
ATOM   2153  C   ASN B 429       6.117  -1.831 -32.934  1.00 40.62           C
ANISOU 2153  C   ASN B 429    4391  6708  4334   -590 -1479  -612          C
ATOM   2154  O   ASN B 429       5.847  -2.720 -32.118  1.00 40.12           O
ANISOU 2154  O   ASN B 429    4238  6603  4402   -701 -1423  -708          O
ATOM   2155  N   PRO B 430       7.376  -1.594 -33.358  1.00 38.69           N
ANISOU 2155  N   PRO B 430    4362  6345  3995   -554 -1365  -592          N
ATOM   2156  CA  PRO B 430       8.524  -2.378 -32.884  1.00 36.44           C
ANISOU 2156  CA  PRO B 430    4197  5886  3762   -622 -1177  -688          C
ATOM   2157  CB  PRO B 430       9.721  -1.573 -33.388  1.00 36.11           C
ANISOU 2157  CB  PRO B 430    4322  5772  3625   -531 -1078  -599          C
ATOM   2158  CG  PRO B 430       9.217  -1.000 -34.683  1.00 38.86           C
ANISOU 2158  CG  PRO B 430    4726  6273  3765   -501 -1232  -528          C
ATOM   2159  CD  PRO B 430       7.784  -0.603 -34.373  1.00 39.49           C
ANISOU 2159  CD  PRO B 430    4600  6481  3923   -451 -1407  -472          C
ATOM   2160  C   PRO B 430       8.614  -2.593 -31.371  1.00 34.07           C
ANISOU 2160  C   PRO B 430    3795  5462  3688   -612 -1058  -701          C
ATOM   2161  O   PRO B 430       8.953  -3.700 -30.951  1.00 33.84           O
ANISOU 2161  O   PRO B 430    3804  5342  3711   -716  -973  -815          O
ATOM   2162  N   MSE B 431       8.323  -1.571 -30.566  1.00 32.32           N
ANISOU 2162  N   MSE B 431    3467  5227  3587   -484 -1051  -588          N
ATOM   2163  CA  MSE B 431       8.460  -1.693 -29.110  1.00 30.33           C
ANISOU 2163  CA  MSE B 431    3144  4860  3520   -467  -933  -597          C
ATOM   2164  CB  MSE B 431       8.410  -0.314 -28.423  1.00 30.13           C
ANISOU 2164  CB  MSE B 431    3074  4793  3580   -299  -911  -470          C
ATOM   2165  CG  MSE B 431       9.687   0.570 -28.662  1.00 28.94           C
ANISOU 2165  CG  MSE B 431    3090  4524  3381   -227  -832  -394          C
ATOM   2166  SE  MSE B 431      11.365  -0.168 -27.993  0.90 30.04          SE
ANISOU 2166  SE  MSE B 431    3345  4495  3575   -303  -647  -469          SE
ATOM   2167  CE  MSE B 431      10.912  -0.117 -26.095  1.00 24.52           C
ANISOU 2167  CE  MSE B 431    2526  3717  3074   -261  -588  -475          C
ATOM   2168  C   MSE B 431       7.432  -2.651 -28.519  1.00 30.68           C
ANISOU 2168  C   MSE B 431    3039  4964  3655   -580  -963  -679          C
ATOM   2169  O   MSE B 431       7.735  -3.405 -27.597  1.00 29.00           O
ANISOU 2169  O   MSE B 431    2836  4642  3540   -644  -854  -738          O
ATOM   2170  N   HIS B 432       6.223  -2.634 -29.071  1.00 32.59           N
ANISOU 2170  N   HIS B 432    3139  5384  3859   -612 -1115  -677          N
ATOM   2171  CA  HIS B 432       5.147  -3.532 -28.631  1.00 33.91           C
ANISOU 2171  CA  HIS B 432    3137  5640  4109   -754 -1154  -751          C
ATOM   2172  CB  HIS B 432       3.767  -2.933 -28.954  1.00 36.00           C
ANISOU 2172  CB  HIS B 432    3166  6133  4378   -703 -1318  -688          C
ATOM   2173  CG  HIS B 432       3.389  -1.817 -28.034  1.00 37.73           C
ANISOU 2173  CG  HIS B 432    3252  6360  4722   -503 -1267  -573          C
ATOM   2174  ND1 HIS B 432       3.912  -0.546 -28.149  1.00 38.20           N
ANISOU 2174  ND1 HIS B 432    3408  6352  4753   -297 -1254  -461          N
ATOM   2175  CE1 HIS B 432       3.416   0.220 -27.191  1.00 39.33           C
ANISOU 2175  CE1 HIS B 432    3427  6494  5023   -146 -1198  -394          C
ATOM   2176  NE2 HIS B 432       2.611  -0.513 -26.443  1.00 40.30           N
ANISOU 2176  NE2 HIS B 432    3363  6697  5252   -246 -1161  -453          N
ATOM   2177  CD2 HIS B 432       2.578  -1.793 -26.950  1.00 40.85           C
ANISOU 2177  CD2 HIS B 432    3447  6806  5268   -481 -1207  -560          C
ATOM   2178  C   HIS B 432       5.320  -4.919 -29.218  1.00 33.99           C
ANISOU 2178  C   HIS B 432    3258  5618  4040   -966 -1169  -895          C
ATOM   2179  O   HIS B 432       4.875  -5.903 -28.645  1.00 34.07           O
ANISOU 2179  O   HIS B 432    3212  5601  4134  -1120 -1134  -973          O
ATOM   2180  N   GLN B 433       5.985  -4.971 -30.363  1.00 34.16           N
ANISOU 2180  N   GLN B 433    3456  5630  3893   -972 -1208  -928          N
```

FIGURE 18-65

```
ATOM   2181  CA  GLN B 433       6.441  -6.214 -30.990  1.00 35.06           C
ANISOU 2181  CA  GLN B 433    3747   5667   3907  -1135  -1189  -1076        C
ATOM   2182  CB  GLN B 433       7.210  -5.810 -32.268  1.00 35.84           C
ANISOU 2182  CB  GLN B 433    4029   5789   3799  -1070  -1217  -1069        C
ATOM   2183  CG  GLN B 433       7.217  -6.698 -33.462  1.00 39.05           C
ANISOU 2183  CG  GLN B 433    4591   6231   4014  -1213  -1290  -1208        C
ATOM   2184  CD  GLN B 433       5.848  -7.071 -33.976  1.00 42.97           C
ANISOU 2184  CD  GLN B 433    4958   6913   4453  -1371  -1501  -1267        C
ATOM   2185  OE1 GLN B 433       5.439  -8.218 -33.828  1.00 44.60           O
ANISOU 2185  OE1 GLN B 433    5176   7077   4694  -1566  -1513  -1404        O
ATOM   2186  NE2 GLN B 433       5.138  -6.124 -34.603  1.00 44.73           N
ANISOU 2186  NE2 GLN B 433    5063   7344   4587  -1294  -1676  -1164        N
ATOM   2187  C   GLN B 433       7.344  -6.960 -29.970  1.00 32.64           C
ANISOU 2187  C   GLN B 433    3545   5136   3721  -1150   -995  -1123        C
ATOM   2188  O   GLN B 433       7.122  -8.135 -29.653  1.00 33.52           O
ANISOU 2188  O   GLN B 433    3691   5166   3879  -1305   -963  -1228        O
ATOM   2189  N   LEU B 434       8.341  -6.245 -29.452  1.00 30.05           N
ANISOU 2189  N   LEU B 434    3268   4710   3441   -990   -877  -1037        N
ATOM   2190  CA  LEU B 434       9.293  -6.738 -28.427  1.00 28.11           C
ANISOU 2190  CA  LEU B 434    3102   4275   3305   -960   -710  -1051        C
ATOM   2191  CB  LEU B 434      10.386  -5.685 -28.177  1.00 24.78           C
ANISOU 2191  CB  LEU B 434    2718   3801   2896   -791   -627   -949        C
ATOM   2192  CG  LEU B 434      11.320  -5.482 -29.364  1.00 25.69           C
ANISOU 2192  CG  LEU B 434    2976   3925   2859   -752   -609   -959        C
ATOM   2193  CD1 LEU B 434      12.113  -4.184 -29.212  1.00 22.35           C
ANISOU 2193  CD1 LEU B 434    2551   3492   2449   -617   -559   -833        C
ATOM   2194  CD2 LEU B 434      12.245  -6.705 -29.605  1.00 21.91           C
ANISOU 2194  CD2 LEU B 434    2655   3326   2345   -797   -500  -1079        C
ATOM   2195  C   LEU B 434       8.644  -7.100 -27.082  1.00 27.61           C
ANISOU 2195  C   LEU B 434    2919   4169   3404  -1009   -667  -1038        C
ATOM   2196  O   LEU B 434       8.945  -8.142 -26.504  1.00 27.00           O
ANISOU 2196  O   LEU B 434    2924   3952   3382  -1083   -579  -1101        O
ATOM   2197  N   LEU B 435       7.790  -6.207 -26.587  1.00 27.73           N
ANISOU 2197  N   LEU B 435    2752   4297   3485   -949   -716   -950        N
ATOM   2198  CA  LEU B 435       7.020  -6.426 -25.375  1.00 28.98           C
ANISOU 2198  CA  LEU B 435    2775   4458   3779   -991   -669   -930        C
ATOM   2199  CB  LEU B 435       6.102  -5.222 -25.124  1.00 28.92           C
ANISOU 2199  CB  LEU B 435    2567   4606   3816   -876   -730   -833        C
ATOM   2200  CG  LEU B 435       5.273  -5.249 -23.842  1.00 32.08           C
ANISOU 2200  CG  LEU B 435    2806   5035   4346   -886   -657   -802        C
ATOM   2201  CD1 LEU B 435       6.159  -5.150 -22.588  1.00 31.09           C
ANISOU 2201  CD1 LEU B 435    2790   4739   4284   -805   -505   -770        C
ATOM   2202  CD2 LEU B 435       4.251  -4.124 -23.876  1.00 32.55           C
ANISOU 2202  CD2 LEU B 435    2657   5276   4437   -759   -732   -723        C
ATOM   2203  C   LEU B 435       6.201  -7.743 -25.431  1.00 30.18           C
ANISOU 2203  C   LEU B 435    2897   4620   3949  -1216   -695  -1029        C
ATOM   2204  O   LEU B 435       6.344  -8.595 -24.548  1.00 29.89           O
ANISOU 2204  O   LEU B 435    2917   4450   3988  -1295   -589  -1055        O
ATOM   2205  N   ARG B 436       5.363  -7.905 -26.462  1.00 31.87           N
ANISOU 2205  N   ARG B 436    3035   4987   4086  -1327   -841  -1079        N
ATOM   2206  CA  ARG B 436       4.545  -9.104 -26.599  1.00 34.36           C
ANISOU 2206  CA  ARG B 436    3319   5321   4414  -1575   -884  -1182        C
ATOM   2207  CB  ARG B 436       3.584  -9.014 -27.800  1.00 37.45           C
ANISOU 2207  CB  ARG B 436    3591   5932   4704  -1679  -1087  -1225        C
ATOM   2208  CG  ARG B 436       2.381  -8.053 -27.651  1.00 42.59           C
ANISOU 2208  CG  ARG B 436    3929   6839   5416  -1610  -1192  -1127        C
ATOM   2209  CD  ARG B 436       1.953  -7.793 -26.187  1.00 48.03           C
ANISOU 2209  CD  ARG B 436    4449   7521   6280  -1555  -1056  -1045        C
ATOM   2210  NE  ARG B 436       0.516  -8.001 -26.006  1.00 55.04           N
ANISOU 2210  NE  ARG B 436    5043   8622   7247  -1697  -1128  -1046        N
ATOM   2211  CZ  ARG B 436      -0.097  -8.150 -24.827  1.00 58.20           C
ANISOU 2211  CZ  ARG B 436    5280   9046   7789  -1739  -1005  -1006        C
ATOM   2212  NH1 ARG B 436       0.594  -8.108 -23.690  1.00 57.05           N
ANISOU 2212  NH1 ARG B 436    5256   8713   7706  -1645   -815   -964        N
ATOM   2213  NH2 ARG B 436      -1.419  -8.336 -24.784  1.00 60.68           N
ANISOU 2213  NH2 ARG B 436    5297   9587   8172  -1880  -1073  -1007        N
ATOM   2214  C   ARG B 436       5.378 -10.388 -26.679  1.00 33.35           C
ANISOU 2214  C   ARG B 436    3452   4963   4256  -1688   -796  -1293        C
ATOM   2215  O   ARG B 436       4.996 -11.405 -26.118  1.00 33.93           O
ANISOU 2215  O   ARG B 436    3548   4941   4401  -1862   -742  -1344        O
ATOM   2216  N   HIS B 437       6.510 -10.333 -27.376  1.00 31.27           N
```

FIGURE 18-66

```
ANISOU 2216  N   HIS B 437     3388   4606   3887  -1584   -771  -1325         N
ATOM   2217  CA  HIS B 437       7.375 -11.493 -27.486  1.00 30.46             C
ANISOU 2217  CA  HIS B 437     3535   4282   3755  -1640   -676  -1429         C
ATOM   2218  CB  HIS B 437       8.585 -11.176 -28.355  1.00 29.42             C
ANISOU 2218  CB  HIS B 437     3569   4112   3499  -1490   -645  -1449         C
ATOM   2219  CG  HIS B 437       9.604 -12.270 -28.367  1.00 29.25             C
ANISOU 2219  CG  HIS B 437     3789   3861   3463  -1483   -520  -1543         C
ATOM   2220  ND1 HIS B 437       9.469 -13.411 -29.135  1.00 30.43             N
ANISOU 2220  ND1 HIS B 437     4121   3919   3524  -1636   -540  -1701         N
ATOM   2221  CE1 HIS B 437      10.511 -14.195 -28.937  1.00 30.95             C
ANISOU 2221  CE1 HIS B 437     4388   3767   3605  -1556   -401  -1752         C
ATOM   2222  NE2 HIS B 437      11.318 -13.608 -28.068  1.00 28.06             N
ANISOU 2222  NE2 HIS B 437     3956   3372   3333  -1368   -306  -1628         N
ATOM   2223  CD2 HIS B 437      10.769 -12.407 -27.692  1.00 28.33             C
ANISOU 2223  CD2 HIS B 437     3765   3589   3411  -1332   -377  -1504         C
ATOM   2224  C   HIS B 437       7.870 -11.985 -26.129  1.00 28.91             C
ANISOU 2224  C   HIS B 437     3395   3896   3694  -1603   -520  -1385         C
ATOM   2225  O   HIS B 437       7.863 -13.189 -25.851  1.00 29.06             O
ANISOU 2225  O   HIS B 437     3551   3745   3744  -1735   -462  -1459         O
ATOM   2226  N   PHE B 438       8.358 -11.040 -25.329  1.00 26.73             N
ANISOU 2226  N   PHE B 438     3039   3636   3480  -1419   -459  -1264         N
ATOM   2227  CA  PHE B 438       8.937 -11.304 -24.028  1.00 25.80             C
ANISOU 2227  CA  PHE B 438     2974   3366   3465  -1349   -329  -1204         C
ATOM   2228  CB  PHE B 438       9.963 -10.216 -23.649  1.00 23.35             C
ANISOU 2228  CB  PHE B 438     2648   3063   3161  -1126   -284  -1110         C
ATOM   2229  CG  PHE B 438      11.265 -10.342 -24.421  1.00 22.62             C
ANISOU 2229  CG  PHE B 438     2709   2894   2992  -1025   -250  -1151         C
ATOM   2230  CD1 PHE B 438      11.950 -11.575 -24.458  1.00 24.84             C
ANISOU 2230  CD1 PHE B 438     3175   2995   3269  -1043   -173  -1228         C
ATOM   2231  CE1 PHE B 438      13.122 -11.730 -25.196  1.00 23.69             C
ANISOU 2231  CE1 PHE B 438     3151   2795   3054   -935   -123  -1274         C
ATOM   2232  CZ  PHE B 438      13.623 -10.638 -25.892  1.00 23.06             C
ANISOU 2232  CZ  PHE B 438     3011   2846   2905   -836   -146  -1233         C
ATOM   2233  CE2 PHE B 438      12.934  -9.427 -25.889  1.00 20.07             C
ANISOU 2233  CE2 PHE B 438     2476   2627   2525   -836   -232  -1152         C
ATOM   2234  CD2 PHE B 438      11.757  -9.288 -25.168  1.00 20.56             C
ANISOU 2234  CD2 PHE B 438     2415   2738   2659   -917   -286  -1115         C
ATOM   2235  C   PHE B 438       7.911 -11.559 -22.925  1.00 27.49             C
ANISOU 2235  C   PHE B 438     3066   3597   3782  -1462   -296  -1158         C
ATOM   2236  O   PHE B 438       8.232 -12.211 -21.936  1.00 27.88             O
ANISOU 2236  O   PHE B 438     3210   3490   3892  -1471   -192  -1132         O
ATOM   2237  N   GLN B 439       6.680 -11.078 -23.096  1.00 29.49             N
ANISOU 2237  N   GLN B 439     3108   4045   4051  -1546   -381  -1143         N
ATOM   2238  CA  GLN B 439       5.604 -11.431 -22.158  1.00 31.31             C
ANISOU 2238  CA  GLN B 439     3202   4318   4377  -1685   -336  -1111         C
ATOM   2239  CB  GLN B 439       4.397 -10.507 -22.312  1.00 31.66             C
ANISOU 2239  CB  GLN B 439     2958   4625   4445  -1684   -425  -1067         C
ATOM   2240  CG  GLN B 439       4.664  -9.127 -21.740  1.00 31.16             C
ANISOU 2240  CG  GLN B 439     2805   4631   4404  -1437   -393   -961         C
ATOM   2241  CD  GLN B 439       3.554  -8.135 -21.987  1.00 35.12             C
ANISOU 2241  CD  GLN B 439     3041   5378   4926  -1380   -482   -914         C
ATOM   2242  OE1 GLN B 439       2.791  -8.271 -22.941  1.00 39.50             O
ANISOU 2242  OE1 GLN B 439     3478   6083   5446  -1486   -616   -957         O
ATOM   2243  NE2 GLN B 439       3.451  -7.121 -21.115  1.00 33.78             N
ANISOU 2243  NE2 GLN B 439     2777   5251   4808  -1202   -413   -827         N
ATOM   2244  C   GLN B 439       5.233 -12.903 -22.334  1.00 33.82             C
ANISOU 2244  C   GLN B 439     3637   4511   4701  -1941   -324  -1206         C
ATOM   2245  O   GLN B 439       4.854 -13.355 -21.370  1.00 33.96             O
ANISOU 2245  O   GLN B 439     3667   4441   4794  -2059   -225  -1176         O
ATOM   2246  N   LYS B 440       5.402 -13.399 -23.562  1.00 35.41             N
ANISOU 2246  N   LYS B 440     3956   4685   4812  -2025   -415  -1321         N
ATOM   2247  CA  LYS B 440       5.169 -14.800 -23.882  1.00 38.51             C
ANISOU 2247  CA  LYS B 440     4517   4922   5193  -2267   -412  -1437         C
ATOM   2248  CB  LYS B 440       5.054 -14.997 -25.392  1.00 40.39             C
ANISOU 2248  CB  LYS B 440     4818   5225   5302  -2360   -556  -1571         C
ATOM   2249  CG  LYS B 440       3.714 -14.593 -25.976  1.00 42.28             C
ANISOU 2249  CG  LYS B 440     4794   5744   5525  -2519   -721  -1588         C
ATOM   2250  CD  LYS B 440       3.577 -15.162 -27.360  1.00 46.14             C
ANISOU 2250  CD  LYS B 440     5410   6249   5872  -2677   -861  -1746         C
ATOM   2251  CE  LYS B 440       3.177 -16.611 -27.299  1.00 48.55             C
ANISOU 2251  CE  LYS B 440     5873   6370   6205  -2981   -837  -1868         C
```

FIGURE 18-67

```
ATOM   2252  NZ  LYS B 440       3.494 -17.274 -28.574  1.00 52.80           N
ANISOU 2252  NZ  LYS B 440     6658   6823   6582  -3080   -924  -2045       N
ATOM   2253  C   LYS B 440       6.248 -15.714 -23.330  1.00 38.27           C
ANISOU 2253  C   LYS B 440     4773   4586   5181  -2209   -273  -1446       C
ATOM   2254  O   LYS B 440       5.963 -16.802 -22.818  1.00 39.92           O
ANISOU 2254  O   LYS B 440     5104   4621   5443  -2385   -203  -1469       O
ATOM   2255  N   ASP B 441       7.490 -15.259 -23.433  1.00 37.00           N
ANISOU 2255  N   ASP B 441     4716   4363   4979  -1961   -233  -1420       N
ATOM   2256  CA  ASP B 441       8.646 -16.065 -23.061  1.00 36.98           C
ANISOU 2256  CA  ASP B 441     4970   4096   4985  -1856   -118  -1430       C
ATOM   2257  CB  ASP B 441       9.051 -17.038 -24.186  1.00 39.34           C
ANISOU 2257  CB  ASP B 441     5510   4241   5196  -1921   -132  -1587       C
ATOM   2258  CG  ASP B 441      10.054 -18.065 -23.712  1.00 41.85           C
ANISOU 2258  CG  ASP B 441     6096   4260   5544  -1824     -5  -1598       C
ATOM   2259  OD1 ASP B 441      10.678 -17.827 -22.647  1.00 45.44           O
ANISOU 2259  OD1 ASP B 441     6535   4664   6067  -1657     74  -1472       O
ATOM   2260  OD2 ASP B 441      10.223 -19.107 -24.371  1.00 44.75           O
ANISOU 2260  OD2 ASP B 441     6700   4440   5864  -1905     13  -1729       O
ATOM   2261  C   ASP B 441       9.820 -15.187 -22.699  1.00 33.68           C
ANISOU 2261  C   ASP B 441     4532   3698   4566  -1573    -72  -1339       C
ATOM   2262  O   ASP B 441      10.467 -14.624 -23.570  1.00 33.22           O
ANISOU 2262  O   ASP B 441     4476   3713   4433  -1450   -108  -1370       O
ATOM   2263  N   ALA B 442      10.076 -15.111 -21.398  1.00 31.93           N
ANISOU 2263  N   ALA B 442     4298   3412   4421  -1490      9  -1227       N
ATOM   2264  CA  ALA B 442      11.092 -14.273 -20.794  1.00 29.34           C
ANISOU 2264  CA  ALA B 442     3931   3110   4105  -1256     44  -1131       C
ATOM   2265  CB  ALA B 442      10.565 -13.725 -19.499  1.00 28.01           C
ANISOU 2265  CB  ALA B 442     3635   3010   3996  -1252     75  -1017       C
ATOM   2266  C   ALA B 442      12.362 -15.072 -20.530  1.00 29.14           C
ANISOU 2266  C   ALA B 442     4112   2874   4085  -1118    122  -1131       C
ATOM   2267  O   ALA B 442      13.360 -14.523 -20.065  1.00 28.18           O
ANISOU 2267  O   ALA B 442     3967   2766   3973   -928    144  -1060       O
ATOM   2268  N   LYS B 443      12.312 -16.375 -20.791  1.00 30.53           N
ANISOU 2268  N   LYS B 443     4490   2851   4260  -1214    161  -1209       N
ATOM   2269  CA  LYS B 443      13.417 -17.281 -20.437  1.00 30.65           C
ANISOU 2269  CA  LYS B 443     4716   2636   4292  -1068    243  -1199       C
ATOM   2270  CB  LYS B 443      13.107 -18.727 -20.819  1.00 32.70           C
ANISOU 2270  CB  LYS B 443     5223   2653   4549  -1211    284  -1301       C
ATOM   2271  CG  LYS B 443      12.149 -19.457 -19.915  1.00 34.47           C
ANISOU 2271  CG  LYS B 443     5515   2754   4829  -1415    319  -1250       C
ATOM   2272  CD  LYS B 443      11.797 -20.833 -20.531  1.00 39.27           C
ANISOU 2272  CD  LYS B 443     6384   3113   5426  -1597    346  -1379       C
ATOM   2273  CE  LYS B 443      10.531 -21.410 -19.929  1.00 42.83           C
ANISOU 2273  CE  LYS B 443     6847   3503   5925  -1897    362  -1351       C
ATOM   2274  NZ  LYS B 443       9.967 -22.468 -20.802  1.00 49.83           N
ANISOU 2274  NZ  LYS B 443     7928   4218   6787  -2143    348  -1509       N
ATOM   2275  C   LYS B 443      14.752 -16.877 -21.049  1.00 29.07           C
ANISOU 2275  C   LYS B 443     4516   2473   4056   -835    255  -1220       C
ATOM   2276  O   LYS B 443      15.765 -16.817 -20.355  1.00 28.19           O
ANISOU 2276  O   LYS B 443     4414   2317   3978   -643    293  -1137       O
ATOM   2277  N   VAL B 444      14.760 -16.582 -22.341  1.00 28.47           N
ANISOU 2277  N   VAL B 444     4419   2495   3904   -857    219  -1324       N
ATOM   2278  CA  VAL B 444      15.989 -16.171 -23.001  1.00 27.62           C
ANISOU 2278  CA  VAL B 444     4298   2443   3753   -657    251  -1342       C
ATOM   2279  CB  VAL B 444      15.844 -16.164 -24.546  1.00 29.10           C
ANISOU 2279  CB  VAL B 444     4535   2697   3822   -721    229  -1480       C
ATOM   2280  CG1 VAL B 444      17.165 -15.772 -25.210  1.00 27.34           C
ANISOU 2280  CG1 VAL B 444     4300   2538   3551   -514    294  -1491       C
ATOM   2281  CG2 VAL B 444      15.361 -17.547 -25.079  1.00 29.33           C
ANISOU 2281  CG2 VAL B 444     4809   2521   3814   -569    251  -1625       C
ATOM   2282  C   VAL B 444      16.469 -14.798 -22.492  1.00 26.53           C
ANISOU 2282  C   VAL B 444     3944   2494   3640   -540    221  -1220       C
ATOM   2283  O   VAL B 444      17.678 -14.605 -22.233  1.00 26.44           O
ANISOU 2283  O   VAL B 444     3908   2485   3653   -353    265  -1171       O
ATOM   2284  N   LEU B 445      15.527 -13.866 -22.343  1.00 24.58           N
ANISOU 2284  N   LEU B 445     3544   2404   3392   -651    144  -1177       N
ATOM   2285  CA  LEU B 445      15.783 -12.541 -21.821  1.00 23.69           C
ANISOU 2285  CA  LEU B 445     3257   2443   3302   -569    112  -1072       C
ATOM   2286  CB  LEU B 445      14.471 -11.724 -21.792  1.00 22.83           C
ANISOU 2286  CB  LEU B 445     3011   2476   3188   -699     34  -1048       C
ATOM   2287  CG  LEU B 445      14.528 -10.302 -21.202  1.00 20.40           C
```

FIGURE 18-68

```
ANISOU 2287  CG  LEU B 445    2549  2300  2903   -624     1   -949       C
ATOM   2288  CD1 LEU B 445    15.452  -9.445 -22.022  1.00 20.80          C
ANISOU 2288  CD1 LEU B 445    2565  2433  2905   -525    -8   -942       C
ATOM   2289  CD2 LEU B 445    13.139  -9.660 -21.107  1.00 21.01          C
ANISOU 2289  CD2 LEU B 445    2499  2498  2987   -724   -59   -929       C
ATOM   2290  C   LEU B 445    16.386 -12.568 -20.405  1.00 23.63          C
ANISOU 2290  C   LEU B 445    3244  2369  3367   -464   143   -970       C
ATOM   2291  O   LEU B 445    17.378 -11.894 -20.145  1.00 23.04          O
ANISOU 2291  O   LEU B 445    3098  2354  3304   -332   144   -914       O
ATOM   2292  N   PHE B 446    15.749 -13.322 -19.503  1.00 24.55          N
ANISOU 2292  N   PHE B 446    3434  2372  3522   -540   163   -944       N
ATOM   2293  CA  PHE B 446    16.165 -13.405 -18.103  1.00 24.13          C
ANISOU 2293  CA  PHE B 446    3400  2257  3510   -456   185   -840       C
ATOM   2294  CB  PHE B 446    15.065 -14.052 -17.240  1.00 24.76          C
ANISOU 2294  CB  PHE B 446    3545  2251  3610   -600   213   -806       C
ATOM   2295  CG  PHE B 446    13.941 -13.121 -16.834  1.00 24.29          C
ANISOU 2295  CG  PHE B 446    3329  2348  3552   -706   187   -774       C
ATOM   2296  CD1 PHE B 446    13.834 -11.833 -17.342  1.00 23.90          C
ANISOU 2296  CD1 PHE B 446    3118  2476  3486   -675   130   -782       C
ATOM   2297  CE1 PHE B 446    12.781 -10.995 -16.975  1.00 24.51          C
ANISOU 2297  CE1 PHE B 446    3058  2686  3570   -740   113   -754       C
ATOM   2298  CZ  PHE B 446    11.834 -11.441 -16.088  1.00 25.45          C
ANISOU 2298  CZ  PHE B 446    3177  2782  3710   -847   166   -718       C
ATOM   2299  CE2 PHE B 446    11.922 -12.724 -15.582  1.00 26.97          C
ANISOU 2299  CE2 PHE B 446    3531  2804  3914   -908   228   -704       C
ATOM   2300  CD2 PHE B 446    12.973 -13.555 -15.954  1.00 26.27          C
ANISOU 2300  CD2 PHE B 446    3601  2560  3821   -831   232   -730       C
ATOM   2301  C   PHE B 446    17.483 -14.179 -17.956  1.00 24.88          C
ANISOU 2301  C   PHE B 446    3609  2223  3621   -283   225   -826       C
ATOM   2302  O   PHE B 446    18.356 -13.744 -17.220  1.00 24.61          O
ANISOU 2302  O   PHE B 446    3518  2231  3603   -148   207   -746       O
ATOM   2303  N   GLN B 447    17.622 -15.313 -18.650  1.00 26.27          N
ANISOU 2303  N   GLN B 447    3944  2245  3792   -281   275   -907       N
ATOM   2304  CA  GLN B 447    18.836 -16.149 -18.568  1.00 27.60          C
ANISOU 2304  CA  GLN B 447    4228  2275  3983    -85   326   -899       C
ATOM   2305  CB  GLN B 447    18.612 -17.566 -19.132  1.00 29.38          C
ANISOU 2305  CB  GLN B 447    4694  2267  4204   -123   392   -993       C
ATOM   2306  CG  GLN B 447    17.510 -18.396 -18.464  1.00 30.32          C
ANISOU 2306  CG  GLN B 447    4963  2215  4340   -306   406   -972       C
ATOM   2307  CD  GLN B 447    17.823 -18.852 -17.033  1.00 33.13          C
ANISOU 2307  CD  GLN B 447    5407  2450  4733   -211   422   -829       C
ATOM   2308  OE1 GLN B 447    18.625 -18.249 -16.326  1.00 34.35          O
ANISOU 2308  OE1 GLN B 447    5450  2708  4895    -47   387   -731       O
ATOM   2309  NE2 GLN B 447    17.167 -19.921 -16.603  1.00 33.37          N
ANISOU 2309  NE2 GLN B 447    5644  2258  4776   -332   469   -814       N
ATOM   2310  C   GLN B 447    20.092 -15.516 -19.196  1.00 27.69          C
ANISOU 2310  C   GLN B 447    4114  2418  3988     88   332   -910       C
ATOM   2311  O   GLN B 447    21.206 -15.860 -18.819  1.00 28.70          O
ANISOU 2311  O   GLN B 447    4248  2505  4150    282   355   -863       O
ATOM   2312  N   ASN B 448    19.912 -14.574 -20.117  1.00 28.11          N
ANISOU 2312  N   ASN B 448    4044  2639  3997     20   310   -961       N
ATOM   2313  CA  ASN B 448    21.036 -13.924 -20.791  1.00 28.81          C
ANISOU 2313  CA  ASN B 448    4012  2863  4073    147   333   -967       C
ATOM   2314  CB  ASN B 448    20.855 -13.960 -22.313  1.00 30.00          C
ANISOU 2314  CB  ASN B 448    4206  3050  4141     92   375  -1087       C
ATOM   2315  CG  ASN B 448    21.087 -15.348 -22.884  1.00 33.62          C
ANISOU 2315  CG  ASN B 448    4871  3323  4581    157   462  -1194       C
ATOM   2316  OD1 ASN B 448    22.214 -15.833 -22.902  1.00 36.46          O
ANISOU 2316  OD1 ASN B 448    5249  3635  4969    354   538  -1194       O
ATOM   2317  ND2 ASN B 448    20.022 -16.002 -23.324  1.00 35.23          N
ANISOU 2317  ND2 ASN B 448    5229  3417  4739     -5   449  -1287       N
ATOM   2318  C   ASN B 448    21.345 -12.521 -20.310  1.00 27.59          C
ANISOU 2318  C   ASN B 448    3659  2892  3933    147   269   -877       C
ATOM   2319  O   ASN B 448    22.364 -11.957 -20.700  1.00 28.46          O
ANISOU 2319  O   ASN B 448    3654  3115  4046    238   290   -863       O
ATOM   2320  N   TRP B 449    20.496 -11.979 -19.431  1.00 27.14          N
ANISOU 2320  N   TRP B 449    3567  2857  3886     45   203   -819       N
ATOM   2321  CA  TRP B 449    20.598 -10.569 -18.976  1.00 25.11          C
ANISOU 2321  CA  TRP B 449    3159  2749  3634     23   140   -751       C
ATOM   2322  CB  TRP B 449    19.384 -10.193 -18.115  1.00 23.06          C
ANISOU 2322  CB  TRP B 449    2904  2486  3374    -89    95   -715       C
```

FIGURE 18-69

```
ATOM   2323  CG  TRP B 449      19.356  -8.762 -17.660  1.00 22.27           C
ANISOU 2323  CG  TRP B 449     2686   2504   3269   -109     39   -663       C
ATOM   2324  CD1 TRP B 449      19.742  -8.290 -16.438  1.00 20.41           C
ANISOU 2324  CD1 TRP B 449     2424   2285   3047    -68     -1   -596       C
ATOM   2325  NE1 TRP B 449      19.559  -6.921 -16.377  1.00 20.85           N
ANISOU 2325  NE1 TRP B 449     2400   2431   3090   -109    -42   -580       N
ATOM   2326  CE2 TRP B 449      19.051  -6.475 -17.580  1.00 20.31           C
ANISOU 2326  CE2 TRP B 449     2300   2412   3004   -163    -32   -620       C
ATOM   2327  CD2 TRP B 449      18.911  -7.599 -18.423  1.00 20.86           C
ANISOU 2327  CD2 TRP B 449     2430   2431   3064   -171     12   -676       C
ATOM   2328  CE3 TRP B 449      18.388  -7.415 -19.723  1.00 22.46           C
ANISOU 2328  CE3 TRP B 449     2627   2683   3225   -229     16   -727       C
ATOM   2329  CZ3 TRP B 449      18.032  -6.099 -20.146  1.00 19.45           C
ANISOU 2329  CZ3 TRP B 449     2176   2397   2819   -261    -26   -701       C
ATOM   2330  CH2 TRP B 449      18.184  -5.005 -19.271  1.00 20.17           C
ANISOU 2330  CH2 TRP B 449     2218   2512   2935   -242    -59   -641       C
ATOM   2331  CZ2 TRP B 449      18.683  -5.166 -17.992  1.00 19.60           C
ANISOU 2331  CZ2 TRP B 449     2154   2396   2896   -202    -64   -609       C
ATOM   2332  C   TRP B 449      21.897 -10.183 -18.247  1.00 25.56           C
ANISOU 2332  C   TRP B 449     3119   2864   3729    148    117   -678       C
ATOM   2333  O   TRP B 449      22.382  -9.027 -18.344  1.00 25.79           O
ANISOU 2333  O   TRP B 449     3020   3020   3758    135     84   -649       O
ATOM   2334  N   GLY B 450      22.478 -11.120 -17.510  1.00 25.38           N
ANISOU 2334  N   GLY B 450     3157   2749   3739    265    124   -642       N
ATOM   2335  CA  GLY B 450      23.632 -10.745 -16.694  1.00 23.99           C
ANISOU 2335  CA  GLY B 450     2870   2652   3595    375     71   -565       C
ATOM   2336  C   GLY B 450      23.294 -10.879 -15.215  1.00 22.88           C
ANISOU 2336  C   GLY B 450     2794   2456   3443    373      4   -488       C
ATOM   2337  O   GLY B 450      22.203 -10.500 -14.778  1.00 21.96           O
ANISOU 2337  O   GLY B 450     2726   2323   3294    250    -10   -485       O
ATOM   2338  N   ILE B 451      24.230 -11.444 -14.467  1.00 23.43           N
ANISOU 2338  N   ILE B 451     2862   2506   3532    521    -32   -423       N
ATOM   2339  CA  ILE B 451      24.085 -11.705 -13.026  1.00 23.62           C
ANISOU 2339  CA  ILE B 451     2972   2480   3523    547    -99   -335       C
ATOM   2340  CB  ILE B 451      24.108 -13.262 -12.731  1.00 25.59           C
ANISOU 2340  CB  ILE B 451     3405   2536   3781    668    -54   -296       C
ATOM   2341  CG1 ILE B 451      23.397 -13.628 -11.415  1.00 23.95           C
ANISOU 2341  CG1 ILE B 451     3355   2232   3512    625    -81   -211       C
ATOM   2342  CD1 ILE B 451      21.902 -13.753 -11.539  1.00 21.00           C
ANISOU 2342  CD1 ILE B 451     3094   1771   3115    435     -5   -253       C
ATOM   2343  CG2 ILE B 451      25.512 -13.822 -12.743  1.00 26.15           C
ANISOU 2343  CG2 ILE B 451     3411   2625   3899    895    -78   -254       C
ATOM   2344  C   ILE B 451      25.203 -10.957 -12.295  1.00 23.68           C
ANISOU 2344  C   ILE B 451     2829   2639   3529    616   -211   -274       C
ATOM   2345  O   ILE B 451      26.284 -10.721 -12.867  1.00 24.64           O
ANISOU 2345  O   ILE B 451     2790   2871   3701    694   -221   -284       O
ATOM   2346  N   GLU B 452      24.948 -10.545 -11.062  1.00 22.87           N
ANISOU 2346  N   GLU B 452     2770   2558   3363    573   -294   -217       N
ATOM   2347  CA  GLU B 452      25.953  -9.818 -10.284  1.00 23.14           C
ANISOU 2347  CA  GLU B 452     2678   2738   3377    610   -425   -170       C
ATOM   2348  CB  GLU B 452      25.784  -8.289 -10.406  1.00 22.01           C
ANISOU 2348  CB  GLU B 452     2434   2709   3218    450   -462   -223       C
ATOM   2349  CG  GLU B 452      24.512  -7.724  -9.739  1.00 20.85           C
ANISOU 2349  CG  GLU B 452     2420   2510   2993    324   -449   -239       C
ATOM   2350  CD  GLU B 452      24.217  -6.272 -10.076  1.00 22.01           C
ANISOU 2350  CD  GLU B 452     2499   2725   3137    190   -457   -300       C
ATOM   2351  OE1 GLU B 452      25.104  -5.613 -10.663  1.00 27.18           O
ANISOU 2351  OE1 GLU B 452     3010   3475   3841    169   -493   -317       O
ATOM   2352  OE2 GLU B 452      23.097  -5.773  -9.748  1.00 23.75           O
ANISOU 2352  OE2 GLU B 452     2812   2904   3310    108   -421   -326       O
ATOM   2353  C   GLU B 452      25.850 -10.194  -8.828  1.00 24.13           C
ANISOU 2353  C   GLU B 452     2934   2823   3413    655   -507    -83       C
ATOM   2354  O   GLU B 452      24.765 -10.560  -8.354  1.00 23.91           O
ANISOU 2354  O   GLU B 452     3081   2678   3325    593   -450    -69       O
ATOM   2355  N  AHIS B 453      26.975 -10.085  -8.119  0.50 25.47           N
ANISOU 2355  N  AHIS B 453     3010   3104   3564    753   -642    -21       N
ATOM   2356  N  BHIS B 453      26.985 -10.127  -8.136  0.50 25.61           N
ANISOU 2356  N  BHIS B 453     3029   3119   3584    758   -640    -20       N
ATOM   2357  CA AHIS B 453      27.020 -10.189  -6.668  0.50 26.91           C
ANISOU 2357  CA AHIS B 453     3303   3295   3629    785   -756     64       C
ATOM   2358  CA BHIS B 453      27.023 -10.168  -6.690  0.50 27.08           C
```

FIGURE 18-70

```
ANISOU 2358  CA  BHIS B 453     3319  3317  3651    783   -755     61        C
ATOM   2359  CB  AHIS B 453      28.450 -10.463  -6.189  0.50 28.79           C
ANISOU 2359  CB  AHIS B 453     3408  3656  3874    952   -909    143        C
ATOM   2360  CB  BHIS B 453      28.476 -10.182  -6.188  0.50 29.00           C
ANISOU 2360  CB  BHIS B 453     3408  3713  3899    919   -922    129        C
ATOM   2361  CG  AHIS B 453      28.526 -10.925  -4.767  0.50 30.03           C
ANISOU 2361  CG  AHIS B 453     3716  3797  3897   1033  -1027    254        C
ATOM   2362  CG  BHIS B 453      29.316 -11.302  -6.740  0.50 30.90           C
ANISOU 2362  CG  BHIS B 453     3578  3926  4237   1140   -898    180        C
ATOM   2363  ND1 AHIS B 453      29.035 -10.142  -3.753  0.50 30.65           N
ANISOU 2363  ND1 AHIS B 453     3748  4029  3869    987  -1204    274        N
ATOM   2364  ND1 BHIS B 453      29.448 -12.521  -6.107  0.50 32.82           N
ANISOU 2364  ND1 BHIS B 453     3973  4053  4444   1327   -921    290        N
ATOM   2365  CE1 AHIS B 453      28.956 -10.802  -2.613  0.50 31.81           C
ANISOU 2365  CE1 AHIS B 453     4076  4127  3883   1080  -1278    384        C
ATOM   2366  CE1 BHIS B 453      30.259 -13.295  -6.810  0.50 33.79           C
ANISOU 2366  CE1 BHIS B 453     3997  4166  4676   1525   -885    307        C
ATOM   2367  NE2 AHIS B 453      28.403 -11.980  -2.849  0.50 31.22           N
ANISOU 2367  NE2 AHIS B 453     4168  3857  3836   1177  -1145    441        N
ATOM   2368  NE2 BHIS B 453      30.665 -12.623  -7.871  0.50 32.37           N
ANISOU 2368  NE2 BHIS B 453     3598  4108  4594   1462   -832    212        N
ATOM   2369  CD2 AHIS B 453      28.125 -12.081  -4.187  0.50 29.97           C
ANISOU 2369  CD2 AHIS B 453     3930  3629  3828   1144   -992    352        C
ATOM   2370  CD2 BHIS B 453      30.092 -11.374  -7.852  0.50 31.63           C
ANISOU 2370  CD2 BHIS B 453     3473  4089  4457   1217   -845    138        C
ATOM   2371  C   AHIS B 453      26.479  -8.902  -6.033  0.50 26.48           C
ANISOU 2371  C   AHIS B 453     3268  3310  3482    609   -804     15        C
ATOM   2372  C   BHIS B 453      26.269  -8.928  -6.168  0.50 26.24           C
ANISOU 2372  C   BHIS B 453     3253  3258  3458    595   -774      5        C
ATOM   2373  O   AHIS B 453      26.801  -7.795  -6.474  0.50 26.15           O
ANISOU 2373  O   AHIS B 453     3082  3376  3477    510   -837    -54        O
ATOM   2374  O   BHIS B 453      26.205  -7.888  -6.829  0.50 25.07           O
ANISOU 2374  O   BHIS B 453     2993  3176  3357    478   -757    -78        O
ATOM   2375  N   ILE B 454       25.653  -9.052  -5.003  1.00 27.27           N
ANISOU 2375  N   ILE B 454      3565  3340  3458    574   -794     52        N
ATOM   2376  CA  ILE B 454       24.998  -7.895  -4.372  1.00 27.11           C
ANISOU 2376  CA  ILE B 454      3599  3362  3338    428   -809     -5        C
ATOM   2377  CB  ILE B 454       23.458  -7.972  -4.438  1.00 26.13           C
ANISOU 2377  CB  ILE B 454      3614  3124  3189    336   -643    -36        C
ATOM   2378  CG1 ILE B 454       22.894  -9.039  -3.497  1.00 26.52           C
ANISOU 2378  CG1 ILE B 454      3869  3071  3135    383   -593     61        C
ATOM   2379  CD1 ILE B 454       21.346  -8.995  -3.430  1.00 25.42           C
ANISOU 2379  CD1 ILE B 454      3835  2857  2966    266   -427     30        C
ATOM   2380  CG2 ILE B 454       22.973  -8.138  -5.878  1.00 24.81           C
ANISOU 2380  CG2 ILE B 454      3361  2901  3162    300   -521    -96        C
ATOM   2381  C   ILE B 454       25.494  -7.622  -2.952  1.00 29.39           C
ANISOU 2381  C   ILE B 454      3966  3732  3468    447   -963     45        C
ATOM   2382  O   ILE B 454       26.002  -8.522  -2.286  1.00 30.77           O
ANISOU 2382  O   ILE B 454      4208  3900  3584    574  -1039    150        O
ATOM   2383  N   ASP B 455       25.404  -6.364  -2.524  1.00 30.94           N
ANISOU 2383  N   ASP B 455      4162  4002  3593    326  -1021    -33        N
ATOM   2384  CA  ASP B 455       25.620  -6.005  -1.121  1.00 33.96           C
ANISOU 2384  CA  ASP B 455      4670  4448  3787    311  -1152    -13        C
ATOM   2385  CB  ASP B 455       25.973  -4.520  -0.989  1.00 35.01           C
ANISOU 2385  CB  ASP B 455      4741  4672  3890    174  -1250   -124        C
ATOM   2386  CG  ASP B 455       27.250  -4.149  -1.740  1.00 38.55           C
ANISOU 2386  CG  ASP B 455      4937  5236  4473    156  -1370   -141        C
ATOM   2387  OD1 ASP B 455       28.218  -4.942  -1.722  1.00 41.76           O
ANISOU 2387  OD1 ASP B 455      5228  5723  4918    276  -1471    -55        O
ATOM   2388  OD2 ASP B 455       27.285  -3.060  -2.363  1.00 42.88           O
ANISOU 2388  OD2 ASP B 455      5401  5798  5094     27  -1354   -234        O
ATOM   2389  C   ASP B 455       24.357  -6.303  -0.319  1.00 33.96           C
ANISOU 2389  C   ASP B 455      4908  4349  3646    293  -1024     10        C
ATOM   2390  O   ASP B 455       23.262  -6.210  -0.836  1.00 32.87           O
ANISOU 2390  O   ASP B 455      4798  4127  3563    235   -851    -36        O
ATOM   2391  N   ASN B 456       24.516  -6.670   0.945  1.00 36.21           N
ANISOU 2391  N   ASN B 456      5355  4657  3744    343  -1109     87        N
ATOM   2392  CA  ASN B 456       23.386  -6.753   1.864  1.00 36.87           C
ANISOU 2392  CA  ASN B 456      5670  4678  3659    306   -986    102        C
ATOM   2393  CB  ASN B 456       23.798  -7.463   3.160  1.00 39.34           C
ANISOU 2393  CB  ASN B 456      6165  5017  3764    394  -1096    229        C
```

FIGURE 18-71

```
ATOM   2394  CG  ASN B 456      24.239  -8.874   2.934  1.00 41.30           C
ANISOU 2394  CG  ASN B 456     6415   5195   4082    538  -1111    377       C
ATOM   2395  OD1 ASN B 456      23.568  -9.643   2.250  1.00 44.21           O
ANISOU 2395  OD1 ASN B 456     6797   5430   4570    545   -942    407       O
ATOM   2396  ND2 ASN B 456      25.373  -9.238   3.516  1.00 45.13           N
ANISOU 2396  ND2 ASN B 456     6893   5765   4491    658  -1320    471       N
ATOM   2397  C   ASN B 456      22.849  -5.350   2.191  1.00 35.93           C
ANISOU 2397  C   ASN B 456     5597   4597   3458    185   -957    -37       C
ATOM   2398  O   ASN B 456      23.527  -4.564   2.854  1.00 36.85           O
ANISOU 2398  O   ASN B 456     5741   4804   3458    149  -1118    -88       O
ATOM   2399  N   VAL B 457      21.652  -5.044   1.700  1.00 34.16           N
ANISOU 2399  N   VAL B 457     5380   4302   3299    127   -759   -100       N
ATOM   2400  CA  VAL B 457      20.941  -3.805   2.045  1.00 33.91           C
ANISOU 2400  CA  VAL B 457     5421   4277   3188     49   -691   -223       C
ATOM   2401  CB  VAL B 457      20.748  -2.905   0.801  1.00 32.48           C
ANISOU 2401  CB  VAL B 457     5070   4073   3197     -6   -646   -327       C
ATOM   2402  CG1 VAL B 457      20.040  -1.606   1.166  1.00 32.79           C
ANISOU 2402  CG1 VAL B 457     5203   4095   3159    -56   -577   -451       C
ATOM   2403  CG2 VAL B 457      22.108  -2.600   0.143  1.00 33.09           C
ANISOU 2403  CG2 VAL B 457     4980   4206   3385    -23   -828   -340       C
ATOM   2404  C   VAL B 457      19.575  -4.186   2.625  1.00 33.78           C
ANISOU 2404  C   VAL B 457     5553   4211   3070     49   -478   -196       C
ATOM   2405  O   VAL B 457      18.791  -4.831   1.940  1.00 32.79           O
ANISOU 2405  O   VAL B 457     5360   4029   3068     45   -328   -158       O
ATOM   2406  N   MSE B 458      19.303  -3.798   3.876  1.00 34.81           N
ANISOU 2406  N   MSE B 458     5882   4374   2971     43   -464   -218       N
ATOM   2407  CA  MSE B 458      18.039  -4.135   4.545  1.00 35.03           C
ANISOU 2407  CA  MSE B 458     6051   4379   2879     40   -244   -187       C
ATOM   2408  CB  MSE B 458      18.056  -3.708   6.020  1.00 37.27           C
ANISOU 2408  CB  MSE B 458     6581   4716   2866     45   -267   -210       C
ATOM   2409  CG  MSE B 458      16.872  -4.222   6.828  1.00 37.38           C
ANISOU 2409  CG  MSE B 458     6752   4723   2726     45    -30   -149       C
ATOM   2410  SE  MSE B 458      16.820  -3.511   8.603  0.90 41.33          SE
ANISOU 2410  SE  MSE B 458     7579   5297   2828     55    -30   -211      SE
ATOM   2411  CE  MSE B 458      15.420  -4.680   9.317  1.00 44.38           C
ANISOU 2411  CE  MSE B 458     8103   5675   3084     45    298    -58       C
ATOM   2412  C   MSE B 458      16.868  -3.480   3.818  1.00 33.79           C
ANISOU 2412  C   MSE B 458     5784   4197   2856     10    -53   -282       C
ATOM   2413  O   MSE B 458      16.995  -2.362   3.336  1.00 32.16           O
ANISOU 2413  O   MSE B 458     5505   3991   2722     -1    -98   -401       O
ATOM   2414  N   GLY B 459      15.744  -4.194   3.715  1.00 34.01           N
ANISOU 2414  N   GLY B 459     5796   4205   2922     -6    153   -221       N
ATOM   2415  CA  GLY B 459      14.570  -3.680   2.991  1.00 33.33           C
ANISOU 2415  CA  GLY B 459     5569   4123   2974    -25    328   -296       C
ATOM   2416  C   GLY B 459      14.548  -4.009   1.501  1.00 31.85           C
ANISOU 2416  C   GLY B 459     5161   3902   3041    -49    307   -289       C
ATOM   2417  O   GLY B 459      13.682  -3.523   0.781  1.00 30.68           O
ANISOU 2417  O   GLY B 459     4875   3768   3012    -57    409   -348       O
ATOM   2418  N   MSE B 460      15.478  -4.860   1.057  1.00 31.24           N
ANISOU 2418  N   MSE B 460     5054   3784   3033    -50    177   -214       N
ATOM   2419  CA  MSE B 460      15.677  -5.150  -0.354  1.00 31.07           C
ANISOU 2419  CA  MSE B 460     4850   3729   3225    -65    137   -221       C
ATOM   2420  CB  MSE B 460      16.629  -4.100  -0.868  1.00 30.09           C
ANISOU 2420  CB  MSE B 460     4650   3629   3156    -42    -20   -303       C
ATOM   2421  CG  MSE B 460      16.615  -3.833  -2.309  1.00 32.45           C
ANISOU 2421  CG  MSE B 460     4767   3917   3643    -59    -30   -347       C
ATOM   2422  SE  MSE B 460      17.913  -2.375  -2.609  0.90 34.00          SE
ANISOU 2422  SE  MSE B 460     4919   4140   3859    -59   -219   -436      SE
ATOM   2423  CE  MSE B 460      16.991  -0.929  -1.707  1.00 33.99           C
ANISOU 2423  CE  MSE B 460     5050   4135   3729    -54   -133   -542       C
ATOM   2424  C   MSE B 460      16.331  -6.512  -0.539  1.00 28.84           C
ANISOU 2424  C   MSE B 460     4594   3383   2980    -52     79   -112       C
ATOM   2425  O   MSE B 460      17.138  -6.910   0.282  1.00 30.15           O
ANISOU 2425  O   MSE B 460     4884   3544   3026     -3    -19    -42       O
ATOM   2426  N   VAL B 461      16.008  -7.206  -1.624  1.00 27.09           N
ANISOU 2426  N   VAL B 461     4265   3111   2918    -87    131   -100       N
ATOM   2427  CA  VAL B 461      16.671  -8.480  -1.957  1.00 26.80           C
ANISOU 2427  CA  VAL B 461     4263   2984   2937    -58     81    -14       C
ATOM   2428  CB  VAL B 461      15.830  -9.766  -1.561  1.00 27.65           C
ANISOU 2428  CB  VAL B 461     4497   2994   3014   -121    226     84       C
ATOM   2429  CG1 VAL B 461      15.820  -9.957  -0.084  1.00 30.27           C
```

FIGURE 18-72

```
ANISOU 2429  CG1 VAL B 461      5027   3330   3145    -99    248    174          C
ATOM   2430  CG2 VAL B 461      14.394  -9.726  -2.097  1.00 27.50              C
ANISOU 2430  CG2 VAL B 461      4380   2992   3077   -246    392     36          C
ATOM   2431  C   VAL B 461      17.010  -8.528  -3.436  1.00 24.89              C
ANISOU 2431  C   VAL B 461      3858   2724   2874    -57     39    -71          C
ATOM   2432  O   VAL B 461      16.458  -7.760  -4.216  1.00 22.95              O
ANISOU 2432  O   VAL B 461      3485   2528   2709   -103     75   -156          O
ATOM   2433  N   GLY B 462      17.912  -9.440  -3.809  1.00 24.45              N
ANISOU 2433  N   GLY B 462      3821   2599   2872     11    -31    -19          N
ATOM   2434  CA  GLY B 462      18.142  -9.764  -5.208  1.00 23.12              C
ANISOU 2434  CA  GLY B 462      3536   2394   2854     12    -34    -67          C
ATOM   2435  C   GLY B 462      17.109 -10.760  -5.728  1.00 23.17              C
ANISOU 2435  C   GLY B 462      3586   2297   2922    -82     97    -61          C
ATOM   2436  O   GLY B 462      16.340 -11.359  -4.962  1.00 23.84              O
ANISOU 2436  O   GLY B 462      3793   2324   2942   -146    191      2          O
ATOM   2437  N   VAL B 463      17.080 -10.925  -7.043  1.00 22.89              N
ANISOU 2437  N   VAL B 463      3453   2241   3003   -108    105   -129          N
ATOM   2438  CA  VAL B 463      16.154 -11.866  -7.677  1.00 23.22              C
ANISOU 2438  CA  VAL B 463      3530   2185   3106   -220    206   -145          C
ATOM   2439  CB  VAL B 463      14.824 -11.131  -8.120  1.00 22.55              C
ANISOU 2439  CB  VAL B 463      3313   2204   3052   -353    274   -216          C
ATOM   2440  CG1 VAL B 463      15.089 -10.058  -9.145  1.00 20.58              C
ANISOU 2440  CG1 VAL B 463      2902   2062   2857   -321    205   -302          C
ATOM   2441  CG2 VAL B 463      13.796 -12.107  -8.634  1.00 23.79              C
ANISOU 2441  CG2 VAL B 463      3493   2283   3263   -503    366   -230          C
ATOM   2442  C   VAL B 463      16.893 -12.591  -8.810  1.00 22.85              C
ANISOU 2442  C   VAL B 463      3485   2051   3146   -163    174   -184          C
ATOM   2443  O   VAL B 463      17.576 -11.960  -9.618  1.00 21.88              O
ANISOU 2443  O   VAL B 463      3242   2006   3066   -101    110   -243          O
ATOM   2444  N   LEU B 464      16.772 -13.917  -8.835  1.00 24.48              N
ANISOU 2444  N   LEU B 464      3847   2086   3370   -184    230   -147          N
ATOM   2445  CA  LEU B 464      17.398 -14.757  -9.860  1.00 24.70              C
ANISOU 2445  CA  LEU B 464      3920   1996   3469   -121    225   -193          C
ATOM   2446  CB  LEU B 464      17.692 -16.167  -9.278  1.00 26.50              C
ANISOU 2446  CB  LEU B 464      4383   2003   3684    -60    262   -101          C
ATOM   2447  CG  LEU B 464      18.614 -16.282  -8.045  1.00 27.20              C
ANISOU 2447  CG  LEU B 464      4556   2079   3698    112    196     31          C
ATOM   2448  CD1 LEU B 464      18.909 -17.751  -7.716  1.00 26.95              C
ANISOU 2448  CD1 LEU B 464      4774   1800   3666    194    234    122          C
ATOM   2449  CD2 LEU B 464      19.925 -15.482  -8.186  1.00 25.91              C
ANISOU 2449  CD2 LEU B 464      4231   2069   3545    291     74     17          C
ATOM   2450  C   LEU B 464      16.470 -14.848 -11.075  1.00 24.29              C
ANISOU 2450  C   LEU B 464      3811   1943   3475   -279    275   -305          C
ATOM   2451  O   LEU B 464      15.296 -14.566 -10.935  1.00 23.51              O
ANISOU 2451  O   LEU B 464      3661   1902   3369   -438    321   -317          O
ATOM   2452  N   PRO B 465      16.996 -15.222 -12.270  1.00 25.25              N
ANISOU 2452  N   PRO B 465      3932   2015   3645   -232    265   -388          N
ATOM   2453  CA  PRO B 465      16.120 -15.432 -13.438  1.00 25.68              C
ANISOU 2453  CA  PRO B 465      3964   2062   3731   -391    297   -499          C
ATOM   2454  CB  PRO B 465      17.050 -16.084 -14.460  1.00 25.85              C
ANISOU 2454  CB  PRO B 465      4061   1984   3778   -277    298   -570          C
ATOM   2455  CG  PRO B 465      18.388 -15.510 -14.133  1.00 24.55              C
ANISOU 2455  CG  PRO B 465      3812   1904   3610    -63    245   -516          C
ATOM   2456  CD  PRO B 465      18.421 -15.441 -12.622  1.00 25.27              C
ANISOU 2456  CD  PRO B 465      3945   1989   3669    -26    225   -389          C
ATOM   2457  C   PRO B 465      14.846 -16.281 -13.209  1.00 28.21              C
ANISOU 2457  C   PRO B 465      4391   2269   4059   -603    369   -498          C
ATOM   2458  O   PRO B 465      13.803 -15.960 -13.790  1.00 27.91              O
ANISOU 2458  O   PRO B 465      4244   2328   4033   -771    372   -565          O
ATOM   2459  N   ASP B 466      14.925 -17.337 -12.388  1.00 30.80              N
ANISOU 2459  N   ASP B 466      4922   2403   4379   -599    424   -415          N
ATOM   2460  CA  ASP B 466      13.752 -18.159 -12.058  1.00 33.52              C
ANISOU 2460  CA  ASP B 466      5376   2631   4730   -825    507   -396          C
ATOM   2461  CB  ASP B 466      14.126 -19.605 -11.623  1.00 35.98              C
ANISOU 2461  CB  ASP B 466      5985   2643   5044   -799    566   -329          C
ATOM   2462  CG  ASP B 466      14.980 -19.668 -10.343  1.00 37.63              C
ANISOU 2462  CG  ASP B 466      6297   2804   5198   -600    556   -174          C
ATOM   2463  OD1 ASP B 466      15.185 -18.631  -9.683  1.00 38.27              O
ANISOU 2463  OD1 ASP B 466      6230   3080   5230   -509    509   -123          O
ATOM   2464  OD2 ASP B 466      15.460 -20.776  -9.985  1.00 41.34              O
ANISOU 2464  OD2 ASP B 466      7013   3029   5664   -519    587   -101          O
```

FIGURE 18-73

```
ATOM   2465  C   ASP B 466      12.853 -17.487 -11.009  1.00 33.70           C
ANISOU 2465  C   ASP B 466     5289   2800   4716   -926    547   -316       C
ATOM   2466  O   ASP B 466      11.911 -18.095 -10.495  1.00 35.21           O
ANISOU 2466  O   ASP B 466     5552   2920   4904  -1111    636   -270       O
ATOM   2467  N   MSE B 467      13.146 -16.229 -10.700  1.00 32.05           N
ANISOU 2467  N   MSE B 467     4911   2790   4475   -810    493   -302       N
ATOM   2468  CA  MSE B 467      12.363 -15.426  -9.749  1.00 32.32           C
ANISOU 2468  CA  MSE B 467     4839   2978   4464   -867    537   -247       C
ATOM   2469  CB  MSE B 467      10.852 -15.367 -10.098  1.00 33.45           C
ANISOU 2469  CB  MSE B 467     4846   3217   4648  -1096    603   -295       C
ATOM   2470  CG  MSE B 467      10.480 -14.569 -11.341  1.00 34.23           C
ANISOU 2470  CG  MSE B 467     4734   3476   4798  -1122    530   -411       C
ATOM   2471  SE  MSE B 467      11.051 -12.703 -11.393  0.90 35.66          SE
ANISOU 2471  SE  MSE B 467     4726   3873   4950   -913    438   -429      SE
ATOM   2472  CE  MSE B 467      10.370 -12.081  -9.735  1.00 33.79           C
ANISOU 2472  CE  MSE B 467     4462   3731   4645   -908    538   -336       C
ATOM   2473  C   MSE B 467      12.545 -15.812  -8.285  1.00 32.77           C
ANISOU 2473  C   MSE B 467     5059   2956   4437   -824    593   -111       C
ATOM   2474  O   MSE B 467      11.814 -15.332  -7.424  1.00 33.07           O
ANISOU 2474  O   MSE B 467     5047   3099   4420   -886    661    -63       O
ATOM   2475  N   THR B 468      13.511 -16.674  -8.005  1.00 33.28           N
ANISOU 2475  N   THR B 468     5323   2840   4482   -705    569    -45       N
ATOM   2476  CA  THR B 468      13.885 -16.983  -6.629  1.00 33.89           C
ANISOU 2476  CA  THR B 468     5568   2851   4457   -623    589     98       C
ATOM   2477  CB  THR B 468      14.768 -18.251  -6.562  1.00 35.34           C
ANISOU 2477  CB  THR B 468     5996   2785   4646   -509    572    172       C
ATOM   2478  OG1 THR B 468      13.977 -19.388  -6.930  1.00 37.79           O
ANISOU 2478  OG1 THR B 468     6452   2897   5009   -697    675    166       O
ATOM   2479  CG2 THR B 468      15.313 -18.475  -5.164  1.00 36.57           C
ANISOU 2479  CG2 THR B 468     6321   2896   4679   -382    556    334       C
ATOM   2480  C   THR B 468      14.591 -15.751  -6.022  1.00 32.35           C
ANISOU 2480  C   THR B 468     5263   2840   4187   -460    495    111       C
ATOM   2481  O   THR B 468      15.453 -15.146  -6.652  1.00 30.75           O
ANISOU 2481  O   THR B 468     4946   2713   4024   -334    390     46       O
ATOM   2482  N   PRO B 469      14.192 -15.361  -4.801  1.00 32.67           N
ANISOU 2482  N   PRO B 469     5345   2955   4113   -481    542    189       N
ATOM   2483  CA  PRO B 469      14.887 -14.289  -4.133  1.00 31.19           C
ANISOU 2483  CA  PRO B 469     5102   2914   3836   -342    447    195       C
ATOM   2484  CB  PRO B 469      13.971 -13.957  -2.953  1.00 32.02           C
ANISOU 2484  CB  PRO B 469     5259   3094   3815   -428    558    252       C
ATOM   2485  CG  PRO B 469      13.209 -15.162  -2.692  1.00 35.33           C
ANISOU 2485  CG  PRO B 469     5828   3365   4231   -568    694    337       C
ATOM   2486  CD  PRO B 469      13.071 -15.891  -4.001  1.00 34.33           C
ANISOU 2486  CD  PRO B 469     5660   3121   4262   -648    695    268       C
ATOM   2487  C   PRO B 469      16.256 -14.732  -3.650  1.00 31.84           C
ANISOU 2487  C   PRO B 469     5312   2920   3863   -153    327    282       C
ATOM   2488  O   PRO B 469      16.421 -15.890  -3.258  1.00 34.25           O
ANISOU 2488  O   PRO B 469     5817   3054   4141   -128    356    388       O
ATOM   2489  N   SER B 470      17.223 -13.819  -3.690  1.00 30.20           N
ANISOU 2489  N   SER B 470     4990   2841   3645    -24    191    241       N
ATOM   2490  CA  SER B 470      18.571 -14.100  -3.234  1.00 30.87           C
ANISOU 2490  CA  SER B 470     5139   2908   3684    161     53    318       C
ATOM   2491  CB  SER B 470      19.482 -14.433  -4.402  1.00 29.68           C
ANISOU 2491  CB  SER B 470     4890   2716   3672    269    -11    267       C
ATOM   2492  OG  SER B 470      20.792 -14.608  -3.929  1.00 30.33           O
ANISOU 2492  OG  SER B 470     4987   2820   3717    461   -149    343       O
ATOM   2493  C   SER B 470      19.131 -12.899  -2.510  1.00 30.64           C
ANISOU 2493  C   SER B 470     5033   3057   3553    216    -65    302       C
ATOM   2494  O   SER B 470      18.928 -11.761  -2.930  1.00 29.05           O
ANISOU 2494  O   SER B 470     4674   2979   3385    159    -76    194       O
ATOM   2495  N   THR B 471      19.865 -13.168  -1.437  1.00 32.50           N
ANISOU 2495  N   THR B 471     5393   3296   3659    329   -164    411       N
ATOM   2496  CA  THR B 471      20.614 -12.129  -0.716  1.00 32.89           C
ANISOU 2496  CA  THR B 471     5386   3511   3599    384   -315    395       C
ATOM   2497  CB  THR B 471      20.490 -12.340   0.813  1.00 34.91           C
ANISOU 2497  CB  THR B 471     5860   3771   3632    403   -333    511       C
ATOM   2498  OG1 THR B 471      20.876 -13.675   1.140  1.00 37.72           O
ANISOU 2498  OG1 THR B 471     6384   3985   3961    514   -348    662       O
ATOM   2499  CG2 THR B 471      19.028 -12.160   1.273  1.00 34.90           C
ANISOU 2499  CG2 THR B 471     5958   3753   3549    246   -138    495       C
ATOM   2500  C   THR B 471      22.099 -12.082  -1.145  1.00 32.75           C
```

FIGURE 18-74

```
ANISOU 2500  C   THR B 471    5227  3559  3656   534  -494   396       C
ATOM   2501  O   THR B 471    22.890 -11.337  -0.583  1.00 34.16       O
ANISOU 2501  O   THR B 471    5345  3877  3756   575  -648   389       O
ATOM   2502  N   GLU B 472    22.465 -12.869  -2.157  1.00 31.92       N
ANISOU 2502  N   GLU B 472    5064  3360  3702   609  -467   396       N
ATOM   2503  CA  GLU B 472    23.861 -12.976  -2.589  1.00 31.44       C
ANISOU 2503  CA  GLU B 472    4859  3365  3724   773  -605   407       C
ATOM   2504  CB  GLU B 472    24.370 -14.411  -2.376  1.00 33.51       C
ANISOU 2504  CB  GLU B 472    5266  3476  3992   956  -618   540       C
ATOM   2505  CG  GLU B 472    24.422 -14.846  -0.927  1.00 37.90       C
ANISOU 2505  CG  GLU B 472    6031  4005  4363  1022  -691   691       C
ATOM   2506  CD  GLU B 472    23.763 -16.204  -0.707  1.00 44.50       C
ANISOU 2506  CD  GLU B 472    7139  4591  5179  1042  -560   804       C
ATOM   2507  OE1 GLU B 472    24.485 -17.177  -0.350  1.00 46.85       O
ANISOU 2507  OE1 GLU B 472    7556  4788  5457  1242  -630   939       O
ATOM   2508  OE2 GLU B 472    22.521 -16.302  -0.892  1.00 44.38       O
ANISOU 2508  OE2 GLU B 472    7216  4477  5169   856  -389   762       O
ATOM   2509  C   GLU B 472    24.062 -12.542  -4.036  1.00 28.34       C
ANISOU 2509  C   GLU B 472    4255  3014  3498   741  -565   283       C
ATOM   2510  O   GLU B 472    25.024 -11.859  -4.337  1.00 27.47       O
ANISOU 2510  O   GLU B 472    3954  3050  3434   785  -672   244       O
ATOM   2511  N   MSE B 473    23.145 -12.942  -4.916  1.00 26.75       N
ANISOU 2511  N   MSE B 473    4093  2693  3379   652  -412   224       N
ATOM   2512  CA  MSE B 473    23.244 -12.649  -6.358  1.00 25.55       C
ANISOU 2512  CA  MSE B 473    3777  2567  3364   621  -362   111       C
ATOM   2513  CB  MSE B 473    23.499 -13.920  -7.189  1.00 25.85       C
ANISOU 2513  CB  MSE B 473    3877  2448  3495   728  -290   117       C
ATOM   2514  CG  MSE B 473    24.655 -14.796  -6.777  1.00 28.02       C
ANISOU 2514  CG  MSE B 473    4194  2678  3776   959  -368   220       C
ATOM   2515  SE  MSE B 473    26.394 -14.027  -6.988  0.90 30.87      SE
ANISOU 2515  SE  MSE B 473    4253  3284  4190  1120  -526   214      SE
ATOM   2516  CE  MSE B 473    26.496 -13.771  -8.933  1.00 22.35       C
ANISOU 2516  CE  MSE B 473    2999  2234  3260  1079  -399    59       C
ATOM   2517  C   MSE B 473    21.954 -12.044  -6.864  1.00 23.67       C
ANISOU 2517  C   MSE B 473    3524  2330  3138   431  -255    20       C
ATOM   2518  O   MSE B 473    20.913 -12.197  -6.250  1.00 23.75       O
ANISOU 2518  O   MSE B 473    3657  2283  3082   333  -183    45       O
ATOM   2519  N   SER B 474    22.018 -11.384  -8.012  1.00 23.00       N
ANISOU 2519  N   SER B 474    3283  2317  3138   384  -240   -79       N
ATOM   2520  CA  SER B 474    20.815 -10.819  -8.621  1.00 21.94       C
ANISOU 2520  CA  SER B 474    3118  2194  3023   228  -154  -159       C
ATOM   2521  CB  SER B 474    20.425  -9.496  -7.949  1.00 20.28       C
ANISOU 2521  CB  SER B 474    2863  2099  2745   152  -190  -179       C
ATOM   2522  OG  SER B 474    19.094  -9.121  -8.284  1.00 20.72       O
ANISOU 2522  OG  SER B 474    2910  2154  2809    30   -97  -231       O
ATOM   2523  C   SER B 474    21.036 -10.602 -10.103  1.00 22.22       C
ANISOU 2523  C   SER B 474    3031  2262  3151   217  -130  -246       C
ATOM   2524  O   SER B 474    22.178 -10.392 -10.544  1.00 22.87       O
ANISOU 2524  O   SER B 474    3006  2412  3273   308  -185  -253       O
ATOM   2525  N   MSE B 475    19.942 -10.646 -10.871  1.00 22.60       N
ANISOU 2525  N   MSE B 475    3085  2278  3225   101   -49  -308       N
ATOM   2526  CA  MSE B 475    19.951 -10.117 -12.224  1.00 22.94       C
ANISOU 2526  CA  MSE B 475    3014  2384  3318    64   -37  -391       C
ATOM   2527  CB  MSE B 475    18.539 -10.126 -12.829  1.00 21.81       C
ANISOU 2527  CB  MSE B 475    2880  2226  3181   -76    26  -446       C
ATOM   2528  CG  MSE B 475    18.108 -11.548 -13.200  1.00 24.19       C
ANISOU 2528  CG  MSE B 475    3308  2381  3504  -112    93  -465       C
ATOM   2529  SE  MSE B 475    16.546 -11.727 -14.313  0.90 27.36      SE
ANISOU 2529  SE  MSE B 475    3688  2786  3921  -305   143  -557      SE
ATOM   2530  CE  MSE B 475    15.247 -11.070 -13.061  1.00 18.34       C
ANISOU 2530  CE  MSE B 475    2500  1718  2750  -406   169  -500       C
ATOM   2531  C   MSE B 475    20.526  -8.725 -12.161  1.00 22.17       C
ANISOU 2531  C   MSE B 475    2788  2424  3212    70  -108  -396       C
ATOM   2532  O   MSE B 475    20.131  -7.953 -11.287  1.00 21.81       O
ANISOU 2532  O   MSE B 475    2749  2419  3118    30  -137  -377       O
ATOM   2533  N   ARG B 476    21.484  -8.425 -13.055  1.00 22.25       N
ANISOU 2533  N   ARG B 476    2693  2497  3262   116  -127  -422       N
ATOM   2534  CA  ARG B 476    22.159  -7.132 -13.117  1.00 22.50       C
ANISOU 2534  CA  ARG B 476    2605  2648  3297    98  -188  -424       C
ATOM   2535  CB  ARG B 476    23.037  -7.065 -14.384  1.00 22.64       C
ANISOU 2535  CB  ARG B 476    2515  2725  3361   130  -162  -454       C
```

FIGURE 18-75

```
ATOM   2536  CG  ARG B 476      23.641  -5.664 -14.657  1.00 24.65           C
ANISOU 2536  CG  ARG B 476    2649   3092   3623     68   -205   -454        C
ATOM   2537  CD  ARG B 476      24.241  -5.462 -16.092  1.00 25.76           C
ANISOU 2537  CD  ARG B 476    2697   3299   3792     63   -145   -481        C
ATOM   2538  NE  ARG B 476      23.541  -6.128 -17.231  1.00 27.18           N
ANISOU 2538  NE  ARG B 476    2943   3428   3957     63    -58   -533        N
ATOM   2539  CZ  ARG B 476      22.619  -5.553 -18.020  1.00 27.94           C
ANISOU 2539  CZ  ARG B 476    3071   3528   4018    -25    -39   -562        C
ATOM   2540  NH1 ARG B 476      22.175  -4.295 -17.792  1.00 26.67           N
ANISOU 2540  NH1 ARG B 476    2896   3395   3843   -102    -85   -540        N
ATOM   2541  NH2 ARG B 476      22.108  -6.250 -19.027  1.00 19.87           N
ANISOU 2541  NH2 ARG B 476    2107   2475   2969    -28     19   -615        N
ATOM   2542  C   ARG B 476      21.228  -5.892 -12.998  1.00 21.11           C
ANISOU 2542  C   ARG B 476    2425   2504   3091     -6   -197   -447        C
ATOM   2543  O   ARG B 476      20.346  -5.675 -13.836  1.00 20.87           O
ANISOU 2543  O   ARG B 476    2391   2470   3068    -64   -149   -485        O
ATOM   2544  N   GLY B 477      21.432  -5.093 -11.949  1.00 21.59           N
ANISOU 2544  N   GLY B 477    2495   2597   3111    -19   -262   -426        N
ATOM   2545  CA  GLY B 477      20.682  -3.845 -11.726  1.00 20.28           C
ANISOU 2545  CA  GLY B 477    2344   2444   2916    -89   -267   -452        C
ATOM   2546  C   GLY B 477      19.265  -4.001 -11.186  1.00 19.95           C
ANISOU 2546  C   GLY B 477    2384   2360   2837   -110   -204   -459        C
ATOM   2547  O   GLY B 477      18.600  -2.995 -10.954  1.00 20.31           O
ANISOU 2547  O   GLY B 477    2442   2415   2859   -137   -196   -482        O
ATOM   2548  N   ILE B 478      18.805  -5.242 -10.986  1.00 19.45           N
ANISOU 2548  N   ILE B 478    2374   2245   2770    -98   -152   -437        N
ATOM   2549  CA  ILE B 478      17.425  -5.543 -10.523  1.00 17.96           C
ANISOU 2549  CA  ILE B 478    2239   2031   2556   -143    -73   -436        C
ATOM   2550  CB  ILE B 478      16.747  -6.700 -11.323  1.00 18.46           C
ANISOU 2550  CB  ILE B 478    2303   2046   2665   -189     -7   -446.       C
ATOM   2551  CG1 ILE B 478      17.035  -6.649 -12.849  1.00 16.97           C
ANISOU 2551  CG1 ILE B 478    2037   1879   2532   -198    -24   -493        C
ATOM   2552  CD1 ILE B 478      16.569  -5.382 -13.592  1.00 12.97           C
ANISOU 2552  CD1 ILE B 478    1440   1453   2034   -221    -43   -526        C
ATOM   2553  CG2 ILE B 478      15.216  -6.762 -11.010  1.00 18.15           C
ANISOU 2553  CG2 ILE B 478    2259   2020   2616   -267     75   -451        C
ATOM   2554  C   ILE B 478      17.351  -5.901  -9.018  1.00 18.54           C
ANISOU 2554  C   ILE B 478    2425   2075   2545   -124    -62   -387        C
ATOM   2555  O   ILE B 478      18.093  -6.760  -8.523  1.00 18.41           O
ANISOU 2555  O   ILE B 478    2476   2015   2504    -76    -93   -336        O
ATOM   2556  N   ARG B 479      16.435  -5.252  -8.299  1.00 18.71           N
ANISOU 2556  N   ARG B 479    2473   2124   2512   -148    -11   -398        N
ATOM   2557  CA  ARG B 479      16.205  -5.537  -6.881  1.00 19.06           C
ANISOU 2557  CA  ARG B 479    2640   2153   2450   -139     24   -354        C
ATOM   2558  CB  ARG B 479      16.835  -4.454  -5.980  1.00 19.31           C
ANISOU 2558  CB  ARG B 479    2727   2220   2388   -100    -54   -375        C
ATOM   2559  CG  ARG B 479      18.364  -4.281  -6.108  1.00 17.90           C
ANISOU 2559  CG  ARG B 479    2524   2056   2221    -65   -199   -368        C
ATOM   2560  CD  ARG B 479      19.159  -5.504  -5.595  1.00 20.83           C
ANISOU 2560  CD  ARG B 479    2956   2400   2558    -12   -249   -287        C
ATOM   2561  NE  ARG B 479      20.603  -5.259  -5.641  1.00 22.94           N
ANISOU 2561  NE  ARG B 479    3160   2718   2838     31   -392   -279        N
ATOM   2562  CZ  ARG B 479      21.370  -5.399  -6.728  1.00 22.88           C
ANISOU 2562  CZ  ARG B 479    3022   2729   2941     52   -425   -288        C
ATOM   2563  NH1 ARG B 479      20.850  -5.826  -7.888  1.00 18.51           N
ANISOU 2563  NH1 ARG B 479    2416   2135   2482     38   -335   -309        N
ATOM   2564  NH2 ARG B 479      22.673  -5.109  -6.657  1.00 21.36           N
ANISOU 2564  NH2 ARG B 479    2746   2610   2759     82   -549   -278        N
ATOM   2565  C   ARG B 479      14.714  -5.617  -6.625  1.00 19.99           C
ANISOU 2565  C   ARG B 479    2751   2287   2555    131    157   -358        C
ATOM   2566  O   ARG B 479      13.908  -5.004  -7.352  1.00 19.57           O
ANISOU 2566  O   ARG B 479    2588   2283   2564   -214    195   -407        O
ATOM   2567  N   VAL B 480      14.344  -6.383  -5.600  1.00 20.85           N
ANISOU 2567  N   VAL B 480    2971   2367   2583   -214    231   -299        N
ATOM   2568  CA  VAL B 480      12.969  -6.481  -5.147  1.00 21.50           C
ANISOU 2568  CA  VAL B 480    3043   2486   2640   -275    379   -291        C
ATOM   2569  CB  VAL B 480      12.437  -7.952  -5.221  1.00 22.40           C
ANISOU 2569  CB  VAL B 480    3194   2531   2785   -375    465   -227        C
ATOM   2570  CG1 VAL B 480      11.090  -8.086  -4.576  1.00 22.44           C
ANISOU 2570  CG1 VAL B 480    3183   2592   2754   -458    630   -204        C
ATOM   2571  CG2 VAL B 480      12.380  -8.430  -6.680  1.00 20.69           C
```

FIGURE 18-76

```
ANISOU 2571  CG2 VAL B 480    2869  2287  2705  -430   428  -266       C
ATOM   2572  C   VAL B 480    12.858  -5.880  -3.738  1.00 23.73       C
ANISOU 2572  C   VAL B 480    3442  2803  2771  -231   424  -282       C
ATOM   2573  O   VAL B 480    13.635  -6.213  -2.833  1.00 23.83       O
ANISOU 2573  O   VAL B 480    3604  2779  2670  -198   372  -230       O
ATOM   2574  N   SER B 481    11.899  -4.968  -3.571  1.00 24.34       N
ANISOU 2574  N   SER B 481    3455  2956  2838  -217   517  -336       N
ATOM   2575  CA  SER B 481    11.641  -4.340  -2.293  1.00 26.50       C
ANISOU 2575  CA  SER B 481    3846  3264  2958  -169   590  -350       C
ATOM   2576  CB  SER B 481    10.803  -3.087  -2.498  1.00 26.56       C
ANISOU 2576  CB  SER B 481    3755  3338  2998  -108   659  -436       C
ATOM   2577  OG  SER B 481    10.413  -2.542  -1.251  1.00 29.55       O
ANISOU 2577  OG  SER B 481    4258  3749  3221   -56   765  -461       O
ATOM   2578  C   SER B 481    10.922  -5.271  -1.311  1.00 29.41       C
ANISOU 2578  C   SER B 481    4304  3643  3226  -230   745  -270       C
ATOM   2579  O   SER B 481    10.009  -6.006  -1.679  1.00 29.10       O
ANISOU 2579  O   SER B 481    4167  3623  3266  -319   857  -233       O
ATOM   2580  N   LYS B 482    11.350  -5.230  -0.054  1.00 32.28       N
ANISOU 2580  N   LYS B 482    4862  3998  3405  -194   747  -241       N
ATOM   2581  CA  LYS B 482    10.679  -5.956   1.007  1.00 36.48       C
ANISOU 2581  CA  LYS B 482    5512  4545  3803  -246   910  -159       C
ATOM   2582  CB  LYS B 482    11.708  -6.552   1.973  1.00 37.56       C
ANISOU 2582  CB  LYS B 482    5882  4620  3770  -223   813   -72       C
ATOM   2583  CG  LYS B 482    12.493  -7.739   1.427  1.00 39.17       C
ANISOU 2583  CG  LYS B 482    6106  4718  4059  -250   700    19       C
ATOM   2584  CD  LYS B 482    13.494  -8.227   2.457  1.00 46.13       C
ANISOU 2584  CD  LYS B 482    7211  5556  4762  -192   592   114       C
ATOM   2585  CE  LYS B 482    13.409  -9.749   2.690  1.00 50.34       C
ANISOU 2585  CE  LYS B 482    7871  5976  5278  -245   653   267       C
ATOM   2586  NZ  LYS B 482    14.542 -10.223   3.564  1.00 55.51       N
ANISOU 2586  NZ  LYS B 482    8732  6587  5770  -151   505   373       N
ATOM   2587  C   LYS B 482     9.701  -5.045   1.766  1.00 39.13       C
ANISOU 2587  C   LYS B 482    5851  4981  4035  -202  1082  -221       C
ATOM   2588  O   LYS B 482     9.060  -5.500   2.711  1.00 41.48       O
ANISOU 2588  O   LYS B 482    6242  5315  4202  -242  1250  -160       O
ATOM   2589  N   MSE B 483     9.603  -3.764   1.371  1.00 39.66       N
ANISOU 2589  N   MSE B 483    5832  5082  4154  -113  1050  -338       N
ATOM   2590  CA  MSE B 483     8.689  -2.788   2.016  1.00 42.78       C
ANISOU 2590  CA  MSE B 483    6232  5558  4464   -32  1217  -416       C
ATOM   2591  CB  MSE B 483     9.114  -1.322   1.779  1.00 42.34       C
ANISOU 2591  CB  MSE B 483    6198  5470  4417    85  1113  -544       C
ATOM   2592  CG  MSE B 483    10.519  -0.958   2.191  1.00 42.80       C
ANISOU 2592  CG  MSE B 483    6451  5447  4363    95   911  -575       C
ATOM   2593  SE  MSE B 483    10.790  -1.343   4.076  0.90 53.78       SE
ANISOU 2593  SE  MSE B 483    8155  6858  5420    89   969  -539       SE
ATOM   2594  CE  MSE B 483     9.681  -0.017   5.008  1.00 43.83       C
ANISOU 2594  CE  MSE B 483    6998  5650  4003   213  1203  -680       C
ATOM   2595  C   MSE B 483     7.253  -2.929   1.531  1.00 44.09       C
ANISOU 2595  C   MSE B 483    6165  5828  4760   -57  1407  -409       C
ATOM   2596  O   MSE B 483     7.028  -2.888   0.312  1.00 43.61       O
ANISOU 2596  O   MSE B 483    5899  5777  4893   -73  1342  -423       O
ATOM   2597  OXT MSE B 483     6.311  -3.041   2.339  1.00 46.48       O
ANISOU 2597  OXT MSE B 483    6471  6220  4971   -61  1623  -390       O
ATOM   2598  N   ILE D 319    63.442 -23.655 -17.970  1.00 53.76       N
ANISOU 2598  N   ILE D 319    7685  4667  8075   274   727  -949       N
ATOM   2599  CA  ILE D 319    62.501 -23.137 -16.919  1.00 52.62       C
ANISOU 2599  CA  ILE D 319    7506  4623  7863    88   628  -790       C
ATOM   2600  CB  ILE D 319    62.826 -23.727 -15.487  1.00 53.65       C
ANISOU 2600  CB  ILE D 319    7709  4559  8116   134   561  -578       C
ATOM   2601  CG1 ILE D 319    61.736 -23.378 -14.463  1.00 53.18       C
ANISOU 2601  CG1 ILE D 319    7660  4578  7969   -75   499  -438       C
ATOM   2602  CD1 ILE D 319    61.719 -24.322 -13.234  1.00 55.09       C
ANISOU 2602  CD1 ILE D 319    8066  4566  8299   -89   460  -258       C
ATOM   2603  CG2 ILE D 319    64.206 -23.306 -14.994  1.00 52.60       C
ANISOU 2603  CG2 ILE D 319    7451  4467  8067   373   525  -452       C
ATOM   2604  C   ILE D 319    62.352 -21.605 -16.916  1.00 49.28       C
ANISOU 2604  C   ILE D 319    6892  4530  7301    56   600  -732       C
ATOM   2605  O   ILE D 319    61.237 -21.097 -16.682  1.00 48.90       O
ANISOU 2605  O   ILE D 319    6817  4614  7147  -127   555  -712       O
ATOM   2606  N   SER D 320    63.458 -20.898 -17.210  1.00 47.45       N
ANISOU 2606  N   SER D 320    6524  4418  7087   232   634  -713       N
```

FIGURE 18-77

```
ATOM   2607  CA  SER D 320      63.576 -19.403 -17.245  1.00 43.82           C
ANISOU 2607  CA  SER D 320    5886  4238  6528    231   618  -650            C
ATOM   2608  CB  SER D 320      62.853 -18.783 -18.463  1.00 43.61           C
ANISOU 2608  CB  SER D 320    5846  4391  6332    139   666  -791            C
ATOM   2609  OG  SER D 320      62.411 -19.771 -19.397  1.00 46.63           O
ANISOU 2609  OG  SER D 320    6378  4652  6686     96   715  -975            O
ATOM   2610  C   SER D 320      63.164 -18.674 -15.938  1.00 40.81           C
ANISOU 2610  C   SER D 320    5444  3950  6114    147   509  -475            C
ATOM   2611  O   SER D 320      62.342 -17.737 -15.963  1.00 39.35           O
ANISOU 2611  O   SER D 320    5199  3949  5803     29   485  -470            O
ATOM   2612  N   SER D 321      63.744 -19.096 -14.810  1.00 38.96           N
ANISOU 2612  N   SER D 321    5233  3587  5982    223   441  -336            N
ATOM   2613  CA  SER D 321      63.435 -18.492 -13.514  1.00 35.41           C
ANISOU 2613  CA  SER D 321    4761  3214  5478    159   341  -177            C
ATOM   2614  CB  SER D 321      63.252 -19.571 -12.458  1.00 37.05           C
ANISOU 2614  CB  SER D 321    5133  3209  5736    139   291   -64            C
ATOM   2615  OG  SER D 321      64.485 -20.151 -12.113  1.00 39.50           O
ANISOU 2615  OG  SER D 321    5449  3370  6187    334   243     7            O
ATOM   2616  C   SER D 321      64.454 -17.445 -13.030  1.00 33.02           C
ANISOU 2616  C   SER D 321    4299  3045  5202    275   271   -86            C
ATOM   2617  O   SER D 321      64.263 -16.842 -11.978  1.00 31.66           O
ANISOU 2617  O   SER D 321    4115  2947  4966    231   181    25            O
ATOM   2618  N   SER D 322      65.501 -17.202 -13.829  1.00 31.16           N
ANISOU 2618  N   SER D 322    3939  2845  5057    410   324  -145            N
ATOM   2619  CA  SER D 322      66.656 -16.427 -13.420  1.00 28.20           C
ANISOU 2619  CA  SER D 322    3392  2555  4768    525   259   -67            C
ATOM   2620  CB  SER D 322      67.515 -17.350 -12.575  1.00 30.48           C
ANISOU 2620  CB  SER D 322    3710  2670  5202    669   164    29            C
ATOM   2621  OG  SER D 322      68.312 -16.682 -11.683  1.00 28.82           O
ANISOU 2621  OG  SER D 322    3373  2534  5042    733    26   137            O
ATOM   2622  C   SER D 322      67.425 -16.050 -14.688  1.00 27.21           C
ANISOU 2622  C   SER D 322    3127  2506  4706    610   390  -168            C
ATOM   2623  O   SER D 322      67.831 -16.930 -15.437  1.00 28.51           O
ANISOU 2623  O   SER D 322    3324  2557  4949    708   491  -255            O
ATOM   2624  N   PHE D 323      67.651 -14.758 -14.921  1.00 24.48           N
ANISOU 2624  N   PHE D 323    2638  2339  4326    576   402  -155            N
ATOM   2625  CA  PHE D 323      68.250 -14.299 -16.169  1.00 24.11           C
ANISOU 2625  CA  PHE D 323    2478  2379  4303    627   556  -233            C
ATOM   2626  CB  PHE D 323      67.335 -14.608 -17.378  1.00 23.01           C
ANISOU 2626  CB  PHE D 323    2478  2256  4010    561   682  -365            C
ATOM   2627  CG  PHE D 323      65.905 -14.146 -17.190  1.00 21.13           C
ANISOU 2627  CG  PHE D 323    2340  2096  3593    393   614  -364            C
ATOM   2628  CD1 PHE D 323      65.509 -12.883 -17.609  1.00 18.06           C
ANISOU 2628  CD1 PHE D 323    1896  1878  3090    321   629  -351            C
ATOM   2629  CE1 PHE D 323      64.229 -12.463 -17.415  1.00 18.85           C
ANISOU 2629  CE1 PHE D 323    2060  2050  3052    195   564  -350            C
ATOM   2630  CZ  PHE D 323      63.312 -13.289 -16.768  1.00 18.75           C
ANISOU 2630  CZ  PHE D 323    2157  1953  3016    115   496  -360            C
ATOM   2631  CE2 PHE D 323      63.706 -14.538 -16.339  1.00 19.68           C
ANISOU 2631  CE2 PHE D 323    2346  1892  3241    165   489  -361            C
ATOM   2632  CD2 PHE D 323      64.977 -14.960 -16.567  1.00 18.81           C
ANISOU 2632  CD2 PHE D 323    2185  1700  3264    312   540  -365            C
ATOM   2633  C   PHE D 323      68.551 -12.810 -16.119  1.00 23.35           C
ANISOU 2633  C   PHE D 323    2228  2449  4195    574   541  -174            C
ATOM   2634  O   PHE D 323      68.114 -12.092 -15.213  1.00 22.75           O
ANISOU 2634  O   PHE D 323    2155  2426  4064    488   412  -101            O
ATOM   2635  N   SER D 324      69.271 -12.361 -17.128  1.00 24.41           N
ANISOU 2635  N   SER D 324    2245  2654  4374    623   689  -212            N
ATOM   2636  CA  SER D 324      69.624 -10.980 -17.324  1.00 25.05           C
ANISOU 2636  CA  SER D 324    2189  2868  4460    566   717  -160            C
ATOM   2637  CB  SER D 324      71.102 -10.908 -17.645  1.00 26.25           C
ANISOU 2637  CB  SER D 324    2123  3028  4822    674   816  -146            C
ATOM   2638  OG  SER D 324      71.632  -9.664 -17.257  1.00 30.85           O
ANISOU 2638  OG  SER D 324    2540  3694  5489    607   763   -65            O
ATOM   2639  C   SER D 324      68.774 -10.395 -18.480  1.00 24.43           C
ANISOU 2639  C   SER D 324    2213  2890  4180    485   840  -211            C
ATOM   2640  O   SER D 324      68.616 -11.018 -19.533  1.00 26.03           O
ANISOU 2640  O   SER D 324    2506  3084  4301    525   976  -305            O
ATOM   2641  N   PHE D 325      68.185  -9.219 -18.275  1.00 22.46           N
ANISOU 2641  N   PHE D 325    1967  2727  3838    380   779  -155            N
ATOM   2642  CA  PHE D 325      67.496  -8.549 -19.370  1.00 21.87           C
```

FIGURE 18-78

```
ANISOU 2642  CA  PHE D 325    1975  2750  3586    326    877   -178       C
ATOM   2643  CB  PHE D 325     66.033  -9.046 -19.505  1.00 20.62         C
ANISOU 2643  CB  PHE D 325    1995  2598  3243    268    813   -247       C
ATOM   2644  CG  PHE D 325     65.292  -8.433 -20.664  1.00 20.13         C
ANISOU 2644  CG  PHE D 325    2019  2644  2985    231    879   -274       C
ATOM   2645  CD1 PHE D 325     65.624  -8.761 -21.981  1.00 21.66         C
ANISOU 2645  CD1 PHE D 325    2270  2870  3090    285   1038   -341       C
ATOM   2646  CE1 PHE D 325     64.947  -8.172 -23.059  1.00 22.94         C
ANISOU 2646  CE1 PHE D 325    2536  3141  3041    260   1079   -353       C
ATOM   2647  CZ  PHE D 325     63.902  -7.259 -22.812  1.00 21.18         C
ANISOU 2647  CZ  PHE D 325    2337  2986  2723    190    953   -296       C
ATOM   2648  CE2 PHE D 325     63.581  -6.933 -21.498  1.00 16.68         C
ANISOU 2648  CE2 PHE D 325    1694  2379  2264    142    816   -240       C
ATOM   2649  CD2 PHE D 325     64.266  -7.516 -20.443  1.00 17.35         C
ANISOU 2649  CD2 PHE D 325    1699  2364  2528    156    782   -231       C
ATOM   2650  C   PHE D 325     67.564  -7.047 -19.143  1.00 21.28         C
ANISOU 2650  C   PHE D 325    1823  2743  3519    255    845    -83       C
ATOM   2651  O   PHE D 325     67.193  -6.571 -18.081  1.00 20.40         O
ANISOU 2651  O   PHE D 325    1704  2620  3427    202    694    -41       O
ATOM   2652  N   GLY D 326     68.068  -6.315 -20.129  1.00 22.68         N
ANISOU 2652  N   GLY D 326    1956  2980  3681    255    996    -51       N
ATOM   2653  CA  GLY D 326     68.092  -4.857 -20.077  1.00 21.89         C
ANISOU 2653  CA  GLY D 326    1812  2918  3589    180    986     43       C
ATOM   2654  C   GLY D 326     68.926  -4.267 -18.972  1.00 21.89         C
ANISOU 2654  C   GLY D 326    1648  2871  3799    145    884    102       C
ATOM   2655  O   GLY D 326     68.699  -3.141 -18.549  1.00 22.59         O
ANISOU 2655  O   GLY D 326    1733  2957  3894     70    809    157       O
ATOM   2656  N   GLY D 327     69.900  -5.022 -18.502  1.00 23.39         N
ANISOU 2656  N   GLY D 327    1704  3016  4166    204    868     84       N
ATOM   2657  CA  GLY D 327     70.839  -4.538 -17.493  1.00 23.14         C
ANISOU 2657  CA  GLY D 327    1492  2951  4348    176    749    131       C
ATOM   2658  C   GLY D 327     70.329  -4.854 -16.096  1.00 21.75         C
ANISOU 2658  C   GLY D 327    1381  2731  4150    171    514    118       C
ATOM   2659  O   GLY D 327     70.892  -4.379 -15.118  1.00 22.68         O
ANISOU 2659  O   GLY D 327    1397  2828  4394    138    366    145       O
ATOM   2660  N   PHE D 328     69.279  -5.678 -16.009  1.00 19.65         N
ANISOU 2660  N   PHE D 328    1290  2454  3722    196    483     75       N
ATOM   2661  CA  PHE D 328     68.706  -6.111 -14.734  1.00 17.83         C
ANISOU 2661  CA  PHE D 328    1149  2184  3442    190    299     73       C
ATOM   2662  CB  PHE D 328     67.233  -5.642 -14.619  1.00 15.94         C
ANISOU 2662  CB  PHE D 328    1072  1982  3001    117    271     59       C
ATOM   2663  CG  PHE D 328     67.092  -4.187 -14.431  1.00 14.33         C
ANISOU 2663  CG  PHE D 328     847  1811  2787     46    236     88       C
ATOM   2664  CD1 PHE D 328     67.017  -3.642 -13.141  1.00 16.78         C
ANISOU 2664  CD1 PHE D 328    1171  2101  3102      9     76     98       C
ATOM   2665  CE1 PHE D 328     66.918  -2.239 -12.944  1.00 15.67         C
ANISOU 2665  CE1 PHE D 328    1024  1962  2966    -54     42    109       C
ATOM   2666  CZ  PHE D 328     66.886  -1.387 -14.054  1.00 15.40         C
ANISOU 2666  CZ  PHE D 328     971  1944  2938    -80    169    134       C
ATOM   2667  CE2 PHE D 328     66.986  -1.913 -15.341  1.00 14.72         C
ANISOU 2667  CE2 PHE D 328     873  1892  2828    -43    329    144       C
ATOM   2668  CD2 PHE D 328     67.088  -3.328 -15.522  1.00 15.45         C
ANISOU 2668  CD2 PHE D 328     971  1989  2910     21    362    108       C
ATOM   2669  C   PHE D 328     68.769  -7.623 -14.575  1.00 18.64         C
ANISOU 2669  C   PHE D 328    1303  2216  3563    279    290     46       C
ATOM   2670  O   PHE D 328     68.507  -8.386 -15.522  1.00 20.76         O
ANISOU 2670  O   PHE D 328    1636  2471  3780    318    422     -9       O
ATOM   2671  N   THR D 329     69.112  -8.074 -13.376  1.00 18.73         N
ANISOU 2671  N   THR D 329    1307  2172  3639    313    128     82       N
ATOM   2672  CA  THR D 329     69.005  -9.486 -13.040  1.00 18.53         C
ANISOU 2672  CA  THR D 329    1375  2049  3615    390     97     78       C
ATOM   2673  CB  THR D 329     70.023  -9.885 -11.931  1.00 20.11         C
ANISOU 2673  CB  THR D 329    1490  2190  3961    478    -77    142       C
ATOM   2674  OG1 THR D 329     71.364  -9.562 -12.341  1.00 19.13         O
ANISOU 2674  OG1 THR D 329    1128  2092  4050    544    -48    144       O
ATOM   2675  CG2 THR D 329     69.932 -11.382 -11.615  1.00 18.59         C
ANISOU 2675  CG2 THR D 329    1418  1867  3778    573   -104    159       C
ATOM   2676  C   THR D 329     67.566  -9.736 -12.566  1.00 17.59         C
ANISOU 2676  C   THR D 329    1460  1922  3302    307     61     73       C
ATOM   2677  O   THR D 329     67.134  -9.147 -11.597  1.00 17.15         O
ANISOU 2677  O   THR D 329    1450  1898  3166    247    -52    110       O
```

FIGURE 18-79

```
ATOM   2678  N   PHE D 330      66.827 -10.592 -13.275  1.00 17.78           N
ANISOU 2678  N   PHE D 330     1597   1907   3254    299    165     17       N
ATOM   2679  CA  PHE D 330      65.483 -11.015 -12.896  1.00 16.15           C
ANISOU 2679  CA  PHE D 330     1553   1684   2900    211    149      7       C
ATOM   2680  CB  PHE D 330      64.639 -11.297 -14.140  1.00 15.29           C
ANISOU 2680  CB  PHE D 330     1503   1600   2706    164    276    -89       C
ATOM   2681  CG  PHE D 330      64.137 -10.053 -14.865  1.00 14.68           C
ANISOU 2681  CG  PHE D 330     1379   1664   2533    108    322   -115       C
ATOM   2682  CD1 PHE D 330      62.776  -9.790 -14.933  1.00 13.44           C
ANISOU 2682  CD1 PHE D 330     1289   1576   2242     15    315   -144       C
ATOM   2683  CE1 PHE D 330      62.297  -8.658 -15.616  1.00 12.28           C
ANISOU 2683  CE1 PHE D 330     1106   1548   2011    -11    342   -157       C
ATOM   2684  CZ  PHE D 330      63.203  -7.777 -16.224  1.00 10.41           C
ANISOU 2684  CZ  PHE D 330      787   1349   1819     38    392   -129       C
ATOM   2685  CE2 PHE D 330      64.553  -8.017 -16.140  1.00 10.15           C
ANISOU 2685  CE2 PHE D 330      674   1255   1926    107    417   -102       C
ATOM   2686  CD2 PHE D 330      65.026  -9.161 -15.481  1.00 11.56           C
ANISOU 2686  CD2 PHE D 330      868   1328   2197    152    376   -101       C
ATOM   2687  C   PHE D 330      65.588 -12.317 -12.123  1.00 18.49           C
ANISOU 2687  C   PHE D 330     1952   1835   3239    255     88     51       C
ATOM   2688  O   PHE D 330      66.310 -13.222 -12.529  1.00 19.07           O
ANISOU 2688  O   PHE D 330     2014   1802   3429    356    126     32       O
ATOM   2689  N   LYS D 331      64.871 -12.417 -11.004  1.00 18.87           N
ANISOU 2689  N   LYS D 331     2112   1869   3190    188      7    114       N
ATOM   2690  CA  LYS D 331      64.775 -13.663 -10.273  1.00 19.84           C
ANISOU 2690  CA  LYS D 331     2374   1841   3323    209    -35    177       C
ATOM   2691  CB  LYS D 331      65.564 -13.571  -8.961  1.00 21.52           C
ANISOU 2691  CB  LYS D 331     2594   2030   3554    282   -199    293       C
ATOM   2692  CG  LYS D 331      67.070 -13.465  -9.152  1.00 23.54           C
ANISOU 2692  CG  LYS D 331     2684   2273   3989    429   -270    302       C
ATOM   2693  CD  LYS D 331      67.817 -13.640  -7.837  1.00 30.28           C
ANISOU 2693  CD  LYS D 331     3560   3083   4861    514   -470    419       C
ATOM   2694  CE  LYS D 331      69.326 -13.743  -8.063  1.00 32.87           C
ANISOU 2694  CE  LYS D 331     3692   3387   5410    673   -546    426       C
ATOM   2695  NZ  LYS D 331      70.045 -13.890  -6.766  1.00 36.55           N
ANISOU 2695  NZ  LYS D 331     4174   3826   5889    762   -782    540       N
ATOM   2696  C   LYS D 331      63.317 -13.898  -9.984  1.00 19.36           C
ANISOU 2696  C   LYS D 331     2445   1788   3123     64     15    174       C
ATOM   2697  O   LYS D 331      62.675 -13.085  -9.342  1.00 18.88           O
ANISOU 2697  O   LYS D 331     2391   1836   2946    -11    -10    198       O
ATOM   2698  N   ARG D 332      62.778 -15.009 -10.461  1.00 19.97           N
ANISOU 2698  N   ARG D 332     2620   1747   3223     20     93    133       N
ATOM   2699  CA  ARG D 332      61.355 -15.290 -10.281  1.00 19.72           C
ANISOU 2699  CA  ARG D 332     2679   1723   3091   -141    152    120       C
ATOM   2700  CB  ARG D 332      60.867 -16.358 -11.279  1.00 20.07           C
ANISOU 2700  CB  ARG D 332     2784   1649   3191   -199    239     17       C
ATOM   2701  CG  ARG D 332      59.346 -16.450 -11.354  1.00 20.01           C
ANISOU 2701  CG  ARG D 332     2804   1695   3106   -388    297    -30       C
ATOM   2702  CD  ARG D 332      58.875 -17.327 -12.504  1.00 20.70           C
ANISOU 2702  CD  ARG D 332     2929   1692   3243   -458    356   -169       C
ATOM   2703  NE  ARG D 332      59.269 -18.715 -12.316  1.00 22.45           N
ANISOU 2703  NE  ARG D 332     3301   1656   3571   -438    369   -145       N
ATOM   2704  CZ  ARG D 332      59.397 -19.590 -13.307  1.00 25.52           C
ANISOU 2704  CZ  ARG D 332     3753   1907   4035   -430    408   -274       C
ATOM   2705  NH1 ARG D 332      59.137 -19.233 -14.566  1.00 25.47           N
ANISOU 2705  NH1 ARG D 332     3678   2016   3984   -447    433   -436       N
ATOM   2706  NH2 ARG D 332      59.748 -20.829 -13.035  1.00 27.36           N
ANISOU 2706  NH2 ARG D 332     4137   1879   4378   -401    419   -243       N
ATOM   2707  C   ARG D 332      61.108 -15.726  -8.841  1.00 20.88           C
ANISOU 2707  C   ARG D 332     2961   1796   3175   -177    105    260       C
ATOM   2708  O   ARG D 332      61.801 -16.602  -8.331  1.00 21.02           O
ANISOU 2708  O   ARG D 332     3078   1652   3257    -95     52    348       O
ATOM   2709  N   THR D 333      60.149 -15.078  -8.180  1.00 20.24           N
ANISOU 2709  N   THR D 333     2890   1838   2964   -284    127    286       N
ATOM   2710  CA  THR D 333      59.820 -15.426  -6.778  1.00 21.32           C
ANISOU 2710  CA  THR D 333     3176   1927   2997   -328    111    423       C
ATOM   2711  CB  THR D 333      59.888 -14.174  -5.876  1.00 20.56           C
ANISOU 2711  CB  THR D 333     3051   1993   2767   -301     47    456       C
ATOM   2712  OG1 THR D 333      59.095 -13.132  -6.468  1.00 19.68           O
ANISOU 2712  OG1 THR D 333     2807   2049   2621   -363    113    346       O
ATOM   2713  CG2 THR D 333      61.342 -13.644  -5.770  1.00 21.41           C
```

FIGURE 18-80

```
ANISOU 2713  CG2 THR D 333    3092  2109  2933  -143  -107   471           C
ATOM   2714  C   THR D 333    58.450 -16.124  -6.612  1.00 22.28           C
ANISOU 2714  C   THR D 333    3381  2007  3077  -508   241   434           C
ATOM   2715  O   THR D 333    58.187 -16.719  -5.565  1.00 24.07           O
ANISOU 2715  O   THR D 333    3763  2148  3232  -557   263   564           O
ATOM   2716  N   SER D 334    57.595 -16.054  -7.636  1.00 21.08           N
ANISOU 2716  N   SER D 334    3124  1916  2968  -609   321   305           N
ATOM   2717  CA  SER D 334    56.275 -16.727  -7.644  1.00 22.78           C
ANISOU 2717  CA  SER D 334    3368  2099  3187  -801   437   290           C
ATOM   2718  CB  SER D 334    55.169 -15.774  -7.203  1.00 22.34           C
ANISOU 2718  CB  SER D 334    3214  2251  3025  -891   506   277           C
ATOM   2719  OG  SER D 334    54.919 -15.851  -5.848  1.00 26.42           O
ANISOU 2719  OG  SER D 334    3849  2761  3430  -928   557   413           O
ATOM   2720  C   SER D 334    55.889 -17.081  -9.055  1.00 21.71           C
ANISOU 2720  C   SER D 334    3148  1948  3153  -862   459   131           C
ATOM   2721  O   SER D 334    56.317 -16.426  -9.985  1.00 20.94           O
ANISOU 2721  O   SER D 334    2944  1944  3068  -771   412    32           O
ATOM   2722  N   GLY D 335    55.021 -18.077  -9.193  1.00 23.23           N
ANISOU 2722  N   GLY D 335    3391  2027  3407 -1030   533   108           N
ATOM   2723  CA  GLY D 335    54.375 -18.411 -10.458  1.00 21.87           C
ANISOU 2723  CA  GLY D 335    3139  1860  3310 -1132   543   -62           C
ATOM   2724  C   GLY D 335    55.276 -19.178 -11.397  1.00 22.97           C
ANISOU 2724  C   GLY D 335    3362  1826  3539 -1040   501  -149           C
ATOM   2725  O   GLY D 335    56.339 -19.683 -10.997  1.00 21.77           O
ANISOU 2725  O   GLY D 335    3331  1510  3430  -910   477   -63           O
ATOM   2726  N   SER D 336    54.833 -19.252 -12.651  1.00 23.39           N
ANISOU 2726  N   SER D 336    3346  1924  3615 -1097   487  -326           N
ATOM   2727  CA  SER D 336    55.445 -20.058 -13.689  1.00 25.47           C
ANISOU 2727  CA  SER D 336    3699  2029  3950 -1039   472  -454           C
ATOM   2728  CB  SER D 336    55.193 -21.560 -13.460  1.00 28.08           C
ANISOU 2728  CB  SER D 336    4201  2067  4403 -1165   513  -454           C
ATOM   2729  OG  SER D 336    53.803 -21.892 -13.365  1.00 31.54           O
ANISOU 2729  OG  SER D 336    4597  2519  4869 -1418   545  -493           O
ATOM   2730  C   SER D 336    54.844 -19.634 -15.019  1.00 25.72           C
ANISOU 2730  C   SER D 336    3625  2220  3926 -1088   437  -644           C
ATOM   2731  O   SER D 336    53.847 -18.912 -15.056  1.00 25.59           O
ANISOU 2731  O   SER D 336    3468  2403  3851 -1187   417  -664           O
ATOM   2732  N   SER D 337    55.464 -20.046 -16.117  1.00 26.46           N
ANISOU 2732  N   SER D 337    3787  2238  4029 -1003   427  -783           N
ATOM   2733  CA  SER D 337    54.928 -19.730 -17.429  1.00 27.34           C
ANISOU 2733  CA  SER D 337    3839  2495  4056 -1043   381  -965           C
ATOM   2734  CB  SER D 337    55.383 -18.344 -17.922  1.00 25.38           C
ANISOU 2734  CB  SER D 337    3476  2488  3680  -890   361  -946           C
ATOM   2735  OG  SER D 337    56.780 -18.297 -18.126  1.00 26.90           O
ANISOU 2735  OG  SER D 337    3722  2614  3884  -694   409  -919           O
ATOM   2736  C   SER D 337    55.239 -20.809 -18.446  1.00 29.10           C
ANISOU 2736  C   SER D 337    4212  2533  4312 -1040   389 -1148           C
ATOM   2737  O   SER D 337    56.117 -21.653 -18.247  1.00 29.85           O
ANISOU 2737  O   SER D 337    4444  2396  4503  -947   441 -1131           O
ATOM   2738  N   ILE D 338    54.459 -20.799 -19.515  1.00 30.44           N
ANISOU 2738  N   ILE D 338    4360  2804  4402 -1139   325 -1328           N
ATOM   2739  CA  ILE D 338    54.760 -21.558 -20.713  1.00 32.19           C
ANISOU 2739  CA  ILE D 338    4726  2912  4591 -1113   322 -1541           C
ATOM   2740  CB  ILE D 338    53.644 -22.589 -21.052  1.00 34.45           C
ANISOU 2740  CB  ILE D 338    5075  3071  4942 -1359   255 -1712           C
ATOM   2741  CG1 ILE D 338    52.280 -21.909 -21.249  1.00 34.10           C
ANISOU 2741  CG1 ILE D 338    4845  3281  4832 -1530   140 -1749           C
ATOM   2742  CD1 ILE D 338    51.154 -22.880 -21.685  1.00 36.18           C
ANISOU 2742  CD1 ILE D 338    5133  3442  5171 -1794    50 -1941           C
ATOM   2743  CG2 ILE D 338    53.582 -23.654 -19.966  1.00 35.56           C
ANISOU 2743  CG2 ILE D 338    5308  2920  5282 -1470   315 -1615           C
ATOM   2744  C   ILE D 338    55.002 -20.549 -21.828  1.00 31.93           C
ANISOU 2744  C   ILE D 338    4641  3126  4363  -988   294 -1615           C
ATOM   2745  O   ILE D 338    54.712 -19.381 -21.647  1.00 30.28           O
ANISOU 2745  O   ILE D 338    4282  3147  4075  -964   258 -1510           O
ATOM   2746  N   LYS D 339    55.566 -20.983 -22.950  1.00 35.00           N
ANISOU 2746  N   LYS D 339    5170  3459  4671  -897   324 -1788           N
ATOM   2747  CA  LYS D 339    55.850 -20.096 -24.079  1.00 36.41           C
ANISOU 2747  CA  LYS D 339    5338  3859  4637  -776   321 -1851           C
ATOM   2748  CB  LYS D 339    57.326 -20.142 -24.495  1.00 36.95           C
ANISOU 2748  CB  LYS D 339    5494  3859  4687  -549   472 -1853           C
```

FIGURE 18-81

```
ATOM   2749  CG  LYS D 339      58.378 -19.987 -23.447  1.00 37.74           C
ANISOU 2749  CG  LYS D 339     5523   3868   4948   -415    568  -1657       C
ATOM   2750  CD  LYS D 339      59.724 -20.262 -24.109  1.00 42.28           C
ANISOU 2750  CD  LYS D 339     6178   4366   5520   -206    718  -1721       C
ATOM   2751  CE  LYS D 339      60.861 -20.353 -23.116  1.00 43.49           C
ANISOU 2751  CE  LYS D 339     6261   4395   5869    -62    795  -1556       C
ATOM   2752  NZ  LYS D 339      62.013 -21.010 -23.793  1.00 46.57           N
ANISOU 2752  NZ  LYS D 339     6738   4653   6302    127    942  -1667       N
ATOM   2753  C   LYS D 339      55.092 -20.560 -25.307  1.00 39.56           C
ANISOU 2753  C   LYS D 339     5843   4294   4893   -881    222  -2099       C
ATOM   2754  O   LYS D 339      54.885 -21.757 -25.525  1.00 41.85           O
ANISOU 2754  O   LYS D 339     6273   4373   5255   -979    208  -2268       O
ATOM   2755  N   ARG D 340      54.750 -19.599 -26.148  1.00 40.34           N
ANISOU 2755  N   ARG D 340     5894   4653   4779   -847    148  -2123       N
ATOM   2756  CA  ARG D 340      54.128 -19.873 -27.426  1.00 43.61           C
ANISOU 2756  CA  ARG D 340     6421   5149   5002   -912     32  -2354       C
ATOM   2757  CB  ARG D 340      52.616 -19.731 -27.273  1.00 44.40           C
ANISOU 2757  CB  ARG D 340     6374   5372   5123  -1124   -171  -2385       C
ATOM   2758  CG  ARG D 340      51.801 -20.062 -28.490  1.00 48.83           C
ANISOU 2758  CG  ARG D 340     7023   6024   5507  -1227   -350  -2632       C
ATOM   2759  CD  ARG D 340      50.478 -19.350 -28.366  1.00 52.29           C
ANISOU 2759  CD  ARG D 340     7237   6693   5939  -1353   -548  -2586       C
ATOM   2760  NE  ARG D 340      49.496 -19.823 -29.329  1.00 58.76           N
ANISOU 2760  NE  ARG D 340     8095   7584   6649  -1504   -768  -2830       N
ATOM   2761  CZ  ARG D 340      48.306 -19.252 -29.509  1.00 62.04           C
ANISOU 2761  CZ  ARG D 340     8317   8227   7030  -1600   -982  -2837       C
ATOM   2762  NH1 ARG D 340      47.964 -18.181 -28.792  1.00 60.08           N
ANISOU 2762  NH1 ARG D 340     7836   8142   6848  -1546   -980  -2613       N
ATOM   2763  NH2 ARG D 340      47.457 -19.748 -30.409  1.00 66.38           N
ANISOU 2763  NH2 ARG D 340     8900   8838   7483  -1742  -1208  -3077       N
ATOM   2764  C   ARG D 340      54.699 -18.825 -28.379  1.00 43.42           C
ANISOU 2764  C   ARG D 340     6432   5344   4723   -731     75  -2320       C
ATOM   2765  O   ARG D 340      54.666 -17.628 -28.079  1.00 41.49           O
ANISOU 2765  O   ARG D 340     6042   5281   4442   -669     66  -2130       O
ATOM   2766  N   GLU D 341      55.293 -19.272 -29.480  1.00 45.77           N
ANISOU 2766  N   GLU D 341     6935   5607   4850   -638    147  -2495       N
ATOM   2767  CA  GLU D 341      55.826 -18.341 -30.477  1.00 46.72           C
ANISOU 2767  CA  GLU D 341     7119   5932   4699   -477    212  -2464       C
ATOM   2768  CB  GLU D 341      56.762 -19.062 -31.453  1.00 49.50           C
ANISOU 2768  CB  GLU D 341     7709   6182   4915   -352    375  -2651       C
ATOM   2769  CG  GLU D 341      57.526 -18.146 -32.413  1.00 51.74           C
ANISOU 2769  CG  GLU D 341     8071   6657   4932   -174    514  -2591       C
ATOM   2770  CD  GLU D 341      58.919 -18.672 -32.742  1.00 55.51           C
ANISOU 2770  CD  GLU D 341     8666   6998   5426      1    793  -2654       C
ATOM   2771  OE1 GLU D 341      59.022 -19.726 -33.415  1.00 59.55           O
ANISOU 2771  OE1 GLU D 341     9387   7379   5861     12    832  -2909       O
ATOM   2772  OE2 GLU D 341      59.911 -18.027 -32.326  1.00 54.92           O
ANISOU 2772  OE2 GLU D 341     8468   6945   5454    128    973  -2457       O
ATOM   2773  C   GLU D 341      54.668 -17.653 -31.202  1.00 47.34           C
ANISOU 2773  C   GLU D 341     7175   6260   4552   -555    -12  -2501       C
ATOM   2774  O   GLU D 341      53.755 -18.308 -31.666  1.00 49.11           O
ANISOU 2774  O   GLU D 341     7462   6479   4718   -696   -188  -2701       O
ATOM   2775  N   GLU D 342      54.698 -16.327 -31.260  1.00 46.37           N
ANISOU 2775  N   GLU D 342     6952   6343   4322   -463    -17  -2304       N
ATOM   2776  CA  GLU D 342      53.581 -15.557 -31.814  1.00 48.18           C
ANISOU 2776  CA  GLU D 342     7130   6809   4367   -510   -246  -2296       C
ATOM   2777  CB  GLU D 342      52.718 -14.978 -30.691  1.00 45.85           C
ANISOU 2777  CB  GLU D 342     6568   6567   4287   -600   -362  -2136       C
ATOM   2778  CG  GLU D 342      51.598 -15.878 -30.201  1.00 49.03           C
ANISOU 2778  CG  GLU D 342     6868   6895   4866   -815   -524  -2272       C
ATOM   2779  CD  GLU D 342      50.813 -15.233 -29.079  1.00 48.12           C
ANISOU 2779  CD  GLU D 342     6483   6849   4951   -882   -591  -2102       C
ATOM   2780  OE1 GLU D 342      50.844 -15.791 -27.956  1.00 52.42           O
ANISOU 2780  OE1 GLU D 342     6943   7228   5746   -975   -507  -2058       O
ATOM   2781  OE2 GLU D 342      50.194 -14.158 -29.301  1.00 51.11           O
ANISOU 2781  OE2 GLU D 342     6748   7440   5233   -829   -716  -2007       O
ATOM   2782  C   GLU D 342      54.051 -14.407 -32.683  1.00 47.55           C
ANISOU 2782  C   GLU D 342     7135   6921   4011   -343   -190  -2174       C
ATOM   2783  O   GLU D 342      55.108 -13.831 -32.436  1.00 45.79           O
ANISOU 2783  O   GLU D 342     6900   6671   3827   -217     22  -2008       O
ATOM   2784  N   GLU D 343      53.237 -14.060 -33.674  1.00 49.19           N
```

FIGURE 18-82

```
ANISOU 2784  N   GLU D 343    7421  7319  3949  -350  -391 -2247       N
ATOM   2785  CA  GLU D 343     53.517 -12.924 -34.539  1.00 49.57      C
ANISOU 2785  CA  GLU D 343    7571  7555  3708  -200  -366 -2109       C
ATOM   2786  CB  GLU D 343     53.181 -13.255 -35.991  1.00 53.34      C
ANISOU 2786  CB  GLU D 343    8304  8158  3805  -185  -494 -2308       C
ATOM   2787  CG  GLU D 343     53.423 -14.707 -36.327  1.00 57.34      C
ANISOU 2787  CG  GLU D 343    8979  8503  4305  -258  -446 -2603       C
ATOM   2788  CD  GLU D 343     54.110 -14.904 -37.652  1.00 62.14      C
ANISOU 2788  CD  GLU D 343    9908  9165  4538  -141  -320 -2734       C
ATOM   2789  OE1 GLU D 343     53.678 -14.282 -38.648  1.00 66.06      O
ANISOU 2789  OE1 GLU D 343   10542  9875  4684   -85  -464 -2723       O
ATOM   2790  OE2 GLU D 343     55.074 -15.699 -37.694  1.00 62.92      O
ANISOU 2790  OE2 GLU D 343   10127  9092  4688   -95   -77 -2850       O
ATOM   2791  C   GLU D 343     52.733 -11.701 -34.073  1.00 47.50      C
ANISOU 2791  C   GLU D 343    7105  7439  3503  -187  -523 -1896       C
ATOM   2792  O   GLU D 343     51.494 -11.696 -34.101  1.00 48.59      O
ANISOU 2792  O   GLU D 343    7137  7683  3642  -274  -791 -1960       O
ATOM   2793  N   VAL D 344     53.461 -10.674 -33.637  1.00 44.51      N
ANISOU 2793  N   VAL D 344    6664  7057  3190   -77  -355 -1653       N
ATOM   2794  CA  VAL D 344     52.851  -9.406 -33.207  1.00 42.32      C
ANISOU 2794  CA  VAL D 344    6222  6892  2967   -33  -471 -1441       C
ATOM   2795  CB  VAL D 344     53.315  -8.974 -31.787  1.00 38.72      C
ANISOU 2795  CB  VAL D 344    5564  6310  2839   -38  -329 -1273       C
ATOM   2796  CG1 VAL D 344     52.789  -9.950 -30.744  1.00 37.84      C
ANISOU 2796  CG1 VAL D 344    5295  6085  2998  -187  -384 -1388       C
ATOM   2797  CG2 VAL D 344     54.852  -8.867 -31.698  1.00 37.43      C
ANISOU 2797  CG2 VAL D 344    5480  6029  2712    42   -33 -1181       C
ATOM   2798  C   VAL D 344     53.142  -8.313 -34.227  1.00 43.10      C
ANISOU 2798  C   VAL D 344    6482  7128  2765   114  -449 -1292       C
ATOM   2799  O   VAL D 344     54.177  -8.360 -34.880  1.00 43.50      O
ANISOU 2799  O   VAL D 344    6721  7153  2653   187  -238 -1280       O
ATOM   2800  N   LEU D 345     52.223  -7.349 -34.352  1.00 43.51      N
ANISOU 2800  N   LEU D 345    6459  7320  2751   163  -657 -1172       N
ATOM   2801  CA  LEU D 345     52.330  -6.227 -35.300  1.00 45.05      C
ANISOU 2801  CA  LEU D 345    6817  7642  2659   308  -675  -998       C
ATOM   2802  CB  LEU D 345     51.020  -6.033 -36.060  1.00 47.61      C
ANISOU 2802  CB  LEU D 345    7160  8159  2770   333 -1020 -1052       C
ATOM   2803  CG  LEU D 345     50.743  -6.475 -37.488  1.00 51.69      C
ANISOU 2803  CG  LEU D 345    7938  8822  2881   358 -1172 -1200       C
ATOM   2804  CD1 LEU D 345     49.400  -5.893 -37.870  1.00 52.98      C
ANISOU 2804  CD1 LEU D 345    8021  9173  2935   408 -1542 -1167       C
ATOM   2805  CD2 LEU D 345     51.809  -6.018 -38.456  1.00 52.76      C
ANISOU 2805  CD2 LEU D 345    8377  8975  2694   479  -945 -1081       C
ATOM   2806  C   LEU D 345     52.638  -4.914 -34.591  1.00 43.02      C
ANISOU 2806  C   LEU D 345    6443  7334  2567   390  -577  -726       C
ATOM   2807  O   LEU D 345     51.867  -4.483 -33.736  1.00 41.31      O
ANISOU 2807  O   LEU D 345    6010  7119  2567   375  -711  -671       O
ATOM   2808  N   THR D 346     53.739  -4.270 -34.977  1.00 43.51      N
ANISOU 2808  N   THR D 346    6654  7353  2525   471  -339  -564       N
ATOM   2809  CA  THR D 346     54.144  -3.000 -34.387  1.00 42.63      C
ANISOU 2809  CA  THR D 346    6463  7169  2566   535  -233  -311       C
ATOM   2810  CB  THR D 346     55.658  -2.699 -34.549  1.00 42.01      C
ANISOU 2810  CB  THR D 346    6490  6988  2482   557   105  -189       C
ATOM   2811  OG1 THR D 346     55.892  -2.121 -35.833  1.00 44.89      O
ANISOU 2811  OG1 THR D 346    7110  7447  2499   650   159   -72       O
ATOM   2812  CG2 THR D 346     56.495  -3.942 -34.379  1.00 40.99      C
ANISOU 2812  CG2 THR D 346    6357  6779  2440   484   289  -371       C
ATOM   2813  C   THR D 346     53.350  -1.816 -34.938  1.00 44.91      C
ANISOU 2813  C   THR D 346    6813  7567  2686   654  -424  -137       C
ATOM   2814  O   THR D 346     52.564  -1.953 -35.884  1.00 47.19      O
ANISOU 2814  O   THR D 346    7219  8008  2701   699  -638  -198       O
ATOM   2815  N   GLY D 347     53.580  -0.657 -34.312  1.00 44.77      N
ANISOU 2815  N   GLY D 347    6714  7455  2839   706  -353    76       N
ATOM   2816  CA  GLY D 347     52.914   0.595 -34.643  1.00 47.06      C
ANISOU 2816  CA  GLY D 347    7049  7795  3037   837  -509   273       C
ATOM   2817  C   GLY D 347     53.311   1.122 -35.999  1.00 50.85      C
ANISOU 2817  C   GLY D 347    7832  8341  3149   933  -452   421       C
ATOM   2818  O   GLY D 347     52.763   2.128 -36.458  1.00 53.05      O
ANISOU 2818  O   GLY D 347    8198  8660  3297  1060  -596   601       O
ATOM   2819  N   ASN D 348     54.272   0.453 -36.638  1.00 51.99      N
ANISOU 2819  N   ASN D 348    8144  8489  3120   885  -232   354       N
```

FIGURE 18-83

```
ATOM    2820  CA  ASN D 348      54.607   0.740 -38.029  1.00 55.74           C
ANISOU  2820  CA  ASN D 348     8937   9058   3184    967   -164    458       C
ATOM    2821  CB  ASN D 348      56.043   1.273 -38.165  1.00 56.17           C
ANISOU  2821  CB  ASN D 348     9099   8991   3252    953    220    639       C
ATOM    2822  CG  ASN D 348      56.246   2.063 -39.453  1.00 61.46           C
ANISOU  2822  CG  ASN D 348    10094   9733   3527   1057    289    857       C
ATOM    2823  OD1 ASN D 348      55.428   2.921 -39.808  1.00 64.89           O
ANISOU  2823  OD1 ASN D 348    10617  10214   3824   1167     67   1018       O
ATOM    2824  ND2 ASN D 348      57.326   1.760 -40.175  1.00 64.62           N
ANISOU  2824  ND2 ASN D 348    10677  10143   3734   1033    603    867       N
ATOM    2825  C   ASN D 348      54.350  -0.455 -38.966  1.00 57.47           C
ANISOU  2825  C   ASN D 348     9315   9429   3090    945   -253    215       C
ATOM    2826  O   ASN D 348      54.970  -0.582 -40.028  1.00 59.79           O
ANISOU  2826  O   ASN D 348     9882   9784   3050    980    -93    233       O
ATOM    2827  N   LEU D 349      53.412  -1.315 -38.557  1.00 56.20           N
ANISOU  2827  N   LEU D 349     8987   9325   3042    880   -504    -17       N
ATOM    2828  CA  LEU D 349      52.992  -2.499 -39.333  1.00 57.58           C
ANISOU  2828  CA  LEU D 349     9285   9625   2966    836   -647   -288       C
ATOM    2829  CB  LEU D 349      52.211  -2.097 -40.591  1.00 61.54           C
ANISOU  2829  CB  LEU D 349    10023  10324   3035    950   -912   -241       C
ATOM    2830  CG  LEU D 349      50.920  -1.293 -40.393  1.00 62.61           C
ANISOU  2830  CG  LEU D 349    10006  10547   3235   1033  -1273   -131       C
ATOM    2831  CD1 LEU D 349      50.097  -1.301 -41.692  1.00 66.68           C
ANISOU  2831  CD1 LEU D 349    10749  11283   3304   1126  -1593   -171       C
ATOM    2832  CD2 LEU D 349      50.089  -1.802 -39.206  1.00 59.33           C
ANISOU  2832  CD2 LEU D 349     9218  10095   3228    926  -1441   -291       C
ATOM    2833  C   LEU D 349      54.118  -3.484 -39.668  1.00 56.92           C
ANISOU  2833  C   LEU D 349     9346   9481   2800    775   -347   -445       C
ATOM    2834  O   LEU D 349      54.078  -4.191 -40.669  1.00 59.54           O
ANISOU  2834  O   LEU D 349     9905   9914   2802    781   -383   -615       O
ATOM    2835  N   GLN D 350      55.114  -3.533 -38.799  1.00 53.58           N
ANISOU  2835  N   GLN D 350     8781   8890   2685    724    -60   -398       N
ATOM    2836  CA  GLN D 350      56.191  -4.499 -38.940  1.00 52.62           C
ANISOU  2836  CA  GLN D 350     8734   8692   2566    681    227   -551       C
ATOM    2837  CB  GLN D 350      57.506  -3.890 -38.472  1.00 51.26           C
ANISOU  2837  CB  GLN D 350     8493   8390   2594.    694    581   -356       C
ATOM    2838  CG  GLN D 350      58.701  -4.803 -38.614  1.00 50.19           C
ANISOU  2838  CG  GLN D 350     8402   8179   2489    677    898   -492       C
ATOM    2839  CD  GLN D 350      59.992  -4.205 -38.068  1.00 48.94           C
ANISOU  2839  CD  GLN D 350     8115   7899   2580    676   1225   -304       C
ATOM    2840  OE1 GLN D 350      60.012  -3.105 -37.519  1.00 43.94           O
ANISOU  2840  OE1 GLN D 350     7366   7218   2111    672   1213    -78       O
ATOM    2841  NE2 GLN D 350      61.086  -4.936 -38.238  1.00 49.94           N
ANISOU  2841  NE2 GLN D 350     8258   7972   2745    684   1516   -409       N
ATOM    2842  C   GLN D 350      55.865  -5.750 -38.123  1.00 50.95           C
ANISOU  2842  C   GLN D 350     8341   8395   2625    565    135   -811       C
ATOM    2843  O   GLN D 350      55.432  -5.662 -36.975  1.00 47.85           O
ANISOU  2843  O   GLN D 350     7690   7924   2565    503     31   -786       O
ATOM    2844  N   THR D 351      56.049  -6.915 -38.728  1.00 52.61           N
ANISOU  2844  N   THR D 351     8702   8610   2676    537    178  -1062       N
ATOM    2845  CA  THR D 351      55.779  -8.175 -38.044  1.00 51.53           C
ANISOU  2845  CA  THR D 351     8435   8362   2782    422    105  -1310       C
ATOM    2846  CB  THR D 351      55.468  -9.299 -39.050  1.00 54.66           C
ANISOU  2846  CB  THR D 351     9064   8813   2891    395     11  -1608       C
ATOM    2847  OG1 THR D 351      54.324  -8.936 -39.833  1.00 58.05           O
ANISOU  2847  OG1 THR D 351     9596   9433   3026    407   -315  -1629       O
ATOM    2848  CG2 THR D 351      55.210 -10.608 -38.356  1.00 53.78           C
ANISOU  2848  CG2 THR D 351     8837   8552   3047    266    -52  -1856       C
ATOM    2849  C   THR D 351      56.988  -8.559 -37.210  1.00 49.24           C
ANISOU  2849  C   THR D 351     8023   7884   2800    411    412  -1292       C
ATOM    2850  O   THR D 351      58.117  -8.534 -37.699  1.00 50.66           O
ANISOU  2850  O   THR D 351     8325   8042   2884    486    705  -1256       O
ATOM    2851  N   LEU D 352      56.742  -8.897 -35.949  1.00 46.43           N
ANISOU  2851  N   LEU D 352     7422   7404   2813    322    345  -1309       N
ATOM    2852  CA  LEU D 352      57.770  -9.440 -35.074  1.00 44.39           C
ANISOU  2852  CA  LEU D 352     7042   6963   2860    309    574  -1318       C
ATOM    2853  CB  LEU D 352      58.010  -8.535 -33.873  1.00 41.23           C
ANISOU  2853  CB  LEU D 352     6404   6502   2761    301    608  -1090       C
ATOM    2854  CG  LEU D 352      58.524  -7.106 -34.038  1.00 41.08           C
ANISOU  2854  CG  LEU D 352     6381   6541   2689    379    724   -827       C
ATOM    2855  CD1 LEU D 352      58.549  -6.426 -32.663  1.00 36.89           C
```

FIGURE 18-84

```
ANISOU 2855  CD1 LEU D 352    5605   5920   2491    342    695   -670        C
ATOM   2856  CD2 LEU D 352     59.892  -7.044 -34.742  1.00 42.81           C
ANISOU 2856  CD2 LEU D 352    6718   6745   2804    456   1049   -782        C
ATOM   2857  C   LEU D 352     57.361 -10.814 -34.566  1.00 44.29           C
ANISOU 2857  C   LEU D 352    6985   6825   3018    206    476  -1554        C
ATOM   2858  O   LEU D 352     56.238 -11.002 -34.099  1.00 43.77           O
ANISOU 2858  O   LEU D 352    6813   6774   3042    103    230  -1608        O
ATOM   2859  N   LYS D 353     58.278 -11.768 -34.669  1.00 44.79           N
ANISOU 2859  N   LYS D 353    7127   6756   3136    236    681  -1689        N
ATOM   2860  CA  LYS D 353     58.073 -13.104 -34.159  1.00 45.15           C
ANISOU 2860  CA  LYS D 353    7153   6632   3369    151    628  -1896        C
ATOM   2861  CB  LYS D 353     58.797 -14.122 -35.043  1.00 47.86           C
ANISOU 2861  CB  LYS D 353    7721   6897   3567    219    805  -2118        C
ATOM   2862  CG  LYS D 353     58.258 -15.538 -34.984  1.00 49.96           C
ANISOU 2862  CG  LYS D 353    8068   7007   3906    117    685  -2393        C
ATOM   2863  CD  LYS D 353     59.022 -16.428 -35.977  1.00 54.00           C
ANISOU 2863  CD  LYS D 353    8834   7446   4239    215    880  -2623        C
ATOM   2864  CE  LYS D 353     58.155 -17.546 -36.539  1.00 59.44           C
ANISOU 2864  CE  LYS D 353    9711   8070   4806    104    687  -2938        C
ATOM   2865  NZ  LYS D 353     58.831 -18.247 -37.687  1.00 64.80           N
ANISOU 2865  NZ  LYS D 353   10681   8712   5227    217    872  -3177        N
ATOM   2866  C   LYS D 353     58.643 -13.117 -32.754  1.00 42.12           C
ANISOU 2866  C   LYS D 353    6545   6092   3366    139    721  -1761        C
ATOM   2867  O   LYS D 353     59.852 -13.025 -32.567  1.00 41.20           O
ANISOU 2867  O   LYS D 353    6392   5905   3356    236    956  -1680        O
ATOM   2868  N   ILE D 354     57.766 -13.202 -31.758  1.00 40.54           N
ANISOU 2868  N   ILE D 354    6187   5851   3365     21    534  -1732        N
ATOM   2869  CA  ILE D 354     58.192 -13.268 -30.366  1.00 38.30           C
ANISOU 2869  CA  ILE D 354    5716   5424   3411      2    591  -1611        C
ATOM   2870  CB  ILE D 354     57.745 -12.007 -29.553  1.00 36.18           C
ANISOU 2870  CB  ILE D 354    5261   5254   3233    -19    498  -1388        C
ATOM   2871  CG1 ILE D 354     56.211 -11.875 -29.518  1.00 36.29           C
ANISOU 2871  CG1 ILE D 354    5222   5374   3193   -132    243  -1432        C
ATOM   2872  CD1 ILE D 354     55.700 -10.892 -28.478  1.00 34.52           C
ANISOU 2872  CD1 ILE D 354    4800   5199   3117   -155    163  -1250        C
ATOM   2873  CG2 ILE D 354     58.399 -10.725 -30.109  1.00 35.98           C
ANISOU 2873  CG2 ILE D 354    5252   5350   3070     93    613  -1218        C
ATOM   2874  C   ILE D 354     57.669 -14.549 -29.696  1.00 38.61           C
ANISOU 2874  C   ILE D 354    5744   5289   3636   -119    500  -1757        C
ATOM   2875  O   ILE D 354     56.645 -15.128 -30.109  1.00 40.64           O
ANISOU 2875  O   ILE D 354    6070   5566   3808   -231    333  -1922        O
ATOM   2876  N   ARG D 355     58.383 -15.004 -28.679  1.00 36.91           N
ANISOU 2876  N   ARG D 355    5447   4900   3678    -99    603  -1695        N
ATOM   2877  CA  ARG D 355     57.871 -16.064 -27.832  1.00 37.02           C
ANISOU 2877  CA  ARG D 355    5439   4735   3891   -219    522  -1768        C
ATOM   2878  CB  ARG D 355     58.994 -16.964 -27.340  1.00 37.88           C
ANISOU 2878  CB  ARG D 355    5582   4617   4194   -134    680  -1782        C
ATOM   2879  CG  ARG D 355     59.574 -17.833 -28.449  1.00 45.02           C
ANISOU 2879  CG  ARG D 355    6685   5434   4986    -48    798  -1993        C
ATOM   2880  CD  ARG D 355     60.668 -18.706 -27.904  1.00 52.28           C
ANISOU 2880  CD  ARG D 355    7615   6120   6130     61    947  -1997        C
ATOM   2881  NE  ARG D 355     61.771 -18.840 -28.849  1.00 59.10           N
ANISOU 2881  NE  ARG D 355    8572   6983   6901    238   1156  -2087        N
ATOM   2882  CZ  ARG D 355     62.978 -19.295 -28.524  1.00 61.64           C
ANISOU 2882  CZ  ARG D 355    8855   7157   7409    394   1324  -2061        C
ATOM   2883  NH1 ARG D 355     63.241 -19.653 -27.265  1.00 59.91           N
ANISOU 2883  NH1 ARG D 355    8522   6776   7463    396   1281  -1939        N
ATOM   2884  NH2 ARG D 355     63.920 -19.396 -29.461  1.00 64.91           N
ANISOU 2884  NH2 ARG D 355    9340   7592   7731    555   1536  -2157        N
ATOM   2885  C   ARG D 355     57.115 -15.449 -26.673  1.00 33.46           C
ANISOU 2885  C   ARG D 355    4803   4335   3576   -315    404  -1608        C
ATOM   2886  O   ARG D 355     57.717 -14.849 -25.782  1.00 30.78           O
ANISOU 2886  O   ARG D 355    4346   3982   3366   -256    470  -1430        O
ATOM   2887  N   VAL D 356     55.792 -15.577 -26.725  1.00 33.25           N
ANISOU 2887  N   VAL D 356    4744   4375   3512   -463    229  -1682        N
ATOM   2888  CA  VAL D 356     54.908 -14.994 -25.724  1.00 31.29           C
ANISOU 2888  CA  VAL D 356    4314   4199   3375   -555    127  -1554        C
ATOM   2889  CB  VAL D 356     53.495 -14.774 -26.281  1.00 32.47           C
ANISOU 2889  CB  VAL D 356    4410   4515   3413   -668    -69  -1643        C
ATOM   2890  CG1 VAL D 356     52.532 -14.347 -25.167  1.00 31.15           C
ANISOU 2890  CG1 VAL D 356    4036   4403   3395   -768   -146  -1532        C
```

FIGURE 18-85

```
ATOM    2891  CG2 VAL D 356      53.522 -13.735 -27.416  1.00 32.66           C
ANISOU  2891  CG2 VAL D 356     4479   4746   3184   -550   -115  -1624       C
ATOM    2892  C   VAL D 356      54.883 -15.895 -24.485  1.00 30.33           C
ANISOU  2892  C   VAL D 356     4157   3876   3491   -651    160  -1525       C
ATOM    2893  O   VAL D 356      54.610 -17.084 -24.580  1.00 31.63           O
ANISOU  2893  O   VAL D 356     4413   3886   3719   -754    142  -1666       O
ATOM    2894  N   HIS D 357      55.229 -15.330 -23.330  1.00 27.89           N
ANISOU  2894  N   HIS D 357     3738   3555   3304   -612    211  -1339       N
ATOM    2895  CA  HIS D 357      55.108 -16.067 -22.055  1.00 27.09           C
ANISOU  2895  CA  HIS D 357     3613   3286   3396   -703    233  -1277       C
ATOM    2896  CB  HIS D 357      56.157 -15.624 -21.051  1.00 24.13           C
ANISOU  2896  CB  HIS D 357     3198   2855   3116   -585    320  -1100       C
ATOM    2897  CG  HIS D 357      57.530 -16.091 -21.397  1.00 23.18           C
ANISOU  2897  CG  HIS D 357     3173   2605   3030   -441    426  -1120       C
ATOM    2898  ND1 HIS D 357      58.182 -17.076 -20.684  1.00 23.15           N
ANISOU  2898  ND1 HIS D 357     3234   2380   3180   -414    478  -1092       N
ATOM    2899  CE1 HIS D 357      59.360 -17.313 -21.233  1.00 21.17           C
ANISOU  2899  CE1 HIS D 357     3036   2061   2946   -261    573  -1129       C
ATOM    2900  NE2 HIS D 357      59.496 -16.511 -22.275  1.00 25.10           N
ANISOU  2900  NE2 HIS D 357     3515   2730   3291   -203    603  -1175       N
ATOM    2901  CD2 HIS D 357      58.363 -15.742 -22.405  1.00 21.56           C
ANISOU  2901  CD2 HIS D 357     3005   2457   2728   -310    501  -1165       C
ATOM    2902  C   HIS D 357      53.706 -15.975 -21.470  1.00 27.09           C
ANISOU  2902  C   HIS D 357     3488   3362   3441   -872    137  -1264       C
ATOM    2903  O   HIS D 357      53.151 -14.887 -21.336  1.00 26.76           O
ANISOU  2903  O   HIS D 357     3314   3507   3346   -858     85  -1189       O
ATOM    2904  N   GLU D 358      53.130 -17.135 -21.179  1.00 28.20           N
ANISOU  2904  N   GLU D 358     3673   3353   3691  -1033    123  -1343       N
ATOM    2905  CA  GLU D 358      51.766 -17.230 -20.704  1.00 28.28           C
ANISOU  2905  CA  GLU D 358     3553   3425   3768  -1223     54  -1351       C
ATOM    2906  CB  GLU D 358      50.984 -18.208 -21.581  1.00 31.17           C
ANISOU  2906  CB  GLU D 358     3968   3736   4138  -1389    -39  -1564       C
ATOM    2907  CG  GLU D 358      50.973 -17.773 -23.047  1.00 32.95           C
ANISOU  2907  CG  GLU D 358     4233   4120   4167  -1309   -143  -1709       C
ATOM    2908  CD  GLU D 358      50.303 -18.740 -23.964  1.00 39.33           C
ANISOU  2908  CD  GLU D 358     5118   4872   4954  -1465   -257  -1944       C
ATOM    2909  OE1 GLU D 358      50.379 -19.974 -23.732  1.00 41.30           O
ANISOU  2909  OE1 GLU D 358     5483   4874   5336  -1583   -213  -2029       O
ATOM    2910  OE2 GLU D 358      49.688 -18.254 -24.939  1.00 42.18           O
ANISOU  2910  OE2 GLU D 358     5432   5432   5161  -1467   -405  -2049       O
ATOM    2911  C   GLU D 358      51.790 -17.669 -19.252  1.00 27.36           C
ANISOU  2911  C   GLU D 358     3429   3163   3804  -1292    145  -1208       C
ATOM    2912  O   GLU D 358      52.383 -18.677 -18.925  1.00 29.08           O
ANISOU  2912  O   GLU D 358     3791   3148   4112  -1304    210  -1203       O
ATOM    2913  N   GLY D 359      51.167 -16.892 -18.380  1.00 25.52           N
ANISOU  2913  N   GLY D 359     3044   3064   3587  -1322    155  -1086       N
ATOM    2914  CA  GLY D 359      51.052 -17.255 -16.979  1.00 24.48           C
ANISOU  2914  CA  GLY D 359     2916   2823   3560  -1399    247   -946       C
ATOM    2915  C   GLY D 359      51.467 -16.139 -16.057  1.00 22.50           C
ANISOU  2915  C   GLY D 359     2608   2681   3262  -1265    290   -781       C
ATOM    2916  O   GLY D 359      52.317 -15.309 -16.401  1.00 21.03           O
ANISOU  2916  O   GLY D 359     2431   2564   2997  -1090    271   -754       O
ATOM    2917  N   TYR D 360      50.879 -16.137 -14.865  1.00 22.56           N
ANISOU  2917  N   TYR D 360     2564   2692   3315  -1355    359   -674       N
ATOM    2918  CA  TYR D 360      51.277 -15.220 -13.807  1.00 20.82           C
ANISOU  2918  CA  TYR D 360     2328   2542   3042  -1243    405   -527       C
ATOM    2919  CB  TYR D 360      50.251 -15.243 -12.659  1.00 21.78           C
ANISOU  2919  CB  TYR D 360     2374   2709   3191  -1377    496   -447       C
ATOM    2920  CG  TYR D 360      50.774 -14.552 -11.417  1.00 21.58           C
ANISOU  2920  CG  TYR D 360     2399   2706   3092  -1269    551   -301       C
ATOM    2921  CD1 TYR D 360      50.769 -13.146 -11.321  1.00 18.96           C
ANISOU  2921  CD1 TYR D 360     1967   2554   2682  -1140    525   -292       C
ATOM    2922  CE1 TYR D 360      51.265 -12.515 -10.199  1.00 20.05           C
ANISOU  2922  CE1 TYR D 360     2168   2704   2746  -1049    560   -185       C
ATOM    2923  CZ  TYR D 360      51.801 -13.280  -9.164  1.00 20.65           C
ANISOU  2923  CZ  TYR D 360     2411   2630   2805  -1074    608    -71       C
ATOM    2924  OH  TYR D 360      52.295 -12.687  -8.034  1.00 19.63           O
ANISOU  2924  OH  TYR D 360     2362   2519   2577   -986    619     26       O
ATOM    2925  CE2 TYR D 360      51.829 -14.661  -9.238  1.00 22.70           C
ANISOU  2925  CE2 TYR D 360     2775   2709   3141  -1186    635    -54       C
ATOM    2926  CD2 TYR D 360      51.320 -15.292 -10.365  1.00 21.83           C
```

FIGURE 18-86

```
ATOM   2891  CG2 VAL D 356      53.522 -13.735 -27.416  1.00 32.66           C
ANISOU 2891  CG2 VAL D 356    4479   4746   3184   -550   -115  -1624        C
ATOM   2892  C   VAL D 356      54.883 -15.895 -24.485  1.00 30.33           C
ANISOU 2892  C   VAL D 356    4157   3876   3491   -651    160  -1525        C
ATOM   2893  O   VAL D 356      54.610 -17.084 -24.580  1.00 31.63           O
ANISOU 2893  O   VAL D 356    4413   3886   3719   -754    142  -1666        O
ATOM   2894  N   HIS D 357      55.229 -15.330 -23.330  1.00 27.89           N
ANISOU 2894  N   HIS D 357    3738   3555   3304   -612    211  -1339        N
ATOM   2895  CA  HIS D 357      55.108 -16.067 -22.055  1.00 27.09           C
ANISOU 2895  CA  HIS D 357    3613   3286   3396   -703    233  -1277        C
ATOM   2896  CB  HIS D 357      56.157 -15.624 -21.051  1.00 24.13           C
ANISOU 2896  CB  HIS D 357    3198   2855   3116   -585    320  -1100        C
ATOM   2897  CG  HIS D 357      57.530 -16.091 -21.397  1.00 23.18           C
ANISOU 2897  CG  HIS D 357    3173   2605   3030   -441    426  -1120        C
ATOM   2898  ND1 HIS D 357      58.182 -17.076 -20.684  1.00 23.15           N
ANISOU 2898  ND1 HIS D 357    3234   2380   3180   -414    478  -1092        N
ATOM   2899  CE1 HIS D 357      59.360 -17.313 -21.233  1.00 21.17           C
ANISOU 2899  CE1 HIS D 357    3036   2061   2946   -261    573  -1129        C
ATOM   2900  NE2 HIS D 357      59.496 -16.511 -22.275  1.00 25.10           N
ANISOU 2900  NE2 HIS D 357    3515   2730   3291   -203    603  -1175        N
ATOM   2901  CD2 HIS D 357      58.363 -15.742 -22.405  1.00 21.56           C
ANISOU 2901  CD2 HIS D 357    3005   2457   2728   -310    501  -1165        C
ATOM   2902  C   HIS D 357      53.706 -15.975 -21.470  1.00 27.09           C
ANISOU 2902  C   HIS D 357    3488   3362   3441   -872    137  -1264        C
ATOM   2903  O   HIS D 357      53.151 -14.887 -21.336  1.00 26.76           O
ANISOU 2903  O   HIS D 357    3314   3507   3346   -858     85  -1189        O
ATOM   2904  N   GLU D 358      53.130 -17.135 -21.179  1.00 28.20           N
ANISOU 2904  N   GLU D 358    3673   3353   3691  -1033    123  -1343        N
ATOM   2905  CA  GLU D 358      51.766 -17.230 -20.704  1.00 28.28           C
ANISOU 2905  CA  GLU D 358    3553   3425   3768  -1223     54  -1351        C
ATOM   2906  CB  GLU D 358      50.984 -18.208 -21.581  1.00 31.17           C
ANISOU 2906  CB  GLU D 358    3968   3736   4138  -1389    -39  -1564        C
ATOM   2907  CG  GLU D 358      50.973 -17.773 -23.047  1.00 32.95           C
ANISOU 2907  CG  GLU D 358    4233   4120   4167  -1309   -143  -1709        C
ATOM   2908  CD  GLU D 358      50.303 -18.740 -23.964  1.00 39.33           C
ANISOU 2908  CD  GLU D 358    5118   4872   4954  -1465   -257  -1944        C
ATOM   2909  OE1 GLU D 358      50.379 -19.974 -23.732  1.00 41.30           O
ANISOU 2909  OE1 GLU D 358    5483   4874   5336  -1583   -213  -2029        O
ATOM   2910  OE2 GLU D 358      49.688 -18.254 -24.939  1.00 42.18           O
ANISOU 2910  OE2 GLU D 358    5432   5432   5161  -1467   -405  -2049        O
ATOM   2911  C   GLU D 358      51.790 -17.669 -19.252  1.00 27.36           C
ANISOU 2911  C   GLU D 358    3429   3163   3804  -1292    145  -1208        C
ATOM   2912  O   GLU D 358      52.383 -18.677 -18.925  1.00 29.08           O
ANISOU 2912  O   GLU D 358    3791   3148   4112  -1304    210  -1203        O
ATOM   2913  N   GLY D 359      51.167 -16.892 -18.380  1.00 25.52           N
ANISOU 2913  N   GLY D 359    3044   3064   3587  -1322    155  -1086        N
ATOM   2914  CA  GLY D 359      51.052 -17.255 -16.979  1.00 24.48           C
ANISOU 2914  CA  GLY D 359    2916   2823   3560  -1399    247   -946        C
ATOM   2915  C   GLY D 359      51.467 -16.139 -16.057  1.00 22.50           C
ANISOU 2915  C   GLY D 359    2608   2681   3262  -1265    290   -781        C
ATOM   2916  O   GLY D 359      52.317 -15.309 -16.401  1.00 21.03           O
ANISOU 2916  O   GLY D 359    2431   2564   2997  -1090    271   -754        O
ATOM   2917  N   TYR D 360      50.879 -16.137 -14.865  1.00 22.56           N
ANISOU 2917  N   TYR D 360    2564   2692   3315  -1355    359   -674        N
ATOM   2918  CA  TYR D 360      51.277 -15.220 -13.807  1.00 20.82           C
ANISOU 2918  CA  TYR D 360    2328   2542   3042  -1243    405   -527        C
ATOM   2919  CB  TYR D 360      50.251 -15.243 -12.659  1.00 21.78           C
ANISOU 2919  CB  TYR D 360    2374   2709   3191  -1377    496   -447        C
ATOM   2920  CG  TYR D 360      50.774 -14.552 -11.417  1.00 21.58           C
ANISOU 2920  CG  TYR D 360    2399   2706   3092  -1269    551   -301        C
ATOM   2921  CD1 TYR D 360      50.769 -13.146 -11.321  1.00 18.96           C
ANISOU 2921  CD1 TYR D 360    1967   2554   2682  -1140    525   -292        C
ATOM   2922  CE1 TYR D 360      51.265 -12.515 -10.199  1.00 20.05           C
ANISOU 2922  CE1 TYR D 360    2168   2704   2746  -1049    560   -185        C
ATOM   2923  CZ  TYR D 360      51.801 -13.280  -9.164  1.00 20.65           C
ANISOU 2923  CZ  TYR D 360    2411   2630   2805  -1074    608    -71        C
ATOM   2924  OH  TYR D 360      52.295 -12.687  -8.034  1.00 19.63           O
ANISOU 2924  OH  TYR D 360    2362   2519   2577   -986    619     26        O
ATOM   2925  CE2 TYR D 360      51.829 -14.661  -9.238  1.00 22.70           C
ANISOU 2925  CE2 TYR D 360    2775   2709   3141  -1186    635    -54        C
ATOM   2926  CD2 TYR D 360      51.320 -15.292 -10.365  1.00 21.83           C
```

FIGURE 18-87

```
ATOM   2962  CG2 THR D 364      62.554  -9.703  -5.942  1.00 18.12           C
ANISOU 2962  CG2 THR D 364    2332  2049  2504    -49   -289    306          C
ATOM   2963  C   THR D 364      63.528  -8.805  -9.555  1.00 18.43           C
ANISOU 2963  C   THR D 364    1999  2147  2858      8   -112    128          C
ATOM   2964  O   THR D 364      63.977  -9.703 -10.275  1.00 19.45           O
ANISOU 2964  O   THR D 364    2108  2205  3076     54    -61    116          O
ATOM   2965  N   MSE D 365      63.759  -7.504  -9.770  1.00 17.63           N
ANISOU 2965  N   MSE D 365    1808  2119  2769      0   -126    104          N
ATOM   2966  CA  MSE D 365      64.730  -7.023 -10.747  1.00 18.41           C
ANISOU 2966  CA  MSE D 365    1769  2226  2998     40    -88     87          C
ATOM   2967  CB  MSE D 365      64.077  -6.068 -11.759  1.00 17.25           C
ANISOU 2967  CB  MSE D 365    1596  2157  2801      0     10     46          C
ATOM   2968  CG  MSE D 365      62.868  -6.645 -12.487  1.00 16.17           C
ANISOU 2968  CG  MSE D 365    1532  2052  2561    -32    102      1          C
ATOM   2969  SE  MSE D 365      61.845  -5.313 -13.450  0.90 20.72          SE
ANISOU 2969  SE  MSE D 365    2093  2738  3041    -63    163    -30         SE
ATOM   2970  CE  MSE D 365      63.243  -4.311 -14.263  1.00 11.76           C
ANISOU 2970  CE  MSE D 365     852  1592  2023    -26    207      8          C
ATOM   2971  C   MSE D 365      65.810  -6.262  -9.991  1.00 17.87           C
ANISOU 2971  C   MSE D 365    1615  2153  3021     59   -218    116          C
ATOM   2972  O   MSE D 365      65.495  -5.340  -9.241  1.00 17.57           O
ANISOU 2972  O   MSE D 365    1614  2147  2913     15   -292    109          O
ATOM   2973  N   VAL D 366      67.068  -6.639 -10.196  1.00 18.01           N
ANISOU 2973  N   VAL D 366    1510  2130  3203    125   -245    137          N
ATOM   2974  CA  VAL D 366      68.202  -5.950  -9.570  1.00 18.86           C
ANISOU 2974  CA  VAL D 366    1492  2239  3436    133   -384    156          C
ATOM   2975  CB  VAL D 366      68.942  -6.864  -8.537  1.00 20.54           C
ANISOU 2975  CB  VAL D 366    1707  2397  3701    214   -553    207          C
ATOM   2976  CG1 VAL D 366      70.186  -6.172  -7.928  1.00 20.97           C
ANISOU 2976  CG1 VAL D 366    1598  2466  3905    220   -731    215          C
ATOM   2977  CG2 VAL D 366      67.976  -7.296  -7.406  1.00 21.86           C
ANISOU 2977  CG2 VAL D 366    2095  2550  3660    195   -633    237          C
ATOM   2978  C   VAL D 366      69.171  -5.358 -10.585  1.00 19.08           C
ANISOU 2978  C   VAL D 366    1324  2284  3643    133   -294    147          C
ATOM   2979  O   VAL D 366      69.843  -6.084 -11.309  1.00 19.34           O
ANISOU 2979  O   VAL D 366    1258  2296  3796    205   -204    151          O
ATOM   2980  N   GLY D 367      69.241  -4.027 -10.623  1.00 19.12           N
ANISOU 2980  N   GLY D 367    1279  2316  3670     51   -305    134          N
ATOM   2981  CA  GLY D 367      70.244  -3.316 -11.436  1.00 20.13           C
ANISOU 2981  CA  GLY D 367    1215  2451  3984     23   -221    144          C
ATOM   2982  C   GLY D 367      71.337  -2.617 -10.640  1.00 21.77           C
ANISOU 2982  C   GLY D 367    1266  2642  4363    -22   -391    146          C
ATOM   2983  O   GLY D 367      71.408  -2.757  -9.417  1.00 21.83           O
ANISOU 2983  O   GLY D 367    1322  2639  4334    -13   -599    136          O
ATOM   2984  N   LYS D 368      72.214  -1.887 -11.335  1.00 22.99           N
ANISOU 2984  N   LYS D 368    1233  2797  4706    -78   -304    160          N
ATOM   2985  CA  LYS D 368      73.258  -1.124 -10.655  1.00 25.77           C
ANISOU 2985  CA  LYS D 368    1410  3130  5252   -153   -467    150          C
ATOM   2986  CB  LYS D 368      74.267  -0.536 -11.644  1.00 27.60           C
ANISOU 2986  CB  LYS D 368    1403  3363  5721   -218   -307    181          C
ATOM   2987  CG  LYS D 368      75.163  -1.558 -12.320  1.00 33.38           C
ANISOU 2987  CG  LYS D 368    1937  4132  6613   -110   -181    206          C
ATOM   2988  CD  LYS D 368      76.116  -0.834 -13.239  1.00 40.97           C
ANISOU 2988  CD  LYS D 368    2663  5104  7802   -196      4    241          C
ATOM   2989  CE  LYS D 368      76.457  -1.646 -14.479  1.00 44.55           C
ANISOU 2989  CE  LYS D 368    3032  5601  8293    -92    283    264          C
ATOM   2990  NZ  LYS D 368      77.644  -1.037 -15.172  1.00 45.91           N
ANISOU 2990  NZ  LYS D 368    2915  5795  8735   -172    454    304          N
ATOM   2991  C   LYS D 368      72.654   0.026  -9.845  1.00 24.40           C
ANISOU 2991  C   LYS D 368    1379  2920  4973   -257   -603    106          C
ATOM   2992  O   LYS D 368      73.146   0.344  -8.779  1.00 25.32           O
ANISOU 2992  O   LYS D 368    1457  3020  5142   -295   -829     68          O
ATOM   2993  N   ARG D 369      71.581   0.624 -10.361  1.00 22.61           N
ANISOU 2993  N   ARG D 369    1320  2680  4592   -289   -471    106          N
ATOM   2994  CA  ARG D 369      71.084   1.898  -9.820  1.00 22.72           C
ANISOU 2994  CA  ARG D 369    1450  2637  4547   -381   -553     61          C
ATOM   2995  CB  ARG D 369      71.284   3.026 -10.839  1.00 23.23           C
ANISOU 2995  CB  ARG D 369    1454  2643  4728   -474   -393     99          C
ATOM   2996  CG  ARG D 369      72.739   3.461 -11.079  1.00 25.22           C
ANISOU 2996  CG  ARG D 369    1448  2862  5272   -572   -395    123          C
ATOM   2997  CD  ARG D 369      72.724   4.978 -11.254  1.00 27.02           C
```

FIGURE 18-88

```
ANISOU 2997  CD  ARG D 369    1710  2974  5581  -711  -368   125        C
ATOM   2998  NE  ARG D 369   73.878   5.516 -10.578  1.00 30.88         N
ANISOU 2998  NE  ARG D 369    2013  3410  6311  -834  -535    79        N
ATOM   2999  CZ  ARG D 369   73.901   6.588  -9.811  1.00 32.41         C
ANISOU 2999  CZ  ARG D 369    2268  3495  6550  -948  -695     3        C
ATOM   3000  NH1 ARG D 369   72.814   7.329  -9.581  1.00 27.48         N
ANISOU 3000  NH1 ARG D 369    1898  2792  5751  -941  -698   -36        N
ATOM   3001  NH2 ARG D 369   75.066   6.923  -9.282  1.00 37.95         N
ANISOU 3001  NH2 ARG D 369    2761  4164  7495 -1068  -857   -43        N
ATOM   3002  C   ARG D 369   69.625   1.847  -9.399  1.00 21.13         C
ANISOU 3002  C   ARG D 369    1494  2450  4083  -335  -554    28        C
ATOM   3003  O   ARG D 369   69.083   2.830  -8.934  1.00 21.50         O
ANISOU 3003  O   ARG D 369    1657  2450  4063  -381  -605   -21        O
ATOM   3004  N   ALA D 370   68.982   0.695  -9.556  1.00 20.31         N
ANISOU 3004  N   ALA D 370    1467  2407  3845  -245  -491    48        N
ATOM   3005  CA  ALA D 370   67.568   0.560  -9.210  1.00 19.37         C
ANISOU 3005  CA  ALA D 370    1545  2315  3499  -211  -469    22        C
ATOM   3006  CB  ALA D 370   66.677   1.149 -10.287  1.00 17.08         C
ANISOU 3006  CB  ALA D 370    1309  2033  3150  -214  -301    37        C
ATOM   3007  C   ALA D 370   67.248  -0.884  -9.014  1.00 19.29         C
ANISOU 3007  C   ALA D 370    1584  2348  3395  -138  -463    43        C
ATOM   3008  O   ALA D 370   67.922  -1.742  -9.573  1.00 19.71         O
ANISOU 3008  O   ALA D 370    1534  2404  3548   -97  -417    79        O
ATOM   3009  N   THR D 371   66.236  -1.151  -8.200  1.00 19.16         N
ANISOU 3009  N   THR D 371    1728  2356  3196  -124  -499    19        N
ATOM   3010  CA  THR D 371   65.719  -2.493  -8.036  1.00 20.02         C
ANISOU 3010  CA  THR D 371    1913  2488  3207   -77  -468    48        C
ATOM   3011  CB  THR D 371   66.139  -3.157  -6.702  1.00 20.97         C
ANISOU 3011  CB  THR D 371    2102  2591  3274   -49  -635    69        C
ATOM   3012  OG1 THR D 371   65.494  -2.487  -5.624  1.00 23.31         O
ANISOU 3012  OG1 THR D 371    2538  2908  3410   -79  -706    26        O
ATOM   3013  CG2 THR D 371   67.641  -3.122  -6.488  1.00 21.86         C
ANISOU 3013  CG2 THR D 371    2068  2673  3565   -30  -782    86        C
ATOM   3014  C   THR D 371   64.184  -2.423  -8.121  1.00 19.54         C
ANISOU 3014  C   THR D 371    1975  2472  2979   -89  -363    23        C
ATOM   3015  O   THR D 371   63.586  -1.359  -8.003  1.00 19.86         O
ANISOU 3015  O   THR D 371    2053  2526  2966  -111  -349   -18        O
ATOM   3016  N   ALA D 372   63.528  -3.552  -8.324  1.00 19.12         N
ANISOU 3016  N   ALA D 372    1973  2435  2858   -76  -288    43        N
ATOM   3017  CA  ALA D 372   62.076  -3.489  -8.455  1.00 17.32         C
ANISOU 3017  CA  ALA D 372    1816  2263  2502   -99  -191    15        C
ATOM   3018  CB  ALA D 372   61.686  -3.097  -9.920  1.00 17.05         C
ANISOU 3018  CB  ALA D 372    1709  2262  2508   -97   -82    -3        C
ATOM   3019  C   ALA D 372   61.442  -4.786  -8.072  1.00 16.39         C
ANISOU 3019  C   ALA D 372    1780  2143  2304  -114  -155    40        C
ATOM   3020  O   ALA D 372   62.117  -5.809  -7.986  1.00 17.78         O
ANISOU 3020  O   ALA D 372    1965  2259  2533   -92  -189    83        O
ATOM   3021  N   ILE D 373   60.138  -4.749  -7.838  1.00 16.26         N
ANISOU 3021  N   ILE D 373    1816  2184  2177  -149   -81    16        N
ATOM   3022  CA  ILE D 373   59.332  -5.958  -7.815  1.00 14.85         C
ANISOU 3022  CA  ILE D 373    1687  2003  1950  -195    -6    35        C
ATOM   3023  CB  ILE D 373   58.647  -6.199  -6.451  1.00 17.21         C
ANISOU 3023  CB  ILE D 373    2106  2321  2113  -231     8    63        C
ATOM   3024  CG1 ILE D 373   59.646  -6.124  -5.278  1.00 14.71         C
ANISOU 3024  CG1 ILE D 373    1885  1957  1748  -191  -121   110        C
ATOM   3025  CD1 ILE D 373   58.992  -6.294  -3.900  1.00 16.18         C
ANISOU 3025  CD1 ILE D 373    2225  2170  1751  -219   -97   142        C
ATOM   3026  CG2 ILE D 373   57.892  -7.565  -6.465  1.00 14.20         C
ANISOU 3026  CG2 ILE D 373    1774  1909  1713  -304    99   100        C
ATOM   3027  C   ILE D 373   58.275  -5.853  -8.918  1.00 15.49         C
ANISOU 3027  C   ILE D 373    1695  2153  2037  -225    90   -18        C
ATOM   3028  O   ILE D 373   57.564  -4.846  -9.013  1.00 14.66         O
ANISOU 3028  O   ILE D 373    1549  2123  1896  -214   114   -57        O
ATOM   3029  N   LEU D 374   58.168  -6.910  -9.725  1.00 15.28         N
ANISOU 3029  N   LEU D 374    1656  2094  2054  -255   132   -25        N
ATOM   3030  CA  LEU D 374   57.294  -6.952 -10.890  1.00 14.84         C
ANISOU 3030  CA  LEU D 374    1534  2103  2000  -285   188   -85        C
ATOM   3031  CB  LEU D 374   58.116  -7.089 -12.188  1.00 13.81         C
ANISOU 3031  CB  LEU D 374    1370  1943  1933  -240   188  -107        C
ATOM   3032  CG  LEU D 374   57.391  -7.325 -13.533  1.00 16.12         C
ANISOU 3032  CG  LEU D 374    1628  2295  2201  -265   224  -176        C
```

FIGURE 18-89

```
ATOM   3033  CD1 LEU D 374      56.508  -6.147 -13.943  1.00 14.16           C
ANISOU 3033  CD1 LEU D 374    1315  2168  1897  -246   213  -194             C
ATOM   3034  CD2 LEU D 374      58.355  -7.620 -14.697  1.00 15.29           C
ANISOU 3034  CD2 LEU D 374    1528  2150  2131  -214   248  -197             C
ATOM   3035  C   LEU D 374      56.317  -8.127 -10.796  1.00 15.20           C
ANISOU 3035  C   LEU D 374    1607  2138  2030  -383   243  -101             C
ATOM   3036  O   LEU D 374      56.725  -9.266 -10.606  1.00 15.35           O
ANISOU 3036  O   LEU D 374    1699  2048  2084  -411   248   -74             O
ATOM   3037  N   ARG D 375      55.028  -7.827 -10.911  1.00 15.31           N
ANISOU 3037  N   ARG D 375    1554  2256  2009  -434   284  -144             N
ATOM   3038  CA  ARG D 375      54.040  -8.841 -11.218  1.00 16.30           C
ANISOU 3038  CA  ARG D 375    1656  2386  2152  -547   331  -184             C
ATOM   3039  CB  ARG D 375      52.876  -8.773 -10.272  1.00 17.01           C
ANISOU 3039  CB  ARG D 375    1708  2548  2207  -621   404  -172             C
ATOM   3040  CG  ARG D 375      53.151  -9.446  -8.924  1.00 16.88           C
ANISOU 3040  CG  ARG D 375    1823  2439  2152  -666   454   -83             C
ATOM   3041  CD  ARG D 375      52.036  -9.111  -7.966  1.00 17.47           C
ANISOU 3041  CD  ARG D 375    1859  2613  2166  -719   557   -71             C
ATOM   3042  NE  ARG D 375      52.301  -9.670  -6.649  1.00 20.64           N
ANISOU 3042  NE  ARG D 375    2417  2937  2488  -755   610    28             N
ATOM   3043  CZ  ARG D 375      51.689  -9.306  -5.525  1.00 21.86           C
ANISOU 3043  CZ  ARG D 375    2602  3163  2540  -771   710    60             C
ATOM   3044  NH1 ARG D 375      50.773  -8.327  -5.513  1.00 20.93           N
ANISOU 3044  NH1 ARG D 375    2351  3193  2408  -742   774   -10             N
ATOM   3045  NH2 ARG D 375      52.012  -9.927  -4.411  1.00 23.29           N
ANISOU 3045  NH2 ARG D 375    2960  3266  2625  -803   749   164             N
ATOM   3046  C   ARG D 375      53.565  -8.716 -12.664  1.00 17.05           C
ANISOU 3046  C   ARG D 375    1663  2555  2260  -548   300  -271             C
ATOM   3047  O   ARG D 375      53.246  -7.633 -13.155  1.00 16.83           O
ANISOU 3047  O   ARG D 375    1557  2634  2204  -481   270  -291             O
ATOM   3048  N   LYS D 376      53.476  -9.856 -13.325  1.00 18.24           N
ANISOU 3048  N   LYS D 376    1844  2640  2446  -624   301  -323             N
ATOM   3049  CA  LYS D 376      53.192  -9.905 -14.723  1.00 18.60           C
ANISOU 3049  CA  LYS D 376    1849  2743  2477  -625   256  -416             C
ATOM   3050  CB  LYS D 376      54.542 -10.061 -15.399  1.00 19.02           C
ANISOU 3050  CB  LYS D 376    1990  2707  2528  -534   251  -415             C
ATOM   3051  CG  LYS D 376      54.498 -10.388 -16.778  1.00 22.27           C
ANISOU 3051  CG  LYS D 376    2419  3141  2901  -532   226  -511             C
ATOM   3052  CD  LYS D 376      55.680 -11.228 -17.131  1.00 21.43           C
ANISOU 3052  CD  LYS D 376    2420  2893  2831  -488   267  -529             C
ATOM   3053  CE  LYS D 376      55.706 -11.320 -18.640  1.00 23.94           C
ANISOU 3053  CE  LYS D 376    2773  3260  3065  -460   255  -635             C
ATOM   3054  NZ  LYS D 376      54.576 -12.148 -19.074  1.00 23.78           N
ANISOU 3054  NZ  LYS D 376    2758  3250  3028  -589   205  -754             N
ATOM   3055  C   LYS D 376      52.271 -11.109 -14.980  1.00 20.06           C
ANISOU 3055  C   LYS D 376    2022  2897  2704  -780   261  -496             C
ATOM   3056  O   LYS D 376      52.290 -12.068 -14.216  1.00 21.47           O
ANISOU 3056  O   LYS D 376    2269  2952  2938  -868   315  -463             O
ATOM   3057  N   ALA D 377      51.449 -11.038 -16.025  1.00 20.56           N
ANISOU 3057  N   ALA D 377    2002  3067  2743  -817   196  -596             N
ATOM   3058  CA  ALA D 377      50.654 -12.164 -16.502  1.00 22.62           C
ANISOU 3058  CA  ALA D 377    2249  3295  3051  -974   171  -703             C
ATOM   3059  CB  ALA D 377      49.141 -12.016 -16.103  1.00 22.84           C
ANISOU 3059  CB  ALA D 377    2091  3455  3132 -1095   166  -725             C
ATOM   3060  C   ALA D 377      50.830 -12.200 -18.012  1.00 23.29           C
ANISOU 3060  C   ALA D 377    2371  3421  3056  -931    81  -817             C
ATOM   3061  O   ALA D 377      51.732 -11.531 -18.538  1.00 22.97           O
ANISOU 3061  O   ALA D 377    2392  3399  2935  -785    78  -786             O
ATOM   3062  N   THR D 378      49.995 -12.969 -18.713  1.00 24.81           N
ANISOU 3062  N   THR D 378    2534  3628  3263 -1062    10  -949             N
ATOM   3063  CA  THR D 378      50.084 -13.071 -20.188  1.00 25.87           C
ANISOU 3063  CA  THR D 378    2732  3812  3286 -1028   -90 -1078             C
ATOM   3064  CB  THR D 378      49.044 -14.046 -20.745  1.00 27.81           C
ANISOU 3064  CB  THR D 378    2938  4058  3571 -1214  -185 -1242             C
ATOM   3065  OG1 THR D 378      49.107 -15.264 -19.991  1.00 28.15           O
ANISOU 3065  OG1 THR D 378    3047  3892  3755 -1360   -97 -1250             O
ATOM   3066  CG2 THR D 378      49.290 -14.336 -22.254  1.00 28.26           C
ANISOU 3066  CG2 THR D 378    3122  4136  3481 -1179  -287 -1397             C
ATOM   3067  C   THR D 378      49.972 -11.709 -20.898  1.00 25.13           C
ANISOU 3067  C   THR D 378    2574  3913  3059  -881  -169 -1044             C
ATOM   3068  O   THR D 378      48.904 -11.120 -20.958  1.00 26.17           O
```

FIGURE 18-90

```
ANISOU 3068  O   THR D 378    2548  4203  3193   -898   -259  -1050       O
ATOM   3069  N   ARG D 379    51.091 -11.219 -21.423  1.00 24.75          N
ANISOU 3069  N   ARG D 379    2648  3846  2911   -733   -128   -998       N
ATOM   3070  CA  ARG D 379    51.137  -9.937 -22.140  1.00 24.06          C
ANISOU 3070  CA  ARG D 379    2543  3907  2692   -591   -183   -941       C
ATOM   3071  CB  ARG D 379    50.530 -10.069 -23.546  1.00 25.58          C
ANISOU 3071  CB  ARG D 379    2771  4219  2730   -599   -324  -1065       C
ATOM   3072  CG  ARG D 379    51.184 -11.136 -24.401  1.00 26.56          C
ANISOU 3072  CG  ARG D 379    3077  4242  2772   -629   -295  -1197       C
ATOM   3073  CD  ARG D 379    50.803 -11.005 -25.880  1.00 28.25          C
ANISOU 3073  CD  ARG D 379    3373  4594  2766   -594   -431  -1303       C
ATOM   3074  NE  ARG D 379    51.357  -9.774 -26.432  1.00 26.17          N
ANISOU 3074  NE  ARG D 379    3166  4426  2352   -423   -403  -1173       N
ATOM   3075  CZ  ARG D 379    51.005  -9.218 -27.587  1.00 26.90          C
ANISOU 3075  CZ  ARG D 379    3324  4670  2228   -349   -523  -1189       C
ATOM   3076  NH1 ARG D 379    50.097  -9.774 -28.377  1.00 26.03          N
ANISOU 3076  NH1 ARG D 379    3225  4654  2011   -425   -705  -1348       N
ATOM   3077  NH2 ARG D 379    51.574  -8.084 -27.945  1.00 25.85          N
ANISOU 3077  NH2 ARG D 379    3250  4588  1983   -203   -467  -1038       N
ATOM   3078  C   ARG D 379    50.451  -8.817 -21.339  1.00 23.81          C
ANISOU 3078  C   ARG D 379    2351  3979  2718   -548   -204   -834       C
ATOM   3079  O   ARG D 379    49.654  -8.062 -21.877  1.00 24.12          O
ANISOU 3079  O   ARG D 379    2303  4167  2693   -496   -315   -835       O
ATOM   3080  N   ARG D 380    50.796  -8.719 -20.055  1.00 23.74          N
ANISOU 3080  N   ARG D 380    2316  3884  2821   -555   -101   -746       N
ATOM   3081  CA  ARG D 380    50.201  -7.776 -19.126  1.00 24.65          C
ANISOU 3081  CA  ARG D 380    2301  4071  2994   -517    -90   -664       C
ATOM   3082  CB  ARG D 380    48.866  -8.319 -18.591  1.00 25.94          C
ANISOU 3082  CB  ARG D 380    2307  4296  3251   -653   -110   -725       C
ATOM   3083  CG  ARG D 380    48.090  -7.378 -17.662  1.00 27.73          C
ANISOU 3083  CG  ARG D 380    2381  4618  3538   -606    -79   -663       C
ATOM   3084  CD  ARG D 380    46.845  -8.116 -17.110  1.00 32.70          C
ANISOU 3084  CD  ARG D 380    2844  5302  4279   -768    -57   -724       C
ATOM   3085  NE  ARG D 380    46.470  -7.643 -15.763  1.00 41.53          N
ANISOU 3085  NE  ARG D 380    3880  6440  5461   -757     67   -655       N
ATOM   3086  CZ  ARG D 380    45.818  -8.377 -14.862  1.00 44.62          C
ANISOU 3086  CZ  ARG D 380    4194  6818  5941   -906    173   -660       C
ATOM   3087  NH1 ARG D 380    45.450  -9.626 -15.147  1.00 47.78          N
ANISOU 3087  NH1 ARG D 380    4579  7169  6405  -1093    162   -728       N
ATOM   3088  NH2 ARG D 380    45.534  -7.858 -13.668  1.00 46.02          N
ANISOU 3088  NH2 ARG D 380    4324  7025  6138   -874    301   -598       N
ATOM   3089  C   ARG D 380    51.163  -7.516 -17.970  1.00 22.17          C
ANISOU 3089  C   ARG D 380    2048  3640  2735   -477     23   -562       C
ATOM   3090  O   ARG D 380    51.649  -8.448 -17.344  1.00 22.38          O
ANISOU 3090  O   ARG D 380    2142  3543  2819   -550     89   -560       O
ATOM   3091  N   LEU D 381    51.447  -6.242 -17.712  1.00 20.15          N
ANISOU 3091  N   LEU D 381    1778  3415  2461   -357     30   -478       N
ATOM   3092  CA  LEU D 381    52.122  -5.824 -16.482  1.00 18.33          C
ANISOU 3092  CA  LEU D 381    1581  3101  2282   -326    104   -398       C
ATOM   3093  CB  LEU D 381    52.866  -4.501 -16.698  1.00 16.65          C
ANISOU 3093  CB  LEU D 381    1404  2880  2041   -197     98   -324       C
ATOM   3094  CG  LEU D 381    53.665  -3.909 -15.562  1.00 16.21          C
ANISOU 3094  CG  LEU D 381    1388  2738  2032   -163    142   -259       C
ATOM   3095  CD1 LEU D 381    54.864  -3.126 -16.123  1.00 15.32          C
ANISOU 3095  CD1 LEU D 381    1337  2566  1918    -87    146   -198       C
ATOM   3096  CD2 LEU D 381    52.771  -3.029 -14.664  1.00 13.19          C
ANISOU 3096  CD2 LEU D 381     938  2411  1663   -126    146   -254       C
ATOM   3097  C   LEU D 381    51.003  -5.675 -15.465  1.00 18.54          C
ANISOU 3097  C   LEU D 381    1498  3193  2353   -368    130   -404       C
ATOM   3098  O   LEU D 381    50.041  -4.942 -15.713  1.00 18.05          O
ANISOU 3098  O   LEU D 381    1322  3249  2289   -319     87   -421       O
ATOM   3099  N   VAL D 382    51.092  -6.417 -14.358  1.00 18.79          N
ANISOU 3099  N   VAL D 382    1564  3152  2425   -454    205   -387       N
ATOM   3100  CA  VAL D 382    50.030  -6.373 -13.333  1.00 19.66          C
ANISOU 3100  CA  VAL D 382    1578  3326  2564   -508    270   -388       C
ATOM   3101  CB  VAL D 382    49.864  -7.734 -12.561  1.00 20.30          C
ANISOU 3101  CB  VAL D 382    1704  3327  2682   -664    351   -380       C
ATOM   3102  CG1 VAL D 382    48.932  -7.592 -11.345  1.00 21.28          C
ANISOU 3102  CG1 VAL D 382    1755  3516  2814   -713    462   -358       C
ATOM   3103  CG2 VAL D 382    49.384  -8.852 -13.492  1.00 18.12          C
ANISOU 3103  CG2 VAL D 382    1390  3040  2452   -790    311   -458       C
```

FIGURE 18-91

```
ATOM   3104  C   VAL D 382      50.355  -5.218 -12.398  1.00 20.00           C
ANISOU 3104  C   VAL D 382    1654   3367   2580   -399    305   -336        C
ATOM   3105  O   VAL D 382      49.503  -4.363 -12.132  1.00 20.34           O
ANISOU 3105  O   VAL D 382    1594   3506   2628   -338    324   -353        O
ATOM   3106  N   GLN D 383      51.602  -5.188 -11.930  1.00 20.10           N
ANISOU 3106  N   GLN D 383    1804   3265   2570   -368    305   -282        N
ATOM   3107  CA  GLN D 383      52.076  -4.128 -11.044  1.00 20.46           C
ANISOU 3107  CA  GLN D 383    1903   3285   2586   -280    314   -249        C
ATOM   3108  CB  GLN D 383      51.440  -4.281  -9.645  1.00 22.14           C
ANISOU 3108  CB  GLN D 383    2130   3523   2758   -323    407   -245        C
ATOM   3109  CG  GLN D 383      51.782  -3.166  -8.701  1.00 27.86           C
ANISOU 3109  CG  GLN D 383    2924   4230   3430   -231    413   -242        C
ATOM   3110  CD  GLN D 383      50.784  -2.962  -7.567  1.00 35.94           C
ANISOU 3110  CD  GLN D 383    3931   5330   4396   -236    530   -267        C
ATOM   3111  OE1 GLN D 383      50.146  -3.921  -7.057  1.00 37.23           O
ANISOU 3111  OE1 GLN D 383    4080   5526   4539   -341    628   -250        O
ATOM   3112  NE2 GLN D 383      50.628  -1.688  -7.167  1.00 36.75           N
ANISOU 3112  NE2 GLN D 383    4039   5450   4475   -122    537   -310        N
ATOM   3113  C   GLN D 383      53.600  -4.104 -10.977  1.00 18.47           C
ANISOU 3113  C   GLN D 383    1765   2914   2337   -249    266   -202        C
ATOM   3114  O   GLN D 383      54.256  -5.122 -11.078  1.00 18.25           O
ANISOU 3114  O   GLN D 383    1793   2812   2329   -299    259   -182        O
ATOM   3115  N   LEU D 384      54.153  -2.908 -10.828  1.00 18.23           N
ANISOU 3115  N   LEU D 384    1759   2860   2309   -163    230   -190        N
ATOM   3116  CA  LEU D 384      55.575  -2.690 -10.666  1.00 16.87           C
ANISOU 3116  CA  LEU D 384    1658   2587   2165   -139    179   -151        C
ATOM   3117  CB  LEU D 384      56.164  -2.192 -11.983  1.00 16.08           C
ANISOU 3117  CB  LEU D 384    1525   2473   2113    -96    154   -135        C
ATOM   3118  CG  LEU D 384      57.662  -1.872 -12.075  1.00 16.83           C
ANISOU 3118  CG  LEU D 384    1646   2475   2275    -79    119    -94        C
ATOM   3119  CD1 LEU D 384      58.510  -3.146 -12.068  1.00 11.98           C
ANISOU 3119  CD1 LEU D 384    1046   1808   1697   -114    119    -78        C
ATOM   3120  CD2 LEU D 384      57.896  -1.065 -13.332  1.00 12.84           C
ANISOU 3120  CD2 LEU D 384    1111   1973   1792    -36    133    -69        C
ATOM   3121  C   LEU D 384      55.832  -1.650  -9.567  1.00 17.39           C
ANISOU 3121  C   LEU D 384    1779   2622   2207    -96    154   -158        C
ATOM   3122  O   LEU D 384      55.240  -0.552  -9.591  1.00 18.03           O
ANISOU 3122  O   LEU D 384    1836   2732   2282    -36    164   -189        O
ATOM   3123  N   ILE D 385      56.704  -1.988  -8.617  1.00 16.14           N
ANISOU 3123  N   ILE D 385    1702   2399   2032   -119    109   -136        N
ATOM   3124  CA  ILE D 385      57.217  -1.037  -7.649  1.00 16.77           C
ANISOU 3124  CA  ILE D 385    1850   2434   2086    -88     49   -157        C
ATOM   3125  CB  ILE D 385      56.942  -1.448  -6.168  1.00 17.93           C
ANISOU 3125  CB  ILE D 385    2109   2597   2105   -110     57   -164        C
ATOM   3126  CG1 ILE D 385      55.479  -1.806  -6.000  1.00 19.43           C
ANISOU 3126  CG1 ILE D 385    2275   2882   2226   -129    188   -183        C
ATOM   3127  CD1 ILE D 385      55.134  -2.472  -4.673  1.00 20.09           C
ANISOU 3127  CD1 ILE D 385    2475   2988   2170   -170    242   -163        C
ATOM   3128  CG2 ILE D 385      57.252  -0.256  -5.217  1.00 17.45           C
ANISOU 3128  CG2 ILE D 385    2135   2503   1991    -68     -6   -224        C
ATOM   3129  C   ILE D 385      58.712  -0.916  -7.838  1.00 16.33           C
ANISOU 3129  C   ILE D 385    1790   2292   2123    -90    -48   -125        C
ATOM   3130  O   ILE D 385      59.401  -1.917  -7.778  1.00 15.60           O
ANISOU 3130  O   ILE D 385    1701   2171   2056   -114    -80    -82        O
ATOM   3131  N   VAL D 386      59.193   0.302  -8.082  1.00 16.79           N
ANISOU 3131  N   VAL D 386    1830   2302   2249    -66    -89   -145        N
ATOM   3132  CA  VAL D 386      60.628   0.573  -8.316  1.00 16.53           C
ANISOU 3132  CA  VAL D 386    1754   2189   2338    -85   -170   -117        C
ATOM   3133  CB  VAL D 386      60.864   1.322  -9.646  1.00 16.12           C
ANISOU 3133  CB  VAL D 386    1628   2110   2389    -76   -119    -88        C
ATOM   3134  CG1 VAL D 386      62.343   1.365  -9.984  1.00 15.54           C
ANISOU 3134  CG1 VAL D 386    1475   1971   2459   -111   -161    -48        C
ATOM   3135  CG2 VAL D 386      60.077   0.665 -10.776  1.00 15.17           C
ANISOU 3135  CG2 VAL D 386    1471   2064   2228    -55    -21    -62        C
ATOM   3136  C   VAL D 386      61.267   1.429  -7.207  1.00 18.00           C
ANISOU 3136  C   VAL D 386    2001   2310   2527    -99   -288   -165        C
ATOM   3137  O   VAL D 386      60.688   2.436  -6.757  1.00 17.63           O
ANISOU 3137  O   VAL D 386    2022   2246   2432    -78   -286   -229        O
ATOM   3138  N   SER D 387      62.475   1.024  -6.818  1.00 17.98           N
ANISOU 3138  N   SER D 387    1968   2271   2593   -128   -398   -143        N
ATOM   3139  CA  SER D 387      63.295   1.740  -5.874  1.00 19.91           C
```

FIGURE 18-92

```
ANISOU 3139  CA  SER D 387    2246  2456  2863  -157  -549  -194       C
ATOM   3140  CB  SER D 387     63.525   0.862  -4.642  1.00 20.75      C
ANISOU 3140  CB  SER D 387    2441  2593  2848  -148  -662  -190       C
ATOM   3141  OG  SER D 387     64.138   1.637  -3.629  1.00 26.41      O
ANISOU 3141  OG  SER D 387    3222  3268  3545  -174  -828  -263       O
ATOM   3142  C   SER D 387     64.614   2.081  -6.601  1.00 19.75      C
ANISOU 3142  C   SER D 387    2073  2372  3058  -200  -595  -160       C
ATOM   3143  O   SER D 387     65.205   1.226  -7.243  1.00 19.61      O
ANISOU 3143  O   SER D 387    1949  2374  3129  -192  -563   -95       O
ATOM   3144  N   GLY D 388     65.045   3.336  -6.558  1.00 20.44      N
ANISOU 3144  N   GLY D 388    2147  2377  3242  -249  -648  -207       N
ATOM   3145  CA  GLY D 388     66.169   3.760  -7.373  1.00 20.71      C
ANISOU 3145  CA  GLY D 388    2024  2350  3495  -310  -644  -164       C
ATOM   3146  C   GLY D 388     66.910   4.945  -6.819  1.00 22.28      C
ANISOU 3146  C   GLY D 388    2212  2442  3810  -396  -776  -233       C
ATOM   3147  O   GLY D 388     66.412   5.643  -5.960  1.00 22.74      O
ANISOU 3147  O   GLY D 388    2413  2458  3769  -398  -850  -326       O
ATOM   3148  N   LYS D 389     68.118   5.162  -7.318  1.00 23.01      N
ANISOU 3148  N   LYS D 389    2130  2489  4124  -474  -798  -195       N
ATOM   3149  CA  LYS D 389     68.973   6.226  -6.823  1.00 25.51      C
ANISOU 3149  CA  LYS D 389    2401  2696  4597  -588  -939  -262       C
ATOM   3150  CB  LYS D 389     70.436   5.931  -7.166  1.00 27.03      C
ANISOU 3150  CB  LYS D 389    2339  2893  5036  -662  -988  -213       C
ATOM   3151  CG  LYS D 389     71.016   4.768  -6.405  1.00 29.16      C
ANISOU 3151  CG  LYS D 389    2536  3261  5282  -606 -1149  -218       C
ATOM   3152  CD  LYS D 389     72.475   4.525  -6.778  1.00 33.37      C
ANISOU 3152  CD  LYS D 389    2779  3803  6095  -662 -1193  -174       C
ATOM   3153  CE  LYS D 389     73.170   3.650  -5.740  1.00 38.88      C
ANISOU 3153  CE  LYS D 389    3409  4571  6792  -609 -1439  -199       C
ATOM   3154  NZ  LYS D 389     74.315   2.871  -6.313  1.00 42.89      N
ANISOU 3154  NZ  LYS D 389    3629  5130  7536  -578 -1414  -125       N
ATOM   3155  C   LYS D 389     68.574   7.622  -7.336  1.00 25.27      C
ANISOU 3155  C   LYS D 389    2446  2528  4627  -643  -846  -275       C
ATOM   3156  O   LYS D 389     68.815   8.616  -6.671  1.00 27.52      O
ANISOU 3156  O   LYS D 389    2792  2696  4970  -722  -969  -371       O
ATOM   3157  N   ASP D 390     67.957   7.673  -8.502  1.00 23.52      N
ANISOU 3157  N   ASP D 390    2238  2314  4385  -594  -643  -180       N
ATOM   3158  CA  ASP D 390     67.627   8.899  -9.203  1.00 24.41      C
ANISOU 3158  CA  ASP D 390    2418  2292  4565  -626  -538  -147       C
ATOM   3159  CB  ASP D 390     68.851   9.494  -9.933  1.00 25.90      C
ANISOU 3159  CB  ASP D 390    2446  2380  5014  -767  -487   -72       C
ATOM   3160  CG  ASP D 390     69.523   8.504 -10.892  1.00 26.86      C
ANISOU 3160  CG  ASP D 390    2382  2621  5204  -760  -358    41       C
ATOM   3161  OD1 ASP D 390     69.057   8.339 -12.046  1.00 26.07      O
ANISOU 3161  OD1 ASP D 390    2311  2561  5035  -701  -169   145       O
ATOM   3162  OD2 ASP D 390     70.541   7.906 -10.494  1.00 27.91      O
ANISOU 3162  OD2 ASP D 390    2341  2805  5458  -807  -451    19       O
ATOM   3163  C   ASP D 390     66.538   8.541 -10.190  1.00 23.04      C
ANISOU 3163  C   ASP D 390    2310  2197  4248  -508  -363   -61       C
ATOM   3164  O   ASP D 390     66.326   7.369 -10.478  1.00 20.52      O
ANISOU 3164  O   ASP D 390    1944  2019  3834  -443  -313   -25       O
ATOM   3165  N   GLU D 391     65.854   9.559 -10.695  1.00 24.31      N
ANISOU 3165  N   GLU D 391    2582  2254  4399  -480  -285   -32       N
ATOM   3166  CA  GLU D 391     64.698   9.375 -11.545  1.00 25.09      C
ANISOU 3166  CA  GLU D 391    2753  2426  4353  -357  -161    37       C
ATOM   3167  CB  GLU D 391     63.893  10.685 -11.645  1.00 25.59      C
ANISOU 3167  CB  GLU D 391    2964  2345  4414  -303  -142    33       C
ATOM   3168  CG  GLU D 391     63.654  11.247 -13.044  1.00 29.26      C
ANISOU 3168  CG  GLU D 391    3463  2757  4898  -269    -8   185       C
ATOM   3169  CD  GLU D 391     63.469  12.790 -13.016  1.00 31.73      C
ANISOU 3169  CD  GLU D 391    3910  2836  5312  -270   -16   194       C
ATOM   3170  OE1 GLU D 391     63.085  13.318 -11.941  1.00 37.16      O
ANISOU 3170  OE1 GLU D 391    4684  3437  5996  -243  -114    56       O
ATOM   3171  OE2 GLU D 391     63.683  13.469 -14.057  1.00 34.98      O
ANISOU 3171  OE2 GLU D 391    4359  3140  5793  -292    83   339       O
ATOM   3172  C   GLU D 391     65.058   8.781 -12.903  1.00 24.24      C
ANISOU 3172  C   GLU D 391    2553  2399  4260  -360   -18   171       C
ATOM   3173  O   GLU D 391     64.273   8.010 -13.468  1.00 22.69      O
ANISOU 3173  O   GLU D 391    2374  2332  3915  -266    47   200       O
ATOM   3174  N   GLN D 392     66.247   9.114 -13.408  1.00 24.93      N
ANISOU 3174  N   GLN D 392    2538  2412  4524  -473    36   242       N
```

FIGURE 18-93

```
ATOM   3175  CA  GLN D 392      66.743   8.484 -14.629  1.00 25.44           C
ANISOU 3175  CA  GLN D 392     2508   2561   4595   -478    192    356       C
ATOM   3176  CB  GLN D 392      68.044   9.130 -15.089  1.00 27.83           C
ANISOU 3176  CB  GLN D 392     2695   2758   5122   -620    273    435       C
ATOM   3177  CG  GLN D 392      68.528   8.613 -16.433  1.00 30.48           C
ANISOU 3177  CG  GLN D 392     2956   3178   5449   -617    479    558       C
ATOM   3178  CD  GLN D 392      69.873   9.190 -16.862  1.00 32.38           C
ANISOU 3178  CD  GLN D 392     3046   3328   5929   -770    593    641       C
ATOM   3179  OE1 GLN D 392      70.866   9.160 -16.120  1.00 34.05           O
ANISOU 3179  OE1 GLN D 392     3083   3509   6346   -874    503    579       O
ATOM   3180  NE2 GLN D 392      69.915   9.682 -18.098  1.00 36.39           N
ANISOU 3180  NE2 GLN D 392     3617   3803   6407   -787    796    790       N
ATOM   3181  C   GLN D 392      66.861   6.952 -14.515  1.00 23.36           C
ANISOU 3181  C   GLN D 392     2153   2465   4257   -425    183    315       C
ATOM   3182  O   GLN D 392      66.428   6.241 -15.420  1.00 22.71           O
ANISOU 3182  O   GLN D 392     2091   2487   4051   -353    291    361       O
ATOM   3183  N   SER D 393      67.396   6.449 -13.399  1.00 22.65           N
ANISOU 3183  N   SER D 393     1984   2391   4230   -455     43    226       N
ATOM   3184  CA  SER D 393      67.491   5.002 -13.124  1.00 21.47           C
ANISOU 3184  CA  SER D 393     1772   2367   4020   -396     13    192       C
ATOM   3185  CB  SER D 393      68.327   4.756 -11.883  1.00 21.62           C
ANISOU 3185  CB  SER D 393     1702   2368   4143   -443   -165    121       C
ATOM   3186  OG  SER D 393      69.540   5.423 -12.049  1.00 27.86           O
ANISOU 3186  OG  SER D 393     2342   3083   5162   -552   -165    148       O
ATOM   3187  C   SER D 393      66.148   4.332 -12.909  1.00 19.41           C
ANISOU 3187  C   SER D 393     1642   2192   3542   -296     -2    151       C
ATOM   3188  O   SER D 393      65.985   3.151 -13.253  1.00 18.62           O
ANISOU 3188  O   SER D 393     1522   2183   3368   -242     46    156       O
ATOM   3189  N   ILE D 394      65.218   5.075 -12.314  1.00 18.26           N
ANISOU 3189  N   ILE D 394     1621   2007   3310   -275    -63    103       N
ATOM   3190  CA  ILE D 394      63.857   4.613 -12.104  1.00 17.01           C
ANISOU 3190  CA  ILE D 394     1563   1931   2968   -189    -60     64       C
ATOM   3191  CB  ILE D 394      63.049   5.528 -11.111  1.00 17.01           C
ANISOU 3191  CB  ILE D 394     1678   1876   2909   -165   -137    -15       C
ATOM   3192  CG1 ILE D 394      63.665   5.443  -9.702  1.00 17.08           C
ANISOU 3192  CG1 ILE D 394     1698   1854   2938   -213   -281    -98       C
ATOM   3193  CD1 ILE D 394      63.245   6.554  -8.715  1.00 19.53           C
ANISOU 3193  CD1 ILE D 394     2130   2075   3217   -209   -359   -197       C
ATOM   3194  CG2 ILE D 394      61.591   5.140 -11.069  1.00 15.94           C
ANISOU 3194  CG2 ILE D 394     1608   1838   2612    -76    -97    -43       C
ATOM   3195  C   ILE D 394      63.185   4.408 -13.442  1.00 16.42           C
ANISOU 3195  C   ILE D 394     1505   1922   2813   -134     66    130       C
ATOM   3196  O   ILE D 394      62.597   3.330 -13.682  1.00 17.30           O
ANISOU 3196  O   ILE D 394     1618   2138   2819    -93     94    116       O
ATOM   3197  N   ALA D 395      63.298   5.400 -14.315  1.00 16.91           N
ANISOU 3197  N   ALA D 395     1588   1917   2920   -141    135    204       N
ATOM   3198  CA  ALA D 395      62.780   5.347 -15.687  1.00 17.37           C
ANISOU 3198  CA  ALA D 395     1681   2033   2883    -86    242    282       C
ATOM   3199  CB  ALA D 395      63.094   6.656 -16.431  1.00 18.96           C
ANISOU 3199  CB  ALA D 395     1932   2120   3153   -106    307    386       C
ATOM   3200  C   ALA D 395      63.322   4.179 -16.485  1.00 17.20           C
ANISOU 3200  C   ALA D 395     1596   2104   2837    -93    329    304       C
ATOM   3201  O   ALA D 395      62.559   3.518 -17.161  1.00 17.12           O
ANISOU 3201  O   ALA D 395     1624   2193   2688    -37    361    297       O
ATOM   3202  N   GLU D 396      64.642   3.945 -16.431  1.00 18.24           N
ANISOU 3202  N   GLU D 396     1621   2199   3109   -159    365    321       N
ATOM   3203  CA  GLU D 396      65.268   2.754 -17.052  1.00 19.05           C
ANISOU 3203  CA  GLU D 396     1650   2376   3211   -147    455    320       C
ATOM   3204  CB  GLU D 396      66.786   2.709 -16.793  1.00 19.83           C
ANISOU 3204  CB  GLU D 396     1592   2423   3518   -212    479    336       C
ATOM   3205  CG  GLU D 396      67.552   3.855 -17.468  1.00 25.11           C
ANISOU 3205  CG  GLU D 396     2219   3017   4306   -286    591    433       C
ATOM   3206  CD  GLU D 396      69.015   4.000 -17.021  1.00 27.94           C
ANISOU 3206  CD  GLU D 396     2381   3319   4915   -376    586    439       C
ATOM   3207  OE1 GLU D 396      69.468   3.298 -16.076  1.00 34.31           O
ANISOU 3207  OE1 GLU D 396     3089   4143   5805   -369    459    366       O
ATOM   3208  OE2 GLU D 396      69.726   4.828 -17.643  1.00 32.70           O
ANISOU 3208  OE2 GLU D 396     2925   3862   5638   -458    709    525       O
ATOM   3209  C   GLU D 396      64.601   1.433 -16.628  1.00 16.89           C
ANISOU 3209  C   GLU D 396     1399   2181   2836    -97    395    236       C
ATOM   3210  O   GLU D 396      64.337   0.594 -17.467  1.00 17.29           O
```

FIGURE 18-94

```
ANISOU 3210  O   GLU D 396    1477  2301  2790   -57   470   225          O
ATOM   3211  N   ALA D 397    64.318   1.260 -15.340  1.00 16.42          N
ANISOU 3211  N   ALA D 397    1346  2104  2788  -105   265   178          N
ATOM   3212  CA  ALA D 397    63.635   0.071 -14.829  1.00 15.26          C
ANISOU 3212  CA  ALA D 397    1236  2012  2549   -75   218   117          C
ATOM   3213  CB  ALA D 397    63.668   0.033 -13.291  1.00 15.13          C
ANISOU 3213  CB  ALA D 397    1230  1961  2557   -95    85    78          C
ATOM   3214  C   ALA D 397    62.215  -0.057 -15.320  1.00 15.97          C
ANISOU 3214  C   ALA D 397    1408  2176  2484   -43   238    95          C
ATOM   3215  O   ALA D 397    61.786  -1.172 -15.654  1.00 16.45          O
ANISOU 3215  O   ALA D 397    1487  2289  2476   -32   262    58          O
ATOM   3216  N   ILE D 398    61.462   1.059 -15.321  1.00 16.01          N
ANISOU 3216  N   ILE D 398    1457  2178  2446   -26   217   108          N
ATOM   3217  CA  ILE D 398    60.095   1.065 -15.859  1.00 16.25          C
ANISOU 3217  CA  ILE D 398    1533  2291  2348    19   219    92          C
ATOM   3218  CB  ILE D 398    59.352   2.440 -15.637  1.00 16.90          C
ANISOU 3218  CB  ILE D 398    1654  2346  2422    64   182   109          C
ATOM   3219  CG1 ILE D 398    59.198   2.757 -14.154  1.00 16.25          C
ANISOU 3219  CG1 ILE D 398    1581  2218  2376    53   117    51          C
ATOM   3220  CD1 ILE D 398    58.939   4.211 -13.831  1.00 17.39          C
ANISOU 3220  CD1 ILE D 398    1771  2278  2557    94    91    55          C
ATOM   3221  CG2 ILE D 398    57.975   2.398 -16.248  1.00 15.79          C
ANISOU 3221  CG2 ILE D 398    1524  2306  2169   127   170    95          C
ATOM   3222  C   ILE D 398    60.089   0.658 -17.357  1.00 16.35          C
ANISOU 3222  C   ILE D 398    1563  2365  2282    40   294   120          C
ATOM   3223  O   ILE D 398    59.343  -0.227 -17.770  1.00 16.18          O
ANISOU 3223  O   ILE D 398    1555  2424  2169    47   288    69          O
ATOM   3224  N   ILE D 399    60.961   1.269 -18.152  1.00 16.83          N
ANISOU 3224  N   ILE D 399    1632  2386  2379    41   371   196          N
ATOM   3225  CA  ILE D 399    61.094   0.870 -19.567  1.00 16.97          C
ANISOU 3225  CA  ILE D 399    1691  2465  2293    64   463   222          C
ATOM   3226  CB  ILE D 399    62.227   1.668 -20.302  1.00 18.12          C
ANISOU 3226  CB  ILE D 399    1838  2552  2495    49   584   328          C
ATOM   3227  CG1 ILE D 399    61.855   3.147 -20.442  1.00 16.73          C
ANISOU 3227  CG1 ILE D 399    1724  2317  2315    67   562   423          C
ATOM   3228  CD1 ILE D 399    63.062   4.110 -20.649  1.00 18.57          C
ANISOU 3228  CD1 ILE D 399    1936  2437  2683     8   667   531          C
ATOM   3229  CG2 ILE D 399    62.537   1.045 -21.698  1.00 17.41          C
ANISOU 3229  CG2 ILE D 399    1800  2535  2278    75   713   340          C
ATOM   3230  C   ILE D 399    61.312  -0.653 -19.738  1.00 16.98          C
ANISOU 3230  C   ILE D 399    1675  2507  2269    53   495   138          C
ATOM   3231  O   ILE D 399    60.592  -1.306 -20.497  1.00 17.78          O
ANISOU 3231  O   ILE D 399    1832  2687  2237    73   491    87          O
ATOM   3232  N   VAL D 400    62.307  -1.207 -19.045  1.00 16.61          N
ANISOU 3232  N   VAL D 400    1556  2398  2359    26   512   120          N
ATOM   3233  CA  VAL D 400    62.608  -2.659 -19.102  1.00 15.36          C
ANISOU 3233  CA  VAL D 400    1388  2241  2209    32   541    46          C
ATOM   3234  CB  VAL D 400    63.878  -2.999 -18.262  1.00 16.29          C
ANISOU 3234  CB  VAL D 400    1403  2277  2508    26   542    57          C
ATOM   3235  CG1 VAL D 400    64.115  -4.500 -18.195  1.00 13.50          C
ANISOU 3235  CG1 VAL D 400    1055  1897  2178    53   557   -12          C
ATOM   3236  CG2 VAL D 400    65.116  -2.244 -18.837  1.00 13.64          C
ANISOU 3236  CG2 VAL D 400     986  1920  2278    24   654   130          C
ATOM   3237  C   VAL D 400    61.412  -3.538 -18.702  1.00 15.40          C
ANISOU 3237  C   VAL D 400    1440  2279  2133    16   456   -35          C
ATOM   3238  O   VAL D 400    61.069  -4.500 -19.408  1.00 16.47          O
ANISOU 3238  O   VAL D 400    1626  2443  2188    19   485  -105          O
ATOM   3239  N   ALA D 401    60.759  -3.208 -17.597  1.00 14.49          N
ANISOU 3239  N   ALA D 401    1311  2156  2037   -10   363   -33          N
ATOM   3240  CA  ALA D 401    59.557  -3.930 -17.183  1.00 14.67          C
ANISOU 3240  CA  ALA D 401    1359  2218  1996   -43   305   -97          C
ATOM   3241  CB  ALA D 401    59.103  -3.452 -15.809  1.00 13.69          C
ANISOU 3241  CB  ALA D 401    1219  2081  1904   -63   238   -82          C
ATOM   3242  C   ALA D 401    58.398  -3.848 -18.208  1.00 15.39          C
ANISOU 3242  C   ALA D 401    1478  2411  1958   -37   291  -135          C
ATOM   3243  O   ALA D 401    57.713  -4.818 -18.452  1.00 16.06          O
ANISOU 3243  O   ALA D 401    1579  2526  1997   -76   274  -209          O
ATOM   3244  N   MSE D 402    58.174  -2.688 -18.801  1.00 16.28          N
ANISOU 3244  N   MSE D 402    1597  2569  2018    10   285   -82          N
ATOM   3245  CA  MSE D 402    57.144  -2.553 -19.841  1.00 18.26          C
ANISOU 3245  CA  MSE D 402    1875  2926  2137    36   243  -106          C
```

FIGURE 18-95

```
ATOM   3246  CB  MSE D 402      56.928  -1.071 -20.204  1.00 18.49           C
ANISOU 3246  CB  MSE D 402     1919   2974   2132    108    222    -14       C
ATOM   3247  CG  MSE D 402      56.199  -0.248 -19.135  1.00 17.60           C
ANISOU 3247  CG  MSE D 402     1749   2850   2087    130    160     -1       C
ATOM   3248  SE  MSE D 402      56.146   1.624 -19.687  0.90 22.98          SE
ANISOU 3248  SE  MSE D 402     2485   3496   2753    237    146    125      SE
ATOM   3249  CE  MSE D 402      55.076   2.410 -18.255  1.00 21.33           C
ANISOU 3249  CE  MSE D 402     2203   3271   2632    282     78     86       C
ATOM   3250  C   MSE D 402      57.429  -3.401 -21.105  1.00 17.59           C
ANISOU 3250  C   MSE D 402     1861   2875   1947     35    288   -158       C
ATOM   3251  O   MSE D 402      56.527  -4.090 -21.622  1.00 17.86           O
ANISOU 3251  O   MSE D 402     1912   2982   1891      9    226   -245       O
ATOM   3252  N   VAL D 403      58.675  -3.365 -21.578  1.00 17.04           N
ANISOU 3252  N   VAL D 403     1828   2753   1894     59    399   -117       N
ATOM   3253  CA  VAL D 403      59.106  -4.194 -22.698  1.00 17.23           C
ANISOU 3253  CA  VAL D 403     1930   2797   1818     71    477   -179       C
ATOM   3254  CB  VAL D 403      60.556  -3.848 -23.174  1.00 18.02           C
ANISOU 3254  CB  VAL D 403     2039   2850   1958    109    637   -106       C
ATOM   3255  CG1 VAL D 403      61.044  -4.814 -24.226  1.00 17.77           C
ANISOU 3255  CG1 VAL D 403     2091   2834   1828    135    747   -191       C
ATOM   3256  CG2 VAL D 403      60.625  -2.412 -23.711  1.00 17.84           C
ANISOU 3256  CG2 VAL D 403     2047   2857   1873    143    665     26       C
ATOM   3257  C   VAL D 403      58.943  -5.683 -22.346  1.00 17.40           C
ANISOU 3257  C   VAL D 403     1955   2774   1884     20    460   -304       C
ATOM   3258  O   VAL D 403      58.320  -6.447 -23.087  1.00 17.38           O
ANISOU 3258  O   VAL D 403     2019   2816   1768     -1    427   -409       O
ATOM   3259  N   PHE D 404      59.463  -6.068 -21.187  1.00 16.85           N
ANISOU 3259  N   PHE D 404     1821   2605   1975     -4    468   -290       N
ATOM   3260  CA  PHE D 404      59.430  -7.453 -20.709  1.00 16.94           C
ANISOU 3260  CA  PHE D 404     1850   2535   2053    -47    459   -377       C
ATOM   3261  CB  PHE D 404      60.112  -7.514 -19.346  1.00 15.89           C
ANISOU 3261  CB  PHE D 404     1652   2303   2081    -48    451   -311       C
ATOM   3262  CG  PHE D 404      60.205  -8.886 -18.770  1.00 14.98           C
ANISOU 3262  CG  PHE D 404     1571   2077   2043    -77    445   -364       C
ATOM   3263  CD1 PHE D 404      61.249  -9.757 -19.143  1.00 15.77           C
ANISOU 3263  CD1 PHE D 404     1698   2082   2212    -16    525   -400       C
ATOM   3264  CE1 PHE D 404      61.321 -11.039 -18.585  1.00 17.63           C
ANISOU 3264  CE1 PHE D 404     1984   2185   2531    -30    513   -438       C
ATOM   3265  CZ  PHE D 404      60.388 -11.449 -17.653  1.00 16.05           C
ANISOU 3265  CZ  PHE D 404     1812   1951   2336   -121    435   -426       C
ATOM   3266  CE2 PHE D 404      59.342 -10.569 -17.262  1.00 17.50           C
ANISOU 3266  CE2 PHE D 404     1951   2250   2448   -190    374   -393       C
ATOM   3267  CD2 PHE D 404      59.283  -9.297 -17.818  1.00 13.88           C
ANISOU 3267  CD2 PHE D 404     1438   1917   1919   -156    374   -367       C
ATOM   3268  C   PHE D 404      58.010  -8.031 -20.605  1.00 17.76           C
ANISOU 3268  C   PHE D 404     1967   2679   2102   -130    361   -459       C
ATOM   3269  O   PHE D 404      57.797  -9.247 -20.769  1.00 17.49           O
ANISOU 3269  O   PHE D 404     1986   2584   2073   -180    361   -559       O
ATOM   3270  N   SER D 405      57.052  -7.151 -20.315  1.00 18.09           N
ANISOU 3270  N   SER D 405     1951   2814   2110   -146    283   -420       N
ATOM   3271  CA  SER D 405      55.637  -7.523 -20.129  1.00 19.11           C
ANISOU 3271  CA  SER D 405     2039   3005   2216   -228    193   -487       C
ATOM   3272  CB  SER D 405      54.863  -6.332 -19.573  1.00 18.78           C
ANISOU 3272  CB  SER D 405     1906   3051   2179   -203    138   -418       C
ATOM   3273  OG  SER D 405      54.618  -5.349 -20.582  1.00 21.57           O
ANISOU 3273  OG  SER D 405     2269   3504   2423   -125     96   -388       O
ATOM   3274  C   SER D 405      54.985  -8.034 -21.418  1.00 20.52           C
ANISOU 3274  C   SER D 405     2267   3260   2268   -254    138   -600       C
ATOM   3275  O   SER D 405      54.015  -8.769 -21.350  1.00 21.91           O
ANISOU 3275  O   SER D 405     2413   3456   2458   -351     72   -689       O
ATOM   3276  N   GLN D 406      55.571  -7.670 -22.566  1.00 21.23           N
ANISOU 3276  N   GLN D 406     2441   3390   2236   -175    172   -596       N
ATOM   3277  CA  GLN D 406      55.127  -8.012 -23.897  1.00 22.62           C
ANISOU 3277  CA  GLN D 406     2703   3650   2242   -175    117   -699       C
ATOM   3278  CB  GLN D 406      55.211  -9.513 -24.125  1.00 23.49           C
ANISOU 3278  CB  GLN D 406     2891   3667   2369   -252    136   -852       C
ATOM   3279  CG  GLN D 406      56.607 -10.072 -23.936  1.00 22.07           C
ANISOU 3279  CG  GLN D 406     2774   3339   2271   -202    291   -842       C
ATOM   3280  CD  GLN D 406      56.648 -11.573 -24.102  1.00 23.20           C
ANISOU 3280  CD  GLN D 406     3007   3356   2451   -264    309   -996       C
ATOM   3281  OE1 GLN D 406      55.795 -12.289 -23.567  1.00 21.91           O
```

FIGURE 18-96

```
ANISOU 3281  OE1 GLN D 406     2815  3144  2366   -382   229 -1058       O
ATOM   3282  NE2 GLN D 406    57.631 -12.062 -24.863  1.00 22.17         N
ANISOU 3282  NE2 GLN D 406     2989  3163  2270   -186   426 -1061       N
ATOM   3283  C   GLN D 406    53.732  -7.462 -24.252  1.00 24.34         C
ANISOU 3283  C   GLN D 406     2853  4022  2375   -190   -45  -716       C
ATOM   3284  O   GLN D 406    53.072  -8.002 -25.126  1.00 26.35         O
ANISOU 3284  O   GLN D 406     3151  4349  2512   -230  -144  -835       O
ATOM   3285  N   GLU D 407    53.301  -6.400 -23.576  1.00 23.86         N
ANISOU 3285  N   GLU D 407     2683  4006  2376   -150   -80  -607       N
ATOM   3286  CA  GLU D 407    51.981  -5.796 -23.788  1.00 25.52         C
ANISOU 3286  CA  GLU D 407     2793  4360  2543   -134  -232  -609       C
ATOM   3287  CB  GLU D 407    51.717  -4.639 -22.799  1.00 24.44         C
ANISOU 3287  CB  GLU D 407     2544  4227  2515    -71  -223  -490       C
ATOM   3288  CG  GLU D 407    51.472  -5.060 -21.360  1.00 25.08         C
ANISOU 3288  CG  GLU D 407     2519  4243  2767   -157  -170  -504       C
ATOM   3289  CD  GLU D 407    50.431  -4.211 -20.650  1.00 25.93         C
ANISOU 3289  CD  GLU D 407     2476  4430  2946   -117  -219  -468       C
ATOM   3290  OE1 GLU D 407    49.823  -3.328 -21.282  1.00 30.67         O
ANISOU 3290  OE1 GLU D 407     3037  5131  3485    -17  -316  -436       O
ATOM   3291  OE2 GLU D 407    50.193  -4.445 -19.455  1.00 24.61         O
ANISOU 3291  OE2 GLU D 407     2235  4224  2892   -177  -157  -471       O
ATOM   3292  C   GLU D 407    51.805  -5.244 -25.195  1.00 26.98         C
ANISOU 3292  C   GLU D 407     3072  4661  2517    -44  -322  -598       C
ATOM   3293  O   GLU D 407    52.719  -4.653 -25.768  1.00 26.51         O
ANISOU 3293  O   GLU D 407     3136  4577  2359     43  -236  -508       O
ATOM   3294  N   ASP D 408    50.596  -5.404 -25.710  1.00 29.10         N
ANISOU 3294  N   ASP D 408     3273  5062  2720    -68  -498  -681       N
ATOM   3295  CA  ASP D 408    50.199  -4.853 -27.013  1.00 31.78         C
ANISOU 3295  CA  ASP D 408     3697  5539  2839     27  -637  -666       C
ATOM   3296  CB  ASP D 408    48.762  -5.265 -27.372  1.00 34.18         C
ANISOU 3296  CB  ASP D 408     3873  5992  3124    -31  -866  -792       C
ATOM   3297  CG  ASP D 408    48.348  -4.814 -28.781  1.00 39.52         C
ANISOU 3297  CG  ASP D 408     4655  6821  3538     70 -1048  -789       C
ATOM   3298  OD1 ASP D 408    49.101  -5.101 -29.741  1.00 40.65         O
ANISOU 3298  OD1 ASP D 408     5022  6953  3469     91  -999  -816       O
ATOM   3299  OD2 ASP D 408    47.267  -4.173 -28.920  1.00 42.45         O
ANISOU 3299  OD2 ASP D 408     4889  7328  3911    139 -1240  -758       O
ATOM   3300  C   ASP D 408    50.353  -3.342 -27.114  1.00 30.90         C
ANISOU 3300  C   ASP D 408     3607  5449  2686    185  -631  -478       C
ATOM   3301  O   ASP D 408    50.746  -2.852 -28.164  1.00 32.78         O
ANISOU 3301  O   ASP D 408     4008  5725  2721    275  -638  -408       O
ATOM   3302  N   ACYS D 409   50.067  -2.594 -26.052  0.50 29.14         N
ANISOU 3302  N   ACYS D 409    3243  5189  2642    219  -609  -394       N
ATOM   3303  N   BCYS D 409   50.023  -2.637 -26.028  0.50 29.40         N
ANISOU 3303  N   BCYS D 409    3268  5224  2679    214  -613  -401       N
ATOM   3304  CA  ACYS D 409   50.211  -1.138 -26.143  0.50 29.02         C
ANISOU 3304  CA  ACYS D 409    3266  5159  2603    370  -605  -222       C
ATOM   3305  CA  BCYS D 409   50.202  -1.188 -25.910  0.50 29.33         C
ANISOU 3305  CA  BCYS D 409    3279  5184  2680    356  -592  -230       C
ATOM   3306  CB  ACYS D 409   49.420  -0.405 -25.050  0.50 28.83         C
ANISOU 3306  CB  ACYS D 409    3056  5130  2766    418  -640  -186       C
ATOM   3307  CB  BCYS D 409   49.874  -0.714 -24.481  0.50 28.22         C
ANISOU 3307  CB  BCYS D 409    2976  4982  2765    357  -546  -204       C
ATOM   3308  SG  ACYS D 409   50.276  -0.105 -23.502  0.50 27.27         S
ANISOU 3308  SG  ACYS D 409    2828  4756  2776    378  -445  -139       S
ATOM   3309  SG  BCYS D 409   48.105  -0.436 -24.090  0.50 33.35         S
ANISOU 3309  SG  BCYS D 409    3379  5779  3515    404  -720  -257       S
ATOM   3310  C   ACYS D 409   51.667  -0.658 -26.204  0.50 27.74         C
ANISOU 3310  C   ACYS D 409    3260  4860  2420    395  -416  -104       C
ATOM   3311  C   BCYS D 409   51.624  -0.756 -26.258  0.50 28.09         C
ANISOU 3311  C   BCYS D 409    3304  4913  2455    389  -423  -117       C
ATOM   3312  O   ACYS D 409   51.933   0.433 -26.730  0.50 28.22         O
ANISOU 3312  O   ACYS D 409    3420  4902  2398    505  -407    42       O
ATOM   3313  O   BCYS D 409   51.824   0.197 -27.026  0.50 28.90         O
ANISOU 3313  O   BCYS D 409    3525  5025  2431    499  -434    14       O
ATOM   3314  N   MSE D 410    52.594  -1.466 -25.672  1.00 25.88         N
ANISOU 3314  N   MSE D 410     3037  4523  2272    295  -268  -161       N
ATOM   3315  CA  MSE D 410    54.024  -1.213 -25.835  1.00 24.44         C
ANISOU 3315  CA  MSE D 410     2971  4231  2082    304   -88   -74       C
ATOM   3316  CB  MSE D 410    54.833  -2.065 -24.854  1.00 22.88         C
ANISOU 3316  CB  MSE D 410     2718  3922  2054    208    32  -139       C
```

FIGURE 18-97

```
ATOM   3317 CG  MSE D 410      56.350  -1.955 -24.998  1.00 21.58           C
ANISOU 3317 CG  MSE D 410     2626   3656   1917    211    213    -70       C
ATOM   3318 SE  MSE D 410      57.152  -3.307 -26.167  0.90 25.86          SE
ANISOU 3318 SE  MSE D 410     3301   4215   2311    188    331   -187      SE
ATOM   3319 CE  MSE D 410      56.323  -4.892 -25.393  1.00 24.10           C
ANISOU 3319 CE  MSE D 410     2993   3974   2189     79    226   -383       C
ATOM   3320 C   MSE D 410      54.468  -1.456 -27.290  1.00 26.13           C
ANISOU 3320 C   MSE D 410     3363   4505   2058    335    -51    -73       C
ATOM   3321 O   MSE D 410      55.180  -0.626 -27.871  1.00 26.11           O
ANISOU 3321 O   MSE D 410     3474   4473   1973    398     47     65       O
ATOM   3322 N   ILE D 411      54.017  -2.573 -27.865  1.00 26.59           N
ANISOU 3322 N   ILE D 411     3456   4644   2004    284   -125   -229       N
ATOM   3323 CA  ILE D 411      54.312  -2.938 -29.242  1.00 28.85           C
ANISOU 3323 CA  ILE D 411     3929   5002   2031    313   -103   -269       C
ATOM   3324 CB  ILE D 411      53.870  -4.398 -29.528  1.00 29.45           C
ANISOU 3324 CB  ILE D 411     4020   5117   2054    221   -180   -493       C
ATOM   3325 CG1 ILE D 411      54.922  -5.354 -28.950  1.00 30.86           C
ANISOU 3325 CG1 ILE D 411     4192   5151   2384    152      9   -568       C
ATOM   3326 CD1 ILE D 411      54.414  -6.711 -28.627  1.00 33.71           C
ANISOU 3326 CD1 ILE D 411     4508   5477   2824     40    -62   -761       C
ATOM   3327 CG2 ILE D 411      53.748  -4.648 -31.007  1.00 32.12           C
ANISOU 3327 CG2 ILE D 411     4558   5571   2076    263   -237   -560       C
ATOM   3328 C   ILE D 411      53.726  -1.918 -30.235  1.00 30.57           C
ANISOU 3328 C   ILE D 411     4252   5336   2025    427   -227   -151       C
ATOM   3329 O   ILE D 411      54.376  -1.536 -31.219  1.00 31.47           O
ANISOU 3329 O   ILE D 411     4553   5470   1935    489   -128    -62       O
ATOM   3330 N   LYS D 412      52.501  -1.477 -29.956  1.00 30.42           N
ANISOU 3330 N   LYS D 412     4112   5395   2052    462   -436   -143       N
ATOM   3331 CA  LYS D 412      51.861  -0.437 -30.741  1.00 32.14           C
ANISOU 3331 CA  LYS D 412     4405   5709   2097    595   -584    -13       C
ATOM   3332 CB  LYS D 412      50.356  -0.417 -30.473  1.00 32.55           C
ANISOU 3332 CB  LYS D 412     4273   5878   2215    618   -846    -83       C
ATOM   3333 CG  LYS D 412      49.618  -1.672 -30.980  1.00 35.49           C
ANISOU 3333 CG  LYS D 412     4615   6379   2489    522  -1011   -302       C
ATOM   3334 CD  LYS D 412      49.784  -1.869 -32.495  1.00 37.96           C
ANISOU 3334 CD  LYS D 412     5179   6799   2444    570  -1080   -323       C
ATOM   3335 CE  LYS D 412      48.933  -3.010 -33.017  1.00 41.23           C
ANISOU 3335 CE  LYS D 412     5565   7342   2760    474  -1290   -557       C
ATOM   3336 NZ  LYS D 412      49.410  -4.347 -32.577  1.00 40.94           N
ANISOU 3336 NZ  LYS D 412     5511   7204   2841    307  -1155   -748       N
ATOM   3337 C   LYS D 412      52.488   0.954 -30.564  1.00 31.37           C
ANISOU 3337 C   LYS D 412     4368   5501   2052    689   -464    219       C
ATOM   3338 O   LYS D 412      52.263   1.832 -31.384  1.00 34.17           O
ANISOU 3338 O   LYS D 412     4853   5899   2228    808   -535    364       O
ATOM   3339 N   ALA D 413      53.283   1.145 -29.513  1.00 28.83           N
ANISOU 3339 N   ALA D 413     3961   5027   1966    633   -291    254       N
ATOM   3340 CA  ALA D 413      54.009   2.413 -29.275  1.00 28.38           C
ANISOU 3340 CA  ALA D 413     3958   4834   1993    687   -162    453       C
ATOM   3341 CB  ALA D 413      54.311   2.582 -27.805  1.00 25.93           C
ANISOU 3341 CB  ALA D 413     3482   4390   1981    626    -91    433       C
ATOM   3342 C   ALA D 413      55.295   2.553 -30.097  1.00 29.23           C
ANISOU 3342 C   ALA D 413     4248   4891   1969    672     54    557       C
ATOM   3343 O   ALA D 413      55.935   3.610 -30.084  1.00 29.28           O
ANISOU 3343 O   ALA D 413     4316   4781   2026    698    170    734       O
ATOM   3344 N   VAL D 414      55.681   1.491 -30.803  1.00 29.64           N
ANISOU 3344 N   VAL D 414     4382   5018   1860    624    122    442       N
ATOM   3345 CA  VAL D 414      56.838   1.555 -31.696  1.00 31.53           C
ANISOU 3345 CA  VAL D 414     4796   5239   1947    622    349    527       C
ATOM   3346 CB  VAL D 414      57.244   0.153 -32.204  1.00 31.72           C
ANISOU 3346 CB  VAL D 414     4872   5330   1851    568    433    337       C
ATOM   3347 CG1 VAL D 414      58.299   0.242 -33.322  1.00 32.64           C
ANISOU 3347 CG1 VAL D 414     5189   5463   1751    592    677    419       C
ATOM   3348 CG2 VAL D 414      57.755  -0.679 -31.067  1.00 26.96           C
ANISOU 3348 CG2 VAL D 414     4084   4628   1532    474    509    207       C
ATOM   3349 C   VAL D 414      56.567   2.486 -32.871  1.00 34.97           C
ANISOU 3349 C   VAL D 414     5447   5737   2103    730    311    706       C
ATOM   3350 O   VAL D 414      55.529   2.404 -33.514  1.00 37.43           O
ANISOU 3350 O   VAL D 414     5833   6183   2206    804     94    673       O
ATOM   3351 N   ARG D 415      57.504   3.384 -33.133  1.00 37.13           N
ANISOU 3351 N   ARG D 415     5819   5909   2380    735    517    905       N
ATOM   3352 CA  ARG D 415      57.422   4.265 -34.293  1.00 41.20           C
```

FIGURE 18-98

```
ANISOU 3352  CA  ARG D 415     6579  6461  2613   830   529  1110       C
ATOM   3353  CB  ARG D 415    57.470   5.732 -33.856  1.00 41.42        C
ANISOU 3353  CB  ARG D 415     6605  6324  2807   867   539  1341       C
ATOM   3354  CG  ARG D 415    56.268   6.184 -33.006  1.00 40.12        C
ANISOU 3354  CG  ARG D 415     6292  6136  2814   940   267  1312       C
ATOM   3355  CD  ARG D 415    54.948   6.139 -33.791  1.00 40.78        C
ANISOU 3355  CD  ARG D 415     6465  6391  2638  1079   -17  1301       C
ATOM   3356  NE  ARG D 415    53.810   6.480 -32.938  1.00 40.08        N
ANISOU 3356  NE  ARG D 415     6189  6295  2746  1151  -253  1252       N
ATOM   3357  CZ  ARG D 415    53.013   5.596 -32.344  1.00 38.46        C
ANISOU 3357  CZ  ARG D 415     5779  6195  2639  1117  -410  1034       C
ATOM   3358  NH1 ARG D 415    53.202   4.298 -32.529  1.00 38.97        N
ANISOU 3358  NH1 ARG D 415     5819  6364  2626  1012  -379   843       N
ATOM   3359  NH2 ARG D 415    52.011   6.011 -31.573  1.00 36.41        N
ANISOU 3359  NH2 ARG D 415     5342  5928  2563  1190  -586  1008       N
ATOM   3360  C   ARG D 415    58.551   3.952 -35.281  1.00 43.98        C
ANISOU 3360  C   ARG D 415     7110  6845  2756   796   815  1153       C
ATOM   3361  O   ARG D 415    59.724   3.892 -34.899  1.00 43.78        O
ANISOU 3361  O   ARG D 415     6999  6716  2919   706  1074  1170       O
ATOM   3362  N   GLY D 416    58.191   3.744 -36.545  1.00 47.07        N
ANISOU 3362  N   GLY D 416     7743  7387  2756   874   766  1163       N
ATOM   3363  CA  GLY D 416    59.167   3.367 -37.555  1.00 50.12        C
ANISOU 3363  CA  GLY D 416     8322  7829  2894   856  1047  1180       C
ATOM   3364  C   GLY D 416    59.585   1.904 -37.482  1.00 49.71        C
ANISOU 3364  C   GLY D 416     8192  7833  2861   793  1140   902       C
ATOM   3365  O   GLY D 416    59.098   1.128 -36.639  1.00 47.48        O
ANISOU 3365  O   GLY D 416     7713  7542  2783   750   976   701       O
ATOM   3366  N   ASP D 417    60.483   1.527 -38.386  1.00 52.34        N
ANISOU 3366  N   ASP D 417     8692  8219  2976   793  1417   896       N
ATOM   3367  CA  ASP D 417    60.963   0.150 -38.487  1.00 52.48        C
ANISOU 3367  CA  ASP D 417     8681  8279  2981   761  1539   635       C
ATOM   3368  CB  ASP D 417    61.397  -0.171 -39.931  1.00 56.31        C
ANISOU 3368  CB  ASP D 417     9473  8894  3029   820  1741   619       C
ATOM   3369  CG  ASP D 417    60.213  -0.435 -40.865  1.00 59.32        C
ANISOU 3369  CG  ASP D 417    10103  9446  2990   899  1447   528       C
ATOM   3370  OD1 ASP D 417    59.072  -0.585 -40.386  1.00 59.62        O
ANISOU 3370  OD1 ASP D 417    10036  9508  3109   898  1092   434       O
ATOM   3371  OD2 ASP D 417    60.426  -0.508 -42.095  1.00 65.27        O
ANISOU 3371  OD2 ASP D 417    11157 10319  3324   961  1571   544       O
ATOM   3372  C   ASP D 417    62.098  -0.116 -37.495  1.00 49.99        C
ANISOU 3372  C   ASP D 417     8103  7818  3073   676  1773   604       C
ATOM   3373  O   ASP D 417    62.852   0.793 -37.130  1.00 49.00        O
ANISOU 3373  O   ASP D 417     7885  7587  3145   634  1948   804       O
ATOM   3374  N   LEU D 418    62.205  -1.370 -37.064  1.00 48.76        N
ANISOU 3374  N   LEU D 418     7831  7652  3045   649  1760   353       N
ATOM   3375  CA  LEU D 418    63.263  -1.792 -36.159  1.00 47.10        C
ANISOU 3375  CA  LEU D 418     7377  7317  3201   592  1951   302       C
ATOM   3376  CB  LEU D 418    62.671  -2.523 -34.951  1.00 43.74        C
ANISOU 3376  CB  LEU D 418     6747  6820  3051   545  1712   135       C
ATOM   3377  CG  LEU D 418    61.641  -1.770 -34.088  1.00 41.30        C
ANISOU 3377  CG  LEU D 418     6331  6480  2881   518  1426   222       C
ATOM   3378  CD1 LEU D 418    61.103  -2.653 -32.963  1.00 38.43        C
ANISOU 3378  CD1 LEU D 418     5787  6060  2756   466  1240    45       C
ATOM   3379  CD2 LEU D 418    62.198  -0.471 -33.502  1.00 40.54        C
ANISOU 3379  CD2 LEU D 418     6125  6279  2999   488  1516   456       C
ATOM   3380  C   LEU D 418    64.314  -2.643 -36.873  1.00 49.82        C
ANISOU 3380  C   LEU D 418     7792  7692  3447   625  2264   186       C
ATOM   3381  O   LEU D 418    64.020  -3.727 -37.397  1.00 50.62        O
ANISOU 3381  O   LEU D 418     8020  7854  3358   665  2228   -37       O
ATOM   3382  N   ASN D 419    65.543  -2.131 -36.890  1.00 51.58        N
ANISOU 3382  N   ASN D 419     7923  7863  3811   605  2578   331       N
ATOM   3383  CA  ASN D 419    66.641  -2.741 -37.637  1.00 55.38        C
ANISOU 3383  CA  ASN D 419     8453  8383  4204   650  2935   258       C
ATOM   3384  CB  ASN D 419    66.810  -2.036 -38.993  1.00 59.00        C
ANISOU 3384  CB  ASN D 419     9195  8957  4265   688  3148   420       C
ATOM   3385  CG  ASN D 419    65.665  -2.308 -39.945  1.00 61.70        C
ANISOU 3385  CG  ASN D 419     9864  9436  4145   756  2933   329       C
ATOM   3386  OD1 ASN D 419    65.411  -3.454 -40.327  1.00 65.31        O
ANISOU 3386  OD1 ASN D 419    10428  9949  4440   806  2887    70       O
ATOM   3387  ND2 ASN D 419    64.978  -1.249 -40.352  1.00 63.31        N
ANISOU 3387  ND2 ASN D 419    10234  9687  4135   763  2791   539       N
```

FIGURE 18-99

```
ATOM   3388  C   ASN D 419      67.967  -2.719 -36.875  1.00 55.20           C
ANISOU 3388  C   ASN D 419    8127  8253  4594    607  3178    304           C
ATOM   3389  O   ASN D 419      69.023  -2.657 -37.482  1.00 57.94           O
ANISOU 3389  O   ASN D 419    8467  8629  4917    625  3529    357           O
ATOM   3390  N   PHE D 420      67.907  -2.779 -35.544  1.00 53.13           N
ANISOU 3390  N   PHE D 420    7606  7875  4704    552  2988    281           N
ATOM   3391  CA  PHE D 420      69.109  -2.716 -34.699  1.00 52.97           C
ANISOU 3391  CA  PHE D 420    7276  7755  5095    508  3151    324           C
ATOM   3392  CB  PHE D 420      68.768  -2.606 -33.210  1.00 49.23           C
ANISOU 3392  CB  PHE D 420    6582  7166  4956    444  2866    319           C
ATOM   3393  CG  PHE D 420      68.193  -1.287 -32.813  1.00 47.59           C
ANISOU 3393  CG  PHE D 420    6385  6920  4777    366  2702    511           C
ATOM   3394  CD1 PHE D 420      66.832  -1.155 -32.549  1.00 44.55           C
ANISOU 3394  CD1 PHE D 420    6113  6548  4267    372  2390    485           C
ATOM   3395  CE1 PHE D 420      66.292   0.070 -32.189  1.00 42.45           C
ANISOU 3395  CE1 PHE D 420    5858  6235  4036    326  2247    653           C
ATOM   3396  CZ  PHE D 420      67.108   1.173 -32.079  1.00 44.31           C
ANISOU 3396  CZ  PHE D 420    6013  6391  4434    255  2405    848           C
ATOM   3397  CE2 PHE D 420      68.467   1.060 -32.333  1.00 47.66           C
ANISOU 3397  CE2 PHE D 420    6314  6802  4991    223  2712    881           C
ATOM   3398  CD2 PHE D 420      69.007  -0.170 -32.699  1.00 48.65           C
ANISOU 3398  CD2 PHE D 420    6408  6994  5082    287  2863    713           C
ATOM   3399  C   PHE D 420      70.044  -3.885 -34.897  1.00 55.24           C
ANISOU 3399  C   PHE D 420    7475  8045  5470    588  3382    148           C
ATOM   3400  O   PHE D 420      69.616  -5.017 -35.139  1.00 55.65           O
ANISOU 3400  O   PHE D 420    7645  8113  5387    664  3310    -68           O
ATOM   3401  N   VAL D 421      71.326  -3.572 -34.740  1.00 57.63           N
ANISOU 3401  N   VAL D 421    7549  8317  6030    565  3651    242           N
ATOM   3402  CA  VAL D 421      72.446  -4.448 -35.036  1.00 60.77           C
ANISOU 3402  CA  VAL D 421    7821  8726  6542    654  3948    120           C
ATOM   3403  CB  VAL D 421      73.166  -3.930 -36.322  1.00 64.47           C
ANISOU 3403  CB  VAL D 421    8404  9304  6788    666  4360    236           C
ATOM   3404  CG1 VAL D 421      74.630  -4.300 -36.367  1.00 67.05           C
ANISOU 3404  CG1 VAL D 421    8458  9632  7386    714  4721    208           C
ATOM   3405  CG2 VAL D 421      72.428  -4.388 -37.580  1.00 66.03           C
ANISOU 3405  CG2 VAL D 421    8997  9617  6475    754  4400    126           C
ATOM   3406  C   VAL D 421      73.361  -4.471 -33.799  1.00 60.35           C
ANISOU 3406  C   VAL D 421    7378  8567  6985    619  3924    144           C
ATOM   3407  O   VAL D 421      73.403  -3.496 -33.045  1.00 58.87           O
ANISOU 3407  O   VAL D 421    7042  8323  7003    501  3800    305           O
ATOM   3408  N   ASN D 422      74.043  -5.593 -33.555  1.00 62.10           N
ANISOU 3408  N   ASN D 422    7446  8752  7397    728  4012    -23           N
ATOM   3409  CA  ASN D 422      75.069  -5.636 -32.502  1.00 62.56           C
ANISOU 3409  CA  ASN D 422    7120  8730  7918    718  4012      6           C
ATOM   3410  CB  ASN D 422      75.045  -6.970 -31.720  1.00 61.54           C
ANISOU 3410  CB  ASN D 422    6907  8505  7969    834  3835   -189           C
ATOM   3411  CG  ASN D 422      75.460  -8.203 -32.559  1.00 64.42           C
ANISOU 3411  CG  ASN D 422    7361  8885  8231   1012  4080   -391           C
ATOM   3412  OD1 ASN D 422      75.195  -9.336 -32.147  1.00 63.87           O
ANISOU 3412  OD1 ASN D 422    7329  8720  8219   1110  3933   -561           O
ATOM   3413  ND2 ASN D 422      76.118  -7.995 -33.700  1.00 67.10           N
ANISOU 3413  ND2 ASN D 422    7740  9330  8425   1055  4460   -372           N
ATOM   3414  C   ASN D 422      76.469  -5.287 -33.033  1.00 66.36           C
ANISOU 3414  C   ASN D 422    7376  9270  8567    724  4415     91           C
ATOM   3415  O   ASN D 422      76.626  -4.987 -34.223  1.00 69.23           O
ANISOU 3415  O   ASN D 422    7905  9734  8666    733  4718    140           O
ATOM   3416  N   ARG D 423      77.475  -5.324 -32.158  1.00 67.11           N
ANISOU 3416  N   ARG D 423    7093  9311  9095    719  4419    113           N
ATOM   3417  CA  ARG D 423      78.878  -5.054 -32.539  1.00 71.12           C
ANISOU 3417  CA  ARG D 423    7306  9875  9840    720  4794    183           C
ATOM   3418  CB  ARG D 423      79.805  -5.272 -31.338  1.00 70.83           C
ANISOU 3418  CB  ARG D 423    6839  9769 10305    731  4668    172           C
ATOM   3419  CG  ARG D 423      81.105  -4.524 -31.468  1.00 75.85           C
ANISOU 3419  CG  ARG D 423    7115 10456 11248    641  4957    306           C
ATOM   3420  CD  ARG D 423      82.094  -4.875 -30.379  1.00 78.88           C
ANISOU 3420  CD  ARG D 423    7053 10793 12126    681  4832    269           C
ATOM   3421  NE  ARG D 423      83.449  -4.480 -30.778  1.00 83.39           N
ANISOU 3421  NE  ARG D 423    7254 11442 12987    644  5197    346           N
ATOM   3422  CZ  ARG D 423      84.346  -3.929 -29.962  1.00 85.30           C
ANISOU 3422  CZ  ARG D 423    7077 11667 13667    531  5116    429           C
ATOM   3423  NH1 ARG D 423      84.039  -3.684 -28.689  1.00 83.30           N
```

FIGURE 18-100

```
ANISOU 3423  NH1 ARG D 423    6747 11320 13584    452  4676    442       N
ATOM   3424  NH2 ARG D 423      85.547  -3.606 -30.420  1.00 88.44       N
ANISOU 3424  NH2 ARG D 423    7128 12146 14328    490  5478    494       N
ATOM   3425  C   ARG D 423      79.401  -5.843 -33.761  1.00 74.67       C
ANISOU 3425  C   ARG D 423    7845 10417 10109    882  5200     61       C
ATOM   3426  O   ARG D 423      80.280  -5.369 -34.493  1.00 78.15       O
ANISOU 3426  O   ARG D 423    8167 10945 10580    855  5588    155       O
ATOM   3427  N   ALA D 424      78.849  -7.036 -33.971  1.00 74.34       N
ANISOU 3427  N   ALA D 424    8018 10348  9879   1042  5120   -153       N
ATOM   3428  CA  ALA D 424      79.275  -7.945 -35.036  1.00 77.50       C
ANISOU 3428  CA  ALA D 424    8532 10811 10104   1222  5468   -322       C
ATOM   3429  CB  ALA D 424      79.327  -9.375 -34.497  1.00 77.08       C
ANISOU 3429  CB  ALA D 424    8426 10642 10219   1410  5328   -554       C
ATOM   3430  C   ALA D 424      78.429  -7.881 -36.329  1.00 78.58       C
ANISOU 3430  C   ALA D 424    9131 11043  9682   1227  5589   -362       C
ATOM   3431  O   ALA D 424      78.708  -8.612 -37.287  1.00 81.61       O
ANISOU 3431  O   ALA D 424    9666 11484  9858   1375  5881   -520       O
ATOM   3432  N   ASN D 425      77.396  -7.032 -36.340  1.00 76.24       N
ANISOU 3432  N   ASN D 425    9062 10762  9143   1081  5352   -230       N
ATOM   3433  CA  ASN D 425      76.541  -6.773 -37.531  1.00 77.06       C
ANISOU 3433  CA  ASN D 425    9601 10971  8708   1070  5413   -224       C
ATOM   3434  CB  ASN D 425      77.382  -6.619 -38.817  1.00 81.53       C
ANISOU 3434  CB  ASN D 425   10245 11670  9062   1128  5927   -191       C
ATOM   3435  CG  ASN D 425      76.892  -5.487 -39.721  1.00 82.66       C
ANISOU 3435  CG  ASN D 425   10683 11919  8803   1017  6017     23       C
ATOM   3436  OD1 ASN D 425      75.842  -4.884 -39.484  1.00 79.73       O
ANISOU 3436  OD1 ASN D 425   10484 11524  8284    921  5681    122       O
ATOM   3437  ND2 ASN D 425      77.670  -5.189 -40.763  1.00 87.19       N
ANISOU 3437  ND2 ASN D 425   11314 12609  9204   1038  6484    104       N
ATOM   3438  C   ASN D 425      75.343  -7.727 -37.759  1.00 75.53       C
ANISOU 3438  C   ASN D 425    9745 10754  8199   1149  5142   -450       C
ATOM   3439  O   ASN D 425      74.857  -7.888 -38.889  1.00 77.60       O
ANISOU 3439  O   ASN D 425   10357 11113  8012   1196  5244   -527       O
ATOM   3440  N   GLN D 426      74.866  -8.349 -36.685  1.00 72.05       N
ANISOU 3440  N   GLN D 426    9203 10184  7987   1153  4795   -555       N
ATOM   3441  CA  GLN D 426      73.650  -9.164 -36.756  1.00 70.27       C
ANISOU 3441  CA  GLN D 426    9262  9919  7517   1181  4501   -748       C
ATOM   3442  CB  GLN D 426      73.803 -10.451 -35.941  1.00 69.42       C
ANISOU 3442  CB  GLN D 426    9024  9655  7697   1280  4372   -950       C
ATOM   3443  CG  GLN D 426      74.946 -11.353 -36.387  1.00 73.99       C
ANISOU 3443  CG  GLN D 426    9510 10209  8392   1461  4723  -1107       C
ATOM   3444  CD  GLN D 426      75.603 -12.085 -35.226  1.00 74.03       C
ANISOU 3444  CD  GLN D 426    9200 10055  8872   1543  4632  -1157       C
ATOM   3445  OE1 GLN D 426      75.551 -11.640 -34.081  1.00 71.79       O
ANISOU 3445  OE1 GLN D 426    8697  9713  8868   1449  4387  -1016       O
ATOM   3446  NE2 GLN D 426      76.238 -13.210 -35.525  1.00 76.73       N
ANISOU 3446  NE2 GLN D 426    9532 10324  9297   1733  4831  -1361       N
ATOM   3447  C   GLN D 426      72.469  -8.361 -36.228  1.00 66.34       C
ANISOU 3447  C   GLN D 426    8844  9421  6942   1033  4126   -613       C
ATOM   3448  O   GLN D 426      72.648  -7.428 -35.444  1.00 64.20       O
ANISOU 3448  O   GLN D 426    8361  9122  6912    930  4038   -414       O
ATOM   3449  N   ARG D 427      71.267  -8.715 -36.673  1.00 65.24       N
ANISOU 3449  N   ARG D 427    9004  9310  6472   1027  3906   -733       N
ATOM   3450  CA  ARG D 427      70.051  -8.191 -36.069  1.00 61.55       C
ANISOU 3450  CA  ARG D 427    8583  8831  5972    913  3523   -653       C
ATOM   3451  CB  ARG D 427      68.814  -8.575 -36.886  1.00 62.29       C
ANISOU 3451  CB  ARG D 427    9018  9000  5650    917  3336   -797       C
ATOM   3452  CG  ARG D 427      68.261  -7.481 -37.795  1.00 64.44       C
ANISOU 3452  CG  ARG D 427    9512  9421  5551    879  3327   -631       C
ATOM   3453  CD  ARG D 427      66.962  -7.945 -38.473  1.00 65.91       C
ANISOU 3453  CD  ARG D 427   10000  9683  5358    883  3067   -794       C
ATOM   3454  NE  ARG D 427      65.923  -8.303 -37.500  1.00 66.69       N
ANISOU 3454  NE  ARG D 427   10003  9701  5634    809  2687   -872       N
ATOM   3455  CZ  ARG D 427      64.760  -7.663 -37.349  1.00 67.25       C
ANISOU 3455  CZ  ARG D 427   10120  9829  5603    741  2381   -785       C
ATOM   3456  NH1 ARG D 427      64.467  -6.631 -38.135  1.00 69.18       N
ANISOU 3456  NH1 ARG D 427   10527 10201  5557    750  2385   -613       N
ATOM   3457  NH2 ARG D 427      63.886  -8.059 -36.414  1.00 63.74       N
ANISOU 3457  NH2 ARG D 427    9559  9311  5349    671  2080   -864       N
ATOM   3458  C   ARG D 427      69.909  -8.721 -34.642  1.00 57.19       C
ANISOU 3458  C   ARG D 427    7803  8128  5798    883  3273   -704       C
```

FIGURE 18-101

```
ATOM   3459  O   ARG D 427      70.103  -9.914 -34.377  1.00 57.69           O
ANISOU 3459  O   ARG D 427    7840   8092   5987    959   3269   -894        O
ATOM   3460  N   LEU D 428      69.595  -7.815 -33.724  1.00 52.80           N
ANISOU 3460  N   LEU D 428    7098   7547   5418    778   3076   -527        N
ATOM   3461  CA  LEU D 428      69.144  -8.185 -32.399  1.00 48.04           C
ANISOU 3461  CA  LEU D 428    6348   6827   5079    732   2792   -559        C
ATOM   3462  CB  LEU D 428      68.918  -6.930 -31.545  1.00 45.72           C
ANISOU 3462  CB  LEU D 428    5911   6527   4933    622   2636   -347        C
ATOM   3463  CG  LEU D 428      70.023  -5.875 -31.426  1.00 45.49           C
ANISOU 3463  CG  LEU D 428    5686   6505   5093    586   2834   -153        C
ATOM   3464  CD1 LEU D 428      69.597  -4.802 -30.425  1.00 41.45           C
ANISOU 3464  CD1 LEU D 428    5066   5948   4733    475   2612      4        C
ATOM   3465  CD2 LEU D 428      71.353  -6.491 -31.016  1.00 45.37           C
ANISOU 3465  CD2 LEU D 428    5422   6426   5391    651   3013   -200        C
ATOM   3466  C   LEU D 428      67.846  -8.982 -32.525  1.00 46.17           C
ANISOU 3466  C   LEU D 428    6321   6580   4642    717   2547   -732        C
ATOM   3467  O   LEU D 428      67.099  -8.802 -33.495  1.00 46.00           O
ANISOU 3467  O   LEU D 428    6533   6665   4279    710   2512   -766        O
ATOM   3468  N   ASN D 429      67.587  -9.863 -31.556  1.00 43.68           N
ANISOU 3468  N   ASN D 429    5922   6137   4538    708   2374   -834        N
ATOM   3469  CA  ASN D 429      66.288 -10.534 -31.500  1.00 42.36           C
ANISOU 3469  CA  ASN D 429    5910   5947   4237    654   2121   -976        C
ATOM   3470  CB  ASN D 429      66.290 -11.755 -30.550  1.00 41.80           C
ANISOU 3470  CB  ASN D 429    5766   5699   4415    662   2019  -1102        C
ATOM   3471  CG  ASN D 429      66.394 -11.396 -29.062  1.00 40.02           C
ANISOU 3471  CG  ASN D 429    5314   5396   4495    608   1878   -956        C
ATOM   3472  OD1 ASN D 429      66.177 -10.270 -28.644  1.00 40.08           O
ANISOU 3472  OD1 ASN D 429    5232   5473   4524    542   1798   -792        O
ATOM   3473  ND2 ASN D 429      66.713 -12.395 -28.251  1.00 41.75           N
ANISOU 3473  ND2 ASN D 429    5463   5458   4943    644   1840  -1024        N
ATOM   3474  C   ASN D 429      65.147  -9.524 -31.230  1.00 39.73           C
ANISOU 3474  C   ASN D 429    5590   5701   3805    548   1883   -849        C
ATOM   3475  O   ASN D 429      65.412  -8.410 -30.755  1.00 37.87           O
ANISOU 3475  O   ASN D 429    5221   5490   3678    516   1887   -655        O
ATOM   3476  N   PRO D 430      63.894  -9.878 -31.600  1.00 39.17           N
ANISOU 3476  N   PRO D 430    5679   5677   3529    497   1681   -965        N
ATOM   3477  CA  PRO D 430      62.734  -8.984 -31.432  1.00 37.02           C
ANISOU 3477  CA  PRO D 430    5410   5497   3159    420   1451   -863        C
ATOM   3478  CB  PRO D 430      61.553  -9.913 -31.669  1.00 37.39           C
ANISOU 3478  CB  PRO D 430    5577   5550   3079    364   1242  -1062        C
ATOM   3479  CG  PRO D 430      62.081 -10.877 -32.687  1.00 40.79           C
ANISOU 3479  CG  PRO D 430    6190   5964   3346    432   1404  -1251        C
ATOM   3480  CD  PRO D 430      63.507 -11.136 -32.276  1.00 40.91           C
ANISOU 3480  CD  PRO D 430    6084   5865   3594    513   1659  -1213        C
ATOM   3481  C   PRO D 430      62.622  -8.261 -30.087  1.00 33.75           C
ANISOU 3481  C   PRO D 430    4783   5029   3011    363   1338   -704        C
ATOM   3482  O   PRO D 430      62.364  -7.059 -30.075  1.00 33.39           O
ANISOU 3482  O   PRO D 430    4712   5054   2922    350   1292   -543        O
ATOM   3483  N   MSE D 431      62.848  -8.958 -28.971  1.00 31.86           N
ANISOU 3483  N   MSE D 431    4412   4658   3035    338   1298   -746        N
ATOM   3484  CA  MSE D 431      62.743  -8.348 -27.632  1.00 28.73           C
ANISOU 3484  CA  MSE D 431    3838   4212   2866    286   1187   -615        C
ATOM   3485  CB  MSE D 431      62.750  -9.420 -26.522  1.00 27.66           C
ANISOU 3485  CB  MSE D 431    3625   3936   2949    257   1113   -693        C
ATOM   3486  CG  MSE D 431      61.493 -10.315 -26.470  1.00 27.35           C
ANISOU 3486  CG  MSE D 431    3673   3880   2840    179    946   -835        C
ATOM   3487  SE  MSE D 431      59.849  -9.332 -26.102  0.90 31.03          SE
ANISOU 3487  SE  MSE D 431    4095   4475   3220     81    709   -763       SE
ATOM   3488  CE  MSE D 431      60.279  -8.893 -24.268  1.00 22.81           C
ANISOU 3488  CE  MSE D 431    2865   3332   2469     58    684   -614        C
ATOM   3489  C   MSE D 431      63.805  -7.287 -27.358  1.00 28.34           C
ANISOU 3489  C   MSE D 431    3663   4159   2948    313   1319   -441        C
ATOM   3490  O   MSE D 431      63.527  -6.285 -26.719  1.00 26.80           O
ANISOU 3490  O   MSE D 431    3388   3975   2822    271   1226   -314        O
ATOM   3491  N   HIS D 432      65.023  -7.514 -27.840  1.00 30.47           N
ANISOU 3491  N   HIS D 432    3907   4407   3264    380   1540   -445        N
ATOM   3492  CA  HIS D 432      66.103  -6.525 -27.751  1.00 31.28           C
ANISOU 3492  CA  HIS D 432    3877   4513   3497    388   1692   -287        C
ATOM   3493  CB  HIS D 432      67.466  -7.225 -27.838  1.00 32.69           C
ANISOU 3493  CB  HIS D 432    3946   4634   3841    464   1905   -335        C
ATOM   3494  CG  HIS D 432      67.822  -7.950 -26.579  1.00 33.74           C
```

FIGURE 18-102

```
ANISOU 3494  CG   HIS D 432    3924  4646  4251    475  1799  -373       C
ATOM   3495  ND1  HIS D 432     67.295  -9.184 -26.261  1.00 34.66       N
ANISOU 3495  ND1  HIS D 432    4117  4682  4371    496  1690  -514       N
ATOM   3496  CE1  HIS D 432     67.748  -9.561 -25.077  1.00 34.47       C
ANISOU 3496  CE1  HIS D 432    3947  4553  4597    508  1603  -490       C
ATOM   3497  NE2  HIS D 432     68.534  -8.608 -24.606  1.00 33.88       N
ANISOU 3497  NE2  HIS D 432    3695  4499  4680    491  1632  -354       N
ATOM   3498  CD2  HIS D 432     68.587  -7.583 -25.521  1.00 33.50       C
ANISOU 3498  CD2  HIS D 432    3682  4555  4490    461  1760  -279       C
ATOM   3499  C    HIS D 432     65.961  -5.388 -28.772  1.00 32.02       C
ANISOU 3499  C    HIS D 432    4081  4712  3373    380  1782  -166       C
ATOM   3500  O    HIS D 432     66.410  -4.265 -28.541  1.00 31.60       O
ANISOU 3500  O    HIS D 432    3939  4650  3418    343  1831    -4       O
ATOM   3501  N    GLN D 433     65.317  -5.703 -29.889  1.00 33.25       N
ANISOU 3501  N    GLN D 433    4447  4957  3229    412  1790  -247       N
ATOM   3502  CA   GLN D 433     64.893  -4.737 -30.897  1.00 34.81       C
ANISOU 3502  CA   GLN D 433    4806  5264  3155    417  1816  -136       C
ATOM   3503  CB   GLN D 433     64.124  -5.526 -31.969  1.00 37.14       C
ANISOU 3503  CB   GLN D 433    5332  5652  3127    458  1766  -297       C
ATOM   3504  CG   GLN D 433     64.229  -5.159 -33.425  1.00 40.17       C
ANISOU 3504  CG   GLN D 433    5942  6157  3166    513  1917  -256       C
ATOM   3505  CD   GLN D 433     65.636  -4.990 -33.941  1.00 42.73       C
ANISOU 3505  CD   GLN D 433    6242  6477  3518    553  2269  -184       C
ATOM   3506  OE1  GLN D 433     66.081  -3.868 -34.122  1.00 42.34       O
ANISOU 3506  OE1  GLN D 433    6173  6441  3473    532  2393    22       O
ATOM   3507  NE2  GLN D 433     66.331  -6.095 -34.227  1.00 44.78       N
ANISOU 3507  NE2  GLN D 433    6506  6712  3797    612  2445  -355       N
ATOM   3508  C    GLN D 433     63.985  -3.705 -30.188  1.00 33.00       C
ANISOU 3508  C    GLN D 433    4532  5029  2979    363  1591   -12       C
ATOM   3509  O    GLN D 433     64.238  -2.508 -30.244  1.00 33.66       O
ANISOU 3509  O    GLN D 433    4602  5106  3081    347  1644   167       O
ATOM   3510  N    LEU D 434     62.956  -4.188 -29.488  1.00 30.54       N
ANISOU 3510  N    LEU D 434    4191  4705  2709    334  1355  -111       N
ATOM   3511  CA   LEU D 434     62.019  -3.349 -28.723  1.00 28.54       C
ANISOU 3511  CA   LEU D 434    3877  4447  2519    298  1147   -27       C
ATOM   3512  CB   LEU D 434     60.860  -4.193 -28.170  1.00 26.57       C
ANISOU 3512  CB   LEU D 434    3605  4209  2281    263   932  -173       C
ATOM   3513  CG   LEU D 434     59.960  -4.841 -29.225  1.00 28.19       C
ANISOU 3513  CG   LEU D 434    3969  4522  2219    278   838  -304       C
ATOM   3514  CD1  LEU D 434     59.179  -6.004 -28.622  1.00 25.09       C
ANISOU 3514  CD1  LEU D 434    3526  4099  1908    213   690  -476       C
ATOM   3515  CD2  LEU D 434     59.035  -3.808 -29.879  1.00 26.55       C
ANISOU 3515  CD2  LEU D 434    3849  4430  1809    316   706  -203       C
ATOM   3516  C    LEU D 434     62.664  -2.581 -27.568  1.00 27.04       C
ANISOU 3516  C    LEU D 434    3514  4152  2609    258  1167    91       C
ATOM   3517  O    LEU D 434     62.423  -1.387 -27.390  1.00 25.53       O
ANISOU 3517  O    LEU D 434    3318  3948  2436    251  1119   227       O
ATOM   3518  N    LEU D 435     63.462  -3.285 -26.775  1.00 26.54       N
ANISOU 3518  N    LEU D 435    3318  4005  2760    239  1220    31       N
ATOM   3519  CA   LEU D 435     64.256  -2.688 -25.702  1.00 26.16       C
ANISOU 3519  CA   LEU D 435    3103  3862  2975    200  1234   119       C
ATOM   3520  CB   LEU D 435     65.092  -3.789 -25.043  1.00 25.47       C
ANISOU 3520  CB   LEU D 435    2895  3705  3077    208  1276    27       C
ATOM   3521  CG   LEU D 435     65.725  -3.556 -23.679  1.00 24.89       C
ANISOU 3521  CG   LEU D 435    2647  3540  3271    171  1207    70       C
ATOM   3522  CD1  LEU D 435     64.682  -3.442 -22.582  1.00 20.95       C
ANISOU 3522  CD1  LEU D 435    2152  3019  2787    132   993    52       C
ATOM   3523  CD2  LEU D 435     66.673  -4.719 -23.380  1.00 26.46       C
ANISOU 3523  CD2  LEU D 435    2748  3683  3624    217  1274    -9       C
ATOM   3524  C    LEU D 435     65.136  -1.488 -26.142  1.00 27.72       C
ANISOU 3524  C    LEU D 435    3277  4043  3215    183  1392   280       C
ATOM   3525  O    LEU D 435     65.062  -0.432 -25.523  1.00 27.64       O
ANISOU 3525  O    LEU D 435    3216  3976  3311    140  1321   381       O
ATOM   3526  N    ARG D 436     65.954  -1.635 -27.191  1.00 30.12       N
ANISOU 3526  N    ARG D 436    3621  4384  3438    211  1617   302       N
ATOM   3527  CA   ARG D 436     66.820  -0.532 -27.661  1.00 32.34       C
ANISOU 3527  CA   ARG D 436    3877  4644  3766    175  1803   469       C
ATOM   3528  CB   ARG D 436     67.825  -0.970 -28.749  1.00 34.74       C
ANISOU 3528  CB   ARG D 436    4200  5003  3997    211  2095   466       C
ATOM   3529  CG   ARG D 436     68.788  -2.119 -28.428  1.00 38.82       C
ANISOU 3529  CG   ARG D 436    4552  5499  4700    249  2201   339       C
```

FIGURE 18-103

```
ATOM    3530  CD   ARG D 436      69.651  -1.978 -27.166  1.00 45.47           C
ANISOU  3530  CD   ARG D 436     5125   6244   5908    197   2148    361       C
ATOM    3531  NE   ARG D 436      70.087  -3.302 -26.682  1.00 50.46           N
ANISOU  3531  NE   ARG D 436     5647   6850   6677    269   2131    214       N
ATOM    3532  CZ   ARG D 436      70.128  -3.695 -25.402  1.00 51.20           C
ANISOU  3532  CZ   ARG D 436     5607   6868   6978    261   1938    168       C
ATOM    3533  NH1  ARG D 436      69.776  -2.873 -24.420  1.00 50.06           N
ANISOU  3533  NH1  ARG D 436     5415   6676   6930    180   1748    238       N
ATOM    3534  NH2  ARG D 436      70.533  -4.928 -25.097  1.00 53.27           N
ANISOU  3534  NH2  ARG D 436     5801   7095   7346    344   1938     52       N
ATOM    3535  C    ARG D 436      66.028   0.663 -28.204  1.00 32.58           C
ANISOU  3535  C    ARG D 436     4070   4692   3616    169   1749    610       C
ATOM    3536  O    ARG D 436      66.482   1.801 -28.113  1.00 33.26           O
ANISOU  3536  O    ARG D 436     4125   4705   3810    112   1815    763       O
ATOM    3537  N    HIS D 437      64.874   0.396 -28.813  1.00 32.38           N
ANISOU  3537  N    HIS D 437     4222   4757   3325    230   1627    560       N
ATOM    3538  CA   HIS D 437      63.992   1.447 -29.316  1.00 32.23           C
ANISOU  3538  CA   HIS D 437     4358   4760   3127    257   1533    689       C
ATOM    3539  CB   HIS D 437      62.776   0.835 -29.996  1.00 32.33           C
ANISOU  3539  CB   HIS D 437     4528   4902   2856    329   1377    588       C
ATOM    3540  CG   HIS D 437      61.792   1.845 -30.505  1.00 32.58           C
ANISOU  3540  CG   HIS D 437     4705   4969   2705    384   1241    716       C
ATOM    3541  ND1  HIS D 437      62.005   2.587 -31.652  1.00 33.44           N
ANISOU  3541  ND1  HIS D 437     5004   5109   2594    423   1364    882       N
ATOM    3542  CE1  HIS D 437      60.975   3.389 -31.850  1.00 32.84           C
ANISOU  3542  CE1  HIS D 437     5028   5050   2399    489   1178    978       C
ATOM    3543  NE2  HIS D 437      60.100   3.192 -30.877  1.00 31.03           N
ANISOU  3543  NE2  HIS D 437     4663   4812   2316    493    955    869       N
ATOM    3544  CD2  HIS D 437      60.589   2.233 -30.023  1.00 28.67           C
ANISOU  3544  CD2  HIS D 437     4193   4482   2217    419    996    711       C
ATOM    3545  C    HIS D 437      63.529   2.367 -28.191  1.00 31.00           C
ANISOU  3545  C    HIS D 437     4111   4501   3166    224   1360    750       C
ATOM    3546  O    HIS D 437      63.642   3.606 -28.303  1.00 31.79           O
ANISOU  3546  O    HIS D 437     4259   4524   3297    208   1393    917       O
ATOM    3547  N    PHE D 438      63.015   1.763 -27.119  1.00 28.21           N
ANISOU  3547  N    PHE D 438     3643   4136   2938    213   1191    616       N
ATOM    3548  CA   PHE D 438      62.438   2.523 -26.020  1.00 27.04           C
ANISOU  3548  CA   PHE D 438     3427   3908   2940    198   1026    640       C
ATOM    3549  CB   PHE D 438      61.377   1.704 -25.284  1.00 24.52           C
ANISOU  3549  CB   PHE D 438     3057   3643   2616    215    836    490       C
ATOM    3550  CG   PHE D 438      60.176   1.379 -26.140  1.00 23.90           C
ANISOU  3550  CG   PHE D 438     3093   3692   2294    282    727    446       C
ATOM    3551  CD1  PHE D 438      59.391   2.399 -26.676  1.00 23.65           C
ANISOU  3551  CD1  PHE D 438     3161   3687   2138    351    643    555       C
ATOM    3552  CE1  PHE D 438      58.280   2.110 -27.459  1.00 24.54           C
ANISOU  3552  CE1  PHE D 438     3360   3932   2032    417    509    512       C
ATOM    3553  CZ   PHE D 438      57.941   0.772 -27.715  1.00 25.28           C
ANISOU  3553  CZ   PHE D 438     3448   4125   2034    392    465    343       C
ATOM    3554  CE2  PHE D 438      58.734  -0.261 -27.196  1.00 23.25           C
ANISOU  3554  CE2  PHE D 438     3113   3818   1903    320    569    233       C
ATOM    3555  CD2  PHE D 438      59.836   0.052 -26.416  1.00 22.04           C
ANISOU  3555  CD2  PHE D 438     2868   3543   1964    276    694    292       C
ATOM    3556  C    PHE D 438      63.462   3.158 -25.072  1.00 27.33           C
ANISOU  3556  C    PHE D 438     3326   3806   3251    116   1082    694       C
ATOM    3557  O    PHE D 438      63.182   4.188 -24.467  1.00 27.54           O
ANISOU  3557  O    PHE D 438     3351   3740   3375    103    998    758       O
ATOM    3558  N    GLN D 439      64.639   2.551 -24.975  1.00 27.93           N
ANISOU  3558  N    GLN D 439     3289   3867   3455     69   1218    661       N
ATOM    3559  CA   GLN D 439      65.790   3.129 -24.318  1.00 28.89           C
ANISOU  3559  CA   GLN D 439     3266   3877   3835    -18   1287    717       C
ATOM    3560  CB   GLN D 439      66.920   2.062 -24.200  1.00 29.69           C
ANISOU  3560  CB   GLN D 439     3213   4002   4067    -32   1401    637       C
ATOM    3561  CG   GLN D 439      66.621   0.950 -23.141  1.00 26.15           C
ANISOU  3561  CG   GLN D 439     2686   3563   3686     -6   1239    487       C
ATOM    3562  CD   GLN D 439      67.662  -0.160 -23.094  1.00 28.79           C
ANISOU  3562  CD   GLN D 439     2888   3909   4142     14   1338    414       C
ATOM    3563  OE1  GLN D 439      68.317  -0.497 -24.104  1.00 32.54           O
ANISOU  3563  OE1  GLN D 439     3363   4430   4572     44   1542    425       O
ATOM    3564  NE2  GLN D 439      67.822  -0.748 -21.912  1.00 28.30           N
ANISOU  3564  NE2  GLN D 439     2720   3805   4230     12   1198    340       N
ATOM    3565  C    GLN D 439      66.284   4.385 -25.045  1.00 31.94           C
```

FIGURE 18-104

```
ANISOU 3565  C   GLN D 439    3715  4193  4229   -65  1434   895       C
ATOM   3566  O   GLN D 439    66.781   5.320 -24.410  1.00 32.63       O
ANISOU 3566  O   GLN D 439    3727  4152  4519  -149  1421   959       O
ATOM   3567  N   LYS D 440    66.162   4.415 -26.374  1.00 34.31       N
ANISOU 3567  N   LYS D 440    4167  4567  4301   -18  1575   976       N
ATOM   3568  CA  LYS D 440    66.529   5.601 -27.135  1.00 37.03       C
ANISOU 3568  CA  LYS D 440    4613  4841  4618   -60  1725  1173       C
ATOM   3569  CB  LYS D 440    66.617   5.319 -28.642  1.00 39.69       C
ANISOU 3569  CB  LYS D 440    5117  5293  4672    -5  1921  1245       C
ATOM   3570  CG  LYS D 440    67.882   4.548 -29.032  1.00 43.01       C
ANISOU 3570  CG  LYS D 440    5411  5768  5163   -42  2176  1205       C
ATOM   3571  CD  LYS D 440    68.388   4.877 -30.420  1.00 49.43       C
ANISOU 3571  CD  LYS D 440    6372  6631  5777   -42  2461  1354       C
ATOM   3572  CE  LYS D 440    69.683   4.104 -30.681  1.00 52.40       C
ANISOU 3572  CE  LYS D 440    6580  7061  6271   -70  2732  1294       C
ATOM   3573  NZ  LYS D 440    70.294   4.407 -32.006  1.00 56.62       N
ANISOU 3573  NZ  LYS D 440    7243  7651  6617   -78  3064  1439       N
ATOM   3574  C   LYS D 440    65.556   6.741 -26.849  1.00 36.89       C
ANISOU 3574  C   LYS D 440    4715  4726  4575   -33  1555  1259       C
ATOM   3575  O   LYS D 440    65.993   7.846 -26.543  1.00 37.86       O
ANISOU 3575  O   LYS D 440    4824  4692  4869  -113  1589  1372       O
ATOM   3576  N   ASP D 441    64.250   6.442 -26.917  1.00 35.37       N
ANISOU 3576  N   ASP D 441    4626  4620  4192    79  1370  1193       N
ATOM   3577  CA  ASP D 441    63.183   7.396 -26.655  1.00 34.86       C
ANISOU 3577  CA  ASP D 441    4660  4486  4100   145  1196  1252       C
ATOM   3578  CB  ASP D 441    62.914   8.221 -27.913  1.00 37.92       C
ANISOU 3578  CB  ASP D 441    5267  4866  4275   207  1267  1450       C
ATOM   3579  CG  ASP D 441    61.804   9.261 -27.730  1.00 40.30       C
ANISOU 3579  CG  ASP D 441    5676  5081  4554   307  1084  1529       C
ATOM   3580  OD1 ASP D 441    61.425   9.618 -26.576  1.00 39.22       O
ANISOU 3580  OD1 ASP D 441    5443  4850  4609   306   947  1449       O
ATOM   3581  OD2 ASP D 441    61.301   9.721 -28.784  1.00 45.16       O
ANISOU 3581  OD2 ASP D 441    6486  5729  4944   401  1080  1674       O
ATOM   3582  C   ASP D 441    61.900   6.717 -26.136  1.00 32.31       C
ANISOU 3582  C   ASP D 441    4311  4270  3697   235   971  1096       C
ATOM   3583  O   ASP D 441    61.199   6.013 -26.871  1.00 32.02       O
ANISOU 3583  O   ASP D 441    4348  4382  3436   310   920  1048       O
ATOM   3584  N   ALA D 442    61.576   6.945 -24.867  1.00 29.74       N
ANISOU 3584  N   ALA D 442    3881  3867  3552   220   839  1014       N
ATOM   3585  CA  ALA D 442    60.377   6.300 -24.287  1.00 27.57       C
ANISOU 3585  CA  ALA D 442    3558  3693  3225   289   658   871       C
ATOM   3586  CB  ALA D 442    60.695   5.663 -22.929  1.00 24.90       C
ANISOU 3586  CB  ALA D 442    3063  3329  3068   217   615   728       C
ATOM   3587  C   ALA D 442    59.104   7.154 -24.217  1.00 27.63       C
ANISOU 3587  C   ALA D 442    3630  3685  3182   404   506   909       C
ATOM   3588  O   ALA D 442    58.109   6.710 -23.648  1.00 27.53       O
ANISOU 3588  O   ALA D 442    3547  3753  3160   452   372   793       O
ATOM   3589  N   LYS D 443    59.122   8.344 -24.818  1.00 29.38       N
ANISOU 3589  N   LYS D 443    3983  3804  3377   452   535  1077       N
ATOM   3590  CA  LYS D 443    57.985   9.293 -24.817  1.00 30.50       C
ANISOU 3590  CA  LYS D 443    4196  3903  3492   591   395  1137       C
ATOM   3591  CB  LYS D 443    58.290  10.528 -25.671  1.00 33.67       C
ANISOU 3591  CB  LYS D 443    4779  4162  3853   630   465  1361       C
ATOM   3592  CG  LYS D 443    59.229  11.526 -25.065  1.00 36.65       C
ANISOU 3592  CG  LYS D 443    5167  4298  4461   529   567  1432       C
ATOM   3593  CD  LYS D 443    59.650  12.550 -26.133  1.00 45.40       C
ANISOU 3593  CD  LYS D 443    6473  5274  5503   538   680  1678       C
ATOM   3594  CE  LYS D 443    60.962  13.265 -25.747  1.00 47.82       C
ANISOU 3594  CE  LYS D 443    6766  5359  6046   363   843  1750       C
ATOM   3595  NZ  LYS D 443    61.530  14.054 -26.889  1.00 50.87       N
ANISOU 3595  NZ  LYS D 443    7337  5634  6356   332  1010  2003       N
ATOM   3596  C   LYS D 443    56.646   8.725 -25.307  1.00 30.23       C
ANISOU 3596  C   LYS D 443    4154  4060  3271   716   235  1077       C
ATOM   3597  O   LYS D 443    55.631   8.934 -24.669  1.00 29.75       O
ANISOU 3597  O   LYS D 443    4018  4015  3270   802   100  1008       O
ATOM   3598  N   VAL D 444    56.638   8.041 -26.453  1.00 30.26       N
ANISOU 3598  N   VAL D 444    4234  4210  3051   726   252  1098       N
ATOM   3599  CA  VAL D 444    55.407   7.466 -26.998  1.00 29.10       C
ANISOU 3599  CA  VAL D 444    4078  4254  2725   825    78  1029       C
ATOM   3600  CB  VAL D 444    55.585   6.963 -28.484  1.00 31.06       C
ANISOU 3600  CB  VAL D 444    4485  4636  2681   840   109  1084       C
```

FIGURE 18-105

```
ATOM   3601  CG1 VAL D 444      54.288   6.421 -29.035  1.00 29.96           C
ANISOU 3601  CG1 VAL D 444    4330   4691   2363    934   -109    999        C
ATOM   3602  CG2 VAL D 444      56.115   8.078 -29.394  1.00 30.95           C
ANISOU 3602  CG2 VAL D 444    4684   4520   2557    891    208   1324        C
ATOM   3603  C   VAL D 444      54.875   6.360 -26.079  1.00 27.62           C
ANISOU 3603  C   VAL D 444    3699   4166   2629    768      3    815        C
ATOM   3604  O   VAL D 444      53.680   6.285 -25.819  1.00 27.97           O
ANISOU 3604  O   VAL D 444    3650   4300   2679    844   -156    743        O
ATOM   3605  N   LEU D 445      55.788   5.542 -25.567  1.00 25.93           N
ANISOU 3605  N   LEU D 445    3422   3927   2503    636    126    725        N
ATOM   3606  CA  LEU D 445      55.501   4.447 -24.647  1.00 23.92           C
ANISOU 3606  CA  LEU D 445    3016   3731   2341    563     89    546        C
ATOM   3607  CB  LEU D 445      56.804   3.645 -24.334  1.00 21.91           C
ANISOU 3607  CB  LEU D 445    2738   3423   2166    439    243    496        C
ATOM   3608  CG  LEU D 445      56.751   2.511 -23.313  1.00 20.89           C
ANISOU 3608  CG  LEU D 445    2483   3313   2143    358    226    342        C
ATOM   3609  CD1 LEU D 445      55.801   1.381 -23.778  1.00 20.54           C
ANISOU 3609  CD1 LEU D 445    2418   3414   1973    353    132    220        C
ATOM   3610  CD2 LEU D 445      58.144   1.953 -22.982  1.00 18.80           C
ANISOU 3610  CD2 LEU D 445    2194   2968   1982    270    365    327        C
ATOM   3611  C   LEU D 445      54.862   4.932 -23.354  1.00 23.22           C
ANISOU 3611  C   LEU D 445    2811   3585   2427    587     19    499        C
ATOM   3612  O   LEU D 445      53.820   4.424 -22.965  1.00 24.32           O
ANISOU 3612  O   LEU D 445    2843   3827   2571    605    -83    395        O
ATOM   3613  N   PHE D 446      55.525   5.867 -22.678  1.00 22.66           N
ANISOU 3613  N   PHE D 446    2760   3351   2500    576     85    565        N
ATOM   3614  CA  PHE D 446      55.043   6.489 -21.438  1.00 21.33           C
ANISOU 3614  CA  PHE D 446    2518   3103   2482    609     39    517        C
ATOM   3615  CB  PHE D 446      56.138   7.400 -20.838  1.00 20.56           C
ANISOU 3615  CB  PHE D 446    2473   2806   2534    555    124    577        C
ATOM   3616  CG  PHE D 446      57.229   6.646 -20.076  1.00 19.42           C
ANISOU 3616  CG  PHE D 446    2266   2630   2484    414    198    502        C
ATOM   3617  CD1 PHE D 446      57.332   5.253 -20.143  1.00 17.40           C
ANISOU 3617  CD1 PHE D 446    1945   2496   2168    352    213    418        C
ATOM   3618  CE1 PHE D 446      58.339   4.559 -19.453  1.00 20.22           C
ANISOU 3618  CE1 PHE D 446    2246   2816   2619    249    265    363        C
ATOM   3619  CZ  PHE D 446      59.301   5.271 -18.691  1.00 19.91           C
ANISOU 3619  CZ  PHE D 446    2198   2633   2733    192    291    386        C
ATOM   3620  CE2 PHE D 446      59.217   6.678 -18.646  1.00 19.69           C
ANISOU 3620  CE2 PHE D 446    2236   2480   2765    229    279    458        C
ATOM   3621  CD2 PHE D 446      58.186   7.346 -19.330  1.00 18.60           C
ANISOU 3621  CD2 PHE D 446    2170   2362   2535    345    240    519        C
ATOM   3622  C   PHE D 446      53.719   7.274 -21.629  1.00 22.61           C
ANISOU 3622  C   PHE D 446    2672   3302   2617    769    -82    546        C
ATOM   3623  O   PHE D 446      52.788   7.129 -20.834  1.00 21.26           O
ANISOU 3623  O   PHE D 446    2384   3189   2505    810   -143    444        O
ATOM   3624  N   GLN D 447      53.634   8.092 -22.683  1.00 24.31           N
ANISOU 3624  N   GLN D 447    3009   3485   2743    868   -111    691        N
ATOM   3625  CA  GLN D 447      52.434   8.923 -22.930  1.00 26.58           C
ANISOU 3625  CA  GLN D 447    3294   3792   3015   1051   -242    741        C
ATOM   3626  CB  GLN D 447      52.727  10.052 -23.948  1.00 28.74           C
ANISOU 3626  CB  GLN D 447    3759   3946   3215   1147   -240    948        C
ATOM   3627  CG  GLN D 447      53.822  11.037 -23.521  1.00 28.97           C
ANISOU 3627  CG  GLN D 447    3898   3721   3387   1085   -109   1039        C
ATOM   3628  CD  GLN D 447      53.417  11.958 -22.367  1.00 31.94           C
ANISOU 3628  CD  GLN D 447    4237   3939   3959   1160   -136    984        C
ATOM   3629  OE1 GLN D 447      52.467  11.685 -21.632  1.00 31.98           O
ANISOU 3629  OE1 GLN D 447    4103   4036   4012   1229   -210    849        O
ATOM   3630  NE2 GLN D 447      54.147  13.060 -22.209  1.00 32.72           N
ANISOU 3630  NE2 GLN D 447    4465   3791   4174   1139    -64   1083        N
ATOM   3631  C   GLN D 447      51.172   8.138 -23.353  1.00 27.31           C
ANISOU 3631  C   GLN D 447    3261   4112   3003   1115   -388    657        C
ATOM   3632  O   GLN D 447      50.059   8.620 -23.205  1.00 28.77           O
ANISOU 3632  O   GLN D 447    3359   4341   3230   1259   -502    646        O
ATOM   3633  N   ASN D 448      51.353   6.919 -23.839  1.00 27.07           N
ANISOU 3633  N   ASN D 448    3210   4218   2855   1005   -385    585        N
ATOM   3634  CA  ASN D 448      50.262   6.088 -24.336  1.00 27.76           C
ANISOU 3634  CA  ASN D 448    3189   4515   2844   1027   -531    492        C
ATOM   3635  CB  ASN D 448      50.574   5.642 -25.776  1.00 28.82           C
ANISOU 3635  CB  ASN D 448    3470   4742   2740   1014   -568    545        C
ATOM   3636  CG  ASN D 448      50.346   6.749 -26.784  1.00 28.94           C
```

FIGURE 18-106

```
ANISOU 3636  CG   ASN D 448    3635   4738   2623   1181   -656    726        C
ATOM   3637  OD1  ASN D 448    49.218    7.083 -27.082  1.00 31.76            O
ANISOU 3637  OD1  ASN D 448    3924   5192   2950   1320   -840    738        O
ATOM   3638  ND2  ASN D 448    51.414    7.321 -27.300  1.00 26.91            N
ANISOU 3638  ND2  ASN D 448    3577   4353   2295   1168   -523    876        N
ATOM   3639  C    ASN D 448    49.972    4.866 -23.458  1.00 27.61            C
ANISOU 3639  C    ASN D 448    3000   4579   2912    892   -508    312        C
ATOM   3640  O    ASN D 448    49.042    4.091 -23.740  1.00 28.34            O
ANISOU 3640  O    ASN D 448    2973   4834   2960    874   -623    214        O
ATOM   3641  N    TRP D 449    50.740    4.720 -22.378  1.00 26.08            N
ANISOU 3641  N    TRP D 449    2795   4267   2845    793   -369    274        N
ATOM   3642  CA   TRP D 449    50.617    3.569 -21.487  1.00 26.10            C
ANISOU 3642  CA   TRP D 449    2678   4318   2922    661   -326    133        C
ATOM   3643  CB   TRP D 449    51.844    3.464 -20.552  1.00 22.77            C
ANISOU 3643  CB   TRP D 449    2311   3748   2592    562   -183    131        C
ATOM   3644  CG   TRP D 449    51.796    2.288 -19.626  1.00 22.86            C
ANISOU 3644  CG   TRP D 449    2234   3788   2662    436   -140     15        C
ATOM   3645  CD1  TRP D 449    51.346    2.273 -18.330  1.00 19.13            C
ANISOU 3645  CD1  TRP D 449    1674   3305   2290    418   -109    -46        C
ATOM   3646  NE1  TRP D 449    51.479    1.021 -17.799  1.00 18.46            N
ANISOU 3646  NE1  TRP D 449    1555   3239   2218    288    -65   -120        N
ATOM   3647  CE2  TRP D 449    52.025    0.180 -18.738  1.00 19.96            C
ANISOU 3647  CE2  TRP D 449    1806   3444   2335    226    -70   -126        C
ATOM   3648  CD2  TRP D 449    52.254    0.945 -19.905  1.00 22.60            C
ANISOU 3648  CD2  TRP D 449    2219   3784   2585    316   -109    -47        C
ATOM   3649  CE3  TRP D 449    52.810    0.315 -21.036  1.00 22.07            C
ANISOU 3649  CE3  TRP D 449    2239   3740   2407    283   -102    -46        C
ATOM   3650  CZ3  TRP D 449    53.121   -1.038 -20.960  1.00 20.32            C
ANISOU 3650  CZ3  TRP D 449    2018   3518   2186    172    -64   -135        C
ATOM   3651  CH2  TRP D 449    52.904   -1.767 -19.775  1.00 19.50            C
ANISOU 3651  CH2  TRP D 449    1836   3385   2187     86    -36   -201        C
ATOM   3652  CZ2  TRP D 449    52.368   -1.173 -18.652  1.00 19.23            C
ANISOU 3652  CZ2  TRP D 449    1723   3343   2240    108    -34   -191        C
ATOM   3653  C    TRP D 449    49.301    3.488 -20.696  1.00 26.80            C
ANISOU 3653  C    TRP D 449    2575   4500   3107    694   -385     42        C
ATOM   3654  O    TRP D 449    48.820    2.383 -20.387  1.00 28.17            O
ANISOU 3654  O    TRP D 449    2636   4768   3300    585   -389    -67        O
ATOM   3655  N    GLY D 450    48.724    4.626 -20.338  1.00 27.01            N
ANISOU 3655  N    GLY D 450    2562   4494   3209    839   -413     84        N
ATOM   3656  CA   GLY D 450    47.550    4.564 -19.465  1.00 26.85            C
ANISOU 3656  CA   GLY D 450    2343   4561   3298    873   -423    -10        C
ATOM   3657  C    GLY D 450    47.850    5.155 -18.104  1.00 26.36            C
ANISOU 3657  C    GLY D 450    2299   4371   3347    887   -298    -33        C
ATOM   3658  O    GLY D 450    48.936    4.913 -17.524  1.00 24.35            O
ANISOU 3658  O    GLY D 450    2156   4003   3095    777   -201    -34        O
ATOM   3659  N    ILE D 451    46.877    5.919 -17.597  1.00 26.86            N
ANISOU 3659  N    ILE D 451    2250   4457   3500   1030   -308    -60        N
ATOM   3660  CA   ILE D 451    47.001    6.664 -16.348  1.00 26.37            C
ANISOU 3660  CA   ILE D 451    2221   4274   3526   1082   -198    -98        C
ATOM   3661  CB   ILE D 451    46.969    8.237 -16.581  1.00 27.89            C
ANISOU 3661  CB   ILE D 451    2507   4318   3770   1289   -238    -20        C
ATOM   3662  CG1  ILE D 451    47.657    9.008 -15.440  1.00 25.93            C
ANISOU 3662  CG1  ILE D 451    2392   3875   3584   1293   -129    -57        C
ATOM   3663  CD1  ILE D 451    49.176    9.125 -15.584  1.00 21.81            C
ANISOU 3663  CD1  ILE D 451    2069   3187   3030   1167   -106     13        C
ATOM   3664  CG2  ILE D 451    45.544    8.748 -16.801  1.00 27.64            C
ANISOU 3664  CG2  ILE D 451    2298   4397   3809   1490   -315    -36        C
ATOM   3665  C    ILE D 451    45.874    6.181 -15.432  1.00 27.18            C
ANISOU 3665  C    ILE D 451    2116   4514   3696   1077   -132   -215        C
ATOM   3666  O    ILE D 451    44.791    5.803 -15.904  1.00 28.28            O
ANISOU 3666  O    ILE D 451    2060   4822   3862   1110   -204   -243        O
ATOM   3667  N    GLU D 452    46.130    6.140 -14.131  1.00 26.29            N
ANISOU 3667  N    GLU D 452    2042   4341   3606   1022      4   -283        N
ATOM   3668  CA   GLU D 452    45.061    5.692 -13.194  1.00 27.65            C
ANISOU 3668  CA   GLU D 452    2028   4647   3830   1011    109   -385        C
ATOM   3669  CB   GLU D 452    45.256    4.198 -12.798  1.00 26.19            C
ANISOU 3669  CB   GLU D 452    1818   4538   3597    781    176   -418        C
ATOM   3670  CG   GLU D 452    46.647    3.878 -12.149  1.00 24.41            C
ANISOU 3670  CG   GLU D 452    1815   4166   3293    656    231   -398        C
ATOM   3671  CD   GLU D 452    46.830    2.423 -11.743  1.00 24.76            C
ANISOU 3671  CD   GLU D 452    1852   4259   3296    455    291   -414        C
```

FIGURE 18-107

```
ATOM   3672  OE1 GLU D 452      45.888   1.618 -11.901  1.00 31.91           O
ANISOU 3672  OE1 GLU D 452    2587  5300  4236   384   309  -448             O
ATOM   3673  OE2 GLU D 452      47.908   2.057 -11.253  1.00 23.36           O
ANISOU 3673  OE2 GLU D 452    1834  3978  3064   366   315  -392             O
ATOM   3674  C   GLU D 452      45.042   6.574 -11.949  1.00 27.37           C
ANISOU 3674  C   GLU D 452    2061  4513  3825  1111   234  -449             C
ATOM   3675  O   GLU D 452      46.052   7.169 -11.604  1.00 26.55           O
ANISOU 3675  O   GLU D 452    2164  4236  3690  1111   242  -433             O
ATOM   3676  N  AHIS D 453      43.898   6.648 -11.278  0.50 29.37           N
ANISOU 3676  N  AHIS D 453    2137  4881  4142  1189   336  -532             N
ATOM   3677  N  BHIS D 453      43.885   6.656 -11.308  0.50 29.06           N
ANISOU 3677  N  BHIS D 453    2095  4843  4104  1192   332  -531             N
ATOM   3678  CA AHIS D 453      43.836   7.247  -9.942  0.50 30.28           C
ANISOU 3678  CA AHIS D 453    2326  4928  4250  1259   493  -622             C
ATOM   3679  CA BHIS D 453      43.774   7.182  -9.955  0.50 29.69           C
ANISOU 3679  CA BHIS D 453    2237  4868  4178  1254   495  -623             C
ATOM   3680  CB AHIS D 453      42.418   7.692  -9.572  0.50 32.76           C
ANISOU 3680  CB AHIS D 453    2411  5367  4670  1432   592  -703             C
ATOM   3681  CB BHIS D 453      42.302   7.269  -9.541  0.50 31.70           C
ANISOU 3681  CB BHIS D 453    2229  5287  4527  1371   609  -705             C
ATOM   3682  CG AHIS D 453      42.349   8.492  -8.302  0.50 34.48           C
ANISOU 3682  CG AHIS D 453    2734  5498  4869  1546   757  -810             C
ATOM   3683  CG BHIS D 453      41.496   8.296 -10.288  0.50 33.06           C
ANISOU 3683  CG BHIS D 453    2263  5469  4828  1622   512  -693             C
ATOM   3684  ND1AHIS D 453      41.699   8.043  -7.170  0.50 37.07           N
ANISOU 3684  ND1AHIS D 453    2974  5946  5164  1508   969  -904             N
ATOM   3685  ND1BHIS D 453      40.830   8.013 -11.463  0.50 33.68           N
ANISOU 3685  ND1BHIS D 453    2135  5683  4978  1653   357  -636             N
ATOM   3686  CE1AHIS D 453      41.803   8.950  -6.214  0.50 37.81           C
ANISOU 3686  CE1AHIS D 453    3219  5928  5219  1638  1082 -1002             C
ATOM   3687  CE1BHIS D 453      40.176   9.092 -11.868  0.50 34.95           C
ANISOU 3687  CE1BHIS D 453    2210  5823  5246  1913   285  -627             C
ATOM   3688  NE2AHIS D 453      42.505   9.967  -6.682  0.50 37.40           N
ANISOU 3688  NE2AHIS D 453    3344  5671  5195  1747   942  -976             N
ATOM   3689  NE2BHIS D 453      40.397  10.065 -11.001  0.50 33.44           N
ANISOU 3689  NE2BHIS D 453    2168  5472  5067  2049   403  -686             N
ATOM   3690  CD2AHIS D 453      42.863   9.704  -7.982  0.50 34.66           C
ANISOU 3690  CD2AHIS D 453    2960  5318  4892  1690   748  -845             C
ATOM   3691  CD2BHIS D 453      41.208   9.589  -9.998  0.50 33.77           C
ANISOU 3691  CD2BHIS D 453    2392  5449  4990  1865   542  -736             C
ATOM   3692  C  AHIS D 453      44.368   6.267  -8.900  0.50 29.31           C
ANISOU 3692  C  AHIS D 453    2300  4818  4018  1058   615  -655             C
ATOM   3693  C  BHIS D 453      44.521   6.231  -8.998  0.50 28.61           C
ANISOU 3693  C  BHIS D 453    2231  4715  3923  1044   596  -643             C
ATOM   3694  O  AHIS D 453      44.077   5.067  -8.933  0.50 29.41           O
ANISOU 3694  O  AHIS D 453    2203  4957  4013   899   649  -643             O
ATOM   3695  O  BHIS D 453      44.536   5.005  -9.196  0.50 27.91           O
ANISOU 3695  O  BHIS D 453    2079  4722  3805   868   596  -612             O
ATOM   3696  N   ILE D 454      45.164   6.783  -7.978  1.00 28.76           N
ANISOU 3696  N   ILE D 454    2449  4605  3874  1063   667  -695             N
ATOM   3697  CA  ILE D 454      45.777   5.937  -6.964  1.00 28.13           C
ANISOU 3697  CA  ILE D 454    2498  4524  3669   893   751  -712             C
ATOM   3698  CB  ILE D 454      47.332   5.999  -7.018  1.00 26.26           C
ANISOU 3698  CB  ILE D 454    2490  4116  3371   803   634  -662             C
ATOM   3699  CG1 ILE D 454      47.890   7.250  -6.344  1.00 24.68           C
ANISOU 3699  CG1 ILE D 454    2478  3746  3152   906   625  -733             C
ATOM   3700  CD1 ILE D 454      49.392   7.303  -6.398  1.00 25.66           C
ANISOU 3700  CD1 ILE D 454    2783  3717  3249   801   503  -689             C
ATOM   3701  CG2 ILE D 454      47.826   5.855  -8.457  1.00 23.15           C
ANISOU 3701  CG2 ILE D 454    2062  3692  3042   772   483  -559             C
ATOM   3702  C   ILE D 454      45.222   6.230  -5.576  1.00 30.71           C
ANISOU 3702  C   ILE D 454    2860  4884  3925   953   938  -822             C
ATOM   3703  O   ILE D 454      44.661   7.306  -5.345  1.00 32.07           O
ANISOU 3703  O   ILE D 454    3011  5025  4150  1141   991  -901             O
ATOM   3704  N   ASP D 455      45.333   5.234  -4.691  1.00 32.26           N
ANISOU 3704  N   ASP D 455    3111  5146  4000   800  1047  -821             N
ATOM   3705  CA  ASP D 455      45.106   5.380  -3.250  1.00 34.47           C
ANISOU 3705  CA  ASP D 455    3507  5446  4142   822  1227  -911             C
ATOM   3706  CB  ASP D 455      44.729   4.030  -2.628  1.00 35.56           C
ANISOU 3706  CB  ASP D 455    3602  5719  4189   648  1374  -865             C
ATOM   3707  CG  ASP D 455      43.446   3.430  -3.228  1.00 39.76           C
```

FIGURE 18-108

```
ANISOU 3707  CG   ASP D 455    3816  6426  4866   618  1465  -844      C
ATOM   3708  OD1  ASP D 455    42.493   4.181  -3.532  1.00 42.46      O
ANISOU 3708  OD1  ASP D 455    3961  6837  5333   779  1511  -908      O
ATOM   3709  OD2  ASP D 455    43.394   2.189  -3.401  1.00 44.22      O
ANISOU 3709  OD2  ASP D 455    4320  7051  5432   431  1479  -765      O
ATOM   3710  C    ASP D 455    46.372   5.899  -2.568  1.00 34.03      C
ANISOU 3710  C    ASP D 455    3751  5221  3959   814  1139  -945      C
ATOM   3711  O    ASP D 455    47.494   5.599  -2.992  1.00 31.59      O
ANISOU 3711  O    ASP D 455    3543  4815  3646   712   975  -870      O
ATOM   3712  N    ASN D 456    46.191   6.679  -1.505  1.00 36.31      N
ANISOU 3712  N    ASN D 456    4174  5475  4146   921  1248 -1069      N
ATOM   3713  CA   ASN D 456    47.306   7.068  -0.637  1.00 36.72      C
ANISOU 3713  CA   ASN D 456    4519  5389  4046   891  1168 -1127      C
ATOM   3714  CB   ASN D 456    46.871   8.172   0.341  1.00 39.40      C
ANISOU 3714  CB   ASN D 456    4986  5683  4301  1056  1292 -1302      C
ATOM   3715  CG   ASN D 456    46.475   9.447  -0.357  1.00 40.47      C
ANISOU 3715  CG   ASN D 456    5043  5708  4625  1250  1255 -1367      C
ATOM   3716  OD1  ASN D 456    47.200   9.934  -1.227  1.00 42.70      O
ANISOU 3716  OD1  ASN D 456    5348  5842  5034  1246  1067 -1312      O
ATOM   3717  ND2  ASN D 456    45.322   9.995   0.010  1.00 40.50      N
ANISOU 3717  ND2  ASN D 456    4954  5779  4655  1427  1445 -1475      N
ATOM   3718  C    ASN D 456    47.813   5.870   0.159  1.00 36.38      C
ANISOU 3718  C    ASN D 456    4600  5409  3814   717  1191 -1062      C
ATOM   3719  O    ASN D 456    47.117   5.374   1.047  1.00 39.46      O
ANISOU 3719  O    ASN D 456    5005  5924  4065   698  1387 -1084      O
ATOM   3720  N    VAL D 457    49.004   5.398  -0.170  1.00 34.18      N
ANISOU 3720  N    VAL D 457    4405  5046  3536   597  1001  -974      N
ATOM   3721  CA   VAL D 457    49.676   4.338   0.582  1.00 33.74      C
ANISOU 3721  CA   VAL D 457    4497  5014  3310   455   975  -903      C
ATOM   3722  CB   VAL D 457    49.883   3.059  -0.286  1.00 32.28      C
ANISOU 3722  CB   VAL D 457    4179  4866  3220   319   921  -748      C
ATOM   3723  CG1  VAL D 457    50.617   1.967   0.500  1.00 32.61      C
ANISOU 3723  CG1  VAL D 457    4387  4904  3098   195   883  -661      C
ATOM   3724  CG2  VAL D 457    48.541   2.522  -0.807  1.00 33.51      C
ANISOU 3724  CG2  VAL D 457    4097  5162  3471   308  1091  -717      C
ATOM   3725  C    VAL D 457    51.031   4.904   1.032  1.00 32.68      C
ANISOU 3725  C    VAL D 457    4580  4731  3105   444   773  -949      C
ATOM   3726  O    VAL D 457    51.822   5.334   0.185  1.00 30.77      O
ANISOU 3726  O    VAL D 457    4297  4375  3018   437   604  -926      O
ATOM   3727  N    MSE D 458    51.279   4.935   2.348  1.00 33.57      N
ANISOU 3727  N    MSE D 458    4921  4852  2984   440   792 -1018      N
ATOM   3728  CA   MSE D 458    52.542   5.460   2.892  1.00 33.03      C
ANISOU 3728  CA   MSE D 458    5058  4656  2837   420   576 -1082      C
ATOM   3729  CB   MSE D 458    52.509   5.541   4.421  1.00 35.52      C
ANISOU 3729  CB   MSE D 458    5638  5013  2845   439   627 -1182      C
ATOM   3730  CG   MSE D 458    53.711   6.288   5.016  1.00 34.66      C
ANISOU 3730  CG   MSE D 458    5739  4772  2659   428   383 -1294      C
ATOM   3731  SE   MSE D 458    53.851   6.197   6.940  0.90 39.03     SE
ANISOU 3731  SE   MSE D 458    6670  5394  2765   437   388 -1406     SE
ATOM   3732  CE   MSE D 458    55.169   7.548   7.238  1.00 40.64      C
ANISOU 3732  CE   MSE D 458    7044  5395  3003   434    59 -1605      C
ATOM   3733  C    MSE D 458    53.711   4.597   2.449  1.00 31.60      C
ANISOU 3733  C    MSE D 458    4852  4434  2721   297   378  -943      C
ATOM   3734  O    MSE D 458    53.591   3.367   2.390  1.00 31.80      O
ANISOU 3734  O    MSE D 458    4832  4541  2711   221   428  -811      O
ATOM   3735  N    GLY D 459    54.833   5.231   2.119  1.00 30.97      N
ANISOU 3735  N    GLY D 459    4791  4220  2755   277   165  -973      N
ATOM   3736  CA   GLY D 459    56.032   4.514   1.643  1.00 29.96      C
ANISOU 3736  CA   GLY D 459    4609  4050  2725   178   -21  -853      C
ATOM   3737  C    GLY D 459    56.149   4.354   0.118  1.00 28.53      C
ANISOU 3737  C    GLY D 459    4203  3839  2800   157   -25  -754      C
ATOM   3738  O    GLY D 459    57.067   3.695  -0.379  1.00 27.21      O
ANISOU 3738  O    GLY D 459    3968  3645  2726    88  -141  -656      O
ATOM   3739  N    MSE D 460    55.240   4.983  -0.620  1.00 28.31      N
ANISOU 3739  N    MSE D 460    4064  3815  2879   230    96  -784      N
ATOM   3740  CA   MSE D 460    55.042   4.734  -2.044  1.00 28.35      C
ANISOU 3740  CA   MSE D 460    3874  3830  3069   225   124  -688      C
ATOM   3741  CB   MSE D 460    54.078   3.573  -2.174  1.00 27.77      C
ANISOU 3741  CB   MSE D 460    3709  3898  2944   200   267  -617      C
ATOM   3742  CG   MSE D 460    54.112   2.810  -3.436  1.00 30.07      C
ANISOU 3742  CG   MSE D 460    3842  4216  3368   152   259  -511      C
```

FIGURE 18-109

```
ATOM   3743  SE   MSE D 460      52.689   1.457  -3.282  0.90 33.52           SE
ANISOU 3743  SE   MSE D 460     4185  4819  3732    100    451   -464         SE
ATOM   3744  CE   MSE D 460      53.605   0.285  -1.992  1.00 34.15            C
ANISOU 3744  CE   MSE D 460     4467  4874  3636     -1    401   -395          C
ATOM   3745  C    MSE D 460      54.378   5.961  -2.667  1.00 26.69            C
ANISOU 3745  C    MSE D 460     3605  3566  2972    333    177   -750          C
ATOM   3746  O    MSE D 460      53.553   6.615  -2.027  1.00 27.88            O
ANISOU 3746  O    MSE D 460     3813  3730  3051    427    275   -855          O
ATOM   3747  N    VAL D 461      54.750   6.277  -3.901  1.00 24.21            N
ANISOU 3747  N    VAL D 461     3187  3185  2826    331    120   -682          N
ATOM   3748  CA   VAL D 461      54.111   7.350  -4.657  1.00 23.60            C
ANISOU 3748  CA   VAL D 461     3055  3051  2861    443    159   -701          C
ATOM   3749  CB   VAL D 461      54.973   8.683  -4.716  1.00 24.29            C
ANISOU 3749  CB   VAL D 461     3246  2931  3053    454     54   -748          C
ATOM   3750  CG1  VAL D 461      54.919   9.441  -3.418  1.00 26.49            C
ANISOU 3750  CG1  VAL D 461     3693  3135  3236    497     49   -907          C
ATOM   3751  CG2  VAL D 461      56.409   8.417  -5.145  1.00 21.55            C
ANISOU 3751  CG2  VAL D 461     2887  2510  2790    322    -73   -669          C
ATOM   3752  C    VAL D 461      53.857   6.895  -6.082  1.00 21.54            C
ANISOU 3752  C    VAL D 461     2635  2848  2701    440    169   -582          C
ATOM   3753  O    VAL D 461      54.504   5.950  -6.569  1.00 20.30            O
ANISOU 3753  O    VAL D 461     2431  2727  2556    340    127   -497          O
ATOM   3754  N    GLY D 462      52.960   7.610  -6.757  1.00 21.64            N
ANISOU 3754  N    GLY D 462     2577  2862  2782    561    213   -581          N
ATOM   3755  CA   GLY D 462      52.766   7.470  -8.213  1.00 20.05            C
ANISOU 3755  CA   GLY D 462     2259  2696  2664    580    191   -472          C
ATOM   3756  C    GLY D 462      53.780   8.244  -9.042  1.00 19.20            C
ANISOU 3756  C    GLY D 462     2210  2429  2656    563    109   -399          C
ATOM   3757  O    GLY D 462      54.540   9.061  -8.544  1.00 19.52            O
ANISOU 3757  O    GLY D 462     2363  2313  2739    543     65   -439          O
ATOM   3758  N    VAL D 463      53.780   8.004 -10.337  1.00 18.47            N
ANISOU 3758  N    VAL D 463     2045  2375  2599    563     93   -292          N
ATOM   3759  CA   VAL D 463      54.761   8.620 -11.196  1.00 18.33            C
ANISOU 3759  CA   VAL D 463     2080  2223  2662    531     49   -199          C
ATOM   3760  CB   VAL D 463      56.088   7.738 -11.343  1.00 18.13            C
ANISOU 3760  CB   VAL D 463     2045  2200  2645    374     27   -152          C
ATOM   3761  CG1  VAL D 463      55.844   6.407 -12.051  1.00 15.46            C
ANISOU 3761  CG1  VAL D 463     1612  2021  2239    337     52   -108          C
ATOM   3762  CG2  VAL D 463      57.144   8.490 -12.103  1.00 18.20            C
ANISOU 3762  CG2  VAL D 463     2096  2063  2755    329     12    -63          C
ATOM   3763  C    VAL D 463      54.076   8.889 -12.517  1.00 18.79            C
ANISOU 3763  C    VAL D 463     2091  2324  2726    630     47   -103          C
ATOM   3764  O    VAL D 463      53.343   8.039 -13.061  1.00 18.59            O
ANISOU 3764  O    VAL D 463     1963  2463  2636    645     53    -87          O
ATOM   3765  N    LEU D 464      54.245  10.107 -12.999  1.00 19.85            N
ANISOU 3765  N    LEU D 464     2307  2300  2934    701     29    -42          N
ATOM   3766  CA   LEU D 464      53.639  10.532 -14.258  1.00 20.22            C
ANISOU 3766  CA   LEU D 464     2344  2365  2972    816      9     71          C
ATOM   3767  CB   LEU D 464      53.298  12.015 -14.196  1.00 21.24            C
ANISOU 3767  CB   LEU D 464     2572  2308  3190    958     -6     86          C
ATOM   3768  CG   LEU D 464      52.392  12.555 -13.082  1.00 21.78            C
ANISOU 3768  CG   LEU D 464     2634  2349  3293   1085     11    -55          C
ATOM   3769  CD1  LEU D 464      52.192  14.033 -13.307  1.00 21.48            C
ANISOU 3769  CD1  LEU D 464     2714  2089  3357   1234     -8    -13          C
ATOM   3770  CD2  LEU D 464      51.033  11.835 -13.039  1.00 19.48            C
ANISOU 3770  CD2  LEU D 464     2173  2290  2938   1184     22   -109          C
ATOM   3771  C    LEU D 464      54.600  10.221 -15.434  1.00 20.13            C
ANISOU 3771  C    LEU D 464     2363  2346  2938    720     16    205          C
ATOM   3772  O    LEU D 464      55.774   9.957 -15.215  1.00 19.34            O
ANISOU 3772  O    LEU D 464     2286  2186  2877    580     42    209          O
ATOM   3773  N    PRO D 465      54.096  10.203 -16.684  1.00 21.70            N
ANISOU 3773  N    PRO D 465     2556  2622  3065    799     -8    311          N
ATOM   3774  CA   PRO D 465      54.985   9.992 -17.845  1.00 22.57            C
ANISOU 3774  CA   PRO D 465     2723  2726  3126    722     25    440          C
ATOM   3775  CB   PRO D 465      54.069  10.254 -19.037  1.00 23.86            C
ANISOU 3775  CB   PRO D 465     2910  2970  3187    865    -34    540          C
ATOM   3776  CG   PRO D 465      52.699   9.890 -18.550  1.00 23.05            C
ANISOU 3776  CG   PRO D 465     2677  3013  3067    968   -105    429          C
ATOM   3777  CD   PRO D 465      52.675  10.307 -17.092  1.00 22.87            C
ANISOU 3777  CD   PRO D 465     2637  2889  3164    965    -71    311          C
ATOM   3778  C    PRO D 465      56.248  10.874 -17.928  1.00 25.04            C
```

FIGURE 18-110

```
ANISOU 3778  C    PRO D 465     3145  2825  3544    637    84   529        C
ATOM   3779  O    PRO D 465     57.278  10.395 -18.414  1.00 25.30          O
ANISOU 3779  O    PRO D 465     3176  2867  3570    517   149   583        O
ATOM   3780  N    ASP D 466     56.170  12.133 -17.480  1.00 26.78          N
ANISOU 3780  N    ASP D 466     3452  2849  3874    696    69   538        N
ATOM   3781  CA   ASP D 466     57.344  13.009 -17.382  1.00 28.69          C
ANISOU 3781  CA   ASP D 466     3786  2862  4253    586   117   599        C
ATOM   3782  CB   ASP D 466     56.953  14.498 -17.491  1.00 31.09          C
ANISOU 3782  CB   ASP D 466     4230  2938  4643    702    98   670        C
ATOM   3783  CG   ASP D 466     56.078  14.998 -16.330  1.00 32.24          C
ANISOU 3783  CG   ASP D 466     4380  3024  4845    822    37   512        C
ATOM   3784  OD1  ASP D 466     55.823  14.292 -15.330  1.00 30.53          O
ANISOU 3784  OD1  ASP D 466     4070  2932  4599    800    19   349        O
ATOM   3785  OD2  ASP D 466     55.642  16.161 -16.413  1.00 38.19          O
ANISOU 3785  OD2  ASP D 466     5248  3591  5673    948    19   556        O
ATOM   3786  C    ASP D 466     58.190  12.757 -16.130  1.00 28.75          C
ANISOU 3786  C    ASP D 466     3742  2819  4363    442   111   460        C
ATOM   3787  O    ASP D 466     59.120  13.523 -15.851  1.00 29.86          O
ANISOU 3787  O    ASP D 466     3937  2764  4644    338   125   475        O
ATOM   3788  N    MSE D 467     57.871  11.674 -15.404  1.00 27.82          N
ANISOU 3788  N    MSE D 467     3523  2874  4173    430    82   334        N
ATOM   3789  CA   MSE D 467     58.653  11.191 -14.238  1.00 27.18          C
ANISOU 3789  CA   MSE D 467     3395  2788  4144    304    55   213        C
ATOM   3790  CB   MSE D 467     60.143  11.016 -14.581  1.00 27.16          C
ANISOU 3790  CB   MSE D 467     3352  2728  4238    142    90   280        C
ATOM   3791  CG   MSE D 467     60.473   9.801 -15.486  1.00 26.75          C
ANISOU 3791  CG   MSE D 467     3210  2847  4106    108   154   349        C
ATOM   3792  SE   MSE D 467     59.696   8.138 -14.902  0.90 30.05         SE
ANISOU 3792  SE   MSE D 467     3540  3499  4378    144   116   232        SE
ATOM   3793  CE   MSE D 467     60.578   8.025 -13.137  1.00 28.88          C
ANISOU 3793  CE   MSE D 467     3369  3279  4325     39    26   100        C
ATOM   3794  C    MSE D 467     58.470  12.021 -12.971  1.00 27.94          C
ANISOU 3794  C    MSE D 467     3565  2749  4304    327    -1    81        C
ATOM   3795  O    MSE D 467     59.154  11.804 -11.978  1.00 28.10          O
ANISOU 3795  O    MSE D 467     3577  2745  4357    227   -48   -18        O
ATOM   3796  N    THR D 468     57.548  12.977 -13.020  1.00 28.97          N
ANISOU 3796  N    THR D 468     3776  2788  4443    470    -3    77        N
ATOM   3797  CA   THR D 468     57.137  13.732 -11.838  1.00 30.36          C
ANISOU 3797  CA   THR D 468     4035  2848  4652    533   -37   -73        C
ATOM   3798  CB   THR D 468     56.270  14.949 -12.237  1.00 32.44          C
ANISOU 3798  CB   THR D 468     4395  2963  4969    710   -26   -37        C
ATOM   3799  OG1  THR D 468     57.079  15.883 -12.965  1.00 35.37          O
ANISOU 3799  OG1  THR D 468     4863  3109  5468    645   -20    91        O
ATOM   3800  CG2  THR D 468     55.697  15.678 -11.014  1.00 36.00          C
ANISOU 3800  CG2  THR D 468     4932  3304  5441    809   -40  -217        C
ATOM   3801  C    THR D 468     56.377  12.807 -10.868  1.00 28.96          C
ANISOU 3801  C    THR D 468     3791  2867  4345    575   -35  -208        C
ATOM   3802  O    THR D 468     55.453  12.082 -11.295  1.00 27.88          O
ANISOU 3802  O    THR D 468     3558  2917  4118    657    -2  -178        O
ATOM   3803  N    PRO D 469     56.760  12.819  -9.568  1.00 28.78          N
ANISOU 3803  N    PRO D 469     3824  2804  4307    512   -72  -354        N
ATOM   3804  CA   PRO D 469     56.011  12.034  -8.581  1.00 28.00          C
ANISOU 3804  CA   PRO D 469     3694  2876  4068    554   -47  -469        C
ATOM   3805  CB   PRO D 469     56.847  12.161  -7.306  1.00 28.47          C
ANISOU 3805  CB   PRO D 469     3854  2854  4107    451  -118  -600        C
ATOM   3806  CG   PRO D 469     57.615  13.422  -7.471  1.00 30.60          C
ANISOU 3806  CG   PRO D 469     4223  2871  4532    407  -176  -605        C
ATOM   3807  CD   PRO D 469     57.864  13.578  -8.946  1.00 30.30          C
ANISOU 3807  CD   PRO D 469     4118  2793  4602    395  -144  -421        C
ATOM   3808  C    PRO D 469     54.628  12.624  -8.344  1.00 28.95          C
ANISOU 3808  C    PRO D 469     3830  3009  4161    746    18  -541        C
ATOM   3809  O    PRO D 469     54.422  13.821  -8.471  1.00 31.03          O
ANISOU 3809  O    PRO D 469     4181  3092  4515    846    15  -558        O
ATOM   3810  N    SER D 470     53.680  11.773  -8.007  1.00 28.12          N
ANISOU 3810  N    SER D 470     3630  3107  3946    799    84  -579        N
ATOM   3811  CA   SER D 470     52.325  12.211  -7.789  1.00 28.32          C
ANISOU 3811  CA   SER D 470     3619  3181  3962   1162   -647            C
ATOM   3812  CB   SER D 470     51.519  12.098  -9.070  1.00 27.33          C
ANISOU 3812  CB   SER D 470     3351  3150  3883   1084   164  -524        C
ATOM   3813  OG   SER D 470     50.209  12.579  -8.834  1.00 30.16          O
ANISOU 3813  OG   SER D 470     3644  3556  4261   1280   230  -595        O
```

FIGURE 18-111

```
ATOM   3814  C    SER D 470      51.727  11.317  -6.739  1.00 28.11           C
ANISOU 3814  C    SER D 470     3546   3336   3798    967    247   -746       C
ATOM   3815  O    SER D 470      51.955  10.097  -6.738  1.00 26.67           O
ANISOU 3815  O    SER D 470     3294   3298   3541    842    249   -697       O
ATOM   3816  N    THR D 471      50.970  11.922  -5.847  1.00 29.88           N
ANISOU 3816  N    THR D 471     3821   3542   3989   1095    330   -882       N
ATOM   3817  CA   THR D 471      50.235  11.190  -4.825  1.00 31.76           C
ANISOU 3817  CA   THR D 471     4022   3958   4090   1099    454   -973       C
ATOM   3818  CB   THR D 471      50.322  11.895  -3.438  1.00 34.06           C
ANISOU 3818  CB   THR D 471     4508   4151   4283   1147    504  -1155       C
ATOM   3819  OG1  THR D 471      49.928  13.268  -3.563  1.00 36.80           O
ANISOU 3819  OG1  THR D 471     4916   4323   4743   1327    515  -1233       O
ATOM   3820  CG2  THR D 471      51.762  11.842  -2.895  1.00 34.68           C
ANISOU 3820  CG2  THR D 471     4765   4112   4299    980    369  -1177       C
ATOM   3821  C    THR D 471      48.769  10.996  -5.221  1.00 32.22           C
ANISOU 3821  C    THR D 471     3872   4182   4189   1237    567   -962       C
ATOM   3822  O    THR D 471      47.976  10.500  -4.422  1.00 33.96           O
ANISOU 3822  O    THR D 471     4032   4552   4321   1256    707  -1035       O
ATOM   3823  N    GLU D 472      48.430  11.356  -6.463  1.00 31.70           N
ANISOU 3823  N    GLU D 472     3692   4098   4254   1325    502   -862       N
ATOM   3824  CA   GLU D 472      47.035  11.363  -6.926  1.00 32.30           C
ANISOU 3824  CA   GLU D 472     3552   4318   4400   1483    566   -856       C
ATOM   3825  CB   GLU D 472      46.564  12.792  -7.215  1.00 34.20           C
ANISOU 3825  CB   GLU D 472     3825   4402   4768   1721    548   -885       C
ATOM   3826  CG   GLU D 472      46.472  13.710  -6.001  1.00 39.23           C
ANISOU 3826  CG   GLU D 472     4619   4902   5385   1834    650  -1059       C
ATOM   3827  CD   GLU D 472      47.149  15.074  -6.249  1.00 44.76           C
ANISOU 3827  CD   GLU D 472     5528   5294   6185   1917    554  -1063       C
ATOM   3828  OE1  GLU D 472      46.462  16.121  -6.201  1.00 47.87           O
ANISOU 3828  OE1  GLU D 472     5937   5570   6681   2147    593  -1130       O
ATOM   3829  OE2  GLU D 472      48.384  15.090  -6.500  1.00 45.99           O
ANISOU 3829  OE2  GLU D 472     5826   5316   6333   1749    444   -998       O
ATOM   3830  C    GLU D 472      46.839  10.501  -8.164  1.00 29.96           C
ANISOU 3830  C    GLU D 472     3083   4165   4136   1413    484   -717       C
ATOM   3831  O    GLU D 472      45.842   9.804  -8.275  1.00 29.57           O
ANISOU 3831  O    GLU D 472     2827   4313   4094   1424    541   -722       O
ATOM   3832  N    MSE D 473      47.796  10.559  -9.100  1.00 28.19           N
ANISOU 3832  N    MSE D 473     2943   3839   3930   1336    355   -601       N
ATOM   3833  CA   MSE D 473      47.703   9.800 -10.341  1.00 26.31           C
ANISOU 3833  CA   MSE D 473     2581   3719   3695   1276    272   -481       C
ATOM   3834  CB   MSE D 473      47.452  10.726 -11.552  1.00 27.81           C
ANISOU 3834  CB   MSE D 473     2766   3834   3967   1434    167   -380       C
ATOM   3835  CG   MSE D 473      46.264  11.657 -11.443  1.00 26.21           C
ANISOU 3835  CG   MSE D 473     2472   3630   3858   1680    188   -429       C
ATOM   3836  SE   MSE D 473      44.516  10.785 -11.482  0.90 29.78          SE
ANISOU 3836  SE   MSE D 473     2569   4404   4342   1752    231   -487      SE
ATOM   3837  CE   MSE D 473      44.552  10.081 -13.324  1.00 24.55           C
ANISOU 3837  CE   MSE D 473     1821   3865   3642   1686     30   -325       C
ATOM   3838  C    MSE D 473      48.978   9.045 -10.570  1.00 24.24           C
ANISOU 3838  C    MSE D 473     2418   3421   3371   1074    225   -417       C
ATOM   3839  O    MSE D 473      50.039   9.420 -10.051  1.00 23.22           O
ANISOU 3839  O    MSE D 473     2450   3138   3233   1006    216   -432       O
ATOM   3840  N    SER D 474      48.890   8.004 -11.387  1.00 22.74           N
ANISOU 3840  N    SER D 474     2125   3368   3148    983    187   -352       N
ATOM   3841  CA   SER D 474      50.092   7.287 -11.803  1.00 20.80           C
ANISOU 3841  CA   SER D 474     1959   3086   2859    820    146   -285       C
ATOM   3842  CB   SER D 474      50.489   6.264 -10.751  1.00 19.28           C
ANISOU 3842  CB   SER D 474     1787   2935   2604    675    208   -343       C
ATOM   3843  OG   SER D 474      51.820   5.854 -10.984  1.00 16.43           O
ANISOU 3843  OG   SER D 474     1518   2493   2230    553    164   -287       O
ATOM   3844  C    SER D 474      49.928   6.603 -13.137  1.00 20.73           C
ANISOU 3844  C    SER D 474     1868   3182   2825    789     81   -205       C
ATOM   3845  O    SER D 474      48.821   6.295 -13.530  1.00 21.95           O
ANISOU 3845  O    SER D 474     1877   3482   2983    843     62   -221       O
ATOM   3846  N    MSE D 475      51.037   6.376 -13.838  1.00 20.98           N
ANISOU 3846  N    MSE D 475     1989   3147   2833    702     46   -127       N
ATOM   3847  CA   MSE D 475      51.056   5.443 -14.964  1.00 21.48           C
ANISOU 3847  CA   MSE D 475     2006   3317   2838    639      5    -80       C
ATOM   3848  CB   MSE D 475      52.472   5.270 -15.530  1.00 19.83           C
ANISOU 3848  CB   MSE D 475     1910   3013   2612    548     10     -6       C
ATOM   3849  CG   MSE D 475      52.894   6.455 -16.381  1.00 20.37           C
```

FIGURE 18-112

```
ANISOU 3849  CG   MSE D 475    2076  2969  2696   631   -15   102        C
ATOM   3850  SE   MSE D 475    54.525   6.239 -17.395  0.90 22.90        SE
ANISOU 3850  SE   MSE D 475    2500  3209  2992   523    29   211        SE
ATOM   3851  CE   MSE D 475    55.763   6.073 -15.923  1.00 15.43        C
ANISOU 3851  CE   MSE D 475    1566  2140  2155   395    75   144        C
ATOM   3852  C    MSE D 475    50.505   4.108 -14.458  1.00 21.28        C
ANISOU 3852  C    MSE D 475    1873  3425  2786   535    40  -159        C
ATOM   3853  O    MSE D 475    50.898   3.647 -13.399  1.00 20.98        O
ANISOU 3853  O    MSE D 475    1867  3355  2749   451   102  -203        O
ATOM   3854  N    ARG D 476    49.570   3.531 -15.206  1.00 22.47        N
ANISOU 3854  N    ARG D 476    1904  3721  2914   539    -9  -173        N
ATOM   3855  CA   ARG D 476    48.834   2.320 -14.818  1.00 22.84        C
ANISOU 3855  CA   ARG D 476    1826  3891  2961   432    23  -248        C
ATOM   3856  CB   ARG D 476    47.933   1.869 -15.985  1.00 23.67        C
ANISOU 3856  CB   ARG D 476    1807  4140  3046   439   -79  -261        C
ATOM   3857  CG   ARG D 476    47.287   0.475 -15.783  1.00 27.51        C
ANISOU 3857  CG   ARG D 476    2172  4732  3549   284   -56  -339        C
ATOM   3858  CD   ARG D 476    46.787  -0.218 -17.071  1.00 27.82        C
ANISOU 3858  CD   ARG D 476    2140  4882  3546   238  -183  -369        C
ATOM   3859  NE   ARG D 476    47.530   0.020 -18.335  1.00 32.26        N
ANISOU 3859  NE   ARG D 476    2845  5411  4002   288  -273  -313        N
ATOM   3860  CZ   ARG D 476    48.407  -0.822 -18.879  1.00 31.84        C
ANISOU 3860  CZ   ARG D 476    2916  5306  3876   190  -263  -319        C
ATOM   3861  NH1  ARG D 476    48.759  -1.946 -18.240  1.00 32.87        N
ANISOU 3861  NH1  ARG D 476    3064  5384  4042    43  -180  -370        N
ATOM   3862  NH2  ARG D 476    48.962  -0.521 -20.040  1.00 28.92        N
ANISOU 3862  NH2  ARG D 476    2666  4927  3395   249  -323  -268        N
ATOM   3863  C    ARG D 476    49.715   1.168 -14.282  1.00 20.44        C
ANISOU 3863  C    ARG D 476    1601  3533  2632   271    84  -261        C
ATOM   3864  O    ARG D 476    50.603   0.659 -14.985  1.00 19.53        O
ANISOU 3864  O    ARG D 476    1567  3372  2481   213    57  -227        O
ATOM   3865  N    GLY D 477    49.476   0.777 -13.028  1.00 20.13        N
ANISOU 3865  N    GLY D 477    1544  3497  2606   212   174  -303        N
ATOM   3866  CA   GLY D 477    50.241  -0.307 -12.377  1.00 19.10        C
ANISOU 3866  CA   GLY D 477    1500  3308  2451    77   223  -300        C
ATOM   3867  C    GLY D 477    51.654   0.032 -11.943  1.00 18.37        C
ANISOU 3867  C    GLY D 477    1558  3076  2345    81   215  -259        C
ATOM   3868  O    GLY D 477    52.351  -0.837 -11.447  1.00 18.98        O
ANISOU 3868  O    GLY D 477    1702  3100  2407    -7   233  -246        O
ATOM   3869  N    ILE D 478    52.094   1.285 -12.110  1.00 18.42        N
ANISOU 3869  N    ILE D 478    1614  3013  2371   179   180  -235        N
ATOM   3870  CA   ILE D 478    53.467   1.698 -11.747  1.00 17.40        C
ANISOU 3870  CA   ILE D 478    1602  2752  2259   167   158  -203        C
ATOM   3871  CB   ILE D 478    54.167   2.509 -12.862  1.00 17.64        C
ANISOU 3871  CB   ILE D 478    1662  2712  2328   215   115  -140        C
ATOM   3872  CG1  ILE D 478    53.884   1.926 -14.282  1.00 18.18        C
ANISOU 3872  CG1  ILE D 478    1682  2862  2363   211    98  -108        C
ATOM   3873  CD1  ILE D 478    54.456   0.525 -14.545  1.00 17.82        C
ANISOU 3873  CD1  ILE D 478    1642  2831  2299   109   115  -115        C
ATOM   3874  CG2  ILE D 478    55.699   2.688 -12.556  1.00 16.84        C
ANISOU 3874  CG2  ILE D 478    1638  2484  2276   163    98  -107        C
ATOM   3875  C    ILE D 478    53.516   2.522 -10.450  1.00 18.27        C
ANISOU 3875  C    ILE D 478    1780  2801  2362   205   175  -248        C
ATOM   3876  O    ILE D 478    52.759   3.501 -10.278  1.00 19.57        O
ANISOU 3876  O    ILE D 478    1928  2971  2538   304   192  -284        O
ATOM   3877  N    ARG D 479    54.407   2.131  -9.538  1.00 17.66        N
ANISOU 3877  N    ARG D 479    1785  2662  2261   138   160  -252        N
ATOM   3878  CA   ARG D 479    54.620   2.867  -8.297  1.00 18.17        C
ANISOU 3878  CA   ARG D 479    1947  2665  2291   163   152  -308        C
ATOM   3879  CB   ARG D 479    53.947   2.147  -7.108  1.00 19.25        C
ANISOU 3879  CB   ARG D 479    2115  2880  2318   131   225  -348        C
ATOM   3880  CG   ARG D 479    52.436   1.937  -7.217  1.00 19.34        C
ANISOU 3880  CG   ARG D 479    2015  3018  2313   163   334  -376        C
ATOM   3881  CD   ARG D 479    51.652   3.264  -7.152  1.00 22.05        C
ANISOU 3881  CD   ARG D 479    2332  3364  2683   298   368  -442        C
ATOM   3882  NE   ARG D 479    50.213   3.019  -7.118  1.00 23.03        N
ANISOU 3882  NE   ARG D 479    2316  3626  2807   332   477  -475        N
ATOM   3883  CZ   ARG D 479    49.448   2.766  -8.182  1.00 24.23        C
ANISOU 3883  CZ   ARG D 479    2306  3868  3033   347   466  -451        C
ATOM   3884  NH1  ARG D 479    49.944   2.768  -9.423  1.00 22.96        N
ANISOU 3884  NH1  ARG D 479    2127  3672  2923   344   360  -392        N
```

FIGURE 18-113

```
ATOM    3885  NH2 ARG D 479      48.161   2.542  -7.998  1.00 26.72           N
ANISOU  3885  NH2 ARG D 479    2471   4316   3365     367    563   -491       N
ATOM    3886  C   ARG D 479      56.113   3.010  -8.047  1.00 18.00           C
ANISOU  3886  C   ARG D 479    2000   2531   2310     111     60   -286       C
ATOM    3887  O   ARG D 479      56.893   2.152  -8.450  1.00 17.43           O
ANISOU  3887  O   ARG D 479    1902   2452   2268      49     31   -230       O
ATOM    3888  N   VAL D 480      56.506   4.091  -7.376  1.00 18.88           N
ANISOU  3888  N   VAL D 480    2194   2547   2431     138     13   -340       N
ATOM    3889  CA  VAL D 480      57.872   4.288  -6.941  1.00 18.12           C
ANISOU  3889  CA  VAL D 480    2153   2351   2382      77    -95   -341       C
ATOM    3890  CB  VAL D 480      58.424   5.658  -7.477  1.00 19.53           C
ANISOU  3890  CB  VAL D 480    2339   2392   2689      91   -137   -344       C
ATOM    3891  CG1 VAL D 480      59.811   6.004  -6.914  1.00 16.90           C
ANISOU  3891  CG1 VAL D 480    2041   1951   2430       9   -261   -368       C
ATOM    3892  CG2 VAL D 480      58.462   5.665  -8.979  1.00 16.55           C
ANISOU  3892  CG2 VAL D 480    1871   2019   2398     100    -88   -246       C
ATOM    3893  C   VAL D 480      57.914   4.199  -5.402  1.00 20.38           C
ANISOU  3893  C   VAL D 480    2561   2642   2541      65   -138   -419       C
ATOM    3894  O   VAL D 480      57.129   4.864  -4.687  1.00 20.96           O
ANISOU  3894  O   VAL D 480    2713   2720   2531     126    -92   -507       O
ATOM    3895  N   SER D 481      58.821   3.365  -4.894  1.00 20.39           N
ANISOU  3895  N   SER D 481    2584   2645   2517       1   -225   -387       N
ATOM    3896  CA  SER D 481      59.058   3.257  -3.454  1.00 22.99           C
ANISOU  3896  CA  SER D 481    3052   2978   2703     -11   -302   -444       C
ATOM    3897  CB  SER D 481      59.874   1.996  -3.174  1.00 22.03           C
ANISOU  3897  CB  SER D 481    2928   2881   2562     -61   -385   -362       C
ATOM    3898  OG  SER D 481      60.138   1.858  -1.810  1.00 21.23           O
ANISOU  3898  OG  SER D 481    2978   2789   2300     -66   -480   -399       O
ATOM    3899  C   SER D 481      59.757   4.490  -2.835  1.00 25.71           C
ANISOU  3899  C   SER D 481    3483   3214   3072     -19   -429   -546       C
ATOM    3900  O   SER D 481      60.658   5.061  -3.420  1.00 25.93           O
ANISOU  3900  O   SER D 481    3439   3147   3265     -59   -511   -535       O
ATOM    3901  N   LYS D 482      59.321   4.900  -1.655  1.00 29.14           N
ANISOU  3901  N   LYS D 482    4076   3658   3339      13   -436   -651       N
ATOM    3902  CA  LYS D 482      60.019   5.935  -0.899  1.00 33.36           C
ANISOU  3902  CA  LYS D 482    4723   4086   3866      -7   -583   -772       C
ATOM    3903  CB  LYS D 482      59.022   6.840  -0.155  1.00 34.30           C
ANISOU  3903  CB  LYS D 482    4994   4191   3848      75   -492   -915       C
ATOM    3904  CG  LYS D 482      58.218   7.746  -1.062  1.00 35.12           C
ANISOU  3904  CG  LYS D 482    5025   4233   4086     151   -361   -933       C
ATOM    3905  CD  LYS D 482      57.186   8.541  -0.242  1.00 38.57           C
ANISOU  3905  CD  LYS D 482    5604   4663   4387     260   -254  -1083       C
ATOM    3906  CE  LYS D 482      57.252  10.056  -0.537  1.00 45.10           C
ANISOU  3906  CE  LYS D 482    6478   5298   5359     308   -284  -1185       C
ATOM    3907  NZ  LYS D 482      56.099  10.810   0.069  1.00 47.81           N
ANISOU  3907  NZ  LYS D 482    6933   5632   5603     453   -143  -1329       N
ATOM    3908  C   LYS D 482      61.038   5.332   0.072  1.00 35.24           C
ANISOU  3908  C   LYS D 482    5039   4343   4008     -65   -774   -772       C
ATOM    3909  O   LYS D 482      61.727   6.074   0.758  1.00 37.45           O
ANISOU  3909  O   LYS D 482    5410   4546   4275     -99   -937   -880       O
ATOM    3910  N   MSE D 483      61.139   3.993   0.102  1.00 35.93           N
ANISOU  3910  N   MSE D 483    5093   4523   4037     -74   -766   -651       N
ATOM    3911  CA  MSE D 483      62.049   3.244   0.994  1.00 38.63           C
ANISOU  3911  CA  MSE D 483    5507   4890   4278    -103   -953   -617       C
ATOM    3912  CB  MSE D 483      61.526   1.809   1.265  1.00 38.49           C
ANISOU  3912  CB  MSE D 483    5539   4971   4113     -80   -858   -492       C
ATOM    3913  CG  MSE D 483      60.174   1.672   1.929  1.00 38.95           C
ANISOU  3913  CG  MSE D 483    5746   5112   3940     -43   -667   -517       C
ATOM    3914  SE  MSE D 483      60.058   2.796   3.498  0.90 48.19          SE
ANISOU  3914  SE  MSE D 483    7190   6282   4839     -11   -748   -705      SE
ATOM    3915  CE  MSE D 483      61.347   1.963   4.722  1.00 38.88           C
ANISOU  3915  CE  MSE D 483    6178   5122   3472     -35  -1049   -643       C
ATOM    3916  C   MSE D 483      63.440   3.077   0.385  1.00 39.71           C
ANISOU  3916  C   MSE D 483    5470   4969   4647    -156  -1120   -557       C
ATOM    3917  O   MSE D 483      63.582   2.646  -0.783  1.00 39.13           O
ANISOU  3917  O   MSE D 483    5221   4891   4756    -163  -1031   -463       O
ATOM    3918  OXT MSE D 483      64.451   3.268   1.060  1.00 42.00           O
ANISOU  3918  OXT MSE D 483    5786   5231   4942    -190  -1344   -601       O
ATOM    3919  N   SER E 320      17.288 -30.979 -15.413  1.00 45.14           N
ANISOU  3919  N   SER E 320    4874   5333   6943   -1348    253  -1314       N
ATOM    3920  CA  SER E 320      18.777 -31.109 -15.580  1.00 43.13           C
```

FIGURE 18-114

```
ANISOU 3920  CA  SER E 320    4877  4914  6598 -1261   271 -1210       C
ATOM   3921  CB  SER E 320   19.237 -30.250 -16.770  1.00 42.79        C
ANISOU 3921  CB  SER E 320    4873  4954  6429 -1088   116 -1208       C
ATOM   3922  OG  SER E 320   20.570 -30.562 -17.153  1.00 42.94        O
ANISOU 3922  OG  SER E 320    5102  4848  6364 -1042   136 -1161       O
ATOM   3923  C   SER E 320   19.579 -30.728 -14.308  1.00 40.67        C
ANISOU 3923  C   SER E 320    4675  4506  6270 -1199   402 -1051       C
ATOM   3924  O   SER E 320   20.651 -30.104 -14.400  1.00 38.93        O
ANISOU 3924  O   SER E 320    4584  4241  5966 -1052   384  -962       O
ATOM   3925  N   SER E 321   19.089 -31.107 -13.126  1.00 39.80        N
ANISOU 3925  N   SER E 321    4515  4379  6227 -1326   537 -1019       N
ATOM   3926  CA  SER E 321   19.714 -30.590 -11.897  1.00 37.65        C
ANISOU 3926  CA  SER E 321    4321  4074  5908 -1264   645  -884       C
ATOM   3927  CB  SER E 321   18.684 -29.870 -11.033  1.00 38.56        C
ANISOU 3927  CB  SER E 321    4239  4357  6053 -1282   719  -919       C
ATOM   3928  OG  SER E 321   17.883 -30.781 -10.335  1.00 42.51        O
ANISOU 3928  OG  SER E 321    4667  4871  6613 -1506   844  -940       O
ATOM   3929  C   SER E 321   20.577 -31.528 -11.043  1.00 35.74        C
ANISOU 3929  C   SER E 321    4273  3651  5656 -1347   751  -758       C
ATOM   3930  O   SER E 321   20.985 -31.157  -9.954  1.00 35.15        O
ANISOU 3930  O   SER E 321    4249  3580  5525 -1318   835  -651       O
ATOM   3931  N   SER E 322   20.888 -32.716 -11.566  1.00 34.84        N
ANISOU 3931  N   SER E 322    4269  3374  5595 -1437   733  -776       N
ATOM   3932  CA  SER E 322   21.599 -33.753 -10.828  1.00 33.04        C
ANISOU 3932  CA  SER E 322    4224  2938  5393 -1514   809  -653       C
ATOM   3933  CB  SER E 322   20.570 -34.509  -9.996  1.00 35.56        C
ANISOU 3933  CB  SER E 322    4485  3245  5779 -1754   925  -626       C
ATOM   3934  OG  SER E 322   21.115 -35.024  -8.821  1.00 37.24        O
ANISOU 3934  OG  SER E 322    4855  3332  5961 -1811  1016  -441       O
ATOM   3935  C   SER E 322   22.235 -34.682 -11.863  1.00 31.91        C
ANISOU 3935  C   SER E 322    4198  2615  5311 -1502   734  -725       C
ATOM   3936  O   SER E 322   21.534 -35.240 -12.700  1.00 32.42        O
ANISOU 3936  O   SER E 322    4194  2677  5448 -1608   693  -870       O
ATOM   3937  N   PHE E 323   23.554 -34.840 -11.834  1.00 29.63        N
ANISOU 3937  N   PHE E 323    4068  2192  4996 -1371   715  -650       N
ATOM   3938  CA  PHE E 323   24.244 -35.599 -12.891  1.00 29.75        C
ANISOU 3938  CA  PHE E 323    4174  2063  5065 -1325   650  -758       C
ATOM   3939  CB  PHE E 323   24.149 -34.903 -14.263  1.00 28.38        C
ANISOU 3939  CB  PHE E 323    3911  2061  4813 -1241   558  -915       C
ATOM   3940  CG  PHE E 323   24.548 -33.447 -14.229  1.00 26.56        C
ANISOU 3940  CG  PHE E 323    3636  2007  4449 -1083   532  -845       C
ATOM   3941  CD1 PHE E 323   25.862 -33.076 -14.466  1.00 22.90        C
ANISOU 3941  CD1 PHE E 323    3264  1521  3918  -932   519  -808       C
ATOM   3942  CE1 PHE E 323   26.235 -31.770 -14.412  1.00 24.39        C
ANISOU 3942  CE1 PHE E 323    3422  1843  4002  -815   501  -741       C
ATOM   3943  CZ  PHE E 323   25.292 -30.792 -14.111  1.00 23.48        C
ANISOU 3943  CZ  PHE E 323    3191  1869  3862  -821   488  -715       C
ATOM   3944  CE2 PHE E 323   23.978 -31.148 -13.862  1.00 24.40        C
ANISOU 3944  CE2 PHE E 323    3199  2025  4048  -947   500  -764       C
ATOM   3945  CD2 PHE E 323   23.615 -32.469 -13.928  1.00 24.02        C
ANISOU 3945  CD2 PHE E 323    3176  1861  4091 -1090   526  -826       C
ATOM   3946  C   PHE E 323   25.685 -35.852 -12.537  1.00 29.09        C
ANISOU 3946  C   PHE E 323    4245  1828  4982 -1184   651  -658       C
ATOM   3947  O   PHE E 323   26.186 -35.304 -11.578  1.00 27.33        O
ANISOU 3947  O   PHE E 323    4053  1639  4692 -1113   681  -508       O
ATOM   3948  N   SER E 324   26.322 -36.718 -13.318  1.00 31.14        N
ANISOU 3948  N   SER E 324    4586  1925  5321 -1147   614  -765       N
ATOM   3949  CA  SER E 324   27.734 -37.036 -13.197  1.00 31.70        C
ANISOU 3949  CA  SER E 324    4771  1855  5418  -989   600  -719       C
ATOM   3950  CB  SER E 324   27.870 -38.553 -13.286  1.00 34.12        C
ANISOU 3950  CB  SER E 324    5192  1860  5913 -1047   596  -770       C
ATOM   3951  OG  SER E 324   29.065 -38.980 -12.669  1.00 38.99        O
ANISOU 3951  OG  SER E 324    5921  2300  6591  -905   581  -655       O
ATOM   3952  C   SER E 324   28.506 -36.359 -14.344  1.00 30.11        C
ANISOU 3952  C   SER E 324    4525  1797  5118  -844   560  -855       C
ATOM   3953  O   SER E 324   28.106 -36.436 -15.500  1.00 31.59        O
ANISOU 3953  O   SER E 324    4663  2058  5282  -883   530 -1033       O
ATOM   3954  N   PHE E 325   29.598 -35.683 -14.036  1.00 28.89        N
ANISOU 3954  N   PHE E 325    4383  1701  4891  -694   561  -773       N
ATOM   3955  CA  PHE E 325   30.474 -35.145 -15.073  1.00 27.03        C
ANISOU 3955  CA  PHE E 325    4117  1587  4568  -576   545  -888       C
```

FIGURE 18-115

```
ATOM   3956  CB  PHE E 325      30.028 -33.721 -15.485  1.00 25.71           C
ANISOU 3956  CB  PHE E 325    3861   1671   4236   -581    531   -870        C
ATOM   3957  CG  PHE E 325      30.847 -33.123 -16.611  1.00 24.39           C
ANISOU 3957  CG  PHE E 325    3676   1643   3950   -499    524   -964        C
ATOM   3958  CD1 PHE E 325      30.800 -33.667 -17.896  1.00 26.53           C
ANISOU 3958  CD1 PHE E 325    3946   1946   4189   -527    510  -1154        C
ATOM   3959  CE1 PHE E 325      31.557 -33.143 -18.941  1.00 26.12           C
ANISOU 3959  CE1 PHE E 325    3882   2048   3996   -474    523  -1236        C
ATOM   3960  CZ  PHE E 325      32.370 -32.062 -18.716  1.00 25.88           C
ANISOU 3960  CZ  PHE E 325    3837   2119   3876   -402    549  -1121        C
ATOM   3961  CE2 PHE E 325      32.432 -31.495 -17.417  1.00 23.76           C
ANISOU 3961  CE2 PHE E 325    3565   1800   3661   -371    553   -942        C
ATOM   3962  CD2 PHE E 325      31.668 -32.040 -16.383  1.00 22.30           C
ANISOU 3962  CD2 PHE E 325    3395   1484   3596   -415    540   -870        C
ATOM   3963  C   PHE E 325      31.902 -35.144 -14.575  1.00 26.40           C
ANISOU 3963  C   PHE E 325    4074   1446   4509   -425    553   -823        C
ATOM   3964  O   PHE E 325      32.194 -34.540 -13.538  1.00 26.23           O
ANISOU 3964  O   PHE E 325    4054   1463   4449   -387    556   -660        O
ATOM   3965  N   GLY E 326      32.796 -35.792 -15.322  1.00 27.37           N
ANISOU 3965  N   GLY E 326    4212   1496   4692   -336    554   -970        N
ATOM   3966  CA  GLY E 326      34.235 -35.778 -15.041  1.00 26.54           C
ANISOU 3966  CA  GLY E 326    4100   1366   4617   -174    556   -952        C
ATOM   3967  C   GLY E 326      34.617 -36.415 -13.719  1.00 27.28           C
ANISOU 3967  C   GLY E 326    4264   1264   4837   -114    519   -785        C
ATOM   3968  O   GLY E 326      35.626 -36.061 -13.130  1.00 26.73           O
ANISOU 3968  O   GLY E 326    4170   1232   4755      5    500   -704        O
ATOM   3969  N   GLY E 327      33.802 -37.361 -13.255  1.00 28.74           N
ANISOU 3969  N   GLY E 327    4538   1245   5136   -209    504   -726        N
ATOM   3970  CA  GLY E 327      34.068 -38.077 -12.017  1.00 29.31           C
ANISOU 3970  CA  GLY E 327    4711   1111   5316   -173    461   -535        C
ATOM   3971  C   GLY E 327      33.462 -37.392 -10.811  1.00 28.45           C
ANISOU 3971  C   GLY E 327    4617   1109   5084   -268    472   -313        C
ATOM   3972  O   GLY E 327      33.702 -37.801  -9.695  1.00 29.85           O
ANISOU 3972  O   GLY E 327    4879   1173   5289   -249    436   -125        O
ATOM   3973  N   PHE E 328      32.672 -36.346 -11.040  1.00 27.12           N
ANISOU 3973  N   PHE E 328    4367   1164   4775   -365    519   -340        N
ATOM   3974  CA  PHE E 328      32.019 -35.572  -9.968  1.00 26.05           C
ANISOU 3974  CA  PHE E 328    4218   1162   4519   -453    548   -181        C
ATOM   3975  CB  PHE E 328      32.455 -34.102 -10.014  1.00 23.69           C
ANISOU 3975  CB  PHE E 328    3822   1103   4075   -380    554   -197        C
ATOM   3976  CG  PHE E 328      33.877 -33.872  -9.572  1.00 23.60           C
ANISOU 3976  CG  PHE E 328    3813   1108   4048   -226    510   -147        C
ATOM   3977  CD1 PHE E 328      34.167 -33.591  -8.245  1.00 22.43           C
ANISOU 3977  CD1 PHE E 328    3694   1000   3828   -211    488     14        C
ATOM   3978  CE1 PHE E 328      35.475 -33.394  -7.831  1.00 23.44           C
ANISOU 3978  CE1 PHE E 328    3804   1160   3943    -72    429     48        C
ATOM   3979  CZ  PHE E 328      36.506 -33.431  -8.745  1.00 21.73           C
ANISOU 3979  CZ  PHE E 328    3523    942   3793     50    409    -84        C
ATOM   3980  CE2 PHE E 328      36.228 -33.706 -10.080  1.00 22.34           C
ANISOU 3980  CE2 PHE E 328    3575    984   3929     31    451   -248        C
ATOM   3981  CD2 PHE E 328      34.921 -33.932 -10.485  1.00 21.48           C
ANISOU 3981  CD2 PHE E 328    3500    839   3823   -105    492   -276        C
ATOM   3982  C   PHE E 328      30.497 -35.621 -10.086  1.00 26.19           C
ANISOU 3982  C   PHE E 328    4206   1214   4532   -642    600   -207        C
ATOM   3983  O   PHE E 328      29.950 -35.431 -11.172  1.00 26.07           O
ANISOU 3983  O   PHE E 328    4118   1269   4517   -682    603   -365        O
ATOM   3984  N   THR E 329      29.819 -35.857  -8.968  1.00 26.51           N
ANISOU 3984  N   THR E 329    4290   1228   4553   -764    638    -54        N
ATOM   3985  CA  THR E 329      28.360 -35.708  -8.900  1.00 26.59           C
ANISOU 3985  CA  THR E 329    4228   1329   4544   -949    705    -80        C
ATOM   3986  CB  THR E 329      27.755 -36.554  -7.740  1.00 28.57           C
ANISOU 3986  CB  THR E 329    4571   1463   4820  -1117    762     93        C
ATOM   3987  OG1 THR E 329      28.147 -37.920  -7.876  1.00 29.01           O
ANISOU 3987  OG1 THR E 329    4767   1221   5033  -1129    723    133        O
ATOM   3988  CG2 THR E 329      26.239 -36.497  -7.744  1.00 28.98           C
ANISOU 3988  CG2 THR E 329    4518   1619   4875  -1326    845     36        C
ATOM   3989  C   THR E 329      28.025 -34.221  -8.688  1.00 25.15           C
ANISOU 3989  C   THR E 329    3921   1415   4220   -919    731    -98        C
ATOM   3990  O   THR E 329      28.444 -33.613  -7.696  1.00 24.93           O
ANISOU 3990  O   THR E 329    3907   1473   4091   -873    746     12        O
ATOM   3991  N   PHE E 330      27.315 -33.629  -9.642  1.00 24.51           N
```

FIGURE 18-116

```
ANISOU 3991  N   PHE E 330     3721  1458  4135   -936   723  -244          N
ATOM   3992  CA  PHE E 330      26.858 -32.240  -9.556  1.00 23.01          C
ANISOU 3992  CA  PHE E 330     3410  1483  3850   -900   734  -274          C
ATOM   3993  CB  PHE E 330      26.817 -31.604 -10.941  1.00 21.72          C
ANISOU 3993  CB  PHE E 330     3173  1403  3676   -825   666  -409          C
ATOM   3994  CG  PHE E 330      28.177 -31.190 -11.498  1.00 21.21          C
ANISOU 3994  CG  PHE E 330     3166  1329  3566   -677   621  -415          C
ATOM   3995  CD1 PHE E 330      28.458 -29.852 -11.723  1.00 15.46          C
ANISOU 3995  CD1 PHE E 330     2388   729  2756   -587   599  -415          C
ATOM   3996  CE1 PHE E 330      29.657 -29.480 -12.246  1.00 17.14          C
ANISOU 3996  CE1 PHE E 330     2641   946  2926   -487   576  -422          C
ATOM   3997  CZ  PHE E 330      30.629 -30.427 -12.567  1.00 16.73          C
ANISOU 3997  CZ  PHE E 330     2657   787  2913   -450   574  -450          C
ATOM   3998  CE2 PHE E 330      30.376 -31.764 -12.358  1.00 17.20          C
ANISOU 3998  CE2 PHE E 330     2768   698  3069   -508   583  -460          C
ATOM   3999  CD2 PHE E 330      29.154 -32.149 -11.835  1.00 21.06          C
ANISOU 3999  CD2 PHE E 330     3238  1164  3598   -632   606  -432          C
ATOM   4000  C   PHE E 330      25.453 -32.252  -9.007  1.00 24.29          C
ANISOU 4000  C   PHE E 330     3474  1732  4023  -1056   804  -281          C
ATOM   4001  O   PHE E 330      24.630 -33.022  -9.465  1.00 26.43          O
ANISOU 4001  O   PHE E 330     3710  1954  4378  -1183   811  -348          O
ATOM   4002  N   LYS E 331      25.180 -31.429  -7.999  1.00 24.67          N
ANISOU 4002  N   LYS E 331     3469  1917  3990  -1057   863  -230          N
ATOM   4003  CA  LYS E 331      23.812 -31.224  -7.513  1.00 26.44          C
ANISOU 4003  CA  LYS E 331     3552  2275  4217  -1188   945  -275          C
ATOM   4004  CB  LYS E 331      23.617 -31.802  -6.093  1.00 27.86          C
ANISOU 4004  CB  LYS E 331     3795  2455  4336  -1333  1061  -141          C
ATOM   4005  CG  LYS E 331      23.960 -33.297  -5.951  1.00 31.24          C
ANISOU 4005  CG  LYS E 331     4390  2659  4822  -1444  1064   -17          C
ATOM   4006  CD  LYS E 331      23.547 -33.844  -4.584  1.00 33.05          C
ANISOU 4006  CD  LYS E 331     4681  2905  4972  -1626  1184   138          C
ATOM   4007  CE  LYS E 331      23.640 -35.361  -4.566  1.00 38.36          C
ANISOU 4007  CE  LYS E 331     5513  3318  5742  -1762  1182   262          C
ATOM   4008  NZ  LYS E 331      22.905 -35.921  -3.365  1.00 42.80          N
ANISOU 4008  NZ  LYS E 331     6117  3916  6230  -2004  1321   413          N
ATOM   4009  C   LYS E 331      23.523 -29.732  -7.509  1.00 25.02          C
ANISOU 4009  C   LYS E 331     3240  2275  3994  -1072   934  -357          C
ATOM   4010  O   LYS E 331      24.129 -28.997  -6.727  1.00 24.10          O
ANISOU 4010  O   LYS E 331     3157  2208  3793   -994   956  -308          O
ATOM   4011  N   ARG E 332      22.604 -29.291  -8.370  1.00 25.04          N
ANISOU 4011  N   ARG E 332     3089  2363  4061  -1059   886  -484          N
ATOM   4012  CA  ARG E 332      22.229 -27.881  -8.446  1.00 24.35          C
ANISOU 4012  CA  ARG E 332     2874  2411  3969   -932   855  -562          C
ATOM   4013  CB  ARG E 332      21.285 -27.616  -9.610  1.00 25.25          C
ANISOU 4013  CB  ARG E 332     2839  2593  4163   -905   757  -680          C
ATOM   4014  CG  ARG E 332      21.014 -26.115  -9.816  1.00 21.87          C
ANISOU 4014  CG  ARG E 332     2303  2255  3752   -736   689  -736          C
ATOM   4015  CD  ARG E 332      20.462 -25.836 -11.209  1.00 20.39          C
ANISOU 4015  CD  ARG E 332     2030  2105  3611   -667   535  -801          C
ATOM   4016  NE  ARG E 332      19.065 -26.242 -11.251  1.00 24.14          N
ANISOU 4016  NE  ARG E 332     2301  2699  4172   -764   543  -916          N
ATOM   4017  CZ  ARG E 332      18.397 -26.578 -12.351  1.00 23.40          C
ANISOU 4017  CZ  ARG E 332     2117  2660  4116   -788   424  -991          C
ATOM   4018  NH1 ARG E 332      18.988 -26.571 -13.538  1.00 21.11          N
ANISOU 4018  NH1 ARG E 332     1938  2320  3762   -722   293  -959          N
ATOM   4019  NH2 ARG E 332      17.126 -26.891 -12.252  1.00 20.98          N
ANISOU 4019  NH2 ARG E 332     1594  2479  3898   -885   440 -1109          N
ATOM   4020  C   ARG E 332      21.525 -27.438  -7.198  1.00 26.32          C
ANISOU 4020  C   ARG E 332     3014  2794  4193   -986   977  -590          C
ATOM   4021  O   ARG E 332      20.536 -28.054  -6.779  1.00 27.98          O
ANISOU 4021  O   ARG E 332     3124  3075  4432  -1144  1068  -625          O
ATOM   4022  N   THR E 333      22.010 -26.355  -6.605  1.00 25.21          N
ANISOU 4022  N   THR E 333     2884  2698  3998   -911   988  -593          N
ATOM   4023  CA  THR E 333      21.397 -25.862  -5.375  1.00 26.76          C
ANISOU 4023  CA  THR E 333     2975  3042  4151   -911  1115  -652          C
ATOM   4024  CB  THR E 333      22.430 -25.785  -4.254  1.00 26.26          C
ANISOU 4024  CB  THR E 333     3060  2971  3947   -914  1174  -557          C
ATOM   4025  OG1 THR E 333      23.540 -25.025  -4.725  1.00 26.60          O
ANISOU 4025  OG1 THR E 333     3196  2922  3989   -755  1066  -537          O
ATOM   4026  CG2 THR E 333      22.913 -27.195  -3.863  1.00 26.22          C
ANISOU 4026  CG2 THR E 333     3215  2876  3869  -1058  1210  -394          C
```

FIGURE 18-117

```
ATOM   4027  C   THR E 333      20.663 -24.526  -5.541  1.00 26.87           C
ANISOU 4027  C   THR E 333    2805  3156  4249   -774  1087   -809           C
ATOM   4028  O   THR E 333      19.854 -24.162  -4.697  1.00 28.07           O
ANISOU 4028  O   THR E 333    2810  3455  4401   -809  1199   -916           O
ATOM   4029  N   SER E 334      20.951 -23.808  -6.627  1.00 26.17           N
ANISOU 4029  N   SER E 334    2727  2986  4232   -617   940   -820           N
ATOM   4030  CA  SER E 334      20.279 -22.542  -6.963  1.00 27.33           C
ANISOU 4030  CA  SER E 334    2719  3177  4488   -459   871   -942           C
ATOM   4031  CB  SER E 334      21.102 -21.370  -6.495  1.00 26.24           C
ANISOU 4031  CB  SER E 334    2660  2977  4331   -331   863   -947           C
ATOM   4032  OG  SER E 334      20.687 -20.972  -5.253  1.00 30.33           O
ANISOU 4032  OG  SER E 334    3084  3610  4830   -352   996  -1061           O
ATOM   4033  C   SER E 334      20.227 -22.353  -8.446  1.00 27.14           C
ANISOU 4033  C   SER E 334    2699  3081  4532   -363   695   -914           C
ATOM   4034  O   SER E 334      21.097 -22.860  -9.148  1.00 24.82           O
ANISOU 4034  O   SER E 334    2565  2688  4175   -384   635   -806           O
ATOM   4035  N   GLY E 335      19.259 -21.545  -8.895  1.00 28.15           N
ANISOU 4035  N   GLY E 335    2651  3264  4780   -243   609  -1014           N
ATOM   4036  CA  GLY E 335      19.198 -21.137 -10.292  1.00 27.93           C
ANISOU 4036  CA  GLY E 335    2635  3180  4796   -127   415   -971           C
ATOM   4037  C   GLY E 335      18.565 -22.157 -11.198  1.00 28.12           C
ANISOU 4037  C   GLY E 335    2593  3273  4817   -224   346   -983           C
ATOM   4038  O   GLY E 335      17.901 -23.072 -10.736  1.00 29.23           O
ANISOU 4038  O   GLY E 335    2627  3506  4972   -375   446  -1053           O
ATOM   4039  N   SER E 336      18.775 -21.971 -12.500  1.00 28.38           N
ANISOU 4039  N   SER E 336    2694  3267  4823   -150   176   -918           N
ATOM   4040  CA  SER E 336      18.131 -22.753 -13.569  1.00 29.07           C
ANISOU 4040  CA  SER E 336    2710  3437  4900   -217    65   -954           C
ATOM   4041  CB  SER E 336      16.621 -22.473 -13.635  1.00 31.46           C
ANISOU 4041  CB  SER E 336    2727  3891  5336   -168    -9  -1092           C
ATOM   4042  OG  SER E 336      16.347 -21.090 -13.798  1.00 31.69           O
ANISOU 4042  OG  SER E 336    2690  3901  5451    54  -132  -1084           O
ATOM   4043  C   SER E 336      18.788 -22.347 -14.882  1.00 28.45           C
ANISOU 4043  C   SER E 336    2781  3302  4725   -127  -102   -846           C
ATOM   4044  O   SER E 336      19.493 -21.345 -14.949  1.00 28.13           O
ANISOU 4044  O   SER E 336    2857  3166  4665    -7  -138   -747           O
ATOM   4045  N   SER E 337      18.584 -23.140 -15.920  1.00 28.83           N
ANISOU 4045  N   SER E 337    2834  3415  4705   -205  -194   -868           N
ATOM   4046  CA  SER E 337      19.123 -22.804 -17.221  1.00 28.54           C
ANISOU 4046  CA  SER E 337    2932  3371  4540   -140  -346   -774           C
ATOM   4047  CB  SER E 337      20.569 -23.278 -17.364  1.00 26.18           C
ANISOU 4047  CB  SER E 337    2866  2970  4113   -211  -249   -695           C
ATOM   4048  OG  SER E 337      20.653 -24.681 -17.263  1.00 28.38           O
ANISOU 4048  OG  SER E 337    3156  3248  4378   -372  -156   -782           O
ATOM   4049  C   SER E 337      18.249 -23.305 -18.353  1.00 29.78           C
ANISOU 4049  C   SER E 337    2982  3676  4656   -176  -510   -851           C
ATOM   4050  O   SER E 337      17.378 -24.160 -18.157  1.00 30.45           O
ANISOU 4050  O   SER E 337    2905  3849  4814   -290  -483   -990           O
ATOM   4051  N   ILE E 338      18.476 -22.729 -19.525  1.00 30.64           N
ANISOU 4051  N   ILE E 338    3181  3820  4639    -89  -681   -757           N
ATOM   4052  CA  ILE E 338      17.938 -23.221 -20.783  1.00 31.77           C
ANISOU 4052  CA  ILE E 338    3281  4120  4670   -132  -851   -814           C
ATOM   4053  CB  ILE E 338      17.005 -22.176 -21.446  1.00 33.98           C
ANISOU 4053  CB  ILE E 338    3438  4503  4968    41 -1101   -760           C
ATOM   4054  CG1 ILE E 338      17.737 -20.850 -21.743  1.00 32.53           C
ANISOU 4054  CG1 ILE E 338    3435  4204  4721   199 -1175   -540           C
ATOM   4055  CD1 ILE E 338      16.899 -19.806 -22.508  1.00 34.27           C
ANISOU 4055  CD1 ILE E 338    3577  4492  4952   387 -1453   -443           C
ATOM   4056  CG2 ILE E 338      15.748 -21.966 -20.580  1.00 34.20           C
ANISOU 4056  CG2 ILE E 338    3181  4582  5232   103 -1106   -883           C
ATOM   4057  C   ILE E 338      19.151 -23.626 -21.656  1.00 31.96           C
ANISOU 4057  C   ILE E 338    3543  4122  4476   -205  -826   -751           C
ATOM   4058  O   ILE E 338      20.274 -23.333 -21.307  1.00 29.56           O
ANISOU 4058  O   ILE E 338    3404  3692  4137   -193  -705   -650           O
ATOM   4059  N   LYS E 339      18.931 -24.339 -22.747  1.00 35.06           N
ANISOU 4059  N   LYS E 339    3939  4655  4729   -290  -928   -838           N
ATOM   4060  CA  LYS E 339      20.029 -24.773 -23.631  1.00 36.58           C
ANISOU 4060  CA  LYS E 339    4335  4861  4705   -363  -892   -821           C
ATOM   4061  CB  LYS E 339      20.084 -26.290 -23.805  1.00 36.71           C
ANISOU 4061  CB  LYS E 339    4342  4894  4712   -536  -805  -1027           C
ATOM   4062  CG  LYS E 339      20.066 -27.164 -22.598  1.00 37.43           C
```

FIGURE 18-118

```
ANISOU 4062  CG  LYS E 339    4380  4835  5006  -627  -622 -1118       C
ATOM   4063  CD  LYS E 339   19.853 -28.608 -23.095  1.00 40.71        C
ANISOU 4063  CD  LYS E 339    4778  5276  5414  -797  -606 -1331       C
ATOM   4064  CE  LYS E 339   19.579 -29.601 -21.976  1.00 42.52        C
ANISOU 4064  CE  LYS E 339    4945  5354  5856  -921  -452 -1418       C
ATOM   4065  NZ  LYS E 339   19.132 -30.907 -22.530  1.00 45.89        N
ANISOU 4065  NZ  LYS E 339    5332  5798  6308 -1093  -469 -1635       N
ATOM   4066  C   LYS E 339   19.787 -24.253 -25.032  1.00 39.73        C
ANISOU 4066  C   LYS E 339    4775  5437  4882  -315 -1112  -753       C
ATOM   4067  O   LYS E 339   18.632 -24.092 -25.473  1.00 41.88        O
ANISOU 4067  O   LYS E 339    4892  5855  5167  -273 -1310  -795       O
ATOM   4068  N   ARG E 340   20.885 -24.049 -25.745  1.00 40.42        N
ANISOU 4068  N   ARG E 340    5065  5535  4757  -334 -1077  -656       N
ATOM   4069  CA  ARG E 340   20.863 -23.611 -27.123  1.00 43.90        C
ANISOU 4069  CA  ARG E 340    5594  6160  4925  -320 -1258  -568       C
ATOM   4070  CB  ARG E 340   20.961 -22.081 -27.170  1.00 44.64        C
ANISOU 4070  CB  ARG E 340    5770  6188  5002  -170 -1365  -292       C
ATOM   4071  CG  ARG E 340   20.849 -21.453 -28.545  1.00 49.08        C
ANISOU 4071  CG  ARG E 340    6441  6929  5279  -142 -1581  -134       C
ATOM   4072  CD  ARG E 340   21.496 -20.082 -28.498  1.00 51.89        C
ANISOU 4072  CD  ARG E 340    6964  7138  5614   -49 -1589   158       C
ATOM   4073  NE  ARG E 340   21.220 -19.278 -29.683  1.00 56.36        N
ANISOU 4073  NE  ARG E 340    7638  7837  5940     5 -1831   373       N
ATOM   4074  CZ  ARG E 340   21.825 -18.121 -29.947  1.00 59.39        C
ANISOU 4074  CZ  ARG E 340    8212  8114  6241    48 -1858   658       C
ATOM   4075  NH1 ARG E 340   22.748 -17.647 -29.115  1.00 56.32        N
ANISOU 4075  NH1 ARG E 340    7907  7494  5997    38 -1655   729       N
ATOM   4076  NH2 ARG E 340   21.514 -17.438 -31.051  1.00 63.84        N
ANISOU 4076  NH2 ARG E 340    8887  8799  6569    90 -2097   878       N
ATOM   4077  C   ARG E 340   22.067 -24.271 -27.797  1.00 44.15        C
ANISOU 4077  C   ARG E 340    5797  6240  4738  -444 -1118  -630       C
ATOM   4078  O   ARG E 340   23.203 -24.110 -27.355  1.00 42.69        O
ANISOU 4078  O   ARG E 340    5728  5923  4568  -452  -937  -561       O
ATOM   4079  N   GLU E 341   21.819 -25.062 -28.834  1.00 46.84        N
ANISOU 4079  N   GLU E 341    6132  6780  4884  -542 -1197  -791       N
ATOM   4080  CA  GLU E 341   22.906 -25.647 -29.629  1.00 47.97        C
ANISOU 4080  CA  GLU E 341    6424  7010  4792  -651 -1074  -881       C
ATOM   4081  CB  GLU E 341   22.392 -26.781 -30.528  1.00 50.34        C
ANISOU 4081  CB  GLU E 341    6666  7504  4956  -770 -1150 -1154       C
ATOM   4082  CG  GLU E 341   23.492 -27.439 -31.354  1.00 53.33        C
ANISOU 4082  CG  GLU E 341    7181  7984  5099  -876 -1010 -1297       C
ATOM   4083  CD  GLU E 341   23.258 -28.925 -31.594  1.00 57.92        C
ANISOU 4083  CD  GLU E 341    7691  8590  5726  -998  -966 -1652       C
ATOM   4084  OE1 GLU E 341   22.554 -29.280 -32.578  1.00 60.51        O
ANISOU 4084  OE1 GLU E 341    7977  9149  5864 -1070 -1129 -1802       O
ATOM   4085  OE2 GLU E 341   23.805 -29.734 -30.804  1.00 56.96        O
ANISOU 4085  OE2 GLU E 341    7564  8249  5831 -1021  -776 -1779       O
ATOM   4086  C   GLU E 341   23.631 -24.578 -30.459  1.00 48.77        C
ANISOU 4086  C   GLU E 341    6704  7214  4614  -626 -1112  -642       C
ATOM   4087  O   GLU E 341   22.992 -23.827 -31.186  1.00 51.13        O
ANISOU 4087  O   GLU E 341    7019  7655  4752  -576 -1330  -491       O
ATOM   4088  N   GLU E 342   24.961 -24.539 -30.346  1.00 47.41        N
ANISOU 4088  N   GLU E 342    6657  6969  4389  -668  -901  -607       N
ATOM   4089  CA  GLU E 342   25.803 -23.487 -30.926  1.00 48.38        C
ANISOU 4089  CA  GLU E 342    6949  7146  4286  -674  -880  -363       C
ATOM   4090  CB  GLU E 342   26.214 -22.470 -29.845  1.00 46.46        C
ANISOU 4090  CB  GLU E 342    6731  6650  4270  -584  -806  -148       C
ATOM   4091  CG  GLU E 342   25.137 -21.435 -29.509  1.00 48.29        C
ANISOU 4091  CG  GLU E 342    6913  6795  4640  -445 -1019    45       C
ATOM   4092  CD  GLU E 342   25.495 -20.511 -28.349  1.00 45.94        C
ANISOU 4092  CD  GLU E 342    6626  6233  4596  -356  -937   198       C
ATOM   4093  OE1 GLU E 342   24.616 -20.290 -27.494  1.00 46.26        O
ANISOU 4093  OE1 GLU E 342    6536  6152  4889  -245 -1012   183       O
ATOM   4094  OE2 GLU E 342   26.637 -19.996 -28.287  1.00 46.95        O
ANISOU 4094  OE2 GLU E 342    6881  6288  4671  -406  -794   315       O
ATOM   4095  C   GLU E 342   27.072 -24.059 -31.538  1.00 48.22        C
ANISOU 4095  C   GLU E 342    7028  7239  4056  -797  -676  -486       C
ATOM   4096  O   GLU E 342   27.501 -25.153 -31.181  1.00 47.12        O
ANISOU 4096  O   GLU E 342    6828  7042  4033  -837  -521  -734       O
ATOM   4097  N   GLU E 343   27.682 -23.303 -32.446  1.00 49.43        N
ANISOU 4097  N   GLU E 343    7330  7543  3907  -857  -673  -307       N
```

FIGURE 18-119

```
ATOM    4098  CA   GLU E 343      28.980 -23.660 -32.998  1.00 49.39           C
ANISOU  4098  CA   GLU E 343     7407   7663   3698   -977   -452   -405       C
ATOM    4099  CB   GLU E 343      28.974 -23.575 -34.524  1.00 53.28           C
ANISOU  4099  CB   GLU E 343     8011   8493   3737  -1090   -528   -387       C
ATOM    4100  CG   GLU E 343      28.356 -24.787 -35.191  1.00 55.60           C
ANISOU  4100  CG   GLU E 343     8229   8984   3914  -1138   -598   -712       C
ATOM    4101  CD   GLU E 343      28.384 -24.690 -36.695  1.00 61.06           C
ANISOU  4101  CD   GLU E 343     9037  10045   4118  -1260   -671   -706       C
ATOM    4102  OE1  GLU E 343      29.354 -24.119 -37.237  1.00 63.45           O
ANISOU  4102  OE1  GLU E 343     9471  10471   4165  -1353   -536   -563       O
ATOM    4103  OE2  GLU E 343      27.437 -25.188 -37.339  1.00 64.46           O
ANISOU  4103  OE2  GLU E 343     9423  10659   4409  -1277   -862   -848       O
ATOM    4104  C    GLU E 343      30.096 -22.797 -32.435  1.00 47.41           C
ANISOU  4104  C    GLU E 343     7226   7262   3525   -983   -284   -209       C
ATOM    4105  O    GLU E 343      30.107 -21.573 -32.600  1.00 47.73           O
ANISOU  4105  O    GLU E 343     7377   7275   3484   -980   -360     94       O
ATOM    4106  N    VAL E 344      31.046 -23.454 -31.778  1.00 44.90           N
ANISOU  4106  N    VAL E 344     6843   6842   3375   -993    -63   -387       N
ATOM    4107  CA   VAL E 344      32.197 -22.761 -31.209  1.00 43.05           C
ANISOU  4107  CA   VAL E 344     6643   6486   3226  -1012    109   -252       C
ATOM    4108  CB   VAL E 344      32.331 -23.057 -29.702  1.00 39.90           C
ANISOU  4108  CB   VAL E 344     6131   5809   3220   -906    177   -321       C
ATOM    4109  CG1  VAL E 344      31.101 -22.518 -28.950  1.00 38.32           C
ANISOU  4109  CG1  VAL E 344     5899   5435   3226   -792    -14   -182       C
ATOM    4110  CG2  VAL E 344      32.487 -24.553 -29.465  1.00 38.73           C
ANISOU  4110  CG2  VAL E 344     5876   5650   3188   -889    269   -644       C
ATOM    4111  C    VAL E 344      33.490 -23.102 -31.963  1.00 44.32           C
ANISOU  4111  C    VAL E 344     6833   6849   3159  -1141    328   -377       C
ATOM    4112  O    VAL E 344      33.591 -24.158 -32.616  1.00 44.99           O
ANISOU  4112  O    VAL E 344     6878   7105   3111  -1182    386   -649       O
ATOM    4113  N    LEU E 345      34.471 -22.206 -31.883  1.00 43.87           N
ANISOU  4113  N    LEU E 345     6834   6773   3060  -1212    457   -199       N
ATOM    4114  CA   LEU E 345      35.747 -22.449 -32.550  1.00 45.58           C
ANISOU  4114  CA   LEU E 345     7050   7199   3071  -1345    689   -320       C
ATOM    4115  CB   LEU E 345      36.032 -21.390 -33.626  1.00 48.71           C
ANISOU  4115  CB   LEU E 345     7610   7796   3101  -1510    700    -58       C
ATOM    4116  CG   LEU E 345      35.431 -21.671 -35.017  1.00 53.49           C
ANISOU  4116  CG   LEU E 345     8310   8712   3302  -1592    600    -90       C
ATOM    4117  CD1  LEU E 345      35.111 -20.382 -35.775  1.00 57.03           C
ANISOU  4117  CD1  LEU E 345     8960   9243   3466  -1690    468    304       C
ATOM    4118  CD2  LEU E 345      36.333 -22.561 -35.889  1.00 56.50           C
ANISOU  4118  CD2  LEU E 345     8642   9402   3424  -1714    825   -394       C
ATOM    4119  C    LEU E 345      36.896 -22.595 -31.559  1.00 43.09           C
ANISOU  4119  C    LEU E 345     6618   6736   3019  -1317    884   -414       C
ATOM    4120  O    LEU E 345      37.045 -21.789 -30.628  1.00 41.78           O
ANISOU  4120  O    LEU E 345     6453   6357   3066  -1279    869   -231       O
ATOM    4121  N    THR E 346      37.683 -23.651 -31.742  1.00 42.92           N
ANISOU  4121  N    THR E 346     6486   6827   2994  -1323   1054   -721       N
ATOM    4122  CA   THR E 346      38.811 -23.942 -30.852  1.00 41.13           C
ANISOU  4122  CA   THR E 346     6122   6488   3017  -1274   1224   -845       C
ATOM    4123  CB   THR E 346      39.287 -25.407 -30.977  1.00 40.99           C
ANISOU  4123  CB   THR E 346     5972   6534   3070  -1207   1337  -1229       C
ATOM    4124  OG1  THR E 346      39.774 -25.630 -32.308  1.00 42.56           O
ANISOU  4124  OG1  THR E 346     6186   7057   2929  -1338   1471  -1380       O
ATOM    4125  CG2  THR E 346      38.155 -26.375 -30.640  1.00 38.07           C
ANISOU  4125  CG2  THR E 346     5595   6009   2863  -1084   1175  -1361       C
ATOM    4126  C    THR E 346      39.986 -23.035 -31.189  1.00 43.36           C
ANISOU  4126  C    THR E 346     6415   6908   3153  -1428   1402   -722       C
ATOM    4127  O    THR E 346      40.054 -22.483 -32.302  1.00 45.98           O
ANISOU  4127  O    THR E 346     6857   7467   3144  -1588   1441   -607       O
ATOM    4128  N    GLY E 347      40.919 -22.907 -30.244  1.00 42.34           N
ANISOU  4128  N    GLY E 347     6167   6654   3267  -1393   1511   -749       N
ATOM    4129  CA   GLY E 347      42.178 -22.198 -30.484  1.00 44.62           C
ANISOU  4129  CA   GLY E 347     6414   7080   3459  -1551   1710   -693       C
ATOM    4130  C    GLY E 347      42.936 -22.690 -31.716  1.00 48.49           C
ANISOU  4130  C    GLY E 347     6856   7916   3651  -1680   1913   -899       C
ATOM    4131  O    GLY E 347      43.950 -22.101 -32.104  1.00 50.47           O
ANISOU  4131  O    GLY E 347     7071   8338   3766  -1851   2101   -856       O
ATOM    4132  N    ASN E 348      42.442 -23.772 -32.316  1.00 49.38           N
ANISOU  4132  N    ASN E 348     6961   8138   3665  -1611   1882  -1139       N
ATOM    4133  CA   ASN E 348      43.017 -24.343 -33.522  1.00 53.66           C
```

FIGURE 18-120

```
ANISOU 4133  CA  ASN E 348    7459  9021  3906 -1720  2064 -1385       C
ATOM   4134  CB  ASN E 348    43.303 -25.835 -33.302  1.00 53.90       C
ANISOU 4134  CB  ASN E 348    7316  9024  4141 -1548  2123 -1804       C
ATOM   4135  CG  ASN E 348    44.284 -26.389 -34.308  1.00 57.89       C
ANISOU 4135  CG  ASN E 348    7705  9868  4422 -1639  2373 -2119       C
ATOM   4136  OD1 ASN E 348    45.044 -25.643 -34.912  1.00 61.94       O
ANISOU 4136  OD1 ASN E 348    8216 10630  4689 -1832  2550 -2031       O
ATOM   4137  ND2 ASN E 348    44.272 -27.699 -34.497  1.00 59.86       N
ANISOU 4137  ND2 ASN E 348    7856 10127  4760 -1508  2399 -2498       N
ATOM   4138  C   ASN E 348    42.113 -24.173 -34.739  1.00 55.81       C
ANISOU 4138  C   ASN E 348    7918  9505  3784 -1834  1968 -1293       C
ATOM   4139  O   ASN E 348    42.448 -24.620 -35.833  1.00 59.14       O
ANISOU 4139  O   ASN E 348    8330 10245  3896 -1941  2104 -1495       O
ATOM   4140  N   LEU E 349    40.962 -23.532 -34.544  1.00 54.75       N
ANISOU 4140  N   LEU E 349    7942  9207  3654 -1805  1726 -1000       N
ATOM   4141  CA  LEU E 349    39.927 -23.424 -35.585  1.00 56.68       C
ANISOU 4141  CA  LEU E 349    8352  9623  3560 -1871  1566  -904       C
ATOM   4142  CB  LEU E 349    40.470 -22.725 -36.850  1.00 60.70       C
ANISOU 4142  CB  LEU E 349    8981 10485  3599 -2117  1702  -766       C
ATOM   4143  CG  LEU E 349    41.305 -21.440 -36.688  1.00 61.95       C
ANISOU 4143  CG  LEU E 349    9196 10613  3728 -2277  1827  -450       C
ATOM   4144  CD1 LEU E 349    42.160 -21.185 -37.940  1.00 65.27       C
ANISOU 4144  CD1 LEU E 349    9667 11441  3693 -2540  2062  -454       C
ATOM   4145  CD2 LEU E 349    40.447 -20.215 -36.321  1.00 60.69       C
ANISOU 4145  CD2 LEU E 349    9223 10201  3636 -2262  1587    -7       C
ATOM   4146  C   LEU E 349    39.218 -24.767 -35.944  1.00 56.66       C
ANISOU 4146  C   LEU E 349    8297  9686  3545 -1769  1484 -1246       C
ATOM   4147  O   LEU E 349    38.866 -24.994 -37.106  1.00 59.07       O
ANISOU 4147  O   LEU E 349    8682 10278  3484 -1869  1460 -1327       O
ATOM   4148  N   GLN E 350    39.005 -25.636 -34.947  1.00 53.61       N
ANISOU 4148  N   GLN E 350    7787  9033  3550 -1586  1436 -1439       N
ATOM   4149  CA  GLN E 350    38.133 -26.811 -35.108  1.00 53.10       C
ANISOU 4149  CA  GLN E 350    7691  8940  3543 -1494  1316 -1711       C
ATOM   4150  CB  GLN E 350    38.663 -28.028 -34.332  1.00 51.62       C
ANISOU 4150  CB  GLN E 350    7339  8560  3716 -1348  1419 -2042       C
ATOM   4151  CG  GLN E 350    37.873 -29.328 -34.565  1.00 52.67       C
ANISOU 4151  CG  GLN E 350    7445  8647  3921 -1280  1324 -2357       C
ATOM   4152  CD  GLN E 350    38.338 -30.499 -33.702  1.00 50.84       C
ANISOU 4152  CD  GLN E 350    7077  8154  4087 -1123  1397 -2632       C
ATOM   4153  OE1 GLN E 350    39.291 -30.387 -32.937  1.00 49.10       O
ANISOU 4153  OE1 GLN E 350    6767  7811  4078 -1049  1513 -2603       O
ATOM   4154  NE2 GLN E 350    37.658 -31.631 -33.831  1.00 50.04       N
ANISOU 4154  NE2 GLN E 350    6962  7961  4090 -1076  1317 -2896       N
ATOM   4155  C   GLN E 350    36.738 -26.435 -34.620  1.00 51.00       C
ANISOU 4155  C   GLN E 350    7502  8477  3398 -1419  1039 -1482       C
ATOM   4156  O   GLN E 350    36.586 -25.851 -33.553  1.00 48.42       O
ANISOU 4156  O   GLN E 350    7168  7889  3341 -1337   973 -1266       O
ATOM   4157  N   THR E 351    35.720 -26.751 -35.413  1.00 52.50       N
ANISOU 4157  N   THR E 351    7754  8813  3381 -1451   877 -1545       N
ATOM   4158  CA  THR E 351    34.345 -26.457 -35.043  1.00 51.35       C
ANISOU 4158  CA  THR E 351    7647  8521  3345 -1378   610 -1367       C
ATOM   4159  CB  THR E 351    33.426 -26.373 -36.272  1.00 54.37       C
ANISOU 4159  CB  THR E 351    8122  9185  3350 -1464   430 -1351       C
ATOM   4160  OG1 THR E 351    33.904 -25.359 -37.160  1.00 57.38       O
ANISOU 4160  OG1 THR E 351    8642  9811  3347 -1597   470 -1106       O
ATOM   4161  CG2 THR E 351    31.995 -26.030 -35.851  1.00 54.10       C
ANISOU 4161  CG2 THR E 351    8091  9006  3461 -1372   144 -1173       C
ATOM   4162  C   THR E 351    33.814 -27.529 -34.107  1.00 48.97       C
ANISOU 4162  C   THR E 351    7225  7955  3425 -1251   560 -1586       C
ATOM   4163  O   THR E 351    33.904 -28.716 -34.421  1.00 49.72       O
ANISOU 4163  O   THR E 351    7258  8093  3539 -1254   623 -1930       O
ATOM   4164  N   LEU E 352    33.273 -27.098 -32.966  1.00 45.92       N
ANISOU 4164  N   LEU E 352    6814  7296  3339 -1150   455 -1389       N
ATOM   4165  CA  LEU E 352    32.556 -27.983 -32.059  1.00 44.43       C
ANISOU 4165  CA  LEU E 352    6531  6865  3485 -1055   383 -1532       C
ATOM   4166  CB  LEU E 352    33.221 -28.020 -30.676  1.00 41.32       C
ANISOU 4166  CB  LEU E 352    6073  6188  3439  -957   494 -1483       C
ATOM   4167  CG  LEU E 352    34.668 -28.498 -30.506  1.00 41.46       C
ANISOU 4167  CG  LEU E 352    6040  6188  3524  -941   718 -1642       C
ATOM   4168  CD1 LEU E 352    35.062 -28.343 -29.037  1.00 38.52       C
ANISOU 4168  CD1 LEU E 352    5612  5540  3485  -837   755 -1527       C
```

FIGURE 18-121

```
ATOM   4169  CD2 LEU E 352      34.921 -29.937 -30.990  1.00 42.58           C
ANISOU 4169  CD2 LEU E 352    6127   6363   3689   -938    799  -2023        C
ATOM   4170  C   LEU E 352      31.099 -27.545 -31.923  1.00 44.26           C
ANISOU 4170  C   LEU E 352    6514   6808   3497  -1026    139  -1372        C
ATOM   4171  O   LEU E 352      30.819 -26.372 -31.696  1.00 43.64           O
ANISOU 4171  O   LEU E 352    6483   6697   3400   -997     47  -1074        O
ATOM   4172  N   LYS E 353      30.182 -28.496 -32.077  1.00 45.32           N
ANISOU 4172  N   LYS E 353    6585   6943   3691  -1035     36  -1586        N
ATOM   4173  CA  LYS E 353      28.773 -28.271 -31.800  1.00 45.51           C
ANISOU 4173  CA  LYS E 353    6559   6921   3812  -1002   -182  -1491        C
ATOM   4174  CB  LYS E 353      27.921 -29.158 -32.701  1.00 47.91           C
ANISOU 4174  CB  LYS E 353    6823   7400   3979  -1081   -305  -1748        C
ATOM   4175  CG  LYS E 353      26.524 -28.628 -33.009  1.00 50.14           C
ANISOU 4175  CG  LYS E 353    7063   7798   4190  -1071   -572  -1626        C
ATOM   4176  CD  LYS E 353      25.789 -29.583 -33.964  1.00 53.59           C
ANISOU 4176  CD  LYS E 353    7450   8440   4472  -1172   -688  -1924        C
ATOM   4177  CE  LYS E 353      24.859 -28.824 -34.921  1.00 59.05           C
ANISOU 4177  CE  LYS E 353    8155   9414   4866  -1182   -955  -1782        C
ATOM   4178  NZ  LYS E 353      24.338 -29.667 -36.045  1.00 61.33           N
ANISOU 4178  NZ  LYS E 353    8416   9973   4912  -1300  -1066  -2081        N
ATOM   4179  C   LYS E 353      28.524 -28.604 -30.336  1.00 42.55           C
ANISOU 4179  C   LYS E 353    6095   6234   3837   -922   -146  -1482        C
ATOM   4180  O   LYS E 353      28.662 -29.747 -29.922  1.00 42.17           O
ANISOU 4180  O   LYS E 353    5995   6049   3977   -931    -59  -1705        O
ATOM   4181  N   ILE E 354      28.186 -27.597 -29.545  1.00 41.27           N
ANISOU 4181  N   ILE E 354    5923   5956   3801   -845   -209  -1222        N
ATOM   4182  CA  ILE E 354      27.891 -27.795 -28.136  1.00 39.35           C
ANISOU 4182  CA  ILE E 354    5599   5456   3897   -780   -175  -1195        C
ATOM   4183  CB  ILE E 354      28.992 -27.170 -27.205  1.00 37.50           C
ANISOU 4183  CB  ILE E 354    5404   5064   3781   -718    -28  -1037        C
ATOM   4184  CG1 ILE E 354      29.069 -25.650 -27.368  1.00 37.51           C
ANISOU 4184  CG1 ILE E 354    5473   5114   3665   -685    -92   -761        C
ATOM   4185  CD1 ILE E 354      29.800 -24.918 -26.225  1.00 35.25           C
ANISOU 4185  CD1 ILE E 354    5197   4643   3554   -625     11   -607        C
ATOM   4186  CG2 ILE E 354      30.370 -27.816 -27.461  1.00 36.99           C
ANISOU 4186  CG2 ILE E 354    5377   5012   3665   -747    157  -1184        C
ATOM   4187  C   ILE E 354      26.513 -27.229 -27.775  1.00 39.58           C
ANISOU 4187  C   ILE E 354    5544   5471   4023   -734   -358  -1077        C
ATOM   4188  O   ILE E 354      26.029 -26.280 -28.412  1.00 40.69           O
ANISOU 4188  O   ILE E 354    5712   5749   4001   -707   -510   -920        O
ATOM   4189  N   ARG E 355      25.880 -27.817 -26.764  1.00 38.29           N
ANISOU 4189  N   ARG E 355    5277   5147   4124   -726   -345  -1150        N
ATOM   4190  CA  ARG E 355      24.674 -27.225 -26.217  1.00 38.79           C
ANISOU 4190  CA  ARG E 355    5231   5189   4318   -672   -479  -1049        C
ATOM   4191  CB  ARG E 355      23.713 -28.293 -25.719  1.00 39.53           C
ANISOU 4191  CB  ARG E 355    5192   5223   4605   -741   -490  -1232        C
ATOM   4192  CG  ARG E 355      23.039 -29.024 -26.844  1.00 45.52           C
ANISOU 4192  CG  ARG E 355    5905   6160   5230   -836   -612  -1430        C
ATOM   4193  CD  ARG E 355      22.085 -30.055 -26.303  1.00 53.44           C
ANISOU 4193  CD  ARG E 355    6770   7084   6450   -932   -613  -1609        C
ATOM   4194  NE  ARG E 355      22.114 -31.290 -27.088  1.00 59.58           N
ANISOU 4194  NE  ARG E 355    7564   7903   7169  -1061   -606  -1876        N
ATOM   4195  CZ  ARG E 355      21.599 -32.454 -26.686  1.00 62.66           C
ANISOU 4195  CZ  ARG E 355    7882   8169   7757  -1181   -561  -2064        C
ATOM   4196  NH1 ARG E 355      21.011 -32.555 -25.495  1.00 61.48           N
ANISOU 4196  NH1 ARG E 355    7637   7868   7853  -1201   -510  -1999        N
ATOM   4197  NH2 ARG E 355      21.672 -33.527 -27.477  1.00 65.58           N
ANISOU 4197  NH2 ARG E 355    8278   8563   8076  -1295   -561  -2326        N
ATOM   4198  C   ARG E 355      25.064 -26.273 -25.116  1.00 36.09           C
ANISOU 4198  C   ARG E 355    4905   4689   4118   -577   -408   -850        C
ATOM   4199  O   ARG E 355      25.478 -26.709 -24.035  1.00 34.96           O
ANISOU 4199  O   ARG E 355    4749   4377   4156   -577   -270   -877        O
ATOM   4200  N   VAL E 356      24.969 -24.977 -25.411  1.00 35.53           N
ANISOU 4200  N   VAL E 356    4875   4668   3958   -499   -510   -651        N
ATOM   4201  CA  VAL E 356      25.331 -23.934 -24.460  1.00 32.64           C
ANISOU 4201  CA  VAL E 356    4532   4149   3721   -411   -457   -475        C
ATOM   4202  CB  VAL E 356      25.631 -22.604 -25.178  1.00 33.72           C
ANISOU 4202  CB  VAL E 356    4781   4333   3698   -360   -549   -256        C
ATOM   4203  CG1 VAL E 356      25.785 -21.456 -24.168  1.00 31.57           C
ANISOU 4203  CG1 VAL E 356    4517   3879   3601   -265   -523    -99        C
ATOM   4204  CG2 VAL E 356      26.875 -22.756 -26.040  1.00 33.21           C
```

FIGURE 18-122

```
ANISOU 4204  CG2 VAL E 356    4859   4358   3403   -450   -446   -246        C
ATOM   4205  C   VAL E 356    24.208 -23.765 -23.447  1.00 31.55             C
ANISOU 4205  C   VAL E 356    4242   3932   3814   -346   -509   -488        C
ATOM   4206  O   VAL E 356    23.059 -23.558 -23.834  1.00 32.82             O
ANISOU 4206  O   VAL E 356    4300   4190   3980   -309   -675   -500        O
ATOM   4207  N   HIS E 357    24.545 -23.882 -22.160  1.00 28.73             N
ANISOU 4207  N   HIS E 357    3860   3421   3635   -336   -366   -497        N
ATOM   4208  CA  HIS E 357    23.592 -23.583 -21.092  1.00 27.88             C
ANISOU 4208  CA  HIS E 357    3613   3252   3728   -280   -380   -505        C
ATOM   4209  CB  HIS E 357    23.842 -24.457 -19.864  1.00 26.86             C
ANISOU 4209  CB  HIS E 357    3453   3014   3739   -344   -211   -589        C
ATOM   4210  CG  HIS E 357    23.454 -25.890 -20.068  1.00 25.78             C
ANISOU 4210  CG  HIS E 357    3270   2906   3619   -465   -186   -748        C
ATOM   4211  ND1 HIS E 357    22.343 -26.453 -19.475  1.00 27.87             N
ANISOU 4211  ND1 HIS E 357    3387   3180   4021   -525   -182   -843        N
ATOM   4212  CE1 HIS E 357    22.243 -27.719 -19.843  1.00 27.26             C
ANISOU 4212  CE1 HIS E 357    3312   3100   3943   -648   -160   -977        C
ATOM   4213  NE2 HIS E 357    23.247 -27.995 -20.658  1.00 28.04             N
ANISOU 4213  NE2 HIS E 357    3549   3196   3910   -650   -149   -990        N
ATOM   4214  CD2 HIS E 357    24.014 -26.867 -20.820  1.00 26.06             C
ANISOU 4214  CD2 HIS E 357    3383   2956   3561   -544   -159   -844        C
ATOM   4215  C   HIS E 357    23.597 -22.112 -20.736  1.00 27.57             C
ANISOU 4215  C   HIS E 357    3590   3142   3745   -155   -429   -350        C
ATOM   4216  O   HIS E 357    24.660 -21.522 -20.518  1.00 26.56             O
ANISOU 4216  O   HIS E 357    3583   2922   3587   -140   -349   -249        O
ATOM   4217  N   GLU E 358    22.399 -21.527 -20.715  1.00 28.31             N
ANISOU 4217  N   GLU E 358    3550   3275   3930    -63   -567   -348        N
ATOM   4218  CA  GLU E 358    22.216 -20.116 -20.449  1.00 28.24             C
ANISOU 4218  CA  GLU E 358    3543   3178   4010     80   -644   -222        C
ATOM   4219  CB  GLU E 358    21.452 -19.463 -21.593  1.00 30.21             C
ANISOU 4219  CB  GLU E 358    3775   3519   4186    174   -884   -133        C
ATOM   4220  CG  GLU E 358    22.112 -19.703 -22.953  1.00 31.27             C
ANISOU 4220  CG  GLU E 358    4073   3757   4051     94   -943    -48        C
ATOM   4221  CD  GLU E 358    21.291 -19.234 -24.129  1.00 35.58             C
ANISOU 4221  CD  GLU E 358    4604   4435   4480    170  -1200     41        C
ATOM   4222  OE1 GLU E 358    20.044 -19.336 -24.097  1.00 36.53             O
ANISOU 4222  OE1 GLU E 358    4532   4641   4708    242  -1341    -49        O
ATOM   4223  OE2 GLU E 358    21.915 -18.767 -25.108  1.00 40.00             O
ANISOU 4223  OE2 GLU E 358    5342   5029   4827    150  -1264    206        O
ATOM   4224  C   GLU E 358    21.481 -19.944 -19.121  1.00 28.03             C
ANISOU 4224  C   GLU E 358    3350   3095   4206    136   -577   -318        C
ATOM   4225  O   GLU E 358    20.399 -20.505 -18.923  1.00 28.19             O
ANISOU 4225  O   GLU E 358    3188   3214   4310    121   -606   -448        O
ATOM   4226  N   GLY E 359    22.095 -19.173 -18.223  1.00 26.47             N
ANISOU 4226  N   GLY E 359    3210   2755   4092    185   -480   -269        N
ATOM   4227  CA  GLY E 359    21.487 -18.828 -16.971  1.00 25.81             C
ANISOU 4227  CA  GLY E 359    2985   2630   4193    246   -409   -364        C
ATOM   4228  C   GLY E 359    22.386 -19.086 -15.810  1.00 23.40             C
ANISOU 4228  C   GLY E 359    2743   2248   3898    169   -211   -393        C
ATOM   4229  O   GLY E 359    23.253 -19.970 -15.866  1.00 23.25             O
ANISOU 4229  O   GLY E 359    2827   2236   3772     53   -119   -381        O
ATOM   4230  N   TYR E 360    22.143 -18.340 -14.742  1.00 23.60             N
ANISOU 4230  N   TYR E 360    2697   2212   4057    243   -154   -447        N
ATOM   4231  CA  TYR E 360    22.840 -18.486 -13.476  1.00 22.59             C
ANISOU 4231  CA  TYR E 360    2606   2041   3936    180     21   -491        C
ATOM   4232  CB  TYR E 360    22.563 -17.303 -12.523  1.00 24.19             C
ANISOU 4232  CB  TYR E 360    2742   2170   4279    292     47   -560        C
ATOM   4233  CG  TYR E 360    23.051 -17.586 -11.112  1.00 23.41             C
ANISOU 4233  CG  TYR E 360    2647   2087   4160    212    225   -639        C
ATOM   4234  CD1 TYR E 360    24.414 -17.521 -10.793  1.00 22.30             C
ANISOU 4234  CD1 TYR E 360    2665   1873   3936    153    290   -572        C
ATOM   4235  CE1 TYR E 360    24.866 -17.828  -9.505  1.00 23.08             C
ANISOU 4235  CE1 TYR E 360    2769   2011   3991     82    427   -634        C
ATOM   4236  CZ  TYR E 360    23.948 -18.220  -8.543  1.00 23.76             C
ANISOU 4236  CZ  TYR E 360    2717   2212   4098     51    519   -752        C
ATOM   4237  OH  TYR E 360    24.387 -18.506  -7.272  1.00 25.07             O
ANISOU 4237  OH  TYR E 360    2903   2436   4185    -28    647   -795        O
ATOM   4238  CE2 TYR E 360    22.593 -18.299  -8.837  1.00 23.70             C
ANISOU 4238  CE2 TYR E 360    2542   2282   4181     91    483   -829        C
ATOM   4239  CD2 TYR E 360    22.156 -17.984 -10.118  1.00 24.20             C
ANISOU 4239  CD2 TYR E 360    2586   2303   4305    179    326   -777        C
```

FIGURE 18-123

```
ATOM   4240  C   TYR E 360      22.448 -19.792 -12.804  1.00 22.00           C
ANISOU 4240  C   TYR E 360     2446   2074   3840     52    139   -585       C
ATOM   4241  O   TYR E 360      21.253 -20.113 -12.717  1.00 23.47           O
ANISOU 4241  O   TYR E 360     2461   2361   4097     47    124   -681       O
ATOM   4242  N   GLU E 361      23.457 -20.544 -12.352  1.00 20.15           N
ANISOU 4242  N   GLU E 361     2328   1813   3516    -52    249   -550       N
ATOM   4243  CA  GLU E 361      23.240 -21.781 -11.604  1.00 20.24           C
ANISOU 4243  CA  GLU E 361     2302   1881   3506   -182    365   -600       C
ATOM   4244  CB  GLU E 361      23.280 -23.001 -12.533  1.00 20.04           C
ANISOU 4244  CB  GLU E 361     2319   1870   3425   -274    330   -587       C
ATOM   4245  CG  GLU E 361      22.084 -23.147 -13.487  1.00 20.79           C
ANISOU 4245  CG  GLU E 361     2284   2055   3561   -270    215   -651       C
ATOM   4246  CD  GLU E 361      22.262 -24.295 -14.477  1.00 22.54           C
ANISOU 4246  CD  GLU E 361     2567   2285   3713   -366    176   -664       C
ATOM   4247  OE1 GLU E 361      23.309 -24.332 -15.160  1.00 21.63           O
ANISOU 4247  OE1 GLU E 361     2597   2118   3502   -350    153   -602       O
ATOM   4248  OE2 GLU E 361      21.336 -25.150 -14.592  1.00 25.55           O
ANISOU 4248  OE2 GLU E 361     2839   2731   4140   -464    173   -754       O
ATOM   4249  C   GLU E 361      24.332 -21.935 -10.561  1.00 19.23           C
ANISOU 4249  C   GLU E 361     2283   1704   3319   -225    479   -560       C
ATOM   4250  O   GLU E 361      25.489 -21.586 -10.802  1.00 18.49           O
ANISOU 4250  O   GLU E 361     2312   1537   3174   -195    463   -490       O
ATOM   4251  N   GLU E 362      23.965 -22.487  -9.413  1.00 19.76           N
ANISOU 4251  N   GLU E 362     2298   1827   3381   -307    593   -601       N
ATOM   4252  CA  GLU E 362      24.937 -22.899  -8.402  1.00 19.50           C
ANISOU 4252  CA  GLU E 362     2372   1771   3266   -364    684   -547       C
ATOM   4253  CB  GLU E 362      24.684 -22.172  -7.076  1.00 19.25           C
ANISOU 4253  CB  GLU E 362     2279   1811   3225   -354    772   -615       C
ATOM   4254  CG  GLU E 362      25.760 -22.371  -6.025  1.00 21.30           C
ANISOU 4254  CG  GLU E 362     2650   2069   3375   -395    835   -559       C
ATOM   4255  CD  GLU E 362      25.377 -21.770  -4.703  1.00 25.48           C
ANISOU 4255  CD  GLU E 362     3112   2708   3863   -409    932   -651       C
ATOM   4256  OE1 GLU E 362      25.884 -20.702  -4.358  1.00 29.65           O
ANISOU 4256  OE1 GLU E 362     3651   3221   4393   -334    920   -709       O
ATOM   4257  OE2 GLU E 362      24.528 -22.338  -4.008  1.00 33.55           O
ANISOU 4257  OE2 GLU E 362     4062   3839   4848   -507   1030   -680       O
ATOM   4258  C   GLU E 362      24.871 -24.422  -8.213  1.00 19.37           C
ANISOU 4258  C   GLU E 362     2397   1748   3215   -498    738   -502       C
ATOM   4259  O   GLU E 362      23.795 -24.978  -8.171  1.00 20.68           O
ANISOU 4259  O   GLU E 362     2465   1971   3423   -582    771   -549       O
ATOM   4260  N   PHE E 363      26.034 -25.068  -8.098  1.00 19.27           N
ANISOU 4260  N   PHE E 363     2522   1656   3143   -514    741   -414       N
ATOM   4261  CA  PHE E 363      26.136 -26.509  -7.875  1.00 20.25           C
ANISOU 4261  CA  PHE E 363     2717   1722   3257   -621    778   -353       C
ATOM   4262  CB  PHE E 363      26.740 -27.207  -9.116  1.00 19.58           C
ANISOU 4262  CB  PHE E 363     2705   1534   3201   -599    705   -347       C
ATOM   4263  CG  PHE E 363      25.919 -27.074 -10.368  1.00 19.78           C
ANISOU 4263  CG  PHE E 363     2651   1593   3274   -596    638   -432       C
ATOM   4264  CD1 PHE E 363      24.935 -28.007 -10.676  1.00 22.26           C
ANISOU 4264  CD1 PHE E 363     2909   1905   3645   -708    644   -486       C
ATOM   4265  CE1 PHE E 363      24.176 -27.899 -11.843  1.00 22.61           C
ANISOU 4265  CE1 PHE E 363     2868   2006   3717   -706    560   -575       C
ATOM   4266  CZ  PHE E 363      24.434 -26.853 -12.731  1.00 21.83           C
ANISOU 4266  CZ  PHE E 363     2762   1956   3576   -585    467   -582       C
ATOM   4267  CE2 PHE E 363      25.409 -25.906 -12.425  1.00 21.29           C
ANISOU 4267  CE2 PHE E 363     2764   1866   3461   -485    474   -512       C
ATOM   4268  CD2 PHE E 363      26.145 -26.028 -11.248  1.00 21.29           C
ANISOU 4268  CD2 PHE E 363     2826   1817   3445   -493    560   -452       C
ATOM   4269  C   PHE E 363      27.072 -26.809  -6.708  1.00 20.24           C
ANISOU 4269  C   PHE E 363     2818   1699   3172   -634    823   -258       C
ATOM   4270  O   PHE E 363      28.019 -26.078  -6.466  1.00 18.19           O
ANISOU 4270  O   PHE E 363     2595   1448   2868   -549    797   -245       O
ATOM   4271  N   THR E 364      26.798 -27.908  -6.012  1.00 21.35           N
ANISOU 4271  N   THR E 364     3007   1811   3294   -749    880   -184       N
ATOM   4272  CA  THR E 364      27.846 -28.619  -5.311  1.00 21.53           C
ANISOU 4272  CA  THR E 364     3165   1757   3258   -747    870    -57       C
ATOM   4273  CB  THR E 364      27.360 -29.262  -3.994  1.00 23.12           C
ANISOU 4273  CB  THR E 364     3410   2001   3374   -884    958     47       C
ATOM   4274  OG1 THR E 364      26.505 -30.365  -4.288  1.00 23.16           O
ANISOU 4274  OG1 THR E 364     3422   1920   3459  -1022    996     71       O
ATOM   4275  CG2 THR E 364      26.661 -28.251  -3.101  1.00 21.80           C
```

FIGURE 18-124

```
ANISOU 4275  CG2 THR E 364    3139  2030  3113  -919  1046   -24      C
ATOM   4276  C   THR E 364    28.359 -29.730  -6.241  1.00 21.92      C
ANISOU 4276  C   THR E 364    3296  1633  3398  -732   808   -30      C
ATOM   4277  O   THR E 364    27.586 -30.289  -7.010  1.00 21.17      O
ANISOU 4277  O   THR E 364    3168  1488  3387  -800   812   -88      O
ATOM   4278  N   MSE E 365    29.664 -30.009  -6.154  1.00 21.90      N
ANISOU 4278  N   MSE E 365    3384  1553  3386  -638   750    34      N
ATOM   4279  CA  MSE E 365    30.337 -31.060  -6.894  1.00 23.37      C
ANISOU 4279  CA  MSE E 365    3644  1570  3666  -594   695    41      C
ATOM   4280  CB  MSE E 365    31.472 -30.506  -7.757  1.00 21.74      C
ANISOU 4280  CB  MSE E 365    3414  1378  3470  -454   639   -36      C
ATOM   4281  CG  MSE E 365    31.045 -29.545  -8.842  1.00 23.13      C
ANISOU 4281  CG  MSE E 365    3502  1647  3639  -443   640  -154      C
ATOM   4282 SE   MSE E 365    32.526 -28.585  -9.625  0.90 23.40     SE
ANISOU 4282 SE   MSE E 365    3512  1739  3638  -313   602  -208     SE
ATOM   4283  CE  MSE E 365    33.771 -30.022  -9.974  1.00 18.37      C
ANISOU 4283  CE  MSE E 365    2937   958  3086  -233   569  -221      C
ATOM   4284  C   MSE E 365    30.960 -31.945  -5.849  1.00 24.00      C
ANISOU 4284  C   MSE E 365    3840  1550  3729  -592   674   197      C
ATOM   4285  O   MSE E 365    31.712 -31.448  -5.007  1.00 24.02      O
ANISOU 4285  O   MSE E 365    3857  1634  3635  -529   647   264      O
ATOM   4286  N   VAL E 366    30.647 -33.239  -5.897  1.00 24.70      N
ANISOU 4286  N   VAL E 366    4015  1459  3911  -665   674   257      N
ATOM   4287  CA  VAL E 366    31.225 -34.211  -4.985  1.00 26.44      C
ANISOU 4287  CA  VAL E 366    4372  1538  4136  -656   631   436      C
ATOM   4288  CB  VAL E 366    30.132 -34.805  -4.045  1.00 28.13      C
ANISOU 4288  CB  VAL E 366    4654  1731  4302  -858   710   576      C
ATOM   4289  CG1 VAL E 366    30.702 -35.906  -3.156  1.00 29.65      C
ANISOU 4289  CG1 VAL E 366    5023  1742  4502  -858   650   802      C
ATOM   4290  CG2 VAL E 366    29.493 -33.697  -3.201  1.00 27.64      C
ANISOU 4290  CG2 VAL E 366    4506  1933  4062  -936   796   572      C
ATOM   4291  C   VAL E 366    31.984 -35.333  -5.738  1.00 27.40      C
ANISOU 4291  C   VAL E 366    4567  1412  4432  -557   553   413      C
ATOM   4292  O   VAL E 366    31.382 -36.089  -6.501  1.00 27.59      O
ANISOU 4292  O   VAL E 366    4608  1292  4584  -633   575   335      O
ATOM   4293  N   GLY E 367    33.293 -35.428  -5.493  1.00 28.19      N
ANISOU 4293  N   GLY E 367    4697  1473  4542  -388   461   462      N
ATOM   4294  CA  GLY E 367    34.123 -36.526  -5.992  1.00 30.20      C
ANISOU 4294  CA  GLY E 367    5014  1486  4973  -261   380   446      C
ATOM   4295  C   GLY E 367    34.685 -37.405  -4.894  1.00 33.69      C
ANISOU 4295  C   GLY E 367    5595  1766  5439  -206   286   673      C
ATOM   4296  O   GLY E 367    34.376 -37.209  -3.720  1.00 34.80      O
ANISOU 4296  O   GLY E 367    5797  1996  5427  -292   292   858      O
ATOM   4297  N   LYS E 368    35.498 -38.390  -5.273  1.00 35.94      N
ANISOU 4297  N   LYS E 368    5932  1812  5911   -57   196   658      N
ATOM   4298  CA  LYS E 368    36.162 -39.264  -4.312  1.00 38.97      C
ANISOU 4298  CA  LYS E 368    6451  2010  6347    42    69   884      C
ATOM   4299  CB  LYS E 368    36.914 -40.385  -5.031  1.00 41.21      C
ANISOU 4299  CB  LYS E 368    6767  1990  6901   219   -19   796      C
ATOM   4300  CG  LYS E 368    36.054 -41.402  -5.755  1.00 44.82      C
ANISOU 4300  CG  LYS E 368    7315  2166  7548    97    41   717      C
ATOM   4301  CD  LYS E 368    36.966 -42.427  -6.402  1.00 52.13      C
ANISOU 4301  CD  LYS E 368    8260  2799  8749   311   -54   600      C
ATOM   4302  CE  LYS E 368    36.378 -43.018  -7.678  1.00 55.25      C
ANISOU 4302  CE  LYS E 368    8645  3030  9319   233    28   339      C
ATOM   4303  NZ  LYS E 368    37.081 -44.304  -8.039  1.00 58.01      N
ANISOU 4303  NZ  LYS E 368    9071  2998  9973   415   -68   265      N
ATOM   4304  C   LYS E 368    37.163 -38.513  -3.429  1.00 38.51      C
ANISOU 4304  C   LYS E 368    6337  2165  6130   175   -25   979      C
ATOM   4305  O   LYS E 368    37.330 -38.848  -2.254  1.00 40.15      O
ANISOU 4305  O   LYS E 368    6662  2346  6248   176  -113  1226      O
ATOM   4306  N   ARG E 369    37.827 -37.509  -4.010  1.00 36.39      N
ANISOU 4306  N   ARG E 369    5893  2111  5823   272   -10   786      N
ATOM   4307  CA  ARG E 369    39.003 -36.893  -3.397  1.00 36.20      C
ANISOU 4307  CA  ARG E 369    5782  2263  5708  -115   816              C
ATOM   4308  CB  ARG E 369    40.271 -37.288  -4.170  1.00 37.98      C
ANISOU 4308  CB  ARG E 369    5899  2401  6129   655  -198   665      C
ATOM   4309  CG  ARG E 369    40.565 -38.794  -4.243  1.00 41.98      C
ANISOU 4309  CG  ARG E 369    6520  2561  6871   788  -303   738      C
ATOM   4310  CD  ARG E 369    42.027 -39.098  -3.979  1.00 47.29      C
ANISOU 4310  CD  ARG E 369    7105  3211  7651  1057  -473   743      C
```

FIGURE 18-125

```
ATOM   4311  NE  ARG E 369      42.155 -39.943  -2.787  1.00 54.15           N
ANISOU 4311  NE  ARG E 369    8144   3905   8525   1121   -641   1046        N
ATOM   4312  CZ  ARG E 369      42.934 -39.702  -1.733  1.00 55.72           C
ANISOU 4312  CZ  ARG E 369    8323   4243   8606   1231   -801   1209        C
ATOM   4313  NH1 ARG E 369      43.718 -38.625  -1.680  1.00 54.95           N
ANISOU 4313  NH1 ARG E 369    8026   4461   8393   1288   -814   1079        N
ATOM   4314  NH2 ARG E 369      42.930 -40.558  -0.724  1.00 58.26           N
ANISOU 4314  NH2 ARG E 369    8832   4383   8920   1274   -956   1510        N
ATOM   4315  C   ARG E 369      38.934 -35.380  -3.308  1.00 33.75           C
ANISOU 4315  C   ARG E 369    5345   2273   5207    348    -39    717        C
ATOM   4316  O   ARG E 369      39.914 -34.725  -2.945  1.00 34.16           O
ANISOU 4316  O   ARG E 369    5295   2491   5191    450   -111    692        O
ATOM   4317  N   ALA E 370      37.792 -34.814  -3.675  1.00 31.33           N
ANISOU 4317  N   ALA E 370    5030   2041   4833    176     99    647        N
ATOM   4318  CA  ALA E 370      37.559 -33.400  -3.527  1.00 28.93           C
ANISOU 4318  CA  ALA E 370    4628   1995   4370    100    169    566        C
ATOM   4319  CB  ALA E 370      38.363 -32.620  -4.535  1.00 27.23           C
ANISOU 4319  CB  ALA E 370    4264   1875   4207    190    183    368        C
ATOM   4320  C   ALA E 370      36.067 -33.095  -3.648  1.00 28.11           C
ANISOU 4320  C   ALA E 370    4547   1924   4208    -87    299    547        C
ATOM   4321  O   ALA E 370      35.301 -33.902  -4.202  1.00 28.06           O
ANISOU 4321  O   ALA E 370    4597   1757   4307   -159    342    541        O
ATOM   4322  N   THR E 371      35.662 -31.950  -3.090  1.00 27.19           N
ANISOU 4322  N   THR E 371    4377   2016   3936   -165    354    524        N
ATOM   4323  CA  THR E 371      34.304 -31.425  -3.247  1.00 26.56           C
ANISOU 4323  CA  THR E 371    4270   2009   3814   -313    474    464        C
ATOM   4324  CB  THR E 371      33.385 -31.679  -2.005  1.00 28.20           C
ANISOU 4324  CB  THR E 371    4554   2275   3886   -460    531    605        C
ATOM   4325  OG1 THR E 371      33.794 -30.847  -0.909  1.00 29.59           O
ANISOU 4325  OG1 THR E 371    4714   2648   3883   -451    514    632        O
ATOM   4326  CG2 THR E 371      33.393 -33.154  -1.572  1.00 28.40           C
ANISOU 4326  CG2 THR E 371    4730   2103   3955   -493    486    799        C
ATOM   4327  C   THR E 371      34.395 -29.935  -3.534  1.00 25.42           C
ANISOU 4327  C   THR E 371    4005   2038   3615   -293    508    318        C
ATOM   4328  O   THR E 371      35.432 -29.303  -3.270  1.00 26.43           O
ANISOU 4328  O   THR E 371    4090   2253   3699   -209    452    292        O
ATOM   4329  N   ALA E 372      33.332 -29.363  -4.091  1.00 23.65           N
ANISOU 4329  N   ALA E 372    3723   1856   3408   -370    590    222        N
ATOM   4330  CA  ALA E 372      33.374 -27.962  -4.454  1.00 21.68           C
ANISOU 4330  CA  ALA E 372    3378   1723   3137   -344    611     98        C
ATOM   4331  CB  ALA E 372      34.062 -27.763  -5.828  1.00 20.08           C
ANISOU 4331  CB  ALA E 372    3135   1466   3029   -263    579     10        C
ATOM   4332  C   ALA E 372      32.005 -27.314  -4.448  1.00 20.75           C
ANISOU 4332  C   ALA E 372    3202   1678   3005   -430    691     32        C
ATOM   4333  O   ALA E 372      30.976 -28.000  -4.439  1.00 20.60           O
ANISOU 4333  O   ALA E 372    3192   1627   3010   -519    740     58        O
ATOM   4334  N   ILE E 373      32.007 -25.988  -4.420  1.00 19.68           N
ANISOU 4334  N   ILE E 373    2997   1635   2845   -402    704    -60        N
ATOM   4335  CA  ILE E 373      30.801 -25.212  -4.699  1.00 20.41           C
ANISOU 4335  CA  ILE E 373    3008   1776   2971   -434    756   -152        C
ATOM   4336  CB  ILE E 373      30.356 -24.310  -3.515  1.00 21.75           C
ANISOU 4336  CB  ILE E 373    3130   2078   3058   -463    816   -213        C
ATOM   4337  CG1 ILE E 373      30.315 -25.102  -2.203  1.00 22.01           C
ANISOU 4337  CG1 ILE E 373    3221   2184   2956   -546    858   -120        C
ATOM   4338  CD1 ILE E 373      29.912 -24.273  -0.985  1.00 23.87           C
ANISOU 4338  CD1 ILE E 373    3410   2587   3072   -587    931   -202        C
ATOM   4339  CG2 ILE E 373      28.992 -23.701  -3.819  1.00 22.34           C
ANISOU 4339  CG2 ILE E 373    3098   2190   3199   -479    868   -317        C
ATOM   4340  C   ILE E 373      31.126 -24.332  -5.891  1.00 19.23           C
ANISOU 4340  C   ILE E 373    2823   1587   2896   -361    711   -221        C
ATOM   4341  O   ILE E 373      32.156 -23.665  -5.899  1.00 18.51           O
ANISOU 4341  O   ILE E 373    2742   1500   2792   -313    680   -234        O
ATOM   4342  N   LEU E 374      30.252 -24.362  -6.898  1.00 18.79           N
ANISOU 4342  N   LEU E 374    2728   1502   2910   -368    705   -257        N
ATOM   4343  CA  LEU E 374      30.467 -23.673  -8.178  1.00 17.10           C
ANISOU 4343  CA  LEU E 374    2503   1253   2742   -312    653   -288        C
ATOM   4344  CB  LEU E 374      30.623 -24.697  -9.314  1.00 17.63           C
ANISOU 4344  CB  LEU E 374    2605   1264   2828   -322    623   -275        C
ATOM   4345  CG  LEU E 374      30.560 -24.218 -10.764  1.00 17.47           C
ANISOU 4345  CG  LEU E 374    2579   1243   2816   -294    572   -302        C
ATOM   4346  CD1 LEU E 374      31.820 -23.383 -11.076  1.00 17.18           C
```

FIGURE 18-126

```
ANISOU 4346  CD1 LEU E 374    2575  1203  2747   -255   564  -283       C
ATOM   4347  CD2 LEU E 374    30.469 -25.360 -11.696  1.00 17.08         C
ANISOU 4347  CD2 LEU E 374    2553  1165  2772   -323   556  -327       C
ATOM   4348  C   LEU E 374    29.286 -22.786  -8.498  1.00 16.92         C
ANISOU 4348  C   LEU E 374    2401  1258  2770   -295   642  -348       C
ATOM   4349  O   LEU E 374    28.126 -23.249  -8.481  1.00 15.98         O
ANISOU 4349  O   LEU E 374    2218  1172  2681   -335   659  -377       O
ATOM   4350  N   ARG E 375    29.570 -21.498  -8.726  1.00 16.55         N
ANISOU 4350  N   ARG E 375    2349  1192  2748   -236   611  -368       N
ATOM   4351  CA  ARG E 375    28.615 -20.620  -9.352  1.00 17.49         C
ANISOU 4351  CA  ARG E 375    2408  1298  2938   -184   562  -403       C
ATOM   4352  CB  ARG E 375    28.483 -19.295  -8.633  1.00 18.68         C
ANISOU 4352  CB  ARG E 375    2524  1428  3145   -130   572  -466       C
ATOM   4353  CG  ARG E 375    27.717 -19.389  -7.371  1.00 20.56         C
ANISOU 4353  CG  ARG E 375    2678  1751  3384   -149   650  -557       C
ATOM   4354  CD  ARG E 375    27.873 -18.091  -6.582  1.00 21.88         C
ANISOU 4354  CD  ARG E 375    2826  1893  3596    -98   670  -652       C
ATOM   4355  NE  ARG E 375    27.046 -18.192  -5.379  1.00 25.86         N
ANISOU 4355  NE  ARG E 375    3235  2515  4078   -123   763  -765       N
ATOM   4356  CZ  ARG E 375    27.146 -17.421  -4.310  1.00 26.86         C
ANISOU 4356  CZ  ARG E 375    3334  2677  4193   -112   819  -885       C
ATOM   4357  NH1 ARG E 375    28.046 -16.437  -4.266  1.00 25.55         N
ANISOU 4357  NH1 ARG E 375    3231  2415  4060    -78   782  -912       N
ATOM   4358  NH2 ARG E 375    26.320 -17.641  -3.296  1.00 29.10         N
ANISOU 4358  NH2 ARG E 375    3524  3103  4428   -151   921  -990       N
ATOM   4359  C   ARG E 375    29.014 -20.386 -10.800  1.00 18.25         C
ANISOU 4359  C   ARG E 375    2561  1348  3024   -160   485  -343       C
ATOM   4360  O   ARG E 375    30.185 -20.109 -11.131  1.00 17.38         O
ANISOU 4360  O   ARG E 375    2525  1203  2875   -168   486  -298       O
ATOM   4361  N   LYS E 376    28.012 -20.433 -11.660  1.00 18.54         N
ANISOU 4361  N   LYS E 376    2552  1405  3088   -138   418  -348       N
ATOM   4362  CA  LYS E 376    28.255 -20.335 -13.071  1.00 19.40         C
ANISOU 4362  CA  LYS E 376    2719  1506  3147   -130   341  -288       C
ATOM   4363  CB  LYS E 376    28.315 -21.771 -13.583  1.00 20.73         C
ANISOU 4363  CB  LYS E 376    2900  1723  3255   -198   357  -310       C
ATOM   4364  CG  LYS E 376    28.136 -21.939 -15.015  1.00 24.60         C
ANISOU 4364  CG  LYS E 376    3416  2255  3675   -204   277  -295       C
ATOM   4365  CD  LYS E 376    27.437 -23.258 -15.295  1.00 25.85         C
ANISOU 4365  CD  LYS E 376    3527  2461  3833   -265   272  -374       C
ATOM   4366  CE  LYS E 376    27.641 -23.566 -16.743  1.00 24.77         C
ANISOU 4366  CE  LYS E 376    3442  2383  3587   -287   210  -382       C
ATOM   4367  NZ  LYS E 376    26.874 -22.594 -17.523  1.00 26.75         N
ANISOU 4367  NZ  LYS E 376    3667  2688  3807   -233    84  -331       N
ATOM   4368  C   LYS E 376    27.119 -19.526 -13.719  1.00 19.69         C
ANISOU 4368  C   LYS E 376    2697  1543  3240    -55   230  -279       C
ATOM   4369  O   LYS E 376    26.022 -19.438 -13.178  1.00 19.19         O
ANISOU 4369  O   LYS E 376    2517  1510  3263    -17   221  -351       O
ATOM   4370  N   ALA E 377    27.402 -18.913 -14.861  1.00 19.87         N
ANISOU 4370  N   ALA E 377    2797  1542  3209    -31   144  -188       N
ATOM   4371  CA  ALA E 377    26.369 -18.220 -15.644  1.00 21.63         C
ANISOU 4371  CA  ALA E 377    2981  1768  3469     54     0  -149       C
ATOM   4372  CB  ALA E 377    26.452 -16.693 -15.458  1.00 21.14         C
ANISOU 4372  CB  ALA E 377    2959  1567  3505    144   -50   -82       C
ATOM   4373  C   ALA E 377    26.594 -18.616 -17.102  1.00 21.95         C
ANISOU 4373  C   ALA E 377    3102  1884  3355      9   -75   -74       C
ATOM   4374  O   ALA E 377    27.330 -19.549 -17.351  1.00 21.69         O
ANISOU 4374  O   ALA E 377    3116  1904  3222    -80     1  -102       O
ATOM   4375  N   THR E 378    25.972 -17.923 -18.050  1.00 23.90         N
ANISOU 4375  N   THR E 378    3362  2140  3578     76  -228    13       N
ATOM   4376  CA  THR E 378    26.139 -18.227 -19.483  1.00 25.60         C
ANISOU 4376  CA  THR E 378    3662  2460  3605     26  -310    87       C
ATOM   4377  CB  THR E 378    25.299 -17.275 -20.380  1.00 27.85         C
ANISOU 4377  CB  THR E 378    3960  2747  3875    127  -515   214       C
ATOM   4378  OG1 THR E 378    23.947 -17.261 -19.926  1.00 29.57         O
ANISOU 4378  OG1 THR E 378    4001  2984  4250    234  -608   120       O
ATOM   4379  CG2 THR E 378    25.304 -17.743 -21.851  1.00 30.08         C
ANISOU 4379  CG2 THR E 378    4315  3193  3920     64  -612   270       C
ATOM   4380  C   THR E 378    27.615 -18.190 -19.933  1.00 25.01         C
ANISOU 4380  C   THR E 378    3737  2377  3386    -74  -208   164       C
ATOM   4381  O   THR E 378    28.215 -17.115 -20.060  1.00 25.04         O
ANISOU 4381  O   THR E 378    3843  2284  3387    -70  -212   297       O
```

FIGURE 18- 127

```
ATOM    4382  N   ARG E 379      28.184 -19.373 -20.172  1.00 24.99           N
ANISOU  4382  N   ARG E 379     3740   2472   3282   -166   -114     69       N
ATOM    4383  CA  ARG E 379      29.589 -19.500 -20.611  1.00 25.62           C
ANISOU  4383  CA  ARG E 379     3921   2580   3232   -258     -1     97       C
ATOM    4384  CB  ARG E 379      29.750 -19.126 -22.102  1.00 27.18           C
ANISOU  4384  CB  ARG E 379     4227   2889   3212   -308    -73    210       C
ATOM    4385  CG  ARG E 379      28.814 -19.879 -23.053  1.00 28.80           C
ANISOU  4385  CG  ARG E 379     4399   3250   3295   -310   -189    143       C
ATOM    4386  CD  ARG E 379      29.241 -19.684 -24.521  1.00 29.35           C
ANISOU  4386  CD  ARG E 379     4591   3475   3087   -391   -225    235       C
ATOM    4387  NE  ARG E 379      30.539 -20.308 -24.733  1.00 29.26           N
ANISOU  4387  NE  ARG E 379     4615   3531   2972   -495    -44    147       N
ATOM    4388  CZ  ARG E 379      31.290 -20.180 -25.826  1.00 30.78           C
ANISOU  4388  CZ  ARG E 379     4907   3869   2920   -596      5    198       C
ATOM    4389  NH1 ARG E 379      30.879 -19.451 -26.857  1.00 32.74           N
ANISOU  4389  NH1 ARG E 379     5258   4210   2972   -620   -124    368       N
ATOM    4390  NH2 ARG E 379      32.460 -20.789 -25.883  1.00 28.70           N
ANISOU  4390  NH2 ARG E 379     4634   3667   2604   -672    184     78       N
ATOM    4391  C   ARG E 379      30.531 -18.661 -19.737  1.00 25.30           C
ANISOU  4391  C   ARG E 379     3915   2410   3286   -262     92    154       C
ATOM    4392  O   ARG E 379      31.356 -17.912 -20.253  1.00 26.75           O
ANISOU  4392  O   ARG E 379     4194   2579   3389   -319    119    264       O
ATOM    4393  N   ARG E 380      30.394 -18.803 -18.417  1.00 25.10           N
ANISOU  4393  N   ARG E 380     3810   2304   3421   -220    143     73       N
ATOM    4394  CA  ARG E 380      31.158 -18.022 -17.438  1.00 25.31           C
ANISOU  4394  CA  ARG E 380     3851   2220   3547   -222    216     92       C
ATOM    4395  CB  ARG E 380      30.500 -16.655 -17.212  1.00 26.33           C
ANISOU  4395  CB  ARG E 380     3995   2220   3788   -147    126    171       C
ATOM    4396  CG  ARG E 380      31.262 -15.682 -16.289  1.00 27.56           C
ANISOU  4396  CG  ARG E 380     4176   2243   4052   -160    190    176       C
ATOM    4397  CD  ARG E 380      30.391 -14.433 -16.058  1.00 30.89           C
ANISOU  4397  CD  ARG E 380     4602   2511   4622    -58     88    218       C
ATOM    4398  NE  ARG E 380      30.622 -13.828 -14.744  1.00 38.11           N
ANISOU  4398  NE  ARG E 380     5478   3322   5681    -38    149    120       N
ATOM    4399  CZ  ARG E 380      29.754 -13.045 -14.114  1.00 42.71           C
ANISOU  4399  CZ  ARG E 380     6009   3793   6425     71     96     61       C
ATOM    4400  NH1 ARG E 380      28.579 -12.763 -14.675  1.00 45.06           N
ANISOU  4400  NH1 ARG E 380     6275   4064   6780    186    -32    102       N
ATOM    4401  NH2 ARG E 380      30.059 -12.552 -12.914  1.00 44.78           N
ANISOU  4401  NH2 ARG E 380     6238   3985   6791     72    166    -57       N
ATOM    4402  C   ARG E 380      31.203 -18.783 -16.134  1.00 23.46           C
ANISOU  4402  C   ARG E 380     3532   1980   3404   -208    293    -29       C
ATOM    4403  O   ARG E 380      30.167 -19.189 -15.617  1.00 24.09           O
ANISOU  4403  O   ARG E 380     3534   2067   3551   -163    264    -91       O
ATOM    4404  N   LEU E 381      32.405 -19.005 -15.619  1.00 22.65           N
ANISOU  4404  N   LEU E 381     3438   1877   3293   -254    389    -57       N
ATOM    4405  CA  LEU E 381      32.583 -19.406 -14.222  1.00 21.63           C
ANISOU  4405  CA  LEU E 381     3250   1728   3240   -238    446   -133       C
ATOM    4406  CB  LEU E 381      33.941 -20.107 -14.030  1.00 21.33           C
ANISOU  4406  CB  LEU E 381     3212   1732   3162   -278    523   -167       C
ATOM    4407  CG  LEU E 381      34.244 -20.753 -12.662  1.00 19.23           C
ANISOU  4407  CG  LEU E 381     2900   1465   2942   -259    560   -221       C
ATOM    4408  CD1 LEU E 381      35.081 -21.997 -12.834  1.00 13.40           C
ANISOU  4408  CD1 LEU E 381     2152    765   2174   -259    593   -258       C
ATOM    4409  CD2 LEU E 381      34.922 -19.699 -11.796  1.00 17.93           C
ANISOU  4409  CD2 LEU E 381     2726   1273   2813   -272    577   -225       C
ATOM    4410  C   LEU E 381      32.513 -18.135 -13.379  1.00 21.99           C
ANISOU  4410  C   LEU E 381     3292   1685   3378   -213    439   -126       C
ATOM    4411  O   LEU E 381      33.301 -17.199 -13.572  1.00 23.59           O
ANISOU  4411  O   LEU E 381     3544   1833   3586   -250    450    -79       O
ATOM    4412  N   VAL E 382      31.546 -18.064 -12.477  1.00 21.86           N
ANISOU  4412  N   VAL E 382     3214   1654   3439   -161    427   -184       N
ATOM    4413  CA  VAL E 382      31.417 -16.882 -11.602  1.00 21.55           C
ANISOU  4413  CA  VAL E 382     3160   1532   3496   -127    428   -223       C
ATOM    4414  CB  VAL E 382      29.957 -16.691 -11.098  1.00 21.88           C
ANISOU  4414  CB  VAL E 382     3114   1573   3625    -48    398   -294       C
ATOM    4415  CG1 VAL E 382      29.859 -15.541 -10.076  1.00 22.19           C
ANISOU  4415  CG1 VAL E 382     3128   1534   3770     -6    417   -382       C
ATOM    4416  CG2 VAL E 382      29.020 -16.449 -12.269  1.00 20.93           C
ANISOU  4416  CG2 VAL E 382     2990   1431   3530     11    293   -231       C
ATOM    4417  C   VAL E 382      32.403 -17.045 -10.441  1.00 20.98           C
```

FIGURE 18-128

```
ANISOU 4417  C   VAL E 382    3076  1491  3404  -172   502  -285       C
ATOM   4418  O   VAL E 382    33.214 -16.165 -10.189  1.00 21.61       O
ANISOU 4418  O   VAL E 382    3184  1514  3514  -203   515  -294       O
ATOM   4419  N   GLN E 383    32.352 -18.188  -9.762  1.00 20.35       N
ANISOU 4419  N   GLN E 383    2959  1500  3272  -184   541  -319       N
ATOM   4420  CA  GLN E 383    33.239 -18.459  -8.653  1.00 20.51       C
ANISOU 4420  CA  GLN E 383    2970  1571  3251  -214   585  -358       C
ATOM   4421  CB  GLN E 383    32.825 -17.601  -7.432  1.00 22.63       C
ANISOU 4421  CB  GLN E 383    3202  1840  3555  -201   605  -454       C
ATOM   4422  CG  GLN E 383    33.753 -17.779  -6.252  1.00 28.07       C
ANISOU 4422  CG  GLN E 383    3885  2608  4173  -239   631  -498       C
ATOM   4423  CD  GLN E 383    33.698 -16.625  -5.265  1.00 36.66       C
ANISOU 4423  CD  GLN E 383    4948  3689  5291  -243   647  -622       C
ATOM   4424  OE1 GLN E 383    32.636 -15.998  -5.049  1.00 36.66       O
ANISOU 4424  OE1 GLN E 383    4916  3654  5358  -202   662  -698       O
ATOM   4425  NE2 GLN E 383    34.860 -16.332  -4.649  1.00 38.02       N
ANISOU 4425  NE2 GLN E 383    5121  3901  5423  -289   640  -665       N
ATOM   4426  C   GLN E 383    33.243 -19.938  -8.326  1.00 19.34       C
ANISOU 4426  C   GLN E 383    2817  1492  3040  -225   604  -337       C
ATOM   4427  O   GLN E 383    32.239 -20.609  -8.509  1.00 18.92       O
ANISOU 4427  O   GLN E 383    2748  1449  2993  -222   605  -329       O
ATOM   4428  N   LEU E 384    34.387 -20.445  -7.868  1.00 18.66       N
ANISOU 4428  N   LEU E 384    2739  1443  2907  -238   610  -326       N
ATOM   4429  CA  LEU E 384    34.544 -21.825  -7.460  1.00 18.10       C
ANISOU 4429  CA  LEU E 384    2681  1403  2795  -235   612  -288       C
ATOM   4430  CB  LEU E 384    35.331 -22.585  -8.546  1.00 18.49       C
ANISOU 4430  CB  LEU E 384    2743  1425  2855  -217   599  -264       C
ATOM   4431  CG  LEU E 384    35.671 -24.077  -8.334  1.00 18.11       C
ANISOU 4431  CG  LEU E 384    2716  1358  2806  -190   586  -231       C
ATOM   4432  CD1 LEU E 384    34.428 -24.981  -8.395  1.00 15.62       C
ANISOU 4432  CD1 LEU E 384    2432   995  2509  -217   597  -207       C
ATOM   4433  CD2 LEU E 384    36.728 -24.517  -9.342  1.00 17.92       C
ANISOU 4433  CD2 LEU E 384    2677  1325  2807  -156   583  -260       C
ATOM   4434  C   LEU E 384    35.349 -21.856  -6.147  1.00 19.39       C
ANISOU 4434  C   LEU E 384    2837  1632  2899  -236   602  -293       C
ATOM   4435  O   LEU E 384    36.373 -21.166  -6.044  1.00 19.75       O
ANISOU 4435  O   LEU E 384    2857  1702  2944  -238   586  -328       O
ATOM   4436  N   ILE E 385    34.898 -22.664  -5.175  1.00 19.03       N
ANISOU 4436  N   ILE E 385    2812  1624  2793  -249   609  -252       N
ATOM   4437  CA  ILE E 385    35.659 -22.991  -3.966  1.00 19.96       C
ANISOU 4437  CA  ILE E 385    2941  1820  2821  -245   576  -221       C
ATOM   4438  CB  ILE E 385    34.993 -22.480  -2.627  1.00 21.28       C
ANISOU 4438  CB  ILE E 385    3107  2094  2884  -296   612  -260       C
ATOM   4439  CG1 ILE E 385    34.558 -21.029  -2.788  1.00 21.71       C
ANISOU 4439  CG1 ILE E 385    3111  2146  2993  -305   650  -390       C
ATOM   4440  CD1 ILE E 385    33.762 -20.478  -1.643  1.00 22.98       C
ANISOU 4440  CD1 ILE E 385    3249  2408  3075  -344   707  -479       C
ATOM   4441  CG2 ILE E 385    36.012 -22.510  -1.462  1.00 21.32       C
ANISOU 4441  CG2 ILE E 385    3118  2212  2770  -293   553  -247       C
ATOM   4442  C   ILE E 385    35.839 -24.504  -3.882  1.00 20.24       C
ANISOU 4442  C   ILE E 385    3032  1811  2849  -222   542  -109       C
ATOM   4443  O   ILE E 385    34.856 -25.249  -3.881  1.00 19.69       O
ANISOU 4443  O   ILE E 385    3003  1695  2782  -261   578   -57       O
ATOM   4444  N   VAL E 386    37.097 -24.943  -3.810  1.00 19.46       N
ANISOU 4444  N   VAL E 386    2924  1714  2754  -158   472   -79       N
ATOM   4445  CA  VAL E 386    37.410 -26.350  -3.752  1.00 20.14       C
ANISOU 4445  CA  VAL E 386    3063  1721  2866  -106   420    23       C
ATOM   4446  CB  VAL E 386    38.383 -26.761  -4.859  1.00 20.24       C
ANISOU 4446  CB  VAL E 386    3030  1666  2993   -20   390   -23       C
ATOM   4447  CG1 VAL E 386    38.441 -28.280  -4.958  1.00 19.96       C
ANISOU 4447  CG1 VAL E 386    3061  1495  3030    41   346    60       C
ATOM   4448  CG2 VAL E 386    37.960 -26.147  -6.192  1.00 19.11       C
ANISOU 4448  CG2 VAL E 386    2855  1498  2906   -57   463  -116       C
ATOM   4449  C   VAL E 386    37.999 -26.803  -2.420  1.00 21.41       C
ANISOU 4449  C   VAL E 386    3261  1950  2925   -78   336   123       C
ATOM   4450  O   VAL E 386    38.857 -26.159  -1.871  1.00 19.90       O
ANISOU 4450  O   VAL E 386    3012  1873  2674   -54   282    81       O
ATOM   4451  N   SER E 387    37.500 -27.932  -1.919  1.00 23.78       N
ANISOU 4451  N   SER E 387    3661  2176  3199   -93   320   261       N
ATOM   4452  CA  SER E 387    38.069 -28.605  -0.755  1.00 26.40       C
ANISOU 4452  CA  SER E 387    4058  2542  3430   -55   216   407       C
```

FIGURE 18-129

```
ATOM   4453  CB  SER E 387      36.995 -28.748   0.300  1.00 26.98           C
ANISOU 4453  CB  SER E 387     4226   2682   3345    -183    274    511      C
ATOM   4454  OG  SER E 387      37.539 -29.206   1.517  1.00 32.13           O
ANISOU 4454  OG  SER E 387     4952   3411   3846    -163    169    663      O
ATOM   4455  C   SER E 387      38.555 -29.968  -1.228  1.00 27.98           C
ANISOU 4455  C   SER E 387     4311   2549   3769      49    138    502      C
ATOM   4456  O   SER E 387      37.824 -30.693  -1.905  1.00 28.28           O
ANISOU 4456  O   SER E 387     4407   2428   3912      14    195    518      O
ATOM   4457  N   GLY E 388      39.787 -30.324  -0.904  1.00 30.49           N
ANISOU 4457  N   GLY E 388     4601   2877   4108     182      2    545      N
ATOM   4458  CA  GLY E 388      40.414 -31.510  -1.506  1.00 31.87           C
ANISOU 4458  CA  GLY E 388     4792   2855   4464     322    -77    582      C
ATOM   4459  C   GLY E 388      41.481 -32.119  -0.645  1.00 35.20           C
ANISOU 4459  C   GLY E 388     5224   3281   4870     465   -259    711      C
ATOM   4460  O   GLY E 388      42.053 -31.431   0.193  1.00 35.40           O
ANISOU 4460  O   GLY E 388     5192   3507   4752     473   -333    715      O
ATOM   4461  N   LYS E 389      41.744 -33.416  -0.854  1.00 37.79           N
ANISOU 4461  N   LYS E 389     5625   3381   5354     584   -343    808      N
ATOM   4462  CA  LYS E 389      42.695 -34.177  -0.038  1.00 41.58           C
ANISOU 4462  CA  LYS E 389     6134   3817   5846     751   -547    967      C
ATOM   4463  CB  LYS E 389      42.453 -35.683  -0.179  1.00 43.32           C
ANISOU 4463  CB  LYS E 389     6511   3710   6238     824   -607   1121      C
ATOM   4464  CG  LYS E 389      41.149 -36.173   0.475  1.00 45.67           C
ANISOU 4464  CG  LYS E 389     7029   3907   6418     632   -541   1336      C
ATOM   4465  CD  LYS E 389      40.990 -37.698   0.334  1.00 48.65           C
ANISOU 4465  CD  LYS E 389     7573   3918   6995     695   -610   1495      C
ATOM   4466  CE  LYS E 389      39.920 -38.253   1.282  1.00 53.15           C
ANISOU 4466  CE  LYS E 389     8371   4404   7418     499   -579   1774      C
ATOM   4467  NZ  LYS E 389      39.307 -39.499   0.737  1.00 55.21           N
ANISOU 4467  NZ  LYS E 389     8779   4293   7904     458   -545   1839      N
ATOM   4468  C   LYS E 389      44.154 -33.830  -0.362  1.00 41.93           C
ANISOU 4468  C   LYS E 389     5968   3976   5988     934   -650    813      C
ATOM   4469  O   LYS E 389      45.009 -33.920   0.510  1.00 43.82           O
ANISOU 4469  O   LYS E 389     6171   4312   6166    1049   -828    906      O
ATOM   4470  N   ASP E 390      44.426 -33.440  -1.615  1.00 40.64           N
ANISOU 4470  N   ASP E 390     5659   3817   5965     951   -538    578      N
ATOM   4471  CA  ASP E 390      45.777 -33.057  -2.081  1.00 40.81           C
ANISOU 4471  CA  ASP E 390     5452   3968   6088    1091   -589    396      C
ATOM   4472  CB  ASP E 390      46.690 -34.296  -2.287  1.00 43.89           C
ANISOU 4472  CB  ASP E 390     5794   4180   6703    1343   -735    406      C
ATOM   4473  CG  ASP E 390      46.218 -35.219  -3.405  1.00 44.30           C
ANISOU 4473  CG  ASP E 390     5913   3965   6955    1376   -637    329      C
ATOM   4474  OD1 ASP E 390      45.353 -34.826  -4.203  1.00 44.98           O
ANISOU 4474  OD1 ASP E 390     6038   4044   7009    1213   -458    233      O
ATOM   4475  OD2 ASP E 390      46.724 -36.355  -3.504  1.00 48.47           O
ANISOU 4475  OD2 ASP E 390     6450   4282   7682    1574   -751    352      O
ATOM   4476  C   ASP E 390      45.746 -32.154  -3.336  1.00 38.51           C
ANISOU 4476  C   ASP E 390     5031   3767   5836     995   -404    157      C
ATOM   4477  O   ASP E 390      44.671 -31.829  -3.839  1.00 36.33           O
ANISOU 4477  O   ASP E 390     4845   3447   5510     841   -259    138      O
ATOM   4478  N   GLU E 391      46.925 -31.763  -3.828  1.00 38.93           N
ANISOU 4478  N   GLU E 391     4869   3952   5972    1081   -414    -16      N
ATOM   4479  CA  GLU E 391      47.081 -30.789  -4.922  1.00 37.97           C
ANISOU 4479  CA  GLU E 391     4618   3953   5855     972   -246   -219      C
ATOM   4480  CB  GLU E 391      48.560 -30.441  -5.133  1.00 38.98           C
ANISOU 4480  CB  GLU E 391     4490   4258   6064    1066   -286   -380      C
ATOM   4481  CG  GLU E 391      48.856 -28.960  -4.994  1.00 40.24           C
ANISOU 4481  CG  GLU E 391     4543   4643   6104     900   -222   -461      C
ATOM   4482  CD  GLU E 391      50.336 -28.644  -4.975  1.00 43.40           C
ANISOU 4482  CD  GLU E 391     4675   5236   6579     973   -281   -608      C
ATOM   4483  OE1 GLU E 391      50.699 -27.575  -4.425  1.00 48.91           O
ANISOU 4483  OE1 GLU E 391     5289   6112   7182     857   -298   -644      O
ATOM   4484  OE2 GLU E 391      51.139 -29.445  -5.512  1.00 49.31           O
ANISOU 4484  OE2 GLU E 391     5283   5963   7491    1142   -308   -707      O
ATOM   4485  C   GLU E 391      46.489 -31.257  -6.243  1.00 36.17           C
ANISOU 4485  C   GLU E 391     4442   3579   5722     947   -104   -312      C
ATOM   4486  O   GLU E 391      45.845 -30.480  -6.927  1.00 34.25           O
ANISOU 4486  O   GLU E 391     4226   3383   5403     790     37   -371      O
ATOM   4487  N   GLN E 392      46.733 -32.515  -6.596  1.00 36.79           N
ANISOU 4487  N   GLN E 392     4532   3478   5968    1108   -154   -333      N
ATOM   4488  CA  GLN E 392      46.180 -33.135  -7.801  1.00 36.36           C
```

FIGURE 18-130

```
ANISOU 4488  CA  GLN E 392    4533  3272  6008  1095   -38  -442       C
ATOM   4489  CB  GLN E 392    46.833 -34.495  -8.032  1.00 39.07       C
ANISOU 4489  CB  GLN E 392    4841  3428  6575  1320  -124  -506       C
ATOM   4490  CG  GLN E 392    46.093 -35.431  -8.959  1.00 42.17       C
ANISOU 4490  CG  GLN E 392    5347  3596  7078  1314   -46  -586       C
ATOM   4491  CD  GLN E 392    46.480 -36.877  -8.682  1.00 51.76       C
ANISOU 4491  CD  GLN E 392    6607  4534  8524  1534  -183  -558       C
ATOM   4492  OE1 GLN E 392    46.212 -37.410  -7.595  1.00 55.83       O
ANISOU 4492  OE1 GLN E 392    7265  4895  9053  1576  -325  -322       O
ATOM   4493  NE2 GLN E 392    47.145 -37.513  -9.647  1.00 54.63       N
ANISOU 4493  NE2 GLN E 392    6850  4836  9072  1680  -143  -798       N
ATOM   4494  C   GLN E 392    44.645 -33.273  -7.800  1.00 33.83       C
ANISOU 4494  C   GLN E 392    4427  2818  5610   940    22  -326       C
ATOM   4495  O   GLN E 392    44.020 -33.044  -8.836  1.00 31.93       O
ANISOU 4495  O   GLN E 392    4205  2580  5345   834   152  -432       O
ATOM   4496  N   SER E 393    44.058 -33.650  -6.657  1.00 32.93       N
ANISOU 4496  N   SER E 393    4460  2605  5446   923   -72  -113       N
ATOM   4497  CA  SER E 393    42.611 -33.725  -6.519  1.00 31.18       C
ANISOU 4497  CA  SER E 393    4411  2291  5146   759    -8    -5       C
ATOM   4498  CB  SER E 393    42.242 -34.366  -5.185  1.00 33.05       C
ANISOU 4498  CB  SER E 393    4797  2419  5340   763  -120   238       C
ATOM   4499  OG  SER E 393    42.910 -35.606  -5.020  1.00 36.61       O
ANISOU 4499  OG  SER E 393    5282  2665  5964   946  -249   295       O
ATOM   4500  C   SER E 393    41.941 -32.337  -6.624  1.00 28.79       C
ANISOU 4500  C   SER E 393    4086  2181  4671   581   102   -36       C
ATOM   4501  O   SER E 393    40.854 -32.192  -7.202  1.00 27.10       O
ANISOU 4501  O   SER E 393    3935  1933  4428   456   198   -62       O
ATOM   4502  N   ILE E 394    42.586 -31.323  -6.062  1.00 27.47       N
ANISOU 4502  N   ILE E 394    3824  2208  4405   574    76   -41       N
ATOM   4503  CA  ILE E 394    42.091 -29.953  -6.192  1.00 26.15       C
ANISOU 4503  CA  ILE E 394    3629  2193  4112   427   170   -88       C
ATOM   4504  CB  ILE E 394    42.826 -28.959  -5.223  1.00 26.34       C
ANISOU 4504  CB  ILE E 394    3570  2404  4034   417   111   -78       C
ATOM   4505  CG1 ILE E 394    42.490 -29.298  -3.766  1.00 28.07       C
ANISOU 4505  CG1 ILE E 394    3891  2627  4148   416    14    91       C
ATOM   4506  CD1 ILE E 394    43.465 -28.723  -2.752  1.00 28.88       C
ANISOU 4506  CD1 ILE E 394    3905  2906  4162   452   -94    95       C
ATOM   4507  CG2 ILE E 394    42.405 -27.519  -5.487  1.00 24.76       C
ANISOU 4507  CG2 ILE E 394    3340  2317  3749   276   210  -152       C
ATOM   4508  C   ILE E 394    42.142 -29.511  -7.661  1.00 24.62       C
ANISOU 4508  C   ILE E 394    3365  2030  3959   387   283  -247       C
ATOM   4509  O   ILE E 394    41.175 -28.957  -8.182  1.00 22.84       O
ANISOU 4509  O   ILE E 394    3189  1810  3678   272   366  -261       O
ATOM   4510  N   ALA E 395    43.257 -29.804  -8.328  1.00 25.55       N
ANISOU 4510  N   ALA E 395    3364  2176  4169   487   282  -366       N
ATOM   4511  CA  ALA E 395    43.459 -29.462  -9.732  1.00 25.07       C
ANISOU 4511  CA  ALA E 395    3232  2174  4119   445   397  -519       C
ATOM   4512  CB  ALA E 395    44.872 -29.811 -10.162  1.00 27.09       C
ANISOU 4512  CB  ALA E 395    3321  2497  4473   567   394  -657       C
ATOM   4513  C   ALA E 395    42.439 -30.156 -10.642  1.00 25.59       C
ANISOU 4513  C   ALA E 395    3403  2112  4209   408   454  -551       C
ATOM   4514  O   ALA E 395    41.894 -29.517 -11.549  1.00 23.95       O
ANISOU 4514  O   ALA E 395    3210  1966  3923   300   540  -600       O
ATOM   4515  N   GLU E 396    42.193 -31.454 -10.389  1.00 27.00       N
ANISOU 4515  N   GLU E 396    3657  2108  4496   495   393  -519       N
ATOM   4516  CA  GLU E 396    41.166 -32.229 -11.086  1.00 27.69       C
ANISOU 4516  CA  GLU E 396    3848  2051  4623   447   430  -554       C
ATOM   4517  CB  GLU E 396    41.104 -33.664 -10.542  1.00 29.27       C
ANISOU 4517  CB  GLU E 396    4134  2013  4973   547   344  -494       C
ATOM   4518  CG  GLU E 396    42.271 -34.530 -10.972  1.00 32.63       C
ANISOU 4518  CG  GLU E 396    4474  2363  5563   729   311  -631       C
ATOM   4519  CD  GLU E 396    42.372 -35.851 -10.218  1.00 36.07       C
ANISOU 4519  CD  GLU E 396    5002  2534  6168   858   191  -529       C
ATOM   4520  OE1 GLU E 396    41.525 -36.109  -9.323  1.00 38.71       O
ANISOU 4520  OE1 GLU E 396    5482  2756  6470   779   143  -330       O
ATOM   4521  OE2 GLU E 396    43.304 -36.647 -10.530  1.00 42.02       O
ANISOU 4521  OE2 GLU E 396    5684  3188  7095  1039   148  -649       O
ATOM   4522  C   GLU E 396    39.785 -31.557 -11.059  1.00 25.08       C
ANISOU 4522  C   GLU E 396    3601  1751  4176   284   471  -475       C
ATOM   4523  O   GLU E 396    39.134 -31.458 -12.082  1.00 25.02       O
ANISOU 4523  O   GLU E 396    3608  1763  4135   209   531  -560       O
```

FIGURE 18-131

```
ATOM   4524  N   ALA E 397      39.382 -31.055  -9.898  1.00 24.77           N
ANISOU 4524  N   ALA E 397    3603  1741  4069    238    435   -329          N
ATOM   4525  CA  ALA E 397      38.105 -30.350  -9.702  1.00 22.83           C
ANISOU 4525  CA  ALA E 397    3407  1538  3729    104    473   -267          C
ATOM   4526  CB  ALA E 397      37.845 -30.182  -8.227  1.00 22.80           C
ANISOU 4526  CB  ALA E 397    3447  1548  3667     81    431   -123          C
ATOM   4527  C   ALA E 397      38.054 -29.011 -10.421  1.00 21.75           C
ANISOU 4527  C   ALA E 397    3209  1549  3504     43    529   -331          C
ATOM   4528  O   ALA E 397      37.043 -28.663 -11.030  1.00 22.91           O
ANISOU 4528  O   ALA E 397    3380  1710  3614    -37    562   -349          O
ATOM   4529  N   ILE E 398      39.136 -28.247 -10.344  1.00 20.67           N
ANISOU 4529  N   ILE E 398    2993  1518  3341     75    531   -358          N
ATOM   4530  CA  ILE E 398      39.245 -27.004 -11.079  1.00 19.58           C
ANISOU 4530  CA  ILE E 398    2812  1492  3134      8    585   -403          C
ATOM   4531  CB  ILE E 398      40.575 -26.213 -10.741  1.00 19.57           C
ANISOU 4531  CB  ILE E 398    2713  1599  3124     24    586   -429          C
ATOM   4532  CG1 ILE E 398      40.619 -25.880  -9.246  1.00 18.51           C
ANISOU 4532  CG1 ILE E 398    2582  1481  2970     32    523   -352          C
ATOM   4533  CD1 ILE E 398      41.963 -25.363  -8.757  1.00 20.95           C
ANISOU 4533  CD1 ILE E 398    2779  1896  3284     56    495   -393          C
ATOM   4534  CG2 ILE E 398      40.655 -24.936 -11.565  1.00 17.52           C
ANISOU 4534  CG2 ILE E 398    2432  1422  2802    -73    651   -453          C
ATOM   4535  C   ILE E 398      39.063 -27.223 -12.597  1.00 19.20           C
ANISOU 4535  C   ILE E 398    2768  1457  3070    -19    639   -494          C
ATOM   4536  O   ILE E 398      38.259 -26.545 -13.226  1.00 17.87           O
ANISOU 4536  O   ILE E 398    2634  1320  2835    -95    659   -479          O
ATOM   4537  N   ILE E 399      39.791 -28.190 -13.148  1.00 20.46           N
ANISOU 4537  N   ILE E 399    2890  1594  3288     52    653   -593          N
ATOM   4538  CA  ILE E 399      39.703 -28.555 -14.570  1.00 20.68           C
ANISOU 4538  CA  ILE E 399    2920  1655  3284     28    710   -714          C
ATOM   4539  CB  ILE E 399      40.619 -29.774 -14.904  1.00 22.08           C
ANISOU 4539  CB  ILE E 399    3039  1784  3565    141    723   -855          C
ATOM   4540  CG1 ILE E 399      42.093 -29.371 -14.774  1.00 21.85           C
ANISOU 4540  CG1 ILE E 399    2876  1872  3554    198    754   -907          C
ATOM   4541  CD1 ILE E 399      43.088 -30.515 -14.781  1.00 23.92           C
ANISOU 4541  CD1 ILE E 399    3050  2078  3961    353    742  -1039          C
ATOM   4542  CG2 ILE E 399      40.306 -30.345 -16.312  1.00 21.12           C
ANISOU 4542  CG2 ILE E 399    2936  1684  3405    110    780  -1011          C
ATOM   4543  C   ILE E 399      38.254 -28.856 -14.984  1.00 21.30           C
ANISOU 4543  C   ILE E 399    3087  1671  3335    -37    690   -699          C
ATOM   4544  O   ILE E 399      37.753 -28.319 -15.969  1.00 21.55           O
ANISOU 4544  O   ILE E 399    3137  1788  3263   -112    713   -722          O
ATOM   4545  N   VAL E 400      37.593 -29.728 -14.229  1.00 21.79           N
ANISOU 4545  N   VAL E 400    3203  1590  3488    -18    641   -655          N
ATOM   4546  CA  VAL E 400      36.210 -30.104 -14.507  1.00 21.47           C
ANISOU 4546  CA  VAL E 400    3221  1492  3445    -94    623   -654          C
ATOM   4547  CB  VAL E 400      35.728 -31.255 -13.542  1.00 21.73           C
ANISOU 4547  CB  VAL E 400    3313  1344  3600    -85    586   -598          C
ATOM   4548  CG1 VAL E 400      34.263 -31.478 -13.660  1.00 19.99           C
ANISOU 4548  CG1 VAL E 400    3126  1090  3380   -194    578   -590          C
ATOM   4549  CG2 VAL E 400      36.493 -32.517 -13.815  1.00 21.84           C
ANISOU 4549  CG2 VAL E 400    3339  1224  3736      3    579   -696          C
ATOM   4550  C   VAL E 400      35.249 -28.902 -14.461  1.00 20.50           C
ANISOU 4550  C   VAL E 400    3099  1460  3229   -173    613   -571          C
ATOM   4551  O   VAL E 400      34.363 -28.774 -15.302  1.00 20.28           O
ANISOU 4551  O   VAL E 400    3080  1476  3150   -232    600   -610          O
ATOM   4552  N   ALA E 401      35.406 -28.048 -13.458  1.00 19.91           N
ANISOU 4552  N   ALA E 401    3010  1412  3141   -166    607   -470          N
ATOM   4553  CA  ALA E 401      34.606 -26.819 -13.352  1.00 19.36           C
ANISOU 4553  CA  ALA E 401    2933  1408  3014   -214    597   -410          C
ATOM   4554  CB  ALA E 401      34.872 -26.101 -12.008  1.00 17.52           C
ANISOU 4554  CB  ALA E 401    2687  1183  2788   -199    596   -333          C
ATOM   4555  C   ALA E 401      34.832 -25.862 -14.533  1.00 19.87           C
ANISOU 4555  C   ALA E 401    2992  1566  2990   -237    605   -427          C
ATOM   4556  O   ALA E 401      33.877 -25.259 -15.044  1.00 19.29           O
ANISOU 4556  O   ALA E 401    2928  1525  2877   -270    570   -403          O
ATOM   4557  N   MSE E 402      36.089 -25.714 -14.954  1.00 20.42           N
ANISOU 4557  N   MSE E 402    3042  1687  3029   -222    647   -461          N
ATOM   4558  CA  MSE E 402      36.416 -24.804 -16.059  1.00 21.29           C
ANISOU 4558  CA  MSE E 402    3161  1895  3034   -271    672   -454          C
ATOM   4559  CB  MSE E 402      37.926 -24.599 -16.154  1.00 21.70           C
```

FIGURE 18-132

```
ANISOU 4559  CB   MSE E 402     3161  2012  3074   -271    741   -491           C
ATOM   4560  CG   MSE E 402     38.500 -23.683 -15.106  1.00 22.22              C
ANISOU 4560  CG   MSE E 402     3194  2063  3185   -274    741   -428           C
ATOM   4561  SE   MSE E 402     40.412 -23.696 -15.293  0.90 27.13              SE
ANISOU 4561  SE   MSE E 402     3703  2793  3811   -278    825   -514           SE
ATOM   4562  CE   MSE E 402     40.877 -22.320 -13.992  1.00 24.57              C
ANISOU 4562  CE   MSE E 402     3347  2452  3536   -321    801   -441           C
ATOM   4563  C    MSE E 402     35.859 -25.299 -17.400  1.00 20.61              C
ANISOU 4563  C    MSE E 402     3105  1865  2859   -305    663   -518           C
ATOM   4564  O    MSE E 402     35.362 -24.495 -18.187  1.00 19.44              O
ANISOU 4564  O    MSE E 402     2995  1781  2610   -352    634   -461           O
ATOM   4565  N    VAL E 403     35.951 -26.621 -17.650  1.00 20.69              N
ANISOU 4565  N    VAL E 403     3106  1848  2909   -277    678   -639           N
ATOM   4566  CA   VAL E 403     35.357 -27.238 -18.838  1.00 21.22              C
ANISOU 4566  CA   VAL E 403     3197  1968  2897   -315    663   -740           C
ATOM   4567  CB   VAL E 403     35.749 -28.745 -19.039  1.00 22.85              C
ANISOU 4567  CB   VAL E 403     3389  2108  3184   -275    696   -911           C
ATOM   4568  CG1  VAL E 403     34.962 -29.365 -20.219  1.00 22.24              C
ANISOU 4568  CG1  VAL E 403     3339  2087  3026   -332    670  -1042           C
ATOM   4569  CG2  VAL E 403     37.257 -28.917 -19.283  1.00 22.02              C
ANISOU 4569  CG2  VAL E 403     3230  2058  3078   -225    785  -1003           C
ATOM   4570  C    VAL E 403     33.831 -27.076 -18.810  1.00 21.70              C
ANISOU 4570  C    VAL E 403     3278  2007  2959   -349    573   -688           C
ATOM   4571  O    VAL E 403     33.223 -26.611 -19.775  1.00 22.35              O
ANISOU 4571  O    VAL E 403     3382  2190  2919   -393    524   -677           O
ATOM   4572  N    PHE E 404     33.229 -27.437 -17.677  1.00 21.32              N
ANISOU 4572  N    PHE E 404     3216  1843  3042   -331    550   -651           N
ATOM   4573  CA   PHE E 404     31.791 -27.400 -17.481  1.00 21.21              C
ANISOU 4573  CA   PHE E 404     3184  1815  3059   -366    483   -626           C
ATOM   4574  CB   PHE E 404     31.482 -27.898 -16.078  1.00 20.30              C
ANISOU 4574  CB   PHE E 404     3054  1582  3076   -361    502   -585           C
ATOM   4575  CG   PHE E 404     30.035 -27.900 -15.746  1.00 19.75              C
ANISOU 4575  CG   PHE E 404     2939  1514  3051   -412    461   -575           C
ATOM   4576  CD1  PHE E 404     29.247 -29.023 -16.055  1.00 19.38              C
ANISOU 4576  CD1  PHE E 404     2879  1427  3057   -483    446   -667           C
ATOM   4577  CE1  PHE E 404     27.907 -29.040 -15.754  1.00 19.00              C
ANISOU 4577  CE1  PHE E 404     2759  1402  3058   -547    417   -672           C
ATOM   4578  CZ   PHE E 404     27.319 -27.946 -15.109  1.00 19.40              C
ANISOU 4578  CZ   PHE E 404     2745  1515  3110   -518    407   -596           C
ATOM   4579  CE2  PHE E 404     28.097 -26.822 -14.789  1.00 17.30              C
ANISOU 4579  CE2  PHE E 404     2507  1267  2799   -435    418   -512           C
ATOM   4580  CD2  PHE E 404     29.458 -26.815 -15.107  1.00 15.18              C
ANISOU 4580  CD2  PHE E 404     2315   974  2477   -394    445   -496           C
ATOM   4581  C    PHE E 404     31.176 -26.003 -17.703  1.00 21.45              C
ANISOU 4581  C    PHE E 404     3204  1924  3023   -364    423   -525           C
ATOM   4582  O    PHE E 404     30.026 -25.880 -18.163  1.00 22.44              O
ANISOU 4582  O    PHE E 404     3300  2097  3129   -384    344   -535           O
ATOM   4583  N    SER E 405     31.953 -24.969 -17.400  1.00 21.06              N
ANISOU 4583  N    SER E 405     3173  1878  2951   -336    451   -437           N
ATOM   4584  CA   SER E 405     31.531 -23.571 -17.521  1.00 21.22              C
ANISOU 4584  CA   SER E 405     3201  1919  2941   -322    396   -331           C
ATOM   4585  CB   SER E 405     32.564 -22.651 -16.867  1.00 20.19              C
ANISOU 4585  CB   SER E 405     3090  1748  2835   -309    450   -261           C
ATOM   4586  OG   SER E 405     33.724 -22.537 -17.685  1.00 22.95              O
ANISOU 4586  OG   SER E 405     3477  2159  3084   -349    505   -260           O
ATOM   4587  C    SER E 405     31.306 -23.154 -18.975  1.00 22.42              C
ANISOU 4587  C    SER E 405     3398  2173  2949   -348    331   -301           C
ATOM   4588  O    SER E 405     30.560 -22.202 -19.254  1.00 23.42              O
ANISOU 4588  O    SER E 405     3532  2307  3060   -324    239   -211           O
ATOM   4589  N    GLN E 406     31.952 -23.865 -19.900  1.00 23.01              N
ANISOU 4589  N    GLN E 406     3502  2329  2912   -392    374   -379           N
ATOM   4590  CA   GLN E 406     31.820 -23.613 -21.329  1.00 23.93              C
ANISOU 4590  CA   GLN E 406     3671  2581  2840   -437    323   -363           C
ATOM   4591  CB   GLN E 406     30.363 -23.731 -21.769  1.00 23.93              C
ANISOU 4591  CB   GLN E 406     3642  2627  2824   -428    184   -375           C
ATOM   4592  CG   GLN E 406     29.800 -25.108 -21.530  1.00 25.61              C
ANISOU 4592  CG   GLN E 406     3790  2817  3125   -445    190   -542           C
ATOM   4593  CD   GLN E 406     28.374 -25.265 -22.015  1.00 26.20              C
ANISOU 4593  CD   GLN E 406     3807  2964  3185   -456     52   -581           C
ATOM   4594  OE1  GLN E 406     27.534 -24.417 -21.751  1.00 27.21              O
ANISOU 4594  OE1  GLN E 406     3891  3085  3361   -406    -42   -484           O
```

FIGURE 18-133

```
ATOM   4595  NE2 GLN E 406      28.100 -26.358 -22.741  1.00 26.20           N
ANISOU 4595  NE2 GLN E 406     3793   3035   3128   -519     35   -744       N
ATOM   4596  C   GLN E 406      32.420 -22.265 -21.765  1.00 24.66           C
ANISOU 4596  C   GLN E 406     3837   2702   2830   -463    327   -203       C
ATOM   4597  O   GLN E 406      32.100 -21.780 -22.848  1.00 26.26           O
ANISOU 4597  O   GLN E 406     4104   3005   2869   -497    254   -125       O
ATOM   4598  N   GLU E 407      33.294 -21.675 -20.941  1.00 23.80           N
ANISOU 4598  N   GLU E 407     3726   2506   2810   -459    407   -149       N
ATOM   4599  CA  GLU E 407      33.961 -20.391 -21.287  1.00 25.17           C
ANISOU 4599  CA  GLU E 407     3974   2678   2913   -513    429      1       C
ATOM   4600  CB  GLU E 407      34.926 -19.945 -20.188  1.00 24.30           C
ANISOU 4600  CB  GLU E 407     3829   2469   2934   -515    519      5       C
ATOM   4601  CG  GLU E 407      34.281 -19.528 -18.878  1.00 24.55           C
ANISOU 4601  CG  GLU E 407     3821   2356   3150   -436    467     19       C
ATOM   4602  CD  GLU E 407      34.947 -18.299 -18.237  1.00 25.54           C
ANISOU 4602  CD  GLU E 407     3969   2380   3355   -464    499     96       C
ATOM   4603  OE1 GLU E 407      35.873 -17.724 -18.827  1.00 30.35           O
ANISOU 4603  OE1 GLU E 407     4626   3019   3887   -559    558    160       O
ATOM   4604  OE2 GLU E 407      34.530 -17.876 -17.153  1.00 23.13           O
ANISOU 4604  OE2 GLU E 407     3631   1969   3188   -407    470     83       O
ATOM   4605  C   GLU E 407      34.732 -20.428 -22.598  1.00 27.34           C
ANISOU 4605  C   GLU E 407     4309   3114   2966   -616    494     10       C
ATOM   4606  O   GLU E 407      35.326 -21.447 -22.949  1.00 27.53           O
ANISOU 4606  O   GLU E 407     4289   3241   2928   -640    584   -143       O
ATOM   4607  N   ASP E 408      34.720 -19.296 -23.313  1.00 30.09           N
ANISOU 4607  N   ASP E 408     4761   3478   3194   -677    453    192       N
ATOM   4608  CA  ASP E 408      35.466 -19.149 -24.567  1.00 32.41           C
ANISOU 4608  CA  ASP E 408     5129   3945   3239   -807    529    238       C
ATOM   4609  CB  ASP E 408      35.129 -17.845 -25.296  1.00 34.46           C
ANISOU 4609  CB  ASP E 408     5534   4184   3374   -865    434    495       C
ATOM   4610  CG  ASP E 408      35.833 -17.727 -26.652  1.00 38.94           C
ANISOU 4610  CG  ASP E 408     6196   4964   3636  -1025    519    562       C
ATOM   4611  OD1 ASP E 408      35.458 -18.436 -27.618  1.00 39.82           O
ANISOU 4611  OD1 ASP E 408     6324   5271   3536  -1043    486    487       O
ATOM   4612  OD2 ASP E 408      36.777 -16.908 -26.746  1.00 42.86           O
ANISOU 4612  OD2 ASP E 408     6747   5443   4095  -1150    628    682       O
ATOM   4613  C   ASP E 408      36.971 -19.282 -24.378  1.00 32.45           C
ANISOU 4613  C   ASP E 408     5078   4004   3248   -892    721    155       C
ATOM   4614  O   ASP E 408      37.656 -19.768 -25.273  1.00 34.09           O
ANISOU 4614  O   ASP E 408     5278   4400   3273   -979    829     69       O
ATOM   4615  N  ACYS E 409      37.497 -18.881 -23.224  0.50 31.13           N
ANISOU 4615  N  ACYS E 409     4853   3694   3283   -867    764    157       N
ATOM   4616  N  BCYS E 409      37.455 -18.823 -23.224  0.50 31.33           N
ANISOU 4616  N  BCYS E 409     4884   3713   3309   -867    757    167       N
ATOM   4617  CA ACYS E 409      38.945 -18.986 -22.993  0.50 31.70           C
ANISOU 4617  CA ACYS E 409     4839   3830   3375   -943    929     67       C
ATOM   4618  CA BCYS E 409      38.853 -18.961 -22.819  0.50 31.92           C
ANISOU 4618  CA BCYS E 409     4865   3831   3435   -926    915     70       C
ATOM   4619  CB ACYS E 409      39.418 -17.964 -21.963  0.50 31.37           C
ANISOU 4619  CB ACYS E 409     4782   3631   3504   -966    941    149       C
ATOM   4620  CB BCYS E 409      39.050 -18.424 -21.402  0.50 30.51           C
ANISOU 4620  CB BCYS E 409     4633   3474   3486   -876    897     85       C
ATOM   4621  SG ACYS E 409      39.457 -18.589 -20.296  0.50 30.93           S
ANISOU 4621  SG ACYS E 409     4597   3457   3698   -823    915      5       S
ATOM   4622  SG BCYS E 409      39.461 -16.682 -21.315  0.50 36.34           S
ANISOU 4622  SG BCYS E 409     5462   4091   4256  -1005    908    284       S
ATOM   4623  C  ACYS E 409      39.403 -20.401 -22.601  0.50 30.56           C
ANISOU 4623  C  ACYS E 409     4560   3745   3307   -857    994   -170       C
ATOM   4624  C  BCYS E 409      39.290 -20.414 -22.846  0.50 31.07           C
ANISOU 4624  C  BCYS E 409     4642   3832   3331   -867    989   -162       C
ATOM   4625  O  ACYS E 409      40.607 -20.690 -22.587  0.50 31.33           O
ANISOU 4625  O  ACYS E 409     4558   3935   3409   -897   1126   -280       O
ATOM   4626  O  BCYS E 409      40.354 -20.744 -23.379  0.50 32.50           O
ANISOU 4626  O  BCYS E 409     4760   4166   3424   -938   1128   -266       O
ATOM   4627  N   MSE E 410      38.447 -21.267 -22.266  1.00 28.89           N
ANISOU 4627  N   MSE E 410     4337   3470   3171   -740    899   -246       N
ATOM   4628  CA  MSE E 410      38.702 -22.687 -22.159  1.00 27.78           C
ANISOU 4628  CA  MSE E 410     4109   3364   3084   -665    940   -452       C
ATOM   4629  CB  MSE E 410      37.602 -23.336 -21.317  1.00 25.84           C
ANISOU 4629  CB  MSE E 410     3858   2970   2988   -556    826   -475       C
ATOM   4630  CG  MSE E 410      37.745 -24.812 -21.107  1.00 24.62           C
```

FIGURE 18-134

```
ANISOU 4630  CG  MSE E 410    3640  2790  2925  -480   849  -661      C
ATOM   4631  SE  MSE E 410    36.814 -25.805 -22.457  0.90 25.74      SE
ANISOU 4631  SE  MSE E 410    3827  3028  2924  -506   808  -801      SE
ATOM   4632  CE  MSE E 410    35.017 -25.128 -22.097  1.00 23.87      C
ANISOU 4632  CE  MSE E 410    3650  2703  2716  -500   633  -631      C
ATOM   4633  C   MSE E 410    38.792 -23.291 -23.566  1.00 29.33      C
ANISOU 4633  C   MSE E 410    4324  3746  3072  -725   995  -564      C
ATOM   4634  O   MSE E 410    39.716 -24.018 -23.894  1.00 29.96      O
ANISOU 4634  O   MSE E 410    4323  3928  3131  -726  1112  -737      O
ATOM   4635  N   ILE E 411    37.828 -22.957 -24.405  1.00 30.56      N
ANISOU 4635  N   ILE E 411    4583  3960  3069  -769   906  -474      N
ATOM   4636  CA  ILE E 411    37.776 -23.470 -25.766  1.00 32.47      C
ANISOU 4636  CA  ILE E 411    4859  4406  3073  -837   938  -578      C
ATOM   4637  CB  ILE E 411    36.401 -23.150 -26.397  1.00 32.92      C
ANISOU 4637  CB  ILE E 411    5019  4490  3001  -847   769  -462      C
ATOM   4638  CG1 ILE E 411    35.373 -24.172 -25.895  1.00 33.37      C
ANISOU 4638  CG1 ILE E 411    5025  4439  3216  -745   664  -594      C
ATOM   4639  CD1 ILE E 411    33.977 -23.673 -25.783  1.00 34.15      C
ANISOU 4639  CD1 ILE E 411    5163  4473  3339  -708   481  -458      C
ATOM   4640  CG2 ILE E 411    36.431 -23.283 -27.907  1.00 35.77      C
ANISOU 4640  CG2 ILE E 411    5446  5105  3040  -954   792  -507      C
ATOM   4641  C   ILE E 411    38.973 -22.985 -26.599  1.00 34.59      C
ANISOU 4641  C   ILE E 411    5130  4868  3144  -972  1100  -571      C
ATOM   4642  O   ILE E 411    39.547 -23.735 -27.392  1.00 36.40      O
ANISOU 4642  O   ILE E 411    5312  5278  3240 -1009  1214  -766      O
ATOM   4643  N   LYS E 412    39.383 -21.744 -26.380  1.00 34.85      N
ANISOU 4643  N   LYS E 412    5209  4862  3172 -1052  1123  -363      N
ATOM   4644  CA  LYS E 412    40.525 -21.193 -27.085  1.00 36.94      C
ANISOU 4644  CA  LYS E 412    5471  5303  3261 -1213  1291  -333      C
ATOM   4645  CB  LYS E 412    40.472 -19.660 -27.055  1.00 37.70      C
ANISOU 4645  CB  LYS E 412    5690  5312  3323 -1323  1253   -33      C
ATOM   4646  CG  LYS E 412    39.344 -19.044 -27.912  1.00 38.14      C
ANISOU 4646  CG  LYS E 412    5929  5383  3179 -1358  1097   184      C
ATOM   4647  CD  LYS E 412    39.476 -19.441 -29.388  1.00 42.37      C
ANISOU 4647  CD  LYS E 412    6522  6218  3360 -1478  1167   132      C
ATOM   4648  CE  LYS E 412    38.440 -18.757 -30.263  1.00 43.95      C
ANISOU 4648  CE  LYS E 412    6909  6454  3335 -1517   992   376      C
ATOM   4649  NZ  LYS E 412    37.050 -19.198 -29.938  1.00 43.30      N
ANISOU 4649  NZ  LYS E 412    6823  6258  3371 -1341   770   345      N
ATOM   4650  C   LYS E 412    41.870 -21.724 -26.575  1.00 37.07      C
ANISOU 4650  C   LYS E 412    5308  5363  3414 -1197  1460  -534      C
ATOM   4651  O   LYS E 412    42.886 -21.588 -27.252  1.00 39.36      O
ANISOU 4651  O   LYS E 412    5545  5853  3557 -1327  1633  -594      O
ATOM   4652  N   ALA E 413    41.872 -22.336 -25.390  1.00 35.02      N
ANISOU 4652  N   ALA E 413    4949  4932  3426 -1041  1408  -635      N
ATOM   4653  CA  ALA E 413    43.087 -22.942 -24.833  1.00 34.68      C
ANISOU 4653  CA  ALA E 413    4723  4918  3536  -985  1526  -827      C
ATOM   4654  CB  ALA E 413    43.016 -22.990 -23.309  1.00 31.70      C
ANISOU 4654  CB  ALA E 413    4291  4318  3437  -852  1426  -795      C
ATOM   4655  C   ALA E 413    43.387 -24.329 -25.422  1.00 35.53      C
ANISOU 4655  C   ALA E 413    4738  5144  3617  -907  1600 -1111      C
ATOM   4656  O   ALA E 413    44.438 -24.908 -25.156  1.00 36.10      O
ANISOU 4656  O   ALA E 413    4646  5265  3807  -844  1701 -1297      O
ATOM   4657  N   VAL E 414    42.471 -24.854 -26.229  1.00 36.17      N
ANISOU 4657  N   VAL E 414    4917  5270  3556  -905  1543 -1161      N
ATOM   4658  CA  VAL E 414    42.703 -26.137 -26.896  1.00 37.60      C
ANISOU 4658  CA  VAL E 414    5026  5559  3703  -846  1616 -1457      C
ATOM   4659  CB  VAL E 414    41.425 -26.689 -27.557  1.00 37.84      C
ANISOU 4659  CB  VAL E 414    5176  5586  3615  -840  1499 -1498      C
ATOM   4660  CG1 VAL E 414    41.758 -27.878 -28.499  1.00 39.24      C
ANISOU 4660  CG1 VAL E 414    5290  5919  3703  -822  1602 -1834      C
ATOM   4661  CG2 VAL E 414    40.407 -27.088 -26.498  1.00 33.57      C
ANISOU 4661  CG2 VAL E 414    4671  4769  3316  -713  1324 -1430      C
ATOM   4662  C   VAL E 414    43.829 -26.037 -27.933  1.00 41.28      C
ANISOU 4662  C   VAL E 414    5406  6318  3960  -969  1828 -1600      C
ATOM   4663  O   VAL E 414    43.854 -25.126 -28.772  1.00 41.91      O
ANISOU 4663  O   VAL E 414    5575  6580  3769 -1151  1889 -1455      O
ATOM   4664  N   ARG E 415    44.752 -26.995 -27.862  1.00 43.28      N
ANISOU 4664  N   ARG E 415    5485  6615  4345  -866  1940 -1885      N
ATOM   4665  CA  ARG E 415    45.838 -27.092 -28.822  1.00 47.04      C
ANISOU 4665  CA  ARG E 415    5837  7389  4648  -962  2163 -2091      C
```

FIGURE 18-135

```
ATOM     4666  CB  ARG E 415      47.205 -27.002 -28.123  1.00 47.50           C
ANISOU   4666  CB  ARG E 415     5672   7467   4909   -912   2278  -2175       C
ATOM     4667  CG  ARG E 415      47.450 -25.686 -27.389  1.00 46.34           C
ANISOU   4667  CG  ARG E 415     5545   7256   4804  -1020   2250  -1881       C
ATOM     4668  CD  ARG E 415      47.536 -24.502 -28.344  1.00 49.52           C
ANISOU   4668  CD  ARG E 415     6053   7875   4887  -1292   2366  -1695       C
ATOM     4669  NE  ARG E 415      47.747 -23.254 -27.607  1.00 48.95           N
ANISOU   4669  NE  ARG E 415     6011   7694   4895  -1396   2332  -1427       N
ATOM     4670  CZ  ARG E 415      46.795 -22.365 -27.330  1.00 46.89           C
ANISOU   4670  CZ  ARG E 415     5952   7256   4608  -1446   2181  -1130       C
ATOM     4671  NH1 ARG E 415      45.553 -22.573 -27.751  1.00 46.50           N
ANISOU   4671  NH1 ARG E 415     6082   7142   4444  -1404   2044  -1050       N
ATOM     4672  NH2 ARG E 415      47.094 -21.257 -26.644  1.00 44.45           N
ANISOU   4672  NH2 ARG E 415     5654   6838   4397  -1538   2164   -932       N
ATOM     4673  C   ARG E 415      45.722 -28.376 -29.633  1.00 49.40           C
ANISOU   4673  C   ARG E 415     6100   7778   4892   -885   2213  -2430       C
ATOM     4674  O   ARG E 415      45.571 -29.466 -29.075  1.00 49.22           O
ANISOU   4674  O   ARG E 415     6023   7550   5130   -691   2135  -2605       O
ATOM     4675  N   GLY E 416      45.791 -28.237 -30.952  1.00 52.08           N
ANISOU   4675  N   GLY E 416     6480   8422   4887  -1048   2344  -2521       N
ATOM     4676  CA  GLY E 416      45.624 -29.371 -31.844  1.00 54.89           C
ANISOU   4676  CA  GLY E 416     6816   8897   5143  -1004   2397  -2865       C
ATOM     4677  C   GLY E 416      44.169 -29.796 -31.969  1.00 53.94           C
ANISOU   4677  C   GLY E 416     6874   8627   4993   -972   2190  -2820       C
ATOM     4678  O   GLY E 416      43.287 -29.229 -31.316  1.00 51.70           O
ANISOU   4678  O   GLY E 416     6715   8147   4783   -967   2007  -2522       O
ATOM     4679  N   ASP E 417      43.932 -30.798 -32.812  1.00 56.14           N
ANISOU   4679  N   ASP E 417     7149   9009   5171   -954   2224  -3142       N
ATOM     4680  CA  ASP E 417      42.594 -31.308 -33.083  1.00 55.99           C
ANISOU   4680  CA  ASP E 417     7273   8893   5107   -947   2041  -3164       C
ATOM     4681  CB  ASP E 417      42.535 -31.971 -34.471  1.00 59.31           C
ANISOU   4681  CB  ASP E 417     7703   9606   5227  -1034   2138  -3503       C
ATOM     4682  CG  ASP E 417      42.443 -30.958 -35.618  1.00 61.53           C
ANISOU   4682  CG  ASP E 417     8097  10274   5009  -1270   2196  -3338       C
ATOM     4683  OD1 ASP E 417      42.191 -29.761 -35.352  1.00 58.40           O
ANISOU   4683  OD1 ASP E 417     7803   9867   4522  -1359   2119  -2936       O
ATOM     4684  OD2 ASP E 417      42.607 -31.366 -36.801  1.00 64.87           O
ANISOU   4684  OD2 ASP E 417     8516  11011   5120  -1369   2315  -3613       O
ATOM     4685  C   ASP E 417      42.153 -32.295 -32.013  1.00 54.22           C
ANISOU   4685  C   ASP E 417     7020   8277   5303   -748   1903  -3244       C
ATOM     4686  O   ASP E 417      42.985 -32.986 -31.415  1.00 54.68           O
ANISOU   4686  O   ASP E 417     6940   8187   5651   -592   1974  -3422       O
ATOM     4687  N   LEU E 418      40.845 -32.359 -31.782  1.00 52.57           N
ANISOU   4687  N   LEU E 418     6940   7908   5127   -756   1703  -3107       N
ATOM     4688  CA  LEU E 418      40.294 -33.303 -30.826  1.00 51.40           C
ANISOU   4688  CA  LEU E 418     6787   7397   5344   -610   1576  -3164       C
ATOM     4689  CB  LEU E 418      39.353 -32.585 -29.850  1.00 48.14           C
ANISOU   4689  CB  LEU E 418     6464   6792   5037   -613   1398  -2795       C
ATOM     4690  CG  LEU E 418      39.926 -31.400 -29.056  1.00 45.99           C
ANISOU   4690  CG  LEU E 418     6170   6504   4798   -611   1421  -2486       C
ATOM     4691  CD1 LEU E 418      38.849 -30.744 -28.220  1.00 44.92           C
ANISOU   4691  CD1 LEU E 418     6125   6198   4746   -616   1247  -2179       C
ATOM     4692  CD2 LEU E 418      41.082 -31.819 -28.178  1.00 46.73           C
ANISOU   4692  CD2 LEU E 418     6131   6455   5169   -468   1509  -2568       C
ATOM     4693  C   LEU E 418      39.612 -34.486 -31.533  1.00 53.69           C
ANISOU   4693  C   LEU E 418     7109   7665   5627   -615   1533  -3488       C
ATOM     4694  O   LEU E 418      38.647 -34.299 -32.289  1.00 54.45           O
ANISOU   4694  O   LEU E 418     7301   7912   5477   -742   1440  -3471       O
ATOM     4695  N   ASN E 419      40.129 -35.693 -31.277  1.00 55.13           N
ANISOU   4695  N   ASN E 419     7208   7649   6090   -474   1588  -3786       N
ATOM     4696  CA  ASN E 419      39.644 -36.931 -31.904  1.00 57.91           C
ANISOU   4696  CA  ASN E 419     7578   7933   6493   -469   1567  -4150       C
ATOM     4697  CB  ASN E 419      40.546 -37.300 -33.088  1.00 61.18           C
ANISOU   4697  CB  ASN E 419     7904   8639   6703   -488   1763  -4536       C
ATOM     4698  CG  ASN E 419      40.444 -36.311 -34.223  1.00 62.11           C
ANISOU   4698  CG  ASN E 419     8073   9206   6320   -687   1822  -4458       C
ATOM     4699  OD1 ASN E 419      39.366 -36.093 -34.773  1.00 61.35           O
ANISOU   4699  OD1 ASN E 419     8092   9224   5995   -820   1694  -4388       O
ATOM     4700  ND2 ASN E 419      41.572 -35.692 -34.576  1.00 64.20           N
ANISOU   4700  ND2 ASN E 419     8248   9736   6409   -717   2012  -4458       N
ATOM     4701  C   ASN E 419      39.519 -38.140 -30.958  1.00 58.48           C
```

FIGURE 18-136

```
ANISOU 4701  C   ASN E 419    7640  7561  7019  -310  1493 -4262       C
ATOM   4702  O   ASN E 419   39.706 -39.289 -31.387  1.00 60.83        O
ANISOU 4702  O   ASN E 419    7906  7757  7451  -247  1539 -4636       O
ATOM   4703  N   PHE E 420   39.191 -37.883 -29.687  1.00 56.70        N
ANISOU 4703  N   PHE E 420    7451  7072  7023  -252  1380 -3940       N
ATOM   4704  CA  PHE E 420   39.084 -38.931 -28.651  1.00 57.43        C
ANISOU 4704  CA  PHE E 420    7556  6734  7531  -114  1302 -3962       C
ATOM   4705  CB  PHE E 420   38.919 -38.322 -27.244  1.00 54.05        C
ANISOU 4705  CB  PHE E 420    7156  6122  7256   -69  1207 -3556       C
ATOM   4706  CG  PHE E 420   40.157 -37.660 -26.718  1.00 53.02        C
ANISOU 4706  CG  PHE E 420    6924  6072  7150    40  1288 -3429       C
ATOM   4707  CD1 PHE E 420   40.232 -36.271 -26.623  1.00 49.71        C
ANISOU 4707  CD1 PHE E 420    6500  5880  6506   -48  1302 -3156       C
ATOM   4708  CE1 PHE E 420   41.378 -35.643 -26.140  1.00 48.97        C
ANISOU 4708  CE1 PHE E 420    6301  5865  6440    27  1377 -3055       C
ATOM   4709  CZ  PHE E 420   42.477 -36.409 -25.744  1.00 51.30        C
ANISOU 4709  CZ  PHE E 420    6475  6032  6983   212  1429 -3226       C
ATOM   4710  CE2 PHE E 420   42.419 -37.803 -25.839  1.00 54.45        C
ANISOU 4710  CE2 PHE E 420    6879  6193  7615   329  1405 -3490       C
ATOM   4711  CD2 PHE E 420   41.259 -38.425 -26.323  1.00 54.30        C
ANISOU 4711  CD2 PHE E 420    6985  6074  7573   234  1341 -3591       C
ATOM   4712  C   PHE E 420   37.958 -39.927 -28.902  1.00 59.71        C
ANISOU 4712  C   PHE E 420    7933  6829  7924  -188  1203 -4135       C
ATOM   4713  O   PHE E 420   36.885 -39.562 -29.385  1.00 59.38        O
ANISOU 4713  O   PHE E 420    7955  6933  7674  -352  1122 -4078       O
ATOM   4714  N   VAL E 421   38.221 -41.179 -28.526  1.00 62.76        N
ANISOU 4714  N   VAL E 421    8318  6873  8656   -62  1198 -4339       N
ATOM   4715  CA  VAL E 421   37.341 -42.318 -28.779  1.00 66.10        C
ANISOU 4715  CA  VAL E 421    8817  7058  9241  -128  1126 -4568       C
ATOM   4716  CB  VAL E 421   37.809 -43.068 -30.056  1.00 69.65        C
ANISOU 4716  CB  VAL E 421    9215  7633  9617  -116  1235 -5067       C
ATOM   4717  CG1 VAL E 421   37.690 -44.582 -29.918  1.00 73.52        C
ANISOU 4717  CG1 VAL E 421    9747  7695 10491   -41  1203 -5363       C
ATOM   4718  CG2 VAL E 421   37.063 -42.546 -31.282  1.00 70.73        C
ANISOU 4718  CG2 VAL E 421    9372  8169  9332  -327  1231 -5178       C
ATOM   4719  C   VAL E 421   37.312 -43.237 -27.547  1.00 66.76        C
ANISOU 4719  C   VAL E 421    8958  6647  9763   -10  1048 -4463       C
ATOM   4720  O   VAL E 421   38.339 -43.406 -26.881  1.00 67.09        O
ANISOU 4720  O   VAL E 421    8949  6536 10006   185  1081 -4409       O
ATOM   4721  N   ASN E 422   36.145 -43.820 -27.243  1.00 67.53        N
ANISOU 4721  N   ASN E 422    9155  6503  9999  -136   942 -4424       N
ATOM   4722  CA  ASN E 422   35.987 -44.671 -26.041  1.00 68.08        C
ANISOU 4722  CA  ASN E 422    9309  6098 10459   -68   865 -4271       C
ATOM   4723  CB  ASN E 422   34.522 -44.727 -25.572  1.00 67.27        C
ANISOU 4723  CB  ASN E 422    9296  5877 10386  -278   760 -4080       C
ATOM   4724  CG  ASN E 422   33.535 -44.977 -26.713  1.00 69.70        C
ANISOU 4724  CG  ASN E 422    9604  6341 10538  -481   739 -4363       C
ATOM   4725  OD1 ASN E 422   32.448 -44.388 -26.738  1.00 68.72        O
ANISOU 4725  OD1 ASN E 422    9477  6388 10245  -657   670 -4214       O
ATOM   4726  ND2 ASN E 422   33.905 -45.848 -27.657  1.00 72.67        N
ANISOU 4726  ND2 ASN E 422    9970  6669 10973  -451   789 -4791       N
ATOM   4727  C   ASN E 422   36.580 -46.085 -26.139  1.00 71.50        C
ANISOU 4727  C   ASN E 422    9766  6157 11244    78   884 -4587       C
ATOM   4728  O   ASN E 422   36.751 -46.632 -27.227  1.00 74.15        O
ANISOU 4728  O   ASN E 422   10065  6559 11547    73   946 -5000       O
ATOM   4729  N   ARG E 427   33.161 -42.328 -30.481  1.00 65.32        N
ANISOU 4729  N   ARG E 427    8875  7278  8664  -761   800 -4699       N
ATOM   4730  CA  ARG E 427   33.763 -40.998 -30.490  1.00 62.98        C
ANISOU 4730  CA  ARG E 427    8546  7283  8101  -712   849 -4431       C
ATOM   4731  CB  ARG E 427   33.673 -40.369 -31.883  1.00 65.03        C
ANISOU 4731  CB  ARG E 427    8792  8005  7911  -823   864 -4564       C
ATOM   4732  CG  ARG E 427   34.458 -39.089 -31.984  1.00 64.47        C
ANISOU 4732  CG  ARG E 427    8699  8216  7579  -784   943 -4317       C
ATOM   4733  CD  ARG E 427   33.754 -38.015 -32.796  1.00 67.22        C
ANISOU 4733  CD  ARG E 427    9082  8944  7515  -926   854 -4158       C
ATOM   4734  NE  ARG E 427   34.445 -36.739 -32.601  1.00 67.49        N
ANISOU 4734  NE  ARG E 427    9116  9147  7382  -892   917 -3843       N
ATOM   4735  CZ  ARG E 427   35.598 -36.405 -33.186  1.00 69.71        C
ANISOU 4735  CZ  ARG E 427    9366  9652  7467  -875  1082 -3922       C
ATOM   4736  NH1 ARG E 427   36.196 -37.243 -34.034  1.00 71.76        N
ANISOU 4736  NH1 ARG E 427    9587 10022  7658  -875  1208 -4324       N
```

FIGURE 18-137

```
ATOM   4737  NH2 ARG E 427      36.152 -35.226 -32.920  1.00 67.88           N
ANISOU 4737  NH2 ARG E 427    9137   9538   7117   -868   1131  -3614        N
ATOM   4738  C   ARG E 427      33.075 -40.091 -29.485  1.00 58.80           C
ANISOU 4738  C   ARG E 427    8035   6711   7596   -740    749  -3994        C
ATOM   4739  O   ARG E 427      31.865 -39.867 -29.575  1.00 58.91           O
ANISOU 4739  O   ARG E 427    8061   6791   7533   -873    626  -3912        O
ATOM   4740  N   LEU E 428      33.848 -39.555 -28.545  1.00 55.36           N
ANISOU 4740  N   LEU E 428    7586   6185   7263   -612    800  -3735        N
ATOM   4741  CA  LEU E 428      33.293 -38.797 -27.419  1.00 50.88           C
ANISOU 4741  CA  LEU E 428    7034   5531   6765   -619    721  -3349        C
ATOM   4742  CB  LEU E 428      34.399 -38.397 -26.432  1.00 48.72           C
ANISOU 4742  CB  LEU E 428    6740   5151   6618   -464    792  -3144        C
ATOM   4743  CG  LEU E 428      35.420 -39.432 -25.919  1.00 49.33           C
ANISOU 4743  CG  LEU E 428    6806   4945   6991   -304    858  -3284        C
ATOM   4744  CD1 LEU E 428      36.268 -38.834 -24.795  1.00 44.63           C
ANISOU 4744  CD1 LEU E 428    6182   4285   6491   -173    879  -3013        C
ATOM   4745  CD2 LEU E 428      34.776 -40.760 -25.451  1.00 49.60           C
ANISOU 4745  CD2 LEU E 428    6906   4603   7335   -323    795  -3387        C
ATOM   4746  C   LEU E 428      32.532 -37.565 -27.894  1.00 49.08           C
ANISOU 4746  C   LEU E 428    6802   5617   6229   -725    643  -3163        C
ATOM   4747  O   LEU E 428      32.874 -36.983 -28.932  1.00 49.55           O
ANISOU 4747  O   LEU E 428    6855   5985   5989   -757    677  -3230        O
ATOM   4748  N   ASN E 429      31.494 -37.179 -27.148  1.00 46.94           N
ANISOU 4748  N   ASN E 429    6534   5270   6032   -780    538  -2933        N
ATOM   4749  CA  ASN E 429      30.814 -35.909 -27.424  1.00 45.15           C
ANISOU 4749  CA  ASN E 429    6294   5299   5563   -837    448  -2718        C
ATOM   4750  CB  ASN E 429      29.427 -35.795 -26.731  1.00 44.53           C
ANISOU 4750  CB  ASN E 429    6183   5130   5604   -909    324  -2571        C
ATOM   4751  CG  ASN E 429      29.505 -35.650 -25.216  1.00 43.04           C
ANISOU 4751  CG  ASN E 429    5995   4702   5656   -844    356  -2335        C
ATOM   4752  OD1 ASN E 429      30.552 -35.375 -24.647  1.00 44.36           O
ANISOU 4752  OD1 ASN E 429    6185   4799   5871   -736    441  -2227        O
ATOM   4753  ND2 ASN E 429      28.369 -35.826 -24.559  1.00 44.32           N
ANISOU 4753  ND2 ASN E 429    6122   4763   5956   -921    286  -2262        N
ATOM   4754  C   ASN E 429      31.770 -34.724 -27.176  1.00 42.35           C
ANISOU 4754  C   ASN E 429    5946   5058   5088   -750    517  -2486        C
ATOM   4755  O   ASN E 429      32.811 -34.903 -26.528  1.00 41.08           O
ANISOU 4755  O   ASN E 429    5779   4756   5072   -648    619  -2464        O
ATOM   4756  N   PRO E 430      31.476 -33.549 -27.774  1.00 41.73           N
ANISOU 4756  N   PRO E 430    5879   5236   4742   -793    458  -2330        N
ATOM   4757  CA  PRO E 430      32.316 -32.355 -27.629  1.00 39.46           C
ANISOU 4757  CA  PRO E 430    5608   5050   4333   -744    520  -2107        C
ATOM   4758  CB  PRO E 430      31.423 -31.252 -28.194  1.00 40.25           C
ANISOU 4758  CB  PRO E 430    5736   5353   4205   -805    385  -1924        C
ATOM   4759  CG  PRO E 430      30.653 -31.948 -29.274  1.00 42.76           C
ANISOU 4759  CG  PRO E 430    6052   5820   4376   -896    299  -2151        C
ATOM   4760  CD  PRO E 430      30.346 -33.303 -28.705  1.00 43.03           C
ANISOU 4760  CD  PRO E 430    6044   5611   4695   -894    315  -2363        C
ATOM   4761  C   PRO E 430      32.774 -32.033 -26.201  1.00 36.38           C
ANISOU 4761  C   PRO E 430    5201   4442   4180   -650    563  -1910        C
ATOM   4762  O   PRO E 430      33.960 -31.739 -25.993  1.00 35.32           O
ANISOU 4762  O   PRO E 430    5056   4315   4049   -592    673  -1876        O
ATOM   4763  N   MSE E 431      31.873 -32.122 -25.223  1.00 34.13           N
ANISOU 4763  N   MSE E 431    4901   3985   4083   -644    482  -1799        N
ATOM   4764  CA  MSE E 431      32.236 -31.766 -23.826  1.00 31.35           C
ANISOU 4764  CA  MSE E 431    4538   3456   3919   -566    515  -1608        C
ATOM   4765  CB  MSE E 431      30.985 -31.620 -22.945  1.00 30.30           C
ANISOU 4765  CB  MSE E 431    4383   3219   3912   -594    423  -1477        C
ATOM   4766  CG  MSE E 431      30.087 -30.421 -23.323  1.00 29.63           C
ANISOU 4766  CG  MSE E 431    4282   3300   3676   -624    317  -1334        C
ATOM   4767  SE  MSE E 431      30.966 -28.722 -22.996  0.90 32.22          SE
ANISOU 4767  SE  MSE E 431    4642   3693   3906   -556    353  -1079       SE
ATOM   4768  CE  MSE E 431      31.056 -28.819 -21.067  1.00 26.36           C
ANISOU 4768  CE  MSE E 431    3867   2715   3434   -492    401   -968        C
ATOM   4769  C   MSE E 431      33.244 -32.741 -23.208  1.00 30.85           C
ANISOU 4769  C   MSE E 431    4469   3203   4050   -485    609  -1710        C
ATOM   4770  O   MSE E 431      34.119 -32.348 -22.445  1.00 29.27           O
ANISOU 4770  O   MSE E 431    4255   2950   3916   -408    662  -1595        O
ATOM   4771  N   HIS E 432      33.128 -34.014 -23.562  1.00 32.32           N
ANISOU 4771  N   HIS E 432    4662   3283   4336   -499    617  -1934        N
ATOM   4772  CA  HIS E 432      34.063 -35.044 -23.091  1.00 34.03           C
```

FIGURE 18-138

```
ANISOU 4772  CA   HIS E 432     4877  3292  4760    -399    685  -2050       C
ATOM   4773  CB   HIS E 432      33.392 -36.424 -23.076  1.00 36.39          C
ANISOU 4773  CB   HIS E 432     5209  3369  5248    -441    649  -2222       C
ATOM   4774  CG   HIS E 432      32.433 -36.595 -21.940  1.00 38.68          C
ANISOU 4774  CG   HIS E 432     5527  3471  5699    -494    584  -2041       C
ATOM   4775  ND1  HIS E 432      31.189 -35.998 -21.920  1.00 39.39          N
ANISOU 4775  ND1  HIS E 432     5597  3668  5702    -607    513  -1936       N
ATOM   4776  CE1  HIS E 432      30.584 -36.288 -20.782  1.00 39.89          C
ANISOU 4776  CE1  HIS E 432     5675  3550  5932    -643    494  -1795       C
ATOM   4777  NE2  HIS E 432      31.391 -37.043 -20.058  1.00 41.36          N
ANISOU 4777  NE2  HIS E 432     5911  3505  6297    -559    536  -1776       N
ATOM   4778  CD2  HIS E 432      32.561 -37.241 -20.754  1.00 40.10          C
ANISOU 4778  CD2  HIS E 432     5748  3382  6107    -450    584  -1933       C
ATOM   4779  C    HIS E 432      35.358 -35.061 -23.901  1.00 35.10          C
ANISOU 4779  C    HIS E 432     4973  3565  4797    -332    791  -2220       C
ATOM   4780  O    HIS E 432      36.402 -35.469 -23.410  1.00 35.53          O
ANISOU 4780  O    HIS E 432     4993  3505  5002    -212    850  -2259       O
ATOM   4781  N    GLN E 433      35.258 -34.625 -25.152  1.00 35.90          N
ANISOU 4781  N    GLN E 433     5072  3931  4639    -414    811  -2323       N
ATOM   4782  CA   GLN E 433      36.394 -34.264 -25.999  1.00 36.69          C
ANISOU 4782  CA   GLN E 433     5128  4254  4558    -397    931  -2434       C
ATOM   4783  CB   GLN E 433      35.808 -33.686 -27.294  1.00 38.40          C
ANISOU 4783  CB   GLN E 433     5382  4764  4444    -531    907  -2469       C
ATOM   4784  CG   GLN E 433      36.487 -33.958 -28.567  1.00 42.26          C
ANISOU 4784  CG   GLN E 433     5849  5489  4720    -569   1019  -2729       C
ATOM   4785  CD   GLN E 433      36.743 -35.422 -28.835  1.00 46.49          C
ANISOU 4785  CD   GLN E 433     6351  5891  5423    -510   1069  -3088       C
ATOM   4786  OE1  GLN E 433      37.885 -35.864 -28.762  1.00 46.73          O
ANISOU 4786  OE1  GLN E 433     6307  5883  5565    -406   1191  -3246       O
ATOM   4787  NE2  GLN E 433      35.701 -36.170 -29.196  1.00 49.59          N
ANISOU 4787  NE2  GLN E 433     6786  6216  5839    -577    974  -3240       N
ATOM   4788  C    GLN E 433      37.266 -33.209 -25.278  1.00 33.83          C
ANISOU 4788  C    GLN E 433     4728  3932  4195    -345    981  -2204       C
ATOM   4789  O    GLN E 433      38.456 -33.403 -25.081  1.00 34.24          O
ANISOU 4789  O    GLN E 433     4705  3974  4330    -254   1077  -2284       O
ATOM   4790  N    LEU E 434      36.650 -32.110 -24.866  1.00 31.07          N
ANISOU 4790  N    LEU E 434     4418  3619  3768    -399    908  -1937       N
ATOM   4791  CA   LEU E 434      37.329 -31.034 -24.128  1.00 28.78          C
ANISOU 4791  CA   LEU E 434     4102  3346  3486    -372    939  -1719       C
ATOM   4792  CB   LEU E 434      36.367 -29.855 -23.924  1.00 26.01          C
ANISOU 4792  CB   LEU E 434     3811  3033  3038    -442    841  -1468       C
ATOM   4793  CG   LEU E 434      35.966 -29.145 -25.222  1.00 25.54          C
ANISOU 4793  CG   LEU E 434     3805  3209  2689    -551    822  -1442       C
ATOM   4794  CD1  LEU E 434      34.729 -28.299 -25.018  1.00 24.35          C
ANISOU 4794  CD1  LEU E 434     3706  3042  2504    -583    681  -1235       C
ATOM   4795  CD2  LEU E 434      37.121 -28.319 -25.799  1.00 22.38          C
ANISOU 4795  CD2  LEU E 434     3397  2995  2113    -602    943  -1400       C
ATOM   4796  C    LEU E 434      37.900 -31.483 -22.783  1.00 27.76          C
ANISOU 4796  C    LEU E 434     3927  2997  3622    -250    939  -1675       C
ATOM   4797  O    LEU E 434      39.014 -31.136 -22.430  1.00 27.07          O
ANISOU 4797  O    LEU E 434     3771  2946  3569    -196   1008  -1653       O
ATOM   4798  N    LEU E 435      37.110 -32.250 -22.042  1.00 27.99          N
ANISOU 4798  N    LEU E 435     3994  2811  3829    -220    856  -1657       N
ATOM   4799  CA   LEU E 435      37.487 -32.722 -20.719  1.00 27.82          C
ANISOU 4799  CA   LEU E 435     3960  2577  4035    -116    832  -1578       C
ATOM   4800  CB   LEU E 435      36.316 -33.464 -20.074  1.00 27.22          C
ANISOU 4800  CB   LEU E 435     3951  2294  4097    -145    746  -1530       C
ATOM   4801  CG   LEU E 435      36.445 -33.810 -18.591  1.00 28.04          C
ANISOU 4801  CG   LEU E 435     4075  2192  4388     -72    705  -1378       C
ATOM   4802  CD1  LEU E 435      36.646 -32.562 -17.667  1.00 24.26          C
ANISOU 4802  CD1  LEU E 435     3574  1799  3846     -69    694  -1159       C
ATOM   4803  CD2  LEU E 435      35.226 -34.633 -18.191  1.00 25.93          C
ANISOU 4803  CD2  LEU E 435     3877  1742  4232    -145    648  -1354       C
ATOM   4804  C    LEU E 435      38.771 -33.577 -20.768  1.00 29.75          C
ANISOU 4804  C    LEU E 435     4131  2762  4410      14    896  -1756       C
ATOM   4805  O    LEU E 435      39.778 -33.201 -20.144  1.00 28.71          O
ANISOU 4805  O    LEU E 435     3929  2650  4330      95    921  -1690       O
ATOM   4806  N    ARG E 436      38.741 -34.676 -21.534  1.00 32.34          N
ANISOU 4806  N    ARG E 436     4465  3030  4795      35    920  -1999       N
ATOM   4807  CA   ARG E 436      39.909 -35.546 -21.722  1.00 35.45          C
ANISOU 4807  CA   ARG E 436     4775  3363  5331     178    982  -2217       C
```

FIGURE 18-139

```
ATOM   4808  CB  ARG E 436      39.663 -36.647 -22.752  1.00 39.05           C
ANISOU 4808  CB  ARG E 436     5249   3770   5817    172   1014  -2522       C
ATOM   4809  CG  ARG E 436      38.505 -37.569 -22.494  1.00 44.53           C
ANISOU 4809  CG  ARG E 436     6055   4209   6656    124    920  -2530       C
ATOM   4810  CD  ARG E 436      38.611 -38.440 -21.233  1.00 52.12           C
ANISOU 4810  CD  ARG E 436     7061   4819   7923    242    842  -2421       C
ATOM   4811  NE  ARG E 436      37.245 -38.756 -20.802  1.00 57.30           N
ANISOU 4811  NE  ARG E 436     7831   5312   8631    112    760  -2299       N
ATOM   4812  CZ  ARG E 436      36.618 -38.200 -19.764  1.00 57.95           C
ANISOU 4812  CZ  ARG E 436     7958   5361   8701     53    702  -2012       C
ATOM   4813  NH1 ARG E 436      37.239 -37.329 -18.967  1.00 55.93           N
ANISOU 4813  NH1 ARG E 436     7660   5194   8395    119    701  -1810       N
ATOM   4814  NH2 ARG E 436      35.361 -38.551 -19.498  1.00 60.15           N
ANISOU 4814  NH2 ARG E 436     8312   5518   9024    -81    651  -1946       N
ATOM   4815  C   ARG E 436      41.160 -34.801 -22.148  1.00 35.22           C
ANISOU 4815  C   ARG E 436     4619   3580   5182    206   1094  -2273       C
ATOM   4816  O   ARG E 436      42.231 -35.071 -21.622  1.00 35.85           O
ANISOU 4816  O   ARG E 436     4598   3608   5416    348   1111  -2313       O
ATOM   4817  N   HIS E 437      41.028 -33.904 -23.128  1.00 34.80           N
ANISOU 4817  N   HIS E 437     4568   3798   4857     67   1165  -2278       N
ATOM   4818  CA  HIS E 437      42.118 -33.014 -23.525  1.00 34.74           C
ANISOU 4818  CA  HIS E 437     4454   4042   4705     38   1285  -2284       C
ATOM   4819  CB  HIS E 437      41.679 -32.053 -24.633  1.00 34.55           C
ANISOU 4819  CB  HIS E 437     4489   4283   4357   -146   1338  -2235       C
ATOM   4820  CG  HIS E 437      42.748 -31.068 -25.013  1.00 35.10           C
ANISOU 4820  CG  HIS E 437     4468   4599   4270   -217   1471  -2204       C
ATOM   4821  ND1 HIS E 437      43.851 -31.420 -25.764  1.00 37.41           N
ANISOU 4821  ND1 HIS E 437     4626   5075   4513   -200   1631  -2455       N
ATOM   4822  CE1 HIS E 437      44.631 -30.366 -25.924  1.00 38.18           C
ANISOU 4822  CE1 HIS E 437     4658   5375   4475   -302   1736  -2358       C
ATOM   4823  NE2 HIS E 437      44.081 -29.345 -25.292  1.00 35.48           N
ANISOU 4823  NE2 HIS E 437     4413   4960   4108   -374   1640  -2054       N
ATOM   4824  CD2 HIS E 437      42.906 -29.759 -24.711  1.00 32.73           C
ANISOU 4824  CD2 HIS E 437     4181   4382   3872   -313   1477  -1962       C
ATOM   4825  C   HIS E 437      42.749 -32.194 -22.375  1.00 33.02           C
ANISOU 4825  C   HIS E 437     4176   3799   4570     79   1259  -2066       C
ATOM   4826  O   HIS E 437      43.972 -32.101 -22.278  1.00 33.79           O
ANISOU 4826  O   HIS E 437     4129   3988   4720    145   1337  -2148       O
ATOM   4827  N   PHE E 438      41.926 -31.574 -21.532  1.00 31.16           N
ANISOU 4827  N   PHE E 438     4035   3462   4342     33   1153  -1812       N
ATOM   4828  CA  PHE E 438      42.449 -30.736 -20.445  1.00 29.88           C
ANISOU 4828  CA  PHE E 438     3826   3289   4236     53   1124  -1624       C
ATOM   4829  CB  PHE E 438      41.489 -29.603 -20.094  1.00 26.95           C
ANISOU 4829  CB  PHE E 438     3561   2923   3757    -63   1061  -1384       C
ATOM   4830  CG  PHE E 438      41.464 -28.502 -21.121  1.00 27.09           C
ANISOU 4830  CG  PHE E 438     3604   3149   3541   -212   1134  -1338       C
ATOM   4831  CD1 PHE E 438      42.603 -27.741 -21.370  1.00 25.13           C
ANISOU 4831  CD1 PHE E 438     3262   3064   3221   -267   1241  -1344       C
ATOM   4832  CE1 PHE E 438      42.595 -26.732 -22.328  1.00 25.50           C
ANISOU 4832  CE1 PHE E 438     3355   3289   3044   -424   1312  -1272       C
ATOM   4833  CZ  PHE E 438      41.445 -26.464 -23.056  1.00 25.46           C
ANISOU 4833  CZ  PHE E 438     3487   3307   2880   -504   1254  -1191       C
ATOM   4834  CE2 PHE E 438      40.295 -27.218 -22.825  1.00 25.44           C
ANISOU 4834  CE2 PHE E 438     3552   3162   2953   -438   1138  -1209       C
ATOM   4835  CD2 PHE E 438      40.308 -28.232 -21.858  1.00 26.06           C
ANISOU 4835  CD2 PHE E 438     3586   3055   3260   -305   1090  -1283       C
ATOM   4836  C   PHE E 438      42.892 -31.546 -19.216  1.00 30.99           C
ANISOU 4836  C   PHE E 438     3923   3228   4624    221   1042  -1610       C
ATOM   4837  O   PHE E 438      43.758 -31.116 -18.459  1.00 30.57           O
ANISOU 4837  O   PHE E 438     3776   3208   4631    221   1032  -1547       O
ATOM   4838  N   GLN E 439      42.333 -32.746 -19.058  1.00 32.94           N
ANISOU 4838  N   GLN E 439     4237   3267   5012    299    977  -1674       N
ATOM   4839  CA  GLN E 439      42.793 -33.691 -18.041  1.00 34.33           C
ANISOU 4839  CA  GLN E 439     4390   3229   5424    468    892  -1664       C
ATOM   4840  CB  GLN E 439      41.809 -34.835 -17.889  1.00 34.98           C
ANISOU 4840  CB  GLN E 439     4604   3055   5634    485    819  -1673       C
ATOM   4841  CG  GLN E 439      40.528 -34.421 -17.151  1.00 33.80           C
ANISOU 4841  CG  GLN E 439     4583   2832   5428    365    747  -1440       C
ATOM   4842  CD  GLN E 439      39.593 -35.607 -16.908  1.00 35.82           C
ANISOU 4842  CD  GLN E 439     4957   2826   5828    357    684  -1441       C
ATOM   4843  OE1 GLN E 439      39.605 -36.585 -17.663  1.00 36.28           O
```

FIGURE 18-140

```
ANISOU 4843  OE1 GLN E 439      5025   2780   5979    391    705  -1646    O
ATOM   4844  NE2 GLN E 439      38.782 -35.521 -15.849  1.00 34.67          N
ANISOU 4844  NE2 GLN E 439      4899   2575   5700    299    617  -1224    N
ATOM   4845  C   GLN E 439      44.181 -34.224 -18.355  1.00 36.88          C
ANISOU 4845  C   GLN E 439      4548   3601   5863    621    947  -1875    C
ATOM   4846  O   GLN E 439      44.947 -34.537 -17.454  1.00 38.31          O
ANISOU 4846  O   GLN E 439      4655   3695   6205    771    873  -1834    O
ATOM   4847  N   LYS E 440      44.506 -34.307 -19.639  1.00 38.67          N
ANISOU 4847  N   LYS E 440      4708   3989   5997    585   1074  -2109    N
ATOM   4848  CA  LYS E 440      45.830 -34.701 -20.085  1.00 41.00          C
ANISOU 4848  CA  LYS E 440      4811   4387   6378    713   1162  -2352    C
ATOM   4849  CB  LYS E 440      45.760 -35.237 -21.517  1.00 43.24          C
ANISOU 4849  CB  LYS E 440      5080   4772   6575    674   1289  -2647    C
ATOM   4850  CG  LYS E 440      44.974 -36.564 -21.628  1.00 44.39          C
ANISOU 4850  CG  LYS E 440      5348   4632   6884    748   1215  -2766    C
ATOM   4851  CD  LYS E 440      45.302 -37.362 -22.891  1.00 47.55          C
ANISOU 4851  CD  LYS E 440      5680   5105   7282    784   1335  -3147    C
ATOM   4852  CE  LYS E 440      44.512 -38.715 -22.929  1.00 50.57          C
ANISOU 4852  CE  LYS E 440      6192   5155   7866    848   1250  -3276    C
ATOM   4853  NZ  LYS E 440      45.145 -39.840 -23.728  1.00 54.88          N
ANISOU 4853  NZ  LYS E 440      6641   5641   8568    993   1329  -3685    N
ATOM   4854  C   LYS E 440      46.860 -33.566 -19.953  1.00 41.06          C
ANISOU 4854  C   LYS E 440      4658   4652   6290    666   1236  -2303    C
ATOM   4855  O   LYS E 440      48.025 -33.808 -19.611  1.00 42.57          O
ANISOU 4855  O   LYS E 440      4664   4881   6629    813   1240  -2407    O
ATOM   4856  N   ASP E 441      46.435 -32.336 -20.226  1.00 39.79          N
ANISOU 4856  N   ASP E 441      4560   4659   5898    463   1287  -2149    N
ATOM   4857  CA  ASP E 441      47.317 -31.180 -20.142  1.00 40.18          C
ANISOU 4857  CA  ASP E 441      4482   4932   5855    373   1365  -2091    C
ATOM   4858  CB  ASP E 441      48.154 -31.013 -21.419  1.00 43.33          C
ANISOU 4858  CB  ASP E 441      4737   5607   6118    295   1564  -2319    C
ATOM   4859  CG  ASP E 441      49.325 -30.041 -21.231  1.00 46.39          C
ANISOU 4859  CG  ASP E 441      4939   6211   6477    220   1653  -2302    C
ATOM   4860  OD1 ASP E 441      49.448 -29.440 -20.140  1.00 48.49          O
ANISOU 4860  OD1 ASP E 441      5197   6410   6818    225   1551  -2118    O
ATOM   4861  OD2 ASP E 441      50.129 -29.879 -22.174  1.00 51.62          O
ANISOU 4861  OD2 ASP E 441      5456   7122   7035    143   1834  -2486    O
ATOM   4862  C   ASP E 441      46.537 -29.904 -19.828  1.00 37.74          C
ANISOU 4862  C   ASP E 441      4310   4644   5386    194   1329  -1822    C
ATOM   4863  O   ASP E 441      45.864 -29.332 -20.693  1.00 37.25          O
ANISOU 4863  O   ASP E 441      4355   4675   5122     36   1387  -1775    O
ATOM   4864  N   ALA E 442      46.636 -29.476 -18.570  1.00 35.71          N
ANISOU 4864  N   ALA E 442      4047   4299   5223    231   1222  -1652    N
ATOM   4865  CA  ALA E 442      45.931 -28.299 -18.098  1.00 33.38          C
ANISOU 4865  CA  ALA E 442      3868   3993   4822     92   1177  -1423    C
ATOM   4866  CB  ALA E 442      45.419 -28.529 -16.675  1.00 31.22          C
ANISOU 4866  CB  ALA E 442      3665   3526   4672    185   1020  -1271    C
ATOM   4867  C   ALA E 442      46.776 -27.016 -18.181  1.00 33.32          C
ANISOU 4867  C   ALA E 442      3761   4170   4728    -46   1265  -1384    C
ATOM   4868  O   ALA E 442      46.260 -25.945 -17.903  1.00 32.99          O
ANISOU 4868  O   ALA E 442      3816   4112   4608   -168   1240  -1212    O
ATOM   4869  N   LYS E 443      48.043 -27.134 -18.584  1.00 34.87          N
ANISOU 4869  N   LYS E 443      3760   4535   4953    -31   1371  -1554    N
ATOM   4870  CA  LYS E 443      49.006 -26.014 -18.612  1.00 35.36          C
ANISOU 4870  CA  LYS E 443      3692   4779   4964   -175   1466  -1542    C
ATOM   4871  CB  LYS E 443      50.372 -26.455 -19.164  1.00 38.05          C
ANISOU 4871  CB  LYS E 443      3778   5324   5355   -134   1599  -1786    C
ATOM   4872  CG  LYS E 443      51.263 -27.243 -18.219  1.00 40.17          C
ANISOU 4872  CG  LYS E 443      3849   5559   5857     88   1500  -1903    C
ATOM   4873  CD  LYS E 443      52.487 -27.764 -18.987  1.00 43.53          C
ANISOU 4873  CD  LYS E 443      4010   6196   6334    144   1649  -2186    C
ATOM   4874  CE  LYS E 443      53.103 -28.956 -18.285  1.00 48.78          C
ANISOU 4874  CE  LYS E 443      4515   6765   7255    440   1522  -2328    C
ATOM   4875  NZ  LYS E 443      54.154 -29.631 -19.120  1.00 53.55          N
ANISOU 4875  NZ  LYS E 443      4860   7551   7935    536   1667  -2646    N
ATOM   4876  C   LYS E 443      48.554 -24.806 -19.413  1.00 33.77          C
ANISOU 4876  C   LYS E 443      3618   4659   4554   -414   1561  -1408    C
ATOM   4877  O   LYS E 443      48.684 -23.694 -18.948  1.00 33.32          O
ANISOU 4877  O   LYS E 443      3574   4600   4484   -537   1551  -1276    O
ATOM   4878  N   VAL E 444      48.057 -25.015 -20.627  1.00 33.39          N
ANISOU 4878  N   VAL E 444      3664   4680   4342   -482   1645  -1446    N
```

FIGURE 18-141

```
ATOM   4879  CA  VAL E 444      47.578 -23.901 -21.443  1.00 32.51           C
ANISOU 4879  CA  VAL E 444    3697   4640   4016   -699   1710  -1287        C
ATOM   4880  CB  VAL E 444      47.325 -24.320 -22.913  1.00 33.98           C
ANISOU 4880  CB  VAL E 444    3940   4981   3988   -767   1820  -1385        C
ATOM   4881  CG1 VAL E 444      46.849 -23.117 -23.727  1.00 33.93           C
ANISOU 4881  CG1 VAL E 444    4100   5048   3745   -989   1863  -1177        C
ATOM   4882  CG2 VAL E 444      48.595 -24.935 -23.530  1.00 35.29           C
ANISOU 4882  CG2 VAL E 444    3886   5374   4147   -757   1997  -1653        C
ATOM   4883  C   VAL E 444      46.325 -23.248 -20.824  1.00 30.69           C
ANISOU 4883  C   VAL E 444    3666   4204   3792   -710   1557  -1054        C
ATOM   4884  O   VAL E 444      46.204 -22.012 -20.791  1.00 30.76           O
ANISOU 4884  O   VAL E 444    3753   4195   3741   -856   1561   -883        O
ATOM   4885  N   LEU E 445      45.419 -24.090 -20.332  1.00 28.79           N
ANISOU 4885  N   LEU E 445    3497   3803   3639   -557   1429  -1058        N
ATOM   4886  CA  LEU E 445      44.175 -23.667 -19.699  1.00 27.40           C
ANISOU 4886  CA  LEU E 445    3476   3448   3487   -543   1291   -880        C
ATOM   4887  CB  LEU E 445      43.334 -24.905 -19.324  1.00 26.06           C
ANISOU 4887  CB  LEU E 445    3348   3141   3410   -390   1191   -938        C
ATOM   4888  CG  LEU E 445      42.005 -24.714 -18.603  1.00 24.67           C
ANISOU 4888  CG  LEU E 445    3297   2800   3277   -363   1061   -794        C
ATOM   4889  CD1 LEU E 445      41.045 -23.943 -19.450  1.00 23.86           C
ANISOU 4889  CD1 LEU E 445    3319   2724   3024   -467   1044   -683        C
ATOM   4890  CD2 LEU E 445      41.388 -26.048 -18.167  1.00 23.79           C
ANISOU 4890  CD2 LEU E 445    3204   2560   3276   -238    987   -863        C
ATOM   4891  C   LEU E 445      44.416 -22.841 -18.438  1.00 26.46           C
ANISOU 4891  C   LEU E 445    3330   3240   3486   -548   1230   -777        C
ATOM   4892  O   LEU E 445      43.801 -21.786 -18.261  1.00 26.04           O
ANISOU 4892  O   LEU E 445    3381   3112   3400   -630   1188   -624        O
ATOM   4893  N   PHE E 446      45.272 -23.353 -17.551  1.00 26.46           N
ANISOU 4893  N   PHE E 446    3188   3241   3625   -447   1211   -870        N
ATOM   4894  CA  PHE E 446      45.576 -22.697 -16.274  1.00 25.67           C
ANISOU 4894  CA  PHE E 446    3046   3084   3625   -444   1141   -806        C
ATOM   4895  CB  PHE E 446      46.347 -23.663 -15.363  1.00 26.39           C
ANISOU 4895  CB  PHE E 446    2995   3178   3856   -282   1079   -912        C
ATOM   4896  CG  PHE E 446      45.490 -24.679 -14.652  1.00 24.94           C
ANISOU 4896  CG  PHE E 446    2898   2839   3740   -131    959   -875        C
ATOM   4897  CD1 PHE E 446      44.152 -24.830 -14.944  1.00 24.46           C
ANISOU 4897  CD1 PHE E 446    2999   2671   3625   -146    932   -796        C
ATOM   4898  CE1 PHE E 446      43.370 -25.769 -14.271  1.00 25.96           C
ANISOU 4898  CE1 PHE E 446    3262   2721   3881    -40    838   -760        C
ATOM   4899  CZ  PHE E 446      43.927 -26.577 -13.306  1.00 26.29           C
ANISOU 4899  CZ  PHE E 446    3242   2714   4034     92    761   -778        C
ATOM   4900  CE2 PHE E 446      45.274 -26.429 -12.996  1.00 28.95           C
ANISOU 4900  CE2 PHE E 446    3418   3158   4423    134    764   -850        C
ATOM   4901  CD2 PHE E 446      46.045 -25.494 -13.676  1.00 27.06           C
ANISOU 4901  CD2 PHE E 446    3080   3073   4128     20    868   -912        C
ATOM   4902  C   PHE E 446      46.389 -21.403 -16.496  1.00 26.52           C
ANISOU 4902  C   PHE E 446    3097   3289   3693   -623   1230   -777        C
ATOM   4903  O   PHE E 446      46.081 -20.387 -15.902  1.00 26.04           O
ANISOU 4903  O   PHE E 446    3101   3142   3650   -697   1185   -672        O
ATOM   4904  N   GLN E 447      47.407 -21.441 -17.364  1.00 28.42           N
ANISOU 4904  N   GLN E 447    3213   3703   3882   -703   1367   -882        N
ATOM   4905  CA  GLN E 447      48.255 -20.272 -17.631  1.00 30.21           C
ANISOU 4905  CA  GLN E 447    3374   4031   4073   -906   1474   -858        C
ATOM   4906  CB  GLN E 447      49.558 -20.665 -18.370  1.00 32.70           C
ANISOU 4906  CB  GLN E 447    3479   4581   4365   -956   1632  -1034        C
ATOM   4907  CG  GLN E 447      50.469 -21.664 -17.619  1.00 33.25           C
ANISOU 4907  CG  GLN E 447    3317   4717   4599   -768   1585  -1223        C
ATOM   4908  CD  GLN E 447      51.134 -21.082 -16.361  1.00 34.07           C
ANISOU 4908  CD  GLN E 447    3297   4813   4836   -777   1499  -1223        C
ATOM   4909  OE1 GLN E 447      50.681 -20.084 -15.801  1.00 33.58           O
ANISOU 4909  OE1 GLN E 447    3351   4637   4770   -881   1442  -1088        O
ATOM   4910  NE2 GLN E 447      52.215 -21.716 -15.914  1.00 33.89           N
ANISOU 4910  NE2 GLN E 447    3028   4913   4937   -660   1480  -1391        N
ATOM   4911  C   GLN E 447      47.535 -19.110 -18.348  1.00 30.32           C
ANISOU 4911  C   GLN E 447    3585   3978   3959  -1087   1508   -671        C
ATOM   4912  O   GLN E 447      47.924 -17.962 -18.215  1.00 31.49           O
ANISOU 4912  O   GLN E 447    3740   4105   4121  -1252   1546   -595        O
ATOM   4913  N   ASN E 448      46.468 -19.409 -19.073  1.00 30.31           N
ANISOU 4913  N   ASN E 448    3744   3928   3845  -1051   1477   -595        N
ATOM   4914  CA  ASN E 448      45.761 -18.409 -19.873  1.00 30.88           C
```

FIGURE 18-142

```
ANISOU 4914  CA  ASN E 448    4004  3947  3783 -1195  1485  -407        C
ATOM   4915  CB  ASN E 448    45.584 -18.920 -21.309  1.00 32.53        C
ANISOU 4915  CB  ASN E 448    4268  4311  3782 -1240  1569  -424        C
ATOM   4916  CG  ASN E 448    46.858 -18.826 -22.104  1.00 35.40        C
ANISOU 4916  CG  ASN E 448    4506  4905  4040 -1401  1764  -514        C
ATOM   4917  OD1 ASN E 448    47.280 -17.741 -22.458  1.00 39.32        O
ANISOU 4917  OD1 ASN E 448    5044  5427  4468 -1605  1846  -389        O
ATOM   4918  ND2 ASN E 448    47.482 -19.960 -22.378  1.00 37.31        N
ANISOU 4918  ND2 ASN E 448    4588  5308  4280 -1312  1845  -737        N
ATOM   4919  C   ASN E 448    44.419 -17.982 -19.291  1.00 29.13        C
ANISOU 4919  C   ASN E 448    3941  3507  3618 -1115  1326  -267        C
ATOM   4920  O   ASN E 448    43.766 -17.081 -19.821  1.00 29.93        O
ANISOU 4920  O   ASN E 448    4198  3528  3646 -1201  1297   -98        O
ATOM   4921  N   TRP E 449    44.039 -18.593 -18.176  1.00 27.59        N
ANISOU 4921  N   TRP E 449    3703  3222  3558  -952  1225  -333        N
ATOM   4922  CA  TRP E 449    42.729 -18.370 -17.542  1.00 26.76        C
ANISOU 4922  CA  TRP E 449    3713  2942  3513  -861  1090  -243        C
ATOM   4923  CB  TRP E 449    42.475 -19.424 -16.454  1.00 24.28        C
ANISOU 4923  CB  TRP E 449    3331  2590  3304  -695  1016  -340        C
ATOM   4924  CG  TRP E 449    41.137 -19.316 -15.787  1.00 23.02        C
ANISOU 4924  CG  TRP E 449    3262  2290  3195  -614   905  -273        C
ATOM   4925  CD1 TRP E 449    40.863 -18.715 -14.596  1.00 21.45        C
ANISOU 4925  CD1 TRP E 449    3066  1994  3092  -591   847  -256        C
ATOM   4926  NE1 TRP E 449    39.515 -18.822 -14.298  1.00 20.39        N
ANISOU 4926  NE1 TRP E 449    3000  1770  2976  -516   770  -215        N
ATOM   4927  CE2 TRP E 449    38.885 -19.504 -15.306  1.00 21.49        C
ANISOU 4927  CE2 TRP E 449    3183  1943  3039  -494   763  -200        C
ATOM   4928  CD2 TRP E 449    39.876 -19.846 -16.270  1.00 24.86        C
ANISOU 4928  CD2 TRP E 449    3576  2486  3383  -553   846  -240        C
ATOM   4929  CE3 TRP E 449    39.491 -20.568 -17.422  1.00 23.76        C
ANISOU 4929  CE3 TRP E 449    3472  2418  3138  -550   858  -261        C
ATOM   4930  CZ3 TRP E 449    38.128 -20.936 -17.561  1.00 23.43        C
ANISOU 4930  CZ3 TRP E 449    3491  2323  3088  -492   771  -235        C
ATOM   4931  CH2 TRP E 449    37.172 -20.568 -16.574  1.00 21.37        C
ANISOU 4931  CH2 TRP E 449    3244  1947  2927  -437   692  -188        C
ATOM   4932  CZ2 TRP E 449    37.535 -19.864 -15.450  1.00 20.61        C
ANISOU 4932  CZ2 TRP E 449    3121  1786  2923  -435   694  -175        C
ATOM   4933  C   TRP E 449    42.490 -16.955 -16.983  1.00 27.51        C
ANISOU 4933  C   TRP E 449    3882  2888  3683  -936  1047  -131        C
ATOM   4934  O   TRP E 449    41.353 -16.459 -16.959  1.00 28.76        O
ANISOU 4934  O   TRP E 449    4157  2914  3855  -897   959   -29        O
ATOM   4935  N   GLY E 450    43.527 -16.296 -16.504  1.00 28.21        N
ANISOU 4935  N   GLY E 450    3890  2989  3838 -1037  1102  -166        N
ATOM   4936  CA  GLY E 450    43.293 -14.993 -15.886  1.00 27.79        C
ANISOU 4936  CA  GLY E 450    3907  2766  3884 -1103  1057   -93        C
ATOM   4937  C   GLY E 450    43.612 -15.062 -14.403  1.00 26.81        C
ANISOU 4937  C   GLY E 450    3678  2623  3885 -1038  1007  -216        C
ATOM   4938  O   GLY E 450    43.219 -16.005 -13.720  1.00 25.75        O
ANISOU 4938  O   GLY E 450    3501  2518  3763  -889   946  -282        O
ATOM   4939  N   ILE E 451    44.331 -14.049 -13.925  1.00 27.46        N
ANISOU 4939  N   ILE E 451    3725  2659  4049 -1166  1031  -243        N
ATOM   4940  CA  ILE E 451    44.805 -13.944 -12.563  1.00 26.27        C
ANISOU 4940  CA  ILE E 451    3467  2521  3994 -1141   984  -372        C
ATOM   4941  CB  ILE E 451    46.380 -13.916 -12.516  1.00 27.56        C
ANISOU 4941  CB  ILE E 451    3449  2845  4177 -1267  1061  -479        C
ATOM   4942  CG1 ILE E 451    46.919 -14.436 -11.178  1.00 27.57        C
ANISOU 4942  CG1 ILE E 451    3300  2949  4228 -1173   981  -627        C
ATOM   4943  CD1 ILE E 451    47.068 -15.951 -11.141  1.00 22.34        C
ANISOU 4943  CD1 ILE E 451    2547  2426  3515  -998   952  -669        C
ATOM   4944  CG2 ILE E 451    46.958 -12.547 -12.840  1.00 28.46        C
ANISOU 4944  CG2 ILE E 451    3590  2876  4349 -1500  1134  -445        C
ATOM   4945  C   ILE E 451    44.170 -12.690 -11.957  1.00 26.81        C
ANISOU 4945  C   ILE E 451    3641  2382  4162 -1182   931  -349        C
ATOM   4946  O   ILE E 451    43.942 -11.712 -12.669  1.00 27.27        O
ANISOU 4946  O   ILE E 451    3818  2296  4248 -1289   957  -238        O
ATOM   4947  N   GLU E 452    43.846 -12.740 -10.657  1.00 26.34        N
ANISOU 4947  N   GLU E 452    3548  2306  4155 -1090   853  -453        N
ATOM   4948  CA  GLU E 452    43.223 -11.616  -9.949  1.00 27.25        C
ANISOU 4948  CA  GLU E 452    3743  2237  4375 -1105   806  -486        C
ATOM   4949  CB  GLU E 452    41.711 -11.797  -9.805  1.00 26.07        C
ANISOU 4949  CB  GLU E 452    3691  1990  4224  -947   745  -441        C
```

FIGURE 18-143

```
ATOM   4950  CG  GLU E 452      41.266 -12.939  -8.853  1.00 25.31           C
ANISOU 4950  CG  GLU E 452    3530   2030   4058   -801    701   -515        C
ATOM   4951  CD  GLU E 452      39.756 -13.124  -8.803  1.00 24.53           C
ANISOU 4951  CD  GLU E 452    3504   1856   3961   -674    661   -476        C
ATOM   4952  OE1 GLU E 452      39.068 -12.217  -9.314  1.00 25.81           O
ANISOU 4952  OE1 GLU E 452    3753   1850   4202   -676    647   -420        O
ATOM   4953  OE2 GLU E 452      39.251 -14.177  -8.283  1.00 23.51           O
ANISOU 4953  OE2 GLU E 452    3341   1829   3761   -574    642   -494        O
ATOM   4954  C   GLU E 452      43.848 -11.432  -8.580  1.00 28.43           C
ANISOU 4954  C   GLU E 452    3783   2458   4563  -1127    771   -662        C
ATOM   4955  O   GLU E 452      44.286 -12.399  -7.949  1.00 27.98           O
ANISOU 4955  O   GLU E 452    3614   2584   4434  -1053    740   -731        O
ATOM   4956  N   HIS E 453      43.923 -10.180  -8.146  1.00 30.69           N
ANISOU 4956  N   HIS E 453    4104   2592   4964  -1232    766   -734        N
ATOM   4957  CA  HIS E 453      44.200  -9.865  -6.747  1.00 32.45           C
ANISOU 4957  CA  HIS E 453    4251   2864   5216  -1241    715   -926        C
ATOM   4958  CB  HIS E 453      44.444  -8.372  -6.528  1.00 34.20           C
ANISOU 4958  CB  HIS E 453    4517   2885   5593  -1398    727  -1017        C
ATOM   4959  CG  HIS E 453      45.250  -8.092  -5.296  1.00 39.68           C
ANISOU 4959  CG  HIS E 453    5086   3695   6296  -1476    688  -1238        C
ATOM   4960  ND1 HIS E 453      44.724  -7.482  -4.169  1.00 43.34           N
ANISOU 4960  ND1 HIS E 453    5574   4092   6801  -1445    640  -1415        N
ATOM   4961  CE1 HIS E 453      45.664  -7.391  -3.246  1.00 44.55           C
ANISOU 4961  CE1 HIS E 453    5596   4407   6924  -1535    601  -1598        C
ATOM   4962  NE2 HIS E 453      46.769  -7.945  -3.718  1.00 42.51           N
ANISOU 4962  NE2 HIS E 453    5213   4316   6621  -1609    617  -1544        N
ATOM   4963  CD2 HIS E 453      46.540  -8.383  -4.997  1.00 40.32           C
ANISOU 4963  CD2 HIS E 453    5000   3982   6338  -1576    682  -1329        C
ATOM   4964  C   HIS E 453      43.055 -10.310  -5.860  1.00 31.39           C
ANISOU 4964  C   HIS E 453    4153   2749   5027  -1069    658   -973        C
ATOM   4965  O   HIS E 453      41.890 -10.357  -6.286  1.00 30.46           O
ANISOU 4965  O   HIS E 453    4134   2517   4921   -967    656   -882        O
ATOM   4966  N   ILE E 454      43.380 -10.638  -4.618  1.00 31.87           N
ANISOU 4966  N   ILE E 454    4122   2971   5015  -1043    609  -1116        N
ATOM   4967  CA  ILE E 454      42.346 -11.093  -3.700  1.00 31.42           C
ANISOU 4967  CA  ILE E 454    4094   2967   4875   -909    573  -1161        C
ATOM   4968  CB  ILE E 454      42.380 -12.627  -3.506  1.00 30.33           C
ANISOU 4968  CB  ILE E 454    3911   3030   4585   -798    542  -1074        C
ATOM   4969  CG1 ILE E 454      43.610 -13.057  -2.681  1.00 31.20           C
ANISOU 4969  CG1 ILE E 454    3893   3350   4610   -830    478  -1157        C
ATOM   4970  CD1 ILE E 454      43.581 -14.534  -2.282  1.00 29.25           C
ANISOU 4970  CD1 ILE E 454    3622   3268   4225   -703    423  -1067        C
ATOM   4971  CG2 ILE E 454      42.334 -13.309  -4.878  1.00 29.40           C
ANISOU 4971  CG2 ILE E 454    3820   2871   4478   -764    580   -902        C
ATOM   4972  C   ILE E 454      42.322 -10.396  -2.359  1.00 32.96           C
ANISOU 4972  C   ILE E 454    4262   3196   5064   -942    541  -1372        C
ATOM   4973  O   ILE E 454      43.289  -9.765  -1.929  1.00 34.56           O
ANISOU 4973  O   ILE E 454    4398   3432   5303  -1065    521  -1505        O
ATOM   4974  N   ASP E 455      41.171 -10.489  -1.720  1.00 33.18           N
ANISOU 4974  N   ASP E 455    4337   3225   5046   -841    545  -1419        N
ATOM   4975  CA  ASP E 455      41.040 -10.071  -0.349  1.00 34.92           C
ANISOU 4975  CA  ASP E 455    4527   3541   5200   -856    525  -1632        C
ATOM   4976  CB  ASP E 455      39.607  -9.614  -0.072  1.00 35.97           C
ANISOU 4976  CB  ASP E 455    4721   3562   5384   -767    570  -1709        C
ATOM   4977  CG  ASP E 455      39.150  -8.513  -1.016  1.00 38.40           C
ANISOU 4977  CG  ASP E 455    5103   3558   5931   -768    596  -1692        C
ATOM   4978  OD1 ASP E 455      39.930  -7.575  -1.295  1.00 43.88           O
ANISOU 4978  OD1 ASP E 455    5809   4103   6759   -885    588  -1746        O
ATOM   4979  OD2 ASP E 455      38.012  -8.581  -1.493  1.00 39.86           O
ANISOU 4979  OD2 ASP E 455    5332   3641   6173   -656    616  -1617        O
ATOM   4980  C   ASP E 455      41.428 -11.210   0.583  1.00 34.38           C
ANISOU 4980  C   ASP E 455    4395   3761   4905   -821    470  -1620        C
ATOM   4981  O   ASP E 455      41.239 -12.372   0.267  1.00 33.22           O
ANISOU 4981  O   ASP E 455    4259   3693   4672   -739    463  -1447        O
ATOM   4982  N   ASN E 456      42.001 -10.857   1.727  1.00 36.29           N
ANISOU 4982  N   ASN E 456    4579   4155   5054   -888    421  -1805        N
ATOM   4983  CA  ASN E 456      42.242 -11.804   2.805  1.00 36.41           C
ANISOU 4983  CA  ASN E 456    4556   4451   4827   -852    350  -1799        C
ATOM   4984  CB  ASN E 456      43.157 -11.172   3.870  1.00 38.96           C
ANISOU 4984  CB  ASN E 456    4797   4935   5071   -959    274  -2023        C
ATOM   4985  CG  ASN E 456      44.549 -10.827   3.334  1.00 40.45           C
```

FIGURE 18-144

```
ANISOU 4985  CG  ASN E 456    4881  5107  5382 -1060   220 -2046       C
ATOM   4986  OD1 ASN E 456    45.178 -11.638   2.635  1.00 41.16       O
ANISOU 4986  OD1 ASN E 456    4920  5233  5486 -1020   191 -1874       O
ATOM   4987  ND2 ASN E 456    45.040  -9.624   3.669  1.00 39.97       N
ANISOU 4987  ND2 ASN E 456    4777  4994  5418 -1199   215 -2279       N
ATOM   4988  C   ASN E 456    40.922 -12.229   3.444  1.00 35.91       C
ANISOU 4988  C   ASN E 456    4561  4451  4631  -773   404 -1790       C
ATOM   4989  O   ASN E 456    40.246 -11.425   4.099  1.00 37.52       O
ANISOU 4989  O   ASN E 456    4782  4643  4833  -794   455 -1984       O
ATOM   4990  N   VAL E 457    40.543 -13.483   3.230  1.00 33.98       N
ANISOU 4990  N   VAL E 457    4351  4269  4291  -689   402 -1578       N
ATOM   4991  CA  VAL E 457    39.365 -14.080   3.867  1.00 33.82       C
ANISOU 4991  CA  VAL E 457    4385  4343  4122  -641   458 -1541       C
ATOM   4992  CB  VAL E 457    38.259 -14.476   2.836  1.00 32.61       C
ANISOU 4992  CB  VAL E 457    4279  4018  4093  -568   540 -1399       C
ATOM   4993  CG1 VAL E 457    37.029 -15.057   3.553  1.00 32.25       C
ANISOU 4993  CG1 VAL E 457    4264  4088  3900  -547   614 -1383       C
ATOM   4994  CG2 VAL E 457    37.839 -13.264   1.956  1.00 34.28       C
ANISOU 4994  CG2 VAL E 457    4492  3983  4548  -564   592 -1495       C
ATOM   4995  C   VAL E 457    39.833 -15.326   4.626  1.00 33.51       C
ANISOU 4995  C   VAL E 457    4356  4530  3847  -623   373 -1398       C
ATOM   4996  O   VAL E 457    40.368 -16.254   4.027  1.00 32.47       O
ANISOU 4996  O   VAL E 457    4224  4372  3741  -570   314 -1210       O
ATOM   4997  N   MSE E 458    39.663 -15.333   5.946  1.00 34.54       N
ANISOU 4997  N   MSE E 458    4498  4881  3746  -664   361 -1491       N
ATOM   4998  CA  MSE E 458    40.077 -16.485   6.758  1.00 34.73       C
ANISOU 4998  CA  MSE E 458    4554  5121  3522  -649   262 -1328       C
ATOM   4999  CB  MSE E 458    39.930 -16.198   8.270  1.00 36.83       C
ANISOU 4999  CB  MSE E 458    4834  5661  3500  -725   252 -1475       C
ATOM   5000  CG  MSE E 458    40.556 -17.267   9.149  1.00 36.65       C
ANISOU 5000  CG  MSE E 458    4852  5870  3203  -714   109 -1293       C
ATOM   5001  SE  MSE E 458    40.273 -16.954  11.015  0.90 41.76       SE
ANISOU 5001  SE  MSE E 458    5537  6903  3425  -827   106 -1458       SE
ATOM   5002  CE  MSE E 458    41.315 -18.332  11.797  1.00 45.02       C
ANISOU 5002  CE  MSE E 458    6009  7547  3550  -781  -137 -1152       C
ATOM   5003  C   MSE E 458    39.307 -17.753   6.367  1.00 33.55       C
ANISOU 5003  C   MSE E 458    4487  4909  3352  -591   305 -1072       C
ATOM   5004  O   MSE E 458    38.099 -17.701   6.110  1.00 32.64       O
ANISOU 5004  O   MSE E 458    4404  4712  3286  -596   437 -1080       O
ATOM   5005  N   GLY E 459    40.010 -18.883   6.316  1.00 33.52       N
ANISOU 5005  N   GLY E 459    4507  4934  3293  -532   189  -859       N
ATOM   5006  CA  GLY E 459    39.389 -20.156   5.923  1.00 33.09       C
ANISOU 5006  CA  GLY E 459    4540  4788  3245  -484   216  -617       C
ATOM   5007  C   GLY E 459    39.465 -20.494   4.445  1.00 31.02       C
ANISOU 5007  C   GLY E 459    4259  4286  3242  -413   236  -537       C
ATOM   5008  O   GLY E 459    38.878 -21.472   4.003  1.00 29.76       O
ANISOU 5008  O   GLY E 459    4166  4024  3119  -382   269  -374       O
ATOM   5009  N   MSE E 460    40.234 -19.707   3.697  1.00 31.09       N
ANISOU 5009  N   MSE E 460    4178  4216  3419  -401   216  -654       N
ATOM   5010  CA  MSE E 460    40.276 -19.773   2.235  1.00 31.27       C
ANISOU 5010  CA  MSE E 460    4178  4037  3665  -358   258  -615       C
ATOM   5011  CB  MSE E 460    39.161 -18.884   1.732  1.00 30.55       C
ANISOU 5011  CB  MSE E 460    4104  3830  3674  -400   385  -715       C
ATOM   5012  CG  MSE E 460    38.666 -19.120   0.368  1.00 31.73       C
ANISOU 5012  CG  MSE E 460    4270  3798  3987  -364   442  -641       C
ATOM   5013  SE  MSE E 460    37.264 -17.775   0.139  0.90 36.29       SE
ANISOU 5013  SE  MSE E 460    4850  4272  4665  -398   558  -792       SE
ATOM   5014  CE  MSE E 460    35.900 -18.531   1.319  1.00 33.17       C
ANISOU 5014  CE  MSE E 460    4495  4021  4089  -418   629  -764       C
ATOM   5015  C   MSE E 460    41.595 -19.181   1.740  1.00 29.41       C
ANISOU 5015  C   MSE E 460    3836  3797  3541  -360   197  -704       C
ATOM   5016  O   MSE E 460    42.123 -18.243   2.345  1.00 30.18       O
ANISOU 5016  O   MSE E 460    3874  3990  3604  -424   166  -859       O
ATOM   5017  N   VAL E 461    42.129 -19.739   0.654  1.00 27.19       N
ANISOU 5017  N   VAL E 461    3522  3418  3392  -302   187  -625       N
ATOM   5018  CA  VAL E 461    43.328 -19.186   0.002  1.00 26.63       C
ANISOU 5018  CA  VAL E 461    3332  3346  3439  -324   164  -711       C
ATOM   5019  CB  VAL E 461    44.678 -19.981   0.317  1.00 27.57       C
ANISOU 5019  CB  VAL E 461    3343  3596  3535  -245    26  -678       C
ATOM   5020  CG1 VAL E 461    45.146 -19.726   1.712  1.00 30.38       C
ANISOU 5020  CG1 VAL E 461    3661  4147  3734  -267   -90  -741       C
```

FIGURE 18-145

```
ATOM   5021  CG2 VAL E 461      44.544 -21.476   0.054  1.00 27.15           C
ANISOU 5021  CG2 VAL E 461    3343   3486   3488   -113    -15   -505        C
ATOM   5022  C   VAL E 461      43.155 -19.117  -1.507  1.00 24.12           C
ANISOU 5022  C   VAL E 461    3020   2866   3278   -326    258   -681        C
ATOM   5023  O   VAL E 461      42.324 -19.841  -2.080  1.00 22.67           O
ANISOU 5023  O   VAL E 461    2916   2584   3112   -275    303   -577        O
ATOM   5024  N   GLY E 462      43.947 -18.249  -2.140  1.00 23.16           N
ANISOU 5024  N   GLY E 462    2816   2728   3258   -401    288   -772        N
ATOM   5025  CA  GLY E 462      44.112 -18.282  -3.598  1.00 21.82           C
ANISOU 5025  CA  GLY E 462    2635   2456   3200   -412    367   -733        C
ATOM   5026  C   GLY E 462      44.981 -19.456  -4.067  1.00 21.42           C
ANISOU 5026  C   GLY E 462    2500   2467   3173   -317    329   -687        C
ATOM   5027  O   GLY E 462      45.717 -20.046  -3.299  1.00 20.90           O
ANISOU 5027  O   GLY E 462    2354   2517   3068   -248    226   -695        O
ATOM   5028  N   VAL E 463      44.888 -19.781  -5.350  1.00 21.09           N
ANISOU 5028  N   VAL E 463    2471   2348   3194   -308    408   -648        N
ATOM   5029  CA  VAL E 463      45.725 -20.807  -5.947  1.00 20.88           C
ANISOU 5029  CA  VAL E 463    2351   2370   3213   -218    396   -648        C
ATOM   5030  CB  VAL E 463      44.939 -22.151  -6.066  1.00 21.07           C
ANISOU 5030  CB  VAL E 463    2475   2306   3226    -91    372   -548        C
ATOM   5031  CG1 VAL E 463      43.726 -22.012  -7.015  1.00 18.51           C
ANISOU 5031  CG1 VAL E 463    2276   1857   2899   -139    466   -501        C
ATOM   5032  CG2 VAL E 463      45.863 -23.303  -6.490  1.00 19.87           C
ANISOU 5032  CG2 VAL E 463    2221   2184   3145     35    338   -572        C
ATOM   5033  C   VAL E 463      46.254 -20.270  -7.294  1.00 20.93           C
ANISOU 5033  C   VAL E 463    2297   2378   3279   -312    513   -699        C
ATOM   5034  O   VAL E 463      45.503 -19.667  -8.067  1.00 20.04           O
ANISOU 5034  O   VAL E 463    2287   2170   3159   -394    595   -659        O
ATOM   5035  N   LEU E 464      47.555 -20.432  -7.522  1.00 21.97           N
ANISOU 5035  N   LEU E 464    2253   2633   3461   -308    516   -787        N
ATOM   5036  CA  LEU E 464      48.217 -20.037  -8.768  1.00 22.38           C
ANISOU 5036  CA  LEU E 464    2222   2733   3549   -412    644   -844        C
ATOM   5037  CB  LEU E 464      49.692 -19.686  -8.481  1.00 23.67           C
ANISOU 5037  CB  LEU E 464    2157   3066   3770   -468    634   -973        C
ATOM   5038  CG  LEU E 464      50.020 -18.579  -7.451  1.00 24.00           C
ANISOU 5038  CG  LEU E 464    2156   3149   3816   -587    574  -1026        C
ATOM   5039  CD1 LEU E 464      51.527 -18.280  -7.395  1.00 23.87           C
ANISOU 5039  CD1 LEU E 464    1881   3320   3868   -665    578  -1172        C
ATOM   5040  CD2 LEU E 464      49.204 -17.298  -7.711  1.00 19.83           C
ANISOU 5040  CD2 LEU E 464    1791   2471   3272   -757    652   -975        C
ATOM   5041  C   LEU E 464      48.096 -21.191  -9.796  1.00 23.25           C
ANISOU 5041  C   LEU E 464    2340   2827   3666   -306    696   -838        C
ATOM   5042  O   LEU E 464      47.759 -22.317  -9.404  1.00 23.03           O
ANISOU 5042  O   LEU E 464    2348   2749   3651   -145    614   -807        O
ATOM   5043  N   PRO E 465      48.325 -20.915 -11.110  1.00 24.19           N
ANISOU 5043  N   PRO E 465    2442   2983   3768   -407    835   -868        N
ATOM   5044  CA  PRO E 465      48.340 -21.987 -12.127  1.00 25.02           C
ANISOU 5044  CA  PRO E 465    2532   3105   3868   -317    897   -912        C
ATOM   5045  CB  PRO E 465      48.816 -21.267 -13.393  1.00 25.21           C
ANISOU 5045  CB  PRO E 465    2515   3230   3834   -493   1061   -949        C
ATOM   5046  CG  PRO E 465      48.349 -19.856 -13.215  1.00 25.13           C
ANISOU 5046  CG  PRO E 465    2621   3143   3785   -666   1072   -842        C
ATOM   5047  CD  PRO E 465      48.511 -19.577 -11.724  1.00 25.08           C
ANISOU 5047  CD  PRO E 465    2570   3111   3849   -623    944   -853        C
ATOM   5048  C   PRO E 465      49.235 -23.225 -11.820  1.00 27.35           C
ANISOU 5048  C   PRO E 465    2659   3471   4261   -129    835  -1023        C
ATOM   5049  O   PRO E 465      48.830 -24.361 -12.130  1.00 26.54           O
ANISOU 5049  O   PRO E 465    2609   3290   4185      9    814  -1032        O
ATOM   5050  N   ASP E 466      50.418 -23.018 -11.230  1.00 29.43           N
ANISOU 5050  N   ASP E 466    2720   3869   4592   -119    795  -1113        N
ATOM   5051  CA  ASP E 466      51.243 -24.148 -10.769  1.00 32.32           C
ANISOU 5051  CA  ASP E 466    2921   4288   5071     93    692  -1202        C
ATOM   5052  CB  ASP E 466      52.739 -23.769 -10.621  1.00 34.50           C
ANISOU 5052  CB  ASP E 466    2906   4779   5422     65    702  -1353        C
ATOM   5053  CG  ASP E 466      53.011 -22.725  -9.515  1.00 36.86           C
ANISOU 5053  CG  ASP E 466    3166   5140   5698    -48    612  -1323        C
ATOM   5054  OD1 ASP E 466      52.104 -22.374  -8.726  1.00 36.45           O
ANISOU 5054  OD1 ASP E 466    3303   4971   5575    -73    529  -1195        O
ATOM   5055  OD2 ASP E 466      54.164 -22.236  -9.438  1.00 40.79           O
ANISOU 5055  OD2 ASP E 466    3426   5820   6251   -123    630  -1452        O
ATOM   5056  C   ASP E 466      50.683 -24.859  -9.498  1.00 32.48           C
```

FIGURE 18-146

```
ANISOU 5056  C   ASP E 466    3053  4182  5108   257   499 -1082        C
ATOM   5057  O   ASP E 466    51.316 -25.787  -8.955  1.00 34.03        O
ANISOU 5057  O   ASP E 466    3140  4392  5398   449   373 -1114        O
ATOM   5058  N   MSE E 467    49.498 -24.434  -9.038  1.00 30.80        N
ANISOU 5058  N   MSE E 467    3052  3848  4801   183   475  -942        N
ATOM   5059  CA  MSE E 467    48.846 -25.020  -7.854  1.00 30.56        C
ANISOU 5059  CA  MSE E 467    3147  3717  4746   291   324  -814        C
ATOM   5060  CB  MSE E 467    48.762 -26.561  -7.943  1.00 31.92        C
ANISOU 5060  CB  MSE E 467    3352  3770  5007   491   255  -788        C
ATOM   5061  CG  MSE E 467    47.737 -27.121  -8.964  1.00 31.71        C
ANISOU 5061  CG  MSE E 467    3477  3592  4981   477   356  -771        C
ATOM   5062 SE   MSE E 467    45.883 -26.433  -8.795  0.90 34.47       SE
ANISOU 5062 SE   MSE E 467    4082  3825  5191   312   402  -618       SE
ATOM   5063  CE  MSE E 467    45.524 -26.906  -6.992  1.00 31.60        C
ANISOU 5063  CE  MSE E 467    3808  3411  4787   390   232  -460        C
ATOM   5064  C   MSE E 467    49.441 -24.599  -6.507  1.00 31.54        C
ANISOU 5064  C   MSE E 467    3189  3953  4840   301   184  -803        C
ATOM   5065  O   MSE E 467    49.044 -25.120  -5.466  1.00 31.93        O
ANISOU 5065  O   MSE E 467    3332  3957  4844   388    53  -692        O
ATOM   5066  N   THR E 468    50.376 -23.644  -6.523  1.00 32.10        N
ANISOU 5066  N   THR E 468    3090  4182  4925   193   214  -918        N
ATOM   5067  CA  THR E 468    50.923 -23.058  -5.298  1.00 32.25        C
ANISOU 5067  CA  THR E 468    3023  4330  4900   163    86  -940        C
ATOM   5068  CB  THR E 468    52.209 -22.245  -5.586  1.00 33.45        C
ANISOU 5068  CB  THR E 468    2925  4665  5118    52   132 -1109        C
ATOM   5069  OG1 THR E 468    53.248 -23.146  -5.974  1.00 36.74        O
ANISOU 5069  OG1 THR E 468    3131  5176  5652   209    99 -1199        O
ATOM   5070  CG2 THR E 468    52.708 -21.493  -4.365  1.00 35.62        C
ANISOU 5070  CG2 THR E 468    3114  5077  5342   -16     5 -1160        C
ATOM   5071  C   THR E 468    49.829 -22.192  -4.665  1.00 30.54        C
ANISOU 5071  C   THR E 468    2997  4041  4564    33    99  -864        C
ATOM   5072  O   THR E 468    49.160 -21.413  -5.371  1.00 28.58        O
ANISOU 5072  O   THR E 468    2848  3706  4305  -106   236  -861        O
ATOM   5073  N   PRO E 469    49.621 -22.346  -3.345  1.00 30.70        N
ANISOU 5073  N   PRO E 469    3072  4103  4490    85   -46  -802        N
ATOM   5074  CA  PRO E 469    48.656 -21.488  -2.669  1.00 30.08        C
ANISOU 5074  CA  PRO E 469    3144  3989  4298   -36   -24  -774        C
ATOM   5075  CB  PRO E 469    48.508 -22.138  -1.284  1.00 31.30        C
ANISOU 5075  CB  PRO E 469    3355  4213  4324    65  -191  -683        C
ATOM   5076  CG  PRO E 469    49.779 -22.851  -1.077  1.00 33.03        C
ANISOU 5076  CG  PRO E 469    3396  4554  4601   203  -334  -705        C
ATOM   5077  CD  PRO E 469    50.246 -23.308  -2.421  1.00 32.56        C
ANISOU 5077  CD  PRO E 469    3238  4425  4708   260  -238  -754        C
ATOM   5078  C   PRO E 469    49.205 -20.071  -2.547  1.00 30.36        C
ANISOU 5078  C   PRO E 469    3079  4112  4345  -212    15  -921        C
ATOM   5079  O   PRO E 469    50.414 -19.874  -2.451  1.00 32.17        O
ANISOU 5079  O   PRO E 469    3111  4488  4626  -230   -38 -1031        O
ATOM   5080  N   SER E 470    48.312 -19.099  -2.559  1.00 28.84        N
ANISOU 5080  N   SER E 470    3014  3820  4123  -340   103  -932        N
ATOM   5081  CA  SER E 470    48.702 -17.729  -2.427  1.00 29.49        C
ANISOU 5081  CA  SER E 470    3037  3929  4238  -515   142 -1067        C
ATOM   5082  CB  SER E 470    48.867 -17.093  -3.809  1.00 28.97        C
ANISOU 5082  CB  SER E 470    2956  3760  4289  -635   295 -1082        C
ATOM   5083  OG  SER E 470    49.175 -15.713  -3.679  1.00 29.55        O
ANISOU 5083  OG  SER E 470    3000  3813  4414  -824   336 -1197        O
ATOM   5084  C   SER E 470    47.631 -16.997  -1.653  1.00 28.74        C
ANISOU 5084  C   SER E 470    3092  3763  4065  -573   150 -1083        C
ATOM   5085  O   SER E 470    46.443 -17.255  -1.843  1.00 26.47        O
ANISOU 5085  O   SER E 470    2958  3353  3748  -526   203  -985        O
ATOM   5086  N   THR E 471    48.069 -16.067  -0.807  1.00 30.16        N
ANISOU 5086  N   THR E 471    3210  4030  4222  -681   102 -1231        N
ATOM   5087  CA  THR E 471    47.155 -15.195  -0.063  1.00 30.86        C
ANISOU 5087  CA  THR E 471    3415  4056  4254  -749   123 -1307        C
ATOM   5088  CB  THR E 471    47.566 -15.088   1.420  1.00 32.72        C
ANISOU 5088  CB  THR E 471    3592  4500  4342  -760   -10 -1427        C
ATOM   5089  OG1 THR E 471    48.951 -14.718   1.504  1.00 37.22        O
ANISOU 5089  OG1 THR E 471    3970  5205  4968  -843   -80 -1556        O
ATOM   5090  CG2 THR E 471    47.380 -16.453   2.138  1.00 32.82        C
ANISOU 5090  CG2 THR E 471    3640  4649  4181  -599  -122 -1281        C
ATOM   5091  C   THR E 471    47.026 -13.797  -0.691  1.00 30.99        C
ANISOU 5091  C   THR E 471    3462  3895  4418  -908   233 -1402        C
```

FIGURE 18-147

```
ATOM   5092  O   THR E 471      46.403 -12.895  -0.095  1.00 32.41           O
ANISOU 5092  O   THR E 471    3716   4003   4595   -969    251  -1512        O
ATOM   5093  N   GLU E 472      47.585 -13.628  -1.893  1.00 30.24           N
ANISOU 5093  N   GLU E 472    3317   3723   4448   -974    310  -1358        N
ATOM   5094  CA  GLU E 472      47.662 -12.324  -2.573  1.00 30.68           C
ANISOU 5094  CA  GLU E 472    3405   3604   4648  -1148    408  -1413        C
ATOM   5095  CB  GLU E 472      49.108 -11.861  -2.654  1.00 32.44           C
ANISOU 5095  CB  GLU E 472    3444   3937   4945  -1303    403  -1532        C
ATOM   5096  CG  GLU E 472      49.779 -11.668  -1.290  1.00 37.76           C
ANISOU 5096  CG  GLU E 472    3990   4801   5555  -1337    276  -1720        C
ATOM   5097  CD  GLU E 472      51.175 -12.305  -1.215  1.00 43.37           C
ANISOU 5097  CD  GLU E 472    4460   5762   6256  -1331    199  -1771        C
ATOM   5098  OE1 GLU E 472      52.173 -11.548  -1.139  1.00 44.91           O
ANISOU 5098  OE1 GLU E 472    4502   6025   6538  -1509    199  -1925        O
ATOM   5099  OE2 GLU E 472      51.270 -13.569  -1.236  1.00 42.62           O
ANISOU 5099  OE2 GLU E 472    4322   5787   6083  -1147    136  -1663        O
ATOM   5100  C   GLU E 472      47.062 -12.382  -3.974  1.00 28.59           C
ANISOU 5100  C   GLU E 472    3251   3164   4447  -1137    517  -1248        C
ATOM   5101  O   GLU E 472      46.385 -11.449  -4.397  1.00 28.12           O
ANISOU 5101  O   GLU E 472    3316   2897   4471  -1205    576  -1225        O
ATOM   5102  N   MSE E 473      47.284 -13.494  -4.682  1.00 27.02           N
ANISOU 5102  N   MSE E 473    3012   3048   4206  -1042    532  -1137        N
ATOM   5103  CA  MSE E 473      46.791 -13.651  -6.073  1.00 25.54           C
ANISOU 5103  CA  MSE E 473    2919   2739   4045  -1038    629   -993        C
ATOM   5104  CB  MSE E 473      47.927 -13.574  -7.115  1.00 25.96           C
ANISOU 5104  CB  MSE E 473    2858   2862   4144  -1159    717   -991        C
ATOM   5105  CG  MSE E 473      48.808 -12.339  -7.049  1.00 27.29           C
ANISOU 5105  CG  MSE E 473    2952   3011   4406  -1379    758  -1091        C
ATOM   5106  SE  MSE E 473      47.910 -10.662  -7.515  0.90 31.81          SE
ANISOU 5106  SE  MSE E 473    3749   3250   5087  -1541    823  -1021       SE
ATOM   5107  CE  MSE E 473      47.552 -10.998  -9.390  1.00 22.17           C
ANISOU 5107  CE  MSE E 473    2643   1969   3812  -1555    942   -793        C
ATOM   5108  C   MSE E 473      46.107 -14.980  -6.236  1.00 23.39           C
ANISOU 5108  C   MSE E 473    2695   2501   3691   -856    603   -890        C
ATOM   5109  O   MSE E 473      46.393 -15.922  -5.503  1.00 22.98           O
ANISOU 5109  O   MSE E 473    2572   2580   3579   -744    522   -910        O
ATOM   5110  N   SER E 474      45.225 -15.055  -7.218  1.00 21.86           N
ANISOU 5110  N   SER E 474    2624   2183   3498   -833    662   -776        N
ATOM   5111  CA  SER E 474      44.566 -16.309  -7.532  1.00 21.14           C
ANISOU 5111  CA  SER E 474    2578   2108   3346   -687    648   -690        C
ATOM   5112  CB  SER E 474      43.337 -16.499  -6.641  1.00 19.96           C
ANISOU 5112  CB  SER E 474    2523   1903   3156   -597    594   -671        C
ATOM   5113  OG  SER E 474      42.904 -17.839  -6.691  1.00 17.66           O
ANISOU 5113  OG  SER E 474    2253   1645   2812   -475    569   -603        O
ATOM   5114  C   SER E 474      44.153 -16.398  -9.009  1.00 21.27           C
ANISOU 5114  C   SER E 474    2672   2053   3359   -708    727   -592        C
ATOM   5115  O   SER E 474      43.946 -15.384  -9.652  1.00 20.89           O
ANISOU 5115  O   SER E 474    2694   1900   3342   -814    775   -549        O
ATOM   5116  N   MSE E 475      44.041 -17.620  -9.536  1.00 21.43           N
ANISOU 5116  N   MSE E 475    2683   2123   3336   -608    732   -558        N
ATOM   5117  CA  MSE E 475      43.337 -17.808 -10.790  1.00 22.35           C
ANISOU 5117  CA  MSE E 475    2894   2181   3417   -609    783   -475        C
ATOM   5118  CB  MSE E 475      43.262 -19.297 -11.154  1.00 21.85           C
ANISOU 5118  CB  MSE E 475    2809   2173   3321   -490    776   -482        C
ATOM   5119  CG  MSE E 475      44.593 -19.830 -11.643  1.00 24.48           C
ANISOU 5119  CG  MSE E 475    3003   2637   3663   -493    828   -563        C
ATOM   5120  SE  MSE E 475      44.487 -21.578 -12.470  0.90 25.13          SE
ANISOU 5120  SE  MSE E 475    3073   2746   3730   -353    842   -603       SE
ATOM   5121  CE  MSE E 475      44.118 -22.622 -10.880  1.00 14.68           C
ANISOU 5121  CE  MSE E 475    1759   1354   2463   -188    701   -580        C
ATOM   5122  C   MSE E 475      41.951 -17.191 -10.626  1.00 21.56           C
ANISOU 5122  C   MSE E 475    2925   1942   3326   -596    747   -409        C
ATOM   5123  O   MSE E 475      41.300 -17.398  -9.596  1.00 20.22           O
ANISOU 5123  O   MSE E 475    2769   1750   3164   -523    691   -430        O
ATOM   5124  N   ARG E 476      41.543 -16.382 -11.605  1.00 22.84           N
ANISOU 5124  N   ARG E 476    3174   2018   3486   -669    779   -331        N
ATOM   5125  CA  ARG E 476      40.252 -15.645 -11.593  1.00 23.43           C
ANISOU 5125  CA  ARG E 476    3359   1948   3596   -642    734   -269        C
ATOM   5126  CB  ARG E 476      40.013 -14.999 -12.975  1.00 24.07           C
ANISOU 5126  CB  ARG E 476    3538   1961   3647   -714    755   -147        C
ATOM   5127  CG  ARG E 476      38.593 -14.426 -13.168  1.00 27.79           C
```

FIGURE 18-148

```
ANISOU 5127  CG  ARG E 476    4110  2292  4159   -646   680   -70        C
ATOM   5128  CD  ARG E 476   38.209 -14.075 -14.619  1.00 28.50          C
ANISOU 5128  CD  ARG E 476    4305  2345  4177   -684   665    79        C
ATOM   5129  NE  ARG E 476   38.636 -14.995 -15.699  1.00 32.45          N
ANISOU 5129  NE  ARG E 476    4797  3003  4528   -722   716   104        N
ATOM   5130  CZ  ARG E 476   37.899 -15.993 -16.202  1.00 31.12          C
ANISOU 5130  CZ  ARG E 476    4629  2913  4282   -642   682    96        C
ATOM   5131  NH1 ARG E 476   36.693 -16.294 -15.685  1.00 30.33          N
ANISOU 5131  NH1 ARG E 476    4521  2762  4240   -526   601    71        N
ATOM   5132  NH2 ARG E 476   38.385 -16.718 -17.191  1.00 25.61          N
ANISOU 5132  NH2 ARG E 476    3925  2354  3452   -687   739    89        N
ATOM   5133  C   ARG E 476   39.015 -16.489 -11.142  1.00 21.83          C
ANISOU 5133  C   ARG E 476    3173  1741  3380   -513   681  -273        C
ATOM   5134  O   ARG E 476   38.679 -17.503 -11.745  1.00 21.04          O
ANISOU 5134  O   ARG E 476    3079  1693  3224   -465   681  -247        O
ATOM   5135  N   GLY E 477   38.372 -16.052 -10.058  1.00 21.70          N
ANISOU 5135  N   GLY E 477    3157  1672  3416   -473   646  -324        N
ATOM   5136  CA  GLY E 477   37.207 -16.716  -9.484  1.00 20.09          C
ANISOU 5136  CA  GLY E 477    2953  1479  3200   -382   617  -338        C
ATOM   5137  C   GLY E 477   37.443 -18.027  -8.755  1.00 19.41          C
ANISOU 5137  C   GLY E 477    2821  1499  3053   -341   617  -363        C
ATOM   5138  O   GLY E 477   36.471 -18.609  -8.296  1.00 19.64          O
ANISOU 5138  O   GLY E 477    2856  1537  3067   -294   607  -361        O
ATOM   5139  N   ILE E 478   38.696 -18.502  -8.647  1.00 18.91          N
ANISOU 5139  N   ILE E 478    2708  1514  2965   -357   623  -381        N
ATOM   5140  CA  ILE E 478   39.017 -19.810  -8.023  1.00 17.77          C
ANISOU 5140  CA  ILE E 478    2530  1443  2777   -297   599  -380        C
ATOM   5141  CB  ILE E 478   40.039 -20.648  -8.855  1.00 18.55          C
ANISOU 5141  CB  ILE E 478    2584  1586  2878   -277   612  -379        C
ATOM   5142  CG1 ILE E 478   39.751 -20.616 -10.374  1.00 17.27          C
ANISOU 5142  CG1 ILE E 478    2459  1391  2711   -306   659  -354        C
ATOM   5143  CD1 ILE E 478   38.418 -21.271 -10.824  1.00 13.13          C
ANISOU 5143  CD1 ILE E 478    2003   811  2174   -270   646  -315        C
ATOM   5144  CG2 ILE E 478   40.182 -22.098  -8.267  1.00 18.35          C
ANISOU 5144  CG2 ILE E 478    2547  1581  2843   -186   567  -361        C
ATOM   5145  C   ILE E 478   39.616 -19.651  -6.599  1.00 18.69          C
ANISOU 5145  C   ILE E 478    2602  1637  2863   -298   561  -430        C
ATOM   5146  O   ILE E 478   40.569 -18.901  -6.395  1.00 18.45          O
ANISOU 5146  O   ILE E 478    2515  1647  2850   -348   556  -490        O
ATOM   5147  N   ARG E 479   39.035 -20.351  -5.617  1.00 18.39          N
ANISOU 5147  N   ARG E 479    2589  1632  2767   -257   533  -405        N
ATOM   5148  CA  ARG E 479   39.554 -20.346  -4.253  1.00 19.06          C
ANISOU 5148  CA  ARG E 479    2644  1820  2777   -256   483  -435        C
ATOM   5149  CB  ARG E 479   38.638 -19.533  -3.312  1.00 19.09          C
ANISOU 5149  CB  ARG E 479    2674  1845  2733   -297   507  -498        C
ATOM   5150  CG  ARG E 479   38.471 -18.073  -3.712  1.00 20.34          C
ANISOU 5150  CG  ARG E 479    2824  1925  2979   -348   545  -592        C
ATOM   5151  CD  ARG E 479   39.752 -17.232  -3.507  1.00 22.85          C
ANISOU 5151  CD  ARG E 479    3081  2279  3322   -408   517  -680        C
ATOM   5152  NE  ARG E 479   39.500 -15.800  -3.765  1.00 25.19          N
ANISOU 5152  NE  ARG E 479    3393  2459  3718   -468   552  -765        N
ATOM   5153  CZ  ARG E 479   39.487 -15.222  -4.979  1.00 27.21          C
ANISOU 5153  CZ  ARG E 479    3679  2582  4078   -498   582  -718        C
ATOM   5154  NH1 ARG E 479   39.709 -15.928  -6.090  1.00 26.37          N
ANISOU 5154  NH1 ARG E 479    3581  2470  3970   -482   595  -610        N
ATOM   5155  NH2 ARG E 479   39.248 -13.924  -5.085  1.00 26.41          N
ANISOU 5155  NH2 ARG E 479    3609  2347  4078   -547   597  -780        N
ATOM   5156  C   ARG E 479   39.697 -21.757  -3.727  1.00 19.49          C
ANISOU 5156  C   ARG E 479    2720  1912  2775   -189   429  -345        C
ATOM   5157  O   ARG E 479   38.976 -22.661  -4.158  1.00 18.74          O
ANISOU 5157  O   ARG E 479    2681  1743  2697   -162   449  -271        O
ATOM   5158  N   VAL E 480   40.609 -21.940  -2.772  1.00 20.82          N
ANISOU 5158  N   VAL E 480    2847  2187  2876   -166   349  -348        N
ATOM   5159  CA  VAL E 480   40.767 -23.248  -2.116  1.00 21.96          C
ANISOU 5159  CA  VAL E 480    3031  2353  2960    -92   271  -232        C
ATOM   5160  CB  VAL E 480   42.207 -23.838  -2.322  1.00 22.03          C
ANISOU 5160  CB  VAL E 480    2948  2393  3028      3   178  -229        C
ATOM   5161  CG1 VAL E 480   42.429 -25.077  -1.472  1.00 22.81          C
ANISOU 5161  CG1 VAL E 480    3098  2500  3069     95    63   -94        C
ATOM   5162  CG2 VAL E 480   42.460 -24.160  -3.772  1.00 20.19          C
ANISOU 5162  CG2 VAL E 480    2677  2061  2932     38   234  -261        C
```

FIGURE 18-149

```
ATOM   5163  C   VAL E 480      40.412 -23.122  -0.620  1.00 23.54           C
ANISOU 5163  C   VAL E 480     3277  2674  2994  -131   235  -206            C
ATOM   5164  O   VAL E 480      40.953 -22.280   0.097  1.00 24.05           O
ANISOU 5164  O   VAL E 480     3287  2864  2988  -167   198  -300            O
ATOM   5165  N   SER E 481      39.492 -23.966  -0.161  1.00 24.81           N
ANISOU 5165  N   SER E 481     3538  2808  3083  -141   253   -88            N
ATOM   5166  CA  SER E 481      39.093 -24.015   1.249  1.00 26.08           C
ANISOU 5166  CA  SER E 481     3757  3104  3048  -193   236   -40            C
ATOM   5167  CB  SER E 481      37.836 -24.872   1.399  1.00 25.78           C
ANISOU 5167  CB  SER E 481     3824  3003  2969  -243   310    83            C
ATOM   5168  OG  SER E 481      37.426 -24.964   2.750  1.00 25.77           O
ANISOU 5168  OG  SER E 481     3886  3155  2752  -316   315   141            O
ATOM   5169  C   SER E 481      40.194 -24.566   2.157  1.00 28.89           C
ANISOU 5169  C   SER E 481     4114  3570  3294  -131    82    47            C
ATOM   5170  O   SER E 481      40.829 -25.579   1.858  1.00 29.34           O
ANISOU 5170  O   SER E 481     4181  3543  3423   -30    -9   161            O
ATOM   5171  N   LYS E 482      40.406 -23.902   3.280  1.00 31.33           N
ANISOU 5171  N   LYS E 482     4407  4070  3426  -183    44   -16            N
ATOM   5172  CA  LYS E 482      41.264 -24.437   4.320  1.00 35.34           C
ANISOU 5172  CA  LYS E 482     4931  4720  3776  -135  -119    86            C
ATOM   5173  CB  LYS E 482      42.004 -23.295   5.021  1.00 36.93           C
ANISOU 5173  CB  LYS E 482     5031  5127  3875  -177  -179   -95            C
ATOM   5174  CG  LYS E 482      43.111 -22.672   4.207  1.00 38.22           C
ANISOU 5174  CG  LYS E 482     5038  5259  4224  -134  -219  -240            C
ATOM   5175  CD  LYS E 482      43.698 -21.521   4.982  1.00 44.98           C
ANISOU 5175  CD  LYS E 482     5803  6309  4977  -211  -267  -433            C
ATOM   5176  CE  LYS E 482      45.223 -21.561   4.968  1.00 47.96           C
ANISOU 5176  CE  LYS E 482     6028  6783  5410  -142  -430  -476            C
ATOM   5177  NZ  LYS E 482      45.777 -20.298   5.551  1.00 50.79           N
ANISOU 5177  NZ  LYS E 482     6280  7307  5710  -250  -458  -708            N
ATOM   5178  C   LYS E 482      40.480 -25.277   5.345  1.00 37.85           C
ANISOU 5178  C   LYS E 482     5402  5097  3882  -186  -120   278            C
ATOM   5179  O   LYS E 482      41.059 -25.722   6.324  1.00 40.42           O
ANISOU 5179  O   LYS E 482     5770  5557  4030  -157  -263   396            O
ATOM   5180  N   MSE E 483      39.178 -25.477   5.113  1.00 38.08           N
ANISOU 5180  N   MSE E 483     5507  5039  3923  -271    35   313            N
ATOM   5181  CA  MSE E 483      38.319 -26.309   5.975  1.00 41.13           C
ANISOU 5181  CA  MSE E 483     6038  5469  4121  -357    73   501            C
ATOM   5182  CB  MSE E 483      36.882 -25.754   6.064  1.00 40.37           C
ANISOU 5182  CB  MSE E 483     5941  5421  3976  -498   279   393            C
ATOM   5183  CG  MSE E 483      36.761 -24.265   6.345  1.00 40.01           C
ANISOU 5183  CG  MSE E 483     5787  5531  3882  -542   350   123            C
ATOM   5184  SE  MSE E 483      37.684 -23.720   7.991  0.90 48.53          SE
ANISOU 5184  SE  MSE E 483     6871  6944  4625  -576   224    65          SE
ATOM   5185  CE  MSE E 483      36.796 -24.873   9.310  1.00 39.30           C
ANISOU 5185  CE  MSE E 483     5885  5939  3108  -711   273   332            C
ATOM   5186  C   MSE E 483      38.246 -27.706   5.373  1.00 42.30           C
ANISOU 5186  C   MSE E 483     6281  5381  4412  -297    34   716            C
ATOM   5187  O   MSE E 483      37.810 -27.893   4.207  1.00 41.41           O
ANISOU 5187  O   MSE E 483     6140  5074  4520  -280   115   669            O
ATOM   5188  OXT MSE E 483      38.610 -28.668   6.048  1.00 45.09           O
ANISOU 5188  OXT MSE E 483     6745  5727  4660  -266   -87   937            O
ATOM   5189  N   SER F 322      34.011   6.452 -60.832  1.00 64.98           N
ANISOU 5189  N   SER F 322    10039 10556  4093 -1803   691  1251            N
ATOM   5190  CA  SER F 322      32.816   6.735 -59.979  1.00 62.59           C
ANISOU 5190  CA  SER F 322     9734 10002  4046 -1536   361  1309            C
ATOM   5191  CB  SER F 322      32.604   8.243 -59.821  1.00 64.65           C
ANISOU 5191  CB  SER F 322    10337  9931  4296 -1631   298  1564            C
ATOM   5192  OG  SER F 322      33.389   8.747 -58.754  1.00 65.13           O
ANISOU 5192  OG  SER F 322    10229  9915  4604 -1806   456  1515            O
ATOM   5193  C   SER F 322      31.562   6.093 -60.548  1.00 61.62           C
ANISOU 5193  C   SER F 322     9683  9900  3831 -1253    68  1295            C
ATOM   5194  O   SER F 322      31.304   6.186 -61.745  1.00 64.33           O
ANISOU 5194  O   SER F 322    10330 10282  3832 -1271    13  1407            O
ATOM   5195  N   PHE F 323      30.793   5.447 -59.672  1.00 57.78           N
ANISOU 5195  N   PHE F 323     8921  9391  3643 -1013  -115  1152            N
ATOM   5196  CA  PHE F 323      29.540   4.774 -60.034  1.00 56.60           C
ANISOU 5196  CA  PHE F 323     8754  9271  3481  -759  -400  1094            C
ATOM   5197  CB  PHE F 323      29.803   3.472 -60.817  1.00 56.49           C
ANISOU 5197  CB  PHE F 323     8646  9535  3285  -767  -321   906            C
ATOM   5198  CG  PHE F 323      30.640   2.458 -60.073  1.00 53.82           C
```

FIGURE 18-150

```
ANISOU 5198  CG  PHE F 323    7956   9345   3148   -799   -105    669        C
ATOM   5199  CD1 PHE F 323    30.039    1.474 -59.298  1.00 49.66            C
ANISOU 5199  CD1 PHE F 323    7167   8820   2880   -621   -219    487        C
ATOM   5200  CE1 PHE F 323    30.800    0.533 -58.628  1.00 48.33            C
ANISOU 5200  CE1 PHE F 323    6732   8755   2877   -621    -52    290        C
ATOM   5201  CZ  PHE F 323    32.182    0.565 -58.719  1.00 49.24            C
ANISOU 5201  CZ  PHE F 323    6772   9006   2930   -778    220    248        C
ATOM   5202  CE2 PHE F 323    32.796    1.537 -59.491  1.00 52.46            C
ANISOU 5202  CE2 PHE F 323    7386   9446   3100   -985    365    404        C
ATOM   5203  CD2 PHE F 323    32.028    2.476 -60.167  1.00 54.43            C
ANISOU 5203  CD2 PHE F 323    7968   9559   3154  -1005    210    625        C
ATOM   5204  C   PHE F 323    28.693    4.508 -58.789  1.00 53.34            C
ANISOU 5204  C   PHE F 323    8069   8746   3453   -555   -559    984        C
ATOM   5205  O   PHE F 323    28.952    5.075 -57.735  1.00 52.04            O
ANISOU 5205  O   PHE F 323    7823   8434   3515   -588   -490   1003        O
ATOM   5206  N   SER F 324    27.717    3.610 -58.913  1.00 52.31            N
ANISOU 5206  N   SER F 324    7801   8693   3380   -371   -751    850        N
ATOM   5207  CA  SER F 324    26.659    3.430 -57.923  1.00 50.15            C
ANISOU 5207  CA  SER F 324    7311   8311   3432   -183   -917    760        C
ATOM   5208  CB  SER F 324    25.461    4.292 -58.342  1.00 52.27            C
ANISOU 5208  CB  SER F 324    7742   8435   3685     -5  -1217    905        C
ATOM   5209  OG  SER F 324    24.546    4.524 -57.289  1.00 51.91            O
ANISOU 5209  OG  SER F 324    7504   8244   3975    161  -1325    848        O
ATOM   5210  C   SER F 324    26.254    1.948 -57.864  1.00 48.44            C
ANISOU 5210  C   SER F 324    6852   8258   3293   -116   -945    520        C
ATOM   5211  O   SER F 324    26.075    1.322 -58.895  1.00 50.04            O
ANISOU 5211  O   SER F 324    7125   8610   3280   -114  -1019    464        O
ATOM   5212  N   PHE F 325    26.129    1.389 -56.660  1.00 45.78            N
ANISOU 5212  N   PHE F 325    6271   7878   3245    -79   -878    379        N
ATOM   5213  CA  PHE F 325    25.670   -0.004 -56.478  1.00 43.79            C
ANISOU 5213  CA  PHE F 325    5824   7722   3091    -32   -896    158        C
ATOM   5214  CB  PHE F 325    26.785   -1.009 -56.819  1.00 43.32            C
ANISOU 5214  CB  PHE F 325    5751   7815   2894   -128   -702     38        C
ATOM   5215  CG  PHE F 325    26.407   -2.453 -56.596  1.00 42.81            C
ANISOU 5215  CG  PHE F 325    5543   7795   2927    -86   -705   -186        C
ATOM   5216  CD1 PHE F 325    25.471   -3.087 -57.424  1.00 45.16            C
ANISOU 5216  CD1 PHE F 325    5857   8167   3136    -52   -875   -288        C
ATOM   5217  CE1 PHE F 325    25.112   -4.424 -57.209  1.00 44.54            C
ANISOU 5217  CE1 PHE F 325    5674   8097   3153    -49   -865   -503        C
ATOM   5218  CZ  PHE F 325    25.706   -5.150 -56.167  1.00 42.37            C
ANISOU 5218  CZ  PHE F 325    5311   7741   3047    -53   -689   -594        C
ATOM   5219  CE2 PHE F 325    26.651   -4.536 -55.348  1.00 40.54            C
ANISOU 5219  CE2 PHE F 325    5059   7456   2890    -58   -547   -487        C
ATOM   5220  CD2 PHE F 325    26.989   -3.188 -55.561  1.00 41.44            C
ANISOU 5220  CD2 PHE F 325    5244   7577   2924    -88   -552   -295        C
ATOM   5221  C   PHE F 325    25.132   -0.224 -55.053  1.00 41.64            C
ANISOU 5221  C   PHE F 325    5353   7325   3145     26   -873     66        C
ATOM   5222  O   PHE F 325    25.807    0.091 -54.067  1.00 39.51            O
ANISOU 5222  O   PHE F 325    5054   6968   2990    -20   -727     92        O
ATOM   5223  N   GLY F 326    23.906   -0.747 -54.969  1.00 41.53            N
ANISOU 5223  N   GLY F 326    5205   7311   3264    109  -1015    -51        N
ATOM   5224  CA  GLY F 326    23.229   -1.041 -53.700  1.00 39.72            C
ANISOU 5224  CA  GLY F 326    4794   6976   3322    140   -970   -158        C
ATOM   5225  C   GLY F 326    23.119    0.104 -52.706  1.00 39.23            C
ANISOU 5225  C   GLY F 326    4733   6746   3427    187   -931    -57        C
ATOM   5226  O   GLY F 326    23.248   -0.105 -51.503  1.00 37.01            O
ANISOU 5226  O   GLY F 326    4384   6376   3302    155   -790   -119        O
ATOM   5227  N   GLY F 327    22.887    1.309 -53.220  1.00 40.74            N
ANISOU 5227  N   GLY F 327    5040   6875   3563    264  -1061     99        N
ATOM   5228  CA  GLY F 327    22.741    2.501 -52.404  1.00 41.28            C
ANISOU 5228  CA  GLY F 327    5152   6754   3780    325  -1040    192        C
ATOM   5229  C   GLY F 327    24.066    3.126 -51.996  1.00 40.95            C
ANISOU 5229  C   GLY F 327    5272   6631   3655    195   -873    305        C
ATOM   5230  O   GLY F 327    24.101    4.024 -51.162  1.00 40.80            O
ANISOU 5230  O   GLY F 327    5305   6440   3756    207   -821    353        O
ATOM   5231  N   PHE F 328    25.160    2.646 -52.578  1.00 40.57            N
ANISOU 5231  N   PHE F 328    5289   6716   3411     64   -781    323        N
ATOM   5232  CA  PHE F 328    26.480    3.152 -52.254  1.00 40.14            C
ANISOU 5232  CA  PHE F 328    5327   6634   3289    -87   -619    398        C
ATOM   5233  CB  PHE F 328    27.337    2.054 -51.593  1.00 38.59            C
ANISOU 5233  CB  PHE F 328    4985   6548   3129   -161   -471    255        C
```

FIGURE 18-151

```
ATOM   5234  CG  PHE F 328      26.937   1.747 -50.172  1.00 36.26           C
ANISOU 5234  CG  PHE F 328    4584   6146   3047   -114   -436    152        C
ATOM   5235  CD1 PHE F 328      27.509   2.439 -49.118  1.00 35.56           C
ANISOU 5235  CD1 PHE F 328    4532   5943   3037   -180   -359    178        C
ATOM   5236  CE1 PHE F 328      27.135   2.179 -47.794  1.00 35.95           C
ANISOU 5236  CE1 PHE F 328    4532   5891   3238   -147   -318     85        C
ATOM   5237  CZ  PHE F 328      26.175   1.205 -47.525  1.00 35.59           C
ANISOU 5237  CZ  PHE F 328    4392   5853   3279    -67   -328    -30        C
ATOM   5238  CE2 PHE F 328      25.579   0.501 -48.591  1.00 35.31           C
ANISOU 5238  CE2 PHE F 328    4292   5930   3195    -16   -406    -67        C
ATOM   5239  CD2 PHE F 328      25.972   0.772 -49.896  1.00 36.57           C
ANISOU 5239  CD2 PHE F 328    4509   6196   3191    -31   -472     21        C
ATOM   5240  C   PHE F 328      27.164   3.747 -53.487  1.00 42.14           C
ANISOU 5240  C   PHE F 328    5784   6945   3284   -188   -612    551        C
ATOM   5241  O   PHE F 328      27.123   3.162 -54.574  1.00 43.04           O
ANISOU 5241  O   PHE F 328    5930   7212   3211   -186   -657    538        O
ATOM   5242  N   THR F 329      27.753   4.931 -53.308  1.00 43.06           N
ANISOU 5242  N   THR F 329    6063   6922   3376   -296   -547    691        N
ATOM   5243  CA  THR F 329      28.590   5.562 -54.324  1.00 44.99           C
ANISOU 5243  CA  THR F 329    6526   7199   3369   -463   -471    842        C
ATOM   5244  CB  THR F 329      28.582   7.124 -54.212  1.00 47.13           C
ANISOU 5244  CB  THR F 329    7067   7201   3639   -520   -492   1036        C
ATOM   5245  OG1 THR F 329      27.239   7.622 -54.309  1.00 47.99           O
ANISOU 5245  OG1 THR F 329    7274   7135   3825   -281   -725   1105        O
ATOM   5246  CG2 THR F 329      29.435   7.782 -55.313  1.00 49.33           C
ANISOU 5246  CG2 THR F 329    7622   7494   3626   -739   -385   1209        C
ATOM   5247  C   THR F 329      30.011   5.037 -54.169  1.00 44.33           C
ANISOU 5247  C   THR F 329    6307   7296   3238   -659   -242    750        C
ATOM   5248  O   THR F 329      30.661   5.270 -53.164  1.00 43.50           O
ANISOU 5248  O   THR F 329    6103   7145   3278   -750   -146    702        O
ATOM   5249  N   PHE F 330      30.485   4.299 -55.160  1.00 45.43           N
ANISOU 5249  N   PHE F 330    6430   7653   3179   -712   -166    704        N
ATOM   5250  CA  PHE F 330      31.856   3.815 -55.144  1.00 45.51           C
ANISOU 5250  CA  PHE F 330    6284   7859   3150   -873     57    599        C
ATOM   5251  CB  PHE F 330      31.974   2.448 -55.811  1.00 44.24           C
ANISOU 5251  CB  PHE F 330    5998   7924   2886   -793     95    438        C
ATOM   5252  CG  PHE F 330      31.265   1.341 -55.083  1.00 41.56           C
ANISOU 5252  CG  PHE F 330    5484   7570   2737   -593    -24    281        C
ATOM   5253  CD1 PHE F 330      31.970   0.227 -54.643  1.00 39.01           C
ANISOU 5253  CD1 PHE F 330    4950   7373   2501   -551     72     97        C
ATOM   5254  CE1 PHE F 330      31.319  -0.811 -53.999  1.00 36.87           C
ANISOU 5254  CE1 PHE F 330    4580   7051   2379   -392    -23    -32        C
ATOM   5255  CZ  PHE F 330      29.941  -0.742 -53.767  1.00 36.29           C
ANISOU 5255  CZ  PHE F 330    4566   6835   2390   -298   -191      0        C
ATOM   5256  CE2 PHE F 330      29.229   0.364 -54.190  1.00 37.65           C
ANISOU 5256  CE2 PHE F 330    4887   6913   2505   -313   -297    159        C
ATOM   5257  CD2 PHE F 330      29.886   1.396 -54.852  1.00 39.87           C
ANISOU 5257  CD2 PHE F 330    5319   7211   2619   -446   -227    310        C
ATOM   5258  C   PHE F 330      32.713   4.818 -55.875  1.00 48.65           C
ANISOU 5258  C   PHE F 330    6873   8264   3348  -1124    219    745        C
ATOM   5259  O   PHE F 330      32.259   5.448 -56.807  1.00 50.59           O
ANISOU 5259  O   PHE F 330    7408   8428   3384  -1150    160    912        O
ATOM   5260  N   LYS F 331      33.946   4.979 -55.416  1.00 50.04           N
ANISOU 5260  N   LYS F 331    6892   8531   3590  -1318    414    680        N
ATOM   5261  CA  LYS F 331      34.964   5.753 -56.116  1.00 53.68           C
ANISOU 5261  CA  LYS F 331    7471   9055   3869  -1620    639    769        C
ATOM   5262  CB  LYS F 331      35.231   7.083 -55.410  1.00 55.11           C
ANISOU 5262  CB  LYS F 331    7777   9006   4157  -1811    660    889        C
ATOM   5263  CG  LYS F 331      34.021   7.996 -55.305  1.00 58.38           C
ANISOU 5263  CG  LYS F 331    8516   9084   4581  -1684    447   1080        C
ATOM   5264  CD  LYS F 331      34.421   9.467 -55.258  1.00 65.79           C
ANISOU 5264  CD  LYS F 331    9739   9778   5479  -1948    534   1252        C
ATOM   5265  CE  LYS F 331      33.390  10.311 -56.018  1.00 69.37           C
ANISOU 5265  CE  LYS F 331   10638   9954   5763  -1842    370   1498        C
ATOM   5266  NZ  LYS F 331      33.674  11.800 -55.808  1.00 74.95           N
ANISOU 5266  NZ  LYS F 331   11678  10334   6466  -2070    432   1671        N
ATOM   5267  C   LYS F 331      36.204   4.910 -56.034  1.00 53.61           C
ANISOU 5267  C   LYS F 331    7117   9344   3907  -1704    845    557        C
ATOM   5268  O   LYS F 331      36.661   4.624 -54.932  1.00 51.96           O
ANISOU 5268  O   LYS F 331    6638   9168   3938  -1666    824    424        O
ATOM   5269  N   ARG F 332      36.740   4.480 -57.175  1.00 55.82           N
```

FIGURE 18-152

```
ANISOU 5269  N    ARG F 332    7406   9846   3958  -1795   1035    512       N
ATOM   5270  CA   ARG F 332    37.975    3.711  -57.141  1.00 56.45           C
ANISOU 5270  CA   ARG F 332    7126  10222   4102  -1854   1251    286       C
ATOM   5271  CB   ARG F 332    38.200    2.902  -58.417  1.00 58.54           C
ANISOU 5271  CB   ARG F 332    7413  10718   4111  -1836   1419    191       C
ATOM   5272  CG   ARG F 332    39.426    1.993  -58.330  1.00 58.83           C
ANISOU 5272  CG   ARG F 332    7035  11059   4257  -1823   1632    -82       C
ATOM   5273  CD   ARG F 332    39.626    1.183  -59.593  1.00 60.93           C
ANISOU 5273  CD   ARG F 332    7343  11542   4265  -1793   1821   -205       C
ATOM   5274  NE   ARG F 332    40.094    1.998  -60.711  1.00 63.73           N
ANISOU 5274  NE   ARG F 332    7925  11986   4305  -2121   2102    -93       N
ATOM   5275  CZ   ARG F 332    39.945    1.662  -61.989  1.00 67.27           C
ANISOU 5275  CZ   ARG F 332    8607  12545   4407  -2151   2238   -103       C
ATOM   5276  NH1  ARG F 332    39.334    0.528  -62.321  1.00 65.85           N
ANISOU 5276  NH1  ARG F 332    8448  12400   4171  -1873   2106   -235       N
ATOM   5277  NH2  ARG F 332    40.400    2.464  -62.946  1.00 71.36           N
ANISOU 5277  NH2  ARG F 332    9373  13127   4613  -2480   2512     18       N
ATOM   5278  C    ARG F 332    39.138    4.648  -56.879  1.00 58.97           C
ANISOU 5278  C    ARG F 332    7335  10596   4475  -2189   1464    297       C
ATOM   5279  O    ARG F 332    39.386    5.586  -57.629  1.00 61.80           O
ANISOU 5279  O    ARG F 332    7943  10911   4627  -2474   1635    449       O
ATOM   5280  N    THR F 333    39.841    4.386  -55.789  1.00 58.21           N
ANISOU 5280  N    THR F 333    6878  10586   4652  -2165   1442    134       N
ATOM   5281  CA   THR F 333    40.945    5.229  -55.366  1.00 60.07           C
ANISOU 5281  CA   THR F 333    6945  10888   4991  -2487   1602    103       C
ATOM   5282  CB   THR F 333    40.955    5.395  -53.809  1.00 57.87           C
ANISOU 5282  CB   THR F 333    6499  10485   5005  -2405   1378     45       C
ATOM   5283  OG1  THR F 333    40.820    4.116  -53.173  1.00 53.94           O
ANISOU 5283  OG1  THR F 333    5755  10082   4659  -2055   1210   -124       O
ATOM   5284  CG2  THR F 333    39.781    6.265  -53.360  1.00 55.42           C
ANISOU 5284  CG2  THR F 333    6572   9793   4692  -2367   1177    257       C
ATOM   5285  C    THR F 333    42.260    4.664  -55.913  1.00 63.49           C
ANISOU 5285  C    THR F 333    7009  11703   5413  -2612   1892   -115       C
ATOM   5286  O    THR F 333    43.229    5.410  -56.156  1.00 66.66           O
ANISOU 5286  O    THR F 333    7310  12223   5793  -2977   2143   -133       O
ATOM   5287  N    SER F 334    42.274    3.351  -56.144  1.00 62.58           N
ANISOU 5287  N    SER F 334    6695  11769   5312  -2317   1875   -291       N
ATOM   5288  CA   SER F 334    43.502    2.644  -56.507  1.00 65.70           C
ANISOU 5288  CA   SER F 334    6674  12530   5758  -2338   2121   -550       C
ATOM   5289  CB   SER F 334    44.291    2.301  -55.244  1.00 65.54           C
ANISOU 5289  CB   SER F 334    6199  12626   6076  -2225   1985   -745       C
ATOM   5290  OG   SER F 334    44.801    3.472  -54.626  1.00 68.04           O
ANISOU 5290  OG   SER F 334    6457  12896   6498  -2553   2002   -685       O
ATOM   5291  C    SER F 334    43.246    1.357  -57.283  1.00 65.13           C
ANISOU 5291  C    SER F 334    6595  12586   5565  -2050   2161   -684       C
ATOM   5292  O    SER F 334    42.223    0.701  -57.097  1.00 62.02           O
ANISOU 5292  O    SER F 334    6381  12018   5168  -1758   1918   -644       O
ATOM   5293  N    GLY F 335    44.195    0.999  -58.142  1.00 68.40           N
ANISOU 5293  N    GLY F 335    6793  13307   5888  -2150   2488   -866       N
ATOM   5294  CA   GLY F 335    44.157   -0.277  -58.850  1.00 68.50           C
ANISOU 5294  CA   GLY F 335    6754  13467   5808  -1876   2563  -1055       C
ATOM   5295  C    GLY F 335    43.389   -0.225  -60.154  1.00 68.74           C
ANISOU 5295  C    GLY F 335    7239  13435   5445  -1951   2668   -925       C
ATOM   5296  O    GLY F 335    43.026    0.858  -60.629  1.00 69.46           O
ANISOU 5296  O    GLY F 335    7680  13399   5314  -2236   2722   -681       O
ATOM   5297  N    SER F 336    43.149   -1.405  -60.731  1.00 68.37           N
ANISOU 5297  N    SER F 336    7212  13464   5303  -1688   2679  -1092       N
ATOM   5298  CA   SER F 336    42.397   -1.531  -61.986  1.00 69.05           C
ANISOU 5298  CA   SER F 336    7727  13513   4996  -1723   2739  -1010       C
ATOM   5299  CB   SER F 336    43.217   -1.023  -63.178  1.00 73.61           C
ANISOU 5299  CB   SER F 336    8375  14331   5263  -2063   3179  -1036       C
ATOM   5300  OG   SER F 336    44.204   -1.967  -63.529  1.00 76.75           O
ANISOU 5300  OG   SER F 336    8413  15033   5715  -1957   3464  -1374       O
ATOM   5301  C    SER F 336    41.939   -2.968  -62.240  1.00 67.73           C
ANISOU 5301  C    SER F 336    7568  13350   4817  -1369   2631  -1214       C
ATOM   5302  O    SER F 336    42.344   -3.898  -61.517  1.00 66.67           O
ANISOU 5302  O    SER F 336    7102  13257   4972  -1096   2562  -1428       O
ATOM   5303  N    SER F 337    41.095   -3.128  -63.279  1.00 68.08           N
ANISOU 5303  N    SER F 337    8018  13336   4512  -1379   2602  -1144       N
ATOM   5304  CA   SER F 337    40.508   -4.417  -63.644  1.00 67.00           C
ANISOU 5304  CA   SER F 337    7973  13170   4315  -1097   2486  -1327       C
```

FIGURE 18-153

```
ATOM   5305  CB  SER F 337      39.336  -4.739 -62.720  1.00 62.53           C
ANISOU 5305  CB  SER F 337    7481  12315   3961   -875   2064  -1229        C
ATOM   5306  OG  SER F 337      38.333  -3.755 -62.848  1.00 60.99           O
ANISOU 5306  OG  SER F 337    7612  11944   3619  -1016   1861   -934        O
ATOM   5307  C   SER F 337      40.018  -4.501 -65.096  1.00 69.66           C
ANISOU 5307  C   SER F 337    8719  13566   4183  -1202   2583  -1314        C
ATOM   5308  O   SER F 337      39.755  -3.477 -65.752  1.00 70.99           O
ANISOU 5308  O   SER F 337    9208  13715   4051  -1462   2625  -1078        O
ATOM   5309  N   ILE F 338      39.898  -5.738 -65.580  1.00 70.19           N
ANISOU 5309  N   ILE F 338    8806  13686   4178   -994   2605  -1570        N
ATOM   5310  CA  ILE F 338      39.155  -6.038 -66.796  1.00 71.90           C
ANISOU 5310  CA  ILE F 338    9439  13908   3972  -1029   2574  -1583        C
ATOM   5311  CB  ILE F 338      40.002  -6.853 -67.853  1.00 76.35           C
ANISOU 5311  CB  ILE F 338    9987  14730   4290  -1023   2965  -1906        C
ATOM   5312  CG1 ILE F 338      40.263  -8.298 -67.393  1.00 75.23           C
ANISOU 5312  CG1 ILE F 338    9575  14570   4439   -678   2951  -2246        C
ATOM   5313  CD1 ILE F 338      40.863  -9.201 -68.486  1.00 80.18           C
ANISOU 5313  CD1 ILE F 338   10254  15401   4810   -623   3291  -2589        C
ATOM   5314  CG2 ILE F 338      41.320  -6.112 -68.205  1.00 78.90           C
ANISOU 5314  CG2 ILE F 338   10131  15320   4527  -1288   3428  -1925        C
ATOM   5315  C   ILE F 338      37.828  -6.734 -66.425  1.00 68.91           C
ANISOU 5315  C   ILE F 338    9200  13287   3697   -806   2150  -1576        C
ATOM   5316  O   ILE F 338      37.757  -7.445 -65.419  1.00 66.10           O
ANISOU 5316  O   ILE F 338    8600  12808   3708   -581   2005  -1683        O
ATOM   5317  N   LYS F 339      36.784  -6.500 -67.226  1.00 69.74           N
ANISOU 5317  N   LYS F 339    9700  13325   3473   -882   1949  -1445        N
ATOM   5318  CA  LYS F 339      35.463  -7.116 -67.021  1.00 67.74           C
ANISOU 5318  CA  LYS F 339    9570  12878   3290   -720   1556  -1458        C
ATOM   5319  CB  LYS F 339      34.333  -6.139 -67.371  1.00 67.59           C
ANISOU 5319  CB  LYS F 339    9864  12753   3064   -831   1250  -1160        C
ATOM   5320  CG  LYS F 339      34.393  -4.798 -66.699  1.00 66.44           C
ANISOU 5320  CG  LYS F 339    9674  12510   3061   -940   1203   -852        C
ATOM   5321  CD  LYS F 339      33.675  -3.720 -67.540  1.00 68.91           C
ANISOU 5321  CD  LYS F 339   10398  12778   3007  -1082   1029   -569        C
ATOM   5322  CE  LYS F 339      34.362  -2.348 -67.345  1.00 70.79           C
ANISOU 5322  CE  LYS F 339   10682  12989   3227  -1292   1208   -308        C
ATOM   5323  NZ  LYS F 339      34.350  -1.864 -65.889  1.00 67.41           N
ANISOU 5323  NZ  LYS F 339    9955  12387   3271  -1227   1105   -208        N
ATOM   5324  C   LYS F 339      35.324  -8.349 -67.910  1.00 70.21           C
ANISOU 5324  C   LYS F 339   10033  13263   3382   -630   1607  -1759        C
ATOM   5325  O   LYS F 339      35.364  -8.238 -69.132  1.00 73.21           O
ANISOU 5325  O   LYS F 339   10707  13787   3321   -763   1726  -1788        O
ATOM   5326  N   ARG F 340      35.143  -9.514 -67.302  1.00 68.86           N
ANISOU 5326  N   ARG F 340    9700  12972   3492   -415   1515  -1980        N
ATOM   5327  CA  ARG F 340      35.046 -10.755 -68.056  1.00 71.85           C
ANISOU 5327  CA  ARG F 340   10224  13375   3699   -321   1570  -2296        C
ATOM   5328  CB  ARG F 340      36.226 -11.677 -67.715  1.00 72.59           C
ANISOU 5328  CB  ARG F 340   10046  13519   4016   -132   1871  -2586        C
ATOM   5329  CG  ARG F 340      36.403 -12.842 -68.679  1.00 76.97           C
ANISOU 5329  CG  ARG F 340   10775  14131   4338    -46   2034  -2942        C
ATOM   5330  CD  ARG F 340      37.468 -13.841 -68.233  1.00 78.54           C
ANISOU 5330  CD  ARG F 340   10696  14325   4818    215   2278  -3243        C
ATOM   5331  NE  ARG F 340      37.621 -14.943 -69.196  1.00 86.31           N
ANISOU 5331  NE  ARG F 340   11880  15342   5571    307   2449  -3605        N
ATOM   5332  CZ  ARG F 340      36.819 -16.011 -69.279  1.00 87.14           C
ANISOU 5332  CZ  ARG F 340   12201  15224   5684    409   2247  -3787        C
ATOM   5333  NH1 ARG F 340      35.781 -16.154 -68.451  1.00 84.58           N
ANISOU 5333  NH1 ARG F 340   11903  14639   5593    422   1877  -3641        N
ATOM   5334  NH2 ARG F 340      37.058 -16.949 -70.188  1.00 89.57           N
ANISOU 5334  NH2 ARG F 340   12702  15565   5765    482   2435  -4134        N
ATOM   5335  C   ARG F 340      33.708 -11.429 -67.754  1.00 70.08           C
ANISOU 5335  C   ARG F 340   10105  12931   3592   -240   1188  -2333        C
ATOM   5336  O   ARG F 340      33.361 -11.615 -66.587  1.00 67.34           O
ANISOU 5336  O   ARG F 340    9563  12392   3630   -132   1021  -2278        O
ATOM   5337  N   GLU F 341      32.949 -11.763 -68.797  1.00 72.62           N
ANISOU 5337  N   GLU F 341   10737  13286   3568   -315   1050  -2429        N
ATOM   5338  CA  GLU F 341      31.665 -12.460 -68.643  1.00 72.00           C
ANISOU 5338  CA  GLU F 341   10745  13030   3582   -280    699  -2511        C
ATOM   5339  CB  GLU F 341      30.833 -12.346 -69.924  1.00 75.35           C
ANISOU 5339  CB  GLU F 341   11521  13561   3548   -419    499  -2531        C
ATOM   5340  CG  GLU F 341      29.378 -12.802 -69.795  1.00 75.43           C
```

FIGURE 18-154

```
ANISOU 5340  CG  GLU F 341    11576 13430  3654   -432    82 -2580       C
ATOM   5341  CD  GLU F 341    28.386 -11.646 -69.818  1.00 75.78         C
ANISOU 5341  CD  GLU F 341    11656 13495  3643   -509  -266 -2273       C
ATOM   5342  OE1 GLU F 341    27.661 -11.539 -70.835  1.00 78.56         O
ANISOU 5342  OE1 GLU F 341    12266 13948  3635   -593  -508 -2290       O
ATOM   5343  OE2 GLU F 341    28.329 -10.858 -68.835  1.00 72.03         O
ANISOU 5343  OE2 GLU F 341    10963 12933  3474   -469  -311 -2029       O
ATOM   5344  C   GLU F 341    31.866 -13.933 -68.254  1.00 72.08         C
ANISOU 5344  C   GLU F 341    10682 12885  3819   -116   781 -2838       C
ATOM   5345  O   GLU F 341    32.667 -14.650 -68.854  1.00 74.94         O
ANISOU 5345  O   GLU F 341    11113 13324  4035    -49  1050 -3099       O
ATOM   5346  N   GLU F 342    31.125 -14.370 -67.245  1.00 69.62         N
ANISOU 5346  N   GLU F 342    10251 12340  3862    -54   560 -2823       N
ATOM   5347  CA  GLU F 342    31.293 -15.693 -66.653  1.00 69.64         C
ANISOU 5347  CA  GLU F 342    10208 12126  4127    103   619 -3074       C
ATOM   5348  CB  GLU F 342    32.322 -15.633 -65.514  1.00 67.97         C
ANISOU 5348  CB  GLU F 342     9720 11849  4259    282   797 -3004       C
ATOM   5349  CG  GLU F 342    33.695 -16.187 -65.890  1.00 72.52         C
ANISOU 5349  CG  GLU F 342    10240 12529  4785    450  1138 -3236       C
ATOM   5350  CD  GLU F 342    34.866 -15.386 -65.320  1.00 73.01         C
ANISOU 5350  CD  GLU F 342     9998 12742  5001    520  1337 -3091       C
ATOM   5351  OE1 GLU F 342    35.691 -14.915 -66.127  1.00 76.14         O
ANISOU 5351  OE1 GLU F 342    10366 13400  5165    460  1597 -3130       O
ATOM   5352  OE2 GLU F 342    34.977 -15.234 -64.084  1.00 71.41         O
ANISOU 5352  OE2 GLU F 342     9591 12405  5135    615  1243 -2952       O
ATOM   5353  C   GLU F 342    29.962 -16.216 -66.134  1.00 67.95         C
ANISOU 5353  C   GLU F 342    10035 11683  4100     41   312 -3093       C
ATOM   5354  O   GLU F 342    29.181 -15.466 -65.550  1.00 65.42         O
ANISOU 5354  O   GLU F 342     9603 11333  3922    -40   100 -2859       O
ATOM   5355  N   GLU F 343    29.706 -17.498 -66.380  1.00 69.90         N
ANISOU 5355  N   GLU F 343    10445 11769  4346     66   308 -3389       N
ATOM   5356  CA  GLU F 343    28.559 -18.194 -65.805  1.00 69.18         C
ANISOU 5356  CA  GLU F 343    10385 11429  4472    -16    79 -3457       C
ATOM   5357  CB  GLU F 343    28.115 -19.373 -66.685  1.00 72.48         C
ANISOU 5357  CB  GLU F 343    11077 11759  4703    -93    38 -3804       C
ATOM   5358  CG  GLU F 343    26.910 -19.055 -67.631  1.00 74.73         C
ANISOU 5358  CG  GLU F 343    11479 12200  4715   -329  -260 -3829       C
ATOM   5359  CD  GLU F 343    26.608 -20.312 -68.539  1.00 78.55         C
ANISOU 5359  CD  GLU F 343    12260 12593  4990   -414  -279 -4224       C
ATOM   5360  OE1 GLU F 343    26.210 -21.396 -67.996  1.00 78.42         O
ANISOU 5360  OE1 GLU F 343    12303 12280  5215   -445  -298 -4412       O
ATOM   5361  OE2 GLU F 343    26.759 -20.210 -69.802  1.00 81.28         O
ANISOU 5361  OE2 GLU F 343    12817 13155  4912   -468  -271 -4349       O
ATOM   5362  C   GLU F 343    28.962 -18.700 -64.434  1.00 66.86         C
ANISOU 5362  C   GLU F 343     9963 10869  4573    140   169 -3421       C
ATOM   5363  O   GLU F 343    30.023 -19.295 -64.287  1.00 68.01         O
ANISOU 5363  O   GLU F 343    10119 10944  4777    342   387 -3549       O
ATOM   5364  N   VAL F 344    28.126 -18.450 -63.434  1.00 64.55         N
ANISOU 5364  N   VAL F 344     9551 10437  4540     58     0 -3253       N
ATOM   5365  CA  VAL F 344    28.351 -18.977 -62.081  1.00 62.97         C
ANISOU 5365  CA  VAL F 344     9292  9954  4679    175    57 -3208       C
ATOM   5366  CB  VAL F 344    28.623 -17.848 -61.021  1.00 59.59         C
ANISOU 5366  CB  VAL F 344     8616  9585  4440    225    51 -2890       C
ATOM   5367  CG1 VAL F 344    29.883 -17.084 -61.375  1.00 59.63         C
ANISOU 5367  CG1 VAL F 344     8500  9834  4323    357   219 -2806       C
ATOM   5368  CG2 VAL F 344    27.435 -16.885 -60.878  1.00 57.61         C
ANISOU 5368  CG2 VAL F 344     8250  9422  4217     29  -159 -2700       C
ATOM   5369  C   VAL F 344    27.175 -19.874 -61.683  1.00 63.62         C
ANISOU 5369  C   VAL F 344     9499  9764  4910     11   -81 -3328       C
ATOM   5370  O   VAL F 344    26.167 -19.933 -62.404  1.00 65.05         O
ANISOU 5370  O   VAL F 344     9736 10016  4963   -196  -243 -3431       O
ATOM   5371  N   LEU F 345    27.309 -20.581 -60.561  1.00 62.81         N
ANISOU 5371  N   LEU F 345     9450  9352  5063     92   -20 -3322       N
ATOM   5372  CA  LEU F 345    26.254 -21.491 -60.114  1.00 64.00         C
ANISOU 5372  CA  LEU F 345     9749  9208  5359    -98   -99 -3437       C
ATOM   5373  CB  LEU F 345    26.623 -22.938 -60.433  1.00 66.98         C
ANISOU 5373  CB  LEU F 345    10440  9302  5705    -18     4 -3726       C
ATOM   5374  CG  LEU F 345    25.588 -24.015 -60.112  1.00 69.00         C
ANISOU 5374  CG  LEU F 345    10916  9216  6083   -256   -48 -3887       C
ATOM   5375  CD1 LEU F 345    25.216 -24.820 -61.343  1.00 72.57         C
ANISOU 5375  CD1 LEU F 345    11584  9653  6334   -394   -85 -4220       C
```

FIGURE 18-155

```
ATOM   5376 CD2 LEU F 345      26.113 -24.915 -59.016  1.00 69.88           C
ANISOU 5376 CD2 LEU F 345    11247  8912  6394   -92    72 -3866            C
ATOM   5377 C   LEU F 345      25.911 -21.302 -58.632  1.00 61.95           C
ANISOU 5377 C   LEU F 345     9405  8757  5376  -129  -105 -3225            C
ATOM   5378 O   LEU F 345      26.775 -21.464 -57.754  1.00 61.11           O
ANISOU 5378 O   LEU F 345     9333  8496  5389    83    -3 -3125            O
ATOM   5379 N   THR F 346      24.649 -20.944 -58.369  1.00 61.45           N
ANISOU 5379 N   THR F 346     9224  8720  5404  -389  -230 -3169            N
ATOM   5380 CA  THR F 346      24.186 -20.634 -57.011  1.00 59.61           C
ANISOU 5380 CA  THR F 346     8895  8347  5406  -459  -215 -2976            C
ATOM   5381 CB  THR F 346      22.830 -19.857 -56.990  1.00 59.00           C
ANISOU 5381 CB  THR F 346     8570  8441  5406  -711  -358 -2918            C
ATOM   5382 OG1 THR F 346      21.739 -20.769 -57.159  1.00 61.25           O
ANISOU 5382 OG1 THR F 346     8940  8578  5755  -989  -400 -3137            O
ATOM   5383 CG2 THR F 346      22.775 -18.783 -58.068  1.00 58.59           C
ANISOU 5383 CG2 THR F 346     8329  8761  5170  -678  -507 -2868            C
ATOM   5384 C   THR F 346      24.058 -21.898 -56.162  1.00 61.14           C
ANISOU 5384 C   THR F 346     9368  8119  5743  -514  -112 -3065            C
ATOM   5385 O   THR F 346      24.144 -23.020 -56.681  1.00 64.20           O
ANISOU 5385 O   THR F 346    10015  8309  6069  -530   -77 -3293            O
ATOM   5386 N   GLY F 347      23.851 -21.703 -54.861  1.00 59.58           N
ANISOU 5386 N   GLY F 347     9155  7768  5717  -548   -58 -2884            N
ATOM   5387 CA  GLY F 347      23.695 -22.800 -53.910  1.00 61.10           C
ANISOU 5387 CA  GLY F 347     9656  7535  6025  -620    47 -2913            C
ATOM   5388 C   GLY F 347      22.384 -23.558 -54.037  1.00 63.56           C
ANISOU 5388 C   GLY F 347    10062  7682  6405 -1000    56 -3100            C
ATOM   5389 O   GLY F 347      22.088 -24.419 -53.209  1.00 65.10           O
ANISOU 5389 O   GLY F 347    10531  7510  6694 -1136   166 -3112            O
ATOM   5390 N   ASN F 348      21.594 -23.215 -55.055  1.00 64.06           N
ANISOU 5390 N   ASN F 348     9904  8019  6416 -1185   -68 -3241            N
ATOM   5391 CA  ASN F 348      20.382 -23.946 -55.409  1.00 66.83           C
ANISOU 5391 CA  ASN F 348    10293  8274  6823 -1558   -97 -3477            C
ATOM   5392 CB  ASN F 348      19.142 -23.043 -55.278  1.00 66.16           C
ANISOU 5392 CB  ASN F 348     9806  8464  6867 -1802  -190 -3437            C
ATOM   5393 CG  ASN F 348      17.840 -23.839 -55.092  1.00 69.65           C
ANISOU 5393 CG  ASN F 348    10255  8745  7462 -2237  -149 -3647            C
ATOM   5394 OD1 ASN F 348      17.773 -24.763 -54.278  1.00 72.02           O
ANISOU 5394 OD1 ASN F 348    10853  8662  7850 -2387    37 -3669            O
ATOM   5395 ND2 ASN F 348      16.799 -23.468 -55.839  1.00 69.91           N
ANISOU 5395 ND2 ASN F 348     9964  9072  7527 -2447  -330 -3802            N
ATOM   5396 C   ASN F 348      20.544 -24.474 -56.834  1.00 69.06           C
ANISOU 5396 C   ASN F 348    10684  8640  6915 -1547  -200 -3738            C
ATOM   5397 O   ASN F 348      19.582 -24.911 -57.473  1.00 71.54           O
ANISOU 5397 O   ASN F 348    10974  8984  7225 -1844  -293 -3970            O
ATOM   5398 N   LEU F 349      21.791 -24.430 -57.308  1.00 68.36           N
ANISOU 5398 N   LEU F 349    10708  8599  6666 -1207  -176 -3713            N
ATOM   5399 CA  LEU F 349      22.186 -24.875 -58.655  1.00 70.41           C
ANISOU 5399 CA  LEU F 349    11104  8949  6701 -1136  -228 -3954            C
ATOM   5400 CB  LEU F 349      22.034 -26.402 -58.833  1.00 74.30           C
ANISOU 5400 CB  LEU F 349    11995  9037  7197 -1269  -153 -4240            C
ATOM   5401 CG  LEU F 349      23.212 -27.314 -58.448  1.00 75.35           C
ANISOU 5401 CG  LEU F 349    12494  8800  7338  -960    11 -4265            C
ATOM   5402 CD1 LEU F 349      23.480 -27.324 -56.942  1.00 73.43           C
ANISOU 5402 CD1 LEU F 349    12321  8288  7290  -860   111 -4005            C
ATOM   5403 CD2 LEU F 349      22.971 -28.730 -58.948  1.00 79.27           C
ANISOU 5403 CD2 LEU F 349    13395  8930  7794 -1104    54 -4593            C
ATOM   5404 C   LEU F 349      21.494 -24.087 -59.774  1.00 70.46           C
ANISOU 5404 C   LEU F 349    10850  9370  6551 -1276  -435 -4021            C
ATOM   5405 O   LEU F 349      21.080 -24.656 -60.785  1.00 73.71           O
ANISOU 5405 O   LEU F 349    11378  9813  6815 -1431  -529 -4288            O
ATOM   5406 N   GLN F 350      21.378 -22.778 -59.579  1.00 67.14           N
ANISOU 5406 N   GLN F 350    10108  9250  6152 -1213  -519 -3778            N
ATOM   5407 CA  GLN F 350      20.865 -21.888 -60.610  1.00 67.20           C
ANISOU 5407 CA  GLN F 350     9898  9645  5989 -1271  -738 -3784            C
ATOM   5408 CB  GLN F 350      19.977 -20.807 -59.982  1.00 65.17           C
ANISOU 5408 CB  GLN F 350     9286  9560  5916 -1363  -855 -3582            C
ATOM   5409 CG  GLN F 350      19.282 -19.897 -60.986  1.00 66.25           C
ANISOU 5409 CG  GLN F 350     9203 10065  5904 -1411 -1134 -3582            C
ATOM   5410 CD  GLN F 350      18.266 -18.962 -60.350  1.00 65.23           C
ANISOU 5410 CD  GLN F 350     8713 10069  6003 -1493 -1259 -3436            C
ATOM   5411 OE1 GLN F 350      18.433 -18.500 -59.215  1.00 63.41           O
```

FIGURE 18-156

```
ANISOU 5411  OE1 GLN F 350    8380  9742  5972 -1419 -1115 -3235           O
ATOM   5412  NE2 GLN F 350      17.205 -18.670 -61.091  1.00 67.82         N
ANISOU 5412  NE2 GLN F 350    8845 10626  6297 -1630 -1540 -3552           N
ATOM   5413  C   GLN F 350      22.031 -21.267 -61.393  1.00 66.19         C
ANISOU 5413  C   GLN F 350    9811  9742  5597  -994  -707 -3697           C
ATOM   5414  O   GLN F 350      23.053 -20.903 -60.811  1.00 63.73         O
ANISOU 5414  O   GLN F 350    9487  9398  5327  -760  -551 -3513           O
ATOM   5415  N   THR F 351      21.873 -21.162 -62.711  1.00 68.30         N
ANISOU 5415  N   THR F 351   10130 10239  5581 -1042  -850 -3841           N
ATOM   5416  CA  THR F 351      22.896 -20.578 -63.589  1.00 68.33         C
ANISOU 5416  CA  THR F 351   10199 10477  5286  -837  -796 -3781           C
ATOM   5417  CB  THR F 351      22.933 -21.313 -64.957  1.00 72.47         C
ANISOU 5417  CB  THR F 351   10986 11065  5483  -903  -838 -4090           C
ATOM   5418  OG1 THR F 351      23.426 -22.645 -64.764  1.00 74.33         O
ANISOU 5418  OG1 THR F 351   11477 10978  5788  -858  -645 -4327           O
ATOM   5419  CG2 THR F 351      23.822 -20.584 -65.965  1.00 72.87         C
ANISOU 5419  CG2 THR F 351   11102 11406  5178  -749  -781 -4024           C
ATOM   5420  C   THR F 351      22.726 -19.054 -63.781  1.00 66.46         C
ANISOU 5420  C   THR F 351    9733 10556  4964  -796  -942 -3503           C
ATOM   5421  O   THR F 351      21.670 -18.577 -64.223  1.00 67.46         O
ANISOU 5421  O   THR F 351    9740 10849  5042  -941 -1208 -3500           O
ATOM   5422  N   LEU F 352      23.774 -18.303 -63.438  1.00 63.82         N
ANISOU 5422  N   LEU F 352    9338 10288  4622  -594  -780 -3279           N
ATOM   5423  CA  LEU F 352      23.783 -16.849 -63.611  1.00 62.08         C
ANISOU 5423  CA  LEU F 352    8962 10317  4309  -548  -879 -3005           C
ATOM   5424  CB  LEU F 352      23.883 -16.122 -62.257  1.00 58.40         C
ANISOU 5424  CB  LEU F 352    8278  9763  4150  -474  -815 -2744           C
ATOM   5425  CG  LEU F 352      22.734 -16.210 -61.252  1.00 57.71         C
ANISOU 5425  CG  LEU F 352    8017  9528  4381  -599  -923 -2723           C
ATOM   5426  CD1 LEU F 352      23.172 -15.633 -59.924  1.00 54.58         C
ANISOU 5426  CD1 LEU F 352    7487  9024  4226  -496  -788 -2494           C
ATOM   5427  CD2 LEU F 352      21.468 -15.522 -61.746  1.00 59.33         C
ANISOU 5427  CD2 LEU F 352    8065  9916  4561  -720 -1217 -2699           C
ATOM   5428  C   LEU F 352      24.939 -16.408 -64.496  1.00 62.47         C
ANISOU 5428  C   LEU F 352    9140 10557  4038  -426  -732 -2963           C
ATOM   5429  O   LEU F 352      26.059 -16.914 -64.364  1.00 62.17         O
ANISOU 5429  O   LEU F 352    9174 10448  4001  -291  -475 -3039           O
ATOM   5430  N   LYS F 353      24.665 -15.457 -65.384  1.00 63.27         N
ANISOU 5430  N   LYS F 353    9272 10900  3869  -470  -892 -2843           N
ATOM   5431  CA  LYS F 353      25.722 -14.814 -66.150  1.00 64.14         C
ANISOU 5431  CA  LYS F 353    9502 11201  3667  -397  -727 -2748           C
ATOM   5432  CB  LYS F 353      25.257 -14.567 -67.589  1.00 67.60         C
ANISOU 5432  CB  LYS F 353   10164 11852  3670  -499  -919 -2806           C
ATOM   5433  CG  LYS F 353      26.308 -14.823 -68.681  1.00 70.46         C
ANISOU 5433  CG  LYS F 353   10783 12357  3632  -480  -672 -2941           C
ATOM   5434  CD  LYS F 353      25.734 -14.438 -70.067  1.00 74.26         C
ANISOU 5434  CD  LYS F 353   11530 13051  3636  -595  -907 -2954           C
ATOM   5435  CE  LYS F 353      26.582 -14.974 -71.227  1.00 78.07         C
ANISOU 5435  CE  LYS F 353   12316 13659  3685  -614  -662 -3177           C
ATOM   5436  NZ  LYS F 353      25.986 -14.635 -72.572  1.00 81.80         N
ANISOU 5436  NZ  LYS F 353   13103 14333  3646  -737  -916 -3190           N
ATOM   5437  C   LYS F 353      26.085 -13.500 -65.445  1.00 61.18         C
ANISOU 5437  C   LYS F 353    8950 10869  3425  -333  -686 -2411           C
ATOM   5438  O   LYS F 353      25.259 -12.592 -65.346  1.00 60.54         O
ANISOU 5438  O   LYS F 353    8789 10834  3380  -374  -920 -2221           O
ATOM   5439  N   ILE F 354      27.308 -13.410 -64.930  1.00 59.64         N
ANISOU 5439  N   ILE F 354    8685 10652  3322  -226  -399 -2355           N
ATOM   5440  CA  ILE F 354      27.766 -12.181 -64.259  1.00 57.21         C
ANISOU 5440  CA  ILE F 354    8224 10380  3133  -191  -340 -2061           C
ATOM   5441  CB  ILE F 354      27.922 -12.336 -62.706  1.00 53.63         C
ANISOU 5441  CB  ILE F 354    7553  9725  3099  -105  -280 -1999           C
ATOM   5442  CG1 ILE F 354      29.041 -13.330 -62.353  1.00 54.06         C
ANISOU 5442  CG1 ILE F 354    7590  9699  3250    27   -30 -2177           C
ATOM   5443  CD1 ILE F 354      29.514 -13.275 -60.917  1.00 51.17         C
ANISOU 5443  CD1 ILE F 354    7045  9181  3215   133    39 -2074           C
ATOM   5444  CG2 ILE F 354      26.599 -12.724 -62.050  1.00 51.74         C
ANISOU 5444  CG2 ILE F 354    7246  9318  3094  -161  -499 -2033           C
ATOM   5445  C   ILE F 354      29.064 -11.642 -64.869  1.00 58.84         C
ANISOU 5445  C   ILE F 354    8491 10766  3100  -178   -75 -2003           C
ATOM   5446  O   ILE F 354      29.891 -12.409 -65.373  1.00 60.22         O
ANISOU 5446  O   ILE F 354    8735 10998  3147  -131   148 -2215           O
```

FIGURE 18-157

```
ATOM   5447  N    ARG F 355      29.226 -10.318 -64.815  1.00 58.63           N
ANISOU 5447  N    ARG F 355     8438  10819   3021    -229     -85   -1728    N
ATOM   5448  CA   ARG F 355      30.437  -9.658 -65.305  1.00 60.49           C
ANISOU 5448  CA   ARG F 355     8713  11221   3050    -274     189   -1647    C
ATOM   5449  CB   ARG F 355      30.117  -8.263 -65.852  1.00 61.44           C
ANISOU 5449  CB   ARG F 355     8992  11418   2933    -394      74   -1361    C
ATOM   5450  CG   ARG F 355      31.245  -7.634 -66.651  1.00 64.96           C
ANISOU 5450  CG   ARG F 355     9569  12047   3066    -511     373   -1292    C
ATOM   5451  CD   ARG F 355      30.886  -6.237 -67.160  1.00 66.33           C
ANISOU 5451  CD   ARG F 355     9972  12237   2992    -636     245    -979    C
ATOM   5452  NE   ARG F 355      30.037  -6.239 -68.360  1.00 71.70           N
ANISOU 5452  NE   ARG F 355    10987  12983   3272    -678      11    -971    N
ATOM   5453  CZ   ARG F 355      29.472  -5.154 -68.895  1.00 73.47           C
ANISOU 5453  CZ   ARG F 355    11472  13191   3252    -738    -203    -704    C
ATOM   5454  NH1  ARG F 355      29.634  -3.953 -68.346  1.00 73.36           N
ANISOU 5454  NH1  ARG F 355    11440  13073   3362    -773    -196    -423    N
ATOM   5455  NH2  ARG F 355      28.736  -5.268 -69.988  1.00 77.30           N
ANISOU 5455  NH2  ARG F 355    12262  13752   3359    -754    -445    -722    N
ATOM   5456  C    ARG F 355      31.472  -9.601 -64.187  1.00 57.93           C
ANISOU 5456  C    ARG F 355     8122  10848   3041    -191     403   -1623    C
ATOM   5457  O    ARG F 355      31.365  -8.802 -63.252  1.00 55.72           O
ANISOU 5457  O    ARG F 355     7705  10480   2987    -196     329   -1419    O
ATOM   5458  N    VAL F 356      32.454 -10.488 -64.286  1.00 59.00           N
ANISOU 5458  N    VAL F 356     8187  11038   3193     -99     649   -1853    N
ATOM   5459  CA   VAL F 356      33.472 -10.669 -63.254  1.00 57.54           C
ANISOU 5459  CA   VAL F 356     7731  10818   3314      26     815   -1887    C
ATOM   5460  CB   VAL F 356      34.034 -12.124 -63.294  1.00 59.07           C
ANISOU 5460  CB   VAL F 356     7892  10969   3584     215     953   -2208    C
ATOM   5461  CG1  VAL F 356      35.263 -12.285 -62.413  1.00 58.90           C
ANISOU 5461  CG1  VAL F 356     7583  10962   3833     377    1122   -2261    C
ATOM   5462  CG2  VAL F 356      32.959 -13.120 -62.889  1.00 58.12           C
ANISOU 5462  CG2  VAL F 356     7884  10597   3601     282     725   -2309    C
ATOM   5463  C    VAL F 356      34.594  -9.647 -63.446  1.00 58.53           C
ANISOU 5463  C    VAL F 356     7742  11144   3352     -77    1059   -1769    C
ATOM   5464  O    VAL F 356      35.136  -9.510 -64.553  1.00 61.27           O
ANISOU 5464  O    VAL F 356     8201  11690   3390    -175    1273   -1838    O
ATOM   5465  N    HIS F 357      34.942  -8.926 -62.380  1.00 56.02           N
ANISOU 5465  N    HIS F 357     7219  10776   3291     -82    1041   -1603    N
ATOM   5466  CA   HIS F 357      36.060  -7.989 -62.470  1.00 57.30           C
ANISOU 5466  CA   HIS F 357     7240  11120   3411    -212    1281   -1516    C
ATOM   5467  CB   HIS F 357      35.754  -6.682 -61.737  1.00 55.20           C
ANISOU 5467  CB   HIS F 357     6955  10760   3259    -343    1148   -1222    C
ATOM   5468  CG   HIS F 357      34.762  -5.810 -62.460  1.00 56.04           C
ANISOU 5468  CG   HIS F 357     7368  10819   3105    -492     995   -1005    C
ATOM   5469  ND1  HIS F 357      35.108  -4.564 -62.960  1.00 57.20           N
ANISOU 5469  ND1  HIS F 357     7641  11040   3052    -709    1109    -802    N
ATOM   5470  CE1  HIS F 357      34.034  -4.029 -63.539  1.00 57.73           C
ANISOU 5470  CE1  HIS F 357     8005  11020   2910    -757     890    -629    C
ATOM   5471  NE2  HIS F 357      33.002  -4.895 -63.453  1.00 56.73           N
ANISOU 5471  NE2  HIS F 357     7904  10798   2853    -597     644    -736    N
ATOM   5472  CD2  HIS F 357      33.429  -6.007 -62.764  1.00 55.77           C
ANISOU 5472  CD2  HIS F 357     7539  10666   2984    -449     720    -964    C
ATOM   5473  C    HIS F 357      37.379  -8.623 -62.026  1.00 57.96           C
ANISOU 5473  C    HIS F 357     7008  11315   3698     -68    1502   -1730    C
ATOM   5474  O    HIS F 357      37.441  -9.312 -61.010  1.00 56.64           O
ANISOU 5474  O    HIS F 357     6685  11010   3825     136    1387   -1810    O
ATOM   5475  N    GLU F 358      38.424  -8.396 -62.813  1.00 60.88           N
ANISOU 5475  N    GLU F 358     7293  11938   3900    -169    1821   -1829    N
ATOM   5476  CA   GLU F 358      39.720  -9.030 -62.584  1.00 62.68           C
ANISOU 5476  CA   GLU F 358     7182  12324   4310     -13    2054   -2080    C
ATOM   5477  CB   GLU F 358      40.114  -9.904 -63.775  1.00 66.22           C
ANISOU 5477  CB   GLU F 358     7711  12931   4519      53    2310   -2364    C
ATOM   5478  CG   GLU F 358      39.357 -11.213 -63.855  1.00 66.22           C
ANISOU 5478  CG   GLU F 358     7904  12729   4529     286    2137   -2540    C
ATOM   5479  CD   GLU F 358      39.723 -12.027 -65.081  1.00 70.08           C
ANISOU 5479  CD   GLU F 358     8515  13362   4752     337    2398   -2837    C
ATOM   5480  OE1  GLU F 358      40.884 -11.947 -65.532  1.00 73.92           O
ANISOU 5480  OE1  GLU F 358     8787  14108   5193     324    2746   -3000    O
ATOM   5481  OE2  GLU F 358      38.844 -12.747 -65.596  1.00 70.92           O
ANISOU 5481  OE2  GLU F 358     8924  13330   4693     377    2265   -2927    O
ATOM   5482  C    GLU F 358      40.822  -8.024 -62.297  1.00 63.33           C
```

FIGURE 18-158

```
ANISOU 5482  C   GLU F 358    6971 12606  4485  -186  2258 -2010         C
ATOM   5483  O   GLU F 358    41.201  -7.245 -63.165  1.00 65.86         O
ANISOU 5483  O   GLU F 358    7365 13110  4550  -452  2506 -1950         O
ATOM   5484  N   GLY F 359    41.349  -8.079 -61.081  1.00 61.35         N
ANISOU 5484  N   GLY F 359    6404 12317  4590   -48  2153 -2027         N
ATOM   5485  CA  GLY F 359    42.408  -7.178 -60.650  1.00 62.41         C
ANISOU 5485  CA  GLY F 359    6211 12637  4866  -213  2303 -1990         C
ATOM   5486  C   GLY F 359    42.221  -6.774 -59.198  1.00 59.15         C
ANISOU 5486  C   GLY F 359    5681 12045  4748  -161  2011 -1834         C
ATOM   5487  O   GLY F 359    41.145  -6.954 -58.626  1.00 55.46         O
ANISOU 5487  O   GLY F 359    5438 11308  4326   -64  1725 -1700         O
ATOM   5488  N   TYR F 360    43.272  -6.231 -58.597  1.00 60.49         N
ANISOU 5488  N   TYR F 360    5491 12378  5116  -241  2091 -1868         N
ATOM   5489  CA  TYR F 360    43.140  -5.679 -57.274  1.00 58.50         C
ANISOU 5489  CA  TYR F 360    5160 11974  5092  -248  1830 -1716         C
ATOM   5490  CB  TYR F 360    44.441  -5.768 -56.483  1.00 61.17         C
ANISOU 5490  CB  TYR F 360    5016 12510  5718  -156  1845 -1890         C
ATOM   5491  CG  TYR F 360    44.405  -5.033 -55.139  1.00 60.37         C
ANISOU 5491  CG  TYR F 360    4845 12280  5811  -223  1588 -1737         C
ATOM   5492  CD1 TYR F 360    44.129  -5.711 -53.941  1.00 57.83         C
ANISOU 5492  CD1 TYR F 360    4525 11766  5682    75  1267 -1742         C
ATOM   5493  CE1 TYR F 360    44.117  -5.040 -52.728  1.00 55.89         C
ANISOU 5493  CE1 TYR F 360    4244 11416  5577     3  1045 -1619         C
ATOM   5494  CZ  TYR F 360    44.376  -3.669 -52.698  1.00 57.61         C
ANISOU 5494  CZ  TYR F 360    4417 11704  5768  -369  1137 -1499         C
ATOM   5495  OH  TYR F 360    44.375  -2.958 -51.515  1.00 56.33         O
ANISOU 5495  OH  TYR F 360    4240 11432  5729  -460   926 -1398         O
ATOM   5496  CE2 TYR F 360    44.640  -2.979 -53.864  1.00 60.25         C
ANISOU 5496  CE2 TYR F 360    4762 12201  5929  -672  1451 -1478         C
ATOM   5497  CD2 TYR F 360    44.645  -3.656 -55.072  1.00 61.36         C
ANISOU 5497  CD2 TYR F 360    4949 12461  5906  -601  1675 -1589         C
ATOM   5498  C   TYR F 360    42.675  -4.246 -57.382  1.00 57.20         C
ANISOU 5498  C   TYR F 360    5212 11733  4789  -608  1840 -1441         C
ATOM   5499  O   TYR F 360    43.193  -3.472 -58.181  1.00 59.56         O
ANISOU 5499  O   TYR F 360    5502 12205  4923  -901  2110 -1412         O
ATOM   5500  N   GLU F 361    41.695  -3.909 -56.553  1.00 53.97         N
ANISOU 5500  N   GLU F 361    5014 11047  4446  -581  1556 -1245         N
ATOM   5501  CA  GLU F 361    41.110  -2.579 -56.522  1.00 52.98         C
ANISOU 5501  CA  GLU F 361    5129 10781  4221  -857  1514  -981         C
ATOM   5502  CB  GLU F 361    39.809  -2.561 -57.329  1.00 51.91         C
ANISOU 5502  CB  GLU F 361    5403 10479  3840  -858  1435  -834         C
ATOM   5503  CG  GLU F 361    40.021  -2.601 -58.835  1.00 54.36         C
ANISOU 5503  CG  GLU F 361    5852 10968  3836  -989  1691  -875         C
ATOM   5504  CD  GLU F 361    38.780  -3.055 -59.586  1.00 54.79         C
ANISOU 5504  CD  GLU F 361    6252 10895  3671  -887  1552  -820         C
ATOM   5505  OE1 GLU F 361    38.124  -4.047 -59.150  1.00 52.19         O
ANISOU 5505  OE1 GLU F 361    5923 10445  3464  -635  1355  -913         O
ATOM   5506  OE2 GLU F 361    38.474  -2.410 -60.614  1.00 54.98         O
ANISOU 5506  OE2 GLU F 361    6559 10938  3391 -1074  1633  -684         O
ATOM   5507  C   GLU F 361    40.862  -2.085 -55.099  1.00 50.53         C
ANISOU 5507  C   GLU F 361    4782 10279  4137  -837  1267  -874         C
ATOM   5508  O   GLU F 361    40.743  -2.868 -54.158  1.00 48.99         O
ANISOU 5508  O   GLU F 361    4492  9997  4125  -585  1074  -955         O
ATOM   5509  N   GLU F 362    40.781  -0.769 -54.967  1.00 50.77         N
ANISOU 5509  N   GLU F 362    4930 10227  4132 -1111  1284  -690         N
ATOM   5510  CA  GLU F 362    40.569  -0.116 -53.696  1.00 49.49         C
ANISOU 5510  CA  GLU F 362    4773  9883  4149 -1141  1086  -593         C
ATOM   5511  CB  GLU F 362    41.853   0.602 -53.290  1.00 52.22         C
ANISOU 5511  CB  GLU F 362    4827 10402  4614 -1376  1204  -662         C
ATOM   5512  CG  GLU F 362    42.289   0.516 -51.833  1.00 53.76         C
ANISOU 5512  CG  GLU F 362    4795 10573  5058 -1278   995  -745         C
ATOM   5513  CD  GLU F 362    43.791   0.759 -51.700  1.00 59.82         C
ANISOU 5513  CD  GLU F 362    5136 11637  5954 -1447  1128  -920         C
ATOM   5514  OE1 GLU F 362    44.203   1.943 -51.674  1.00 63.47         O
ANISOU 5514  OE1 GLU F 362    5597 12108  6413 -1798  1232  -851         O
ATOM   5515  OE2 GLU F 362    44.566  -0.232 -51.658  1.00 61.55         O
ANISOU 5515  OE2 GLU F 362    5018 12080  6288 -1231  1134 -1137         O
ATOM   5516  C   GLU F 362    39.471   0.903 -53.950  1.00 47.93         C
ANISOU 5516  C   GLU F 362    4959  9439  3815 -1279  1021  -345         C
ATOM   5517  O   GLU F 362    39.619   1.764 -54.816  1.00 50.08         O
ANISOU 5517  O   GLU F 362    5385  9735  3909 -1529  1187  -230         O
```

FIGURE 18-159

```
ATOM   5518  N   PHE F 363      38.374   0.793 -53.206  1.00 44.53           N
ANISOU 5518  N   PHE F 363    4688    8767    3465   -1111     788    -267   N
ATOM   5519  CA  PHE F 363      37.236   1.684 -53.350  1.00 43.24           C
ANISOU 5519  CA  PHE F 363    4850    8361    3218   -1169     690     -58   C
ATOM   5520  CB  PHE F 363      35.981   0.878 -53.683  1.00 40.67           C
ANISOU 5520  CB  PHE F 363    4673    7941    2838    -939     548     -53   C
ATOM   5521  CG  PHE F 363      36.051   0.171 -54.979  1.00 40.68           C
ANISOU 5521  CG  PHE F 363    4709    8111    2635    -910     655    -120   C
ATOM   5522  CD1 PHE F 363      35.670   0.807 -56.150  1.00 41.53           C
ANISOU 5522  CD1 PHE F 363    5074    8214    2492   -1035     704      21   C
ATOM   5523  CE1 PHE F 363      35.734   0.141 -57.373  1.00 42.89           C
ANISOU 5523  CE1 PHE F 363    5312    8550    2433   -1019     806     -55   C
ATOM   5524  CZ  PHE F 363      36.189  -1.158 -57.422  1.00 42.89           C
ANISOU 5524  CZ  PHE F 363    5110    8707    2481    -871     874    -284   C
ATOM   5525  CE2 PHE F 363      36.573  -1.800 -56.244  1.00 41.85           C
ANISOU 5525  CE2 PHE F 363    4721    8557    2623    -723     816    -416   C
ATOM   5526  CD2 PHE F 363      36.503  -1.134 -55.038  1.00 39.67           C
ANISOU 5526  CD2 PHE F 363    4392    8132    2547    -749     702    -327   C
ATOM   5527  C   PHE F 363      36.925   2.473 -52.094  1.00 42.77           C
ANISOU 5527  C   PHE F 363    4840    8086    3327   -1199     550      18   C
ATOM   5528  O   PHE F 363      37.135   2.007 -50.973  1.00 41.83           O
ANISOU 5528  O   PHE F 363    4561    7954    3377   -1087     450     -85   O
ATOM   5529  N   THR F 364      36.389   3.667 -52.305  1.00 43.89           N
ANISOU 5529  N   THR F 364    5240    8037    3400   -1337     537     201   N
ATOM   5530  CA  THR F 364      35.644   4.393 -51.289  1.00 42.92           C
ANISOU 5530  CA  THR F 364    5254    7647    3406   -1303     388     282   C
ATOM   5531  CB  THR F 364      35.989   5.912 -51.391  1.00 45.24           C
ANISOU 5531  CB  THR F 364    5738    7796    3655   -1580     468     427   C
ATOM   5532  OG1 THR F 364      36.808   6.290 -50.279  1.00 45.24           O
ANISOU 5532  OG1 THR F 364    5587    7795    3810   -1716     475     338   O
ATOM   5533  CG2 THR F 364      34.757   6.819 -51.449  1.00 46.04           C
ANISOU 5533  CG2 THR F 364    6170    7588    3736   -1510     345     604   C
ATOM   5534  C   THR F 364      34.153   4.071 -51.527  1.00 41.58           C
ANISOU 5534  C   THR F 364    5252    7332    3215   -1076     236     345   C
ATOM   5535  O   THR F 364      33.686   4.150 -52.663  1.00 43.15           O
ANISOU 5535  O   THR F 364    5607    7543    3244   -1066     239     436   O
ATOM   5536  N   MSE F 365      33.435   3.668 -50.475  1.00 39.53           N
ANISOU 5536  N   MSE F 365    4952    6953    3115    -905     109     284   N
ATOM   5537  CA  MSE F 365      31.970   3.467 -50.514  1.00 38.74           C
ANISOU 5537  CA  MSE F 365    4959    6713    3047     -717    -25     317   C
ATOM   5538  CB  MSE F 365      31.558   2.102 -49.967  1.00 36.04           C
ANISOU 5538  CB  MSE F 365    4475    6423    2797    -544     -77     168   C
ATOM   5539  CG  MSE F 365      32.040   0.907 -50.754  1.00 36.93           C
ANISOU 5539  CG  MSE F 365    4478    6743    2812    -498     -25      64   C
ATOM   5540 SE   MSE F 365      31.519  -0.802 -49.939  0.90 39.05          SE
ANISOU 5540 SE   MSE F 365    4645    6991    3203    -298     -87    -113  SE
ATOM   5541  CE  MSE F 365      29.589  -0.577 -49.841  1.00 35.91           C
ANISOU 5541  CE  MSE F 365.   4355    6406    2882    -215    -210     -68   C
ATOM   5542  C   MSE F 365      31.317   4.540 -49.661  1.00 37.78           C
ANISOU 5542  C   MSE F 365    4972    6339    3046    -712     -92     392   C
ATOM   5543  O   MSE F 365      31.692   4.733 -48.500  1.00 37.16           O
ANISOU 5543  O   MSE F 365    4845    6192    3080    -755     -78     332   O
ATOM   5544  N   VAL F 366      30.362   5.267 -50.226  1.00 38.03           N
ANISOU 5544  N   VAL F 366    5182    6223    3045    -647    -175     514   N
ATOM   5545  CA  VAL F 366      29.724   6.334 -49.460  1.00 38.03           C
ANISOU 5545  CA  VAL F 366    5316    5962    3171    -610    -229     570   C
ATOM   5546  CB  VAL F 366      30.225   7.753 -49.873  1.00 40.41           C
ANISOU 5546  CB  VAL F 366    5862    6104    3387    -782    -188     733   C
ATOM   5547  CG1 VAL F 366      29.484   8.835 -49.096  1.00 40.76           C
ANISOU 5547  CG1 VAL F 366    6072    5842    3573    -704    -250     771   C
ATOM   5548  CG2 VAL F 366      31.728   7.887 -49.656  1.00 39.69           C
ANISOU 5548  CG2 VAL F 366    5703    6126    3250   -1053     -37     699   C
ATOM   5549  C   VAL F 366      28.216   6.220 -49.565  1.00 37.81           C
ANISOU 5549  C   VAL F 366    5297    5841    3228    -366    -366     566   C
ATOM   5550  O   VAL F 366      27.635   6.467 -50.626  1.00 39.06           O
ANISOU 5550  O   VAL F 366    5559    5991    3289    -297    -470     667   O
ATOM   5551  N   GLY F 367      27.601   5.809 -48.458  1.00 36.34           N
ANISOU 5551  N   GLY F 367    4995    5600    3214    -276    -367     439   N
ATOM   5552  CA  GLY F 367      26.149   5.662 -48.373  1.00 35.97           C
ANISOU 5552  CA  GLY F 367    4885    5486    3296     -73    -463     389   C
ATOM   5553  C   GLY F 367      25.571   6.755 -47.502  1.00 37.01           C
```

FIGURE 18-160

```
ANISOU 5553  C   GLY F 367    5111  5371  3580    -2  -460   393       C
ATOM   5554  O   GLY F 367    26.298   7.648 -47.027  1.00 37.55       O
ANISOU 5554  O   GLY F 367    5332  5300  3634  -122  -397   444       O
ATOM   5555  N   LYS F 368    24.263   6.678 -47.289  1.00 37.07       N
ANISOU 5555  N   LYS F 368    5015  5327  3743   187  -521   315       N
ATOM   5556  CA  LYS F 368    23.522   7.707 -46.596  1.00 39.14       C
ANISOU 5556  CA  LYS F 368    5344  5357  4169   313  -519   293       C
ATOM   5557  CB  LYS F 368    22.035   7.565 -46.942  1.00 40.86       C
ANISOU 5557  CB  LYS F 368    5388  5594  4542   553  -639   224       C
ATOM   5558  CG  LYS F 368    21.244   8.827 -46.755  1.00 45.35       C
ANISOU 5558  CG  LYS F 368    6044  5921  5265   758  -706   244       C
ATOM   5559  CD  LYS F 368    20.322   9.053 -47.934  1.00 52.09       C
ANISOU 5559  CD  LYS F 368    6847  6803  6142   988  -956   316       C
ATOM   5560  CE  LYS F 368    21.070   9.688 -49.121  1.00 54.74       C
ANISOU 5560  CE  LYS F 368    7484  7077  6236   936 -1094   561       C
ATOM   5561  NZ  LYS F 368    20.132  10.022 -50.240  1.00 57.30       N
ANISOU 5561  NZ  LYS F 368    7821  7398  6554  1192 -1381   650       N
ATOM   5562  C   LYS F 368    23.751   7.641 -45.067  1.00 37.84       C
ANISOU 5562  C   LYS F 368    5174  5115  4090   229  -347   158       C
ATOM   5563  O   LYS F 368    23.754   8.670 -44.375  1.00 38.54       O
ANISOU 5563  O   LYS F 368    5412  4988  4245   237  -298   153       O
ATOM   5564  N   ARG F 369    23.945   6.421 -44.577  1.00 35.65       N
ANISOU 5564  N   ARG F 369    4759  4999  3789   150  -265    51       N
ATOM   5565  CA  ARG F 369    24.089   6.136 -43.170  1.00 35.10       C
ANISOU 5565  CA  ARG F 369    4704  4880  3753    76  -120   -72       C
ATOM   5566  CB  ARG F 369    22.839   5.418 -42.628  1.00 35.16       C
ANISOU 5566  CB  ARG F 369    4548  4914  3898   172   -37  -226       C
ATOM   5567  CG  ARG F 369    21.534   6.240 -42.641  1.00 36.78       C
ANISOU 5567  CG  ARG F 369    4677  4998  4298   364   -46  -284       C
ATOM   5568  CD  ARG F 369    20.626   5.893 -41.434  1.00 39.03       C
ANISOU 5568  CD  ARG F 369    4867  5249  4714   379   152  -479       C
ATOM   5569  NE  ARG F 369    20.476   7.016 -40.493  1.00 39.37       N
ANISOU 5569  NE  ARG F 369    5053  5078  4826   428   260  -540       N
ATOM   5570  CZ  ARG F 369    20.294   6.888 -39.186  1.00 41.20       C
ANISOU 5570  CZ  ARG F 369    5349  5245  5059   356   470  -682       C
ATOM   5571  NH1 ARG F 369    20.260   5.688 -38.625  1.00 40.27       N
ANISOU 5571  NH1 ARG F 369    5187  5244  4870   225   594  -756       N
ATOM   5572  NH2 ARG F 369    20.172   7.967 -38.423  1.00 45.93       N
ANISOU 5572  NH2 ARG F 369    6100  5643  5708   408   562  -750       N
ATOM   5573  C   ARG F 369    25.349   5.297 -42.903  1.00 33.83       C
ANISOU 5573  C   ARG F 369    4557  4853  3444   -89   -92   -70       C
ATOM   5574  O   ARG F 369    25.582   4.876 -41.779  1.00 33.68       O
ANISOU 5574  O   ARG F 369    4575  4816  3407  -150    -7  -158       O
ATOM   5575  N   ALA F 370    26.165   5.072 -43.928  1.00 33.74       N
ANISOU 5575  N   ALA F 370    4525  4977  3319  -148  -165    25       N
ATOM   5576  CA  ALA F 370    27.433   4.376 -43.756  1.00 33.32       C
ANISOU 5576  CA  ALA F 370    4448  5061  3152  -271  -149    14       C
ATOM   5577  CB  ALA F 370    27.219   2.866 -43.786  1.00 32.53       C
ANISOU 5577  CB  ALA F 370    4229  5094  3036  -219  -139   -68       C
ATOM   5578  C   ALA F 370    28.480   4.805 -44.796  1.00 34.46       C
ANISOU 5578  C   ALA F 370    4607  5301  3186  -377  -183   124       C
ATOM   5579  O   ALA F 370    28.141   5.420 -45.821  1.00 35.44       O
ANISOU 5579  O   ALA F 370    4786  5396  3282  -351  -228   227       O
ATOM   5580  N   THR F 371    29.749   4.533 -44.485  1.00 34.41       N
ANISOU 5580  N   THR F 371    4557  5404  3113  -500  -162    97       N
ATOM   5581  CA  THR F 371    30.877   4.693 -45.401  1.00 35.72       C
ANISOU 5581  CA  THR F 371    4675  5719  3179  -628  -147   157       C
ATOM   5582  CB  THR F 371    31.658   6.063 -45.259  1.00 37.27       C
ANISOU 5582  CB  THR F 371    4983  5816  3361  -831  -115   222       C
ATOM   5583  OG1 THR F 371    32.299   6.139 -43.983  1.00 39.27       O
ANISOU 5583  OG1 THR F 371    5217  6048  3656  -912  -125   125       O
ATOM   5584  CG2 THR F 371    30.771   7.277 -45.436  1.00 38.77       C
ANISOU 5584  CG2 THR F 371    5387  5755  3590  -806  -128   324       C
ATOM   5585  C   THR F 371    31.864   3.567 -45.105  1.00 35.06       C
ANISOU 5585  C   THR F 371    4426  5831  3065  -633  -144    55       C
ATOM   5586  O   THR F 371    31.992   3.125 -43.961  1.00 34.68       O
ANISOU 5586  O   THR F 371    4370  5753  3055  -598  -175   -28       O
ATOM   5587  N   ALA F 372    32.582   3.125 -46.131  1.00 35.32       N
ANISOU 5587  N   ALA F 372    4346  6058  3017  -666  -110    60       N
ATOM   5588  CA  ALA F 372    33.520   2.019 -45.996  1.00 34.84       C
ANISOU 5588  CA  ALA F 372    4107  6186  2944  -621  -112   -50       C
```

FIGURE 18-161

```
ATOM    5589  CB  ALA F 372      32.796   0.677 -46.224  1.00 33.58           C
ANISOU  5589  CB  ALA F 372    3933   6046   2781   -434   -136   -111        C
ATOM    5590  C   ALA F 372      34.709   2.162 -46.952  1.00 36.35           C
ANISOU  5590  C   ALA F 372    4157   6590   3064   -749    -25    -55        C
ATOM    5591  O   ALA F 372      34.637   2.846 -47.979  1.00 37.00           O
ANISOU  5591  O   ALA F 372    4314   6683   3060   -860     51     41        O
ATOM    5592  N   ILE F 373      35.809   1.530 -46.579  1.00 36.90           N
ANISOU  5592  N   ILE F 373    4028   6828   3166   -731    -35   -172        N
ATOM    5593  CA  ILE F 373      36.920   1.327 -47.482  1.00 38.46           C
ANISOU  5593  CA  ILE F 373    4023   7274   3317   -805     74   -232        C
ATOM    5594  CB  ILE F 373      38.271   1.774 -46.878  1.00 40.52           C
ANISOU  5594  CB  ILE F 373    4067   7677   3652   -954     71   -316        C
ATOM    5595  CG1 ILE F 373      38.285   3.292 -46.705  1.00 41.82           C
ANISOU  5595  CG1 ILE F 373    4365   7713   3813  -1228    112   -214        C
ATOM    5596  CD1 ILE F 373      38.951   3.744 -45.409  1.00 46.04           C
ANISOU  5596  CD1 ILE F 373    4819   8231   4445  -1323     -5   -292        C
ATOM    5597  CG2 ILE F 373      39.438   1.353 -47.777  1.00 42.20           C
ANISOU  5597  CG2 ILE F 373    3998   8188   3847   -998    208   -427        C
ATOM    5598  C   ILE F 373      36.917  -0.152 -47.827  1.00 37.80           C
ANISOU  5598  C   ILE F 373    3843   7296   3223   -576     62   -341        C
ATOM    5599  O   ILE F 373      37.018  -1.025 -46.943  1.00 36.27           O
ANISOU  5599  O   ILE F 373    3606   7073   3101   -402    -52   -425        O
ATOM    5600  N   LEU F 374      36.771  -0.409 -49.125  1.00 37.99           N
ANISOU  5600  N   LEU F 374    3882   7418   3136   -391    175   -333        N
ATOM    5601  CA  LEU F 374      36.835  -1.740 -49.675  1.00 37.72           C
ANISOU  5601  CA  LEU F 374    3776   7485   3070   -391    197   -455        C
ATOM    5602  CB  LEU F 374      35.600  -2.008 -50.541  1.00 36.81           C
ANISOU  5602  CB  LEU F 374    3865   7278   2844   -346    196   -396        C
ATOM    5603  CG  LEU F 374      35.410  -3.409 -51.127  1.00 35.70           C
ANISOU  5603  CG  LEU F 374    3719   7187   2659   -167    206   -529        C
ATOM    5604  CD1 LEU F 374      35.355  -4.482 -50.037  1.00 32.88           C
ANISOU  5604  CD1 LEU F 374    3345   6714   2434     29     94   -622        C
ATOM    5605  CD2 LEU F 374      34.154  -3.412 -51.980  1.00 36.04           C
ANISOU  5605  CD2 LEU F 374    3956   7151   2586   -180    174   -465        C
ATOM    5606  C   LEU F 374      38.114  -1.935 -50.495  1.00 40.40           C
ANISOU  5606  C   LEU F 374    3881   8101   3369   -441    359   -571        C
ATOM    5607  O   LEU F 374      38.330  -1.244 -51.491  1.00 41.59           O
ANISOU  5607  O   LEU F 374    4056   8354   3393   -631    516   -515        O
ATOM    5608  N   ARG F 375      38.958  -2.863 -50.040  1.00 41.39           N
ANISOU  5608  N   ARG F 375    3788   8340   3600   -264    322   -734        N
ATOM    5609  CA  ARG F 375      40.081  -3.367 -50.817  1.00 44.76           C
ANISOU  5609  CA  ARG F 375    3954   9037   4017   -227    480   -901        C
ATOM    5610  CB  ARG F 375      41.365  -3.461 -49.975  1.00 46.06           C
ANISOU  5610  CB  ARG F 375    3782   9363   4356   -167    416  -1037        C
ATOM    5611  CG  ARG F 375      41.765  -2.160 -49.277  1.00 47.35           C
ANISOU  5611  CG  ARG F 375    3874   9536   4580   -429    379   -955        C
ATOM    5612  CD  ARG F 375      43.214  -2.192 -48.753  1.00 51.18           C
ANISOU  5612  CD  ARG F 375    3943  10275   5227   -420    344  -1131        C
ATOM    5613  NE  ARG F 375      43.464  -1.175 -47.726  1.00 56.01           N
ANISOU  5613  NE  ARG F 375    4529  10837   5914   -618    213  -1075        N
ATOM    5614  CZ  ARG F 375      44.650  -0.608 -47.469  1.00 59.99           C
ANISOU  5614  CZ  ARG F 375    4690  11572   6531   -795    230  -1192        C
ATOM    5615  NH1 ARG F 375      45.730  -0.928 -48.175  1.00 63.23           N
ANISOU  5615  NH1 ARG F 375    4713  12304   7009   -801    399  -1375        N
ATOM    5616  NH2 ARG F 375      44.757   0.294 -46.496  1.00 61.29           N
ANISOU  5616  NH2 ARG F 375    4888  11655   6746   -981     88  -1145        N
ATOM    5617  C   ARG F 375      39.650  -4.740 -51.345  1.00 44.39           C
ANISOU  5617  C   ARG F 375    3991   8951   3922     26    478  -1009        C
ATOM    5618  O   ARG F 375      39.022  -5.515 -50.620  1.00 42.96           O
ANISOU  5618  O   ARG F 375    3945   8574   3804    217    312  -1010        O
ATOM    5619  N   LYS F 376      39.987  -5.036 -52.600  1.00 46.26           N
ANISOU  5619  N   LYS F 376    4176   9365   4035      5    679  -1106        N
ATOM    5620  CA  LYS F 376      39.348  -6.134 -53.320  1.00 46.24           C
ANISOU  5620  CA  LYS F 376    4340   9297   3933    173    694  -1190        C
ATOM    5621  CB  LYS F 376      38.040  -5.601 -53.905  1.00 45.02           C
ANISOU  5621  CB  LYS F 376    4494   9002   3608     21    666  -1020        C
ATOM    5622  CG  LYS F 376      37.218  -6.592 -54.639  1.00 45.84           C
ANISOU  5622  CG  LYS F 376    4788   9030   3597    138    648  -1099        C
ATOM    5623  CD  LYS F 376      36.312  -5.902 -55.630  1.00 45.93           C
ANISOU  5623  CD  LYS F 376    5028   9033   3391    -41    662   -965        C
ATOM    5624  CE  LYS F 376      35.659  -6.942 -56.497  1.00 47.28           C
```

FIGURE 18-162

```
ANISOU 5624  CE  LYS F 376     5357   9181   3425     56    651  -1090       C
ATOM   5625  NZ  LYS F 376     36.674  -7.533 -57.410  1.00 49.17            N
ANISOU 5625  NZ  LYS F 376     5499   9636   3547    101    872  -1286       N
ATOM   5626  C   LYS F 376     40.212  -6.718 -54.445  1.00 49.04            C
ANISOU 5626  C   LYS F 376     4537   9897   4199    227    926  -1392       C
ATOM   5627  O   LYS F 376     40.914  -5.980 -55.142  1.00 51.37            O
ANISOU 5627  O   LYS F 376     4701  10414   4403     20   1140  -1400       O
ATOM   5628  N   ALA F 377     40.148  -8.041 -54.624  1.00 48.89            N
ANISOU 5628  N   ALA F 377     4554   9824   4200    490    905  -1564       N
ATOM   5629  CA  ALA F 377     40.819  -8.718 -55.746  1.00 50.86            C
ANISOU 5629  CA  ALA F 377     4702  10273   4349    573   1136  -1786       C
ATOM   5630  CB  ALA F 377     41.903  -9.649 -55.227  1.00 53.08            C
ANISOU 5630  CB  ALA F 377     4691  10631   4845    884   1125  -2013       C
ATOM   5631  C   ALA F 377     39.807  -9.480 -56.625  1.00 50.17            C
ANISOU 5631  C   ALA F 377     4938  10055   4069    617   1139  -1830       C
ATOM   5632  O   ALA F 377     38.594  -9.335 -56.445  1.00 47.07            O
ANISOU 5632  O   ALA F 377     4807   9454   3625    543    972  -1675       O
ATOM   5633  N   THR F 378     40.302 -10.282 -57.575  1.00 52.64            N
ANISOU 5633  N   THR F 378     5218  10501   4283    731   1331  -2062       N
ATOM   5634  CA  THR F 378     39.443 -11.109 -58.447  1.00 52.30            C
ANISOU 5634  CA  THR F 378     5480  10344   4050    774   1333  -2154       C
ATOM   5635  CB  THR F 378     40.261 -11.862 -59.508  1.00 56.31            C
ANISOU 5635  CB  THR F 378     5911  11045   4441    890   1603  -2444       C
ATOM   5636  OG1 THR F 378     41.023 -10.926 -60.282  1.00 58.56            O
ANISOU 5636  OG1 THR F 378     6043  11640   4566    661   1879  -2434       O
ATOM   5637  CG2 THR F 378     39.345 -12.685 -60.420  1.00 56.32            C
ANISOU 5637  CG2 THR F 378     6258  10920   4219    905   1590  -2552       C
ATOM   5638  C   THR F 378     38.624 -12.111 -57.623  1.00 50.10            C
ANISOU 5638  C   THR F 378     5380   9738   3920    974   1085  -2166       C
ATOM   5639  O   THR F 378     39.174 -13.029 -57.010  1.00 50.63            O
ANISOU 5639  O   THR F 378     5354   9711   4174   1249   1041  -2309       O
ATOM   5640  N   ARG F 379     37.307 -11.917 -57.630  1.00 47.53            N
ANISOU 5640  N   ARG F 379     5314   9237   3507    831    928  -2016       N
ATOM   5641  CA  ARG F 379     36.375 -12.691 -56.812  1.00 45.98            C
ANISOU 5641  CA  ARG F 379     5299   8730   3442    929    717  -1996       C
ATOM   5642  CB  ARG F 379     35.991 -13.986 -57.509  1.00 47.10            C
ANISOU 5642  CB  ARG F 379     5649   8750   3497   1039    741  -2218       C
ATOM   5643  CG  ARG F 379     35.553 -13.795 -58.975  1.00 49.36            C
ANISOU 5643  CG  ARG F 379     6077   9194   3483    864    839  -2280       C
ATOM   5644  CD  ARG F 379     34.872 -15.036 -59.519  1.00 49.19            C
ANISOU 5644  CD  ARG F 379     6310   8999   3381    920    800  -2486       C
ATOM   5645  NE  ARG F 379     33.688 -15.336 -58.716  1.00 48.20            N
ANISOU 5645  NE  ARG F 379     6327   8598   3390    864    582  -2392       N
ATOM   5646  CZ  ARG F 379     32.926 -16.417 -58.847  1.00 48.36            C
ANISOU 5646  CZ  ARG F 379     6569   8396   3409    870    509  -2542       C
ATOM   5647  NH1 ARG F 379     33.204 -17.326 -59.776  1.00 50.81            N
ANISOU 5647  NH1 ARG F 379     7015   8710   3582    951    618  -2802       N
ATOM   5648  NH2 ARG F 379     31.886 -16.587 -58.042  1.00 43.85            N
ANISOU 5648  NH2 ARG F 379     6090   7596   2976    779    346  -2448       N
ATOM   5649  C   ARG F 379     36.840 -12.931 -55.347  1.00 45.52            C
ANISOU 5649  C   ARG F 379     5126   8523   3646   1110    592  -1952       C
ATOM   5650  O   ARG F 379     36.679 -14.029 -54.799  1.00 46.28            O
ANISOU 5650  O   ARG F 379     5352   8383   3849   1302    501  -2041       O
ATOM   5651  N   ARG F 380     37.400 -11.897 -54.717  1.00 44.64            N
ANISOU 5651  N   ARG F 380     4807   8534   3618   1036    579  -1811       N
ATOM   5652  CA  ARG F 380     37.835 -11.998 -53.324  1.00 44.23            C
ANISOU 5652  CA  ARG F 380     4663   8367   3777   1184    430  -1758       C
ATOM   5653  CB  ARG F 380     39.209 -12.663 -53.248  1.00 47.80            C
ANISOU 5653  CB  ARG F 380     4876   8940   4345   1461    483  -1956       C
ATOM   5654  CG  ARG F 380     39.793 -12.813 -51.838  1.00 49.84            C
ANISOU 5654  CG  ARG F 380     5033   9103   4802   1655    286  -1915       C
ATOM   5655  CD  ARG F 380     41.062 -13.651 -51.917  1.00 56.80            C
ANISOU 5655  CD  ARG F 380     5680  10096   5807   1991    313  -2147       C
ATOM   5656  NE  ARG F 380     42.171 -13.087 -51.147  1.00 61.43            N
ANISOU 5656  NE  ARG F 380     5917  10875   6548   2062    223  -2147       N
ATOM   5657  CZ  ARG F 380     43.388 -12.828 -51.635  1.00 64.11            C
ANISOU 5657  CZ  ARG F 380     5845  11552   6964   2111    368  -2317       C
ATOM   5658  NH1 ARG F 380     43.677 -13.067 -52.908  1.00 65.91            N
ANISOU 5658  NH1 ARG F 380     5980  11960   7104   2099    641  -2496       N
ATOM   5659  NH2 ARG F 380     44.326 -12.326 -50.842  1.00 65.00            N
ANISOU 5659  NH2 ARG F 380     5629  11835   7234   2157    247  -2324       N
```

FIGURE 18-163

```
ATOM   5660  C   ARG F 380      37.852 -10.660 -52.621  1.00 41.88           C
ANISOU 5660  C   ARG F 380     4256  8133  3523   993   370 -1553           C
ATOM   5661  O   ARG F 380      38.517  -9.734 -53.075  1.00 42.95           O
ANISOU 5661  O   ARG F 380     4196  8508  3614   848   494 -1530           O
ATOM   5662  N   LEU F 381      37.099 -10.574 -51.519  1.00 39.44           N
ANISOU 5662  N   LEU F 381     4100  7595  3292   975   200 -1415           N
ATOM   5663  CA  LEU F 381      37.138  -9.447 -50.574  1.00 37.48           C
ANISOU 5663  CA  LEU F 381     3781  7350  3109   840   116 -1247           C
ATOM   5664  CB  LEU F 381      35.919  -9.479 -49.643  1.00 35.32           C
ANISOU 5664  CB  LEU F 381     3754  6800  2866   791   -16 -1118           C
ATOM   5665  CG  LEU F 381      35.557  -8.300 -48.733  1.00 33.09           C
ANISOU 5665  CG  LEU F 381     3486  6465  2620   628   -85  -947           C
ATOM   5666  CD1 LEU F 381      34.028  -8.185 -48.630  1.00 28.32           C
ANISOU 5666  CD1 LEU F 381     3096  5671  1992   513  -108  -858           C
ATOM   5667  CD2 LEU F 381      36.185  -8.462 -47.322  1.00 32.20           C
ANISOU 5667  CD2 LEU F 381     3358  6270  2605   750  -225  -936           C
ATOM   5668  C   LEU F 381      38.412  -9.549 -49.763  1.00 38.85           C
ANISOU 5668  C   LEU F 381     3730  7616  3415  1002    44 -1313           C
ATOM   5669  O   LEU F 381      38.661 -10.569 -49.124  1.00 39.13           O
ANISOU 5669  O   LEU F 381     3822  7515  3530  1250   -72 -1389           O
ATOM   5670  N   VAL F 382      39.229  -8.500 -49.829  1.00 39.49           N
ANISOU 5670  N   VAL F 382     3562  7926  3518   858   106 -1289           N
ATOM   5671  CA  VAL F 382      40.512  -8.475 -49.144  1.00 41.58           C
ANISOU 5671  CA  VAL F 382     3538  8340  3920   980    28 -1378           C
ATOM   5672  CB  VAL F 382      41.603  -7.708 -49.966  1.00 43.41           C
ANISOU 5672  CB  VAL F 382     3420  8920  4155   821   228 -1467           C
ATOM   5673  CG1 VAL F 382      42.891  -7.551 -49.173  1.00 44.97           C
ANISOU 5673  CG1 VAL F 382     3263  9301  4525   909   121 -1569           C
ATOM   5674  CG2 VAL F 382      41.887  -8.422 -51.295  1.00 45.12           C
ANISOU 5674  CG2 VAL F 382     3569  9282  4293   909   448 -1638           C
ATOM   5675  C   VAL F 382      40.312  -7.883 -47.743  1.00 40.72           C
ANISOU 5675  C   VAL F 382     3510  8092  3870   921  -175 -1239           C
ATOM   5676  O   VAL F 382      40.756  -8.472 -46.752  1.00 41.67           O
ANISOU 5676  O   VAL F 382     3618  8139  4075  1138  -368 -1279           O
ATOM   5677  N   GLN F 383      39.620  -6.740 -47.677  1.00 39.32           N
ANISOU 5677  N   GLN F 383     3446  7862  3630   645  -138 -1080           N
ATOM   5678  CA  GLN F 383      39.373  -6.002 -46.438  1.00 38.54           C
ANISOU 5678  CA  GLN F 383     3444  7637  3564   546  -287  -961           C
ATOM   5679  CB  GLN F 383      40.628  -5.223 -46.012  1.00 40.51           C
ANISOU 5679  CB  GLN F 383     3390  8104  3898   455  -334 -1014           C
ATOM   5680  CG  GLN F 383      40.645  -4.744 -44.547  1.00 40.45           C
ANISOU 5680  CG  GLN F 383     3469  7978  3921   423  -545  -949           C
ATOM   5681  CD  GLN F 383      41.875  -3.885 -44.209  1.00 43.46           C
ANISOU 5681  CD  GLN F 383     3531  8595  4388   279  -598 -1023           C
ATOM   5682  OE1 GLN F 383      42.401  -3.158 -45.063  1.00 47.32           O
ANISOU 5682  OE1 GLN F 383     3803  9284  4893    65  -416 -1057           O
ATOM   5683  NE2 GLN F 383      42.331  -3.969 -42.958  1.00 43.22           N
ANISOU 5683  NE2 GLN F 383     3486  8538  4398   376  -848 -1052           N
ATOM   5684  C   GLN F 383      38.227  -5.022 -46.652  1.00 36.57           C
ANISOU 5684  C   GLN F 383     3400  7259  3236   306  -212  -801           C
ATOM   5685  O   GLN F 383      38.119  -4.405 -47.720  1.00 37.21           O
ANISOU 5685  O   GLN F 383     3447  7443  3248   144   -58  -768           O
ATOM   5686  N   LEU F 384      37.369  -4.907 -45.642  1.00 34.97           N
ANISOU 5686  N   LEU F 384     3425  6828  3036   299  -318  -709           N
ATOM   5687  CA  LEU F 384      36.306  -3.912 -45.594  1.00 33.66           C
ANISOU 5687  CA  LEU F 384     3428  6527  2834   111  -275  -576           C
ATOM   5688  CB  LEU F 384      34.924  -4.535 -45.873  1.00 31.81           C
ANISOU 5688  CB  LEU F 384     3403  6118  2566   163  -248  -546           C
ATOM   5689  CG  LEU F 384      33.659  -3.661 -45.748  1.00 30.14           C
ANISOU 5689  CG  LEU F 384     3344  5757  2352    32  -224  -435           C
ATOM   5690  CD1 LEU F 384      33.439  -2.719 -46.929  1.00 25.61           C
ANISOU 5690  CD1 LEU F 384     2737  5271  1724  -100  -144  -364           C
ATOM   5691  CD2 LEU F 384      32.413  -4.513 -45.509  1.00 29.87           C
ANISOU 5691  CD2 LEU F 384     3472  5546  2330   101  -229  -452           C
ATOM   5692  C   LEU F 384      36.364  -3.301 -44.207  1.00 33.92           C
ANISOU 5692  C   LEU F 384     3539  6450  2901    56  -390  -531           C
ATOM   5693  O   LEU F 384      36.411  -4.017 -43.192  1.00 34.45           O
ANISOU 5693  O   LEU F 384     3703  6414  2973   195  -514  -559           O
ATOM   5694  N   ILE F 385      36.419  -1.976 -44.173  1.00 34.62           N
ANISOU 5694  N   ILE F 385     3612  6550  2992  -150  -352  -464           N
ATOM   5695  CA  ILE F 385      36.450  -1.228 -42.930  1.00 35.04           C
```

FIGURE 18-164

```
ANISOU 5695  CA  ILE F 385    3759  6494  3061  -238  -445  -436       C
ATOM   5696  CB  ILE F 385    37.718  -0.361 -42.822  1.00 36.95        C
ANISOU 5696  CB  ILE F 385    3794  6908  3338  -401  -473  -480       C
ATOM   5697  CG1 ILE F 385    38.985  -1.211 -43.001  1.00 38.55        C
ANISOU 5697  CG1 ILE F 385    3710  7352  3587  -268  -538  -611       C
ATOM   5698  CD1 ILE F 385    40.287  -0.384 -43.171  1.00 41.49        C
ANISOU 5698  CD1 ILE F 385    3783  7960  4019  -466  -520  -687       C
ATOM   5699  CG2 ILE F 385    37.746   0.385 -41.474  1.00 37.52        C
ANISOU 5699  CG2 ILE F 385    3994  6855  3407  -499  -592  -475       C
ATOM   5700  C   ILE F 385    35.213  -0.350 -42.996  1.00 34.38        C
ANISOU 5700  C   ILE F 385    3874  6223  2965  -350  -364  -332       C
ATOM   5701  O   ILE F 385    35.148   0.522 -43.864  1.00 35.97        O
ANISOU 5701  O   ILE F 385    4050  6456  3159  -485  -273  -270       O
ATOM   5702  N   VAL F 386    34.230  -0.603 -42.119  1.00 32.76        N
ANISOU 5702  N   VAL F 386    3871  5822  2755  -286  -389  -317       N
ATOM   5703  CA  VAL F 386    32.929   0.098 -42.139  1.00 31.18        C
ANISOU 5703  CA  VAL F 386    3822  5448  2576  -341  -310  -251       C
ATOM   5704  CB  VAL F 386    31.707  -0.895 -42.196  1.00 30.22        C
ANISOU 5704  CB  VAL F 386    3791  5226  2465  -223  -267  -266       C
ATOM   5705  CG1 VAL F 386    30.411  -0.170 -42.554  1.00 28.82        C
ANISOU 5705  CG1 VAL F 386    3669  4938  2344  -255  -195  -220       C
ATOM   5706  CG2 VAL F 386    31.928  -2.001 -43.194  1.00 31.56        C
ANISOU 5706  CG2 VAL F 386    3858  5519  2615  -125  -265  -303       C
ATOM   5707  C   VAL F 386    32.736   1.020 -40.921  1.00 31.34        C
ANISOU 5707  C   VAL F 386    3995  5314  2601  -430  -328  -248       C
ATOM   5708  O   VAL F 386    33.123   0.664 -39.792  1.00 31.29        O
ANISOU 5708  O   VAL F 386    4065  5275  2548  -406  -407  -298       O
ATOM   5709  N   SER F 387    32.167   2.205 -41.181  1.00 30.66        N
ANISOU 5709  N   SER F 387    3973  5122  2554  -523  -264  -192       N
ATOM   5710  CA  SER F 387    31.593   3.089 -40.168  1.00 30.93        C
ANISOU 5710  CA  SER F 387    4185  4961  2606  -577  -238  -204       C
ATOM   5711  CB  SER F 387    32.314   4.437 -40.147  1.00 32.15        C
ANISOU 5711  CB  SER F 387    4367  5081  2766  -752  -252  -182       C
ATOM   5712  OG  SER F 387    33.719   4.299 -40.027  1.00 33.45        O
ANISOU 5712  OG  SER F 387    4399  5419  2892  -849  -338  -224       O
ATOM   5713  C   SER F 387    30.123   3.319 -40.541  1.00 30.20        C
ANISOU 5713  C   SER F 387    4150  4737  2589  -496  -148  -176       C
ATOM   5714  O   SER F 387    29.797   3.411 -41.720  1.00 30.80        O
ANISOU 5714  O   SER F 387    4146  4862  2693  -463  -140  -113       O
ATOM   5715  N   GLY F 388    29.239   3.490 -39.556  1.00 29.35        N
ANISOU 5715  N   GLY F 388    4170  4476  2507  -463   -82  -233       N
ATOM   5716  CA  GLY F 388    27.829   3.707 -39.816  1.00 28.50        C
ANISOU 5716  CA  GLY F 388    4063  4258  2506  -376     4  -240       C
ATOM   5717  C   GLY F 388    27.081   4.361 -38.647  1.00 28.60        C
ANISOU 5717  C   GLY F 388    4224  4084  2558  -377   109  -322       C
ATOM   5718  O   GLY F 388    27.550   4.343 -37.526  1.00 27.72        O
ANISOU 5718  O   GLY F 388    4253  3926  2354  -450   122  -378       O
ATOM   5719  N   LYS F 389    25.894   4.911 -38.914  1.00 28.96        N
ANISOU 5719  N   LYS F 389    4235  4030  2737  -281   179  -343       N
ATOM   5720  CA  LYS F 389    25.150   5.640 -37.881  1.00 30.12        C
ANISOU 5720  CA  LYS F 389    4504  3998  2943  -260   308  -446       C
ATOM   5721  CB  LYS F 389    24.270   6.732 -38.500  1.00 31.54        C
ANISOU 5721  CB  LYS F 389    4640  4054  3289  -128   310  -434       C
ATOM   5722  CG  LYS F 389    25.065   7.735 -39.311  1.00 31.37        C
ANISOU 5722  CG  LYS F 389    4699  3977  3246  -167   180  -301       C
ATOM   5723  CD  LYS F 389    24.164   8.721 -39.993  1.00 32.90        C
ANISOU 5723  CD  LYS F 389    4890  4023  3587     1   146  -263       C
ATOM   5724  CE  LYS F 389    24.971   9.802 -40.644  1.00 33.28        C
ANISOU 5724  CE  LYS F 389    5107  3953  3584   -75    49  -123       C
ATOM   5725  NZ  LYS F 389    24.087  10.800 -41.284  1.00 36.05        N
ANISOU 5725  NZ  LYS F 389    5517  4114  4065   121   -12   -67       N
ATOM   5726  C   LYS F 389    24.345   4.720 -36.971  1.00 30.25        C
ANISOU 5726  C   LYS F 389    4529  4017  2950  -255   466  -565       C
ATOM   5727  O   LYS F 389    23.902   5.131 -35.891  1.00 31.37        O
ANISOU 5727  O   LYS F 389    4806  4031  3083  -274   611  -673       O
ATOM   5728  N   ASP F 390    24.204   3.466 -37.393  1.00 29.12        N
ANISOU 5728  N   ASP F 390    4269  4006  2789  -251   455  -550       N
ATOM   5729  CA  ASP F 390    23.576   2.440 -36.575  1.00 29.97        C
ANISOU 5729  CA  ASP F 390    4424  4105  2858  -296   612  -643       C
ATOM   5730  CB  ASP F 390    22.041   2.586 -36.553  1.00 30.71        C
ANISOU 5730  CB  ASP F 390    4366  4164  3137  -237   789  -763       C
```

FIGURE 18-165

```
ATOM   5731  CG  ASP F 390      21.410   2.597 -37.954  1.00 30.11           C
ANISOU 5731  CG  ASP F 390    4012  4192  3236   -122    680   -736          C
ATOM   5732  OD1 ASP F 390      21.906   1.900 -38.876  1.00 31.34           O
ANISOU 5732  OD1 ASP F 390    4099  4466  3341   -128    537   -651          O
ATOM   5733  OD2 ASP F 390      20.396   3.303 -38.134  1.00 27.66           O
ANISOU 5733  OD2 ASP F 390    3554  3847  3110    -10    729   -811          O
ATOM   5734  C   ASP F 390      23.993   1.035 -37.017  1.00 29.58           C
ANISOU 5734  C   ASP F 390    4340  4171  2729   -323    541   -594          C
ATOM   5735  O   ASP F 390      24.751   0.863 -37.972  1.00 28.60           O
ANISOU 5735  O   ASP F 390    4127  4153  2588   -291    379   -507          O
ATOM   5736  N   GLU F 391      23.482   0.046 -36.293  1.00 30.84           N
ANISOU 5736  N   GLU F 391    4594  4290  2833   -389    685   -659          N
ATOM   5737  CA  GLU F 391      23.729  -1.385 -36.518  1.00 30.78           C
ANISOU 5737  CA  GLU F 391    4622  4325  2747   -417    652   -631          C
ATOM   5738  CB  GLU F 391      22.983  -2.177 -35.421  1.00 31.99           C
ANISOU 5738  CB  GLU F 391    4962  4364  2827   -533    875   -709          C
ATOM   5739  CG  GLU F 391      23.324  -3.638 -35.334  1.00 31.45           C
ANISOU 5739  CG  GLU F 391    5056  4259  2634   -576    853   -670          C
ATOM   5740  CD  GLU F 391      22.692  -4.319 -34.139  1.00 33.38           C
ANISOU 5740  CD  GLU F 391    5573  4355  2756   -724   1088   -721          C
ATOM   5741  OE1 GLU F 391      23.273  -5.342 -33.707  1.00 33.05           O
ANISOU 5741  OE1 GLU F 391    5804  4219  2535   -744   1036   -654          O
ATOM   5742  OE2 GLU F 391      21.639  -3.850 -33.633  1.00 30.81           O
ANISOU 5742  OE2 GLU F 391    5202  3997  2506   -814   1329   -829          O
ATOM   5743  C   GLU F 391      23.286  -1.857 -37.909  1.00 30.79           C
ANISOU 5743  C   GLU F 391    4372  4443  2884   -367    585   -630          C
ATOM   5744  O   GLU F 391      24.001  -2.594 -38.588  1.00 30.38           O
ANISOU 5744  O   GLU F 391    4307  4463  2773   -336    456   -576          O
ATOM   5745  N   GLN F 392      22.099  -1.421 -38.324  1.00 32.45           N
ANISOU 5745  N   GLN F 392    4380  4677  3273   -346    666   -706          N
ATOM   5746  CA  GLN F 392      21.515  -1.817 -39.610  1.00 32.48           C
ANISOU 5746  CA  GLN F 392    4144  4800  3398   -304    583   -727          C
ATOM   5747  CB  GLN F 392      20.092  -1.260 -39.718  1.00 34.09           C
ANISOU 5747  CB  GLN F 392    4120  5020  3814   -271    678   -843          C
ATOM   5748  CG  GLN F 392      19.442  -1.344 -41.095  1.00 35.80           C
ANISOU 5748  CG  GLN F 392    4067  5374  4160   -195    528   -866          C
ATOM   5749  CD  GLN F 392      19.152  -2.771 -41.513  1.00 38.28           C
ANISOU 5749  CD  GLN F 392    4332  5752  4461   -309    544   -935          C
ATOM   5750  OE1 GLN F 392      19.360  -3.713 -40.739  1.00 38.79           O
ANISOU 5750  OE1 GLN F 392    4575  5730  4433   -443    686   -960          O
ATOM   5751  NE2 GLN F 392      18.687  -2.945 -42.749  1.00 38.16           N
ANISOU 5751  NE2 GLN F 392    4110  5869  4519   -260    384   -963          N
ATOM   5752  C   GLN F 392      22.369  -1.346 -40.784  1.00 31.31           C
ANISOU 5752  C   GLN F 392    3932  4753  3213   -208    364   -613          C
ATOM   5753  O   GLN F 392      22.674  -2.123 -41.683  1.00 30.61           O
ANISOU 5753  O   GLN F 392    3793  4758  3081   -202    268   -594          O
ATOM   5754  N   SER F 393      22.754  -0.071 -40.752  1.00 31.83           N
ANISOU 5754  N   SER F 393    4026  4785  3285   -152    308   -546          N
ATOM   5755  CA  SER F 393      23.555   0.584 -41.804  1.00 31.84           C
ANISOU 5755  CA  SER F 393    4001  4859  3240    -99    140   -428          C
ATOM   5756  CB  SER F 393      23.778   2.031 -41.404  1.00 32.41           C
ANISOU 5756  CB  SER F 393    4160  4818  3334    -79    137   -379          C
ATOM   5757  OG  SER F 393      22.513   2.621 -41.159  1.00 36.78           O
ANISOU 5757  OG  SER F 393    4636  5288  4050      2    210   -458          O
ATOM   5758  C   SER F 393      24.904  -0.068 -42.095  1.00 31.09           C
ANISOU 5758  C   SER F 393    3969  4851  2992   -139     63   -365          C
ATOM   5759  O   SER F 393      25.370  -0.089 -43.238  1.00 31.67           O
ANISOU 5759  O   SER F 393    3975  5039  3019   -116    -36   -305          O
ATOM   5760  N   ILE F 394      25.531  -0.560 -41.031  1.00 30.78           N
ANISOU 5760  N   ILE F 394    4068  4760  2868   -190    110   -387          N
ATOM   5761  CA  ILE F 394      26.767  -1.307 -41.083  1.00 29.79           C
ANISOU 5761  CA  ILE F 394    3986  4710  2624   -191     33   -359          C
ATOM   5762  CB  ILE F 394      27.351  -1.480 -39.645  1.00 29.65           C
ANISOU 5762  CB  ILE F 394    4156  4598  2511   -226     48   -374          C
ATOM   5763  CG1 ILE F 394      27.823  -0.134 -39.098  1.00 29.52           C
ANISOU 5763  CG1 ILE F 394    4191  4541  2482   -279     24   -348          C
ATOM   5764  CD1 ILE F 394      27.916  -0.060 -37.553  1.00 31.10           C
ANISOU 5764  CD1 ILE F 394    4613  4618  2587   -330     64   -390          C
ATOM   5765  CG2 ILE F 394      28.466  -2.533 -39.621  1.00 29.07           C
ANISOU 5765  CG2 ILE F 394    4119  4590  2336   -174    -54   -367          C
ATOM   5766  C   ILE F 394      26.499  -2.669 -41.731  1.00 29.71           C
```

FIGURE 18-166

```
ANISOU 5766  C   ILE F 394    3929  4753  2607   -158    31  -404       C
ATOM   5767  O   ILE F 394    27.278  -3.120 -42.577  1.00 29.55         O
ANISOU 5767  O   ILE F 394    3847  4847  2533   -116   -47  -388       O
ATOM   5768  N   ALA F 395    25.403  -3.316 -41.324  1.00 30.22         N
ANISOU 5768  N   ALA F 395    4027  4730  2726   -194   137  -478       N
ATOM   5769  CA  ALA F 395    25.009  -4.588 -41.908  1.00 30.57         C
ANISOU 5769  CA  ALA F 395    4048  4791  2775   -201   149  -541       C
ATOM   5770  CB  ALA F 395    23.837  -5.225 -41.145  1.00 31.36         C
ANISOU 5770  CB  ALA F 395    4215  4766  2934   -302   310  -630       C
ATOM   5771  C   ALA F 395    24.716  -4.452 -43.403  1.00 30.78         C
ANISOU 5771  C   ALA F 395    3889  4961  2846   -163    60  -548       C
ATOM   5772  O   ALA F 395    25.104  -5.325 -44.164  1.00 31.52         O
ANISOU 5772  O   ALA F 395    3978  5117  2882   -138    10  -576       O
ATOM   5773  N   GLU F 396    24.072  -3.354 -43.821  1.00 31.71         N
ANISOU 5773  N   GLU F 396    3881  5119  3047   -145    31  -523       N
ATOM   5774  CA  GLU F 396    23.861  -3.029 -45.257  1.00 31.94         C
ANISOU 5774  CA  GLU F 396    3780  5281  3073    -95   -93  -498       C
ATOM   5775  CB  GLU F 396    23.037  -1.743 -45.443  1.00 33.01         C
ANISOU 5775  CB  GLU F 396    3825  5402  3315    -41  -139  -461       C
ATOM   5776  CG  GLU F 396    21.538  -1.987 -45.467  1.00 35.48         C
ANISOU 5776  CG  GLU F 396    3973  5718  3789    -35  -123  -581       C
ATOM   5777  CD  GLU F 396    20.680  -0.802 -44.997  1.00 38.57         C
ANISOU 5777  CD  GLU F 396    4281  6037  4338     44  -103  -589       C
ATOM   5778  OE1 GLU F 396    21.223   0.325 -44.807  1.00 39.47         O
ANISOU 5778  OE1 GLU F 396    4500  6075  4423     99  -126  -482       O
ATOM   5779  OE2 GLU F 396    19.447  -1.008 -44.817  1.00 35.64         O
ANISOU 5779  OE2 GLU F 396    3729  5680  4133     47   -55  -721       O
ATOM   5780  C   GLU F 396    25.163  -2.938 -46.052  1.00 31.50         C
ANISOU 5780  C   GLU F 396    3762  5332  2874    -69  -168  -417       C
ATOM   5781  O   GLU F 396    25.290  -3.588 -47.089  1.00 32.61         O
ANISOU 5781  O   GLU F 396    3871  5579  2942    -56  -221  -449       O
ATOM   5782  N   ALA F 397    26.128  -2.156 -45.567  1.00 30.36         N
ANISOU 5782  N   ALA F 397    3680  5169  2688    -79  -159  -334       N
ATOM   5783  CA  ALA F 397    27.425  -2.017 -46.242  1.00 30.05         C
ANISOU 5783  CA  ALA F 397    3636  5250  2530    -86  -193  -277       C
ATOM   5784  CB  ALA F 397    28.335  -0.987 -45.512  1.00 29.70         C
ANISOU 5784  CB  ALA F 397    3637  5170  2479   -140  -180  -206       C
ATOM   5785  C   ALA F 397    28.164  -3.342 -46.421  1.00 29.77         C
ANISOU 5785  C   ALA F 397    3596  5288  2428    -49  -182  -356       C
ATOM   5786  O   ALA F 397    28.768  -3.583 -47.484  1.00 30.19         O
ANISOU 5786  O   ALA F 397    3600  5481  2390    -35  -195  -364       O
ATOM   5787  N   ILE F 398    28.116  -4.184 -45.387  1.00 29.18         N
ANISOU 5787  N   ILE F 398    3597  5103  2385    -28  -151  -416       N
ATOM   5788  CA  ILE F 398    28.785  -5.500 -45.391  1.00 29.82         C
ANISOU 5788  CA  ILE F 398    3721  5193  2418     45  -156  -491       C
ATOM   5789  CB  ILE F 398    28.763  -6.184 -43.978  1.00 30.01         C
ANISOU 5789  CB  ILE F 398    3908  5042  2453     64  -137  -511       C
ATOM   5790  CG1 ILE F 398    29.506  -5.325 -42.937  1.00 28.78         C
ANISOU 5790  CG1 ILE F 398    3784  4871  2279     53  -173  -446       C
ATOM   5791  CD1 ILE F 398    29.361  -5.799 -41.514  1.00 29.65         C
ANISOU 5791  CD1 ILE F 398    4105  4806  2357     54  -162  -447       C
ATOM   5792  CG2 ILE F 398    29.370  -7.571 -44.042  1.00 30.84         C
ANISOU 5792  CG2 ILE F 398    4096  5109  2512    173  -164  -580       C
ATOM   5793  C   ILE F 398    28.199  -6.428 -46.466  1.00 30.35         C
ANISOU 5793  C   ILE F 398    3770  5297  2466     59  -152  -577       C
ATOM   5794  O   ILE F 398    28.943  -7.040 -47.237  1.00 31.40         O
ANISOU 5794  O   ILE F 398    3877  5526  2528    124  -162  -630       O
ATOM   5795  N   ILE F 399    26.868  -6.485 -46.522  1.00 30.23         N
ANISOU 5795  N   ILE F 399    3752  5216  2518     -8  -136  -610       N
ATOM   5796  CA  ILE F 399    26.139  -7.273 -47.508  1.00 30.68         C
ANISOU 5796  CA  ILE F 399    3781  5309  2565    -31  -156  -710       C
ATOM   5797  CB  ILE F 399    24.585  -7.231 -47.249  1.00 31.14         C
ANISOU 5797  CB  ILE F 399    3785  5298  2749   -126  -136  -763       C
ATOM   5798  CG1 ILE F 399    24.226  -7.902 -45.914  1.00 29.45         C
ANISOU 5798  CG1 ILE F 399    3695  4892  2602   -193   -16  -803       C
ATOM   5799  CD1 ILE F 399    22.950  -7.376 -45.272  1.00 29.44         C
ANISOU 5799  CD1 ILE F 399    3606  4839  2739   -287    62  -831       C
ATOM   5800  CG2 ILE F 399    23.800  -7.896 -48.410  1.00 32.52         C
ANISOU 5800  CG2 ILE F 399    3891  5551  2914   -170  -202  -881       C
ATOM   5801  C   ILE F 399    26.479  -6.784 -48.919  1.00 31.25         C
ANISOU 5801  C   ILE F 399    3772  5569  2531     -6  -226  -685       C
```

FIGURE 18-167

```
ATOM    5802  O    ILE F 399      26.773  -7.594 -49.799  1.00 32.29           O
ANISOU  5802  O    ILE F 399    3926   5770   2572     20   -235   -772        O
ATOM    5803  N    VAL F 400      26.442  -5.468 -49.127  1.00 31.26           N
ANISOU  5803  N    VAL F 400    3717   5633   2527    -17   -266   -569        N
ATOM    5804  CA   VAL F 400      26.703  -4.862 -50.439  1.00 31.99           C
ANISOU  5804  CA   VAL F 400    3791   5879   2484    -16   -326   -512        C
ATOM    5805  CB   VAL F 400      26.552  -3.321 -50.424  1.00 32.28           C
ANISOU  5805  CB   VAL F 400    3826   5904   2535    -32   -369   -359        C
ATOM    5806  CG1  VAL F 400      27.154  -2.712 -51.702  1.00 31.55           C
ANISOU  5806  CG1  VAL F 400    3785   5949   2253    -57   -395   -270        C
ATOM    5807  CG2  VAL F 400      25.081  -2.906 -50.237  1.00 31.82           C
ANISOU  5807  CG2  VAL F 400    3714   5767   2609     -9   -454   -364        C
ATOM    5808  C    VAL F 400      28.110  -5.188 -50.913  1.00 32.53           C
ANISOU  5808  C    VAL F 400    3873   6063   2424      4   -258   -527        C
ATOM    5809  O    VAL F 400      28.320  -5.462 -52.094  1.00 33.48           O
ANISOU  5809  O    VAL F 400    4010   6312   2399      3   -262   -566        O
ATOM    5810  N    ALA F 401      29.054  -5.149 -49.973  1.00 31.73           N
ANISOU  5810  N    ALA F 401    3756   5926   2375     25   -198   -510        N
ATOM    5811  CA   ALA F 401      30.462  -5.417 -50.239  1.00 32.29           C
ANISOU  5811  CA   ALA F 401    3773   6123   2374     61   -131   -547        C
ATOM    5812  CB   ALA F 401      31.316  -4.940 -49.082  1.00 31.23           C
ANISOU  5812  CB   ALA F 401    3591   5955   2320     61   -122   -500        C
ATOM    5813  C    ALA F 401      30.738  -6.885 -50.529  1.00 32.85           C
ANISOU  5813  C    ALA F 401    3863   6199   2419    165   -106   -703        C
ATOM    5814  O    ALA F 401      31.652  -7.205 -51.280  1.00 34.52           O
ANISOU  5814  O    ALA F 401    4018   6556   2542    209    -41   -775        O
ATOM    5815  N    MSE F 402      29.963  -7.768 -49.913  1.00 32.87           N
ANISOU  5815  N    MSE F 402    3957   6031   2501    198   -138   -765        N
ATOM    5816  CA   MSE F 402      30.121  -9.221 -50.081  1.00 34.29           C
ANISOU  5816  CA   MSE F 402    4216   6142   2669    295   -120   -914        C
ATOM    5817  CB   MSE F 402      29.405 -10.001 -48.955  1.00 33.61           C
ANISOU  5817  CB   MSE F 402    4274   5812   2686    294   -135   -936        C
ATOM    5818  CG   MSE F 402      30.159 -10.004 -47.602  1.00 34.31           C
ANISOU  5818  CG   MSE F 402    4411   5796   2829    379   -152   -874        C
ATOM    5819  SE   MSE F 402      29.225 -10.945 -46.127  0.90 35.69          SE
ANISOU  5819  SE   MSE F 402    4858   5634   3068    337   -136   -872       SE
ATOM    5820  CE   MSE F 402      30.613 -10.934 -44.782  1.00 35.68           C
ANISOU  5820  CE   MSE F 402    4931   5574   3050    510   -223   -797        C
ATOM    5821  C    MSE F 402      29.589  -9.629 -51.439  1.00 34.50           C
ANISOU  5821  C    MSE F 402    4268   6255   2587    255   -119  -1011        C
ATOM    5822  O    MSE F 402      30.190 -10.441 -52.110  1.00 36.42           O
ANISOU  5822  O    MSE F 402    4535   6549   2753    337    -73  -1137        O
ATOM    5823  N    VAL F 403      28.465  -9.043 -51.840  1.00 34.25           N
ANISOU  5823  N    VAL F 403    4226   6243   2545    142   -183   -962        N
ATOM    5824  CA   VAL F 403      27.919  -9.227 -53.188  1.00 34.82           C
ANISOU  5824  CA   VAL F 403    4323   6427   2480     94   -232  -1038        C
ATOM    5825  CB   VAL F 403      26.495  -8.620 -53.318  1.00 34.53           C
ANISOU  5825  CB   VAL F 403    4248   6380   2494      0   -356   -989        C
ATOM    5826  CG1  VAL F 403      25.966  -8.754 -54.767  1.00 35.80           C
ANISOU  5826  CG1  VAL F 403    4442   6680   2479    -40   -460  -1064        C
ATOM    5827  CG2  VAL F 403      25.531  -9.291 -52.314  1.00 33.68           C
ANISOU  5827  CG2  VAL F 403    4139   6086   2573    -50   -354  -1061        C
ATOM    5828  C    VAL F 403      28.878  -8.653 -54.249  1.00 35.95           C
ANISOU  5828  C    VAL F 403    4446   6779   2433    106   -179  -1003        C
ATOM    5829  O    VAL F 403      29.190  -9.332 -55.244  1.00 37.21           O
ANISOU  5829  O    VAL F 403    4664   7031   2443    127   -138  -1133        O
ATOM    5830  N    PHE F 404      29.347  -7.420 -54.010  1.00 34.96           N
ANISOU  5830  N    PHE F 404    4259   6715   2308     72   -159   -839        N
ATOM    5831  CA   PHE F 404      30.282  -6.688 -54.895  1.00 36.53           C
ANISOU  5831  CA   PHE F 404    4449   7101   2332     28    -72   -777        C
ATOM    5832  CB   PHE F 404      30.606  -5.293 -54.309  1.00 35.90           C
ANISOU  5832  CB   PHE F 404    4324   7008   2310    -45    -63   -589        C
ATOM    5833  CG   PHE F 404      31.373  -4.375 -55.245  1.00 37.51           C
ANISOU  5833  CG   PHE F 404    4558   7371   2322   -153     35   -495        C
ATOM    5834  CD1  PHE F 404      30.713  -3.660 -56.254  1.00 38.35           C
ANISOU  5834  CD1  PHE F 404    4819   7508   2243   -225    -40   -382        C
ATOM    5835  CE1  PHE F 404      31.414  -2.801 -57.112  1.00 37.22           C
ANISOU  5835  CE1  PHE F 404    4768   7483   1890   -354     72   -274        C
ATOM    5836  CZ   PHE F 404      32.771  -2.645 -56.966  1.00 39.43           C
ANISOU  5836  CZ   PHE F 404    4931   7877   2174   -433    279   -303        C
ATOM    5837  CE2  PHE F 404      33.452  -3.342 -55.961  1.00 39.28           C
```

FIGURE 18-168

```
ANISOU 5837  CE2 PHE F 404    4699   7858   2368    -343    332   -436      C
ATOM   5838  CD2 PHE F 404   32.747  -4.197 -55.097  1.00 38.17             C
ANISOU 5838  CD2 PHE F 404    4522   7571   2408    -192    198   -517      C
ATOM   5839  C   PHE F 404   31.571  -7.463 -55.140  1.00 37.46             C
ANISOU 5839  C   PHE F 404    4505   7327   2403     103     81   -918      C
ATOM   5840  O   PHE F 404   32.134  -7.391 -56.225  1.00 39.22             O
ANISOU 5840  O   PHE F 404    4747   7721   2433      66    186   -960      O
ATOM   5841  N   SER F 405   32.025  -8.203 -54.131  1.00 37.05             N
ANISOU 5841  N   SER F 405    4389   7171   2517     221     94   -995      N
ATOM   5842  CA  SER F 405   33.281  -8.958 -54.222  1.00 39.28             C
ANISOU 5842  CA  SER F 405    4576   7544   2804     352    212  -1143      C
ATOM   5843  CB  SER F 405   33.727  -9.455 -52.845  1.00 38.82             C
ANISOU 5843  CB  SER F 405    4463   7343   2945     492    158  -1160      C
ATOM   5844  OG  SER F 405   33.038 -10.651 -52.515  1.00 40.42             O
ANISOU 5844  OG  SER F 405    4824   7332   3201     585     93  -1254      O
ATOM   5845  C   SER F 405   33.166 -10.136 -55.180  1.00 40.69             C
ANISOU 5845  C   SER F 405    4856   7736   2869     429    260  -1340      C
ATOM   5846  O   SER F 405   34.178 -10.658 -55.653  1.00 42.13             O
ANISOU 5846  O   SER F 405    4962   8038   3005     534    391  -1487      O
ATOM   5847  N   GLN F 406   31.920 -10.534 -55.450  1.00 40.68             N
ANISOU 5847  N   GLN F 406    5011   7615   2832     371    155  -1361      N
ATOM   5848  CA  GLN F 406   31.572 -11.630 -56.381  1.00 42.61             C
ANISOU 5848  CA  GLN F 406    5392   7843   2954     399    169  -1558      C
ATOM   5849  CB  GLN F 406   31.955 -11.281 -57.824  1.00 44.04             C
ANISOU 5849  CB  GLN F 406    5602   8265   2868     332    270  -1606      C
ATOM   5850  CG  GLN F 406   31.191 -10.103 -58.371  1.00 43.15             C
ANISOU 5850  CG  GLN F 406    5540   8242   2614     163    170  -1425      C
ATOM   5851  CD  GLN F 406   31.738  -9.591 -59.677  1.00 44.42             C
ANISOU 5851  CD  GLN F 406    5768   8633   2476      81    291  -1422      C
ATOM   5852  OE1 GLN F 406   32.951  -9.500 -59.865  1.00 43.92             O
ANISOU 5852  OE1 GLN F 406    5611   8710   2369     105    499  -1468      O
ATOM   5853  NE2 GLN F 406   30.838  -9.241 -60.593  1.00 45.45             N
ANISOU 5853  NE2 GLN F 406    6064   8814   2393     -23    159  -1372      N
ATOM   5854  C   GLN F 406   32.173 -12.968 -55.971  1.00 43.95             C
ANISOU 5854  C   GLN F 406    5600   7871   3227     589    226  -1742      C
ATOM   5855  O   GLN F 406   32.433 -13.808 -56.819  1.00 46.15             O
ANISOU 5855  O   GLN F 406    5963   8178   3395     657    304  -1937      O
ATOM   5856  N   GLU F 407   32.373 -13.145 -54.666  1.00 43.66             N
ANISOU 5856  N   GLU F 407    5534   7667   3389     684    177  -1678      N
ATOM   5857  CA  GLU F 407   32.972 -14.356 -54.087  1.00 45.89             C
ANISOU 5857  CA  GLU F 407    5886   7768   3781     902    190  -1811      C
ATOM   5858  CB  GLU F 407   33.245 -14.162 -52.597  1.00 44.16             C
ANISOU 5858  CB  GLU F 407    5633   7413   3733     980    106  -1674      C
ATOM   5859  CG  GLU F 407   34.489 -13.382 -52.270  1.00 44.97             C
ANISOU 5859  CG  GLU F 407    5487   7716   3881    1066    133  -1614      C
ATOM   5860  CD  GLU F 407   35.177 -13.876 -51.008  1.00 45.76             C
ANISOU 5860  CD  GLU F 407    5591   7667   4127    1279     35  -1602      C
ATOM   5861  OE1 GLU F 407   34.788 -14.945 -50.485  1.00 46.21             O
ANISOU 5861  OE1 GLU F 407    5887   7443   4229    1387    -30  -1645      O
ATOM   5862  OE2 GLU F 407   36.126 -13.199 -50.553  1.00 46.06             O
ANISOU 5862  OE2 GLU F 407    5409   7866   4226    1332     14  -1552      O
ATOM   5863  C   GLU F 407   32.093 -15.581 -54.248  1.00 47.47             C
ANISOU 5863  C   GLU F 407    6337   7722   3977     890    155  -1951      C
ATOM   5864  O   GLU F 407   30.874 -15.486 -54.144  1.00 46.49             O
ANISOU 5864  O   GLU F 407    6303   7502   3860     703     80  -1898      O
ATOM   5865  N   ASP F 408   32.713 -16.737 -54.463  1.00 51.07             N
ANISOU 5865  N   ASP F 408    6898   8065   4441    1090    210  -2142      N
ATOM   5866  CA  ASP F 408   31.942 -17.949 -54.697  1.00 53.71             C
ANISOU 5866  CA  ASP F 408    7506   8138   4762    1059    193  -2300      C
ATOM   5867  CB  ASP F 408   32.753 -19.039 -55.396  1.00 56.74             C
ANISOU 5867  CB  ASP F 408    7989   8471   5099    1286    290  -2553      C
ATOM   5868  CG  ASP F 408   31.879 -19.947 -56.264  1.00 60.34             C
ANISOU 5868  CG  ASP F 408    8697   8784   5445    1155    300  -2755      C
ATOM   5869  OD1 ASP F 408   31.500 -19.542 -57.393  1.00 61.41             O
ANISOU 5869  OD1 ASP F 408    8794   9144   5396     993    324  -2821      O
ATOM   5870  OD2 ASP F 408   31.573 -21.074 -55.817  1.00 63.81             O
ANISOU 5870  OD2 ASP F 408    9399   8875   5969    1205    273  -2849      O
ATOM   5871  C   ASP F 408   31.241 -18.477 -53.441  1.00 53.40             C
ANISOU 5871  C   ASP F 408    7660   7761   4869    1016    107  -2210      C
ATOM   5872  O   ASP F 408   30.214 -19.139 -53.548  1.00 54.39             O
ANISOU 5872  O   ASP F 408    7984   7691   4992     852     89  -2287      O
```

FIGURE 18-169

```
ATOM   5873  N   ACYS F 409      31.777 -18.185 -52.260  0.50 52.75           N
ANISOU 5873  N   ACYS F 409    7531   7613   4899   1137     60  -2057        N
ATOM   5874  N   BCYS F 409      31.777 -18.185 -52.260  0.50 52.75           N
ANISOU 5874  N   BCYS F 409    7531   7613   4899   1137     60  -2057        N
ATOM   5875  CA  ACYS F 409      31.089 -18.592 -51.034  0.50 52.65           C
ANISOU 5875  CA  ACYS F 409    7738   7288   4981   1065      2  -1951        C
ATOM   5876  CA  BCYS F 409      31.089 -18.592 -51.034  0.50 52.65           C
ANISOU 5876  CA  BCYS F 409    7738   7288   4981   1065      2  -1951        C
ATOM   5877  CB  ACYS F 409      32.047 -18.636 -49.835  0.50 52.96           C
ANISOU 5877  CB  ACYS F 409    7800   7221   5099   1305    -69  -1839        C
ATOM   5878  CB  BCYS F 409      32.047 -18.636 -49.835  0.50 52.96           C
ANISOU 5878  CB  BCYS F 409    7800   7221   5099   1305    -69  -1839        C
ATOM   5879  SG  ACYS F 409      32.091 -17.163 -48.811  0.50 52.55           S
ANISOU 5879  SG  ACYS F 409    7540   7342   5085   1205   -130  -1593        S
ATOM   5880  SG  BCYS F 409      32.091 -17.163 -48.811  0.50 52.55           S
ANISOU 5880  SG  BCYS F 409    7540   7342   5085   1205   -130  -1593        S
ATOM   5881  C   ACYS F 409      29.827 -17.739 -50.774  0.50 50.12           C
ANISOU 5881  C   ACYS F 409    7348   7022   4672    755    -13  -1821        C
ATOM   5882  C   BCYS F 409      29.827 -17.739 -50.774  0.50 50.12           C
ANISOU 5882  C   BCYS F 409    7348   7022   4672    755    -13  -1821        C
ATOM   5883  O   ACYS F 409      28.886 -18.205 -50.136  0.50 50.44           O
ANISOU 5883  O   ACYS F 409    7577   6823   4766    597     -7  -1802        O
ATOM   5884  O   BCYS F 409      28.886 -18.205 -50.136  0.50 50.44           O
ANISOU 5884  O   BCYS F 409    7577   6823   4766    597     -7  -1802        O
ATOM   5885  N   MSE  F 410      29.811 -16.507 -51.289  1.00 48.14           N
ANISOU 5885  N   MSE  F 410    6837   7079   4377    671    -19  -1743        N
ATOM   5886  CA  MSE  F 410      28.586 -15.667 -51.329  1.00 46.32           C
ANISOU 5886  CA  MSE  F 410    6511   6930   4158    419    -48  -1656        C
ATOM   5887  CB  MSE  F 410      28.941 -14.221 -51.724  1.00 44.79           C
ANISOU 5887  CB  MSE  F 410    6071   7035   3913    406    -68  -1529        C
ATOM   5888  CG  MSE  F 410      27.762 -13.229 -51.931  1.00 42.99           C
ANISOU 5888  CG  MSE  F 410    5730   6910   3694    209   -126  -1442        C
ATOM   5889  SE  MSE  F 410      26.955 -13.098 -53.730  0.90 42.31          SE
ANISOU 5889  SE  MSE  F 410    5600   7035   3439     86   -204  -1557       SE
ATOM   5890  CE  MSE  F 410      28.542 -12.628 -54.751  1.00 41.76           C
ANISOU 5890  CE  MSE  F 410    5476   7222   3170    230   -121  -1549        C
ATOM   5891  C   MSE  F 410      27.565 -16.259 -52.323  1.00 47.69           C
ANISOU 5891  C   MSE  F 410    6753   7090   4276    253    -60  -1820        C
ATOM   5892  O   MSE  F 410      26.393 -16.467 -51.992  1.00 47.49           O
ANISOU 5892  O   MSE  F 410    6775   6944   4327     57    -75  -1837        O
ATOM   5893  N   ILE  F 411      28.020 -16.533 -53.544  1.00 48.99           N
ANISOU 5893  N   ILE  F 411    6915   7393   4304    318    -48  -1959        N
ATOM   5894  CA  ILE  F 411      27.176 -17.189 -54.556  1.00 50.31           C
ANISOU 5894  CA  ILE  F 411    7177   7552   4386    171    -80  -2148        C
ATOM   5895  CB  ILE  F 411      27.852 -17.190 -55.945  1.00 51.34           C
ANISOU 5895  CB  ILE  F 411    7295   7903   4310    257    -53  -2275        C
ATOM   5896  CG1 ILE  F 411      27.605 -15.837 -56.612  1.00 50.21           C
ANISOU 5896  CG1 ILE  F 411    6965   8064   4047    166   -123  -2142        C
ATOM   5897  CD1 ILE  F 411      28.722 -15.359 -57.495  1.00 52.42           C
ANISOU 5897  CD1 ILE  F 411    7190   8586   4140    279    -32  -2145        C
ATOM   5898  CG2 ILE  F 411      27.314 -18.312 -56.826  1.00 53.79           C
ANISOU 5898  CG2 ILE  F 411    7799   8112   4525    167    -66  -2531        C
ATOM   5899  C   ILE  F 411      26.671 -18.575 -54.108  1.00 51.93           C
ANISOU 5899  C   ILE  F 411    7639   7413   4677    105    -50  -2292        C
ATOM   5900  O   ILE  F 411      25.517 -18.904 -54.355  1.00 53.42           O
ANISOU 5900  O   ILE  F 411    7863   7547   4889   -126    -93  -2390        O
ATOM   5901  N   LYS  F 412      27.502 -19.356 -53.416  1.00 52.22           N
ANISOU 5901  N   LYS  F 412    7857   7215   4771    298     14  -2301        N
ATOM   5902  CA  LYS  F 412      27.074 -20.655 -52.866  1.00 53.75           C
ANISOU 5902  CA  LYS  F 412    8365   7019   5038    237     51  -2401        C
ATOM   5903  CB  LYS  F 412      28.288 -21.518 -52.480  1.00 55.14           C
ANISOU 5903  CB  LYS  F 412    8752   6970   5227    556     88  -2438        C
ATOM   5904  CG  LYS  F 412      29.038 -22.152 -53.648  1.00 57.75           C
ANISOU 5904  CG  LYS  F 412    9134   7352   5454    744    126  -2667        C
ATOM   5905  CD  LYS  F 412      28.231 -23.272 -54.325  1.00 61.07           C
ANISOU 5905  CD  LYS  F 412    9825   7547   5831    564    149  -2906        C
ATOM   5906  CE  LYS  F 412      28.940 -23.834 -55.572  1.00 63.36           C
ANISOU 5906  CE  LYS  F 412   10174   7912   5988    740    204  -3162        C
ATOM   5907  NZ  LYS  F 412      28.944 -22.908 -56.735  1.00 61.64           N
ANISOU 5907  NZ  LYS  F 412    9691   8127   5602    663    198  -3197        N
ATOM   5908  C   LYS  F 412      26.100 -20.546 -51.670  1.00 52.80           C
```

FIGURE 18-170

```
ANISOU 5908  C   LYS F 412    8297  6719  5046    18    66 -2268       C
ATOM   5909  O   LYS F 412   25.481 -21.540 -51.279  1.00 54.85        O
ANISOU 5909  O   LYS F 412    8819  6665  5356  -135   119 -2349       O
ATOM   5910  N   ALA F 413   25.965 -19.345 -51.104  1.00 50.11        N
ANISOU 5910  N   ALA F 413    7723  6567  4749   -13    43 -2077       N
ATOM   5911  CA  ALA F 413   25.099 -19.097 -49.933  1.00 48.96        C
ANISOU 5911  CA  ALA F 413    7598  6290  4712  -206    90 -1956       C
ATOM   5912  CB  ALA F 413   25.724 -18.033 -49.014  1.00 46.53        C
ANISOU 5912  CB  ALA F 413    7166  6089  4424   -67    75 -1735       C
ATOM   5913  C   ALA F 413   23.642 -18.733 -50.269  1.00 48.81        C
ANISOU 5913  C   ALA F 413    7393  6390  4762  -515    84 -2024       C
ATOM   5914  O   ALA F 413   22.815 -18.557 -49.364  1.00 48.53        O
ANISOU 5914  O   ALA F 413    7342  6265  4831  -700   159 -1964       O
ATOM   5915  N   VAL F 414   23.341 -18.612 -51.562  1.00 49.08        N
ANISOU 5915  N   VAL F 414    7279  6637  4730  -561    -7 -2158       N
ATOM   5916  CA  VAL F 414   21.970 -18.436 -52.037  1.00 49.54        C
ANISOU 5916  CA  VAL F 414    7153  6817  4854  -830   -65 -2269       C
ATOM   5917  CB  VAL F 414   21.929 -18.102 -53.563  1.00 50.27        C
ANISOU 5917  CB  VAL F 414    7101  7196  4804  -801  -222 -2378       C
ATOM   5918  CG1 VAL F 414   20.491 -17.927 -54.072  1.00 49.09        C
ANISOU 5918  CG1 VAL F 414    6737  7190  4726 -1054  -341 -2505       C
ATOM   5919  CG2 VAL F 414   22.757 -16.861 -53.860  1.00 47.46        C
ANISOU 5919  CG2 VAL F 414    6588  7096  4350  -582  -280 -2198       C
ATOM   5920  C   VAL F 414   21.156 -19.706 -51.750  1.00 52.59        C
ANISOU 5920  C   VAL F 414    7748  6913  5322 -1091    27 -2442       C
ATOM   5921  O   VAL F 414   21.612 -20.824 -52.012  1.00 54.19        O
ANISOU 5921  O   VAL F 414    8243  6888  5458 -1056    66 -2564       O
ATOM   5922  N   ARG F 415   19.960 -19.513 -51.195  1.00 53.57        N
ANISOU 5922  N   ARG F 415    7719  7037  5597 -1355    78 -2459       N
ATOM   5923  CA  ARG F 415   19.009 -20.599 -50.933  1.00 56.86        C
ANISOU 5923  CA  ARG F 415    8279  7213  6113 -1686   189 -2636       C
ATOM   5924  CB  ARG F 415   18.679 -20.667 -49.434  1.00 56.75        C
ANISOU 5924  CB  ARG F 415    8382  6972  6208 -1824   400 -2512       C
ATOM   5925  CG  ARG F 415   19.868 -20.954 -48.513  1.00 56.55        C
ANISOU 5925  CG  ARG F 415    8721  6681  6086 -1584   482 -2321       C
ATOM   5926  CD  ARG F 415   20.259 -22.434 -48.501  1.00 61.81        C
ANISOU 5926  CD  ARG F 415    9852  6947  6685 -1607   548 -2415       C
ATOM   5927  NE  ARG F 415   21.475 -22.674 -47.715  1.00 62.49        N
ANISOU 5927  NE  ARG F 415   10262  6805  6676 -1304   561 -2235       N
ATOM   5928  CZ  ARG F 415   22.689 -22.855 -48.237  1.00 62.58        C
ANISOU 5928  CZ  ARG F 415   10363  6824  6592  -954   445 -2229       C
ATOM   5929  NH1 ARG F 415   22.868 -22.842 -49.557  1.00 61.25        N
ANISOU 5929  NH1 ARG F 415   10028  6864  6379  -878   340 -2390       N
ATOM   5930  NH2 ARG F 415   23.727 -23.063 -47.431  1.00 62.31        N
ANISOU 5930  NH2 ARG F 415   10583  6594  6498  -677   434 -2075       N
ATOM   5931  C   ARG F 415   17.730 -20.345 -51.734  1.00 58.42        C
ANISOU 5931  C   ARG F 415    8134  7663  6402 -1935    70 -2824       C
ATOM   5932  O   ARG F 415   17.145 -19.259 -51.654  1.00 58.20        O
ANISOU 5932  O   ARG F 415    7749  7898  6468 -1933     2 -2757       O
ATOM   5933  N   GLY F 416   17.295 -21.329 -52.509  1.00 61.08        N
ANISOU 5933  N   GLY F 416    8575  7920  6715 -2136    26 -3069       N
ATOM   5934  CA  GLY F 416   16.104 -21.163 -53.341  1.00 62.81        C
ANISOU 5934  CA  GLY F 416    8459  8396  7010 -2372  -136 -3277       C
ATOM   5935  C   GLY F 416   16.429 -20.481 -54.658  1.00 61.99        C
ANISOU 5935  C   GLY F 416    8200  8622  6732 -2155  -406 -3291       C
ATOM   5936  O   GLY F 416   17.592 -20.198 -54.941  1.00 59.93        O
ANISOU 5936  O   GLY F 416    8093  8382  6296 -1854  -424 -3155       O
ATOM   5937  N   ASP F 417   15.403 -20.224 -55.467  1.00 63.90        N
ANISOU 5937  N   ASP F 417    8138  9127  7013 -2314  -618 -3460       N
ATOM   5938  CA  ASP F 417   15.591 -19.601 -56.780  1.00 64.06        C
ANISOU 5938  CA  ASP F 417    8056  9458  6828 -2137  -900 -3476       C
ATOM   5939  CB  ASP F 417   14.602 -20.172 -57.801  1.00 67.95        C
ANISOU 5939  CB  ASP F 417    8438 10082  7298 -2398 -1118 -3786       C
ATOM   5940  CG  ASP F 417   15.090 -21.481 -58.420  1.00 70.01        C
ANISOU 5940  CG  ASP F 417    9098 10118  7385 -2495 -1067 -4000       C
ATOM   5941  OD1 ASP F 417   16.312 -21.756 -58.345  1.00 67.20        O
ANISOU 5941  OD1 ASP F 417    9070  9582  6879 -2269  -919 -3895       O
ATOM   5942  OD2 ASP F 417   14.257 -22.228 -58.994  1.00 73.52        O
ANISOU 5942  OD2 ASP F 417    9518 10568  7849 -2792 -1180 -4292       O
ATOM   5943  C   ASP F 417   15.497 -18.081 -56.723  1.00 62.18        C
ANISOU 5943  C   ASP F 417    7507  9500  6617 -1920 -1034 -3253       C
```

FIGURE 18-171

```
ATOM    5944  O   ASP F 417      14.874 -17.529 -55.816  1.00 61.19           O
ANISOU  5944  O   ASP F 417     7135   9393   6721  -1970   -960  -3173       O
ATOM    5945  N   LEU F 418      16.133 -17.413 -57.685  1.00 61.75           N
ANISOU  5945  N   LEU F 418     7496   9647   6320  -1686  -1210  -3156       N
ATOM    5946  CA  LEU F 418      16.118 -15.948 -57.745  1.00 60.49           C
ANISOU  5946  CA  LEU F 418     7114   9719   6152  -1472  -1351  -2931       C
ATOM    5947  CB  LEU F 418      17.537 -15.398 -57.923  1.00 57.76           C
ANISOU  5947  CB  LEU F 418     6989   9374   5583  -1201  -1274  -2707       C
ATOM    5948  CG  LEU F 418      18.593 -15.816 -56.888  1.00 55.19           C
ANISOU  5948  CG  LEU F 418     6875   8788   5307  -1122   -976  -2599       C
ATOM    5949  CD1 LEU F 418      19.955 -15.240 -57.229  1.00 53.26           C
ANISOU  5949  CD1 LEU F 418     6775   8610   4852   -874   -930  -2422       C
ATOM    5950  CD2 LEU F 418      18.177 -15.419 -55.497  1.00 52.84           C
ANISOU  5950  CD2 LEU F 418     6426   8377   5273  -1162   -838  -2481       C
ATOM    5951  C   LEU F 418      15.138 -15.398 -58.802  1.00 63.79           C
ANISOU  5951  C   LEU F 418     7283  10437   6516  -1492  -1711  -3027       C
ATOM    5952  O   LEU F 418      15.392 -15.465 -60.017  1.00 65.29           O
ANISOU  5952  O   LEU F 418     7619  10766   6424  -1442  -1904  -3087       O
ATOM    5953  N   ASN F 419      14.019 -14.860 -58.308  1.00 65.15           N
ANISOU  5953  N   ASN F 419     7085  10711   6958  -1553  -1798  -3047       N
ATOM    5954  CA  ASN F 419      12.905 -14.410 -59.137  1.00 69.14           C
ANISOU  5954  CA  ASN F 419     7285  11496   7490  -1571  -2166  -3170       C
ATOM    5955  CB  ASN F 419      11.688 -15.328 -58.915  1.00 72.59           C
ANISOU  5955  CB  ASN F 419     7461  11934   8184  -1910  -2173  -3488       C
ATOM    5956  CG  ASN F 419      11.896 -16.734 -59.469  1.00 75.06           C
ANISOU  5956  CG  ASN F 419     8060  12114   8344  -2158  -2126  -3731       C
ATOM    5957  OD1 ASN F 419      12.169 -16.915 -60.657  1.00 76.13           O
ANISOU  5957  OD1 ASN F 419     8378  12363   8185  -2114  -2350  -3807       O
ATOM    5958  ND2 ASN F 419      11.741 -17.738 -58.608  1.00 76.18           N
ANISOU  5958  ND2 ASN F 419     8272  11998   8674  -2427  -1828  -3861       N
ATOM    5959  C   ASN F 419      12.492 -12.941 -58.929  1.00 68.82           C
ANISOU  5959  C   ASN F 419     6962  11617   7568  -1329  -2328  -2971       C
ATOM    5960  O   ASN F 419      11.329 -12.583 -59.159  1.00 71.70           O
ANISOU  5960  O   ASN F 419     6960  12179   8104  -1346  -2585  -3092       O
ATOM    5961  N   PHE F 420      13.438 -12.093 -58.525  1.00 65.87           N
ANISOU  5961  N   PHE F 420     6754  11162   7112  -1099  -2193  -2683       N
ATOM    5962  CA  PHE F 420      13.118 -10.705 -58.172  1.00 65.85           C
ANISOU  5962  CA  PHE F 420     6538  11242   7241   -872  -2295  -2489       C
ATOM    5963  CB  PHE F 420      14.226 -10.056 -57.331  1.00 61.88           C
ANISOU  5963  CB  PHE F 420     6236  10564   6710   -720  -2025  -2217       C
ATOM    5964  CG  PHE F 420      14.370 -10.644 -55.947  1.00 60.67           C
ANISOU  5964  CG  PHE F 420     6083  10193   6774   -865  -1658  -2251       C
ATOM    5965  CD1 PHE F 420      15.369 -11.592 -55.674  1.00 58.71           C
ANISOU  5965  CD1 PHE F 420     6148   9758   6401   -954  -1418  -2253       C
ATOM    5966  CE1 PHE F 420      15.511 -12.143 -54.394  1.00 56.02           C
ANISOU  5966  CE1 PHE F 420     5866   9196   6224  -1073  -1110  -2262       C
ATOM    5967  CZ  PHE F 420      14.657 -11.740 -53.367  1.00 56.93           C
ANISOU  5967  CZ  PHE F 420     5728   9288   6616  -1135   -998  -2278       C
ATOM    5968  CE2 PHE F 420      13.656 -10.794 -53.617  1.00 59.27           C
ANISOU  5968  CE2 PHE F 420     5671   9783   7065  -1048  -1201  -2302       C
ATOM    5969  CD2 PHE F 420      13.516 -10.248 -54.907  1.00 61.33           C
ANISOU  5969  CD2 PHE F 420     5874  10254   7176   -897  -1551  -2282       C
ATOM    5970  C   PHE F 420      12.752  -9.824 -59.370  1.00 68.72           C
ANISOU  5970  C   PHE F 420     6852  11834   7423   -675  -2718  -2421       C
ATOM    5971  O   PHE F 420      13.329  -9.934 -60.459  1.00 69.39           O
ANISOU  5971  O   PHE F 420     7220  11989   7156   -637  -2864  -2384       O
ATOM    5972  N   VAL F 421      11.776  -8.954 -59.131  1.00 70.81           N
ANISOU  5972  N   VAL F 421     6770  12208   7928   -541  -2906  -2410       N
ATOM    5973  CA  VAL F 421      11.229  -8.033 -60.118  1.00 74.14           C
ANISOU  5973  CA  VAL F 421     7105  12827   8236   -313  -3351  -2341       C
ATOM    5974  CB  VAL F 421       9.792  -8.485 -60.500  1.00 78.54           C
ANISOU  5974  CB  VAL F 421     7234  13606   9001   -421  -3660  -2651       C
ATOM    5975  CG1 VAL F 421       8.878  -7.313 -60.807  1.00 82.04           C
ANISOU  5975  CG1 VAL F 421     7378  14217   9575   -122  -4060  -2593       C
ATOM    5976  CG2 VAL F 421       9.832  -9.491 -61.650  1.00 80.93           C
ANISOU  5976  CG2 VAL F 421     7719  14022   9009   -611  -3856  -2839       C
ATOM    5977  C   VAL F 421      11.256  -6.621 -59.499  1.00 73.25           C
ANISOU  5977  C   VAL F 421     6923  12642   8268    -29  -3339  -2091       C
ATOM    5978  O   VAL F 421      11.324  -6.490 -58.270  1.00 71.13           O
ANISOU  5978  O   VAL F 421     6541  12226   8260    -56  -3019  -2067       O
ATOM    5979  N   ASN F 422      11.235  -5.578 -60.335  1.00 75.33           N
```

FIGURE 18-172

```
ANISOU 5979  N   ASN F 422    7301 12982  8339    236 -3678 -1903       N
ATOM   5980  CA  ASN F 422    11.155  -4.182 -59.848  1.00 75.16        C
ANISOU 5980  CA  ASN F 422    7234 12867  8457    526 -3716 -1678       C
ATOM   5981  CB  ASN F 422    11.971  -3.211 -60.732  1.00 75.42        C
ANISOU 5981  CB  ASN F 422    7709 12848  8099    726 -3890 -1361       C
ATOM   5982  CG  ASN F 422    11.733  -3.403 -62.234  1.00 78.66        C
ANISOU 5982  CG  ASN F 422    8283 13451  8152    754 -4312 -1386       C
ATOM   5983  OD1 ASN F 422    12.644  -3.194 -63.032  1.00 78.39        O
ANISOU 5983  OD1 ASN F 422    8691 13389  7703    758 -4323 -1195       O
ATOM   5984  ND2 ASN F 422    10.515  -3.784 -62.621  1.00 82.48        N
ANISOU 5984  ND2 ASN F 422    8411 14140  8786    763 -4655 -1629       N
ATOM   5985  C   ASN F 422     9.730  -3.647 -59.623  1.00 78.75        C
ANISOU 5985  C   ASN F 422    7196 13446  9279    707 -3985 -1818       C
ATOM   5986  O   ASN F 422     8.770  -4.093 -60.259  1.00 82.55        O
ANISOU 5986  O   ASN F 422    7398 14147  9820    676 -4307 -2041       O
ATOM   5987  N   ASN F 425     7.024  -4.833 -63.856  1.00 98.86        N
ANISOU 5987  N   ASN F 425    9351 16900 11312    750 -5734 -2397       N
ATOM   5988  CA  ASN F 425     7.135  -6.277 -63.620  1.00 97.53        C
ANISOU 5988  CA  ASN F 425    9123 16747 11187    326 -5436 -2676       C
ATOM   5989  CB  ASN F 425     5.828  -6.981 -64.027  1.00102.75        C
ANISOU 5989  CB  ASN F 425    9296 17692 12053    177 -5785 -3064       C
ATOM   5990  CG  ASN F 425     5.624  -8.316 -63.314  1.00102.31        C
ANISOU 5990  CG  ASN F 425    9017 17603 12253   -265 -5400 -3381       C
ATOM   5991  OD1 ASN F 425     5.938  -8.463 -62.125  1.00 99.34        O
ANISOU 5991  OD1 ASN F 425    8595 17029 12122   -377 -4908 -3350       O
ATOM   5992  ND2 ASN F 425     5.084  -9.292 -64.040  1.00106.55        N
ANISOU 5992  ND2 ASN F 425    9446 18321 12716   -527 -5632 -3690       N
ATOM   5993  C   ASN F 425     8.361  -6.918 -64.312  1.00 94.87        C
ANISOU 5993  C   ASN F 425    9373 16317 10355    150 -5275 -2581       C
ATOM   5994  O   ASN F 425     8.342  -8.097 -64.685  1.00 95.60        O
ANISOU 5994  O   ASN F 425    9505 16474 10347   -145 -5240 -2830       O
ATOM   5995  N   GLN F 426     9.430  -6.136 -64.450  1.00 91.71        N
ANISOU 5995  N   GLN F 426    9420 15760  9667    322 -5153 -2238       N
ATOM   5996  CA  GLN F 426    10.599  -6.536 -65.229  1.00 89.89        C
ANISOU 5996  CA  GLN F 426    9732 15477  8946    211 -5027 -2133       C
ATOM   5997  CB  GLN F 426    11.215  -5.312 -65.891  1.00 90.44        C
ANISOU 5997  CB  GLN F 426    10206 15499  8656    478 -5188 -1769      C
ATOM   5998  CG  GLN F 426    10.299  -4.689 -66.940  1.00 97.68        C
ANISOU 5998  CG  GLN F 426    11101 16610  9404    704 -5808 -1744      C
ATOM   5999  CD  GLN F 426    10.355  -3.172 -66.960  1.00 99.86        C
ANISOU 5999  CD  GLN F 426    11537 16771  9635   1056 -5984 -1390      C
ATOM   6000  OE1 GLN F 426    10.705  -2.530 -65.963  1.00 97.48        O
ANISOU 6000  OE1 GLN F 426    11179 16268  9590   1145 -5681 -1230      O
ATOM   6001  NE2 GLN F 426     9.997  -2.588 -68.101  1.00105.16        N
ANISOU 6001  NE2 GLN F 426    12440 17552  9963   1259 -6492 -1268      N
ATOM   6002  C   GLN F 426    11.620  -7.231 -64.357  1.00 84.44        C
ANISOU 6002  C   GLN F 426    9182 14578  8323      4 -4459 -2135       C
ATOM   6003  O   GLN F 426    11.740  -6.912 -63.176  1.00 81.85        O
ANISOU 6003  O   GLN F 426    8691 14096  8313     37 -4164 -2056       O
ATOM   6004  N   ARG F 427    12.359  -8.169 -64.948  1.00 83.25        N
ANISOU 6004  N   ARG F 427    9349 14421  7862   -189 -4319 -2232       N
ATOM   6005  CA  ARG F 427    13.309  -9.025 -64.224  1.00 78.32        C
ANISOU 6005  CA  ARG F 427    8863 13606  7291   -373 -3826 -2279       C
ATOM   6006  CB  ARG F 427    13.485 -10.355 -64.972  1.00 80.10        C
ANISOU 6006  CB  ARG F 427    9276 13874  7285   -608 -3811 -2550       C
ATOM   6007  CG  ARG F 427    14.098 -11.462 -64.139  1.00 76.56        C
ANISOU 6007  CG  ARG F 427    8883 13214  6993   -803 -3370 -2682       C
ATOM   6008  CD  ARG F 427    14.519 -12.666 -64.971  1.00 77.87        C
ANISOU 6008  CD  ARG F 427    9339 13376  6870   -982 -3325 -2916       C
ATOM   6009  NE  ARG F 427    15.694 -13.289 -64.368  1.00 73.46        N
ANISOU 6009  NE  ARG F 427    9005 12591  6315  -1013 -2884 -2889       N
ATOM   6010  CZ  ARG F 427    15.669 -14.203 -63.397  1.00 71.27        C
ANISOU 6010  CZ  ARG F 427    8652 12105  6323  -1165 -2616 -3026       C
ATOM   6011  NH1 ARG F 427    14.518 -14.649 -62.913  1.00 72.31        N
ANISOU 6011  NH1 ARG F 427    8487 12227  6763  -1350 -2697 -3217       N
ATOM   6012  NH2 ARG F 427    16.809 -14.675 -62.908  1.00 67.90        N
ANISOU 6012  NH2 ARG F 427    8452 11478  5871  -1132 -2266 -2974       N
ATOM   6013  C   ARG F 427    14.672  -8.348 -64.009  1.00 74.70        C
ANISOU 6013  C   ARG F 427    8734 13001  6647   -251 -3533 -1973       C
ATOM   6014  O   ARG F 427    15.300  -7.904 -64.973  1.00 75.87        O
ANISOU 6014  O   ARG F 427    9220 13212  6395   -172 -3625 -1821       O
```

FIGURE 18-173

```
ATOM   6015  N   LEU F 428      15.131  -8.282 -62.758  1.00 70.08           N
ANISOU 6015  N   LEU F 428    8058 12231  6337   -257  -3177  -1893          N
ATOM   6016  CA  LEU F 428      16.419  -7.647 -62.441  1.00 66.81           C
ANISOU 6016  CA  LEU F 428    7899 11689  5796   -165  -2899  -1630          C
ATOM   6017  CB  LEU F 428      16.562  -7.399 -60.921  1.00 63.57           C
ANISOU 6017  CB  LEU F 428    7303 11097  5755   -149  -2609  -1557          C
ATOM   6018  CG  LEU F 428      15.516  -6.574 -60.147  1.00 63.89           C
ANISOU 6018  CG  LEU F 428    7011 11121  6144    -34  -2730  -1518          C
ATOM   6019  CD1 LEU F 428      15.697  -6.733 -58.634  1.00 62.28           C
ANISOU 6019  CD1 LEU F 428    6672 10736  6257    -96  -2381  -1524          C
ATOM   6020  CD2 LEU F 428      15.535  -5.103 -60.527  1.00 64.62           C
ANISOU 6020  CD2 LEU F 428    7197 11227  6130    203  -2935  -1253          C
ATOM   6021  C   LEU F 428      17.636  -8.433 -62.980  1.00 65.60           C
ANISOU 6021  C   LEU F 428    8076 11517  5330   -268  -2664  -1675          C
ATOM   6022  O   LEU F 428      17.516  -9.608 -63.330  1.00 66.61           O
ANISOU 6022  O   LEU F 428    8239 11668  5402   -417  -2648  -1925          O
ATOM   6023  N   ASN F 429      18.796  -7.770 -63.056  1.00 63.59           N
ANISOU 6023  N   ASN F 429    8056 11222  4884   -191  -2477  -1450          N
ATOM   6024  CA  ASN F 429      20.054  -8.420 -63.463  1.00 62.44           C
ANISOU 6024  CA  ASN F 429    8171 11070  4485   -261  -2205  -1496          C
ATOM   6025  CB  ASN F 429      21.027  -7.413 -64.103  1.00 63.01           C
ANISOU 6025  CB  ASN F 429    8510 11197  4233   -193  -2135  -1245          C
ATOM   6026  CG  ASN F 429      21.529  -6.363 -63.128  1.00 60.93           C
ANISOU 6026  CG  ASN F 429    8175 10809  4167   -113  -1976   -998          C
ATOM   6027  OD1 ASN F 429      22.477  -6.593 -62.368  1.00 58.51           O
ANISOU 6027  OD1 ASN F 429    7839 10412  3980   -137  -1668   -990          O
ATOM   6028  ND2 ASN F 429      20.914  -5.187 -63.169  1.00 62.71           N
ANISOU 6028  ND2 ASN F 429    8387 11023  4418     -6  -2203   -799          N
ATOM   6029  C   ASN F 429      20.718  -9.203 -62.314  1.00 58.73           C
ANISOU 6029  C   ASN F 429    7615 10428  4271   -309  -1860  -1579          C
ATOM   6030  O   ASN F 429      20.508  -8.869 -61.159  1.00 56.33           O
ANISOU 6030  O   ASN F 429    7122 10004  4278   -277  -1781  -1501          O
ATOM   6031  N   PRO F 430      21.502 -10.253 -62.639  1.00 58.55           N
ANISOU 6031  N   PRO F 430    7752 10388  4107   -370  -1665  -1747          N
ATOM   6032  CA  PRO F 430      22.103 -11.214 -61.701  1.00 56.25           C
ANISOU 6032  CA  PRO F 430    7432  9919  4022   -392  -1387  -1860          C
ATOM   6033  CB  PRO F 430      23.143 -11.919 -62.569  1.00 57.92           C
ANISOU 6033  CB  PRO F 430    7882 10184  3943   -387  -1225  -1989          C
ATOM   6034  CG  PRO F 430      22.512 -11.934 -63.934  1.00 61.22           C
ANISOU 6034  CG  PRO F 430    8436 10778  4048   -454  -1472  -2086          C
ATOM   6035  CD  PRO F 430      21.832 -10.598 -64.041  1.00 61.60           C
ANISOU 6035  CD  PRO F 430    8395 10925  4087   -406  -1721  -1851          C
ATOM   6036  C   PRO F 430      22.770 -10.649 -60.433  1.00 53.25           C
ANISOU 6036  C   PRO F 430    6949  9412  3872   -310  -1184  -1672          C
ATOM   6037  O   PRO F 430      22.727 -11.279 -59.364  1.00 51.32           O
ANISOU 6037  O   PRO F 430    6623  8994  3881   -331  -1058  -1737          O
ATOM   6038  N   MSE F 431      23.393  -9.482 -60.550  1.00 52.56           N
ANISOU 6038  N   MSE F 431    6896  9398  3678   -235  -1153  -1444          N
ATOM   6039  CA  MSE F 431      24.056  -8.867 -59.414  1.00 49.48           C
ANISOU 6039  CA  MSE F 431    6418  8904  3479   -176   -983  -1278          C
ATOM   6040  CB  MSE F 431      25.096  -7.852 -59.885  1.00 49.34           C
ANISOU 6040  CB  MSE F 431    6508  8987  3253   -144   -888  -1088          C
ATOM   6041  CG  MSE F 431      26.338  -8.505 -60.487  1.00 49.79           C
ANISOU 6041  CG  MSE F 431    6683  9129  3106   -146   -670  -1196          C
ATOM   6042 SE   MSE F 431      27.421  -9.500 -59.208  0.90 48.52          SE
ANISOU 6042 SE   MSE F 431    6408  8820  3206    -65   -407  -1314         SE
ATOM   6043  CE  MSE F 431      28.095  -8.003 -58.164  1.00 42.60           C
ANISOU 6043  CE  MSE F 431    5533  8047  2607    -51   -331  -1034          C
ATOM   6044  C   MSE F 431      23.033  -8.245 -58.467  1.00 48.53           C
ANISOU 6044  C   MSE F 431    6111  8689  3637   -167  -1099  -1191          C
ATOM   6045  O   MSE F 431      23.151  -8.389 -57.249  1.00 46.67           O
ANISOU 6045  O   MSE F 431    5784  8310  3637   -162   -966  -1179          O
ATOM   6046  N   HIS F 432      22.022  -7.577 -59.025  1.00 50.21           N
ANISOU 6046  N   HIS F 432    6275  8987  3817   -152  -1351  -1142          N
ATOM   6047  CA  HIS F 432      20.939  -6.996 -58.216  1.00 50.13           C
ANISOU 6047  CA  HIS F 432    6049  8909  4088   -120  -1466  -1100          C
ATOM   6048  CB  HIS F 432      20.214  -5.876 -58.970  1.00 52.12           C
ANISOU 6048  CB  HIS F 432    6294  9261  4248    -24  -1753   -971          C
ATOM   6049  CG  HIS F 432      21.028  -4.628 -59.064  1.00 53.16           C
ANISOU 6049  CG  HIS F 432    6589  9363  4245     57  -1703   -709          C
ATOM   6050  ND1 HIS F 432      21.765  -4.303 -60.183  1.00 56.08           N
```

FIGURE 18-174

```
ANISOU 6050  ND1 HIS F 432     7218   9830   4259     47  -1719   -603         N
ATOM   6051  CE1 HIS F 432     22.416  -3.175 -59.964 1.00 55.82               C
ANISOU 6051  CE1 HIS F 432     7296   9724   4188     81  -1633   -377         C
ATOM   6052  NE2 HIS F 432     22.146  -2.768 -58.736 1.00 53.78               N
ANISOU 6052  NE2 HIS F 432     6864   9325   4245    128  -1574   -342         N
ATOM   6053  CD2 HIS F 432     21.287  -3.664 -58.149 1.00 52.46               C
ANISOU 6053  CD2 HIS F 432     6466   9146   4318    116  -1604   -545         C
ATOM   6054  C   HIS F 432     19.976  -8.044 -57.680 1.00 50.25               C
ANISOU 6054  C   HIS F 432     5890   8868   4334   -223  -1472  -1325         C
ATOM   6055  O   HIS F 432     19.291  -7.825 -56.678 1.00 49.54               O
ANISOU 6055  O   HIS F 432     5610   8692   4520   -230  -1440  -1330         O
ATOM   6056  N   GLN F 433     19.961  -9.185 -58.363 1.00 51.26               N
ANISOU 6056  N   GLN F 433     6103   9036   4336   -321  -1489  -1523         N
ATOM   6057  CA  GLN F 433     19.267 -10.386 -57.940 1.00 51.44               C
ANISOU 6057  CA  GLN F 433     6036   8972   4537   -471  -1445  -1757         C
ATOM   6058  CB  GLN F 433     19.368 -11.415 -59.072 1.00 53.59               C
ANISOU 6058  CB  GLN F 433     6472   9312   4577   -558  -1515  -1959         C
ATOM   6059  CG  GLN F 433     18.243 -12.401 -59.174 1.00 56.54               C
ANISOU 6059  CG  GLN F 433     6733   9673   5078   -746  -1618  -2223         C
ATOM   6060  CD  GLN F 433     16.932 -11.816 -59.689 1.00 59.82               C
ANISOU 6060  CD  GLN F 433     6898  10278   5554   -765  -1945  -2270         C
ATOM   6061  OE1 GLN F 433     15.859 -12.218 -59.245 1.00 61.27               O
ANISOU 6061  OE1 GLN F 433     6840  10449   5990   -910  -1990  -2434         O
ATOM   6062  NE2 GLN F 433     17.012 -10.890 -60.639 1.00 62.13               N
ANISOU 6062  NE2 GLN F 433     7249  10744   5612   -622  -2176  -2135         N
ATOM   6063  C   GLN F 433     19.878 -10.921 -56.630 1.00 48.94               C
ANISOU 6063  C   GLN F 433     5764   8437   4393   -497  -1154  -1743         C
ATOM   6064  O   GLN F 433     19.161 -11.164 -55.657 1.00 48.75               O
ANISOU 6064  O   GLN F 433     5604   8301   4617   -588  -1080  -1799         O
ATOM   6065  N   LEU F 434     21.204 -11.080 -56.605 1.00 47.33               N
ANISOU 6065  N   LEU F 434     5750   8183   4051   -415   -991  -1671         N
ATOM   6066  CA  LEU F 434     21.915 -11.611 -55.435 1.00 45.33               C
ANISOU 6066  CA  LEU F 434     5572   7729   3923   -399   -763  -1651         C
ATOM   6067  CB  LEU F 434     23.375 -11.926 -55.764 1.00 44.35               C
ANISOU 6067  CB  LEU F 434     5621   7609   3622   -286   -638  -1633         C
ATOM   6068  CG  LEU F 434     23.737 -13.106 -56.671 1.00 46.26               C
ANISOU 6068  CG  LEU F 434     6031   7847   3701   -298   -613  -1839         C
ATOM   6069  CD1 LEU F 434     25.048 -12.834 -57.429 1.00 45.03               C
ANISOU 6069  CD1 LEU F 434     5961   7831   3320   -170   -529  -1797         C
ATOM   6070  CD2 LEU F 434     23.811 -14.406 -55.887 1.00 45.64               C
ANISOU 6070  CD2 LEU F 434     6075   7510   3756   -328   -486  -1973         C
ATOM   6071  C   LEU F 434     21.877 -10.621 -54.289 1.00 43.61               C
ANISOU 6071  C   LEU F 434     5240   7453   3875   -350   -703  -1470         C
ATOM   6072  O   LEU F 434     21.795 -11.014 -53.136 1.00 42.36               O
ANISOU 6072  O   LEU F 434     5094   7124   3877   -394   -569  -1478         O
ATOM   6073  N   LEU F 435     21.949  -9.337 -54.633 1.00 43.83               N
ANISOU 6073  N   LEU F 435     5202   7609   3845   -265   -801  -1307         N
ATOM   6074  CA  LEU F 435     21.877  -8.246 -53.682 1.00 42.80               C
ANISOU 6074  CA  LEU F 435     4980   7425   3858   -212   -765  -1145         C
ATOM   6075  CB  LEU F 435     22.151  -6.916 -54.393 1.00 43.44               C
ANISOU 6075  CB  LEU F 435     5072   7627   3806   -118   -883   -969         C
ATOM   6076  CG  LEU F 435     22.046  -5.590 -53.631 1.00 43.35               C
ANISOU 6076  CG  LEU F 435     4998   7552   3919    -51   -879   -798         C
ATOM   6077  CD1 LEU F 435     23.280  -5.323 -52.808 1.00 40.78               C
ANISOU 6077  CD1 LEU F 435     4764   7145   3587    -39   -699   -695         C
ATOM   6078  CD2 LEU F 435     21.811  -4.465 -54.623 1.00 46.94               C
ANISOU 6078  CD2 LEU F 435     5485   8107   4244     28  -1070   -665         C
ATOM   6079  C   LEU F 435     20.548  -8.204 -52.917 1.00 43.61               C
ANISOU 6079  C   LEU F 435     4899   7464   4207   -283   -781  -1217         C
ATOM   6080  O   LEU F 435     20.564  -8.107 -51.684 1.00 43.27               O
ANISOU 6080  O   LEU F 435     4845   7285   4311   -301   -630  -1181         O
ATOM   6081  N   ARG F 436     19.419  -8.281 -53.628 1.00 45.19               N
ANISOU 6081  N   ARG F 436     4950   7774   4447   -327   -958  -1331         N
ATOM   6082  CA  ARG F 436     18.092  -8.308 -52.997 1.00 46.39               C
ANISOU 6082  CA  ARG F 436     4861   7907   4858   -409   -963  -1447         C
ATOM   6083  CB  ARG F 436     16.958  -8.209 -54.025 1.00 49.83               C
ANISOU 6083  CB  ARG F 436     5092   8525   5315   -416  -1236  -1567         C
ATOM   6084  CG  ARG F 436     16.930  -6.953 -54.854 1.00 52.80               C
ANISOU 6084  CG  ARG F 436     5452   9031   5579   -222  -1482  -1411         C
ATOM   6085  CD  ARG F 436     16.008  -5.894 -54.293 1.00 58.94               C
ANISOU 6085  CD  ARG F 436     5980   9814   6599   -104  -1555  -1371         C
```

FIGURE 18-175

```
ATOM   6086  NE  ARG F 436      15.996  -4.730 -55.183  1.00 65.22           N
ANISOU 6086  NE  ARG F 436     6825  10696   7261    100  -1823  -1207       N
ATOM   6087  CZ  ARG F 436      16.971  -3.816 -55.263  1.00 66.83           C
ANISOU 6087  CZ  ARG F 436     7266  10826   7300    211  -1789   -971       C
ATOM   6088  NH1 ARG F 436      18.065  -3.900 -54.498  1.00 64.44           N
ANISOU 6088  NH1 ARG F 436     7128  10393   6962    150  -1516   -886       N
ATOM   6089  NH2 ARG F 436      16.854  -2.803 -56.124  1.00 69.94           N
ANISOU 6089  NH2 ARG F 436     7744  11271   7558    377  -2041   -820       N
ATOM   6090  C   ARG F 436      17.859  -9.557 -52.166  1.00 45.64           C
ANISOU 6090  C   ARG F 436     4800   7659   4881   -598   -758  -1602       C
ATOM   6091  O   ARG F 436      17.216  -9.476 -51.121  1.00 45.62           O
ANISOU 6091  O   ARG F 436     4679   7574   5082   -674   -619  -1635       O
ATOM   6092  N   HIS F 437      18.342 -10.706 -52.646  1.00 45.31           N
ANISOU 6092  N   HIS F 437     4943   7568   4705   -678   -729  -1703       N
ATOM   6093  CA  HIS F 437      18.235 -11.973 -51.907  1.00 45.24           C
ANISOU 6093  CA  HIS F 437     5056   7358   4776   -856   -535  -1833       C
ATOM   6094  CB  HIS F 437      18.834 -13.126 -52.703  1.00 45.82           C
ANISOU 6094  CB  HIS F 437     5355   7378   4675   -890   -550  -1948       C
ATOM   6095  CG  HIS F 437      18.890 -14.416 -51.941  1.00 46.87           C
ANISOU 6095  CG  HIS F 437     5698   7245   4866  -1039   -355  -2050       C
ATOM   6096  ND1 HIS F 437      17.806 -15.262 -51.828  1.00 50.23           N
ANISOU 6096  ND1 HIS F 437     6073   7589   5423  -1302   -309  -2247       N
ATOM   6097  CE1 HIS F 437      18.145 -16.317 -51.107  1.00 49.92           C
ANISOU 6097  CE1 HIS F 437     6317   7264   5387  -1394   -120  -2277       C
ATOM   6098  NE2 HIS F 437      19.407 -16.186 -50.746  1.00 46.92           N
ANISOU 6098  NE2 HIS F 437     6143   6795   4890  -1170    -71  -2113       N
ATOM   6099  CD2 HIS F 437      19.897 -15.006 -51.253  1.00 45.46           C
ANISOU 6099  CD2 HIS F 437     5796   6848   4628   -964   -203  -1979       C
ATOM   6100  C   HIS F 437      18.888 -11.907 -50.513  1.00 43.18           C
ANISOU 6100  C   HIS F 437     4945   6899   4562   -822   -311  -1700       C
ATOM   6101  O   HIS F 437      18.278 -12.279 -49.506  1.00 43.17           O
ANISOU 6101  O   HIS F 437     4939   6759   4706   -972   -145  -1753       O
ATOM   6102  N   PHE F 438      20.125 -11.420 -50.468  1.00 41.26           N
ANISOU 6102  N   PHE F 438     4837   6655   4185   -641   -309  -1536       N
ATOM   6103  CA  PHE F 438      20.852 -11.273 -49.206  1.00 39.83           C
ANISOU 6103  CA  PHE F 438     4798   6315   4020   -587   -153  -1408       C
ATOM   6104  CB  PHE F 438      22.361 -11.316 -49.455  1.00 37.85           C
ANISOU 6104  CB  PHE F 438     4709   6069   3602   -417   -169  -1313       C
ATOM   6105  CG  PHE F 438      22.829 -12.660 -49.947  1.00 39.60           C
ANISOU 6105  CG  PHE F 438     5116   6198   3733   -418   -151  -1439       C
ATOM   6106  CD1 PHE F 438      22.572 -13.808 -49.195  1.00 40.19           C
ANISOU 6106  CD1 PHE F 438     5380   6026   3864   -522    -35  -1520       C
ATOM   6107  CE1 PHE F 438      22.977 -15.070 -49.651  1.00 41.92           C
ANISOU 6107  CE1 PHE F 438     5806   6113   4007   -509    -21  -1646       C
ATOM   6108  CZ  PHE F 438      23.645 -15.183 -50.862  1.00 41.42           C
ANISOU 6108  CZ  PHE F 438     5733   6193   3811   -388   -107  -1710       C
ATOM   6109  CE2 PHE F 438      23.898 -14.046 -51.625  1.00 40.68           C
ANISOU 6109  CE2 PHE F 438     5446   6370   3640   -307   -203  -1629       C
ATOM   6110  CD2 PHE F 438      23.490 -12.793 -51.171  1.00 37.92           C
ANISOU 6110  CD2 PHE F 438     4917   6123   3367   -324   -234  -1485       C
ATOM   6111  C   PHE F 438      20.402 -10.089 -48.336  1.00 39.74           C
ANISOU 6111  C   PHE F 438     4583   6259   4070   -568   -108  -1305       C
ATOM   6112  O   PHE F 438      20.540 -10.130 -47.106  1.00 39.25           O
ANISOU 6112  O   PHE F 438     4694   6107   4112   -601     45  -1255       O
ATOM   6113  N   GLN F 439      19.858  -9.049 -48.967  1.00 39.55           N
ANISOU 6113  N   GLN F 439     4408   6467   4154   -505   -247  -1277       N
ATOM   6114  CA  GLN F 439      19.215  -7.958 -48.236  1.00 40.07           C
ANISOU 6114  CA  GLN F 439     4319   6538   4370   -476   -210  -1224       C
ATOM   6115  CB  GLN F 439      18.927  -6.776 -49.172  1.00 40.77           C
ANISOU 6115  CB  GLN F 439     4244   6792   4456   -335   -421  -1156       C
ATOM   6116  CG  GLN F 439      20.154  -5.878 -49.485  1.00 38.76           C
ANISOU 6116  CG  GLN F 439     4134   6557   4035   -195   -480   -960       C
ATOM   6117  CD  GLN F 439      19.884  -4.831 -50.591  1.00 40.21           C
ANISOU 6117  CD  GLN F 439     4240   6875   4164    -74   -700   -876       C
ATOM   6118  OE1 GLN F 439      18.910  -4.924 -51.358  1.00 40.53           O
ANISOU 6118  OE1 GLN F 439     4129   7024   4247    -65   -866   -967       O
ATOM   6119  NE2 GLN F 439      20.765  -3.840 -50.676  1.00 38.72           N
ANISOU 6119  NE2 GLN F 439     4173   6671   3869     12   -714   -700       N
ATOM   6120  C   GLN F 439      17.937  -8.415 -47.506  1.00 41.99           C
ANISOU 6120  C   GLN F 439     4418   6725   4813   -648    -69  -1382       C
ATOM   6121  O   GLN F 439      17.606  -7.892 -46.434  1.00 42.49           O
```

FIGURE 18-176

```
ANISOU 6121  O   GLN F 439     4446   6713   4984   -664     82  -1362        O
ATOM   6122  N   LYS F 440     17.235  -9.393 -48.079  1.00 43.71             N
ANISOU 6122  N   LYS F 440     4556   6978   5073   -798    -100  -1554       N
ATOM   6123  CA  LYS F 440     16.025  -9.948 -47.471  1.00 45.70             C
ANISOU 6123  CA  LYS F 440     4653   7190   5520  -1019     59  -1732        C
ATOM   6124  CB  LYS F 440     15.193 -10.701 -48.516  1.00 47.97             C
ANISOU 6124  CB  LYS F 440     4765   7600   5862  -1159    -81  -1933        C
ATOM   6125  CG  LYS F 440     13.730 -10.810 -48.165  1.00 52.65             C
ANISOU 6125  CG  LYS F 440     5024   8266   6716  -1355     10  -2138        C
ATOM   6126  CD  LYS F 440     13.005 -11.813 -49.037  1.00 57.78             C
ANISOU 6126  CD  LYS F 440     5548   8998   7410  -1567    -98  -2366        C
ATOM   6127  CE  LYS F 440     11.613 -12.094 -48.466  1.00 63.15             C
ANISOU 6127  CE  LYS F 440     5897   9727   8371  -1834     73  -2594        C
ATOM   6128  NZ  LYS F 440     10.726 -12.860 -49.401  1.00 67.40             N
ANISOU 6128  NZ  LYS F 440     6202  10408   8999  -2047    -88  -2852        N
ATOM   6129  C   LYS F 440     16.343 -10.851 -46.265  1.00 45.04             C
ANISOU 6129  C   LYS F 440     4857   6858   5399  -1184    337  -1726        C
ATOM   6130  O   LYS F 440     15.665 -10.779 -45.235  1.00 45.28             O
ANISOU 6130  O   LYS F 440     4834   6818   5553  -1319    556  -1776        O
ATOM   6131  N   ASP F 441     17.363 -11.702 -46.407  1.00 44.15             N
ANISOU 6131  N   ASP F 441     5059   6609   5107  -1164    329  -1670        N
ATOM   6132  CA  ASP F 441     17.851 -12.542 -45.301  1.00 44.37             C
ANISOU 6132  CA  ASP F 441     5434   6370   5057  -1258    537  -1623        C
ATOM   6133  CB  ASP F 441     17.083 -13.877 -45.220  1.00 47.39             C
ANISOU 6133  CB  ASP F 441     5912   6599   5494  -1550    681  -1796        C
ATOM   6134  CG  ASP F 441     17.580 -14.785 -44.081  1.00 49.62             C
ANISOU 6134  CG  ASP F 441     6630   6558   5663  -1643    885  -1723        C
ATOM   6135  OD1 ASP F 441     17.900 -14.261 -42.985  1.00 47.18             O
ANISOU 6135  OD1 ASP F 441     6449   6174   5305  -1586    997  -1590        O
ATOM   6136  OD2 ASP F 441     17.647 -16.033 -44.294  1.00 53.67             O
ANISOU 6136  OD2 ASP F 441     7391   6878   6124  -1769    920  -1801        O
ATOM   6137  C   ASP F 441     19.354 -12.779 -45.422  1.00 42.20             C
ANISOU 6137  C   ASP F 441     5438   6011   4585  -1054    445  -1484        C
ATOM   6138  O   ASP F 441     19.809 -13.476 -46.344  1.00 42.70             O
ANISOU 6138  O   ASP F 441     5580   6080   4565  -1008    336  -1539        O
ATOM   6139  N   ALA F 442     20.119 -12.200 -44.490  1.00 39.94             N
ANISOU 6139  N   ALA F 442     5287   5659   4228   -932    490  -1327        N
ATOM   6140  CA  ALA F 442     21.587 -12.254 -44.552  1.00 37.88             C
ANISOU 6140  CA  ALA F 442     5212   5367   3812   -718    385  -1206        C
ATOM   6141  CB  ALA F 442     22.194 -10.935 -44.070  1.00 35.76             C
ANISOU 6141  CB  ALA F 442     4870   5197   3522   -576    341  -1061        C
ATOM   6142  C   ALA F 442     22.206 -13.431 -43.786  1.00 38.27             C
ANISOU 6142  C   ALA F 442     5637   5147   3758   -720    460  -1181        C
ATOM   6143  O   ALA F 442     23.427 -13.627 -43.815  1.00 37.55             O
ANISOU 6143  O   ALA F 442     5683   5026   3559   -521    361  -1107        O
ATOM   6144  N   LYS F 443     21.364 -14.209 -43.117  1.00 39.15             N
ANISOU 6144  N   LYS F 443     5911   5060   3903   -941    634  -1246        N
ATOM   6145  CA  LYS F 443     21.830 -15.168 -42.119  1.00 40.19             C
ANISOU 6145  CA  LYS F 443     6467   4887   3916   -956    722  -1181        C
ATOM   6146  CB  LYS F 443     20.647 -15.777 -41.368  1.00 42.67             C
ANISOU 6146  CB  LYS F 443     6926   5010   4276  -1279    972  -1253        C
ATOM   6147  CG  LYS F 443     20.361 -15.115 -40.038  1.00 42.60             C
ANISOU 6147  CG  LYS F 443     7000   4958   4230  -1361   1138  -1163        C
ATOM   6148  CD  LYS F 443     19.175 -15.766 -39.380  1.00 45.79             C
ANISOU 6148  CD  LYS F 443     7535   5190   4676  -1716   1431  -1256        C
ATOM   6149  CE  LYS F 443     17.886 -15.276 -40.009  1.00 47.38             C
ANISOU 6149  CE  LYS F 443     7261   5629   5111  -1902   1514  -1439        C
ATOM   6150  NZ  LYS F 443     17.018 -16.416 -40.328  1.00 51.45             N
ANISOU 6150  NZ  LYS F 443     7824   6016   5707  -2211   1655  -1602        N
ATOM   6151  C   LYS F 443     22.727 -16.272 -42.669  1.00 40.29             C
ANISOU 6151  C   LYS F 443     6714   4754   3841   -804    609  -1201        C
ATOM   6152  O   LYS F 443     23.776 -16.559 -42.095  1.00 39.70             O
ANISOU 6152  O   LYS F 443     6892   4543   3650   -607    536  -1092        O
ATOM   6153  N   VAL F 444     22.306 -16.894 -43.771  1.00 40.93             N
ANISOU 6153  N   VAL F 444     6708   4865   3980   -884    583  -1356        N
ATOM   6154  CA  VAL F 444     23.106 -17.948 -44.424  1.00 41.02             C
ANISOU 6154  CA  VAL F 444     6929   4738   3917   -730    491  -1416        C
ATOM   6155  CB  VAL F 444     22.315 -18.633 -45.563  1.00 42.70             C
ANISOU 6155  CB  VAL F 444     7062   4969   4193   -911    498  -1626        C
ATOM   6156  CG1 VAL F 444     23.094 -19.832 -46.148  1.00 43.29             C
ANISOU 6156  CG1 VAL F 444     7417   4842   4187   -760    438  -1715        C
```

FIGURE 18-177

```
ATOM   6157 CG2 VAL F 444      20.936 -19.073 -45.051  1.00 44.72           C
ANISOU 6157 CG2 VAL F 444    7368   5079   4545   -1289    687  -1713       C
ATOM   6158 C   VAL F 444      24.422 -17.346 -44.942  1.00 38.71           C
ANISOU 6158 C   VAL F 444    6494   4651   3563    -400    317  -1349       C
ATOM   6159 O   VAL F 444      25.494 -17.944 -44.813  1.00 39.03           O
ANISOU 6159 O   VAL F 444    6739   4560   3529    -169    245  -1320       O
ATOM   6160 N   LEU F 445      24.333 -16.142 -45.489  1.00 36.36           N
ANISOU 6160 N   LEU F 445    5845   4667   3303    -380    255  -1326       N
ATOM   6161 CA  LEU F 445      25.508 -15.420 -45.967  1.00 34.90           C
ANISOU 6161 CA  LEU F 445    5500   4697   3063    -133    131  -1260       C
ATOM   6162 CB  LEU F 445      25.098 -14.069 -46.554  1.00 32.55           C
ANISOU 6162 CB  LEU F 445    4867   4693   2805    -184     89  -1227       C
ATOM   6163 CG  LEU F 445      26.226 -13.137 -46.999  1.00 31.63           C
ANISOU 6163 CG  LEU F 445    4587   4801   2630       0     -2  -1143       C
ATOM   6164 CD1 LEU F 445      26.905 -13.645 -48.265  1.00 30.39           C
ANISOU 6164 CD1 LEU F 445    4401   4755   2391     115    -50  -1248       C
ATOM   6165 CD2 LEU F 445      25.692 -11.704 -47.173  1.00 30.43           C
ANISOU 6165 CD2 LEU F 445    4199   4843   2521     -73    -28  -1062       C
ATOM   6166 C   LEU F 445      26.542 -15.233 -44.853  1.00 35.09           C
ANISOU 6166 C   LEU F 445    5661   4635   3035      44     94  -1119       C
ATOM   6167 O   LEU F 445      27.710 -15.627 -44.999  1.00 35.50           O
ANISOU 6167 O   LEU F 445    5772   4680   3036     277      8  -1121       O
ATOM   6168 N   PHE F 446      26.090 -14.642 -43.743  1.00 35.06           N
ANISOU 6168 N   PHE F 446    5700   4578   3045     -65    157  -1016       N
ATOM   6169 CA  PHE F 446      26.937 -14.316 -42.610  1.00 35.44           C
ANISOU 6169 CA  PHE F 446    5879   4565   3023      66    102   -884       C
ATOM   6170 CB  PHE F 446      26.155 -13.442 -41.604  1.00 33.86           C
ANISOU 6170 CB  PHE F 446    5673   4356   2836    -109    206   -808       C
ATOM   6171 CG  PHE F 446      26.103 -11.980 -41.978  1.00 30.18           C
ANISOU 6171 CG  PHE F 446    4878   4157   2434    -115    174   -779       C
ATOM   6172 CD1 PHE F 446      26.572 -11.539 -43.229  1.00 28.69           C
ANISOU 6172 CD1 PHE F 446    4433   4194   2273     -20     77   -809       C
ATOM   6173 CE1 PHE F 446      26.527 -10.181 -43.583  1.00 26.71           C
ANISOU 6173 CE1 PHE F 446    3939   4146   2063     -34     47   -761       C
ATOM   6174 CZ  PHE F 446      25.987  -9.247 -42.674  1.00 27.01           C
ANISOU 6174 CZ  PHE F 446    3967   4156   2138    -123    111   -702       C
ATOM   6175 CE2 PHE F 446      25.498  -9.688 -41.439  1.00 24.47           C
ANISOU 6175 CE2 PHE F 446    3871   3634   1792    -215    223   -696       C
ATOM   6176 CD2 PHE F 446      25.556 -11.045 -41.101  1.00 28.12           C
ANISOU 6176 CD2 PHE F 446    4595   3899   2192    -223    257   -724       C
ATOM   6177 C   PHE F 446      27.501 -15.562 -41.943  1.00 38.56           C
ANISOU 6177 C   PHE F 446    6654   4667   3332     191     66   -864       C
ATOM   6178 O   PHE F 446      28.671 -15.593 -41.562  1.00 39.82           O
ANISOU 6178 O   PHE F 446    6870   4828   3433     430    -77   -804       O
ATOM   6179 N   GLN F 447      26.677 -16.596 -41.820  1.00 41.56           N
ANISOU 6179 N   GLN F 447    7294   4789   3708      31    185   -921       N
ATOM   6180 CA  GLN F 447      27.057 -17.775 -41.044  1.00 45.64           C
ANISOU 6180 CA  GLN F 447    8264   4954   4124     121    165   -873       C
ATOM   6181 CB  GLN F 447      25.815 -18.492 -40.478  1.00 47.48           C
ANISOU 6181 CB  GLN F 447    8800   4901   4339    -200    378   -890       C
ATOM   6182 CG  GLN F 447      25.073 -17.727 -39.352  1.00 48.48           C
ANISOU 6182 CG  GLN F 447    8957   5035   4427    -424    529   -798       C
ATOM   6183 CD  GLN F 447      23.680 -18.313 -39.041  1.00 50.68           C
ANISOU 6183 CD  GLN F 447    9403   5119   4735    -807    800   -867       C
ATOM   6184 OE1 GLN F 447      23.423 -19.504 -39.267  1.00 54.85           O
ANISOU 6184 OE1 GLN F 447   10205   5382   5253    -905    862   -931       O
ATOM   6185 NE2 GLN F 447      22.781 -17.469 -38.526  1.00 51.31           N
ANISOU 6185 NE2 GLN F 447    9309   5325   4860   -1031    975   -872       N
ATOM   6186 C   GLN F 447      27.949 -18.752 -41.824  1.00 47.16           C
ANISOU 6186 C   GLN F 447    8540   5061   4318     384     43   -961       C
ATOM   6187 O   GLN F 447      28.431 -19.731 -41.252  1.00 49.81           O
ANISOU 6187 O   GLN F 447    9258   5091   4576     537    -19   -919       O
ATOM   6188 N   ASN F 448      28.178 -18.487 -43.112  1.00 46.16           N
ANISOU 6188 N   ASN F 448    8083   5190   4265     451      9  -1083       N
ATOM   6189 CA  ASN F 448      29.028 -19.362 -43.933  1.00 47.96           C
ANISOU 6189 CA  ASN F 448    8359   5368   4497     707    -74  -1202       C
ATOM   6190 CB  ASN F 448      28.210 -20.041 -45.037  1.00 48.76           C
ANISOU 6190 CB  ASN F 448    8474   5419   4635     530     28  -1384       C
ATOM   6191 CG  ASN F 448      27.331 -21.142 -44.506  1.00 51.36           C
ANISOU 6191 CG  ASN F 448    9217   5346   4949     321    138  -1405       C
ATOM   6192 OD1 ASN F 448      27.684 -22.318 -44.583  1.00 56.22           O
```

FIGURE 18-178

```
ANISOU 6192  OD1 ASN F 448    10163   5660   5540    452    119  -1474       O
ATOM   6193  ND2 ASN F 448     26.186 -20.775 -43.948  1.00 51.17            N
ANISOU 6193  ND2 ASN F 448     9191   5303   4948    -10    270  -1356       N
ATOM   6194  C   ASN F 448     30.261 -18.680 -44.526  1.00 47.16            C
ANISOU 6194  C   ASN F 448     7915   5590   4414    975   -193  -1223       C
ATOM   6195  O   ASN F 448     31.074 -19.318 -45.229  1.00 48.80            O
ANISOU 6195  O   ASN F 448     8107   5803   4633   1217   -243  -1344       O
ATOM   6196  N   TRP F 449     30.404 -17.396 -44.214  1.00 44.74            N
ANISOU 6196  N   TRP F 449     7344   5542   4115    923   -220  -1118       N
ATOM   6197  CA  TRP F 449     31.462 -16.558 -44.749  1.00 43.75            C
ANISOU 6197  CA  TRP F 449     6866   5746   4011   1087   -296  -1130       C
ATOM   6198  CB  TRP F 449     31.109 -15.093 -44.514  1.00 40.74            C
ANISOU 6198  CB  TRP F 449     6250   5589   3640    899   -272  -1021       C
ATOM   6199  CG  TRP F 449     32.099 -14.109 -45.064  1.00 39.18            C
ANISOU 6199  CG  TRP F 449     5708   5720   3459    989   -319  -1021       C
ATOM   6200  CD1 TRP F 449     33.122 -13.516 -44.388  1.00 38.41            C
ANISOU 6200  CD1 TRP F 449     5492   5733   3368   1111   -427   -956       C
ATOM   6201  NE1 TRP F 449     33.798 -12.649 -45.215  1.00 37.76            N
ANISOU 6201  NE1 TRP F 449     5082   5959   3306   1105   -405   -988       N
ATOM   6202  CE2 TRP F 449     33.212 -12.668 -46.456  1.00 38.35            C
ANISOU 6202  CE2 TRP F 449     5092   6121   3360    997   -290  -1060       C
ATOM   6203  CD2 TRP F 449     32.132 -13.577 -46.398  1.00 38.04            C
ANISOU 6203  CD2 TRP F 449     5310   5833   3311    927   -251  -1092       C
ATOM   6204  CE3 TRP F 449     31.347 -13.773 -47.545  1.00 37.88            C
ANISOU 6204  CE3 TRP F 449     5272   5859   3262    804   -169  -1181       C
ATOM   6205  CZ3 TRP F 449     31.668 -13.069 -48.703  1.00 37.87            C
ANISOU 6205  CZ3 TRP F 449     5043   6135   3213    771   -130  -1214       C
ATOM   6206  CH2 TRP F 449     32.756 -12.173 -48.731  1.00 37.69            C
ANISOU 6206  CH2 TRP F 449     4797   6336   3188    831   -137  -1165       C
ATOM   6207  CZ2 TRP F 449     33.536 -11.958 -47.622  1.00 37.45            C
ANISOU 6207  CZ2 TRP F 449     4735   6279   3216    935   -216  -1098       C
ATOM   6208  C   TRP F 449     32.844 -16.878 -44.167  1.00 45.96            C
ANISOU 6208  C   TRP F 449     7170   6002   4289   1417   -454  -1113       C
ATOM   6209  O   TRP F 449     33.846 -16.885 -44.895  1.00 46.57            O
ANISOU 6209  O   TRP F 449     7011   6277   4406   1622   -492  -1216       O
ATOM   6210  N   GLY F 450     32.904 -17.119 -42.858  1.00 47.36            N
ANISOU 6210  N   GLY F 450     7622   5957   4416   1470   -550   -991       N
ATOM   6211  CA  GLY F 450     34.169 -17.491 -42.226  1.00 50.09            C
ANISOU 6211  CA  GLY F 450     8014   6263   4756   1812   -756   -972       C
ATOM   6212  C   GLY F 450     34.684 -16.523 -41.180  1.00 49.91            C
ANISOU 6212  C   GLY F 450     7895   6373   4695   1820   -896   -845       C
ATOM   6213  O   GLY F 450     34.711 -15.310 -41.382  1.00 47.96            O
ANISOU 6213  O   GLY F 450     7334   6410   4479   1663   -853   -827       O
ATOM   6214  N   ILE F 451     35.112 -17.089 -40.061  1.00 52.64            N
ANISOU 6214  N   ILE F 451     8549   6492   4958   2009  -1079   -759       N
ATOM   6215  CA  ILE F 451     35.602 -16.346 -38.912  1.00 53.25            C
ANISOU 6215  CA  ILE F 451     8628   6646   4959   2031  -1254   -644       C
ATOM   6216  CB  ILE F 451     35.053 -16.971 -37.603  1.00 54.82            C
ANISOU 6216  CB  ILE F 451     9395   6461   4973   1996  -1306   -493       C
ATOM   6217  CG1 ILE F 451     33.541 -17.196 -37.695  1.00 53.93            C
ANISOU 6217  CG1 ILE F 451     9533   6138   4820   1646  -1016   -464       C
ATOM   6218  CD1 ILE F 451     32.730 -15.935 -37.885  1.00 50.90            C
ANISOU 6218  CD1 ILE F 451     8876   5986   4479   1312   -825   -462       C
ATOM   6219  CG2 ILE F 451     35.374 -16.122 -36.407  1.00 55.21            C
ANISOU 6219  CG2 ILE F 451     9489   6589   4899   1957  -1461   -380       C
ATOM   6220  C   ILE F 451     37.132 -16.370 -38.907  1.00 55.90            C
ANISOU 6220  C   ILE F 451     8691   7179   5368   2392  -1514   -716       C
ATOM   6221  O   ILE F 451     37.752 -17.379 -39.291  1.00 58.65            O
ANISOU 6221  O   ILE F 451     9074   7433   5779   2709  -1607   -809       O
ATOM   6222  N   GLU F 452     37.737 -15.263 -38.480  1.00 55.67            N
ANISOU 6222  N   GLU F 452     8380   7424   5347   2344  -1628   -694       N
ATOM   6223  CA  GLU F 452     39.200 -15.177 -38.353  1.00 58.58            C
ANISOU 6223  CA  GLU F 452     8434   8023   5801   2651  -1892   -778       C
ATOM   6224  CB  GLU F 452     39.802 -14.454 -39.564  1.00 57.37            C
ANISOU 6224  CB  GLU F 452     7708   8270   5820   2597  -1761   -932       C
ATOM   6225  CG  GLU F 452     39.359 -12.995 -39.696  1.00 53.46            C
ANISOU 6225  CG  GLU F 452     7007   7989   5316   2209  -1603   -881       C
ATOM   6226  CD  GLU F 452     40.063 -12.246 -40.809  1.00 54.15            C
ANISOU 6226  CD  GLU F 452     6579   8455   5541   2140  -1483  -1012       C
ATOM   6227  OE1 GLU F 452     40.983 -12.807 -41.443  1.00 57.04            O
ANISOU 6227  OE1 GLU F 452     6687   8967   6017   2391  -1514  -1163       O
```

FIGURE 18-179

```
ATOM    6228  OE2 GLU F 452      39.690 -11.080 -41.056  1.00 52.63           O
ANISOU  6228  OE2 GLU F 452     6251   8404   5340   1830  -1342   -966       O
ATOM    6229  C   GLU F 452      39.607 -14.457 -37.070  1.00 59.73           C
ANISOU  6229  C   GLU F 452     8632   8226   5839   2623  -2130   -681       C
ATOM    6230  O   GLU F 452      38.882 -13.574 -36.594  1.00 57.59           O
ANISOU  6230  O   GLU F 452     8458   7952   5471   2304  -2021   -587       O
ATOM    6231  N   AHIS F 453     40.760 -14.833 -36.519  0.50 63.60           N
ANISOU  6231  N   AHIS F 453    9051   8768   6344   2968  -2465   -719       N
ATOM    6232  N   BHIS F 453     40.754 -14.846 -36.516  0.50 63.68           N
ANISOU  6232  N   BHIS F 453    9067   8774   6353   2970  -2465   -718       N
ATOM    6233  CA  AHIS F 453     41.336 -14.158 -35.351  0.50 65.33           C
ANISOU  6233  CA  AHIS F 453    9270   9092   6462   2971  -2752   -662       C
ATOM    6234  CA  BHIS F 453     41.340 -14.156 -35.367  0.50 65.46           C
ANISOU  6234  CA  BHIS F 453    9280   9111   6481   2971  -2750   -664       C
ATOM    6235  CB  AHIS F 453     42.466 -15.006 -34.739  0.50 70.02           C
ANISOU  6235  CB  AHIS F 453    9906   9644   7055   3446  -3172   -693       C
ATOM    6236  CB  BHIS F 453     42.520 -14.952 -34.789  0.50 70.22           C
ANISOU  6236  CB  BHIS F 453    9888   9698   7095   3444  -3170   -705       C
ATOM    6237  CG  AHIS F 453     42.950 -14.519 -33.405  0.50 71.64           C
ANISOU  6237  CG  AHIS F 453   10237   9889   7094   3472  -3522   -618       C
ATOM    6238  CG  BHIS F 453     42.131 -16.251 -34.150  0.50 72.40           C
ANISOU  6238  CG  BHIS F 453   10795   9514   7199   3687  -3298   -573       C
ATOM    6239  ND1 AHIS F 453     44.132 -13.826 -33.248  0.50 73.20           N
ANISOU  6239  ND1 AHIS F 453    9938  10466   7409   3561  -3786   -748       N
ATOM    6240  ND1 BHIS F 453     41.800 -16.354 -32.815  0.50 73.75           N
ANISOU  6240  ND1 BHIS F 453   11506   9424   7089   3657  -3486   -390       N
ATOM    6241  CE1 AHIS F 453     44.303 -13.532 -31.971  0.50 74.77           C
ANISOU  6241  CE1 AHIS F 453   10403  10611   7394   3557  -4093   -655       C
ATOM    6242  CE1 BHIS F 453     41.511 -17.612 -32.531  0.50 76.18           C
ANISOU  6242  CE1 BHIS F 453   12349   9316   7280   3883  -3551   -290       C
ATOM    6243  NE2 AHIS F 453     43.277 -14.013 -31.292  0.50 73.86           N
ANISOU  6243  NE2 AHIS F 453   10957  10092   7013   3469  -4011   -461       N
ATOM    6244  NE2 BHIS F 453     41.648 -18.329 -33.632  0.50 76.34           N
ANISOU  6244  NE2 BHIS F 453   12183   9314   7510   4069  -3421   -416       N
ATOM    6245  CD2 AHIS F 453     42.418 -14.639 -32.164  0.50 71.98           C
ANISOU  6245  CD2 AHIS F 453   10857   9646   6844   3407  -3652   -438       C
ATOM    6246  CD2 BHIS F 453     42.038 -17.502 -34.658  0.50 73.83           C
ANISOU  6246  CD2 BHIS F 453   11192   9429   7433   3954  -3259   -597       C
ATOM    6247  C   AHIS F 453     41.856 -12.786 -35.785  0.50 64.34           C
ANISOU  6247  C   AHIS F 453    8588   9388   6470   2743  -2688   -765       C
ATOM    6248  C   BHIS F 453     41.815 -12.774 -35.816  0.50 64.27           C
ANISOU  6248  C   BHIS F 453    8581   9378   6462   2731  -2673   -764       C
ATOM    6249  O   AHIS F 453     42.515 -12.669 -36.821  0.50 64.49           O
ANISOU  6249  O   AHIS F 453    8133   9680   6690   2808  -2604   -919       O
ATOM    6250  O   BHIS F 453     42.409 -12.638 -36.887  0.50 64.21           O
ANISOU  6250  O   BHIS F 453    8108   9637   6652   2778  -2569   -914       O
ATOM    6251  N   ILE F 454      41.544 -11.752 -35.009  1.00 63.53           N
ANISOU  6251  N   ILE F 454     8571   9322   6247   2459  -2702   -686       N
ATOM    6252  CA  ILE F 454      41.980 -10.396 -35.349  1.00 63.62           C
ANISOU  6252  CA  ILE F 454     8126   9678   6370   2202  -2634   -772       C
ATOM    6253  CB  ILE F 454      40.800  -9.375 -35.410  1.00 59.86           C
ANISOU  6253  CB  ILE F 454     7791   9130   5822   1781  -2331   -683       C
ATOM    6254  CG1 ILE F 454      40.225  -9.077 -34.026  1.00 59.78           C
ANISOU  6254  CG1 ILE F 454     8229   8907   5579   1656  -2428   -563       C
ATOM    6255  CD1 ILE F 454      38.978  -8.221 -34.069  1.00 56.89           C
ANISOU  6255  CD1 ILE F 454     8015   8437   5162   1302  -2116   -495       C
ATOM    6256  CG2 ILE F 454      39.713  -9.882 -36.346  1.00 57.55           C
ANISOU  6256  CG2 ILE F 454     7631   8673   5561   1711  -2013   -646       C
ATOM    6257  C   ILE F 454      43.171  -9.893 -34.513  1.00 67.95           C
ANISOU  6257  C   ILE F 454     8445  10453   6920   2290  -2997   -844       C
ATOM    6258  O   ILE F 454      43.466 -10.413 -33.431  1.00 70.35           O
ANISOU  6258  O   ILE F 454     9035  10620   7074   2507  -3324   -789       O
ATOM    6259  N   ASP F 455      43.850  -8.885 -35.059  1.00 69.56           N
ANISOU  6259  N   ASP F 455     8140  11002   7287   2108  -2939   -971       N
ATOM    6260  CA  ASP F 455      45.062  -8.311 -34.481  1.00 74.25           C
ANISOU  6260  CA  ASP F 455     8389  11882   7940   2136  -3255  -1090       C
ATOM    6261  CB  ASP F 455      45.985  -7.824 -35.605  1.00 75.13           C
ANISOU  6261  CB  ASP F 455     7842  12386   8318   2063  -3120  -1280       C
ATOM    6262  CG  ASP F 455      46.888  -8.925 -36.144  1.00 78.46           C
ANISOU  6262  CG  ASP F 455     7952  12945   8915   2492  -3242  -1425       C
ATOM    6263  OD1 ASP F 455      47.431  -9.720 -35.339  1.00 82.36           O
```

FIGURE 18-180

```
ANISOU 6263  OD1 ASP F 455      8541  13377   9374   2866  -3625  -1440        O
ATOM   6264  OD2 ASP F 455     47.073  -8.983 -37.376  1.00 77.63              O
ANISOU 6264  OD2 ASP F 455      7515  13007   8974   2469  -2960  -1531        O
ATOM   6265  C   ASP F 455     44.811  -7.167 -33.493  1.00 74.78              C
ANISOU 6265  C   ASP F 455      8634  11930   7848   1812  -3331  -1036        C
ATOM   6266  O   ASP F 455     45.644  -6.915 -32.603  1.00 78.03              O
ANISOU 6266  O   ASP F 455      8955  12477   8215   1872  -3689  -1103        O
ATOM   6267  N   ASN F 456     43.670  -6.484 -33.647  1.00 72.42              N
ANISOU 6267  N   ASN F 456      8584  11465   7468   1486  -3010   -931        N
ATOM   6268  CA  ASN F 456     43.375  -5.246 -32.898  1.00 72.87              C
ANISOU 6268  CA  ASN F 456      8779  11502   7406   1147  -3004   -908        C
ATOM   6269  CB  ASN F 456     43.194  -5.502 -31.383  1.00 74.89              C
ANISOU 6269  CB  ASN F 456      9517  11553   7382   1230  -3287   -830        C
ATOM   6270  CG  ASN F 456     41.742  -5.352 -30.921  1.00 73.35              C
ANISOU 6270  CG  ASN F 456      9857  11028   6986   1044  -3027   -684        C
ATOM   6271  OD1 ASN F 456     40.804  -5.294 -31.734  1.00 71.27              O
ANISOU 6271  OD1 ASN F 456      9614  10661   6803    923  -2671   -632        O
ATOM   6272  ND2 ASN F 456     41.555  -5.287 -29.604  1.00 75.14              N
ANISOU 6272  ND2 ASN F 456     10508  11099   6942   1020  -3208   -632        N
ATOM   6273  C   ASN F 456     44.415  -4.143 -33.156  1.00 74.75              C
ANISOU 6273  C   ASN F 456      8515  12082   7807    933  -3067  -1065        C
ATOM   6274  O   ASN F 456     45.187  -3.760 -32.261  1.00 77.82              O
ANISOU 6274  O   ASN F 456      8830  12596   8142    912  -3384  -1148        O
ATOM   6275  N   VAL F 457     44.445  -3.683 -34.408  1.00 73.51              N
ANISOU 6275  N   VAL F 457      8021  12072   7836    767  -2766  -1110        N
ATOM   6276  CA  VAL F 457     45.134  -2.453 -34.786  1.00 74.40              C
ANISOU 6276  CA  VAL F 457      7745  12439   8083    443  -2695  -1225        C
ATOM   6277  CB  VAL F 457     45.522  -2.397 -36.298  1.00 73.96              C
ANISOU 6277  CB  VAL F 457      7258  12607   8237    380  -2410  -1296        C
ATOM   6278  CG1 VAL F 457     46.942  -2.910 -36.505  1.00 77.90              C
ANISOU 6278  CG1 VAL F 457      7228  13455   8917    586  -2608  -1493        C
ATOM   6279  CG2 VAL F 457     44.528  -3.164 -37.166  1.00 71.21              C
ANISOU 6279  CG2 VAL F 457      7123  12070   7862    520  -2146  -1181        C
ATOM   6280  C   VAL F 457     44.230  -1.295 -34.377  1.00 72.20              C
ANISOU 6280  C   VAL F 457      7797  11953   7683     96  -2535  -1135        C
ATOM   6281  O   VAL F 457     43.123  -1.523 -33.872  1.00 69.99              O
ANISOU 6281  O   VAL F 457      7977  11379   7238    134  -2467  -1004        O
ATOM   6282  N   MSE F 458     44.696  -0.064 -34.577  1.00 73.06              N
ANISOU 6282  N   MSE F 458      7679  12203   7878   -244  -2463  -1216        N
ATOM   6283  CA  MSE F 458     44.062   1.090 -33.940  1.00 72.35              C
ANISOU 6283  CA  MSE F 458      7904  11914   7672   -546  -2395  -1172        C
ATOM   6284  CB  MSE F 458     44.941   2.335 -34.025  1.00 74.88              C
ANISOU 6284  CB  MSE F 458      7928  12422   8101   -907  -2406  -1306        C
ATOM   6285  CG  MSE F 458     44.687   3.283 -32.866  1.00 77.18              C
ANISOU 6285  CG  MSE F 458      8543  12541   8241  -1133  -2523  -1331        C
ATOM   6286 SE   MSE F 458     44.951   5.167 -33.288  0.90 80.31             SE
ANISOU 6286 SE   MSE F 458      8839  12926   8747  -1693  -2306  -1407       SE
ATOM   6287  CE  MSE F 458     45.046   5.835 -31.442  1.00 81.22              C
ANISOU 6287  CE  MSE F 458      9312  12907   8640  -2642  -1526              C
ATOM   6288  C   MSE F 458     42.672   1.407 -34.465  1.00 66.67              C
ANISOU 6288  C   MSE F 458      7502  10919   6910   -636  -2053  -1019        C
ATOM   6289  O   MSE F 458     42.496   1.655 -35.655  1.00 65.37              O
ANISOU 6289  O   MSE F 458      7177  10798   6862   -727  -1796   -981        O
ATOM   6290  N   GLY F 459     41.699   1.395 -33.554  1.00 63.85              N
ANISOU 6290  N   GLY F 459      7594  10290   6378   -606  -2058   -941        N
ATOM   6291  CA  GLY F 459     40.324   1.802 -33.851  1.00 58.57              C
ANISOU 6291  CA  GLY F 459      7217   9360   5679   -691  -1761   -826        C
ATOM   6292  C   GLY F 459     39.477   0.783 -34.594  1.00 54.89              C
ANISOU 6292  C   GLY F 459      6812   8810   5236   -479  -1592   -722        C
ATOM   6293  O   GLY F 459     38.386   1.107 -35.066  1.00 52.95              O
ANISOU 6293  O   GLY F 459      6711   8400   5008   -543  -1352   -643        O
ATOM   6294  N   AMSE F 460    39.968  -0.449 -34.693  0.50 54.86              N
ANISOU 6294  N   AMSE F 460     6699   8908   5236   -220  -1732   -735        N
ATOM   6295  N   BMSE F 460    39.971  -0.452 -34.680  0.50 54.79              N
ANISOU 6295  N   BMSE F 460     6693   8900   5227   -219  -1735   -736        N
ATOM   6296  CA  AMSE F 460    39.261  -1.491 -35.431  0.50 51.87              C
ANISOU 6296  CA  AMSE F 460     6376   8449   4883    -31  -1585   -662        C
ATOM   6297  CA  BMSE F 460    39.302  -1.517 -35.430  0.50 51.83              C
ANISOU 6297  CA  BMSE F 460     6363   8450   4879    -25  -1593   -665        C
ATOM   6298  CB  AMSE F 460    40.169  -2.121 -36.484  0.50 52.65              C
ANISOU 6298  CB  AMSE F 460     6093   8789   5123    111  -1605   -728        C
```

FIGURE 18-181

```
ATOM   6299  CB  BMSE F 460      40.281  -2.170 -36.413  0.50 52.63           C
ANISOU 6299  CB  BMSE F 460    6078   8800   5119    127  -1634   -737        C
ATOM   6300  CG  AMSE F 460      40.769  -1.118 -37.435  0.50 52.90           C
ANISOU 6300  CG  AMSE F 460    5781   9031   5286   -116  -1474   -781        C
ATOM   6301  CG  BMSE F 460      40.942  -1.184 -37.354  0.50 52.67           C
ANISOU 6301  CG  BMSE F 460    5723   9028   5261    -97  -1512   -797        C
ATOM   6302  SE  AMSE F 460      40.983  -1.865 -39.199  0.45 52.53          SE
ANISOU 6302  SE  AMSE F 460    5430   9166   5364      3  -1264   -808       SE
ATOM   6303  SE  BMSE F 460      39.627  -0.349 -38.511  0.45 48.23          SE
ANISOU 6303  SE  BMSE F 460    5294   8313   4718   -315  -1143   -673       SE
ATOM   6304  CE  AMSE F 460      42.271  -0.575 -39.921  0.50 54.18           C
ANISOU 6304  CE  AMSE F 460    5186   9698   5701   -319  -1174   -914        C
ATOM   6305  CE  BMSE F 460      40.149   1.530 -38.358  0.50 49.90           C
ANISOU 6305  CE  BMSE F 460    5422   8568   4968   -714  -1105   -700        C
ATOM   6306  C   AMSE F 460      38.707  -2.567 -34.517  0.50 51.44           C
ANISOU 6306  C   AMSE F 460    6684   8191   4671    169  -1681   -606        C
ATOM   6307  C   BMSE F 460      38.711  -2.576 -34.510  0.50 51.37           C
ANISOU 6307  C   BMSE F 460    6676   8181   4661    171  -1683   -606        C
ATOM   6308  O   AMSE F 460      39.431  -3.139 -33.701  0.50 54.01           O
ANISOU 6308  O   AMSE F 460    7068   8548   4908    330  -1952   -636        O
ATOM   6309  O   BMSE F 460      39.417  -3.146 -33.677  0.50 53.95           O
ANISOU 6309  O   BMSE F 460    7068   8534   4895    330  -1953   -635        O
ATOM   6310  N   VAL  F 461      37.413  -2.830 -34.656  1.00 48.69           N
ANISOU 6310  N   VAL  F 461    6584   7631   4285    151  -1461   -525        N
ATOM   6311  CA  VAL  F 461      36.770  -3.939 -33.955  1.00 47.45           C
ANISOU 6311  CA  VAL  F 461    6786   7259   3984    298  -1478   -464        C
ATOM   6312  CB  VAL  F 461      35.734  -3.470 -32.897  1.00 47.00           C
ANISOU 6312  CB  VAL  F 461    7111   6980   3768    144  -1360   -424        C
ATOM   6313  CG1 VAL  F 461      36.434  -2.715 -31.786  1.00 49.19           C
ANISOU 6313  CG1 VAL  F 461    7483   7296   3912     62  -1566   -471        C
ATOM   6314  CG2 VAL  F 461      34.645  -2.627 -33.519  1.00 44.93           C
ANISOU 6314  CG2 VAL  F 461    6793   6661   3616    -36  -1068   -416        C
ATOM   6315  C   VAL  F 461      36.194  -4.970 -34.930  1.00 45.12           C
ANISOU 6315  C   VAL  F 461    6467   6905   3770    421  -1327   -434        C
ATOM   6316  O   VAL  F 461      35.935  -4.679 -36.100  1.00 43.35           O
ANISOU 6316  O   VAL  F 461    6011   6774   3686    357  -1162   -447        O
ATOM   6317  N   GLY  F 462      36.044  -6.197 -34.453  1.00 45.10           N
ANISOU 6317  N   GLY  F 462    6732   6740   3664    596  -1399   -395        N
ATOM   6318  CA  GLY  F 462      35.452  -7.240 -35.259  1.00 42.67           C
ANISOU 6318  CA  GLY  F 462    6463   6335   3417    690  -1260   -382        C
ATOM   6319  C   GLY  F 462      33.953  -7.209 -35.132  1.00 40.00           C
ANISOU 6319  C   GLY  F 462    6361   5797   3042    512   -999   -335        C
ATOM   6320  O   GLY  F 462      33.413  -6.646 -34.174  1.00 40.52           O
ANISOU 6320  O   GLY  F 462    6646   5756   2995    370   -939   -306        O
ATOM   6321  N   VAL  F 463      33.287  -7.800 -36.113  1.00 37.67           N
ANISOU 6321  N   VAL  F 463    6002   5468   2845    514   -838   -350        N
ATOM   6322  CA  VAL  F 463      31.848  -8.005 -36.073  1.00 35.82           C
ANISOU 6322  CA  VAL  F 463    5947   5057   2604    360   -600   -333        C
ATOM   6323  CB  VAL  F 463      31.095  -7.040 -37.020  1.00 33.67           C
ANISOU 6323  CB  VAL  F 463    5405   4907   2481    210   -430   -364        C
ATOM   6324  CG1 VAL  F 463      31.567  -7.173 -38.489  1.00 32.45           C
ANISOU 6324  CG1 VAL  F 463    4944   4937   2447    292   -457   -406        C
ATOM   6325  CG2 VAL  F 463      29.608  -7.232 -36.898  1.00 33.01           C
ANISOU 6325  CG2 VAL  F 463    5453   4672   2418     63   -204   -375        C
ATOM   6326  C   VAL  F 463      31.552  -9.483 -36.370  1.00 36.17           C
ANISOU 6326  C   VAL  F 463    6172   4936   2636    457   -567   -337        C
ATOM   6327  O   VAL  F 463      32.101 -10.045 -37.313  1.00 36.03           O
ANISOU 6327  O   VAL  F 463    5987   5003   2702    603   -633   -384        O
ATOM   6328  N   LEU  F 464      30.720 -10.110 -35.536  1.00 36.36           N
ANISOU 6328  N   LEU  F 464    6560   4711   2543    365   -452   -297        N
ATOM   6329  CA  LEU  F 464      30.401 -11.533 -35.679  1.00 37.09           C
ANISOU 6329  CA  LEU  F 464    6903   4585   2604    418   -409   -295        C
ATOM   6330  CB  LEU  F 464      30.195 -12.174 -34.286  1.00 39.07           C
ANISOU 6330  CB  LEU  F 464    7666   4549   2628    385   -405   -204        C
ATOM   6331  CG  LEU  F 464      31.419 -12.196 -33.354  1.00 40.94           C
ANISOU 6331  CG  LEU  F 464    8086   4773   2696    599   -705   -130        C
ATOM   6332  CD1 LEU  F 464      31.091 -12.743 -31.939  1.00 43.14           C
ANISOU 6332  CD1 LEU  F 464    8942   4755   2695    535   -688    -20        C
ATOM   6333  CD2 LEU  F 464      32.590 -12.974 -33.978  1.00 41.49           C
ANISOU 6333  CD2 LEU  F 464    8040   4887   2837    924   -961   -154        C
ATOM   6334  C   LEU  F 464      29.185 -11.752 -36.603  1.00 35.79           C
```

FIGURE 18-182

```
ANISOU 6334  C   LEU F 464    6614  4407  2578   242  -171  -368      C
ATOM   6335  O   LEU F 464    28.472 -10.801 -36.896  1.00 33.02      O
ANISOU 6335  O   LEU F 464    6037  4188  2322    87   -41  -402      O
ATOM   6336  N   PRO F 465    28.971 -12.999 -37.096  1.00 37.43      N
ANISOU 6336  N   PRO F 465    6964  4455  2802   278  -137  -405      N
ATOM   6337  CA  PRO F 465    27.800 -13.306 -37.943  1.00 37.58      C
ANISOU 6337  CA  PRO F 465    6875  4460  2944    89    62  -496      C
ATOM   6338  CB  PRO F 465    27.950 -14.814 -38.211  1.00 39.80      C
ANISOU 6338  CB  PRO F 465    7426  4504  3193   175    38  -526      C
ATOM   6339  CG  PRO F 465    29.420 -15.040 -38.140  1.00 39.49      C
ANISOU 6339  CG  PRO F 465    7412  4494  3099   501  -217  -486      C
ATOM   6340  CD  PRO F 465    29.850 -14.180 -36.969  1.00 39.01      C
ANISOU 6340  CD  PRO F 465    7417  4482  2924   517  -307  -380      C
ATOM   6341  C   PRO F 465    26.410 -12.985 -37.360  1.00 38.58      C
ANISOU 6341  C   PRO F 465    7067  4510  3081  -204   314  -511      C
ATOM   6342  O   PRO F 465    25.432 -12.960 -38.117  1.00 38.80      O
ANISOU 6342  O   PRO F 465    6890  4606  3248  -359   449  -608      O
ATOM   6343  N   ASP F 466    26.316 -12.749 -36.047  1.00 39.71      N
ANISOU 6343  N   ASP F 466    7482  4529  3078  -278   375  -433      N
ATOM   6344  CA  ASP F 466    25.076 -12.246 -35.431  1.00 39.99      C
ANISOU 6344  CA  ASP F 466    7530  4535  3128  -543   642  -469      C
ATOM   6345  CB  ASP F 466    24.733 -13.040 -34.157  1.00 42.38      C
ANISOU 6345  CB  ASP F 466    8343  4540  3221  -688   795  -405      C
ATOM   6346  CG  ASP F 466    25.745 -12.838 -33.026  1.00 43.25      C
ANISOU 6346  CG  ASP F 466    8774  4573  3086  -539   618  -276      C
ATOM   6347  OD1 ASP F 466    26.686 -12.035 -33.161  1.00 40.47      O
ANISOU 6347  OD1 ASP F 466    8215  4411  2751  -348   390  -255      O
ATOM   6348  OD2 ASP F 466    25.589 -13.493 -31.976  1.00 46.27      O
ANISOU 6348  OD2 ASP F 466    9636  4699  3245  -632   706  -198      O
ATOM   6349  C   ASP F 466    25.070 -10.709 -35.183  1.00 38.76      C
ANISOU 6349  C   ASP F 466    7126  4585  3017  -543   641  -473      C
ATOM   6350  O   ASP F 466    24.221 -10.195 -34.450  1.00 39.42      O
ANISOU 6350  O   ASP F 466    7256  4637  3087  -715   852  -505      O
ATOM   6351  N   MSE F 467    26.016 -10.007 -35.819  1.00 37.33      N
ANISOU 6351  N   MSE F 467    6690  4601  2894  -358   423  -453      N
ATOM   6352  CA  MSE F 467    26.170  -8.534 -35.809  1.00 35.96      C
ANISOU 6352  CA  MSE F 467    6277  4607  2779  -345   387  -455      C
ATOM   6353  CB  MSE F 467    24.899  -7.811 -36.252  1.00 35.73      C
ANISOU 6353  CB  MSE F 467    5992  4658  2926  -482   577  -541      C
ATOM   6354  CG  MSE F 467    24.737  -7.701 -37.761  1.00 34.64      C
ANISOU 6354  CG  MSE F 467    5513  4688  2961  -427   503  -584      C
ATOM   6355  SE  MSE F 467    26.345  -7.142 -38.729  0.90 36.20     SE
ANISOU 6355  SE  MSE F 467    5518  5088  3149  -218   224  -515     SE
ATOM   6356  CE  MSE F 467    26.525  -5.301 -38.059  1.00 32.31      C
ANISOU 6356  CE  MSE F 467    4958  4657  2664  -246   217  -475      C
ATOM   6357  C   MSE F 467    26.703  -7.992 -34.476  1.00 37.22      C
ANISOU 6357  C   MSE F 467    6683  4702  2756  -343   341  -397      C
ATOM   6358  O   MSE F 467    26.687  -6.785 -34.186  1.00 35.87      O
ANISOU 6358  O   MSE F 467    6406  4617  2608  -377   355  -413      O
ATOM   6359  N   THR F 468    27.215  -8.919 -33.687  1.00 39.05      N
ANISOU 6359  N   THR F 468    7274  4768  2795  -291   262  -331      N
ATOM   6360  CA  THR F 468    27.716  -8.634 -32.358  1.00 40.94      C
ANISOU 6360  CA  THR F 468    7827  4923  2805  -287   187  -272      C
ATOM   6361  CB  THR F 468    27.372  -9.857 -31.476  1.00 43.19      C
ANISOU 6361  CB  THR F 468    8602  4931  2878  -353   280  -210      C
ATOM   6362  OG1 THR F 468    26.274  -9.513 -30.624  1.00 44.16      O
ANISOU 6362  OG1 THR F 468    8907  4957  2915  -594   586  -247      O
ATOM   6363  CG2 THR F 468    28.546 -10.408 -30.685  1.00 46.31      C
ANISOU 6363  CG2 THR F 468    9341  5221  3032  -165   -11  -103      C
ATOM   6364  C   THR F 468    29.201  -8.251 -32.487  1.00 40.62      C
ANISOU 6364  C   THR F 468    7654  5035  2745   -81  -147  -239      C
ATOM   6365  O   THR F 468    29.894  -8.776 -33.364  1.00 40.74      O
ANISOU 6365  O   THR F 468    7490  5133  2857    84  -302  -238      O
ATOM   6366  N   PRO F 469    29.679  -7.295 -31.671  1.00 41.09      N
ANISOU 6366  N   PRO F 469    7766  5150  2694  -102  -242  -236      N
ATOM   6367  CA  PRO F 469    31.083  -6.882 -31.768  1.00 41.16      C
ANISOU 6367  CA  PRO F 469    7605  5330  2704    54  -555  -230      C
ATOM   6368  CB  PRO F 469    31.077  -5.503 -31.123  1.00 40.81      C
ANISOU 6368  CB  PRO F 469    7543  5347  2614   -81  -534  -273      C
ATOM   6369  CG  PRO F 469    30.006  -5.598 -30.079  1.00 42.91      C
ANISOU 6369  CG  PRO F 469    8187  5411  2707  -237  -295  -271      C
```

FIGURE 18-183

```
ATOM   6370  CD  PRO F 469      28.964  -6.555 -30.615  1.00 42.09           C
ANISOU 6370  CD  PRO F 469    8108   5193   2693   -283    -58   -262        C
ATOM   6371  C   PRO F 469      32.038  -7.820 -30.998  1.00 43.78           C
ANISOU 6371  C   PRO F 469    8232   5571   2832    239   -831   -163        C
ATOM   6372  O   PRO F 469      31.609  -8.515 -30.066  1.00 45.55           O
ANISOU 6372  O   PRO F 469    8901   5569   2839    206   -778    -99        O
ATOM   6373  N   SER F 470      33.313  -7.825 -31.394  1.00 43.90           N
ANISOU 6373  N   SER F 470    8000   5762   2916    433  -1119   -181        N
ATOM   6374  CA  SER F 470      34.346  -8.639 -30.751  1.00 46.64           C
ANISOU 6374  CA  SER F 470    8551   6062   3110    671  -1446   -135        C
ATOM   6375  CB  SER F 470      34.315 -10.073 -31.297  1.00 47.59           C
ANISOU 6375  CB  SER F 470    8779   6031   3271    863  -1454    -97        C
ATOM   6376  OG  SER F 470      35.473 -10.807 -30.918  1.00 49.69           O
ANISOU 6376  OG  SER F 470    9140   6283   3454   1168  -1812    -71        O
ATOM   6377  C   SER F 470      35.752  -8.045 -30.913  1.00 47.35           C
ANISOU 6377  C   SER F 470    8278   6429   3286    805  -1756   -203        C
ATOM   6378  O   SER F 470      36.105  -7.528 -31.963  1.00 45.73           O
ANISOU 6378  O   SER F 470    7626   6442   3306    790  -1714   -278        O
ATOM   6379  N   THR F 471      36.553  -8.143 -29.862  1.00 50.52           N
ANISOU 6379  N   THR F 471    8881   6821   3494    925  -2070   -182        N
ATOM   6380  CA  THR F 471      37.935  -7.704 -29.919  1.00 52.23           C
ANISOU 6380  CA  THR F 471    8738   7311   3795   1058  -2399   -268        C
ATOM   6381  CB  THR F 471      38.370  -7.063 -28.571  1.00 54.64           C
ANISOU 6381  CB  THR F 471    9275   7631   3857    989  -2649   -274        C
ATOM   6382  OG1 THR F 471      38.127  -7.985 -27.503  1.00 57.14           O
ANISOU 6382  OG1 THR F 471   10164   7680   3867   1111  -2776   -156        O
ATOM   6383  CG2 THR F 471      37.604  -5.758 -28.297  1.00 51.68           C
ANISOU 6383  CG2 THR F 471    8940   7250   3448    642  -2391   -311        C
ATOM   6384  C   THR F 471      38.872  -8.866 -30.315  1.00 54.76           C
ANISOU 6384  C   THR F 471    8937   7670   4198   1425  -2659   -278        C
ATOM   6385  O   THR F 471      40.081  -8.673 -30.459  1.00 56.74           O
ANISOU 6385  O   THR F 471    8822   8174   4560   1580  -2936   -374        O
ATOM   6386  N   GLU F 472      38.310 -10.061 -30.502  1.00 55.20           N
ANISOU 6386  N   GLU F 472    9286   7473   4215   1560  -2559   -198        N
ATOM   6387  CA  GLU F 472      39.103 -11.273 -30.764  1.00 58.61           C
ANISOU 6387  CA  GLU F 472    9708   7861   4701   1944  -2804   -203        C
ATOM   6388  CB  GLU F 472      38.944 -12.273 -29.615  1.00 61.64           C
ANISOU 6388  CB  GLU F 472   10735   7900   4787   2108  -2991    -57        C
ATOM   6389  CG  GLU F 472      39.602 -11.834 -28.294  1.00 66.05           C
ANISOU 6389  CG  GLU F 472   11497   8504   5096   2156  -3355    -23        C
ATOM   6390  CD  GLU F 472      39.044 -12.577 -27.088  1.00 68.99           C
ANISOU 6390  CD  GLU F 472   12632   8493   5089   2173  -3414    155        C
ATOM   6391  OE1 GLU F 472      39.536 -12.355 -25.958  1.00 74.88           O
ANISOU 6391  OE1 GLU F 472   13642   9238   5571   2229  -3734    199        O
ATOM   6392  OE2 GLU F 472      38.110 -13.393 -27.270  1.00 70.96           O
ANISOU 6392  OE2 GLU F 472   13234   8438   5289   2110  -3138    248        O
ATOM   6393  C   GLU F 472      38.814 -11.965 -32.106  1.00 56.75           C
ANISOU 6393  C   GLU F 472    9268   7606   4689   2022  -2575   -253        C
ATOM   6394  O   GLU F 472      39.740 -12.338 -32.826  0.50 57.96           O
ANISOU 6394  O   GLU F 472    9067   7930   5026   2279  -2713   -356        O
ATOM   6395  N   AMSE F 473     37.538 -12.106 -32.442  0.50 54.05           N
ANISOU 6395  N   AMSE F 473   9129   7077   4333   1792  -2225   -203        N
ATOM   6396  N   BMSE F 473     37.527 -12.152 -32.413  0.50 54.67           N
ANISOU 6396  N   BMSE F 473   9227   7140   4403   1798  -2228   -198        N
ATOM   6397  CA  AMSE F 473     37.154 -12.767 -33.686  0.50 52.38           C
ANISOU 6397  CA  AMSE F 473   8771   6831   4299   1830  -2013   -259        C
ATOM   6398  CA  BMSE F 473     37.061 -12.837 -33.638  0.50 53.57           C
ANISOU 6398  CA  BMSE F 473   8970   6950   4436   1823  -2000   -249        C
ATOM   6399  CB  AMSE F 473     36.349 -14.042 -33.398  0.50 53.56           C
ANISOU 6399  CB  AMSE F 473   9451   6579   4320   1866  -1917   -167        C
ATOM   6400  CB  BMSE F 473     36.126 -14.020 -33.278  0.50 54.56           C
ANISOU 6400  CB  BMSE F 473   9648   6665   4417   1812  -1876   -149        C
ATOM   6401  CG  AMSE F 473     37.019 -15.032 -32.430  0.50 57.16           C
ANISOU 6401  CG  AMSE F 473  10331   6794   4594   2182  -2241    -77        C
ATOM   6402  CG  BMSE F 473     36.799 -15.413 -33.076  0.50 59.08           C
ANISOU 6402  CG  BMSE F 473  10512   7000   4934   2193  -2125   -118        C
ATOM   6403  SE  AMSE F 473     38.682 -15.802 -33.103  0.45 58.91          SE
ANISOU 6403  SE  AMSE F 473  10192   7173   5018   2733  -2611   -206       SE
ATOM   6404  SE  BMSE F 473     35.701 -16.903 -32.302  0.45 62.74          SE
ANISOU 6404  SE  BMSE F 473  11838   6858   5142   2138  -1994     50       SE
ATOM   6405  CE  AMSE F 473     37.985 -17.029 -34.440  0.50 58.03           C
```

FIGURE 18-184

```
ANISOU 6405  CE  AMSE F 473    10158   6829   5063   2774  -2311   -279        C
ATOM   6406  CE  BMSE F 473    34.039 -16.732 -33.323  0.50 58.44              C
ANISOU 6406  CE  BMSE F 473    11168   6293   4743   1680  -1460    -22        C
ATOM   6407  C   AMSE F 473    36.353 -11.826 -34.583  0.50 48.62              C
ANISOU 6407  C   AMSE F 473     7996   6515   3962   1519  -1691   -310        C
ATOM   6408  C   BMSE F 473    36.326 -11.854 -34.571  0.50 49.21              C
ANISOU 6408  C   BMSE F 473     8085   6580   4033   1518  -1688   -307        C
ATOM   6409  O   AMSE F 473    35.756 -10.854 -34.118  0.50 46.99              O
ANISOU 6409  O   AMSE F 473     7827   6334   3694   1260  -1572   -275        O
ATOM   6410  O   BMSE F 473    35.750 -10.866 -34.112  0.50 47.60              O
ANISOU 6410  O   BMSE F 473     7908   6407   3769   1261  -1572   -274        O
ATOM   6411  N   SER  F 474    36.355 -12.116 -35.876  1.00 47.59              N
ANISOU 6411  N   SER  F 474     7586   6486   4008   1564  -1563   -398        N
ATOM   6412  CA  SER  F 474    35.584 -11.319 -36.852  1.00 44.33              C
ANISOU 6412  CA  SER  F 474     6917   6214   3712   1304  -1290   -437        C
ATOM   6413  CB  SER  F 474    36.392 -10.097 -37.301  1.00 43.46              C
ANISOU 6413  CB  SER  F 474     6360   6443   3709   1243  -1335   -499        C
ATOM   6414  OG  SER  F 474    35.624  -9.222 -38.089  1.00 39.78              O
ANISOU 6414  OG  SER  F 474     5726   6072   3317    997  -1104   -503        O
ATOM   6415  C   SER  F 474    35.225 -12.160 -38.070  1.00 43.77              C
ANISOU 6415  C   SER  F 474     6781   6105   3745   1359  -1143   -510        C
ATOM   6416  O   SER  F 474    35.885 -13.164 -38.345  1.00 45.97              O
ANISOU 6416  O   SER  F 474     7084   6329   4052   1623  -1256   -566        O
ATOM   6417  N   MSE  F 475    34.196 -11.754 -38.806  1.00 41.25              N
ANISOU 6417  N   MSE  F 475     6380   5813   3480   1127   -909   -523        N
ATOM   6418  CA  MSE  F 475    34.003 -12.291 -40.149  1.00 40.97              C
ANISOU 6418  CA  MSE  F 475     6197   5831   3539   1157   -792   -619        C
ATOM   6419  CB  MSE  F 475    32.693 -11.806 -40.771  1.00 38.57              C
ANISOU 6419  CB  MSE  F 475     5849   5536   3270    888   -576   -618        C
ATOM   6420  CG  MSE  F 475    31.457 -12.502 -40.205  1.00 38.53              C
ANISOU 6420  CG  MSE  F 475     6187   5241   3212    749   -456   -585        C
ATOM   6421  SE  MSE  F 475    29.784 -11.880 -40.999  0.90 37.77             SE
ANISOU 6421  SE  MSE  F 475     5943   5203   3204    437   -222   -623       SE
ATOM   6422  CE  MSE  F 475    29.784 -10.021 -40.369  1.00 34.50              C
ANISOU 6422  CE  MSE  F 475     5347   4962   2799    318   -223   -536        C
ATOM   6423  C   MSE  F 475    35.210 -11.913 -41.018  1.00 41.26              C
ANISOU 6423  C   MSE  F 475     5836   6174   3668   1296   -861   -711        C
ATOM   6424  O   MSE  F 475    35.709 -10.786 -40.947  1.00 40.52              O
ANISOU 6424  O   MSE  F 475     5499   6296   3600   1209   -892   -694        O
ATOM   6425  N   ARG  F 476    35.662 -12.871 -41.825  1.00 42.54              N
ANISOU 6425  N   ARG  F 476     5947   6338   3877   1494   -862   -821        N
ATOM   6426  CA  ARG  F 476    36.908 -12.783 -42.592  1.00 43.25              C
ANISOU 6426  CA  ARG  F 476     5676   6704   4054   1670   -906   -942        C
ATOM   6427  CB  ARG  F 476    37.047 -14.035 -43.462  1.00 44.93              C
ANISOU 6427  CB  ARG  F 476     5941   6831   4299   1877   -855  -1078        C
ATOM   6428  CG  ARG  F 476    38.089 -13.966 -44.568  1.00 47.16              C
ANISOU 6428  CG  ARG  F 476     5839   7416   4664   2010   -797  -1241        C
ATOM   6429  CD  ARG  F 476    38.138 -15.267 -45.379  1.00 48.80              C
ANISOU 6429  CD  ARG  F 476     6156   7498   4889   2224   -733  -1397        C
ATOM   6430  NE  ARG  F 476    36.829 -15.772 -45.815  1.00 48.30              N
ANISOU 6430  NE  ARG  F 476     6394   7206   4752   2046   -602  -1383        N
ATOM   6431  CZ  ARG  F 476    36.126 -15.297 -46.843  1.00 47.93              C
ANISOU 6431  CZ  ARG  F 476     6261   7289   4660   1803   -431  -1409        C
ATOM   6432  NH1 ARG  F 476    36.574 -14.273 -47.565  1.00 48.79              N
ANISOU 6432  NH1 ARG  F 476     6042   7730   4765   1693   -345  -1425        N
ATOM   6433  NH2 ARG  F 476    34.962 -15.848 -47.154  1.00 46.79              N
ANISOU 6433  NH2 ARG  F 476     6372   6939   4466   1657   -353  -1419        N
ATOM   6434  C   ARG  F 476    37.030 -11.498 -43.416  1.00 41.10              C
ANISOU 6434  C   ARG  F 476     5060   6740   3817   1453   -777   -953        C
ATOM   6435  O   ARG  F 476    36.182 -11.199 -44.258  1.00 39.12              O
ANISOU 6435  O   ARG  F 476     4810   6511   3545   1266   -612   -945        O
ATOM   6436  N   GLY  F 477    38.082 -10.733 -43.140  1.00 41.43              N
ANISOU 6436  N   GLY  F 477     4825   7009   3906   1471   -870   -969        N
ATOM   6437  CA  GLY  F 477    38.354  -9.486 -43.850  1.00 40.53              C
ANISOU 6437  CA  GLY  F 477     4413   7168   3820   1250   -748   -972        C
ATOM   6438  C   GLY  F 477    37.457  -8.303 -43.526  1.00 37.97              C
ANISOU 6438  C   GLY  F 477     4192   6789   3447    958   -686   -834        C
ATOM   6439  O   GLY  F 477    37.588  -7.235 -44.118  1.00 37.40              O
ANISOU 6439  O   GLY  F 477     3939   6888   3383    765   -584   -814        O
ATOM   6440  N   ILE  F 478    36.549  -8.489 -42.574  1.00 37.64              N
ANISOU 6440  N   ILE  F 478     4456   6494   3350    927   -734   -743        N
```

FIGURE 18-185

```
ATOM    6441  CA   ILE F 478      35.552  -7.457 -42.189  1.00 35.63           C
ANISOU  6441  CA   ILE F 478     4320   6155   3064    685   -661   -635       C
ATOM    6442  CB   ILE F 478      34.126  -8.080 -42.125  1.00 34.02           C
ANISOU  6442  CB   ILE F 478     4389   5711   2826    640   -565   -600       C
ATOM    6443  CG1  ILE F 478      33.806  -8.827 -43.435  1.00 33.55           C
ANISOU  6443  CG1  ILE F 478     4276   5687   2784    683   -466   -676       C
ATOM    6444  CD1  ILE F 478      33.521  -7.945 -44.656  1.00 30.29           C
ANISOU  6444  CD1  ILE F 478     3677   5452   2378    537   -355   -670       C
ATOM    6445  CG2  ILE F 478      33.074  -7.027 -41.766  1.00 33.10           C
ANISOU  6445  CG2  ILE F 478     4345   5524   2706    427   -477   -518       C
ATOM    6446  C    ILE F 478      35.903  -6.782 -40.854  1.00 36.01           C
ANISOU  6446  C    ILE F 478     4438   6165   3079    636   -794   -583       C
ATOM    6447  O    ILE F 478      35.986  -7.446 -39.812  1.00 37.11           O
ANISOU  6447  O    ILE F 478     4791   6153   3155    758   -925   -568       O
ATOM    6448  N    ARG F 479      36.123  -5.467 -40.889  1.00 35.61           N
ANISOU  6448  N    ARG F 479     4243   6236   3052    452   -766   -558       N
ATOM    6449  CA   ARG F 479      36.358  -4.678 -39.648  1.00 35.25           C
ANISOU  6449  CA   ARG F 479     4285   6146   2962    361   -880   -526       C
ATOM    6450  CB   ARG F 479      37.771  -4.102 -39.604  1.00 37.00           C
ANISOU  6450  CB   ARG F 479     4220   6604   3234    340  -1006   -596       C
ATOM    6451  CG   ARG F 479      38.905  -5.105 -39.660  1.00 39.51           C
ANISOU  6451  CG   ARG F 479     4354   7064   3594    589  -1165   -694       C
ATOM    6452  CD   ARG F 479      38.890  -6.113 -38.506  1.00 39.37           C
ANISOU  6452  CD   ARG F 479     4610   6863   3485    811  -1371   -676       C
ATOM    6453  NE   ARG F 479      39.992  -7.062 -38.667  1.00 43.02           N
ANISOU  6453  NE   ARG F 479     4879   7454   4013   1100  -1539   -778       N
ATOM    6454  CZ   ARG F 479      39.943  -8.180 -39.394  1.00 42.54           C
ANISOU  6454  CZ   ARG F 479     4821   7349   3992   1310  -1482   -822       C
ATOM    6455  NH1  ARG F 479      38.836  -8.535 -40.045  1.00 39.17           N
ANISOU  6455  NH1  ARG F 479     4582   6764   3539   1240  -1271   -774       N
ATOM    6456  NH2  ARG F 479      41.014  -8.951 -39.460  1.00 44.32           N
ANISOU  6456  NH2  ARG F 479     4855   7691   4295   1600  -1648   -933       N
ATOM    6457  C    ARG F 479      35.379  -3.518 -39.523  1.00 33.52           C
ANISOU  6457  C    ARG F 479     4176   5824   2735    141   -749   -457       C
ATOM    6458  O    ARG F 479      34.960  -2.946 -40.533  1.00 33.11           O
ANISOU  6458  O    ARG F 479     4023   5824   2735     39   -613   -431       O
ATOM    6459  N    VAL F 480      35.010  -3.170 -38.293  1.00 33.05           N
ANISOU  6459  N    VAL F 480     4342   5614   2601     83   -794   -431       N
ATOM    6460  CA   VAL F 480      34.211  -1.973 -38.054  1.00 31.67           C
ANISOU  6460  CA   VAL F 480     4261   5340   2433   -100   -679   -394       C
ATOM    6461  CB   VAL F 480      32.975  -2.270 -37.150  1.00 31.19           C
ANISOU  6461  CB   VAL F 480     4503   5047   2302   -107   -586   -373       C
ATOM    6462  CG1  VAL F 480      32.299  -0.976 -36.650  1.00 29.99           C
ANISOU  6462  CG1  VAL F 480     4449   4788   2157   -263   -483   -369       C
ATOM    6463  CG2  VAL F 480      31.966  -3.168 -37.871  1.00 30.56           C
ANISOU  6463  CG2  VAL F 480     4439   4902   2268    -46   -452   -362       C
ATOM    6464  C    VAL F 480      35.128  -0.915 -37.429  1.00 32.95           C
ANISOU  6464  C    VAL F 480     4368   5575   2578   -225   -792   -424       C
ATOM    6465  O    VAL F 480      35.745  -1.151 -36.395  1.00 34.11           O
ANISOU  6465  O    VAL F 480     4604   5721   2637   -182   -961   -460       O
ATOM    6466  N    SER F 481      35.233   0.241 -38.068  1.00 33.25           N
ANISOU  6466  N    SER F 481     4278   5667   2688   -388   -713   -411       N
ATOM    6467  CA   SER F 481      36.017   1.336 -37.502  1.00 35.24           C
ANISOU  6467  CA   SER F 481     4499   5958   2933   -559   -797   -452       C
ATOM    6468  CB   SER F 481      36.437   2.355 -38.572  1.00 35.71           C
ANISOU  6468  CB   SER F 481     4370   6117   3082   -738   -702   -431       C
ATOM    6469  OG   SER F 481      37.145   3.457 -37.988  1.00 38.65           O
ANISOU  6469  OG   SER F 481     4738   6495   3454   -948   -769   -482       O
ATOM    6470  C    SER F 481      35.306   2.040 -36.341  1.00 35.43           C
ANISOU  6470  C    SER F 481     4816   5766   2882   -645   -777   -459       C
ATOM    6471  O    SER F 481      34.117   2.366 -36.409  1.00 34.16           O
ANISOU  6471  O    SER F 481     4805   5434   2740   -653   -618   -419       O
ATOM    6472  N    LYS F 482      36.073   2.261 -35.283  1.00 37.40           N
ANISOU  6472  N    LYS F 482     5126   6040   3045   -702   -948   -528       N
ATOM    6473  CA   LYS F 482      35.676   3.070 -34.149  1.00 38.68           C
ANISOU  6473  CA   LYS F 482     5562   6025   3110   -819   -945   -569       C
ATOM    6474  CB   LYS F 482      36.268   2.482 -32.863  1.00 40.92           C
ANISOU  6474  CB   LYS F 482     5998   6331   3219   -756  -1171   -627       C
ATOM    6475  CG   LYS F 482      35.631   1.192 -32.366  1.00 43.46           C
ANISOU  6475  CG   LYS F 482     6540   6556   3418   -560  -1164   -577       C
ATOM    6476  CD   LYS F 482      34.408   1.466 -31.467  1.00 47.95           C
```

FIGURE 18-186

```
ANISOU 6476  CD  LYS F 482    7475  6881  3862   -619  -984  -579       C
ATOM   6477  CE  LYS F 482   33.121   1.568 -32.297  1.00 47.40         C
ANISOU 6477  CE  LYS F 482    7363  6708  3938   -612  -696  -534       C
ATOM   6478  NZ  LYS F 482   32.024   2.121 -31.458  1.00 48.36         N
ANISOU 6478  NZ  LYS F 482    7761  6627  3987   -690  -499  -580       N
ATOM   6479  C   LYS F 482   36.172   4.524 -34.290  1.00 39.57         C
ANISOU 6479  C   LYS F 482    5613  6135  3288  -1061  -935  -613       C
ATOM   6480  O   LYS F 482   35.963   5.337 -33.378  1.00 40.79         O
ANISOU 6480  O   LYS F 482    5995  6137  3367  -1181  -937  -673       O
ATOM   6481  N   MSE F 483   36.839   4.848 -35.404  1.00 38.62         N
ANISOU 6481  N   MSE F 483    5216  6167  3290  -1150  -910  -591       N
ATOM   6482  CA  MSE F 483   37.361   6.208 -35.607  1.00 39.11         C
ANISOU 6482  CA  MSE F 483    5242  6208  3412  -1419  -881  -623       C
ATOM   6483  CB  MSE F 483   38.321   6.273 -36.805  1.00 39.75         C
ANISOU 6483  CB  MSE F 483    4987  6519  3599  -1525  -853  -609       C
ATOM   6484  CG  MSE F 483   39.626   5.497 -36.598  1.00 41.96         C
ANISOU 6484  CG  MSE F 483    4958  7098  3887  -1482 -1052  -714       C
ATOM   6485 SE   MSE F 483   40.539   5.770 -34.876  0.90 50.05        SE
ANISOU 6485 SE   MSE F 483    6036  8169  4812  -1584 -1372  -884      SE
ATOM   6486  CE  MSE F 483   41.373   7.511 -35.168  1.00 48.50         C
ANISOU 6486  CE  MSE F 483    5726  7986  4714  -2058 -1303  -969       C
ATOM   6487  C   MSE F 483   36.227   7.226 -35.749  1.00 37.49         C
ANISOU 6487  C   MSE F 483    5289  5719  3238  -1481  -693  -566       C
ATOM   6488  O   MSE F 483   35.094   6.823 -36.053  1.00 35.28         O
ANISOU 6488  O   MSE F 483    5099  5332  2975  -1307  -572  -494       O
ATOM   6489  OXT MSE F 483   36.389   8.431 -35.532  1.00 37.47         O
ANISOU 6489  OXT MSE F 483    5406  5580  3252  -1689  -668  -602       O
ATOM   6490  O2G MGT A    1  48.431  21.314 -32.822  1.00 51.34         O
ANISOU 6490  O2G MGT A    1   5580  7344  6582   -151   662   268       O
ATOM   6491  PG  MGT A    1  47.642  21.644 -31.468  1.00 49.83         P
ANISOU 6491  PG  MGT A    1   5455  6960  6518   -139   518   275       P
ATOM   6492  O3G MGT A    1  46.906  20.295 -30.960  1.00 45.91         O
ANISOU 6492  O3G MGT A    1   5042  6412  5989     23   408   176       O
ATOM   6493  O1G MGT A    1  48.607  22.186 -30.469  1.00 50.23         O
ANISOU 6493  O1G MGT A    1   5363  7007  6715   -196   508   226       O
ATOM   6494  O3B MGT A    1  46.392  22.571 -31.946  1.00 49.90         O
ANISOU 6494  O3B MGT A    1   5618  6851  6491   -212   497   434       O
ATOM   6495  PB  MGT A    1  46.500  23.966 -32.785  1.00 50.34         P
ANISOU 6495  PB  MGT A    1   5693  6896  6537   -368   593   604       P
ATOM   6496  O2B MGT A    1  46.307  23.569 -34.337  1.00 50.62         O
ANISOU 6496  O2B MGT A    1   5793  7073  6368   -354   675   667       O
ATOM   6497  O1B MGT A    1  47.806  24.652 -32.528  1.00 51.47         O
ANISOU 6497  O1B MGT A    1   5686  7087  6785   -486   681   592       O
ATOM   6498  O3A MGT A    1  45.229  24.838 -32.232  1.00 49.00         O
ANISOU 6498  O3A MGT A    1   5651  6519  6447   -386   490   701       O
ATOM   6499  PA  MGT A    1  43.722  24.280 -31.756  1.00 44.78         P
ANISOU 6499  PA  MGT A    1   5239  5880  5896   -269   352   675       P
ATOM   6500  O2A MGT A    1  43.564  22.796 -32.345  1.00 45.17         O
ANISOU 6500  O2A MGT A    1   5307  6056  5798   -157   346   583       O
ATOM   6501  O1A MGT A    1  42.713  25.256 -32.229  1.00 46.58         O
ANISOU 6501  O1A MGT A    1   5577  6005  6118   -305   327   828       O
ATOM   6502  O5* MGT A    1  43.626  24.206 -30.136  1.00 42.80         O
ANISOU 6502  O5* MGT A    1   4955  5516  5792   -234   258   568       O
ATOM   6503  C5* MGT A    1  43.771  25.451 -29.389  1.00 38.57         C
ANISOU 6503  C5* MGT A    1   4398  4855  5403   -327   250   603       C
ATOM   6504  C4* MGT A    1  44.860  25.368 -28.297  1.00 34.92         C
ANISOU 6504  C4* MGT A    1   3808  4419  5042   -349   242   478       C
ATOM   6505  O4* MGT A    1  44.641  24.152 -27.533  1.00 33.27         O
ANISOU 6505  O4* MGT A    1   3599  4240  4800   -224   161   362       O
ATOM   6506  C3* MGT A    1  46.295  25.288 -28.821  1.00 34.19         C
ANISOU 6506  C3* MGT A    1   3578  4475  4937   -411   343   453       C
ATOM   6507  O3* MGT A    1  47.120  26.048 -27.945  1.00 35.75         O
ANISOU 6507  O3* MGT A    1   3669  4640  5274   -506   342   399       O
ATOM   6508  C2* MGT A    1  46.671  23.831 -28.682  1.00 33.94         C
ANISOU 6508  C2* MGT A    1   3496  4568  4833   -279   318   333       C
ATOM   6509  O2* MGT A    1  48.079  23.737 -28.438  1.00 37.14         O
ANISOU 6509  O2* MGT A    1   3729  5093  5289   -308   364   248       O
ATOM   6510  C1* MGT A    1  45.936  23.471 -27.403  1.00 30.89         C
ANISOU 6510  C1* MGT A    1   3166  4076  4495   -198   191   266       C
ATOM   6511  N9  MGT A    1  45.522  22.046 -27.080  1.00 29.66         N
ANISOU 6511  N9  MGT A    1   3059  3943  4269    -51   124   187       N
```

FIGURE 18-187

```
ATOM   6512  C8  MGT A   1      44.505  21.434 -27.715  1.00 27.88           C
ANISOU 6512  C8  MGT A   1     2948   3695   3949      8    112    221       C
ATOM   6513  N7  MGT A   1      44.411  20.228 -27.155  1.00 27.01           N
ANISOU 6513  N7  MGT A   1     2858   3589   3815    120     53    134       N
ATOM   6514  CM7 MGT A   1      43.375  19.249 -27.561  1.00 25.30           C
ANISOU 6514  CM7 MGT A   1     2758   3341   3512    194     23    127       C
ATOM   6515  C5  MGT A   1      45.336  20.071 -26.191  1.00 27.24           C
ANISOU 6515  C5  MGT A   1     2792   3648   3910    147     21     59       C
ATOM   6516  C4  MGT A   1      46.053  21.249 -26.149  1.00 27.82           C
ANISOU 6516  C4  MGT A   1     2769   3743   4059     34     64     84       C
ATOM   6517  N3  MGT A   1      47.061  21.426 -25.271  1.00 27.51           N
ANISOU 6517  N3  MGT A   1     2607   3751   4096     24     36     11       N
ATOM   6518  C2  MGT A   1      47.423  20.471 -24.405  1.00 28.78           C
ANISOU 6518  C2  MGT A   1     2738   3945   4254    139    -41    -75       C
ATOM   6519  N2  MGT A   1      48.443  20.701 -23.575  1.00 29.71           N
ANISOU 6519  N2  MGT A   1     2722   4129   4439    129    -80   -146       N
ATOM   6520  N1  MGT A   1      46.712  19.246 -24.380  1.00 27.51           N
ANISOU 6520  N1  MGT A   1     2690   3743   4019    264    -84    -86       N
ATOM   6521  C6  MGT A   1      45.678  19.057 -25.295  1.00 26.68           C
ANISOU 6521  C6  MGT A   1     2705   3587   3846    258    -48    -26       C
ATOM   6522  O6  MGT A   1      45.070  17.997 -25.311  1.00 27.25           O
ANISOU 6522  O6  MGT A   1     2870   3620   3863    348    -80    -46       O
ATOM   6523  O2G MGT B   1       8.911   7.379 -30.815  1.00 52.96           O
ANISOU 6523  O2G MGT B   1     6523   7405   6194    480  -1101    341       O
ATOM   6524  PG  MGT B   1       8.686   7.207 -29.221  1.00 49.79           P
ANISOU 6524  PG  MGT B   1     5992   6928   5999    504  -1012    247       P
ATOM   6525  O3G MGT B   1      10.111   6.727 -28.566  1.00 47.34           O
ANISOU 6525  O3G MGT B   1     5764   6484   5738    339   -851    158       O
ATOM   6526  O1G MGT B   1       8.184   8.475 -28.631  1.00 50.87           O
ANISOU 6526  O1G MGT B   1     6159   6948   6223    702  -1015    339       O
ATOM   6527  O3B MGT B   1       7.735   5.911 -29.048  1.00 49.75           O
ANISOU 6527  O3B MGT B   1     5755   7120   6027    437  -1075    126       O
ATOM   6528  PB  MGT B   1       6.305   5.749 -29.792  1.00 51.97           P
ANISOU 6528  PB  MGT B   1     5864   7633   6251    512  -1261    156       P
ATOM   6529  O2B MGT B   1       6.621   5.123 -31.256  1.00 52.42           O
ANISOU 6529  O2B MGT B   1     6011   7805   6099    381  -1353    144       O
ATOM   6530  O1B MGT B   1       5.596   7.053 -29.893  1.00 53.94           O
ANISOU 6530  O1B MGT B   1     6111   7869   6514    750  -1339    301       O
ATOM   6531  O3A MGT B   1       5.465   4.683 -28.886  1.00 50.43           O
ANISOU 6531  O3A MGT B   1     5422   7553   6185    435  -1246     27       O
ATOM   6532  PA  MGT B   1       5.986   3.318 -28.093  1.00 45.51           P
ANISOU 6532  PA  MGT B   1     4771   6888   5634    227  -1122   -129       P
ATOM   6533  O2A MGT B   1       7.298   2.764 -28.782  1.00 43.17           O
ANISOU 6533  O2A MGT B   1     4672   6508   5222     84  -1068   -175       O
ATOM   6534  O1A MGT B   1       4.876   2.329 -28.139  1.00 43.87           O
ANISOU 6534  O1A MGT B   1     4348   6870   5450    131  -1206   -207       O
ATOM   6535  O5* MGT B   1       6.408   3.771 -26.568  1.00 42.04           O
ANISOU 6535  O5* MGT B   1     4356   6273   5345    294   -960   -138       O
ATOM   6536  C5* MGT B   1       5.376   4.024 -25.569  1.00 40.75           C
ANISOU 6536  C5* MGT B   1     4018   6158   5306    403   -935   -137       C
ATOM   6537  C4* MGT B   1       5.580   5.362 -24.810  1.00 38.17           C
ANISOU 6537  C4* MGT B   1     3791   5670   5043    591   -859    -67       C
ATOM   6538  O4* MGT B   1       6.866   5.317 -24.120  1.00 33.12           O
ANISOU 6538  O4* MGT B   1     3324   4841   4420    503   -736   -111       O
ATOM   6539  C3* MGT B   1       5.606   6.610 -25.719  1.00 38.56           C
ANISOU 6539  C3* MGT B   1     3962   5672   5018    750   -947     64       C
ATOM   6540  O3* MGT B   1       4.951   7.705 -25.060  1.00 39.09           O
ANISOU 6540  O3* MGT B   1     4007   5678   5169    978   -922    122       O
ATOM   6541  C2* MGT B   1       7.108   6.900 -25.892  1.00 36.08           C
ANISOU 6541  C2* MGT B   1     3897   5166   4648    655   -875     76       C
ATOM   6542  O2* MGT B   1       7.314   8.312 -26.089  1.00 40.76           O
ANISOU 6542  O2* MGT B   1     4655   5608   5223    807   -882    193       O
ATOM   6543  C1* MGT B   1       7.650   6.495 -24.540  1.00 30.98           C
ANISOU 6543  C1* MGT B   1     3257   4415   4100    578   -738    -22       C
ATOM   6544  N9  MGT B   1       9.078   6.082 -24.348  1.00 28.02           N
ANISOU 6544  N9  MGT B   1     3017   3924   3707    418   -654    -71       N
ATOM   6545  C8  MGT B   1       9.633   4.953 -24.839  1.00 26.32           C
ANISOU 6545  C8  MGT B   1     2789   3772   3439    259   -650   -132       C
ATOM   6546  N7  MGT B   1      10.913   4.962 -24.399  1.00 26.18           N
ANISOU 6546  N7  MGT B   1     2885   3627   3435    179   -562   -155       N
ATOM   6547  CM7 MGT B   1      11.908   3.911 -24.712  1.00 23.88           C
```

FIGURE 18-188

```
ANISOU 6547  CM7 MGT B   1     2618   3350   3106     33   -517   -218       C
ATOM   6548  C5  MGT B   1     11.150   6.053 -23.649  1.00 26.92            C
ANISOU 6548  C5  MGT B   1     3066   3581   3583    257   -521   -117       C
ATOM   6549  C4  MGT B   1      9.951   6.759 -23.616  1.00 26.32            C
ANISOU 6549  C4  MGT B   1     2937   3533   3529    418   -573    -67       C
ATOM   6550  N3  MGT B   1      9.832   7.907 -22.934  1.00 26.49            N
ANISOU 6550  N3  MGT B   1     3046   3417   3601    542   -541    -32       N
ATOM   6551  C2  MGT B   1     10.866   8.432 -22.259  1.00 27.34            C
ANISOU 6551  C2  MGT B   1     3301   3354   3732    486   -471    -49       C
ATOM   6552  N2  MGT B   1     10.701   9.584 -21.612  1.00 27.16            N
ANISOU 6552  N2  MGT B   1     3394   3178   3749    604   -444    -27       N
ATOM   6553  N1  MGT B   1     12.111   7.743 -22.231  1.00 25.77            N
ANISOU 6553  N1  MGT B   1     3131   3144   3516    307   -431    -94       N
ATOM   6554  C6  MGT B   1     12.248   6.556 -22.934  1.00 25.10            C
ANISOU 6554  C6  MGT B   1     2952   3198   3385    209   -450   -125       C
ATOM   6555  O6  MGT B   1     13.319   5.964 -22.921  1.00 23.93            O
ANISOU 6555  O6  MGT B   1     2823   3040   3228     85   -407   -162       O
ATOM   6556  O2G MGT D   1     61.475 -17.770 -25.548  1.00 67.38            O
ANISOU 6556  O2G MGT D   1     9188   7995   8420    107    942  -1582       O
ATOM   6557  PG  MGT D   1     62.375 -16.755 -24.687  1.00 63.67            P
ANISOU 6557  PG  MGT D   1     8522   7594   8077    197    990  -1352       P
ATOM   6558  O3G MGT D   1     61.503 -15.362 -24.545  1.00 60.97            O
ANISOU 6558  O3G MGT D   1     8082   7476   7609     96    876  -1228       O
ATOM   6559  O1G MGT D   1     62.653 -17.429 -23.397  1.00 61.93            O
ANISOU 6559  O1G MGT D   1     8255   7184   8089    201    946  -1268       O
ATOM   6560  O3B MGT D   1     63.673 -16.536 -25.716  1.00 64.52            O
ANISOU 6560  O3B MGT D   1     8633   7752   8130    376   1208  -1392       O
ATOM   6561  PB  MGT D   1     64.918 -15.449 -25.741  1.00 62.58            P
ANISOU 6561  PB  MGT D   1     8215   7622   7940    497   1355  -1237       P
ATOM   6562  O2B MGT D   1     65.139 -15.212 -27.321  1.00 64.91            O
ANISOU 6562  O2B MGT D   1     8631   8045   7988    558   1524  -1348       O
ATOM   6563  O1B MGT D   1     66.180 -15.970 -25.139  1.00 63.51            O
ANISOU 6563  O1B MGT D   1     8220   7601   8311    635   1450  -1195       O
ATOM   6564  O3A MGT D   1     64.421 -13.964 -25.210  1.00 59.32            O
ANISOU 6564  O3A MGT D   1     7676   7379   7485    401   1242  -1049       O
ATOM   6565  PA  MGT D   1     65.432 -12.750 -24.675  1.00 56.96            P
ANISOU 6565  PA  MGT D   1     7170   7154   7317    450   1303   -853       P
ATOM   6566  O2A MGT D   1     64.807 -11.421 -25.326  1.00 57.92            O
ANISOU 6566  O2A MGT D   1     7315   7462   7229    384   1286   -780       O
ATOM   6567  O1A MGT D   1     66.884 -12.915 -25.008  1.00 57.06            O
ANISOU 6567  O1A MGT D   1     7089   7135   7457    589   1504   -851       O
ATOM   6568  O5* MGT D   1     65.125 -12.590 -23.090  1.00 52.24            O
ANISOU 6568  O5* MGT D   1     6467   6494   6888    382   1121   -735       O
ATOM   6569  C5* MGT D   1     66.139 -12.982 -22.146  1.00 47.19            C
ANISOU 6569  C5* MGT D   1     5707   5738   6485    461   1122   -671       C
ATOM   6570  C4* MGT D   1     65.571 -13.910 -21.075  1.00 41.42            C
ANISOU 6570  C4* MGT D   1     5036   4863   5837    416    977   -675       C
ATOM   6571  O4* MGT D   1     64.237 -13.425 -20.723  1.00 38.14            O
ANISOU 6571  O4* MGT D   1     4670   4525   5297    270    847   -650       O
ATOM   6572  C3* MGT D   1     65.400 -15.351 -21.574  1.00 41.82            C
ANISOU 6572  C3* MGT D   1     5242   4761   5887    450   1023   -828       C
ATOM   6573  O3* MGT D   1     66.052 -16.225 -20.646  1.00 42.77            O
ANISOU 6573  O3* MGT D   1     5339   4701   6212    533    987   -785       O
ATOM   6574  C2* MGT D   1     63.880 -15.578 -21.583  1.00 38.52            C
ANISOU 6574  C2* MGT D   1     4952   4355   5329    288    909   -890       C
ATOM   6575  O2* MGT D   1     63.571 -16.924 -21.181  1.00 41.39            O
ANISOU 6575  O2* MGT D   1     5434   4513   5779    262    869   -960       O
ATOM   6576  C1* MGT D   1     63.397 -14.606 -20.531  1.00 32.26            C
ANISOU 6576  C1* MGT D   1     4058   3655   4544    202    787   -739       C
ATOM   6577  N9  MGT D   1     61.985 -14.077 -20.575  1.00 30.62            N
ANISOU 6577  N9  MGT D   1     3877   3566   4190     57    691   -749       N
ATOM   6578  C8  MGT D   1     61.537 -13.152 -21.455  1.00 28.56            C
ANISOU 6578  C8  MGT D   1     3608   3474   3770     36    699   -767       C
ATOM   6579  N7  MGT D   1     60.245 -12.956 -21.135  1.00 28.87            N
ANISOU 6579  N7  MGT D   1     3649   3576   3745    -86    585   -769       N
ATOM   6580  CM7 MGT D   1     59.372 -12.016 -21.848  1.00 27.27            C
ANISOU 6580  CM7 MGT D   1     3432   3551   3377   -125    533   -779       C
ATOM   6581  C5  MGT D   1     59.872 -13.721 -20.082  1.00 29.90            C
ANISOU 6581  C5  MGT D   1     3792   3586   3983   -156    529   -750       C
ATOM   6582  C4  MGT D   1     61.017 -14.436 -19.739  1.00 29.44            C
ANISOU 6582  C4  MGT D   1     3754   3372   4059    -59    592   -730       C
```

FIGURE 18-189

| | | | | | | | |
|---|---|---|---|---|---|---|---|
| ATOM | 6583 | N3 | MGT D | 1 | 61.004 -15.292 -18.702 1.00 29.19 | | N |
| ANISOU | 6583 | N3 | MGT D | 1 | 3760 3183 4146 -86 553 -685 | | N |
| ATOM | 6584 | C2 | MGT D | 1 | 59.915 -15.502 -17.954 1.00 28.05 | | C |
| ANISOU | 6584 | C2 | MGT D | 1 | 3637 3026 3992 -223 481 -658 | | C |
| ATOM | 6585 | N2 | MGT D | 1 | 59.978 -16.375 -16.971 1.00 29.73 | | N |
| ANISOU | 6585 | N2 | MGT D | 1 | 3915 3072 4309 -246 463 -596 | | N |
| ATOM | 6586 | N1 | MGT D | 1 | 58.740 -14.829 -18.230 1.00 27.16 | | N |
| ANISOU | 6586 | N1 | MGT D | 1 | 3479 3073 3767 -332 434 -687 | | N |
| ATOM | 6587 | C6 | MGT D | 1 | 58.701 -13.917 -19.293 1.00 28.79 | | C |
| ANISOU | 6587 | C6 | MGT D | 1 | 3642 3444 3853 -290 443 -733 | | C |
| ATOM | 6588 | O6 | MGT D | 1 | 57.638 -13.327 -19.502 1.00 27.71 | | O |
| ANISOU | 6588 | O6 | MGT D | 1 | 3458 3444 3626 -368 381 -750 | | O |
| ATOM | 6589 | O2G | MGT E | 1 | 23.200 -31.391 -24.125 1.00 70.75 | | O |
| ANISOU | 6589 | O2G | MGT E | 1 | 9036 8796 9051 -973 -263 -1625 | | O |
| ATOM | 6590 | PG | MGT E | 1 | 23.830 -31.142 -22.645 1.00 68.95 | | P |
| ANISOU | 6590 | PG | MGT E | 1 | 8848 8360 8991 -906 -117 -1455 | | P |
| ATOM | 6591 | O3G | MGT E | 1 | 24.816 -29.813 -22.701 1.00 67.49 | | O |
| ANISOU | 6591 | O3G | MGT E | 1 | 8750 8226 8668 -768 -101 -1258 | | O |
| ATOM | 6592 | O1G | MGT E | 1 | 22.748 -30.981 -21.631 1.00 68.11 | | O |
| ANISOU | 6592 | O1G | MGT E | 1 | 8612 8217 9051 -935 -125 -1397 | | O |
| ATOM | 6593 | O3B | MGT E | 1 | 24.889 -32.361 -22.338 1.00 67.54 | | O |
| ANISOU | 6593 | O3B | MGT E | 1 | 8779 7972 8911 -938 27 -1554 | | O |
| ATOM | 6594 | PB | MGT E | 1 | 24.785 -33.870 -22.938 1.00 68.18 | | P |
| ANISOU | 6594 | PB | MGT E | 1 | 8880 7968 9058 -1057 39 -1813 | | P |
| ATOM | 6595 | O2B | MGT E | 1 | 25.148 -33.733 -24.532 1.00 69.37 | | O |
| ANISOU | 6595 | O2B | MGT E | 1 | 9066 8338 8953 -1050 -28 -1961 | | O |
| ATOM | 6596 | O1B | MGT E | 1 | 23.440 -34.487 -22.726 1.00 68.87 | | O |
| ANISOU | 6596 | O1B | MGT E | 1 | 8856 8032 9278 -1201 -15 -1906 | | O |
| ATOM | 6597 | O3A | MGT E | 1 | 25.997 -34.776 -22.240 1.00 65.43 | | O |
| ANISOU | 6597 | O3A | MGT E | 1 | 8646 7350 8863 -1017 183 -1825 | | O |
| ATOM | 6598 | PA | MGT E | 1 | 27.307 -34.306 -21.288 1.00 59.20 | | P |
| ANISOU | 6598 | PA | MGT E | 1 | 7934 6449 8110 -875 286 -1635 | | P |
| ATOM | 6599 | O2A | MGT E | 1 | 28.136 -33.197 -22.107 1.00 58.65 | | O |
| ANISOU | 6599 | O2A | MGT E | 1 | 7884 6588 7811 -779 280 -1588 | | O |
| ATOM | 6600 | O1A | MGT E | 1 | 28.129 -35.492 -20.942 1.00 59.66 | | O |
| ANISOU | 6600 | O1A | MGT E | 1 | 8071 6268 8331 -854 365 -1720 | | O |
| ATOM | 6601 | O5* | MGT E | 1 | 26.816 -33.620 -19.940 1.00 53.22 | | O |
| ANISOU | 6601 | O5* | MGT E | 1 | 7134 5651 7435 -863 299 -1411 | | O |
| ATOM | 6602 | C5* | MGT E | 1 | 26.613 -34.401 -18.761 1.00 47.71 | | C |
| ANISOU | 6602 | C5* | MGT E | 1 | 6458 4745 6925 -918 359 -1351 | | C |
| ATOM | 6603 | C4* | MGT E | 1 | 25.456 -33.830 -17.966 1.00 43.86 | | C |
| ANISOU | 6603 | C4* | MGT E | 1 | 5872 4324 6467 -983 346 -1240 | | C |
| ATOM | 6604 | O4* | MGT E | 1 | 25.786 -32.441 -17.660 1.00 39.94 | | O |
| ANISOU | 6604 | O4* | MGT E | 1 | 5354 3955 5866 -865 338 -1094 | | O |
| ATOM | 6605 | C3* | MGT E | 1 | 24.198 -33.807 -18.837 1.00 44.21 | | C |
| ANISOU | 6605 | C3* | MGT E | 1 | 5798 4523 6477 -1082 252 -1373 | | C |
| ATOM | 6606 | O3* | MGT E | 1 | 23.129 -34.318 -18.052 1.00 47.14 | | O |
| ANISOU | 6606 | O3* | MGT E | 1 | 6089 4833 6988 -1223 283 -1368 | | O |
| ATOM | 6607 | C2* | MGT E | 1 | 23.967 -32.325 -19.118 1.00 42.11 | | C |
| ANISOU | 6607 | C2* | MGT E | 1 | 5461 4470 6071 -979 178 -1280 | | C |
| ATOM | 6608 | O2* | MGT E | 1 | 22.556 -32.080 -19.141 1.00 44.49 | | O |
| ANISOU | 6608 | O2* | MGT E | 1 | 5604 4894 6405 -1051 104 -1318 | | O |
| ATOM | 6609 | C1* | MGT E | 1 | 24.614 -31.665 -17.889 1.00 36.11 | | C |
| ANISOU | 6609 | C1* | MGT E | 1 | 4744 3637 5341 -890 263 -1094 | | C |
| ATOM | 6610 | N9 | MGT E | 1 | 25.074 -30.253 -17.973 1.00 33.69 | | N |
| ANISOU | 6610 | N9 | MGT E | 1 | 4442 3438 4921 -758 232 -977 | | N |
| ATOM | 6611 | C8 | MGT E | 1 | 26.143 -29.848 -18.690 1.00 32.33 | | C |
| ANISOU | 6611 | C8 | MGT E | 1 | 4355 3300 4628 -678 226 -961 | | C |
| ATOM | 6612 | N7 | MGT E | 1 | 26.235 -28.515 -18.497 1.00 30.39 | | N |
| ANISOU | 6612 | N7 | MGT E | 1 | 4097 3125 4326 -592 200 -834 | | N |
| ATOM | 6613 | CM7 | MGT E | 1 | 27.291 -27.689 -19.147 1.00 30.36 | | C |
| ANISOU | 6613 | CM7 | MGT E | 1 | 4173 3175 4187 -519 196 -768 | | C |
| ATOM | 6614 | C5 | MGT E | 1 | 25.270 -28.075 -17.684 1.00 30.41 | | C |
| ANISOU | 6614 | C5 | MGT E | 1 | 4001 3137 4414 -594 187 -790 | | C |
| ATOM | 6615 | C4 | MGT E | 1 | 24.528 -29.207 -17.348 1.00 33.54 | | C |
| ANISOU | 6615 | C4 | MGT E | 1 | 4345 3484 4915 -708 216 -881 | | C |
| ATOM | 6616 | N3 | MGT E | 1 | 23.454 -29.116 -16.532 1.00 32.74 | | N |
| ANISOU | 6616 | N3 | MGT E | 1 | 4124 3405 4909 -756 232 -876 | | N |
| ATOM | 6617 | C2 | MGT E | 1 | 23.082 -27.949 -16.013 1.00 31.10 | | C |
| ANISOU | 6617 | C2 | MGT E | 1 | 3842 3265 4708 -674 218 -805 | | C |
| ATOM | 6618 | N2 | MGT E | 1 | 22.036 -27.912 -15.215 1.00 32.01 | | N |

FIGURE 18-190

```
ANISOU 6618  N2  MGT E   1      3821   3423   4917   -724    252   -831        N
ATOM   6619  N1  MGT E   1      23.783 -26.786 -16.310  1.00 30.29             N
ANISOU 6619  N1  MGT E   1      3801   3183   4526   -545    175   -716        N
ATOM   6620  C6  MGT E   1      24.887 -26.830 -17.148  1.00 31.43             C
ANISOU 6620  C6  MGT E   1      4072   3309   4562   -516    162   -696        C
ATOM   6621  O6  MGT E   1      25.482 -25.774 -17.398  1.00 30.00             O
ANISOU 6621  O6  MGT E   1      3944   3144   4312   -429    135   -607        O
ATOM   6622  O2G MGT F   1      30.350  -3.944 -65.480  1.00 99.58             O
ANISOU 6622  O2G MGT F   1     14031  16156   7647   -644      2   -439        O
ATOM   6623  PG  MGT F   1      28.875  -4.380 -64.937  1.00 97.98             P
ANISOU 6623  PG  MGT F   1     13719  15816   7693   -487   -380   -489        P
ATOM   6624  O3G MGT F   1      28.278  -5.473 -65.973  1.00100.06             O
ANISOU 6624  O3G MGT F   1     14125  16190   7703   -469   -516   -718        O
ATOM   6625  O1G MGT F   1      28.966  -4.930 -63.549  1.00 93.98             O
ANISOU 6625  O1G MGT F   1     12887  15191   7630   -397   -325   -595        O
ATOM   6626  O3B MGT F   1      27.926  -3.048 -65.157  1.00 97.20             O
ANISOU 6626  O3B MGT F   1     13810  15616   7506   -472   -688   -195        O
ATOM   6627  PB  MGT F   1      26.314  -3.046 -64.848  1.00 94.58             P
ANISOU 6627  PB  MGT F   1     13385  15180   7372   -321  -1114   -191        P
ATOM   6628  O2B MGT F   1      25.693  -3.980 -66.039  1.00 96.13             O
ANISOU 6628  O2B MGT F   1     13730  15529   7265   -323  -1304   -385        O
ATOM   6629  O1B MGT F   1      25.707  -1.684 -64.850  1.00 95.46             O
ANISOU 6629  O1B MGT F   1     13630  15170   7470   -262  -1343     89        O
ATOM   6630  O3A MGT F   1      26.194  -3.836 -63.403  1.00 86.47             O
ANISOU 6630  O3A MGT F   1     11980  14048   6828   -253  -1036   -362        O
ATOM   6631  PA  MGT F   1      25.747  -3.160 -61.969  1.00 79.76             P
ANISOU 6631  PA  MGT F   1     10904  13006   6395   -173  -1093   -247        P
ATOM   6632  O2A MGT F   1      25.428  -4.445 -61.045  1.00 77.01             O
ANISOU 6632  O2A MGT F   1     10293  12609   6357   -138  -1050   -494        O
ATOM   6633  O1A MGT F   1      24.575  -2.250 -62.103  1.00 81.05             O
ANISOU 6633  O1A MGT F   1     11113  13096   6587    -75  -1414    -96        O
ATOM   6634  O5* MGT F   1      27.022  -2.434 -61.277  1.00 74.56             O
ANISOU 6634  O5* MGT F   1     10228  12289   5813   -247   -803   -111        O
ATOM   6635  C5* MGT F   1      27.118  -0.995 -61.342  1.00 70.02             C
ANISOU 6635  C5* MGT F   1      9816  11623   5166   -279   -837    152        C
ATOM   6636  C4* MGT F   1      28.554  -0.539 -61.633  1.00 66.55             C
ANISOU 6636  C4* MGT F   1      9491  11251   4545   -450   -529    235        C
ATOM   6637  O4* MGT F   1      29.365  -1.421 -60.821  1.00 62.48             O
ANISOU 6637  O4* MGT F   1      8711  10787   4243   -457   -310     45        O
ATOM   6638  C3* MGT F   1      29.017  -0.716 -63.097  1.00 67.92             C
ANISOU 6638  C3* MGT F   1      9926  11602   4279   -559   -437    229        C
ATOM   6639  O3* MGT F   1      29.464   0.547 -63.638  1.00 71.23             O
ANISOU 6639  O3* MGT F   1     10633  11975   4455   -700   -363    483        O
ATOM   6640  C2* MGT F   1      30.204  -1.684 -63.020  1.00 65.40             C
ANISOU 6640  C2* MGT F   1      9433  11442   3975   -628   -112     11        C
ATOM   6641  O2* MGT F   1      31.280  -1.234 -63.872  1.00 65.11             O
ANISOU 6641  O2* MGT F   1      9573  11538   3626   -817    163     74        O
ATOM   6642  C1* MGT F   1      30.610  -1.563 -61.542  1.00 60.72             C
ANISOU 6642  C1* MGT F   1      8551  10736   3784   -595    -29      0        C
ATOM   6643  N9  MGT F   1      31.361  -2.695 -60.897  1.00 58.13             N
ANISOU 6643  N9  MGT F   1      7951  10481   3654   -540    147   -237        N
ATOM   6644  C8  MGT F   1      30.774  -3.809 -60.424  1.00 56.15             C
ANISOU 6644  C8  MGT F   1      7571  10180   3582   -396     36   -414        C
ATOM   6645  N7  MGT F   1      31.776  -4.546 -59.912  1.00 55.98             N
ANISOU 6645  N7  MGT F   1      7360  10216   3694   -359    232   -573        N
ATOM   6646  CM7 MGT F   1      31.556  -5.890 -59.278  1.00 54.61             C
ANISOU 6646  CM7 MGT F   1      7057   9970   3722   -208    191   -783        C
ATOM   6647  C5  MGT F   1      32.960  -3.927 -60.039  1.00 57.17             C
ANISOU 6647  C5  MGT F   1      7463  10481   3778   -476    459   -522        C
ATOM   6648  C4  MGT F   1      32.671  -2.722 -60.675  1.00 58.35             C
ANISOU 6648  C4  MGT F   1      7834  10615   3719   -617    418   -299        C
ATOM   6649  N3  MGT F   1      33.637  -1.831 -60.974  1.00 59.84             N
ANISOU 6649  N3  MGT F   1      8063  10888   3784   -804    632   -191        N
ATOM   6650  C2  MGT F   1      34.924  -2.053 -60.665  1.00 60.72             C
ANISOU 6650  C2  MGT F   1      7940  11139   3992   -862    890   -315        C
ATOM   6651  N2  MGT F   1      35.834  -1.129 -60.973  1.00 62.34             N
ANISOU 6651  N2  MGT F   1      8169  11434   4084  -1091   1115   -218        N
ATOM   6652  N1  MGT F   1      35.287  -3.254 -60.011  1.00 59.54             N
ANISOU 6652  N1  MGT F   1      7525  11029   4067   -680    912   -549        N
ATOM   6653  C6  MGT F   1      34.299  -4.207 -59.684  1.00 57.63             C
ANISOU 6653  C6  MGT F   1      7300  10661   3935   -485    696   -642        C
```

FIGURE 18-191

```
ATOM    6654  O6  MGT F   1      34.635  -5.252 -59.114  1.00 55.72           O
ANISOU  6654  O6  MGT F   1       6882   10416   3874    -329   718    -828   O
ATOM    6655  OH2 WAT Z   1      22.010 -17.664  -4.923  1.00 24.01           O
ATOM    6656  OH2 WAT Z   2      35.587 -15.501 -13.579  1.00 25.92           O
ATOM    6657  OH2 WAT Z   3      24.874  18.972 -29.481  1.00 17.82           O
ATOM    6658  OH2 WAT Z   4      22.669  -1.536 -24.962  1.00 13.35           O
ATOM    6659  OH2 WAT Z   5      52.591 -14.211  -5.902  1.00 21.48           O
ATOM    6660  OH2 WAT Z   7      13.160   0.537   1.189  1.00 23.18           O
ATOM    6661  OH2 WAT Z   8      25.007  17.823 -32.038  1.00 17.76           O
ATOM    6662  OH2 WAT Z   9      57.764   0.177  -1.188  1.00 25.56           O
ATOM    6663  OH2 WAT Z  10      22.557  -2.907 -16.078  1.00 29.94           O
ATOM    6664  OH2 WAT Z  11       0.415  -4.929 -12.849  1.00 25.54           O
ATOM    6665  OH2 WAT Z  12      21.159   3.266  -9.320  1.00 33.91           O
ATOM    6666  OH2 WAT Z  13      29.894  16.381 -39.221  1.00 27.21           O
ATOM    6667  OH2 WAT Z  14      48.790  14.910 -10.474  1.00 28.71           O
ATOM    6668  OH2 WAT Z  15      51.978 -20.700 -11.448  1.00 26.98           O
ATOM    6669  OH2 WAT Z  16      52.522   8.682 -31.531  1.00 27.48           O
ATOM    6670  OH2 WAT Z  17      71.301  -1.768 -14.451  1.00 22.48           O
ATOM    6671  OH2 WAT Z  18      27.320 -22.307 -20.123  1.00 19.55           O
ATOM    6672  OH2 WAT Z  19      34.964  21.944  -4.871  1.00 23.06           O
ATOM    6673  OH2 WAT Z  21      23.902 -22.328 -16.923  1.00 23.97           O
ATOM    6674  OH2 WAT Z  22      48.357  -2.830 -15.780  1.00 34.81           O
ATOM    6675  OH2 WAT Z  23      58.588   5.961 -27.382  1.00 19.01           O
ATOM    6676  OH2 WAT Z  24      18.628  15.589 -17.793  1.00 30.46           O
ATOM    6677  OH2 WAT Z  25      19.270 -18.539 -13.641  1.00 21.85           O
ATOM    6678  OH2 WAT Z  26      43.558  13.915 -26.424  1.00 17.33           O
ATOM    6679  OH2 WAT Z  27      26.542 -12.581 -16.266  1.00 26.41           O
ATOM    6680  OH2 WAT Z  28      34.875  33.272 -20.697  1.00 21.41           O
ATOM    6681  OH2 WAT Z  29      13.457 -11.350 -34.721  1.00 35.91           O
ATOM    6682  OH2 WAT Z  30      25.564  10.236 -30.803  1.00 24.48           O
ATOM    6683  OH2 WAT Z  31      45.958 -26.847 -21.485  1.00 27.96           O
ATOM    6684  OH2 WAT Z  32      35.988 -22.594   2.913  1.00 21.42           O
ATOM    6685  OH2 WAT Z  33      54.562 -14.794 -17.888  1.00 22.27           O
ATOM    6686  OH2 WAT Z  34      22.529   2.193 -30.694  1.00 27.64           O
ATOM    6687  OH2 WAT Z  35      25.635  -4.794 -32.881  1.00 28.73           O
ATOM    6688  OH2 WAT Z  36      27.823  20.133  -0.039  1.00 36.81           O
ATOM    6689  OH2 WAT Z  37      20.246  12.658 -31.810  1.00 24.61           O
ATOM    6690  OH2 WAT Z  38      28.300 -37.005 -18.759  1.00 51.31           O
ATOM    6691  OH2 WAT Z  39      53.886 -12.268 -21.629  1.00 17.36           O
ATOM    6692  OH2 WAT Z  40      48.741  -7.083 -24.282  1.00 24.97           O
ATOM    6693  OH2 WAT Z  41      56.501 -23.941 -22.749  1.00 33.42           O
ATOM    6694  OH2 WAT Z  42      70.436   0.347 -12.882  1.00 19.32           O
ATOM    6695  OH2 WAT Z  43      25.679   6.098 -19.237  1.00 22.39           O
ATOM    6696  OH2 WAT Z  44      32.839  32.448 -18.714  1.00 35.80           O
ATOM    6697  OH2 WAT Z  45      13.259 -14.963 -26.829  1.00 23.85           O
ATOM    6698  OH2 WAT Z  46      45.572 -27.223 -24.539  1.00 26.82           O
ATOM    6699  OH2 WAT Z  47      18.892  12.226  -9.507  1.00 24.12           O
ATOM    6700  OH2 WAT Z  48      15.179  -6.957   4.889  1.00 33.18           O
ATOM    6701  OH2 WAT Z  49      28.351   4.517 -12.106  1.00 29.12           O
ATOM    6702  OH2 WAT Z  50      69.753  -7.784 -22.150  1.00 24.16           O
ATOM    6703  OH2 WAT Z  51      51.484 -18.920 -13.213  1.00 25.28           O
ATOM    6704  OH2 WAT Z  52      30.860  13.483  -5.891  1.00 23.31           O
ATOM    6705  OH2 WAT Z  53      30.542 -37.628 -17.641  1.00 34.32           O
ATOM    6706  OH2 WAT Z  54      17.077 -19.149 -12.084  1.00 24.17           O
ATOM    6707  OH2 WAT Z  55      31.540 -38.915 -14.093  1.00 29.25           O
ATOM    6708  OH2 WAT Z  56      32.031  10.317  -7.068  1.00 23.87           O
ATOM    6709  OH2 WAT Z  57      63.159 -12.048 -28.694  1.00 38.66           O
ATOM    6710  OH2 WAT Z  60      32.626 -17.204 -22.492  1.00 28.77           O
ATOM    6711  OH2 WAT Z  61      13.024 -14.857 -24.008  1.00 21.66           O
ATOM    6712  OH2 WAT Z  62      16.501   7.671 -21.877  1.00 22.39           O
ATOM    6713  OH2 WAT Z  63      26.459   8.287 -33.540  1.00 44.16           O
ATOM    6714  OH2 WAT Z  64      51.383 -16.236  -0.275  1.00 35.25           O
ATOM    6715  OH2 WAT Z  65      55.449   4.737 -37.070  1.00 38.33           O
ATOM    6716  OH2 WAT Z  66      18.627  -7.775 -42.508  1.00 43.11           O
ATOM    6717  OH2 WAT Z  67      25.172  -1.387 -16.895  1.00 32.89           O
ATOM    6718  OH2 WAT Z  68      63.541   6.400   3.498  1.00 39.85           O
ATOM    6719  OH2 WAT Z  69      58.234   5.010 -30.073  1.00 27.73           O
ATOM    6720  OH2 WAT Z  70      40.724  12.891 -10.774  1.00 30.83           O
ATOM    6721  OH2 WAT Z  71      24.900  12.576 -19.843  1.00 20.19           O
ATOM    6722  OH2 WAT Z  72      49.784  -6.304  -7.577  1.00 31.08           O
ATOM    6723  OH2 WAT Z  73      27.087  40.698 -13.760  1.00 41.38           O
```

FIGURE 18-192

```
ATOM   6724  OH2 WAT Z  74      76.962   7.731  -7.980  1.00 33.08      O
ATOM   6725  OH2 WAT Z  75      23.651  14.328 -38.716  1.00 32.75      O
ATOM   6726  OH2 WAT Z  76      11.075   7.898  -8.738  1.00 37.62      O
ATOM   6727  OH2 WAT Z  77      17.338   4.404 -24.665  1.00 17.00      O
ATOM   6728  OH2 WAT Z  78      16.077 -25.529 -23.013  1.00 30.89      O
ATOM   6729  OH2 WAT Z  79      53.527  14.001 -17.979  1.00 27.27      O
ATOM   6730  OH2 WAT Z  80      34.264  14.194 -45.137  1.00 32.07      O
ATOM   6731  OH2 WAT Z  82      42.478  -8.305  -9.650  1.00 29.55      O
ATOM   6732  OH2 WAT Z  83      15.985  -6.541 -42.463  1.00 28.85      O
ATOM   6733  OH2 WAT Z  84      34.516   8.340 -25.756  1.00 25.94      O
ATOM   6734  OH2 WAT Z  85      58.379  -1.510 -36.376  1.00 38.41      O
ATOM   6735  OH2 WAT Z  86      37.811   8.922 -27.105  1.00 22.11      O
ATOM   6736  OH2 WAT Z  87      -0.391  -3.769 -14.739  1.00 35.30      O
ATOM   6737  OH2 WAT Z  88      43.490  14.702  -6.036  1.00 32.76      O
ATOM   6738  OH2 WAT Z  89      66.881   0.967 -35.813  1.00 29.64      O
ATOM   6739  OH2 WAT Z  90      50.228  23.440 -23.336  1.00 25.56      O
ATOM   6740  OH2 WAT Z  91      18.346 -19.140 -26.919  1.00 38.45      O
ATOM   6741  OH2 WAT Z  93      33.957  31.768 -27.497  1.00 34.70      O
ATOM   6742  OH2 WAT Z  94      15.782  16.563 -13.960  1.00 25.91      O
ATOM   6743  OH2 WAT Z  95      48.925   4.506   4.193  1.00 30.06      O
ATOM   6744  OH2 WAT Z  96      55.094   8.303   2.407  1.00 32.94      O
ATOM   6745  OH2 WAT Z  97      23.845  23.584 -12.034  1.00 27.82      O
ATOM   6746  OH2 WAT Z  98      19.282  13.117 -18.942  1.00 28.06      O
ATOM   6747  OH2 WAT Z  99      21.689 -13.748 -35.649  1.00 30.66      O
ATOM   6748  OH2 WAT Z 100      30.856  27.498 -24.106  1.00 31.84      O
ATOM   6749  OH2 WAT Z 101      46.475  15.139 -23.225  1.00 30.44      O
ATOM   6750  OH2 WAT Z 102      75.808   3.111  -8.446  1.00 33.80      O
ATOM   6751  OH2 WAT Z 103      22.117  -4.088 -48.032  1.00 47.28      O
ATOM   6752  OH2 WAT Z 104      19.417  -9.956 -43.103  1.00 37.00      O
ATOM   6753  OH2 WAT Z 105      50.959  14.958  -6.038  1.00 28.24      O
ATOM   6754  OH2 WAT Z 106      12.824 -14.262 -55.184  1.00 53.76      O
ATOM   6755  OH2 WAT Z 107      24.243 -15.291 -17.663  1.00 39.66      O
ATOM   6756  OH2 WAT Z 108      42.270  21.564 -34.734  1.00 24.55      O
ATOM   6757  OH2 WAT Z 109      16.713 -20.968  -7.090  1.00 27.98      O
ATOM   6758  OH2 WAT Z 110      36.477 -16.419 -21.410  1.00 48.83      O
ATOM   6759  OH2 WAT Z 111      35.351  16.445 -10.062  1.00 50.87      O
ATOM   6760  OH2 WAT Z 112      24.841  -4.261  -4.666  1.00 30.33      O
ATOM   6761  OH2 WAT Z 113       4.786  -8.000 -18.626  1.00 35.35      O
ATOM   6762  OH2 WAT Z 114      10.306  -1.689 -38.133  1.00 26.41      O
ATOM   6763  OH2 WAT Z 115      42.924 -19.244 -23.456  1.00 34.89      O
ATOM   6764  OH2 WAT Z 116      42.206  12.907  -6.861  1.00 25.28      O
ATOM   6765  OH2 WAT Z 117      51.605  13.100 -19.296  1.00 31.95      O
ATOM   6766  OH2 WAT Z 118      16.469  13.514  -8.427  1.00 45.86      O
ATOM   6767  OH2 WAT Z 119      50.036   4.161 -29.744  1.00 25.55      O
ATOM   6768  OH2 WAT Z 120      16.233  10.887 -35.555  1.00 41.62      O
ATOM   6769  OH2 WAT Z 121      22.532   0.490 -33.852  1.00 27.81      O
ATOM   6770  OH2 WAT Z 123      19.367 -19.611 -56.734  1.00 31.09      O
ATOM   6771  OH2 WAT Z 124      46.548 -25.852 -32.207  1.00 41.02      O
ATOM   6772  OH2 WAT Z 125      27.102 -32.879  -5.267  1.00 28.86      O
ATOM   6773  OH2 WAT Z 126      49.465   4.075  -4.211  1.00 29.62      O
ATOM   6774  OH2 WAT Z 127      68.660  -0.401 -18.608  1.00 38.81      O
ATOM   6775  OH2 WAT Z 128      28.488 -14.653  -2.031  1.00 33.34      O
ATOM   6776  OH2 WAT Z 129      38.691  29.556 -29.045  1.00 27.56      O
ATOM   6777  OH2 WAT Z 130      20.046  14.970  -5.630  1.00 35.59      O
ATOM   6778  OH2 WAT Z 131      21.161  -5.035  -2.609  1.00 24.94      O
ATOM   6779  OH2 WAT Z 132      39.421 -26.828   9.622  1.00 57.63      O
ATOM   6780  OH2 WAT Z 133      30.273 -15.692  -5.914  1.00 26.45      O
ATOM   6781  OH2 WAT Z 134      40.038 -33.801 -13.906  1.00 35.26      O
ATOM   6782  OH2 WAT Z 135      50.389   2.298 -27.656  1.00 26.52      O
ATOM   6783  OH2 WAT Z 136      42.086   7.582 -31.511  1.00 36.58      O
ATOM   6784  OH2 WAT Z 137      50.049 -21.915 -25.630  1.00 29.44      O
ATOM   6785  OH2 WAT Z 138      54.096  17.394 -14.365  1.00 26.83      O
ATOM   6786  OH2 WAT Z 139      53.457  22.759 -18.096  1.00 29.22      O
ATOM   6787  OH2 WAT Z 140      47.276 -14.555 -17.579  1.00 28.30      O
ATOM   6788  OH2 WAT Z 141      29.621  27.139  -8.722  1.00 19.74      O
ATOM   6789  OH2 WAT Z 142      21.551 -15.531 -46.177  1.00 37.12      O
ATOM   6790  OH2 WAT Z 143       0.081  -2.053  -6.723  1.00 35.12      O
ATOM   6791  OH2 WAT Z 145       2.708  -6.704 -12.288  1.00 29.20      O
ATOM   6792  OH2 WAT Z 146      48.187  -3.807 -23.913  1.00 39.45      O
ATOM   6793  OH2 WAT Z 147      35.518  -9.414 -58.946  1.00 49.19      O
ATOM   6794  OH2 WAT Z 149      50.661   6.651  -2.459  1.00 31.55      O
```

FIGURE 18-193

```
ATOM   6795  OH2 WAT Z 150       6.977  -4.292   5.382  1.00 33.62      O
ATOM   6796  OH2 WAT Z 151      70.053  -2.697 -21.777  1.00 35.37      O
ATOM   6797  OH2 WAT Z 152      26.405 -25.745 -56.037  1.00 54.31      O
ATOM   6798  OH2 WAT Z 153      21.807 -11.348 -34.300  1.00 36.00      O
ATOM   6799  OH2 WAT Z 155      61.988  12.944  -9.997  1.00 37.17      O
ATOM   6800  OH2 WAT Z 156      48.957  -7.172  -3.666  1.00 35.39      O
ATOM   6801  OH2 WAT Z 157       9.240  15.496 -16.665  1.00 37.22      O
ATOM   6802  OH2 WAT Z 158      22.966  -4.323 -23.838  1.00 42.19      O
ATOM   6803  OH2 WAT Z 159       4.714 -15.721  -5.172  1.00 39.15      O
ATOM   6804  OH2 WAT Z 160      23.677  12.223 -38.115  1.00 37.72      O
ATOM   6805  OH2 WAT Z 161      40.873 -28.484 -31.719  1.00 49.84      O
ATOM   6806  OH2 WAT Z 162      20.764 -17.215 -48.256  1.00 30.64      O
ATOM   6807  OH2 WAT Z 163      46.257   2.134  -5.934  1.00 28.45      O
ATOM   6808  OH2 WAT Z 164       1.102  -0.339 -23.846  1.00 33.06      O
ATOM   6809  OH2 WAT Z 165      56.153 -23.889 -11.833  1.00 51.89      O
ATOM   6810  OH2 WAT Z 166      46.513 -37.594 -25.306  1.00 42.87      O
ATOM   6811  OH2 WAT Z 167      31.205 -31.346 -33.201  1.00 37.47      O
ATOM   6812  OH2 WAT Z 168      46.736 -32.410 -16.066  1.00 48.36      O
ATOM   6813  OH2 WAT Z 169      16.920 -25.816 -15.401  1.00 43.16      O
ATOM   6814  OH2 WAT Z 170      40.084  28.332 -35.998  1.00 31.80      O
ATOM   6815  OH2 WAT Z 171      43.734  19.350 -33.881  1.00 29.51      O
ATOM   6816  OH2 WAT Z 172      26.493  -8.330 -14.753  1.00 32.62      O
ATOM   6817  OH2 WAT Z 173      33.748   4.983 -37.285  1.00 33.47      O
ATOM   6818  OH2 WAT Z 175      56.484 -13.704  -3.695  1.00 32.87      O
ATOM   6819  OH2 WAT Z 176      27.269  -8.161 -63.691  1.00 43.49      O
ATOM   6820  OH2 WAT Z 177      50.087  -8.525  -2.162  1.00 26.01      O
ATOM   6821  OH2 WAT Z 179      36.074 -14.083  -7.400  1.00 33.95      O
ATOM   6822  OH2 WAT Z 180      21.712 -14.738 -31.372  1.00 41.69      O
ATOM   6823  OH2 WAT Z 181      66.636  -9.970  -8.729  1.00 30.38      O
ATOM   6824  OH2 WAT Z 182      65.403 -12.027  -5.047  1.00 39.48      O
ATOM   6825  OH2 WAT Z 183      25.708  11.169 -43.671  1.00 35.61      O
ATOM   6826  OH2 WAT Z 184      51.471 -10.298 -38.366  1.00 45.24      O
ATOM   6827  OH2 WAT Z 185      13.816  14.588 -29.069  1.00 30.39      O
ATOM   6828  OH2 WAT Z 186      25.401  24.637   0.808  1.00 42.63      O
ATOM   6829  OH2 WAT Z 187      24.141   3.660  -9.953  1.00 41.40      O
ATOM   6830  OH2 WAT Z 188      50.530  -7.054 -30.104  1.00 37.25      O
ATOM   6831  OH2 WAT Z 189      17.307 -28.578  -8.340  1.00 37.35      O
ATOM   6832  OH2 WAT Z 190      23.215  -2.485  -9.503  1.00 34.35      O
ATOM   6833  OH2 WAT Z 191      25.409 -36.972 -21.377  1.00 28.84      O
ATOM   6834  OH2 WAT Z 192      32.293   9.056 -52.850  1.00 53.81      O
ATOM   6835  OH2 WAT Z 194       9.854 -20.178  -8.716  1.00 47.33      O
ATOM   6836  OH2 WAT Z 195      45.448   7.502 -21.691  1.00 37.17      O
ATOM   6837  OH2 WAT Z 196      41.211 -41.959 -28.245  1.00 48.32      O
ATOM   6838  OH2 WAT Z 197      35.027 -38.234 -17.129  1.00 46.15      O
ATOM   6839  OH2 WAT Z 198      30.945   3.849 -33.630  1.00 38.01      O
ATOM   6840  OH2 WAT Z 199      10.582   3.216 -30.915  1.00 30.78      O
ATOM   6841  OH2 WAT Z 200      38.611 -12.140 -47.412  1.00 34.67      O
ATOM   6842  OH2 WAT Z 201      17.623  19.014 -29.499  1.00 56.25      O
ATOM   6843  OH2 WAT Z 202      48.293  17.619 -42.569  1.00 39.31      O
ATOM   6844  OH2 WAT Z 203      28.384  15.063  -3.883  1.00 41.61      O
ATOM   6845  OH2 WAT Z 204      35.579   3.773 -42.257  1.00 44.44      O
ATOM   6846  OH2 WAT Z 205      20.437 -13.266 -15.586  1.00 23.67      O
ATOM   6847  OH2 WAT Z 206      38.154   5.184 -40.233  1.00 49.51      O
ATOM   6848  OH2 WAT Z 207      45.198  22.725 -11.680  1.00 41.39      O
ATOM   6849  OH2 WAT Z 208      36.171 -18.123 -57.255  1.00 45.32      O
ATOM   6850  OH2 WAT Z 209      20.057   7.547  -4.988  1.00 40.68      O
ATOM   6851  OH2 WAT Z 210      40.148   3.860 -50.600  1.00 35.38      O
ATOM   6852  OH2 WAT Z 211      45.636  -6.474 -29.807  1.00 52.09      O
ATOM   6853  OH2 WAT Z 212      45.277  22.770  -9.176  1.00 24.03      O
ATOM   6854  OH2 WAT Z 213      33.172   4.773 -32.693  1.00 35.71      O
ATOM   6855  OH2 WAT Z 214      33.650 -19.496 -30.848  1.00 39.27      O
ATOM   6856  OH2 WAT Z 215      46.592  -5.388 -49.721  1.00 39.74      O
ATOM   6857  OH2 WAT Z 216      35.963 -38.228  -8.201  1.00 32.99      O
ATOM   6858  OH2 WAT Z 217      42.449 -15.437   1.419  1.00 33.54      O
ATOM   6859  OH2 WAT Z 218      17.500 -25.027  -8.417  1.00 31.46      O
ATOM   6860  OH2 WAT Z 219      24.656  -8.332 -63.244  1.00 41.72      O
ATOM   6861  OH2 WAT Z 220      30.837   2.476 -36.522  1.00 34.45      O
ATOM   6862  OH2 WAT Z 221      54.803 -22.398 -30.205  1.00 48.05      O
ATOM   6863  OH2 WAT Z 222      46.624  -6.685  -7.840  1.00 45.14      O
ATOM   6864  OH2 WAT Z 223      69.977   0.204  -6.062  1.00 29.12      O
ATOM   6865  OH2 WAT Z 224      27.484   9.235 -45.269  1.00 41.47      O
```

FIGURE 18-194

```
ATOM   6866  OH2 WAT Z 225      39.053  12.272  -7.273  1.00 35.61           O
ATOM   6867  OH2 WAT Z 226      33.654 -11.620 -71.645  1.00 32.99           O
ATOM   6868  OH2 WAT Z 227      37.763 -36.609  -6.731  1.00 39.13           O
ATOM   6869  OH2 WAT Z 228      43.789  -6.817 -64.285  1.00 35.87           O
ATOM   6870  OH2 WAT Z 229      15.841   7.668 -39.846  1.00 42.57           O
ATOM   6871  OH2 WAT Z 230      49.470  -7.674 -32.876  1.00 39.94           O
ATOM   6872  OH2 WAT Z 231      73.132  -6.437 -11.485  1.00 43.64           O
ATOM   6873  OH2 WAT Z 232      69.189 -10.890  -8.124  1.00 43.10           O
ATOM   6874  OH2 WAT Z 233      68.220   1.931  -4.425  1.00 35.19           O
ATOM   6875  OH2 WAT Z 234      -0.117   0.428 -21.467  1.00 53.29           O
ATOM   6876  OH2 WAT Z 235      22.121  -3.444   6.017  1.00 34.04           O
ATOM   6877  OH2 WAT Z 236      12.296  14.675 -22.643  1.00 46.28           O
ATOM   6878  OH2 WAT Z 237      14.515  13.822  -6.990  1.00 44.07           O
ATOM   6879  OH2 WAT Z 238       8.264   1.618 -31.428  1.00 31.10           O
ATOM   6880  OH2 WAT Z 239      18.004  15.205  -9.508  1.00 43.87           O
ATOM   6881  OH2 WAT Z 240      26.138  -4.555  -6.867  1.00 38.79           O
ATOM   6882  OH2 WAT Z 241      44.614   6.587 -19.546  1.00 22.31           O
ATOM   6883  OH2 WAT Z 242      42.232  28.400 -29.247  1.00 39.83           O
ATOM   6884  OH2 WAT Z 243      35.090  10.219 -18.144  1.00 42.61           O
ATOM   6885  OH2 WAT Z 244      42.707   7.488 -22.667  1.00 26.48           O
ATOM   6886  OH2 WAT Z 245       5.481 -13.489 -33.682  1.00 42.88           O
ATOM   6887  OH2 WAT Z 246      24.380   4.187 -32.955  1.00 35.24           O
ATOM   6888  OH2 WAT Z 247      57.349  26.834 -15.600  1.00 57.46           O
ATOM   6889  OH2 WAT Z 248      36.055 -30.582   3.645  1.00 49.07           O
ATOM   6890  OH2 WAT Z 249      34.660 -36.210  -0.590  1.00 38.86           O
ATOM   6891  OH2 WAT Z 250      44.202   2.988 -16.631  1.00 34.41           O
ATOM   6892  OH2 WAT Z 251      28.312 -18.014 -27.408  1.00 47.07           O
ATOM   6893  OH2 WAT Z 252      43.871   7.890 -38.332  1.00 39.41           O
ATOM   6894  OH2 WAT Z 254      35.217 -18.557  -4.263  1.00 39.96           O
ATOM   6895  OH2 WAT Z 256      10.973  15.666 -13.469  1.00 51.73           O
ATOM   6896  OH2 WAT Z 257      63.806   8.757 -23.338  1.00 49.41           O
ATOM   6897  OH2 WAT Z 258      30.195  19.858 -45.928  1.00 40.05           O
ATOM   6898  OH2 WAT Z 259      45.473 -17.828 -14.547  1.00 34.13           O
ATOM   6899  OH2 WAT Z 261      32.026  -1.032 -32.780  1.00 55.96           O
ATOM   6900  OH2 WAT Z 263      11.334 -21.951 -13.454  1.00 54.94           O
ATOM   6901  OH2 WAT Z 264      34.852  11.262 -11.695  1.00 56.14           O
ATOM   6902  OH2 WAT Z 265      50.631 -23.856 -26.444  1.00 33.63           O
ATOM   6903  OH2 WAT Z 266      28.803  -8.481   0.380  1.00 46.99           O
ATOM   6904  OH2 WAT Z 268      60.910 -11.529 -36.250  1.00 42.92           O
ATOM   6905  OH2 WAT Z 269      29.242  24.796 -47.351  1.00 47.76           O
ATOM   6906  OH2 WAT Z 270      25.353 -10.071 -20.464  1.00 44.62           O
ATOM   6907  OH2 WAT Z 271      21.773 -15.534 -15.644  1.00 27.98           O
ATOM   6908  OH2 WAT Z 272      43.832  29.110 -16.193  1.00 29.32           O
ATOM   6909  OH2 WAT Z 274      24.253   7.923 -25.411  1.00 52.09           O
ATOM   6910  OH2 WAT Z 275      41.167  -6.372 -42.144  1.00 44.79           O
ATOM   6911  OH2 WAT Z 276      51.558 -15.128  -4.442  1.00 26.03           O
ATOM   6912  OH2 WAT Z 277      27.750 -30.861 -21.049  1.00 38.16           O
ATOM   6913  OH2 WAT Z 278      54.407   4.151   7.215  1.00 52.58           O
ATOM   6914  OH2 WAT Z 279      34.111  20.624  -3.191  1.00 50.26           O
ATOM   6915  OH2 WAT Z 280      47.178   7.039 -25.319  1.00 49.30           O
ATOM   6916  OH2 WAT Z 281      47.157 -37.019 -13.327  1.00 40.78           O
ATOM   6917  OH2 WAT Z 282      39.719 -34.762  -7.503  1.00 35.67           O
ATOM   6918  OH2 WAT Z 283      22.466 -13.541 -17.364  1.00 61.73           O
ATOM   6919  OH2 WAT Z 284      46.118  -4.589 -17.951  1.00 44.94           O
ATOM   6920  OH2 WAT Z 285      20.024 -16.482  -0.472  1.00 35.25           O
ATOM   6921  OH2 WAT Z 286      20.617  -3.221 -30.981  1.00 26.80           O
ATOM   6922  OH2 WAT Z 287      14.396  11.159  -7.209  1.00 48.86           O
ATOM   6923  OH2 WAT Z 288       1.963   6.454 -25.094  1.00 54.37           O
ATOM   6924  OH2 WAT Z 290      27.856  10.495 -28.946  1.00 31.74           O
ATOM   6925  OH2 WAT Z 291      20.937 -11.628 -24.894  1.00 33.25           O
ATOM   6926  OH2 WAT Z 293      29.682  29.704  -7.204  1.00 42.07           O
END
```

SOLUBLE FRAGMENTS OF INFLUENZA VIRUS PB2 PROTEIN CAPABLE OF BINDING RNA-CAP

CROSS-REFERENCE TO RELATED APPLICATION

This application is a National Stage filing of International Application Serial No. PCT/EP2008/008543, filed Oct. 9, 2008, which claims the benefit of U.S. Provisional Application Ser. Nos. 60/998,398 filed Oct. 9, 2007, 61/070,792 filed Mar. 25, 2008; and 61/123,456 filed Apr. 8, 2008, the disclosures of which are expressly incorporated herein by reference.

TECHNICAL FIELD OF INVENTION

The present invention relates to soluble fragments of the Influenza virus RNA dependent RNA polymerase subunit PB2 and variants thereof, and crystallized complexes thereof comprising an RNA cap analog. This invention also relates to computational methods using the structural coordinates of said complex to screen for and design compounds that interact with the RNA cap binding pocket. In addition, this invention relates to methods identifying compounds that bind to PB2 polypeptide fragments comprising the RNA cap binding pocket, preferably inhibit the interaction with RNA caps or analogs thereof, by using said PB2 polypeptide fragments, preferably in a high-throughput setting. This invention also relates to compounds and pharmaceutical compositions comprising the identified compounds for the treatment of disease conditions due to viral infections caused by negative-sense single stranded RNA viruses.

BACKGROUND OF THE INVENTION

Influenza is responsible for much morbidity and mortality in the world and is considered by many as belonging to the most significant viral threats to humans. Annual Influenza epidemics swipe the globe and occasional new virulent strains cause pandemics of great destructive power. At present the primary means of controlling Influenza virus epidemics is vaccination. However, mutant Influenza viruses are rapidly generated which escape the effects of vaccination. In the light of the fact that it takes approximately 6 months to generate a new Influenza vaccine, alternative therapeutic means, i.e., antiviral medication, are required especially as the first line of defense against a rapidly spreading pandemic.

An excellent starting point for the development of antiviral medication is structural data of essential viral proteins. Thus, the crystal structure determination of the Influenza virus surface antigen neuraminidase (von Itzstein et al., 1993) led directly to the development of neuraminidase inhibitors with anti-viral activity preventing the release of virus from the cells, however, not the virus production. These and their derivatives have subsequently developed into the anti-Influenza drugs, zanamivir (Glaxo) and oseltamivir (Roche), which are currently being stockpiled by many countries as a first line of defense against an eventual pandemic. However, these medicaments provide only a reduction in the duration of the clinical disease. Alternatively, other anti-Influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden et al., 2005). In addition, more unspecific viral drugs, such as ribavirin, have been shown to work for treatment of Influenza infections (Eriksson et al., 1977). However, ribavirin is only approved in a few countries, probably due to severe side effects (Furuta et al., 2005). Clearly, new antiviral compounds are needed, preferably directed against different targets.

Influenza virus as well as Thogotovirus belong to the family of Orthomyxoviridae which, as well as the family of the Bunyaviridae, including the Hantavirus, Nairovirus, Orthobunyavirus, and Phlebovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. For the generation of viral mRNA the polymerase makes use of the so called "cap-snatching" mechanism (Plotch et al., 1981; Kukkonen et al., 2005; Leahy et al., 1997; Noah and Krug, 2005). It binds to the 5' RNA cap of cellular mRNA molecules and cleaves the RNA cap together with a stretch of nucleotides. The capped RNA fragments serve as primers for the synthesis of viral mRNA. The polymerase is composed of three subunits: PB1 (polymerase basic protein), PB2, and PA. While PB1 harbors the endonuclease and polymerase activities, PB2 contains the RNA cap binding domain.

The polymerase complex seems to be an appropriate antiviral drug target since it is essential for synthesis of viral mRNA and viral replication and contains several functional active sites likely to be significantly different from those found in host cell proteins (Magden et al., 2005). Thus, for example, there have been attempts to interfere with the assembly of polymerase subunits by a 25-amino-acid peptide resembling the PA-binding domain within PB1 (Ghanem et al., 2007). Furthermore, the endonuclease activity of the polymerase has been targeted and a series of 4-substituted 2,4-dioxobutanoic acid compounds has been identified as selective inhibitors of this activity in Influenza viruses (Tomassini et al., 1994). In addition, flutimide, a substituted 2,6-diketopiperazine, identified in extracts of *Delitschia confertaspora*, a fungal species, has been shown to inhibit the endonuclease of Influenza virus (Tomassini et al., 1996). Moreover, there have been attempts to interfere with viral transcription by nucleoside analogs, such as 2'-deoxy-2'-fluoroguanosine (Tisdale et al., 1995) and it has been shown that T-705, a substituted pyrazine compound may function as a specific inhibitor of Influenza virus RNA polymerase (Furuta et al., 2005). Finally, by comparison studies between the binding mode of human cap binding protein eIF4E to RNA cap structures and Influenza virus RNP interaction with RNA cap structures Hooker et al. (2003) identified a novel cap analog that selectively interacts with Influenza virus, but not human cap binding protein. However, the major obstacle for identifying compounds that interact with the RNA cap binding pocket of PB2 and potentially interfere with RNA cap binding and thereby RNA polymerase activity was up to now that the structure and identity of said binding pocket was unknown.

Several attempts have been made to elucidate the RNA cap binding site, however, with controversial results. Cross-linking experiments indicated that two separate sequences, one N-(242-282) and one C-terminal (538-577) proximal segment of PB2, constitute the RNA cap-binding site of the Influenza virus RNA polymerase (Honda et al., 1999). Additional cross-linking experiments identified a sequence extending from amino acid 533 to amino acid 564 in the PB2 protein subunit, particularly amino acid residue Trp552, as potential interaction site for the RNA cap (Li et al., 2001).

Furthermore, mutational analysis resulted in potential RNA cap binding amino acid residues Phe363 and Phe404 within PB2 (Fechter et al., 2003).

It is an object of the present invention to provide (i) high resolution structural data of the RNA cap binding pocket of PB2 by X-ray crystallography, (ii) computational as well as in vitro methods, preferably in a high-throughput setting, for identifying compounds that can bind to the RNA binding pocket of PB2, preferably competing with RNA cap binding and thereby interfering with RNA polymerase activity, and (iii) pharmacological compositions comprising such compounds for the treatment of infectious diseases caused by viruses using the cap snatching mechanism for synthesis of viral mRNA.

The present invention allows for the first time for the precise definition of the PB2 RNA cap-binding site within an independently folded domain. It has up to now been highly controversial where the site may be located. It was a common believe that a functional cap binding site requires all three polymerase subunits and possibly also viral RNA (Cianci et al., 1995; Li et al., 2001). The surprising achievement of the present inventors to recombinantly produce soluble PB2 polypeptide fragments comprising a functional RNA cap binding pocket allows to perform in vitro high-throughput screening for inhibitors of a functional site on Influenza virus polymerase using easily obtainable material from a straightforward expression system. Previous work on cap binding inhibitors has, for instance, used complete ribonucleoprotein particles purified from Influenza virions (Hooker et al., 2003). Furthermore, by providing detailed structure coordinates of the RNA cap binding pocket within PB2, the present invention allows to use structure-based approaches to cap-binding inhibitor design, i.e., in silico screening and lead optimization.

SUMMARY OF THE INVENTION

In a first aspect the present invention relates to soluble polypeptide fragment, wherein said polypeptide fragment is (i) derived from the Influenza virus RNA-dependent RNA polymerase subunit PB2 or variant thereof and (ii) capable of binding to a RNA cap or analog thereof.

In a further aspect the present invention relates to a complex comprising the soluble polypeptide fragments of the present invention and a RNA cap or analog thereof.

In a further aspect the present invention relates to an isolated polynucleotide coding for an isolated soluble polypeptide fragment of the present invention.

In a further aspect the present invention relates to a recombinant vector comprising the isolated polynucleotide of the present invention.

In a further aspect the present invention relates to a recombinant host cell comprising the isolated polynucleotide of the present invention or the recombinant vector of the present invention.

In a further aspect the present invention relates to a method for identifying compounds which associate with all or part of the RNA cap binding pocket of PB2 or the binding pocket of a PB2 polypeptide variant, comprising the steps of
(a) constructing a computer model of said binding pocket defined by the structure coordinates of the complex of the present invention as shown in FIG. 18;
(b) selecting a potential binding compound by a method selected from the group consisting of:
 (i) assembling molecular fragments into said compound,
 (ii) selecting a compound from a small molecule database, and
 (iii) de novo ligand design of said compound;
(c) employing computational means to perform a fitting program operation between computer models of the said compound and the said binding pocket in order to provide an energy-minimized configuration of the said compound in the binding pocket; and
(d) evaluating the results of said fitting operation to quantify the association between the said compound and the binding pocket model, whereby evaluating the ability of said compound to associate with the said binding pocket.

In a further aspect the present invention relates to a compound identifiable by the in silico method of the present invention, under the provision that the compound is not $m^7G$, $m^7GMP$, $m^7GTP$, $m^7GpppG$, $m^7GpppGm$, $m^7GpppA$, $m^7GpppAm$, $m^7GpppC$, $m^7GpppCm$, $m^7GpppU$, $m^7GpppUm$, 2-Amino-7-benzyl-9-(4-hydroxy-butyl)-1,9-dihydro-purin-6-one or T-705 and is able to bind to the RNA cap binding pocket of PB2 or variant thereof.

In a further aspect the present invention relates to a compound identifiable by the in silico method of the present invention, under the provision that the compound is not $m^7G$, $m^7GMP$, $m^7GTP$, $m^7GpppG$, $m^7GpppGm$, $m^7GpppA$, $m^7GpppAm$, $m^7GpppC$, $m^7GpppCm$, $m^7GpppU$, $m^7GpppUm$, 2-Amino-7-benzyl-9-(4-hydroxy-butyl)-1,9-dihydro-purin-6-one or T-705 and is able to inhibit binding between the PB2 polypeptide, variant thereof or fragment thereof and the RNA cap or analog thereof.

In a further aspect the present invention relates to a method for identifying compounds which associate with the RNA cap binding pocket of PB2 or binding pockets of PB2 polypeptide variants, comprising the steps of (i) contacting the polypeptide fragment of the present invention or the recombinant host cell of the present invention with a test compound and (ii) analyzing the ability of said test compound to bind to PB2.

In a further aspect the present invention relates to a pharmaceutical composition producible according to the in vitro method of the present invention.

In a further aspect the present invention relates to a compound identifiable by the in vitro method of the present invention, under the provision that the compound is not $m^7G$, $m^7GMP$, $m^7GTP$, $m^7GpppG$, $m^7GpppGm$, $m^7GpppA$, $m^7GpppAm$, $m^7GpppC$, $m^7GpppCm$, $m^7GpppU$, $m^7GpppUm$, 2-Amino-7-benzyl-9-(4-hydroxy-butyl)-1,9-dihydro-purin-6-one or T-705 and is able to bind to the PB2 polypeptide, variant thereof or fragment thereof.

In a further aspect the present invention relates to a compound identifiable by the in vitro method of the present invention under the provision that the compound is not $m^7G$, $m^7GMP$, $m^7GTP$, $m^7GpppG$, $m^7GpppGm$, $m^7GpppA$, $m^7GpppAm$, $m^7GpppC$, $m^7GpppCm$, $m^7GpppU$, $m^7GpppUm$, 2-Amino-7-benzyl-9-(4-hydroxy-butyl)-1,9-dihydro-purin-6-one or T-705 and is able to inhibit binding between the PB2 polypeptide, variant thereof or fragment thereof and the RNA cap or analog thereof.

In a further aspect the present invention relates to an antibody directed against the RNA cap binding domain of PB2.

In a further aspect the present invention relates to a use of a compound of the present invention, a pharmaceutical composition of the present invention or an antibody of the present invention for the manufacture of a medicament for treating, ameliorating, or preventing disease conditions caused by viral infections with negative-sense ssRNA viruses.

FIG. 2A shows a graph illustrating the purification of PB2 polypeptide fragment amino acids 318 to 483 (SEQ ID NO: 11) on a Superdex 75 gel filtration column. The absorption at 280 nm in arbitrary units is plotted versus the elution time and fraction number.

FIG. 2B shows a coomassie stained SDS PAGE gel of fractions 24-34 of the PB2 polypeptide fragment (amino acids 318 to 483) (SEQ ID NO: 11) after gel filtration. The molecular weight markers have sizes 116-66.2-45-35-25-18.4 and 14.4 kD.

FIG. 3A shows the native crystals of the PB2 polypeptide fragment (amino acids 318 to 483) (SEQ ID NO: 11) in complex with $m^7$GTP (5 mM) formed with precipitant solution 1.6 M sodium formate, 0.1 M citric acid pH 4.6.

FIG. 3B shows the crystals of partially seleno-methionylated PB2 polypeptide fragment (amino acids 318 to 483) (SEQ ID NO: 11) in complex with $m^7$GTP (5 mM) formed with precipitant solution 1.6 M sodium formate, 0.1 M citric acid pH 4.6.

FIG. 4 shows the X-ray diffraction pattern obtained on a native crystal on beamline BM14 at the European Synchrotron Radiation Facility. The diffraction pattern indexes in space-group $C222_1$ with cell dimensions a=92.2, b=94.4, c=220.4 Å. The top right inset shows the diffraction extending to 2.4 Å resolution. The bottom right inset shows the frozen crystal used for the data collection, which has an approximate size of 15×15×50 $\mu m^3$.

FIG. 5 shows a ribbon diagram of the structure of the PB2 polypeptide fragment (amino acids 318 to 483) (SEQ ID NO: 11) in complex with $m^7$GTP. Secondary structure elements are labeled as calculated by DSSP (Holm, L. and Sander, C., 1993), with alpha helices in dark grey and beta-strands in light grey. The GTP is shown as a ball and stick model as are the side-chains of Phe323, Phe404 and His357. Significant loops, centered on residues 348 and 420 are labeled, as are the N- and C-terminal residues visible in the structure (respectively 320 and 483).

FIG. 6 shows an alternative view of the structure of the PB2 polypeptide fragment (amino acids 318 to 483) (SEQ ID NO: 11) in complex with $m^7$GTP revealing that the 420-loop projects into the solvent.

FIG. 7 depicts the conformation and the unbiased, experimental electron density of $m^7$GTP surrounded by some of the amino acids that form the RNA cap binding pocket within PB2. The electron density corresponds to a map obtained by RESOLVE using experimental phases and non-crystallographic symmetry averaging contoured at 0.95 sigma.

FIG. 8 depicts the cap analog $m^7$GTP embedded in the RNA cap binding pocket within PB2 with potential interacting atoms. Putative hydrogen bonds are denoted by dotted lines.

FIG. 9 shows an amino acid sequence alignment of the PB2 RNA cap-binding domains from Influenza A (strain A/Victoria/3/1975) SEQ ID NO:1 and B (strain B/Lee/40) SEQ ID NO: 2. The secondary structure of A/Victoria/3/1975 (calculated with DSSP (Holm and Sander, 1993)) is displayed over the sequence alignment. The structure based sequence alignments were plotted with ESPRIPT see website at espript.ibcp.fr/ESPript/cgi-bin/ESPript.cgi). Residues on a solid black background are identical between the two sequences. The triangles indicate the principle residues interacting with the cap analog $m^7$GTP.

FIG. 10 shows an amino acid sequence alignment of the PB2 RNA cap-binding domains from influenza A (strain A/Victoria/3/1975) SEQ ID NO: 1, B (strain B/Lee/40) SEQ ID NO: 2 and C (strain Ann Arbor/1/50) SEQ ID NO: 3. Annotation is as for FIG. 9.

FIG. 11 schematically depicts the interactions between the RNA cap analog $m^7$GTP and the RNA cap binding pocket within PB2. The cap analog $m^7$GTP (labeled M7G) is drawn with dark grey bonds, protein residues with medium grey bonds and water molecules with light grey spheres. Hydrogen bonds are shown as dotted lines with the distance between donor and acceptor in A. Hatched parts of spheres in dark grey indicate residues that are in van der Waals contact with the ligand. The diagram corresponds to the molecule with chain designation B in the co-ordinate file. The four other molecules in the asymmetric unit (chains A, B, D and F) give similar diagrams with minor differences in distances and water positions. The figure was made using LIGPLOT (Wallace et al., 1995).

FIG. 12 shows a coomassie stained SDS PAGE gel of the results of elution of indicated wild-type and single point mutants of the PB2 cap-binding domain, after binding to a $m^7$GTP Sepharose 4B resin at 4° C. Mutants E361A, F404A, H357A and K376A failed to bind to the $m^7$GTP Sepharose 4B resin under conditions where wild-type protein binds, whereas F323A had weak residual binding activity and F325A bound the resin nearly as well as wild-type, however, this binding activity is drastically reduced at 37° C. (cf. Table 3). A H357W mutant was also made as influenzas B and C have this residue at this position. This mutant was solubly purified and found to have slightly enhanced binding to the $m^7$GTP Sepharose 4B resin compared to wild-type. Mutant ΔVQ was generated by replacing residues Val421-Gln426 by three glycines (420-loop) and shows cap-binding activity.

FIG. 13 shows the cap-binding activity of wild-type or mutant recombinant polymerase complexes. Cultures of HEK293T cells were co-transfected with plasmids expressing PB1 and PA (Φ) or cotransfected with plasmids expressing PB1, PB2-His or mutants thereof and PA. Cell extracts were analysed by pull-down with $m^7$GTP-Sepharose at 4° C. The polymerase complexes retained and eluted with $m^7$GTP were revealed by Western-blot with PA-specific antibodies. IN and E indicate input cell extract and eluted protein, respectively. The position of the PA-specific band is indicated to the right and the mobility of molecular weight markers is shown on the left. Mutant ΔVQ was generated by replacing residues Val421-Gln426 by three glycines (420-loop).

FIG. 14 is a graph that shows replication activity of the wild-type or mutant polymerases. Wild-type and mutant mini-RNPs were reconstituted in vivo and purified by affinity chromatography with $Ni^{2+}$-NTA-agarose. The accumulation of progeny RNPs was determined by Western-blot using anti-PA and anti-NP antibodies. The data are presented as percent of the wild-type value and are averages and ranges of two experiments. Mutant ΔVQ was generated by replacing residues Val421-Gln426 by three glycines (420-loop).

FIG. 15 is a graph that shows the in vitro transcription activity of purified wild-type or mutant RNPs using ApG as primer. The data presented are averages and ranges of two experiments. Mutant ΔVQ was generated by replacing residues Val421-Gln426 by three glycines (420-loop).

Figure 16:
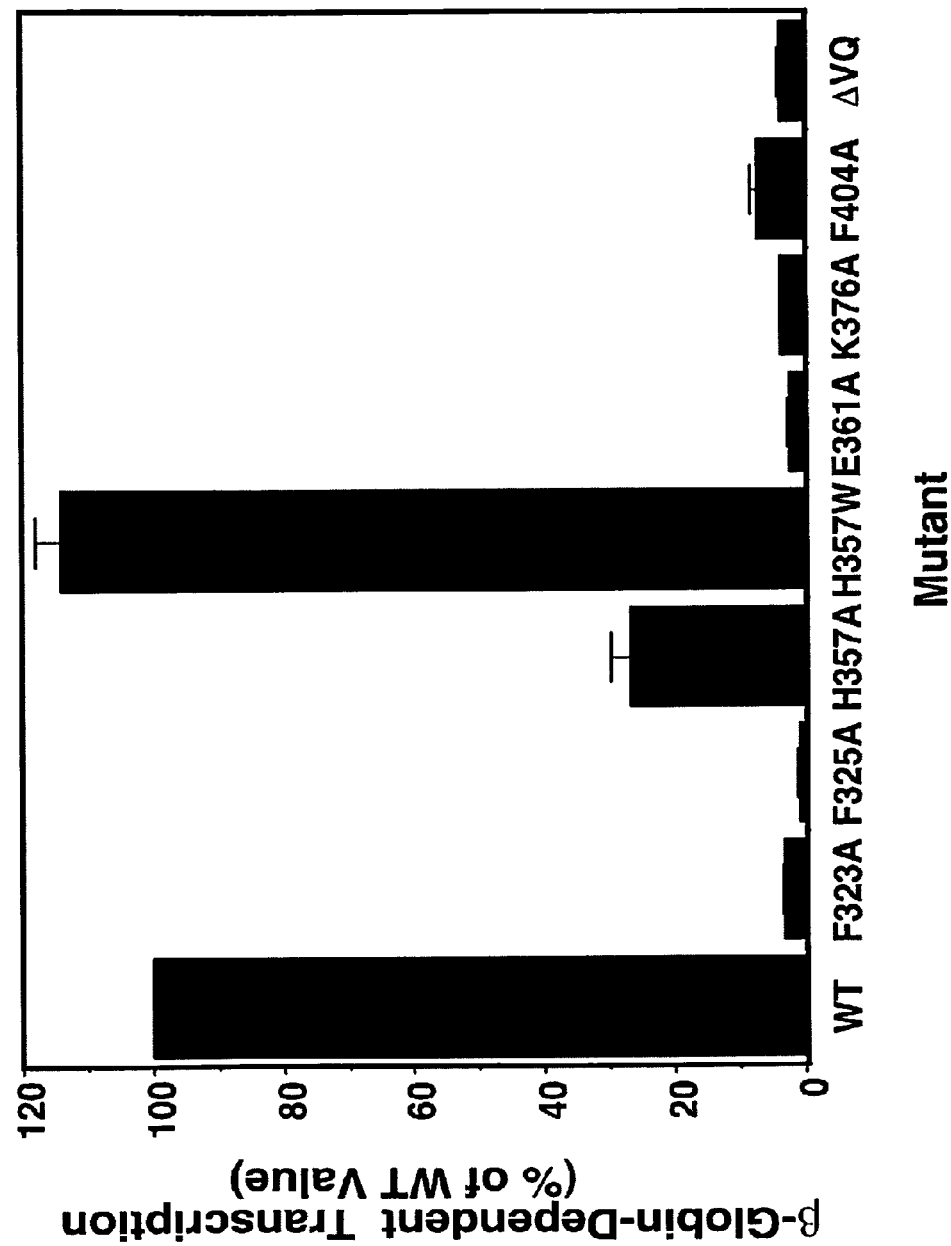

FIG. 16 is a graph that shows the in vitro transcription activity of purified wild-type or mutant RNPs using β-globin mRNA as primer. The data presented are averages and ranges of two experiments. Mutant ΔVQ was generated by replacing residues Val421-Gln426 by three glycines (420-loop).

Figure 17:
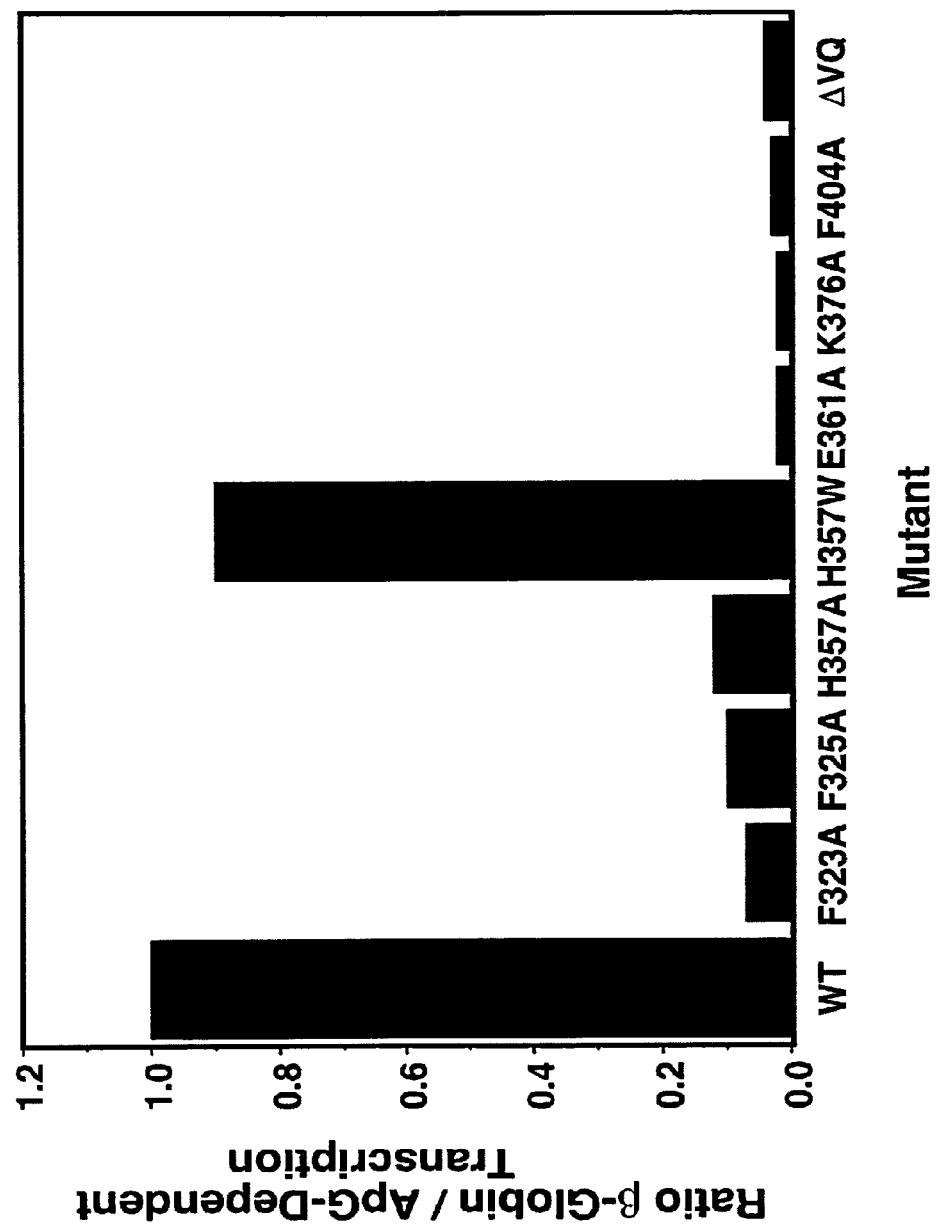

FIG. 17 is a graph that shows the ratio of ApG- versus β-globin mRNA-dependent in vitro transcription activity of purified wild-type or mutant RNPs. The data presented are averages and ranges of two experiments. Mutant ΔVQ was generated by replacing residues Val421-Gln426 by three glycines (420-loop).

Figure 1:
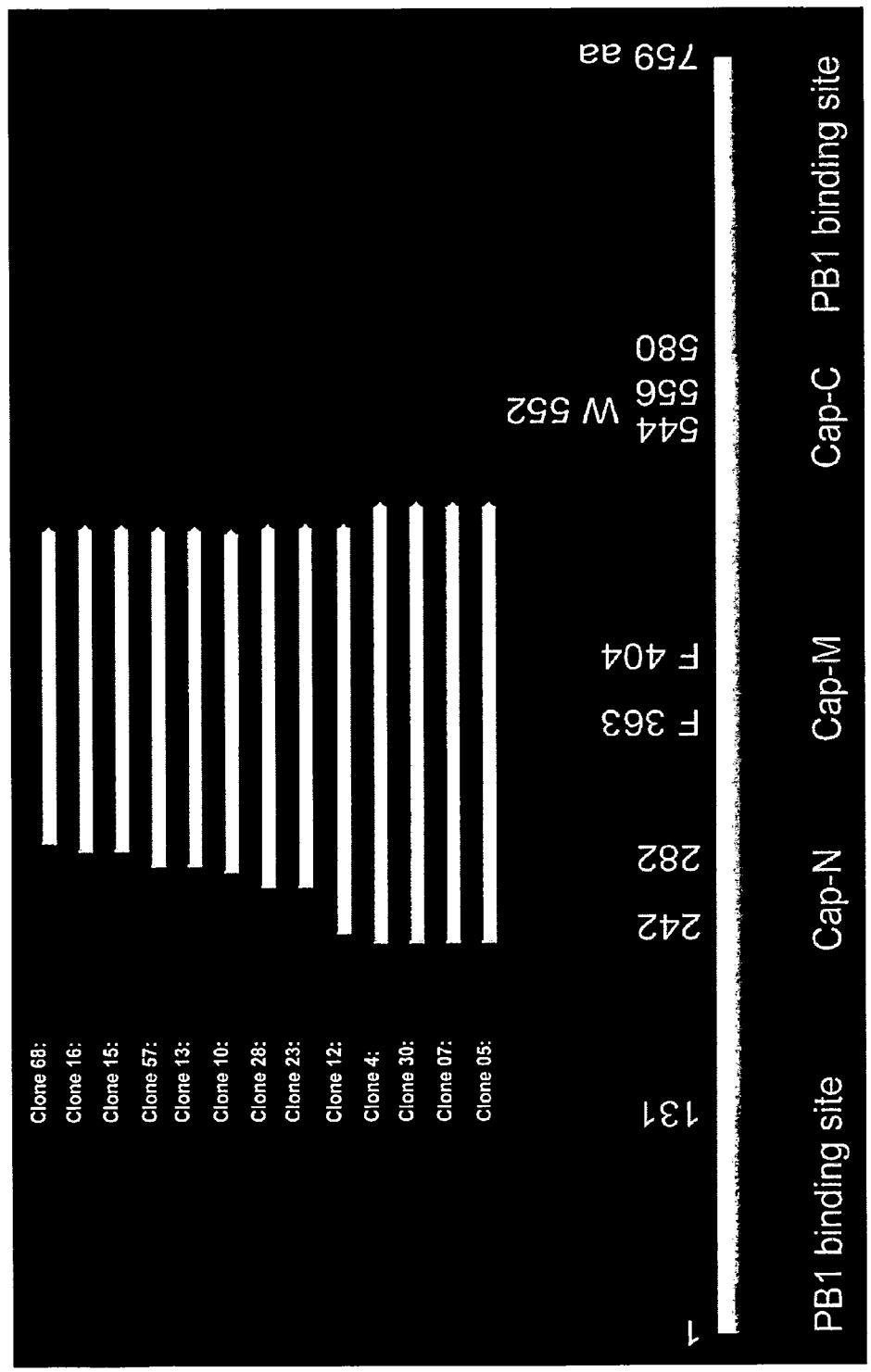
FIG. 1 illustrates full-length PB2 with potential binding sites for the PB1 subunit of the Influenza polymerase and potential RNA cap binding sites as predicted by the prior art (Cap-N/Cap-C see Honda et al. (1999), Cap-C (Trp552) see Li et al. (2001), Cap-M see Fechter et al. (2003). In addition, various PB2 fragments are shown that were generated for bacterial expression. All of these constructs are expressed at high levels and are soluble. From top to bottom the length of PB2 fragments encoded by 13 isolated clones are depicted, which encoded seven unique PB2 fragments. The isolated clones span nucleotides: Clone 68: 886 to 1449, Clone 16: 871 to 1452, Clone 15: 871 to 1452, Clone 57: 844 to 1449, Clone 13: 844 to 1449, Clone 10: 832 to 1443, Clone 28: 805 to 1452, Clone 23: 805 to 1452, Clone 12: 723 to 1425, Clone 4: 706 to 1491, Clone 30: 706 to 1491, Clone 07: 706 to 1491, and Clone 05: 706 to 1491 of SEQ ID NO: 25.

FIG. 18 includes FIG. 18-1 to FIG. 18-194.

FIG. 18 lists the refined atomic structure coordinates for PB2 polypeptide fragment amino acids 318 to 483 of SEQ ID NO.1 with Lys389. The fragment has an amino acid sequence according to SEQ ID NO: 11 in complex with the RNA cap analog 7-methyl-guanosine triphosphate (m$^7$GTP). There are five molecules in the asymmetric unit with chains A, B, D, E, F. The RNA cap analog m$^7$GTP is residue number 1 of each chain. There are 293 water molecules. The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all molecules of the crystal. B is a thermal factor that measures movement of the atom around its atomic center. The anisotropic temperature factors are given in the lines marked "ANISOU". This nomenclature corresponds to the PDB file format.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "polypeptide fragment" refers to a part of a protein which is composed of a single amino acid chain. The term "protein" comprises polypeptide fragments that resume a secondary and tertiary structure and additionally refers to proteins that are made up of several amino acid chains, i.e., several subunits, forming quartenary structures. The term "peptide" refers to short amino acid chains of up to 50 amino acids that do not necessarily assume secondary or tertiary structures. A "peptoid" is a peptidomimetic that results from the oligomeric assembly of N-substituted glycines.

Figure 9:
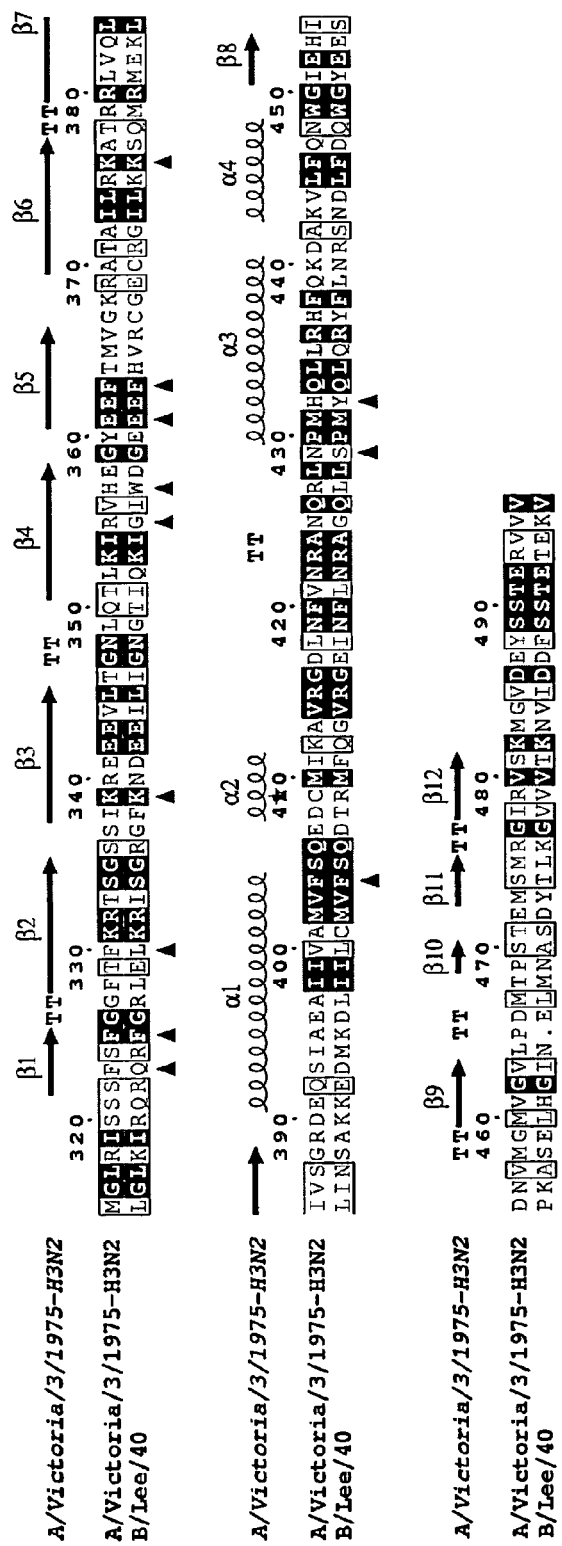
Figure 10:
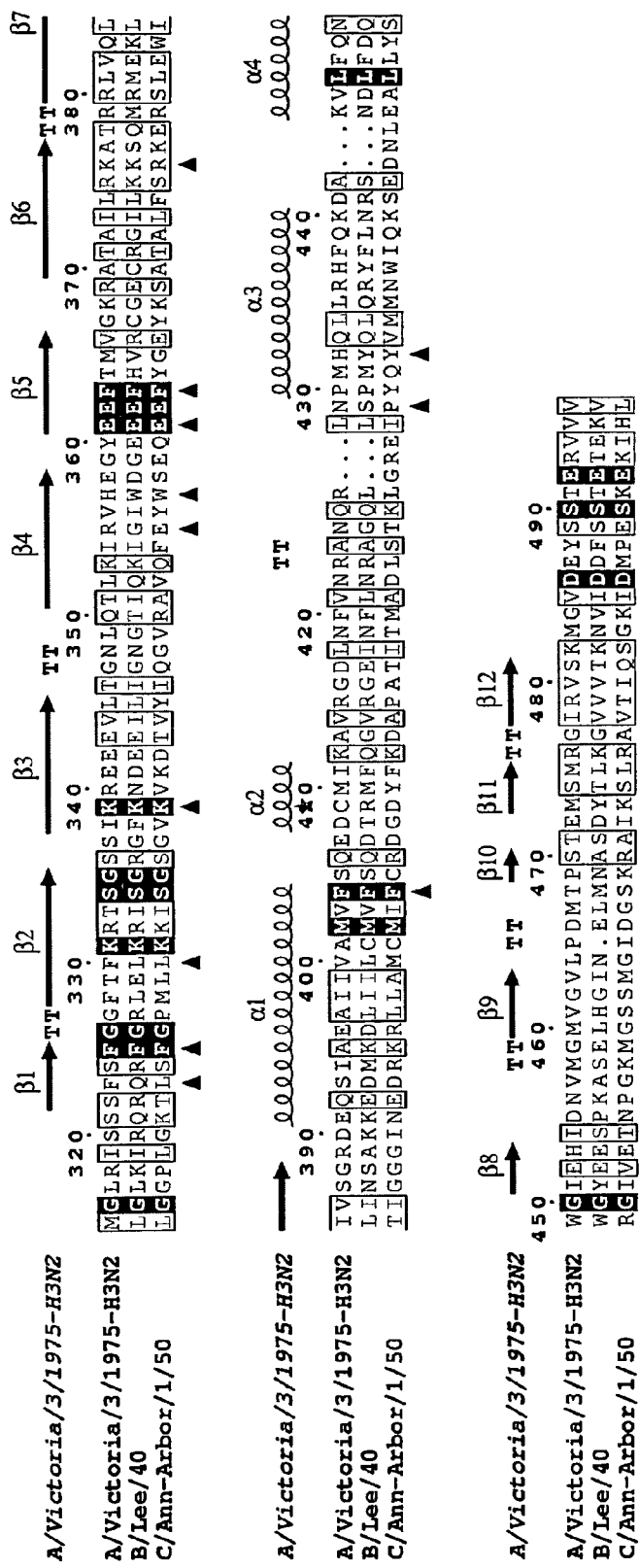
Figure 11:
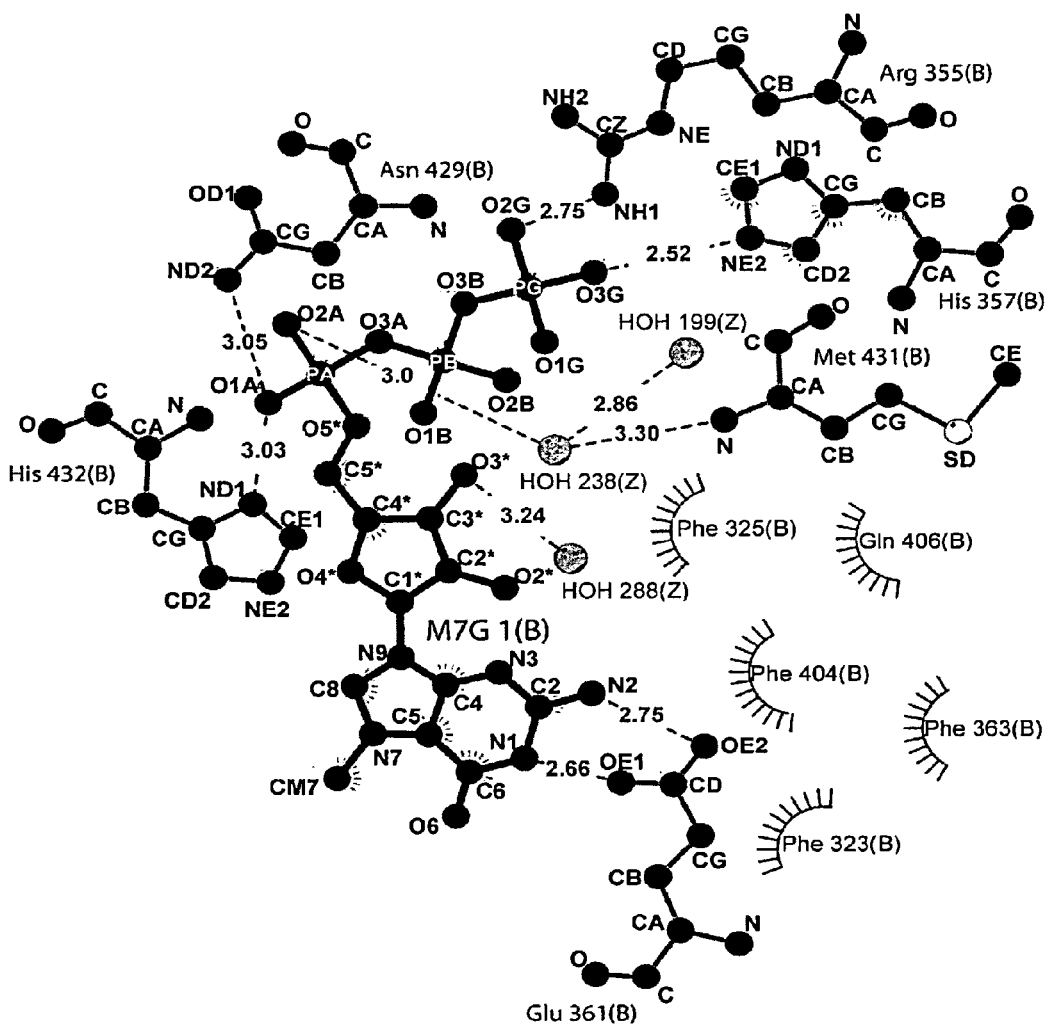

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, see website at ebi.ac.uk/clustalw or ebi.ac.uk/emboss/align/index.html using standard settings, preferably for Align EMBOSS: :needle, Matrix: Blosum62, Gap Open 10.0, Gap Extend 0.5. Those skilled in the art understand that it may be necessary to introduce gaps in either sequence to produce a satisfactory alignment. For example, residues 220 to 510 in the Influenza A virus PB2 subunit (SEQ ID NO: 1) correspond to residues 222 to 511 and 227 to 528 in the Influenza B and C virus PB2 subunits (SEQ ID NO: 2 and 3), respectively. A thus generated alignment for three PB2 subunits is depicted in FIG. 10. Residues in two or more Influenza virus PB2 subunits are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids, more preferably to less than 30% over a length of 10, 20 or 30 amino acids. A part of the best sequence alignment for the amino acid sequences of SEQ ID NO:1 Influenza A (aa 315 to 498), SEQ ID NO: 2 Influenza B (aa 317 to 499), and SEQ ID NO: 3 Influenza C (aa 327 to 516) PB2 subunits is shown in FIGS. 9 and 10.

The present invention includes soluble Influenza virus RNA-dependent RNA polymerase PB2 subunit fragments, which are capable of binding to a RNA cap or analog thereof. The term "RNA-dependent RNA polymerase subunit PB2" preferably refers to the PB2 of Influenza A, Influenza B and Influenza C virus, preferably having an amino acid sequence as set out in SEQ ID NO: 1, 2 or 3. "RNA-dependent RNA polymerase subunit PB2 variants" have at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NOs: 1, 2, or 3. It is preferred that when a naturally occurring PB2 variant is aligned with a PB2 subunit according to SEQ ID NO:1, 2, or 3 that alignment will be over the entire length of the two proteins and, thus, that the alignment score will be determined on this basis. It is, however, possible that the natural variant may comprise C-terminal/N-terminal or internal deletions or additions, e.g. through N- or C-terminal fusions. In this case only the best aligned region is used for the assessment of the similarity and identity, respectively.

Preferably, and as set out in more detail below soluble fragments derived from these variants show the indicated similarity and identity, respectively, preferably within the region required for RNA cap binding. Accordingly, any alignment between SEQ ID NOs: 1, 2, or 3 and a PB2 variant should preferably comprise the RNA cap binding pocket. Thus, the above sequence similarity and identity, respectively, to SEQ ID NO: 1, 2, or 3 occurs at least over a length of 100, 110, 120, 130, 140, 150, 160, 165, 170, 180, 190, 200, 210, 220, 230, 240, 250, 300 or more amino acids, preferably comprising the RNA cap binding pocket. Accordingly, in a preferred embodiment a RNA-dependent RNA polymerase subunit PB2 variant has at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 100 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 110 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 120 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 130 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 140 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 150 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 160 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 165 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 170 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 180 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 190 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 200 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 210 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 220 amino acids, at least 60%, 65%, 70%, 80%, 81%, 82%, 83%, 84%, 0.84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 230 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 240 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 250 amino acids or at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 1 over a length of 300 amino acids.

In a preferred embodiment a RNA-dependent RNA polymerase subunit PB2 variant has at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 100 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 110 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 120 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 130 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 140 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 150 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 160 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 165 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 170 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 180 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 190 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 200 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 210 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 220 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 230 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 240 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 250 amino acids or at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 2 over a length of 300 amino acids.

In a preferred embodiment a RNA-dependent RNA polymerase subunit PB2 variant has at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 100 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 110 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 120 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 130 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 140 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 150 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 160 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 165 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 170 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 180 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 190 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 200 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 210 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 220 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 230 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 240 amino acids, at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 250 amino acids or at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity to SEQ ID NO: 3 over a length of 300 amino acids.

A large number of natural PB2 variants of sequences according to SEQ ID NO: 1, 2, or 3 are known and have been described in the literature. All these PB2 variants are comprised and can be the basis for the soluble fragments of the present invention. Preferred examples for Influenza A, if SEQ ID NO: 1 is used as reference sequence, comprise mutations at one or more of Val227, Arg251, Ile255, Ser271, Gln288, Ile338, Val344, Arg355, Ile373, Leu374, Asn456, Val 461, and/or Ser497. In a preferred embodiment, said variants comprise one or more of the following mutations: Val227Met, Arg251Lys, Ile255Val, Ile255Thr, Ser271Ala, Gln288Leu, Ile338Val, Ile338Thr, Val344Leu, Arg355Lys, Ile373Thr, Leu374Ile, Asn456Ser, Val461Ile, and/or Ser497Asn. Preferred variants of the Influenza A virus PB2 subunit comprise a mutation at position 389 resulting in an amino acid exchange from arginine to lysine (e.g., SEQ ID NO: 11), optionally combined with one or more of the aforementioned mutations. Preferred variants of the Influenza B virus PB2 subunit, if SEQ ID NO: 2 is used as reference sequence, include mutations at one or more of the following amino acid positions: Thr254, Met261, Ile269, Thr301, Ile303, Leu319, Ile346, Lys380, Arg382, Met383, Lys385, Lys397, Asn442, Ser456, Glu467, Leu468, and/or Thr494. In a preferred embodiment the PB2 subunit variant comprises one or more of the following mutations: Thr254Ala, Met261Thr, Ile269Val, Thr301Ala, Ile303Leu, Leu319Gln, Ile346Val, Lys380Gln, Arg382Lys, Met383Leu, Lys385Arg, Lys397Arg, Asn442Ser, Ser456Pro, Glu467Gly, Leu468Ser, and/or Thr494Ile. Preferred variants of the Influenza B virus PB2 subunit, if SEQ ID NO: 3 is used as reference sequence, include mutations at one or more of the following amino acid positions: Leu311, Pro330, and/or Ser436. In a preferred embodiment, said mutations are as follows: Leu311Pro, Pro330Gln, and/or Ser436Thr.

The soluble fragments of the present invention are, thus, based on RNA-dependent RNA polymerase subunit PB2 or variants thereof as defined above. Accordingly, in the following specification the term "soluble polypeptide fragment(s)" and "PB2 polypeptide fragments" always comprises such fragments derived both from the PB2 proteins as set out in SEQ ID NO: 1, 2, or 3 and fragments derived from PB2 protein variants thereof, as set out above, which are capable of binding RNA cap or an analog thereof. However, the specification also uses the term "PB2 polypeptide fragment variants" or "PB2 fragment variants" to specifically refer to soluble PB" fragments, capable of binding to RNA cap or an analog thereof that are derived from RNA-dependent RNA polymerase subunit PB2 variants. The soluble PB2 fragments of the present invention thus, preferably comprise, essentially consist or consist of sequences of naturally occurring Influenza virus subunit PB2. It is, however, also envisioned that the PB2 fragments variants further contain amino acid substitutions at 1, 2, 3, 4, 5, 6, 7, 8, 9, 10, 11, 12, 13, 14, 15 or more amino acid positions, and have at least 60%, 65%, 70%, 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NOs: 1, 2, or 3. It is understood that PB2 fragments of the present invention may comprise additional amino acids not derived from PB2, like, e.g. tags, enzymes etc., such additional amino acids will not be considered in such an alignment, i.e. are excluded from the calculation of the alignment score. In a preferred embodiment the above indicated alignment score is obtained when aligning the sequence of the fragment with SEQ ID NOs:1, 2, or 3 at least over a length of 100, 110, 120, 130, 140, 150, 160, 165, 170, 180, 190, 200, 210, 220, 230, 240, 250, 260, or 270 amino acids, wherein the respective sequence of SEQ ID NO: 1, 2, or 3, preferably comprises the RNA cap binding pocket.

In a preferred embodiment, the soluble PB2 polypeptide fragment variants comprise at least or consist of the amino acid residues corresponding to amino acid residues 323 to 404 of Influenza A virus PB2 (SEQ ID NO: 13) and have at least 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 13, more preferably the PB2 polypeptide fragment variants comprise at least the amino acid residues corresponding to amino acid residues 318 to 483 of Influenza A virus PB2 (SEQ ID NO: 11) and have at least 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 11, more preferably the PB2 polypeptide fragment variants comprise at least the amino acid residues corresponding to amino acid residues 235 to 496 of Influenza A virus PB2 (SEQ ID NO: 4) and have at least 60%, more preferably 65%, more preferably 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 4, more preferably the PB2 polypeptide fragment variants comprise at least the amino acid residues corresponding to amino acid residues 220 to 510 of Influenza A virus PB2 and have at least 60%, more preferably 65%, more preferably 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 1. In preferred embodiments, the Influenza A virus PB2 polypeptide fragment variants of the present invention comprise mutations, preferably naturally occurring mutations such as mutations in one or more of the following amino acid residues when compared to SEQ ID NO: 1: Val227, Arg251, Ile255, Ser271, Gln288, Ile338, Val344, Arg355, Ile373, Leu374, Lys389, Asn456, Val 461, and/or Ser497. In a preferred embodiment, said mutations are as follows: Val227Met, Arg251Lys, Ile255Val, Ile255Thr, Ser271Ala, Gln288Leu, Ile338Val, Ile338Thr, Val344Leu, Arg355Lys, Ile373Thr, Leu374Ile, Lys389, Asn456Ser, Val461Ile, and/or Ser497Asn. A preferred variant of the Influenza A virus PB2 subunit fragment comprises a mutation at position 389 resulting in an amino acid exchange from arginine to lysine (e.g., SEQ ID NO: 11), optionally combined with one or more of the aforementioned mutations.

In a preferred embodiment, the PB2 polypeptide fragment variants comprise at least or consist of the amino acid residues corresponding to amino acid residues 325 to 406 of Influenza B virus PB2 (derived from SEQ ID NO: 2) and have at least 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 2, more preferably the PB2 polypeptide fragment variants comprise at least the amino acid residues corresponding to amino acid residues 320 to 484 of Influenza B virus PB2 (derived from SEQ ID NO: 2) and have at least 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 2, more preferably the PB2 polypeptide fragment variants comprise at least the amino acid residues corresponding to amino acid residues 237 to 497 of Influenza B virus PB2 (derived from SEQ ID NO: 2) and have at least 60%, more preferably 65%, more preferably 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 2, more preferably the PB2 polypeptide fragment variants comprise at least the amino acid residues corresponding to amino acid residues 222 to 511 of Influenza B virus PB2 (derived from SEQ ID NO: 2) and have at least 60%, more preferably 65%, more preferably 70%, more preferably 75%, more preferably 80%, 81%, 82%, 83% m 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NO: 2. In preferred embodiments, the Influenza B virus PB2 polypeptide fragment variants of the present invention comprise mutations, preferably naturally occurring mutations, at one or more of the following amino acid positions compared to SEQ ID NO: 2: Thr254, Met261, Ile269, Thr301, Ile303, Leu319, Ile346, Lys380, Arg382, Met383, Lys385, Lys397, Asn442, Ser456, Glu467, Leu468, and/or Thr494. In a preferred embodiment, said fragment variants comprise one or more of the following mutations: Thr254Ala, Met261Thr, Ile269Val, Thr301Ala, Ile303Leu, Leu319Gln, Ile346Val, Lys380Gln, Arg382Lys, Met383Leu, Lys385Arg, Lys397Arg, Asn442Ser, Ser456Pro, Glu467Gly, Leu468Ser, and/or Thr494Ile.

In a preferred embodiment, the PB2 polypeptide fragment variants comprise at least or consist of the amino acid residues corresponding to amino acid residues 335 to 416 of Influenza C virus PB2 (derived from SEQ ID NO: 3) and have at least 80%, more preferably 85% more preferably 90%, most preferably 95% sequence similarity over the entire length of the fragment with the amino acid sequence set forth in SEQ ID NO: 3, more preferably the PB2 polypeptide fragment variants comprise at least the amino acid residues corresponding to amino acid residues 330 to 501 of Influenza C virus PB2 (derived from SEQ ID NO: 3) and have at least 70%, more preferably 75%, more preferably 80%, more preferably 85%, most preferably 90% sequence similarity over the entire length of the fragment with the amino acid sequence set forth in SEQ ID NO: 3, more preferably the PB2 polypeptide fragment variants comprise at least the amino acid residues corresponding to amino acid residues 242 to 514 of Influenza C virus PB2 (derived from SEQ ID NO: 3) and have at least 60%, more preferably 65%, more preferably 70%, more preferably 75%, more preferably 80%, more preferably 85%, most preferably 90% sequence similarity over the entire length of the fragment with the amino acid sequence set forth in SEQ ID NO: 3, more preferably the PB2 polypeptide fragment variants comprise at least the amino acid residues corresponding to amino acid residues 227 to 528 of Influenza C virus PB2 (derived from SEQ ID NO: 3) and have at least 60%, more preferably 65%, more preferably 70%, more preferably 75%, more preferably 80%, more preferably 85%, most preferably 90% sequence similarity over the entire length of the fragment with the amino acid sequence set forth in SEQ ID NO: 2. In preferred embodiments, the Influenza C virus PB2 polypeptide fragment variants of the present invention comprise mutations, preferably naturally occurring mutations such as mutations in one or more of the following amino acid residues when compared to SEQ ID NO: 3: Leu311, Pro330, and/or Ser436. In a preferred embodiment, the fragment variants comprise one or more of the following mutations: Leu311Pro, Pro330Gln, and/or Ser436Thr.

The term "sequence similarity" means that amino acids at the same position of the best sequence alignment are identical or similar, preferably identical. "Similar amino acids" possess similar characteristics, such as polarity, solubility, hydrophilicity, hydrophobicity, charge, or size. Similar amino acids are preferably leucine, isoleucine, and valine; phenylalanine, tryptophan, and tyrosine; lysine, arginine, and histidine; glutamic acid and aspartic acid; glycine, alanine, and serine; threonine, asparagine, glutamine, and methionine. The skilled person is well aware of sequence similarity searching tools, e.g., available on the World Wide Web (e.g., www.ebi.ac.uk/Tools/similarity.html).

The term "soluble", as used herein, refers to a polypeptide fragment which remains in the supernatant after centrifugation for 30 min at 100,000×g in an aqueous buffer under physiologically isotonic conditions, for example, 0.14 M sodium chloride or sucrose, at a protein concentration of as much as 5 mg/ml in the absence of denaturants such as guanidine or urea in effective concentrations. A protein fragment that is tested for its solubility, is preferably expressed in one of the cellular expression systems indicated below. It is particularly preferred that the expression and, preferably, purification of such a protein fragment is carried out as set out in more detail below in Example 2.

The term "purified" in reference to a polypeptide, does not require absolute purity such as a homogenous preparation, rather it represents an indication that the polypeptide is relatively purer than in the natural environment. Generally, a purified polypeptide is substantially free of other proteins, lipids, carbohydrates, or other materials with which it is naturally associated, preferably at a functionally significant level, for example, at least 85% pure, more preferably at least 95% pure, most preferably at least 99% pure. The expression "purified to an extent to be suitable for crystallization" refers to a protein that is 85% to 100%, preferably 90% to 100%, more preferably 95% to 100% pure and can be concentrated to higher than 3 mg/ml, preferably higher than 10 mg/ml, more preferably higher than 18 mg/ml without precipitation. A skilled artisan can purify a polypeptide using standard techniques for protein purification. A substantially pure polypeptide will yield a single major band on a non-reducing polyacrylamide gel.

The term "associate" as used in the context of identifying compounds with the methods of the present invention refers to a condition of proximity between a moiety (i.e., chemical entity or compound or portions or fragments thereof), and a binding pocket of PB2. The association may be non-covalent, i.e., where the juxtaposition is energetically favored by, for example, hydrogen-bonding, van der Waals, electrostatic, or hydrophobic interactions, or it may be covalent.

The term "RNA cap" refers to a cap structure found on the 5' end of an mRNA molecule and consists of a guanine nucleotide connected to the mRNA via an unusual 5' to 5' triphosphate linkage. This guanosine is methylated on the 7 position. Further modifications include the possible methylation of the 2' hydroxy-groups of the first 3 ribose sugars of the 5' end of the mRNA. "RNA cap analogs" refer to structures that resemble the RNA cap structure. Examples of RNA cap analogs include 7-methyl-guanosine ($m^7G$), 7-methyl-guanosine monophosphate ($m^7GMP$), 7-methyl-guanosine triphosphate ($m^7GTP$), 7-methyl-guanosine linked via a 5' to 5' triphosphate bridge to guanosine ($m^7$ GpppG), 7-methyl-guanosine linked via a 5' to 5' triphosphate bridge to guanosine methylated at the 2' OH position of the ribose ($m^7$ GpppGm), 7-methyl-guanosine linked via a 5' to 5' triphosphate bridge to adenosine ($m^7$ GpppA), 7-methyl-guanosine linked via a 5' to 5' triphosphate bridge to adenosine methylated at the 2' OH position of the ribose ($m^7$ GpppAm), 7-methyl-guanosine linked via a 5' to 5' triphosphate bridge to cytidine ($m^7$ GpppC), 7-methyl-guanosine linked via a 5' to 5' triphosphate bridge to cytidine methylated at the 2' OH position of the ribose ($m^7$ GpppCm), 7-methyl-guanosine linked via a 5' to 5' triphosphate bridge to uridine ($m^7$ GpppU), 7-methyl-guanosine linked via a 5' to 5' triphosphate bridge to uridine methylated at the 2' OH position of the ribose ($m^7$ GpppUm). Thus, in a preferred embodiment of the present invention the cap analog is selected from the group consisting of $m^7G$, $m^7GMP$, $m^7GTP$, $m^7$ GpppN, $m^7$ GpppNm, where N is a nucleotide, preferably G, A, U, or C. In another preferred embodiment, the RNA cap analogs may comprise additional, e.g., 1 to 15 nucleotides, i.e., 1, 2, 3, 4, 5, 6, 7, 8, 9, 10, 11, 12, 13, 14, or 15, wherein the nucleotides are preferably independently selected from the group consisting of A, C, G, U, and/or T. These further nucleotides are, preferably linked via a phosphoester, phophodiester or phosphotrieester bond or a non-hydrolyzable analog thereof to the first nucleotide N in $m^7$ GpppN or $m^7$ GpppNm.

The term "nucleotide" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Kornberg and Baker, DNA Replication, 2nd Ed. (Freeman, San Francisco, 1992) and further include, but are not limited to, synthetic nucleosides having modified base moieties and/or modified sugar moieties, e.g. described generally by Scheit, Nucleotide Analogs (John Wiley, N.Y., 1980).

The term "binding pocket" refers to a three-dimensional structure formed by the polypeptide fragments of the invention, i.e., the RNA cap binding domain of PB2, that is lined with amino acids that directly contact the RNA cap or amino acid residues that position the amino acid residues that are in direct contact with the RNA cap (second layer amino acid residues), e.g., Arg332 and Ser337. As a result of its shape the binding pocket accommodates the RNA cap or analog thereof. The RNA cap binding pocket of PB2 is defined by structure coordinates originating from the analysis of the crystal structure data of the complex between a PB2 polypeptide fragment comprising the RNA cap binding site and a RNA cap analog. The term "binding pocket" also includes binding pockets of PB2 polypeptide fragment variants.

The term "RNA cap binding domain of PB2" refers to the minimal polypeptide fragment of PB2 that comprises the RNA binding pocket in its native three-dimensional structure.

The term "isolated polynucleotide" refers to polynucleotides that were (i) isolated from their natural environment, (ii) amplified by polymerase chain reaction, or (iii) wholly or partially synthesized, and means a single or double-stranded polymer of deoxyribonucleotide or ribonucleotide bases and includes DNA and RNA molecules, both sense and anti-sense strands. The term comprises cDNA, genomic DNA, and recombinant DNA. A polynucleotide may consist of an entire gene, or a portion thereof.

The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

"Recombinant host cell", as used herein, refers to a host cell that comprises a polynucleotide that codes for a polypeptide fragment of interest, i.e., the PB2 polypeptide fragment or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or Hi5 cells, or a mammalian cell. Preferred examples of mammalian cells are Chinese hamster ovary (CHO) cells, green African monkey kidney (COS) cells, human embryonic kidney (HEK293) cells, HELA cells, and the like.

As used herein, the term "crystal" or "crystalline" means a structure (such as a three-dimensional solid aggregate) in which the plane faces intersect at definite angles and in which there is a regular structure (such as internal structure) of the constituent chemical species. The term "crystal" can include any one of: a solid physical crystal form such as an experimentally prepared crystal, a crystal structure derivable from the crystal (including secondary and/or tertiary and/or quaternary structural elements), a 2D and/or 3D model based on the crystal structure, a representation thereof such as a schematic representation thereof or a diagrammatic representation thereof, or a data set thereof for a computer. In one aspect, the crystal is usable in X-ray crystallography techniques. Here, the crystals used can withstand exposure to X-ray beams and are used to produce diffraction pattern data necessary to solve the X-ray crystallographic structure. A crystal may be characterized as being capable of diffracting X-rays in a pattern defined by one of the crystal forms depicted in T. L. Blundell and L. N. Johnson, "Protein Crystallography", Academic Press, New York (1976).

The term "unit cell" refers to a basic parallelepiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal. In a space group designation the capital letter indicates the lattice type and the other symbols represent symmetry operations that can be carried out on the contents of the asymmetric unit without changing its appearance.

The term "structure coordinates" refers to a set of values that define the position of one or more amino acid residues with reference to a system of axes. The term refers to a data set that defines the three-dimensional structure of a molecule or molecules (e.g., Cartesian coordinates, temperature factors, and occupancies). Structural coordinates can be slightly modified and still render nearly identical three-dimensional structures. A measure of a unique set of structural coordinates is the root mean square deviation of the resulting structure. Structural coordinates that render three-dimensional structures (in particular a three-dimensional structure of a binding pocket) that deviate from one another by a root mean square deviation of less than 3 Å, 2 Å, 1.5 Å, 1.0 Å, or 0.5 Å may be viewed by a person of ordinary skill in the art as very similar.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a variant of the PB2 polypeptide fragment or RNA cap binding pocket therein from the backbone of PB2 or the RNA cap binding pocket therein as defined by the structure coordinates of the PB2-m$^7$GTP complex according to FIG. 18.

As used herein, the term "constructing a computer model" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry, and other structure-based constraint models.

The term "fitting program operation" refers to an operation that utilizes the structure coordinates of a chemical entity, binding pocket, molecule or molecular complex, or portion thereof, to associate the chemical entity with the binding pocket, molecule or molecular complex, or portion thereof. This may be achieved by positioning, rotating or translating the chemical entity in the binding pocket to match the shape and electrostatic complementarity of the binding pocket. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the binding pocket.

As used herein, the term "test compound" refers to an agent comprising a compound, molecule, or complex that is being tested for its ability to bind to the polypeptide fragment of interest, i.e., the PB2 polypeptide fragment of the invention or variants thereof comprising the RNA cap binding pocket. Test compounds can be any agents including, but not restricted to, peptides, peptoids, polypeptides, proteins (including antibodies), lipids, metals, nucleotides, nucleotide analogs, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a test compound. The test compound of the invention may also comprise complex mixtures of substances, such as extracts containing natural products, or the products of mixed combinatorial syntheses. These can also be tested and the component that binds to the target polypeptide fragment can be purified from the mixture in a subsequent step. Test compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

The term "in a high-throughput setting" refers to high-throughput screening assays and techniques of various types which are used to screen libraries of test compounds for their ability to bind to the polypeptide fragment of interest. Typically, the high-throughput assays are performed in a multi-well format and include cell-free as well as cell-based assays.

The term "antibody" refers to both monoclonal and polyclonal antibodies, i.e., any immunoglobulin protein or portion thereof which is capable of recognizing an antigen or hapten, i.e., the RNA cap binding domain of PB2 or a peptide thereof. Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide.

The term "pharmaceutically acceptable salt" refers to a salt of a compound identifiable by the methods of the present invention or a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The term "pharmaceutically acceptable carrier" includes, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The present inventors have found that there are Influenza virus RNA-dependent RNA polymerase subunit PB2 derived fragments, which are soluble and capable of binding to a RNA cap or analog thereof and, thus, suitable for a crystallization to obtain structural information but also to carry out binding studies with recombinant proteins. It is one aspect of the invention to provide a soluble polypeptide fragment, wherein said polypeptide fragment is (i) derived from the Influenza virus RNA-dependent RNA polymerase subunit PB2 and (ii) capable of binding to a RNA cap or analog thereof. The RNA-dependent RNA polymerase subunit PB2 from which the soluble fragments of the invention are derived are preferably derived from an Influenza A, B or C virus. The minimal length of the soluble fragment of the present invention is determined by its ability to bind RNA cap or an analog thereof. Accordingly, it is preferred that the PB2 polypeptide fragment of the invention comprises at least or consists of amino acid residues 323 to 404 or 320 to 483 of SEQ ID NO 1 or amino acids corresponding thereto, e.g. in PB2 polypeptide fragment variant; at least or consists of amino acid residues 325 to 406 or 320 to 484 of SEQ ID NO 2 or amino acids corresponding thereto, e.g. in PB2 polypeptide fragment variant; or at least or consists of amino acid residues 335 to 416 or 330 to 501 of SEQ ID NO 3 or amino acids corresponding thereto, e.g. in PB2 polypeptide fragment variant. On the other hand it has been observed that the solubility of the fragments decreases if their length extends beyond certain C- and/or N-terminal boundaries. For Influenza A type derived soluble fragments these boundaries are with reference to SEQ ID NO: 1 preferably for the N-terminus amino acid 220 or an amino acid corresponding thereto in a variant and for the C-terminus amino acid 510 or an amino acid corresponding thereto in a variant. For Influenza B type derived soluble fragments these boundaries are with reference to SEQ ID NO: 2 preferably for the N-terminus amino acid 222 or an amino acid corresponding thereto in a variant and for the C-terminus amino acid 511 or an amino acid corresponding thereto in a variant. For Influenza C type derived soluble fragments these boundaries are with reference to SEQ ID NO: 3 preferably for the N-terminus amino acid 227 or an amino acid corresponding thereto in a variant and for the C-terminus amino acid 528 or an amino acid corresponding thereto in a variant. The term "soluble" in this context refers to polypeptide fragments, which are dissolvable at a concentration of at least 0.1 mg/ml solvent, more preferably at least 0.5 mg/ml, more preferably at least 1 mg/ml, more preferably at 5 mg/ml or more. Suitable solvents are buffer systems comprising Tris.HCl at concentrations ranging from 0.01 M to 3 M, preferably 0.05 M to 2 M, more preferably 0.1 M to 1 M, at pH 3 to pH 9, preferably pH 4 to pH 9, more preferably pH 7 to pH 9 and optionally a reducing agent such as dithiothreitol (DTT) or TCEP.HCl (Tris(2-carboxyethyl) phosphine hydroxychloride) at a concentration of 1 mM to 20 mM.

In a preferred embodiment, said polypeptide fragment is purified to an extent to be suitable for crystallization. Preferably has a purity of at least 95%, 96%, 98%, 99%, 99.1%, 99.2%, 99.3%, 99.4%, 99.5%, 99.6%, 99.7%, 99.8%, 99.9%. Purity of a protein can be assessed by standard methods including SDS polyacrylamide gel electrophoresis and staining by silver staining or HPLC and detection at 280 nm.

In another preferred embodiment, the (i) N-terminus of said polypeptide fragment is identical to or corresponds to amino acid position 220 or higher, e.g. 225, 230, 235, 240, 245, 250, 255, 260, 265, 270, 275, 280, 285, 290, 295, 300, 305, 310, 315, 320, or 323, and the C-terminus is identical to or corresponds to amino acid position 510 or lower, e.g. 505, 500, 495, 490, 489, 488, 487, 486, 485, 484 or 483, of the amino acid sequence of PB2 according to SEQ ID NO: 1, more preferably the N-terminus of said polypeptide fragment is identical to or corresponds to amino acid position 220 and the C-terminus is identical to or corresponds to amino acid position 510, 505, 500, 495, 490, 489, 488, 487, 486, 485, 484 or 483; more preferably the N-terminus of said polypeptide fragment is identical to or corresponds to amino acid position 225 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 230 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 235 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 240 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 245 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 250 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 255 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 260 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 265 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 270 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 275 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 280 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 280 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 285 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 290 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 295 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 300 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 305 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 310 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 315 or higher and the C-terminus is identical to or corresponds to amino acid position 510 or lower, in particular 505, 500, 495, 490, 489, 488, 487, 486, 485, 484 or 483; more preferably the N-terminus of said polypeptide fragment is identical to or corresponds to amino acid position 320 or higher and the C-terminus is identical to or corresponds to amino acid position 510 or lower, in particular 505, 500, 495, 490, 489, 488, 487, 486, 485, 484 or 483; or more preferably the N-terminus of said polypeptide fragment is identical to or corresponds to amino acid position 323 or higher and the C-terminus is identical to or corresponds to amino acid position 510 or lower, in particular 505, 500, 495, 490, 489, 488, 487, 486, 485, 484 or 483;

(ii) N-terminus of said polypeptide fragment is identical to or corresponds to amino acid position 222 or higher, e.g. 225, 230, 235, 240, 245, 250, 255, 260, 265, 270, 275, 280, 285, 290, 295, 300, 305, 310, 315, 320, 325, and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484, of the amino acid sequence of PB2 according to SEQ ID NO: 2, more preferably the N-terminus of said polypeptide fragment is identical to or corresponds to amino acid position 222 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 225 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 230 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 235 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 240 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 245 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 250 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 255 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 260 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 265 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 270 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 275 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 280 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 285 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 290 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 295 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 300 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 305 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 310 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 315 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; more preferably the N-terminus of said polypeptide fragment is identical to or corresponds to amino acid position 320 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484; or more preferably the N-terminus of said polypeptide fragment is identical to or corresponds to amino acid position 325 or higher and the C-terminus is identical to or corresponds to amino acid position 511 or lower, e.g. 510, 505, 500, 499, 498, 497, 496, 495, 494, 493, 492, 491, 490, 489, 488, 487, 486, 485, or 484;

or (iii) N-terminus of said polypeptide fragment is identical to or corresponds to amino acid position 227 or higher, e.g. 230, 235, 240, 245, 250, 255, 260, 265, 270, 275, 280, 285, 290, 295, 300, 305, 310, 315, 320, 325, 330, or 335, and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501, of the amino acid sequence of PB2 according to SEQ ID NO: 3, more preferably the N-terminus of said polypeptide fragment is identical to or corresponds to amino acid position 227 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 230 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 235 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 240 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 245 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 250 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 255 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 260 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 265 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 270 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 275 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 280 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 285 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 290 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 295 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 300 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 305 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 227 or higher and the C-terminus is identical to or corresponds to amino acid position 310 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 315 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 320 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 325 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; more preferably the N-terminus of said polypeptide fragment is identical to or corresponds to amino acid position 330 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501; or more preferably the N-terminus of said polypeptide fragment is identical to or corresponds to amino acid position 335 or higher and the C-terminus is identical to or corresponds to amino acid position 528 or lower, e.g. 525, 520, 519, 518, 517, 516, 515, 514, 513, 512, 511, 510, 509, 508, 507, 506, 505, 504, 503, 502, or 501.

In another embodiment said polypeptide fragment consist, essentially consists or corresponds to an amino acid sequence selected from the group of amino acid sequences according to SEQ ID NO: 4 to 13 and variants thereof, which retain the ability to associate with an RNA cap or analog thereof and are soluble. In preferred embodiments, said polypeptide fragments comprise amino acid substitutions, insertions, or deletions, preferably naturally occurring mutations as set forth above. Preferably the PB2 polypeptide fragment of the invention has or corresponds to the amino acid residues 235 to 496 (SEQ ID NO: 4), 241 to 483 (SEQ ID NO: 5), 268 to 483 (SEQ ID NO: 6), 277 to 480 (SEQ ID NO: 7), 281 to 482 (SEQ ID NO: 8), 290 to 483 (SEQ ID NO: 9), 295 to 482 (SEQ ID NO: 10), 318 to 483 (SEQ ID NO: 11), 320 to 483 (SEQ ID NO: 12), or 323 to 404 (SEQ ID NO: 13).

In another aspect, the invention provides a complex comprising the PB2 polypeptide fragment as described above and a RNA cap or analog thereof. Preferably, the cap analog is selected from the group consisting of $m^7G$, $m^7GMP$, $m^7GTP$, $m^7GpppG$, $m^7GpppGm$, $m^7GpppA$, $m^7GpppAm$, $m^7GpppC$, $m^7GpppCm$, $m^7GpppU$, and $m^7GpppUm$. In one embodiment of the present invention the polypeptide fragment in the complex consists of an amino acid sequence according to SEQ ID NO: 11 and the cap analog is $m^7GTP$, the complex having the structure defined by the structural coordinates as shown in FIG. 18. In a preferred embodiment, any of the complexes of the invention comprise a crystalline form, preferably with space group $C222_1$ and unit cell dimensions of a=9.2 nm, b=9.4 nm; c=22.0 nm±0.3 nm. Preferably said crystal diffracts X-rays to a resolution of 3.0 Å or higher, preferably 2.8 Å or higher, more preferably 2.6 Å or higher, most preferably 2.4 Å or higher.

In one embodiment, the protein solution suitable for crystallization may include in aqueous solution the PB2 polypeptide fragment or variant thereof at a concentration of 5 mg/ml to 20 mg/ml, preferably at 8 mg/ml to 18 mg/ml, more preferably at 11 mg/ml to 15 mg/ml, a RNA cap analog at a concentration between 2 mM and 10 mM, preferably 3 mM and 8 mM, more preferably 4 mM and 6 mM, optionally a buffer system such as Tris·HCl at concentrations ranging from 0.01 M to 3 M, preferably 0.05 M to 2 M, more preferably 0.1 M to 1 M, at pH 3 to pH 9, preferably pH 4 to pH 9, more preferably pH 7 to pH 9 and optionally a reducing agent such as dithiothreitol (DTT) or TCEP.HCl (Tris(2-carboxyethyl) phosphine hydroxychloride) at a concentration of 1 mM to 20 mM. The PB2 polypeptide fragment or variant thereof or the complex comprising the PB2 polypeptide fragment or variant thereof and an RNA cap or analog thereof is preferably 85% to 100% pure, more preferably 90% to 100% pure, even more preferably 95% to 100% pure in the crystallization solution. To produce crystals, the protein solution suitable for crystallization is mixed with an equal volume of a precipitant solution such as sodium formate, ammonium sulphate, polyethylene glycol of various sizes. In a preferred embodiment, the crystallization medium comprises 0.05 to 2 µA preferably 0.8 to 1.2 µl, of protein solution suitable for crystallization mixed with a similar, preferably equal, volume of precipitant solution comprising 1.5 to 2 M sodium formate, and 0.05 to 0.15 M citric acid at pH 4 to pH 5. In another embodiment, the precipitant solution comprises 7% PEG6000, 1 M LiCl, 0.1 M citric acid pH 5.0, 10 mM TCEP.HCl.

Crystals can be grown by any method known to the person skilled in the art including, but not limited to, hanging and sitting drop techniques, sandwich-drop, dialysis, and microbatch or microtube batch devices. It would be readily apparent to one of skill in the art to vary the crystallization conditions disclosed above to identify other crystallization conditions that would produce crystals of PB2 polypeptide fragments of the inventions or variants thereof alone or in complex with a compound. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brij 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Microseeding may be used to increase the size and quality of crystals. In brief, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

The manner of obtaining the structure coordinates as shown in FIG. 18, interpretation of the coordinates and their utility in understanding the protein structure, as described herein, are commonly understood by the skilled person and by reference to standard texts such as J. Drenth, "Principles of protein X-ray crystallography", $2^{nd}$ Ed., Springer Advanced Texts in Chemistry, New York (1999); and G. E. Schulz and R. H. Schirmer, "Principles of Protein Structure", Springer Verlag, New York (1985). For example, X-ray diffraction data is first acquired, often using cryoprotected (e.g., with 20% to 30% glycerol) crystals frozen to 100 K, e.g., using a beamline at a synchrotron facility or a rotating anode as a X-ray source. Then the phase problem is solved by a generally known method, e.g., multiwavelength anomalous diffraction (MAD), multiple isomorphous replacement (MIR), single wavelength anomalous diffraction (SAD), or molecular replacement (MR). The sub-structure may be solved using SHELXD (Schneider and Sheldrick, 2002), phases calculated with SHARP (Vonrhein et al., 2006), and improved with solvent flattening and non-crystallographic symmetry averaging (e.g., with RESOLVE (Terwilliger, 2000). Model autobuilding can be done, e.g., with ARP/wARP (Perrakis et al., 1999) and refinement with, e.g., REFMAC (Murshudov, 1997). Furthermore, the structure coordinates (FIG. 18) of the PB2 fragment provided by the present invention are useful for the structure determination of PB2 polypeptides of other Orthomyxoviridae genera, or PB2 polypeptide variants that have amino acid substitutions, deletions, and/or insertions using the method of molecular replacement.

It is another aspect of the present invention to provide an isolated polynucleotide coding for the above-mentioned PB2 polypeptide fragments and variants thereof. The molecular biology methods applied for obtaining such isolated nucleotide fragments are generally known to the person skilled in the art (for standard molecular biology methods see Sambrook et al., Eds., "Molecular Cloning: A Laboratory Manual", Cold Spring Harbor Laboratory Press, Cold Spring Harbor, N.Y. (1989), which is incorporated herein by reference). For example, RNA can be isolated from Influenza virus infected cells and cDNA generated applying reverse transcription polymerase chain reaction (RT-PCR) using either random primers (e.g., random hexamers of decamers) or primers specific for the generation of the fragments of interest. The fragments of interest can then be amplified by standard PCR using fragment specific primers.

In a preferred embodiment the isolated polynucleotide coding for the preferred embodiments of the soluble PB2 polypeptide fragments are derived from SEQ ID NOs: 23 (Influenza A), 26 (Influenza B), or 27 (Influenza C). In a preferred embodiment, the isolated polynucleotide coding for the soluble Influenza A virus PB2 polypeptide fragment or variant thereof is derived from SEQ ID NO: 25 which comprises an amino acid exchange from arginine to lysine at position 389 when compared to SEQ ID NO: 1. In an even more preferred embodiment, the isolated polynucleotide coding for the Influenza A virus PB2 polypeptide fragment or variants thereof is derived from SEQ ID NO: 26 which is a DNA sequence optimized for *E. coli* codon usage. In that context, derived refers to the fact that SEQ ID NOs: 23, 24, 25, 26, or 27 encode the full-length PB2 polypeptides and, thus, polynucleotides coding for preferred PB2 polypeptide fragments comprise deletions at the 5' and 3' ends of the polynucleotide as required by the respectively encoded PB2 polypeptide fragment.

In one embodiment, the present invention relates to a recombinant vector comprising said isolated polynucleotide. The person skilled in the art is well aware of techniques used for the incorporation of polynucleotide sequences of interest into vectors (also see Sambrook et al., 1989). Such vectors include any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors may be expression vectors suitable for prokaryotic or eukaryotic expression. Said plasmids may include an origin of replication (ori), a multiple cloning site, and regulatory sequences such as promoter (constitutive or inducible), transcription initiation site, ribosomal binding site, transcription termination site, polyadenylation signal, and selection marker such as antibiotic resistance or auxotrophic marker based on complementation of a mutation or deletion. In one embodiment the polynucleotide sequence of interest is operably linked to the regulatory sequences.

In another embodiment, said vector includes nucleotide sequences coding for epitope-, peptide-, or protein-tags that facilitate purification of polypeptide fragments of interest. Such epitope-, peptide-, or protein-tags include, but are not limited to, hemagglutinin- (HA-), FLAG-, myc-tag, poly-His-tag, glutathione-S-transferase- (GST-), maltose-binding-protein- (MBP-), NusA-, and thioredoxin-tag, or fluorescent protein-tags such as (enhanced) green fluorescent protein ((E)GFP), (enhanced) yellow fluorescent protein ((E)YFP), red fluorescent protein (RFP) derived from Discosoma species (DsRed) or monomeric (mRFP), cyan fluorescent protein (CFP), and the like. In a preferred embodiment, the epitope-, peptide-, or protein-tags can be cleaved off the polypeptide fragment of interest, for example, using a protease such as thrombin, Factor Xa, PreScission, TEV protease, and the like. The recognition sites for such proteases are well known to the person skilled in the art. In another embodiment, the vector includes functional sequences that lead to secretion of the polypeptide fragment of interest into the culture medium of the recombinant host cells or into the periplasmic space of bacteria. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

In another aspect, the present invention provides a recombinant host cell comprising said isolated polynucleotide or said recombinant vector. The recombinant host cells may be prokaryotic cells such as archea and bacterial cells or eukaryotic cells such as yeast, plant, insect, or mammalian cells. In a preferred embodiment the host cell is a bacterial cell such as an E. coli cell. The person skilled in the art is well aware of methods for introducing said isolated polynucleotide or said recombinant vector into said host cell. For example, bacterial cells can be readily transformed using, for example, chemical transformation, e.g., the calcium chloride method, or electroporation. Yeast cells may be transformed, for example, using the lithium acetate transformation method or electroporation. Other eukaryotic cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection. In a preferred embodiment of the invention, the recombinant host cell expresses the polynucleotide fragment of interest. In an even more preferred embodiment, said expression leads to soluble polypeptide fragments of the invention. These polypeptide fragments can be purified using protein purification methods well known to the person skilled in the art, optionally taking advantage of the above-mentioned epitope-, peptide-, or protein-tags.

In another aspect, the present invention relates to a method for identifying compounds which associate with all or part of the RNA cap binding pocket of PB2 or a binding pocket of PB2 polypeptide variant, comprising the steps of (a) constructing a computer model of said binding pocket defined by the structure coordinates of the complex as shown in FIG. 18; (b) selecting a potential binding compound by a method selected from the group consisting of:
(i) assembling molecular fragments into said compound,
(ii) selecting a compound from a small molecule database, and
(iii) de novo ligand design of said compound;
(c) employing computational means to perform a fitting program operation between computer models of the said compound and the said binding pocket in order to provide an energy-minimized configuration of the said compound in the binding pocket; and (d) evaluating the results of said fitting operation to quantify the association between the said compound and the binding pocket model, whereby evaluating the ability of said compound to associate with the said binding pocket.

For the first time, the present invention permits the use of molecular design techniques to identify, select, or design potential binding partners for the RNA cap binding pocket of PB2 or RNA cap binding pockets of PB2 polypeptide variants, preferably inhibitors of RNA cap binding, based on the structure coordinates of said binding pocket according to FIG. 18. Such a predictive model is valuable in light of the higher costs associated with the preparation and testing of the many diverse compounds that may possibly bind to said binding pocket. In order to use the structure coordinates generated for the PB2 polypeptide fragment in complex with the RNA cap analog it is necessary to convert the structure coordinates into a three-dimensional shape. This is achieved through the use of commercially available software that is capable of generating three-dimensional graphical representations of molecules or portions thereof from a set of structure coordinates. An example for such a computer program is MODELER (A. Sali and T. L. Blundell, J. Mol. Biol., 234, pp. 779-815 (1993) as implemented in the Insight II Homology software package (Insight II (97.0), Molecular Simulations Incorporated, San Diego, Calif.)).

One skilled in the art may use several methods to screen chemical entities or fragments for their ability to bind to the RNA cap binding pocket of PB2 or PB2 polypeptide variants. This process may begin by a visual inspection of, for example, a three-dimensional computer model of the RNA cap binding pocket of PB2 based on the structural coordinates according to FIG. 18. Selected fragments or chemical compounds may then be positioned in a variety of orientations or docked within the binding pocket. Docking may be accomplished using software such as Cerius, Quanta, and Sybyl (Tripos Associates, St. Louis, Mo.), followed by energy minimization and molecular dynamics with standard molecular dynamics force fields such as OPLS-AA, CHARMM, and AMBER. Additional specialized computer programs that may assist the person skilled in the art in the process of selecting suitable compounds or fragments include, for example, (i) AUTODOCK (D. S. Goodsell et al., "Automated Docking of Substrates to Proteins by Simulated Annealing", Proteins: Struct., Funct., Genet., 8, pp. 195-202 (1990); AUTODOCK is available from The Scripps Research Institute, La Jolla, Calif.) and (ii) DOCK (I. D. Kuntz et al., "A Geometric Approach to Macromolecule-Ligand Interactions", J. Mol. Biol., 161, pp. 269-288 (1982); DOCK is available from the University of California, San Francisco, Calif.).

Once suitable compounds or fragments have been selected, they can be designed or assembled into a single compound or complex. This manual model building is performed using software such as Quanta or Sybyl. Useful programs aiding the skilled person in connecting individual compounds or fragments include, for example, (i) CAVEAT (P. A. Bartlett et al., "CAVEAT: A Program to Facilitate the Structure-Derived Design of Biologically Active Molecules", in Molecular Recognition in Chemical and Biological Problems", Special Publication, Royal Chem. Soc., 78, pp. 182-196 (1989); G. Lauri and P. A. Bartlett, "CAVEAT: A Program to Facilitate the Design of Organic Molecules", J. Comp. Aid. Mol. Des., 8, pp. 51-66 (1994); CAVEAT is available from the University of California, Berkley, Calif.), (ii) 3D Database systems such as ISIS (MDL Information Systems, San Leandro, Calif.; reviewed in Y. C. Martin, "3D Database Searching in Drug Design", J. Med. Chem., 35, pp. 2145-2154 (1992)), and (iii) HOOK (M. B. Eisen et al., "HOOK: A Program for Finding Novel Molecular Architectures that Satisfy the Chemical and Steric Requirements of a Macromolecule Binding Site", Proteins: Struct., Funct., Genet., 19, pp. 199-221 (1994); HOOK is available from Molecular Simulations Incorporated, San Diego, Calif.).

Another approach enabled by this invention, is the computational screening of small molecule databases for compounds that can bind in whole or part to the RNA cap binding pocket of PB2 or binding pockets of PB2 polypeptide variants. In this screening, the quality of fit of such compounds to the binding pocket may be judged either by shape complementarity or by estimated interaction energy (E. C. Meng et al., J. Comp. Chem., 13, pp. 505-524 (1992)).

Alternatively, a potential binding partner for the RNA cap binding pocket of PB2, preferably an inhibitor of RNA cap binding, may be designed de novo on the basis of the 3D structure of the PB2 polypeptide fragment in complex with the RNA cap analog according to FIG. 18. There are various de novo ligand design methods available to the person skilled in the art. Such methods include (i) LUDI (H.-J. Bohm, "The Computer Program LUDI: A New Method for the De Novo Design of Enzyme Inhibitors", J. Comp. Aid. Mol. Des., 6, pp. 61-78 (1992); LUDI is available from Molecular Simulations Incorporated, San Diego, Calif.), (ii) LEGEND (Y. Nishibata and A. Itai, Tetrahedron, 47, pp. 8985-8990 (1991); LEGEND is available from Molecular Simulations Incorporated, San Diego, Calif.), (iii) LeapFrog (available from Tripos Associates, St. Louis, Mo.), (iv) SPROUT (V. Gillet et al., "SPROUT: A Program for Structure Generation", J. Comp. Aid. Mol. Des., 7, pp. 127-153 (1993); SPROUT is available from the University of Leeds, UK), (v) GROUPBUILD (S. H. Rotstein and M. A. Murcko "GroupBuild: A Fragment-Based Method for De Novo Drug Design", J. Med. Chem., 36, pp. 1700-1710 (1993)), and (vi) GROW (J. B. Moon and W. J. Howe, "Computer Design of Bioactive Molecules: A Method for Receptor-Based De Novo Ligand Design", Proteins, 11, pp 314-328 (1991)).

In addition, several molecular modeling techniques (hereby incorporated by reference) that may support the person skilled in the art in de novo design and modeling of potential RNA cap binding pocket interacting compounds have been described and include, for example, N. C. Cohen et al., "Molecular Modeling Software and Methods for Medicinal Chemistry", J. Med. Chem., 33, pp. 883-894 (1990); M. A. Navia and M. A. Murcko, "The Use of Structural Information in Drug Design", Curr. Opin. Struct. Biol., 2, pp. 202-210 (1992); L. M. Balbes et al., "A Perspective in Modern Methods in Computer-Aided Drug Design", Reviews in Computational Chemistry, Vol. 5, K. B. Lipkowitz and D. B. Boyd, Eds., VCH, New York, pp. 37-380 (1994); W. C. Guida, "Software for Structure-Based Drug Design", Curr. Opin. Struct. Biol., 4, pp. 777-781 (1994).

A molecule designed or selected as binding to the RNA cap binding pocket of PB2 or a binding pocket of a PB2 variant may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the binding compound and the binding pocket in a bound state, preferably make a neutral or favorable contribution to the enthalpy of binding. Specific computer programs that can evaluate a compound deformation energy and electrostatic interaction are available in the art. Examples of suitable programs include (i) Gaussian 92, revision C (M. J. Frisch, Gaussian, Incorporated, Pittsburgh, Pa.), (ii) AMBER, version 4.0 (P. A. Kollman, University of California, San Francisco, Calif.), (iii) QUANTA/CHARMM (Molecular Simulations Incorporated, San Diego, Calif.), (iv) OPLS-AA (W. L. Jorgensen, "OPLS Force Fields", Encyclopedia of Computational Chemistry, Schleyer, Ed., Wiley, New York (1998) Vol. 3, pp. 1986-1989), and (v) Insight II/Discover (Biosysm Technologies Incorporated, San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the RNA cap binding pocket of PB2 or a binding pocket of a PB2 variant by the same computer methods described in detail above.

In one embodiment of the above-described method of the invention, the RNA cap binding pocket of PB2 or a binding pocket of a PB2 polypeptide variant comprises amino acids Phe323, His357, and Phe404 of PB2 according to SEQ ID NO: 1 or amino acids corresponding thereto. In another embodiment, said binding pocket comprises amino acids Phe323, Phe404, Phe325, Phe330, and Phe363 according to SEQ ID NO: 1 or amino acids corresponding thereto. In another embodiment, said binding pocket comprises amino acids Phe323, His357, Phe404, Phe325, Phe330, and Phe363 according to SEQ ID NO: 1 or amino acids corresponding thereto. In yet another embodiment, said binding pocket comprises amino acids Phe323, His357, Phe404, Glu361, and Lys376 according to SEQ ID NO: 1 or amino acids corresponding thereto. In yet another embodiment, said binding pocket comprises amino acids Phe323, His357, Phe404, Ser320, Arg332, Ser337, and Gln406 according to SEQ ID NO: 1 or amino acids corresponding thereto. In another embodiment, said binding pocket comprises amino acids Phe323, His357, Phe404, Lys339, Arg355, Asn429, and His432 according to SEQ ID NO: 1 or amino acids corresponding thereto. In another embodiment, said binding pocket comprises amino acids Phe323, His357, Phe404, Phe325, Phe330, Phe363, Glu361, and Lys376 according to SEQ ID NO: 1 or amino acids corresponding thereto. In yet another embodiment, said binding pocket comprises amino acids Phe323, His357, Phe404, Phe325, Phe330, Phe363, Ser320, Arg332, Ser337, and Gln406 according to SEQ ID NO: 1 or amino acids corresponding thereto. In yet another embodiment, said binding pocket comprises amino acids Phe323, His357, Phe404, Phe325, Phe330, Phe363, Lys339, Arg355, Asn429, and His432 according to SEQ ID NO: 1 or amino acids corresponding thereto. In another embodiment, said binding pocket comprises amino acids Phe323, His357, Phe404, Glu361, Lys376, Ser320, Arg332, Ser337, and Gln406 according to SEQ ID NO: 1 or amino acids corresponding thereto. In another embodiment, said binding pocket comprises amino acids Phe323, His357, Phe404, Glu361, Lys376, Lys339, Arg355, Asn429, and His432 according to SEQ ID NO: 1 or amino acids corresponding thereto. In another embodiment, said binding pocket comprises amino acids Phe323, His357, Phe404, Ser320, Arg332, Ser337, Gln406, Lys339, Arg355, Asn429, and His432 according to SEQ ID NO: 1 or amino acids corresponding thereto. In another embodiment, said binding pocket comprises amino acids Phe323, His357, Phe404, Phe325, Phe330, Phe363, Glu361, Lys376, Ser320, Arg332, Ser337, and Gln406 according to SEQ ID NO: 1 or amino acids corresponding thereto. In another embodiment, said binding pocket comprises amino acids Phe323, His357, Phe404, Phe325, Phe330, Phe363, Glu361, Lys376, Lys339, Arg355, Asn429, and His432 according to SEQ ID NO: 1 or amino acids corresponding thereto. In another embodiment, said binding pocket comprises amino acids Phe323, His357, Phe404, Phe325, Phe330, Phe363, Ser320, Arg332, Ser337, Gln406, Lys339, Arg355, Asn429, and His432 according to SEQ ID NO: 1 or amino acids corresponding thereto. In another embodiment, said binding pocket comprises amino acids Phe323, His357, Phe404, Glu361, Lys376, Ser320, Arg332, Ser337, Gln406, Lys339, Arg355, Asn429, and His432 according to SEQ ID NO: 1 or amino acids corresponding thereto. In another embodiment, said binding pocket comprises amino acids Phe323, His357, Phe404, Phe325, Phe330, Phe363, Glu361, Lys376, Ser320, Arg332, Ser337, Gln406, Lys339, Arg355, Asn429, and His432 according to SEQ ID NO: 1 or amino acids corresponding thereto. In another embodiment, said binding pocket comprises amino acids Phe323, His357, Phe404, and Met431 according to SEQ ID NO: 1 or amino acids corresponding thereto. In another embodiment, said binding pocket comprises amino acids Phe323, His357, Phe404, Phe325, Phe330, Phe363, and Met431 according to SEQ ID NO: 1 or amino acids corresponding thereto. In another embodiment, said binding pocket comprises amino acids Phe323, His357, Phe404, Phe325, Phe330, Phe363, Glu361, Lys376, and Met431 according to SEQ ID NO: 1 or amino acids corresponding thereto. In another embodiment, said binding pocket comprises amino acids Phe323, His357, Phe404, Phe325, Phe330, Phe363, Glu361, Lys376, Ser320, Arg332, Ser337, Gln406, and Met431 according to SEQ ID NO: 1 or amino acids corresponding thereto. In another embodiment, said binding pocket comprises amino acids Phe323, His357, Phe404, Phe325, Phe330, Phe363, Glu361, Lys376, Ser320, Arg332, Ser337, Gln406, Lys339, Arg355, Asn429, His432, and Met431 according to SEQ ID NO: 1 or amino acids corresponding thereto. In another embodiment, said binding pocket comprises amino acids Phe323, His357, Phe404, Phe325, Glu361, and Lys376 according to SEQ ID NO: 1 or amino acids corresponding thereto. In another embodiment, said binding pocket comprises amino acids Phe323, His357, Phe404, Phe325, Phe363, Glu361, and Lys376 according to SEQ ID NO: 1 or amino acids corresponding thereto. In another embodiment, said binding pocket comprises amino acids Phe323, His357, Phe404, Glu361, and Lys376 according to SEQ ID NO: 1 or amino acids corresponding thereto. In another embodiment, said binding pocket comprises amino acids Phe323, His357, Phe404, Phe325, Phe330, Phe363, Glu361, and Ser337 according to SEQ ID NO: 1 or amino acids corresponding thereto. In another embodiment, said binding pocket comprises amino acids His357, Phe404, Phe325, Glu361, Lys376, Arg332, Ser337, and Met431 according to SEQ ID NO: 1 or amino acids corresponding thereto. In another embodiment, said binding pocket comprises amino acids His357, Phe404, Phe325, Glu361, Lys376, Arg332, Ser337, Met431, Lys339, Arg355, Asn429, and His432 according to SEQ ID NO: 1 or amino acids corresponding thereto. In another embodiment, said binding pocket comprises amino acids Phe323, His357, Phe404, and Phe325 according to SEQ ID NO: 1 or amino acids corresponding thereto. In another embodiment, said binding pocket comprises amino acids Phe323, His357, Phe404, and Glu361 according to SEQ ID NO: 1 or amino acids corresponding thereto. In another embodiment, said binding pocket comprises amino acids Phe323, His357, Phe404, and Lys376 according to SEQ ID NO: 1 or amino acids corresponding thereto. In another embodiment, said binding pocket comprises amino acids Phe323, His357, Phe404, Glu361, and Lys376 according to SEQ ID NO: 1 or amino acids corresponding thereto. In another embodiment, said binding pocket comprises amino acids Phe323, His357, Phe404, Phe325 and Glu361 according to SEQ ID NO: 1 or amino acids corresponding thereto. In another embodiment, said binding pocket comprises amino acids Phe323, His357, Phe404, Phe325 and Lys376 according to SEQ ID NO: 1 or amino acids corresponding thereto. Furthermore, in other embodiments, the above defined binding pockets may optionally comprise an amino acid corresponding to amino acid Met431 according to SEQ ID NO: 1 or amino acids corresponding thereto.

In a further aspect of the above-described method of the invention, the RNA cap binding pocket of PB2 is defined by the structure coordinates of PB2 SEQ ID NO: 1 amino acids Phe323, His357, and Phe404 according to FIG. 18. In another embodiment, said binding pocket is defined by the structure coordinates of PB2 SEQ ID NO: 1 amino acids Phe323, Phe404, Phe325, Phe330, and Phe363 according to FIG. 18. In another embodiment, said binding pocket is defined by the structure coordinates of PB2 SEQ ID NO: 1 amino acids Phe323, His357, Phe404, Phe325, Phe330, and Phe363 according to FIG. 18. In yet another embodiment, said binding pocket is defined by the structure coordinates of PB2 SEQ ID NO: 1 amino acids Phe323, His357, Phe404, Glu361, and Lys376 according to FIG. 18. In another embodiment, said binding pocket is defined by the structure coordinates of PB2 SEQ ID NO: 1 amino acids Phe323, His357, Phe404, Ser 320, Arg332, Ser337, and Gln406 according to FIG. 18. In another embodiment, said binding pocket is defined by the structure coordinates of PB2 SEQ ID NO: 1 amino acids Phe323, His357, Phe404, Lys339, Arg355, Asn429, and His432 according to FIG. 18. In another embodiment, said binding pocket is defined by the structure coordinates of PB2 SEQ ID NO: 1 amino acids Phe323, His357, Phe404, Phe325, Phe330, Phe363, Glu361, and Lys376 according to FIG. 18. In yet another embodiment, said binding pocket is defined by the structure coordinates of PB2 SEQ ID NO: 1 amino acids Phe323, His357, Phe404, Phe325, Phe330, Phe363, Ser320, Arg332, Ser337, and Gln406 according to FIG. 18. In yet another embodiment, said binding pocket is defined by the structure coordinates of PB2 SEQ ID NO: 1 amino acids Phe323, His357, Phe404, Phe325, Phe330, Phe363, Lys339, Arg355, Asn429, and His432 according to FIG. 18. In another embodiment, said binding pocket is defined by the structure coordinates of PB2 SEQ ID NO: 1 amino acids Phe323, His357, Phe404, Glu361, Lys376, Ser320, Arg332, Ser337, and Gln406 according to FIG. 18. In another embodiment, said binding pocket is defined by the structure coordinates of PB2 SEQ ID NO: 1 amino acids Phe323, His357, Phe404, Glu361, Lys376, Lys339, Arg355, Asn429, and His432 according to FIG. 18. In another embodiment, said binding pocket is defined by the structure coordinates of PB2 SEQ ID NO: 1 amino acids Phe323, His357, Phe404, Ser320, Arg332, Ser337, Gln406, Lys339, Arg355, Asn429, and His432 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, Ser320, Arg332, Ser337, and Gln406 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, Lys339, Arg355, Asn429, and His432 according to FIG. 18. In another embodiment, said binding pocket is defined by the structure coordinates of PB2 SEQ ID NO: 1 amino acids Phe323, His357, Phe404, Phe325, Phe330, Phe363, Ser320, Arg332, Ser337, Gln406, Lys339, Arg355, Asn429, and His432 according to FIG. 18. In another embodiment, said binding pocket is defined by the structure coordinates of PB2 SEQ ID NO: 1 amino acids Phe323, His357, Phe404, Glu361, Lys376, Ser320, Arg332, Ser337, Gln406, Lys339, Arg355, Asn429, and His432 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, Ser320, Arg332, Ser337, Gln406, Lys339, Arg355, Asn429, and His432 according to FIG. 18. In another embodiment, said binding pocket is defined by the structure coordinates of PB2 SEQ ID NO: 1 amino acids Phe323, His357, Phe404, and Met431 according to FIG. 18. In another embodiment, said binding pocket is defined by the structure coordinates of PB2 SEQ ID NO: 1 amino acids Phe323, His357, Phe404, Phe325, Phe330, Phe363, and Met431 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, and Met431 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, Ser320, Arg332, Ser337, Gln406, and Met431 according to FIG. 18. In another embodiment, said binding pocket is defined by the structure coordinates of PB2 SEQ ID NO: 1 amino acids Phe323, His357, Phe404, Phe325, Phe330, Phe363, Glu361, Lys376, Ser320, Arg332, Ser337, Gln406, Lys339, Arg355, Asn429, His432, and Met431 according to FIG. 18. In another embodiment, said binding pocket is defined by the structure coordinates of PB2 SEQ ID NO: 1 amino acids Phe323, His357, Phe404, Phe325, Glu361, and Lys376 according to FIG. 18. In another embodiment, said binding pocket is defined by the structure coordinates of PB2 SEQ ID NO: 1 amino acids Phe323, His357, Phe404, Phe325, Phe363, Glu361, and Lys376 according to FIG. 18. In another embodiment, said binding pocket is defined by the structure coordinates of PB2 SEQ ID NO: 1 amino acids Phe323, His357, Phe404, Glu361, and Lys376 according to FIG. 18. In another embodiment, said binding pocket is defined by the structure coordinates of PB2 SEQ ID NO: 1 amino acids Phe323, His357, Phe404, Phe325, Phe330, Phe363, Glu361, and Ser337 according to FIG. 18. In another embodiment, said binding pocket is defined by the structure coordinates of PB2 SEQ ID NO: 1 amino acids His357, Phe404, Phe325, Glu361, Lys376, Arg332, Ser337, and Met431 according to FIG. 18. In another embodiment, said binding pocket is defined by the structure coordinates of PB2 SEQ ID NO: 1 amino acids His357, Phe404, Phe325, Glu361, Lys376, Arg332, Ser337, Met431, Lys339, Arg355, Asn429, and His432 according to FIG. 18. In another embodiment, said binding pocket is defined by the structure coordinates of PB2 SEQ ID NO: 1 amino acids Phe323, His357, Phe404, and Phe325 according to FIG. 18. In another embodiment, said binding pocket is defined by the structure coordinates of PB2 SEQ ID NO: 1 amino acids Phe323, His357, Phe404, and Lys376 according to FIG. 18. In another embodiment, said binding pocket is defined by the structure coordinates of PB2 SEQ ID NO: 1 amino acids Phe323, His357, Phe404, Glu361, and Lys376 according to FIG. 18. In another embodiment, said binding pocket is defined by the structure coordinates of PB2 SEQ ID NO: 1 amino acids Phe323, His357, Phe404, Phe325, and Glu361 according to FIG. 18. In another embodiment, said binding pocket is defined by the structure coordinates of PB2 SEQ ID NO: 1 amino acids Phe323, His357, Phe404, Phe325, and Lys376 according to FIG. 18. Furthermore, in other embodiments, the binding pockets as defined above may optionally be additionally defined by the structure coordinates of PB2 SEQ ID NO:1 amino acid Met431 according to FIG. 18.

In one aspect, the present invention provides a method for computational screening according to the above-described method for compounds able to associate with a binding pocket that is a variant to the RNA cap binding pocket of PB2 according to FIG. 18. In one embodiment said variant of said binding pocket has a root mean square deviation from the backbone atoms of amino acids Phe323, His357, and Phe404; of amino acids Phe323, Phe404, Phe325, Phe330, and Phe363; of amino acids Phe323, His357, Phe404, Phe325, Phe330, and Phe363; of amino acids Phe323, His357, Phe404, Glu361, and Lys376; of amino acids Phe323, His357, Phe404, Ser 320, Arg332, Ser337, and Gln406; of amino acids Phe323, His357, Phe404, Lys339, Arg355, Asn429, and His432; of amino acids Phe323, His357, Phe404, Phe325, Phe330, Phe363, Glu361, and Lys376; of amino acids Phe323, His357, Phe404, Phe325, Phe330, Phe363, Ser320, Arg332, Ser337, and Gln406; of amino acids Phe323, His357, Phe404, Phe325, Phe330, Phe363, Lys339, Arg355, Asn429, and His432; of amino acids Phe323, His357, Phe404, Glu361, Lys376, Ser320, Arg332, Ser337, and Gln406; of amino acids Phe323, His357, Phe404, Glu361, Lys376, Lys339, Arg355, Asn429, and His432; of amino acids Phe323, His357, Phe404, Ser320, Arg332, Ser337, Gln406, Lys339, Arg355, Asn429, and His432; of amino acids Phe323, His357, Phe404, Phe325, Phe330, Phe363, Glu361, Lys376, Ser320, Arg332, Ser337, and Gln406; of amino acids Phe323, His357, Phe404, Phe325, Phe330, Phe363, Glu361, Lys376, Lys339, Arg355, Asn429, and His432; of amino acids Phe323, His357, Phe404, Phe325, Phe330, Phe363, Ser320, Arg332, Ser337, Gln406, Lys339, Arg355, Asn429, and His432; of amino acids Phe323, His357, Phe404, Glu361, Lys376, Ser320, Arg332, Ser337, Gln406, Lys339, Arg355, Asn429, and His432; of amino acids Phe323, His357, Phe404, Phe325, Phe330, Phe363, Glu361, Lys376, Ser320, Arg332, Ser337, Gln406, Lys339, Arg355, Asn429, and His432, of amino acids Phe323, His357, Phe404, and Met431, of amino acids Phe323, His357, Phe404, Phe325, Phe330, Phe363, and Met431, of amino acids Phe323, His357, Phe404, Phe325, Phe330, Phe363, Glu361, Lys376, and Met431, of amino acids Phe323, His357, Phe404, Phe325, Phe330, Phe363, Glu361, Lys376, Ser320, Arg332, Ser337, Gln406, and Met431, of amino acids Phe323, His357, Phe404, Phe325, Phe330, Phe363, Glu361, Lys376, Ser320, Arg332, Ser337, Gln406, Lys339, Arg355, Asn429, His432, and Met431, of amino acids Phe323, His357, Phe404, Phe325, Glu361, and Lys376, of amino acids Phe323, His357, Phe404, Phe325, Phe363, Glu361, and Lys376, of amino acids Phe323, His357, Phe404, Glu361, and Lys376, of amino acids Phe323, His357, Phe404, Phe325, Phe330, Phe363, Glu361, and Ser337, of amino acids His357, Phe404, Phe325, Glu361, Lys376, Arg332, Ser337, and Met431, of amino acids His357, Phe404, Phe325, Glu361, Lys376, Arg332, Ser337, Met431, Lys339, Arg355, Asn429, and His432, of amino acids Phe323, His357, Phe404, and Phe325, of amino acids Phe323, His357, Phe404, and Glu361, of amino acids Phe323, His357, Phe404, and Lys376, of amino acids Phe323, His357, Phe404, Glu361, and Lys376, of amino acids Phe323, His357, Phe404, Phe325, and Glu361, of amino acids Phe323, His357, Phe404, Phe325, and Lys376, the above amino acid combinations optionally including amino acid Met431 according to FIG. 18 of not more than 3 Å. In another embodiment, the said root mean square deviation is not more than 2.5 Å. In another embodiment, the said root mean square deviation is not more than 2 Å. In another embodiment, the said root mean square deviation is not more than 1.5 Å. In another embodiment, the said root mean square deviation is not more than 1 Å. In another embodiment, the said root mean square deviation is not more than 0.5 Å.

In a preferred embodiment, $m^7GTP$ is sandwiched between His357 on the solvent side and a cluster of five phenylalanines on the protein side, principally Phe323 and Phe404, but also Phe325, Phe330, and Phe363. In this preferred embodiment, specific recognition of the guanosine base is principally achieved by Glu361 hydrogen bonding to N2 and N1 positions of the guanine, which also helps to neutralize the delocalized positive charge of the $m^7GTP$. Also Lys376 makes a long hydrogen bond to the O6. There are two well-ordered, buried water molecules in the ligand pocket which interact with Glu361, Lys376, and Gln406 but not directly with the ligand. Important second layer residues are preferably Arg332 and Ser337 which hydrogen bond to His357. Within hydrogen bonding distance of the N2 of the base is either a water molecule or Ser320. The N7 methyl group is in van der Waals contact with the side-chain of Gln406 (3.4 Å) and the carbonyl oxygen of Phe404 (3.4 Å) is in contact with the side chain of Met431 slightly further away. In this embodiment, the triphosphate is bent round towards the base. The alpha-phosphate interacts with His432 and Asn429 and the gamma-phosphate interacts with basic residues His357, Lys339, and Arg355.

If computer modeling according to the methods described hereinabove indicates binding of a compound to the RNA binding pocket of PB2 or the binding pocket of a PB2 polypeptide variant, said compound may be synthesized and optionally the ability of said compound to bind to said binding pocket may be tested in vitro or in vivo comprising the further step of (e) synthesizing said compound, and optionally (f) contacting said compound with the PB2 polypeptide fragment or variant thereof or the recombinant host cell of the invention and a RNA cap or analog thereof to determine the ability of said compound to inhibit binding between said PB2 polypeptide fragment and said RNA cap or analog thereof. The quality of fit of such compounds to the binding pocket may be judged either by shape complementarity or by estimated interaction energy (E. C. Meng et al., J. Comp. Chem., 13, pp. 505-524 (1992). Methods for synthesizing said compounds are well known to the person skilled in the art or such compounds may be commercially available. Examples for methods for determining said RNA cap binding inhibitory effect of the identified compounds are described hereinafter.

It is another aspect of the invention to provide a compound identifiable by the above-described method, under the provision that said compound is not any of the RNA cap analogs selected from the group consisting of $m^7G$, $m^7GMP$, $m^7GTP$, $m^7$ GpppG, $m^7$ GpppGm, $m^7$ GpppA, $m^7$ GpppAm, $m^7$ GpppC, and $m^7$ GpppCm, $m^7$ GpppU, and $m^7$ GpppUm or the small molecule inhibitors of RNA cap binding 2-Amino-7-benzyl-9-(4-hydroxy-butyl)-1,9-dihydro-purin-6-one (RO0794238, Hooker et al., 2003) or T-705 (Furuta et al., 2005) and is able to bind to the RNA cap binding pocket of PB2. In another aspect, the present invention refers to a compound identifiable by the above-described method, under the provision that said compound is not any of the RNA cap analogs selected from the group consisting of $m^7G$, $m^7GMP$, $m^7GTP$, $m^7$ GpppG, $m^7$ GpppGm, $m^7$ GpppA, $m^7$ GpppAm, $m^7$ GpppC, and $m^7$ GpppCm, $m^7$ GpppU, and $m^7$ GpppUm or the small molecule inhibitors of RNA cap binding 2-Amino-7-benzyl-9-(4-hydroxy-butyl)-1,9-dihydro-purin-6-one or T-705 and is able to inhibit binding between the PB2 polypeptide fragment and the RNA cap or analog thereof. Compounds of the present invention can be any agents including, but not restricted to, peptides, peptoids, polypeptides, proteins (including antibodies), lipids, metals, nucleotides, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds.

In a further aspect, the present invention provides a method for identifying compounds which associate with the RNA cap binding pocket of PB2 or a binding pocket of a PB2 polypeptide variant, comprising the steps of (i) contacting the PB2 polypeptide fragment or the recombinant host cell of the invention with a test compound and (ii) analyzing the ability of said test compound to bind to the PB2 polypeptide fragment or variant thereof.

In one embodiment, the interaction between the PB2 polypeptide fragment or variant thereof and a test compound may be analyzed in form of a pull down assay. For example, the PB2 polypeptide fragment may be purified and may be immobilized on beads. In one embodiment, the PB2 polypeptide fragment immobilized on beads may be contacted, for example, with (i) another purified protein, polypeptide fragment, or peptide, (ii) a mixture of proteins, polypeptide fragments, or peptides, or (iii) a cell or tissue extract, and binding of proteins, polypeptide fragments, or peptides may be verified by polyacrylamide gel electrophoresis in combination with coomassie staining or Western blotting. Unknown binding partners may be identified by mass spectrometric analysis.

In another embodiment, the interaction between the PB2 polypeptide fragment or variant thereof and a test compound may be analyzed in form of an enzyme-linked immunosorbent assay (ELISA)-based experiment. In one embodiment, the PB2 polypeptide fragment or variant thereof according to the invention may be immobilized on the surface of an ELISA plate and contacted with the test compound. Binding of the test compound may be verified, for example, for proteins, polypeptides, peptides, and epitope-tagged compounds by antibodies specific for the test compound or the epitope-tag. These antibodies might be directly coupled to an enzyme or detected with a secondary antibody coupled to said enzyme that—in combination with the appropriate substrates—carries out chemiluminescent reactions (e.g., horseradish peroxidase) or colorimetric reactions (e.g., alkaline phosphatase). In another embodiment, binding of compounds that cannot be detected by antibodies might be verified by labels directly coupled to the test compounds. Such labels may include enzymatic labels, radioisotope or radioactive compounds or elements, fluorescent compounds or metals, chemiluminescent compounds and bioluminescent compounds. In another embodiment, the test compounds might be immobilized on the ELISA plate and contacted with the soluble PB2 polypeptide fragment or variants thereof according to the invention. Binding of said polypeptide may be verified by a PB2 polypeptide fragment specific antibody and chemiluminescence or colorimetric reactions as described above.

In a further embodiment, purified soluble PB2 polypeptide fragments may be incubated with a peptide array and binding of the PB2 polypeptide fragments to specific peptide spots corresponding to a specific peptide sequence may be analyzed, for example, by PB2 polypeptide specific antibodies, antibodies that are directed against an epitope-tag fused to the PB2 polypeptide fragment, or by a fluorescence signal emitted by a fluorescent tag coupled to the PB2 polypeptide fragment.

In another embodiment, the recombinant host cell according to the present invention is contacted with a test compound. This may be achieved by co-expression of test proteins or polypeptides and verification of interaction, for example, by fluorescence resonance energy transfer (FRET) or co-immunoprecipitation. In another embodiment, directly labeled test compounds may be added to the medium of the recombinant host cells. The potential of the test compound to penetrate membranes and bind to the PB2 polypeptide fragment may be, for example, verified by immunoprecipitation of said polypeptide and verification of the presence of the label.

In a preferred embodiment, the above-described method for identifying compounds which associate with the RNA cap binding pocket of PB2 or a binding pocket of a PB2 polypeptide variant comprises the further step of adding a RNA cap or analog thereof. In another embodiment of said method, the ability of said test compound to bind to PB2 in presence of said RNA cap or analog thereof or the ability of said test compound to inhibit binding of said RNA cap or analog thereof to PB2 is analyzed. A compound is considered to inhibit RNA cap or RNA cap analog binding if binding is reduced by the compound at the same molar concentration as the RNA cap or RNA cap analog by more than 20%, by more than 30%, by more than 40%, by more than 50%, preferably by more than 60%, preferably by more than 70%, preferably by more than 80%, preferably by more than 90%. In preferred embodiments, the above-described pull down, ELISA, peptide array, FRET, and co-immunoprecipitation experiments may be carried out in presence of an RNA cap structure or an analog thereof, preferably a labeled RNA cap structure or analog thereof, in presence or in absence of a test compound. In one embodiment, the RNA cap or analog thereof is added prior to addition of said test compound. In a further embodiment, the RNA cap or analog thereof is added concomitantly with addition of said test compound. In yet another embodiment, the RNA cap or analog thereof is added after addition of said test compound.

In a preferred embodiment, the ability of the identifiable test compound to interfere with the interaction of a PB2 polypeptide fragment of the invention to a RNA cap or analog thereof may be tested by incubating said polypeptide fragment with 7-methyl-GTP Sepharose 4B resin (GE Healthcare) in presence or absence of said compound and comparing, preferably quantifying, the amount of bound PB2 polypeptide fragment with and without said compound, e.g., on a coomassie stained SDS PAGE gel or using Western blot analysis.

The ability of the RNA cap or analog thereof to associate with the PB2 fragment or variant thereof according to the present invention in presence or absence of the test compound is evaluated. In one embodiment, this may be achieved using a fluorescein-labeled RNA cap analog, fluorescein-labeled 7-methyl-guanosine monophosphate ($m^7$GMP), in a fluorescence polarization assay as described by Natarajan et al. (2004). Alternatively, in another embodiment a ribose diol-modified fluorescent cap analog, anthraniloyl-$m^7$GTP, may be used in a fluorescence spectroscopic assay as set forth by Ren et al. (1996). In a further embodiment, radioactively labeled RNA caps may be incubated with the PB2 polypeptide fragment or variant thereof in presence or absence of a test compound, wherein the RNA cap may be added prior to, concomitantly with, or after addition of the test compound. The cap binding reaction is UV-crosslinked, denatured, and analyzed by gel electrophoresis as described by Hooker et al. (2003). In another embodiment, the PB2 polypeptide fragments of the invention may be immobilized on a microtiter plate, incubated with a labeled RNA cap or analog thereof in presence or absence of a test compound, wherein the RNA cap or analog thereof may be added prior to, concomitantly with, or after addition of the test compound, and cap binding is analyzed by verifying the presence of the label after thorough washing of the plate. Signal intensities of the RNA cap or RNA cap analog label in wells with test compound to signal intensities of said label without test compound are compared and a compound is considered to inhibit RNA cap or RNA cap analog binding if binding is reduced by more than 50%, preferably by more than 60%, preferably by more than 70%, preferably by more than 80%, preferably by more than 90% as described above.

In a preferred embodiment, the above-described method for identifying compounds which associate with the RNA cap binding pocket of PB2 or a binding pocket of a PB2 polypeptide variant, preferably inhibit binding of RNA caps or analogs thereof, is performed in a high-throughput setting. In a preferred embodiment, said method is carried out in a multi-well microtiter plate as described above using immobilized PB2 polypeptide fragments or variants thereof according to the present invention and labeled RNA caps or analogs thereof. In a preferred embodiment, the test compounds are derived from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal extracts can be used. Additionally, test compounds can be synthetically produced using combinatorial chemistry either as individual compounds or as mixtures. The RNA caps or analogs thereof may be added prior to, concomitantly with, or after the addition of the library compound. The ability of the compound to inhibit RNA cap binding may be assessed as described above.

In another embodiment, the inhibitory effect of the identified compound on the Influenza virus life cycle may be tested in an in vivo setting. A cell line that is susceptible for Influenza virus infection such as 293T human embryonic kidney cells, Madin-Darby canine kidney cells, or chicken embryo fibroblasts may be infected with Influenza virus in presence or absence of the identified compound. In a preferred embodiment, the identified compound may be added to the culture medium of the cells in various concentrations. Viral plaque formation may be used as read out for the infectious capacity of the Influenza virus and may be compared between cells that have been treated with the identified compound and cells that have not been treated.

In a further embodiment of the invention, the test compound applied in any of the above described methods is a small molecule. In a preferred embodiment, said small molecule is derived from a library, e.g., a small molecule inhibitor library. In another embodiment, said test compound is a peptide or protein. In a preferred embodiment, said peptide or protein is derived from a peptide or protein library.

In another embodiment of the above-described methods for computational as well as in vitro identification of compounds that associate with the RNA cap binding pocket of the PB2 polypeptide fragment or variant according to the invention and/or inhibit RNA cap binding to said binding pocket, said methods further comprise the step of formulating the identifiable compound or a pharmaceutically acceptable salt thereof with one or more pharmaceutically acceptable excipient(s) and/or carrier(s). In another aspect the present invention provides a pharmaceutical composition producible according to the aforementioned method. A compound according to the present invention can be administered alone but, in human therapy, will generally be administered in admixture with a suitable pharmaceutical excipient, diluent, or carrier selected with regard to the intended route of administration and standard pharmaceutical practice (see hereinafter).

In the aspect of computational modeling or screening of a binding partner for the RNA cap binding pocket of PB2 or a binding pocket of a PB2 variant, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics", $8^{th}$ Edition, L. S. Goodman, A. Gilman, T. W. Rall, A. S, Nies, & P. Taylor, Eds., Pergamon Press (1985); W. L. Jorgensen & E. M. Duffy, Bioorg. Med. Chem. Lett, 10, pp. 1155-1158 (2000). Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (C. A. Lipinski et al., Adv. Drug Deliv. Rev., 23, pp. 3-25 (1997)). Programs suitable for pharmacophore selection and design include (i) DISCO (Abbot Laboratories, Abbot Park, Ill.), (ii) Catalyst (Bio-CAD Corp., Mountain View, Calif.), and (iii) Chem DBS-3D (Chemical Design Ltd., Oxford, UK).

The pharmaceutical composition contemplated by the present invention may be formulated in various ways well known to one of skill in the art. For example, the pharmaceutical composition of the present invention may be in solid form such as in the form of tablets, pills, capsules (including soft gel capsules), cachets, lozenges, ovules, powder, granules, or suppositories, or in liquid form such as in the form of elixirs, solutions, emulsions, or suspensions.

Solid administration forms may contain excipients such as microcrystalline cellulose, lactose, sodium citrate, calcium carbonate, dibasic calcium phosphate, glycine, and starch (preferably corn, potato, or tapioca starch), disintegrants such as sodium starch glycolate, croscarmellose sodium, and certain complex silicates, and granulation binders such as polyvinylpyrrolidone, hydroxypropylmethyl cellulose (HPMC), hydroxypropylcellulose (HPC), sucrose, gelatin, and acacia. Additionally, lubricating agents such as magnesium stearate, stearic acid, glyceryl behenate, and talc may be included. Solid compositions of a similar type may also be employed as fillers in gelatin capsules. Preferred excipients in this regard include lactose, starch, a cellulose, milk sugar or high molecular weight polyethylene glycols.

For aqueous suspensions, solutions, elixirs, and emulsions suitable for oral administration the compound may be combined with various sweetening or flavoring agents, coloring matter or dyes, with emulsifying and/or suspending agents and with diluents such as water, ethanol, propylene glycol, and glycerin, and combinations thereof.

The pharmaceutical composition of the invention may contain release rate modifiers including, for example, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, and mixtures thereof.

The pharmaceutical composition of the present invention may be in the form of fast dispersing or dissolving dosage formulations (FDDFs) and may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodium stearyl fumarate, sorbitol, xylitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The pharmaceutical composition of the present invention suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

The pharmaceutical composition suitable for intranasal administration and administration by inhalation is best delivered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A.™) or 1,1,1,2,3,3,3-heptafluoropropane (HFA 227EA.™), carbon dioxide, or another suitable gas. The pressurized container, pump, spray or nebulizer may contain a solution or suspension of the active compound, e.g., using a mixture of ethanol and the propellant as the solvent, which may additionally contain a lubricant, e.g., sorbitan trioleate.

In another embodiment the present invention provides a compound identifiable by the methods described above, comprising the step of contacting a PB2 polypeptide fragment or PB2 polypeptide fragment variant of the present invention or a recombinant host cell of the present invention with a test compound, which is different from the RNA cap analogs selected from the group consisting of $m^7G$, $m^7GMP$, $m^7GTP$, $m^7$ GpppG, $m^7$ GpppGm, $m^7$ GpppA, $m^7$ GpppAm, $m^7$ GpppC, m⁷ GpppCm, m⁷ GpppU, and m⁷ GpppUm, and the small molecule inhibitors of cap binding 2-Amino-7-benzyl-9-(4-hydroxy-butyl)-1,9-dihydro-purin-6-one (RO0794238, Hooker et al., 2003) and T-705 (Furuta et al., 2005) and is able to bind to PB2. In a preferred aspect, the present invention relates to a compound identifiable by the methods described above, comprising the step of contacting a PB2 polypeptide fragment or variant thereof or a recombinant host cell of the present invention with a test compound, which is different from the RNA cap analogs selected from the group consisting of $m^7G$, $m^7GMP$, $m^7GTP$, $m^7$ GpppG, $m^7$ GpppGm, $m^7$ GpppA, $m^7$ GpppAm, $m^7$ GpppC, $m^7$ GpppCm, $m^7$ GpppU, and $m^7$ GpppUm, and the small molecule inhibitors of cap binding 2-Amino-7-benzyl-9-(4-hydroxy-butyl)-1,9-dihydro-purin-6-one and T-705 and is able to inhibit binding between PB2 and the RNA cap or analog thereof.

In another aspect, the present invention provides an antibody directed against the RNA cap binding domain of PB2. In a preferred embodiment, said antibody recognizes the RNA cap binding domain of a polypeptide fragment or variant of a fragment indicated above, in particular selected from the group of polypeptides defined by SEQ ID NO: 14 to 22. In particular, said antibody specifically binds to an epitope comprising one or more of above indicated amino acids, which define the binding pocket. In that context, the term epitope has its art recognized meaning and preferably refers to stretches of 4 to 20 amino acids, preferably 5 to 18, 6 to 16, or 7 to 14 amino acids. Accordingly, preferred epitopes have a length of 4 to 20, 5 to 18, preferably 6 to 16 or 7 to 14 amino acids and comprise one or more of Ser320, Phe323, Phe325, Phe330, Arg332, Ser337, Lys339, Arg355, His357, Glu361, Phe363, Lys376, Phe404, Gln406, Met431 and/or His432 of SEQ ID NO: 1 or a corresponding amino acid. The antibody of the present invention may be a monoclonal or polyclonal antibody or portions thereof. Antigen-binding portions may be produced by recombinant DNA techniques or by enzymatic or chemical cleavage of intact antibodies. In some embodiments, antigen-binding portions include Fab, Fab', $F(ab')_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide. The antibody of the present invention is generated according to standard protocols. For example, a polyclonal antibody may be generated by immunizing an animal such as mouse, rat, rabbit, goat, sheep, pig, cattle, or horse with the antigen of interest optionally in combination with an adjuvant such as Freund's complete or incomplete adjuvant, RIBI (muramyl dipeptides), or ISCOM (immunostimulating complexes) according to standard methods well known to the person skilled in the art. The polyclonal antiserum directed against the RNA cap binding domain of PB2 or fragments thereof is obtained from the animal by bleeding or sacrificing the immunized animal. The serum (i) may be used as it is obtained from the animal, (ii) an immunoglobulin fraction may be obtained from the serum, or (iii) the antibodies specific for the RNA cap binding domain of PB2 or fragments thereof may be purified from the serum. Monoclonal antibodies may be generated by methods well known to the person skilled in the art. In brief, the animal is sacrificed after immunization and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. Immortalized cells are screened using the RNA cap binding domain of PB2 or a fragment thereof. Cells that produce antibodies directed against the RNA cap binding domain of PB2 or fragments thereof, e.g., hybridomas, are selected, cloned, and further screened for desirable characteristics including robust growth, high antibody production, and desirable antibody characteristics. Hybridomas can be expanded (i) in vivo in syngeneic animals, (ii) in animals that lack an immune system, e.g., nude mice, or (iii) in cell culture in vitro. Methods of selecting, cloning, and expanding hybridomas are well known to those of ordinary skill in the art. The skilled person may refer to standard texts such as "Antibodies: A Laboratory Manual", E. Harlow and D. Lane, Eds., Cold Spring Harbor Laboratory Press, Cold Spring Harbor, N.Y. (1990), which is incorporated herein by reference, for support regarding generation of antibodies.

In another aspect, the present invention relates to the use of a compound identifiable by the above-described methods that is able to bind to the RNA cap binding pocket of PB2 or a binding pocket of a PB2 polypeptide variant and/or is able to inhibit binding of an RNA cap or analog thereof to said binding pocket, the pharmaceutical composition described above, or the antibody of the present invention for the manufacture of a medicament for treating, ameliorating, or preventing disease conditions caused by viral infections with negative-sense single stranded RNA viruses. In a preferred embodiment, said disease conditions are caused by viral infections with non-segmented negative-sense single stranded RNA viruses, i.e., the order of Mononegavirales, comprising the Bornaviridae, Filoviridae, Paramyxoviridae, and Rhabdoviridae families. In a more preferred embodiment, said disease condition is caused by segmented negative-sense single stranded RNA viruses comprising the family of Orthomyxoviridae, including the genera Influenza A virus, Influenza B virus, Influenza C virus, Thogotovirus, and Isavirus, the families of Arenaviridae and Bunyaviridae, including the genera Hantavirus, Nairovirus, Orthobunyavirus, Phlebovirus, and Tospovirus. In an even more preferred embodiment said disease condition is caused by an infection with a virus species selected from the group consisting of Borna disease virus, Marburg virus, Ebola virus, Sendai virus, Mumps virus, Measles virus, Human respiratory syncytial virus, Turkey rhinotracheitis virus, Vesicular stomatitis Indiana virus, Nipah virus, Henda virus, Rabies virus, Bovine ephemeral fever virus, Infectious hematopoietic necrosis virus, Thogoto virus, Influenza A virus, Influenza B virus, Influenza C virus, Hantaan virus, Crimean-congo hemorrhagic fever virus, Rift Valley fever virus, La Crosse virus, preferably Influenza A virus, Influenza B virus, Influenza C virus, Thogoto virus, or Hantaan virus, more preferably Influenza A virus, Influenza B virus, Influenza C virus, most preferably Influenza A virus.

For treating, ameliorating, or preventing said disease conditions the medicament of the present invention can be administered to an animal patient, preferably a mammalian patient, preferably a human patient, orally, buccally, sublingually, intranasally, via pulmonary routes such as by inhalation, via rectal routes, or parenterally, for example, intracavernosally, intravenously, intra-arterially, intraperitoneally, intrathecally, intraventricularly, intraurethrally intrasternally, intracranially, intramuscularly, or subcutaneously, they may be administered by infusion or needleless injection techniques.

The pharmaceutical compositions of the present invention may be formulated in various ways well known to one of skill in the art. For example, the pharmaceutical composition of the present invention may be in solid form such as in the form of tablets, pills, capsules (including soft gel capsules), cachets, lozenges, ovules, powder, granules, or suppositories, or in liquid form such as in the form of elixirs, solutions, emulsions, or suspensions.

Solid administration forms may contain excipients such as microcrystalline cellulose, lactose, sodium citrate, calcium carbonate, dibasic calcium phosphate, glycine, and starch (preferably corn, potato, or tapioca starch), disintegrants such as sodium starch glycolate, croscarmellose sodium, and certain complex silicates, and granulation binders such as polyvinylpyrrolidone, hydroxypropylmethyl cellulose (HPMC), hydroxypropylcellulose (HPC), sucrose, gelatin, and acacia. Additionally, lubricating agents such as magnesium stearate, stearic acid, glyceryl behenate, and talc may be included. Solid compositions of a similar type may also be employed as fillers in gelatin capsules. Preferred excipients in this regard include lactose, starch, a cellulose, milk sugar or high molecular weight polyethylene glycols.

For aqueous suspensions, solutions, elixirs, and emulsions suitable for oral administration the compound may be combined with various sweetening or flavoring agents, coloring matter or dyes, with emulsifying and/or suspending agents and with diluents such as water, ethanol, propylene glycol, and glycerin, and combinations thereof.

The pharmaceutical composition of the invention may contain release rate modifiers including, for example, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, and mixtures thereof.

The pharmaceutical composition of the present invention may be in the form of fast dispersing or dissolving dosage formulations (FDDFs) and may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, finned silica, silicon dioxide, sodium starch glycolate, sodium stearyl fumarate, sorbitol, xylitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The pharmaceutical composition of the present invention suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

The pharmaceutical composition suitable for intranasal administration and administration by inhalation is best delivered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A.™) or 1,1,1,2,3,3,3-heptafluoropropane (HFA 227EA.™), carbon dioxide, or another suitable gas. The pressurized container, pump, spray or nebulizer may contain a solution or suspension of the active compound, e.g., using a mixture of ethanol and the propellant as the solvent, which may additionally contain a lubricant, e.g., sorbitan trioleate.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation administered in the use of the present invention may be varied or adjusted from about 1 mg to about 1000 mg per $m^2$, preferably about 5 mg to about 150 mg/$m^2$ according to the particular application and the potency of the active component.

The compounds employed in the medical use of the invention are administered at an initial dosage of about 0.05 mg/kg to about 20 mg/kg daily. A daily dose range of about 0.05 mg/kg to about 2 mg/kg is preferred, with a daily dose range of about 0.05 mg/kg to about 1 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

EXAMPLES

The Examples are designed in order to further illustrate the present invention and serve a better understanding. They are not to be construed as limiting the scope of the invention in any way.

Example 1

Generation of PB2 Expression Constructs

An *E. coli* codon optimized PB2 gene (Geneart) SEQ ID NO: 25, based on the amino acid sequence of Influenza A/Victoria/3/1975(H3N2) PB2 (SEQ ID NO: 1) (de la Luna et al., 1989), was cloned into vector pET9a (Novagen) modified to introduce 5' AatII/AscI and 3' NsiI/NotI restriction site pairs for directional exonuclease III truncation, and provide a 3' sequence encoding the C-terminal biotin acceptor peptide GLNDIFEAQKIEWHE. A first unidirectional truncation plasmid library was generated from the 3' end (Tarendeau et al., 2007), pooled and used as the substrate for a 5' deletion reaction. Linearised plasmids encoding inserts of 150 to 250 amino acids were isolated from an agarose gel, religated and used to transform *E. coli* BL21 AI containing the RIL plasmid (Stratagene) for expression screening using hybridization of Alexa488 streptavidin (Invitrogen) to colony blots (Tarendeau et al., 2007). Clones were ranked upon their fluorescence signal and the first 36 tested for expression of purifiable protein by $Ni^2$ affinity chromatography. Thirteen clones were identified and sequenced revealing 7 unique constructs in the region of interest (see FIG. 1):

nt 703-1488 (aa 235-496, SEQ ID NO:4)
nt 721-1449 (aa 241-483, SEQ ID NO:5)
nt 802-1449 (aa 268-483, SEQ ID NO: 6)
nt 829-1440 (aa 277-480, SEQ ID NO:7)
nt 841-1466 (aa 281-482, SEQ ID NO: 8)
nt 848-1449 (aa 290-483, SEQ ID NO:9)
nt 883-1446 (aa 295-482, SEQ ID NO: 10)
nt 952-1449 (aa 318-483, SEQ ID NO:11)

These PB2 polynucleotide fragments were generated by polymerase chain reaction (PCR) using the synthetic gene as template and cloned into the expression vector pETM11 plasmid (EMBL) between NcoI and XhoI sites. The pETM11 expression vector allows for expression of $His_6$-tagged fusion protein. The $His_6$-tag can be cleaved off the fusion protein using TEV protease.

Example 2

Identification of a Minimal Cap-Binding Fragment

PB2 polypeptide fragments 235-496, 241-483, 268-483, and 290-483 (SEQ ID NOs: 4, 5, 6 and 9) were expressed in E. coli using the plasmid constructs described in Example 1 and the general expression and purification protocol described in Example 3. It was found that purified PB2 fragment 235-496 (SEQ ID NO: 4) is only soluble at low concentration, whereas fragments 241-483, 268-483 and 290-483 (SEQ ID NO: 5, 6, and 9) are more soluble and could bind specifically to a $Hi^7GTP$ sepharose column, indicating cap-binding activity. For these assays 0.2 mg of protein was loaded onto 50 µL of 7-methyl-GTP Sepharose 4B resin (GE Healthcare) and incubated for 3 h at 4° C. for binding. After washing with buffer containing 50 mM Tris'HCl (pH 8.0), 200 mM NaCl, 2 mM DTT, the proteins were eluted by centrifugation with the same buffer containing 1 mM $m^7GTP$ and analysed on SDS-PAGE. During the course of these experiments it was noted that a smaller degradation fragment could also bind $m^7GTP$ and this was identified by N-terminal sequencing and mass-spectroscopy to be residues 318-483 (SEQ ID NO: 11) and furthermore this fragment was proteolytically stable. The corresponding polynucleotide fragment (nt 952-1449) was cloned into pETMl 1 as described in Example 1.

Example 3

PB2 Fragment Expression and Purification

Figure 2:
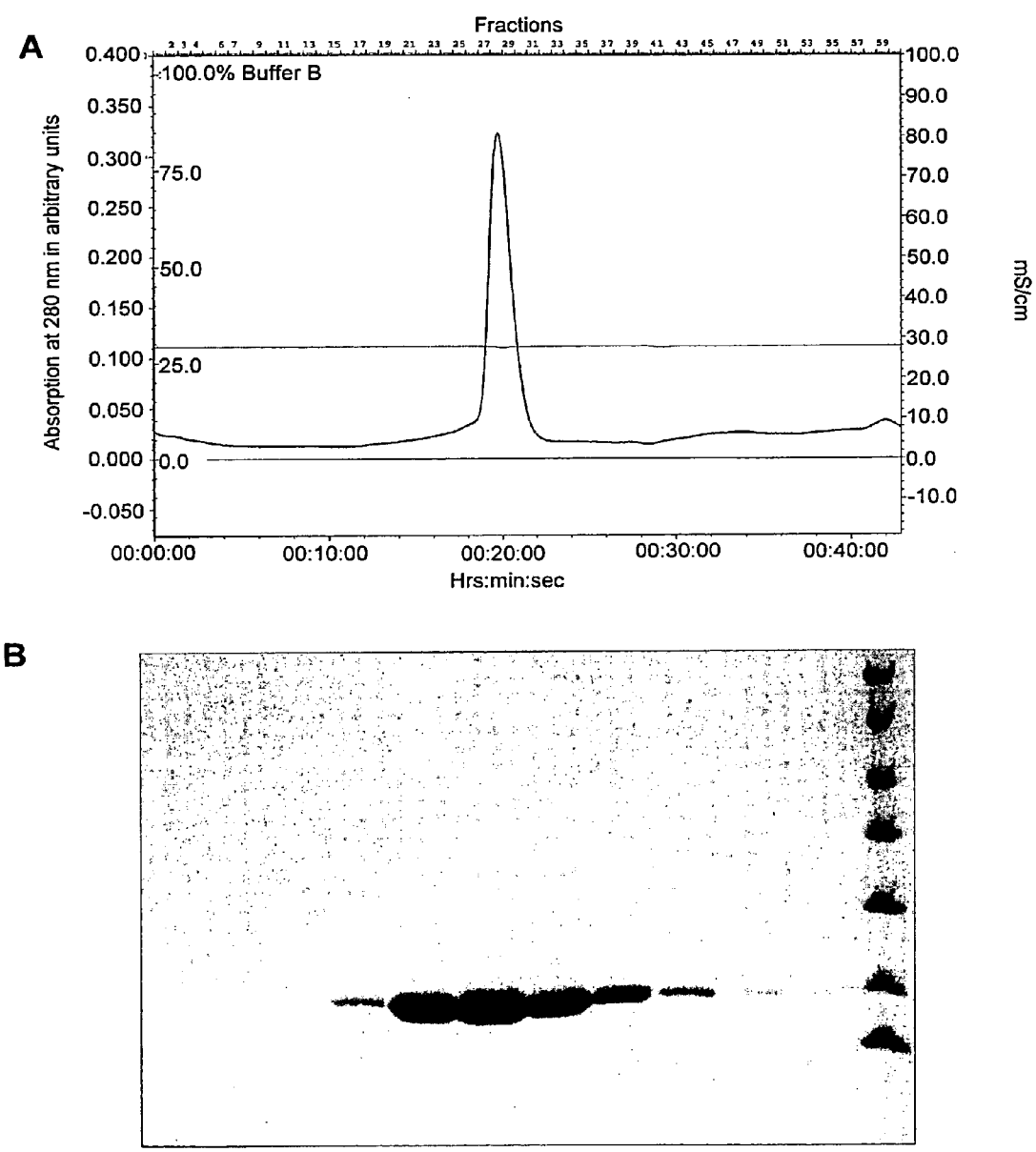
Figure 3:
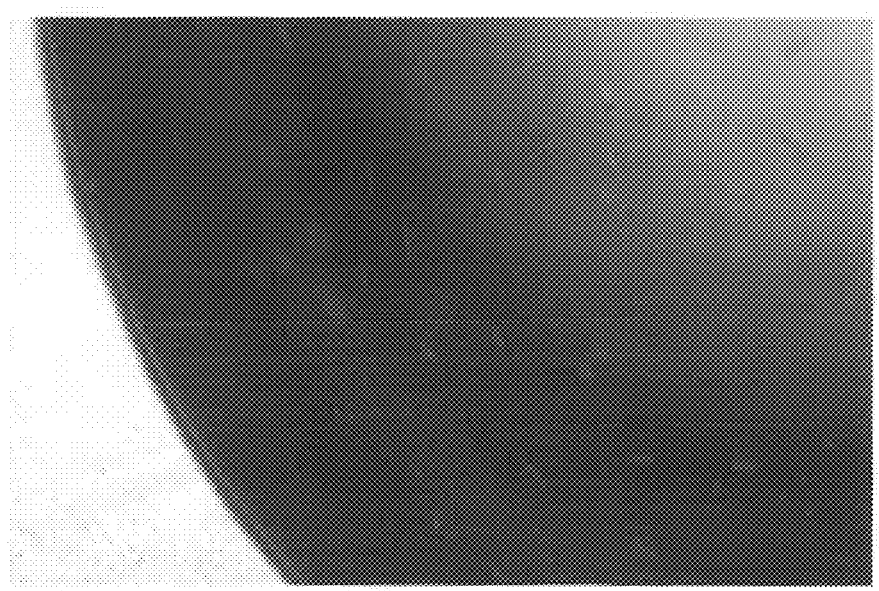
Figure 3:
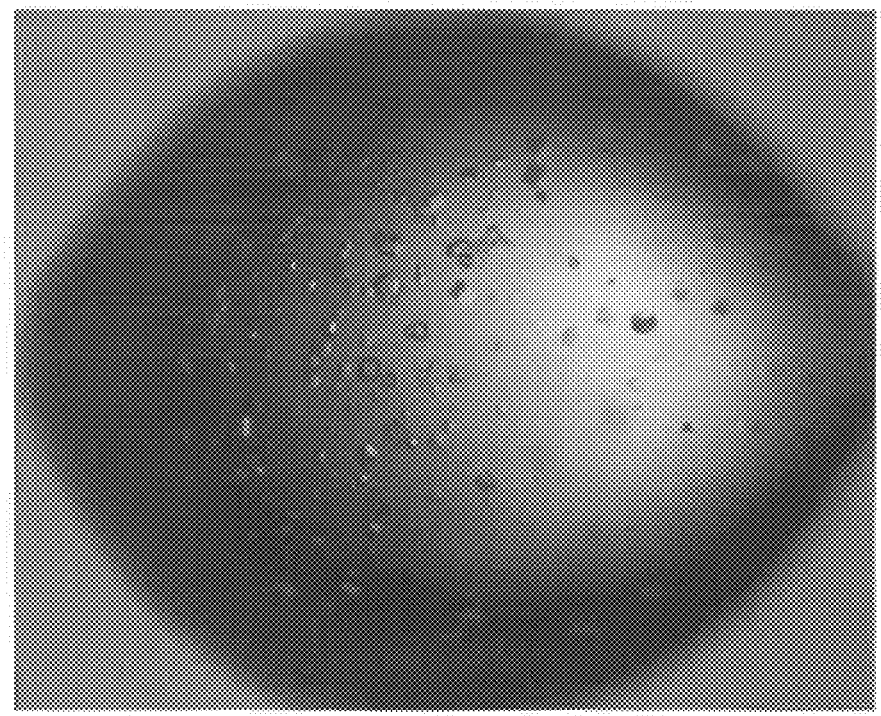

Said plasmids were transformed in E. coli cells using chemical transformation. The protein was expressed in E. coli strain BL21-CodonPlus-RIL (Stratagene) in LB medium. After a 16 to 20 h hours induction at 25° C. with 0.2 mM isopropyl-β-thiogalactopyranoside (IPTG), the cells were harvested and re-suspended in a lysis buffer (50 mM TrisHCl (pH 8.0), 300 mM NaCl, 5 mM 2-mercaptoethanol) and sonicated. After centrifugation, the cleared lysate was directly loaded on a nickel affinity column (Chelating sepharose from GE Healthcare, loaded with $Ni^{2+}$ ions). The Ni-sepharose resin was extensively washed with a 50 mM Tris#HCl (pH 8.0), 1 M NaCl, 15 mM imidazole, 5 mM 2-mercaptoethanol buffer, and then with a 50 mM Tris'HCl (pH 8.0), 200 mM NaCl, 50 mM imidazole, 5 mM 2-mercaptoethanol buffer. The protein was then eluted with a 50 mM Tris'HCl (pH 8.0), 200 mM NaCl, 0.5 M imidazole, 5 mM 2-mercaptoethanol buffer. The purified protein was incubated for TEV protease cleavage overnight at 10° C. After dialysis against 50 mM Tris-HCl (pH 8.0), 200 mM NaCl, 15 mM imidazole, 5 mM 2-mercaptoethanol buffer, a second nickel affinity step was performed to remove His-tag labeled TEV protease. The unbound protein was recovered and concentrated at 5-8 mg/ml for gel filtration on Superdex 75 column (GE Healthcare) in order to improve purity. The result of gel filtration for PB2 polypeptide fragment (amino acids 318 to 483, SEQ ID NO:11) is shown in FIG. 2A. This fragment (amino acids 318 to 483, SEQ ID NO:11) could be concentrated up to 24 mg/ml. The purity of the protein was evaluated by SDS PAGE and coomassie staining (see FIG. 2B). A typical yield is 120 mg of pure protein per liter of bacterial culture.

Example 4

Co-Crystallization of PB2 and $m^7GTP$

For crystallization trials a protein solution of PB2 fragment 318-483 (SEQ ID NO:11) at 11-15 mg/ml in 50 mM Tris-HCl (pH 8.0), 200 mM NaCl, 2 mM dithiothreitol (DTT), 5 mM $m^7GTP$ (Sigma) was used. A robot (Cartesian) was used to screen 576 crystallization conditions using the sitting drop vapor diffusion method, by mixing 100 µl of protein solution with 0.1 µl of different precipitant solutions. Crystals were identified in two distinct conditions. These conditions were manually optimized using the hanging drop vapor diffusion method with 1 µl of protein solution mixed with 1 µl of precipitant solution. The best crystals were obtained with a precipitant solution comprising 0.1 M citric acid pH 4.6, 1.6-1.8 M sodium formate. These crystals were of space group C222i, with unit cell dimensions a=9.2 nm, b=9.4 nm; c=22.0 nm±0.3 nm A. Some of the smaller crystals resulted in X-ray diffraction with a resolution of at least 2.4 A. Larger crystals were found to be unusable in that they were not single crystals. In the second crystallization condition found, the precipitant solution comprises, 7% PEG6000, 1 M LiCl, 0.1 M citric acid pH 5.0, 10 mM TCEP HCl. This condition gives thin plate-like crystals, of undetermined space-group, with evidence of diffraction to at least 3.3 A resolution, but the diffraction quality is much inferior and these crystals were not pursued.

Example 5

Preparation of Seleno-Methionine Labeled Protein

Seleno-methionated protein was produced in minimum M9 medium as described (Van Duyne, 1993). Since fully seleno-methionated protein did not crystallize, partially labeled protein was produced using 50 mg/L of selenomethionine and 5 mg/L of methionine, instead of 60 mg/l of selenomethionine. Expression, lysis, and purification conditions were as for native protein (Example 3). Electrospray mass-spectroscopy showed that, whereas the fully seleno-methionated protein had a MW of 19654 Daltons, corresponding to 11/11 methionines being substituted, the partially labeled protein had an average molecular weight of 19578 (9.4/11, i.e., 85% substituted) with individual peaks being obtained for protein species with 7-11 seleniums.

Example 6

Structure Determination and Refinement

The structure was determined with the single wavelength anomalous diffraction (SAD) method using partially seleno-methionylated protein as described in Example 5. Partially seleno-methionylated protein actually gave rise to larger single crystals than wild-type. Native data was collected at 2.4 Å resolution on a small crystal (size 15×15×50 μm³) of space-group C222₁ and cell dimensions a=92.2, b=94.4, c=220.4 Å on beamline BM14 at the ESRF (FIG. 4). Partially seleno-methionine labeled protein crystals were measured on ID29 at 2.9 Å resolution for structure determination and later at 2.3 Å resolution on ID14-EH1 on a larger crystal for structure refinement. The structure was solved by the SAD method using AUTOSHARP (Vonrhein et al., 2006). 50/55 selenium atom positions were found. Phases and the map were improved with RESOLVE (Terwilliger, 2000) making use of 4-fold non-crystallographic symmetry determined from the selenium positions, although it turned out that there are actually five molecules in the asymmetric unit (solvent content 55%). These are arranged in an unusual way. Four well-ordered molecules (average B-factor about 30 Å2), denoted A-D are arranged with 4-fold point symmetry. The fifth molecule mediates the packing of the tetramers in the crystallographic c-direction but is partially disordered (average B-factor about 51 Å2). After transferring phases to the native data, ARP/wARP (Perrakis et al., 1999) was able to automatically build most of the structure. Clear residual electron density was observed for the m⁷GTP bound to each molecule. Refinement was performed with REFMAC (Murshudov, 1997) using tight NCS restraints for the majority of each molecule and TLS parameters for each molecule as a whole. The final R-factor (R-free) is 0.186 (0.235) with 293 water molecules. According to MOLPROBITY (Lovell et al., 2003), the quality of the structure is excellent, as indicated by this server output:

REMARK 40
REMARK 40 MOLPROBITY STRUCTURE VALIDATION
REMARK 40 MOLPROBITY OUTPUT SCORES:
REMARK 40 ALL-ATOM CLASHSCORE: 8.40
REMARK 40 BAD ROTAMERS: 3.4% 24/708 (TARGET 0-1%)
REMARK 40 RAMACHANDRAN OUTLIERS: 0.0% 0/795 (TARGET 0.2%)
REMARK 40 RAMACHANDRAN FAVORED: 97.7% 777/795 (TARGET 98.0%)

Figure 5:
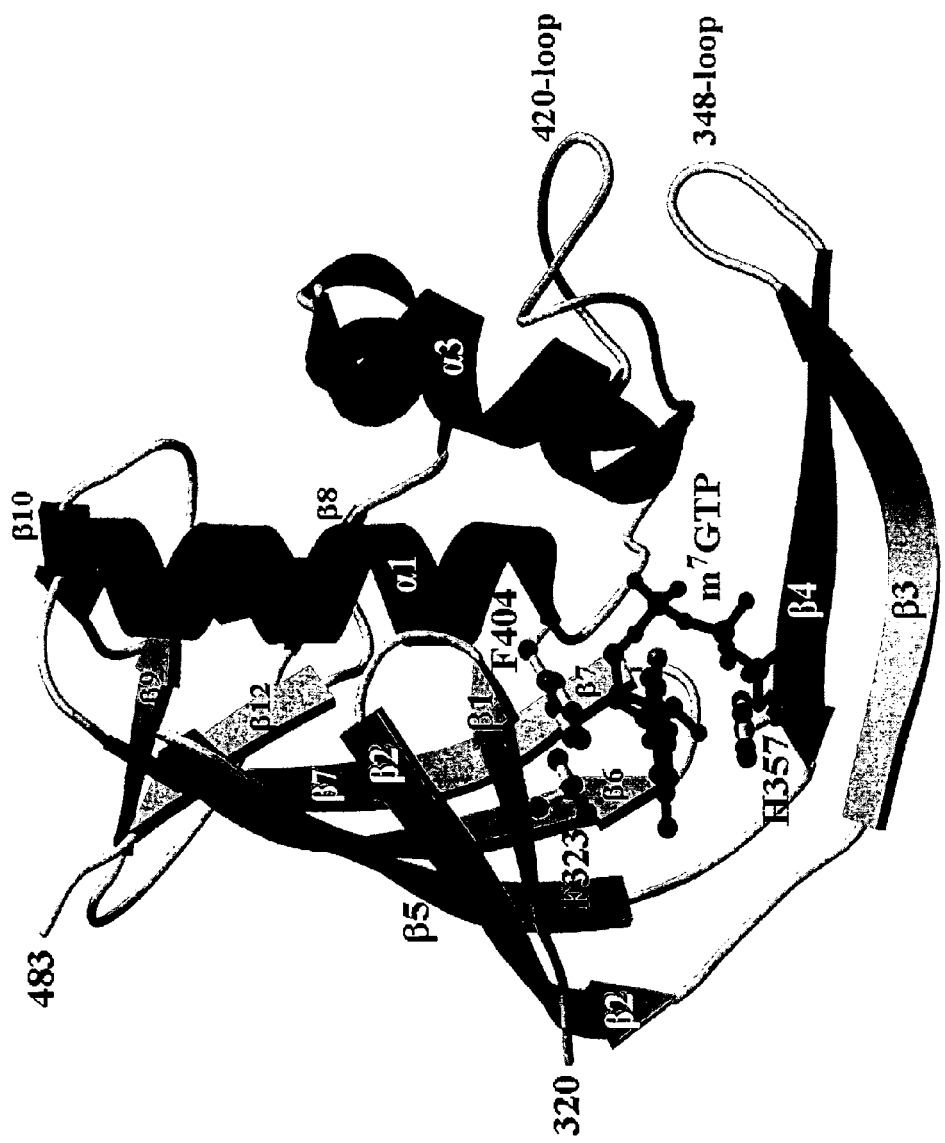
Figure 6:
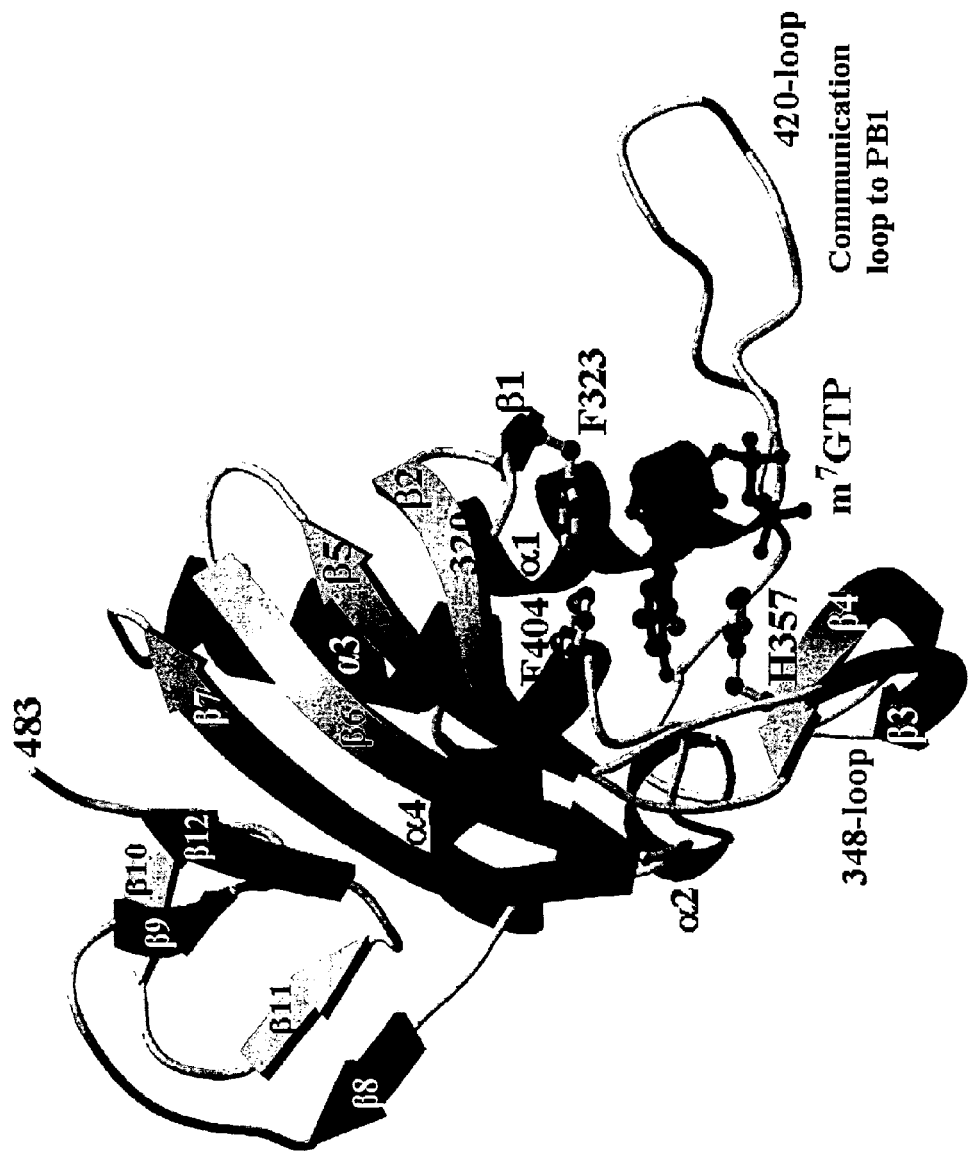
Figure 7:
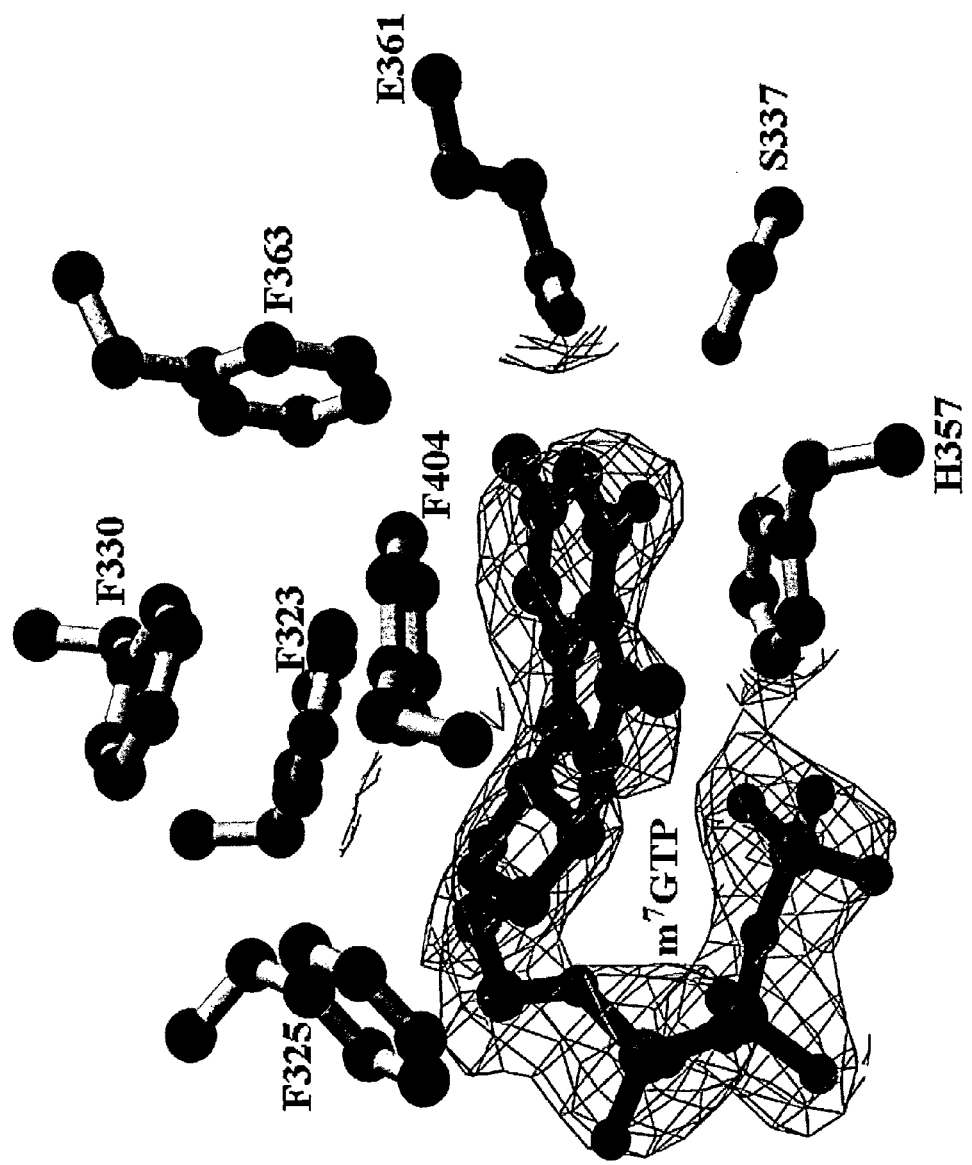
Figure 8:
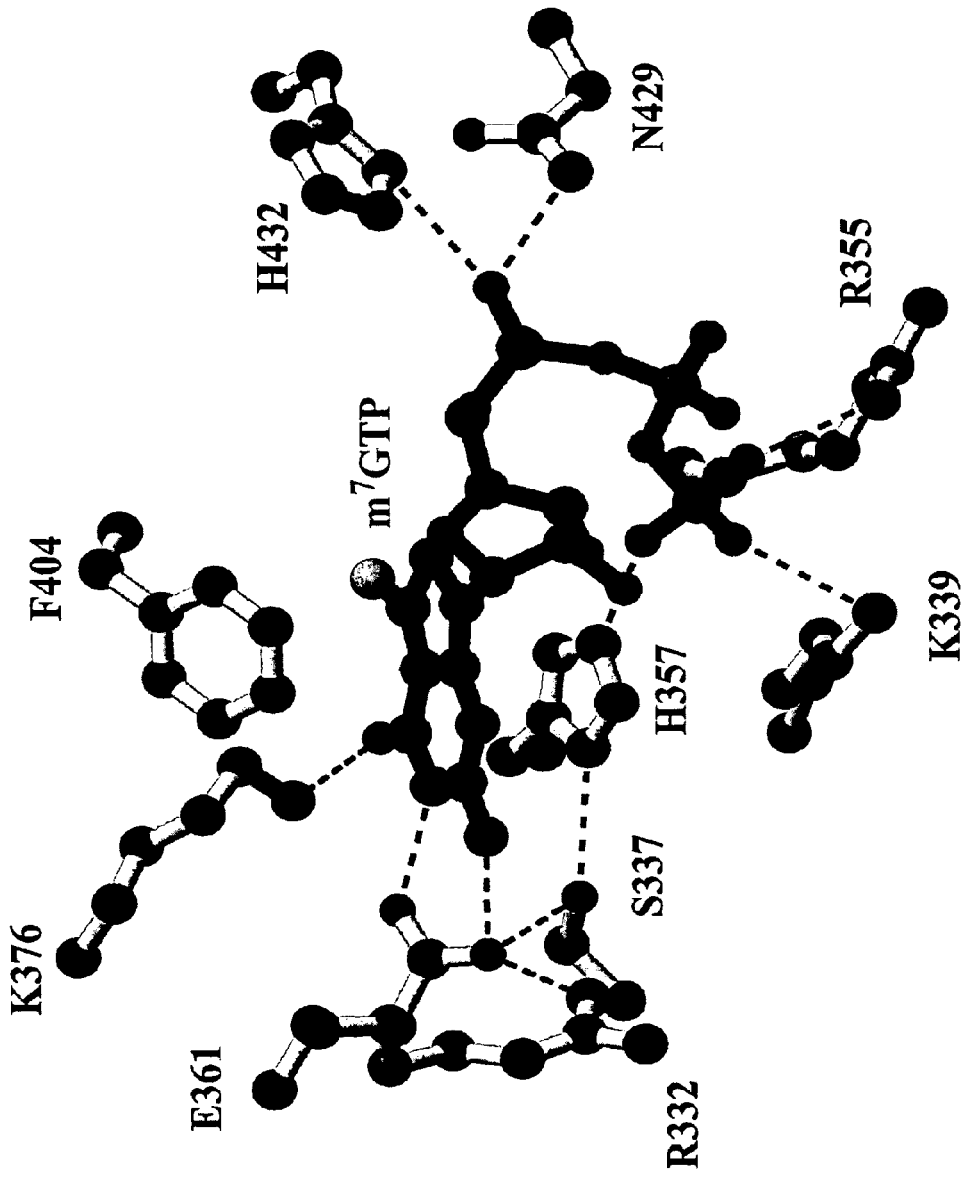

The cap-binding domain of PB2 has a compact, well-ordered mixed α-β fold with a prominent anti-parallel beta-sheet comprising strands β1, β2, β5, β6 and β7 packed onto a helical bundle comprising α1, α2, α3 and α4, with the longest helices α1 and α3 being aligned roughly anti-parallel. The connection between β2 and β5 is extended into a long beta hairpin, comprising strands β3 and β4 and 348-loop, which crosses over to the helical side of the molecule. Between α2 and α3, a poorly ordered loop, designated the 420-loop, juts into the solvent FIGS. 4 and 5). In the Influenza A PB2 cap-binding domain, the m⁷G sits on a hydrophobic platform formed principally by Phe-323 (from β1, more stacked against the ribose) and Phe-404 (from the C-terminal of helix α1, more stacked against the base), but neither are exactly parallel to the base. These two aromatic residues are part of a remarkable cluster of five phenylalanines including also Phe-325, Phe-330 and Phe-363. On the solvent side of the ligand, the sandwich is completed by His-357 (from the C-terminal of β4), a residue type not previously observed in this role. The key acidic residue is Glu-361 which hydrogen bonds to the N1 and N2 positions of the guanine and Lys-376 is also involved in base specific recognition via an interaction with O6 (FIGS. 6, 7, and 10). Unusually for cap-binding proteins, there are no direct interactions with either ribose hydroxyl. The triphosphate is bent round towards the base. The alpha-phosphate interacts with His-432 and Asn-429 and the gamma-phosphate interacts with basic residues His-357, Lys-339 and Arg-355.

Example 7

Mutational Analysis of the Cap-Binding Site

Figure 12:
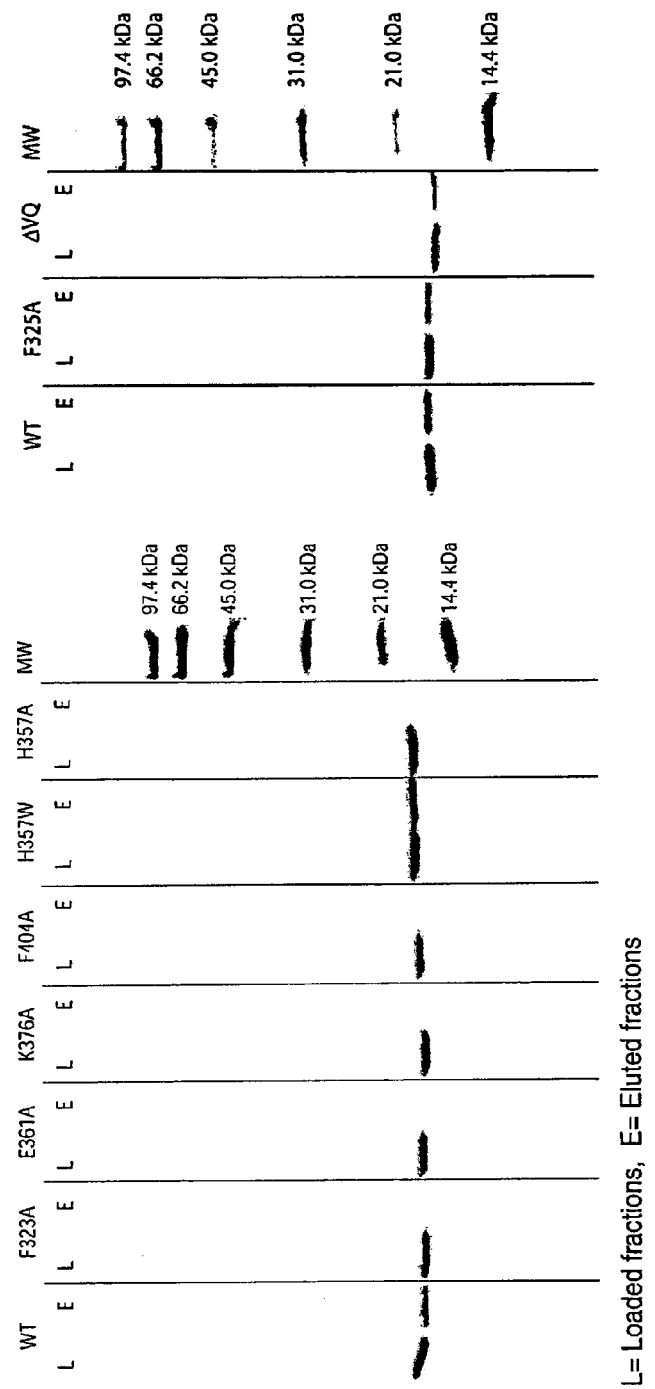

To verify that the structurally observed protein-ligand interactions are important for in vitro cap-binding, we made alanine mutations of seven m⁷GTP-contacting residues (F323, F325, E361, F363, F404, H357, K376) using the QuickChange site directed mutagnesis kit (Stratagene). These single point mutants were expected to show reduced cap-binding activity, which was assessed by their ability to bind to m⁷GTP-Sepharose resin at 4° C. (Table 4, FIG. 12). The mutants were purified as described in Example 3 for wild-type PB2. Mutant F363A expressed poorly and with low solubility in *E. coli*, presumably due to misfolding, and was not further pursued. Mutants H357A, E361A, K376A and F404A expressed well in soluble form but failed to bind to m⁷GTP-Sepharose under the assay conditions, whereas F323A had weak binding activity (FIG. 12). Surprisingly, mutant F325A, though poorly expressed, bound the resin nearly as well as the wild-type. We show that this mutant's activity is strongly temperature-dependent (Table 3). A H357W substitution was also made and consistent with the expected improved stacking with the base, this mutant domain showed enhanced m⁷GTP binding. Results are shown in FIG. 12 and Table 4.

Example 8

Quantitative Analysis of Cap-Binding Affinity Using Surface Plasmon Resonance Measurements To provide a more quantitative comparison of the binding affinity of the various mutants we performed surface plasmon resonance (SPR) measurements with immobilised cap-binding domain and m⁷GTP as the analyte. SPR analysis was performed on a Biacore T100 machine equipped with CM5 sensor chips (Biacore AB, Uppsala, Sweden). Wild-type and mutant PB2 cap-binding domains were diluted to 50 μg/mL in 10 mM sodium acetate, pH 6.0 and immobilized to the sensor surface using standard amine-coupling chemistry. Activated/deactivated sensor surface served as reference. Two-fold serial dilutions of m⁷GTP, m⁷ GpppG and GTP ranging from 0.47-1 mM were injected over the immobilized PB2 proteins and reference surfaces at a flow rate of 30 μL/min. Running buffer was 10 mM Hepes, pH 7.4 containing 150 mM NaCl and 1 mM DTT. To test the effects of temperature upon binding, the experiments were performed at 5, 15, 25 and 37° C. All acquired sensorgrams were processed using double referencing and the equilibrium dissociation constants were determined by steady state affinity evaluation with the Biacore T100 Evaluation Software. These are referred to as 'apparent' dissociation constants as the surface chemistry and molecular orientation associated with immobilisation could affect the values. The errors are those associated with the fitting as reported by the software. Variability between experiments with different immobilizations of proteins was <25% (data not shown). Results for the apparent equilibrium disassociation constant $K_D$ obtained at 25° C. (Table 1) show a trend consistent with the m⁷GTP-Sepharose binding results, with the highest affinity being for the H357W mutant ($K_D$=24±3 μM) followed by the wild-type ($K_D$=177±34 μM), and the E361A and K376A mutants having the lowest affinity ($K_D$>1500 μM).

Table 1: Apparent equilibrium dissociation constants ($K_D$) for interaction between $m^7GTP$ and different point mutants of the PB2 cap-binding domain determined by SPR at 25° C.

| protein | $K_D$ (μM) |
|---|---|
| Wild-type | 177 ± 34 |
| H357W | 24 ± 3 |
| F323A | 285 ± 45 |
| F325A | 418 ± 99 |
| H357A | 831 ± 45 |
| F404A | 1277 ± 120 |
| E361A | >1500 |
| K376A | >1500 |

Taken together, the above data confirm the functional importance of these contact residues to $m^7GTP$ by the PB2 domain in vitro. Additional results for the dinucleotide cap analogue, $m^7$ GpppG, and GTP binding to the wild-type cap-binding domain are shown in Table 2.

Table 2: Apparent equilibrium dissociation constants ($K_D$) for interaction between wild-type cap-binding domain of PB2 and different cap analogues determined by SPR at 25° C., compared to values for $IC_{50}$ measured by inhibition of capped RNA cross-linking by cap analogues (Hooker et al. 2003)

| Analyte | $K_D$ (μM) | $IC_{50}$ (μM) |
|---|---|---|
| $m^7$GpppG | 171 ± 19 | 127 |
| $m^7$GTP | 177 ± 34 | 113 |
| GTP | 1019 ± 100 | 550 |

To investigate the temperature dependence of binding between the cap-binding domain and $m^7GTP$ we made SPR measurements of $K_D$ on wild-type and selected mutant domains at various temperatures up to 37° C. (Table 3). The cap-binding affinity of all proteins tested decreased significantly with increasing temperature. However, whereas the apparent $K_D$ of the wild-type increased by a factor of 2.7 between 5 and 37° C., that of the F325A mutant increased by more than 20 times. Moreover, unlike the wild-type domain, the binding activity of the F325A mutant is irreversibly lost after incubation at 37° C. (data not shown), presumably due to thermal denaturation. This temperature sensitivity therefore provides a consistent rationale for the observed near normal cap-binding activity of the F325A mutant at 4° C., both in the domain and the trimer, and the functional impairment of the F325A mutant polymerase at 37° C. (cf. Example 10).

Table 3: Temperature dependence of dissociation constants ($K_D$) for interaction between $m^7GTP$ and different point mutants of the cap-binding domain.

| | $K_D$ (μM) | | | | |
|---|---|---|---|---|---|
| Temperature | Wild-type | H357W | F323A | H357A | F325A |
| 5° C. | 100 ± 20 | 12 ± 2 | 168 ± 29 | 394 ± 26 | 170 ± 44 |
| 15° C. | 133 ± 26 | 16 ± 3 | 215 ± 38 | 551 ± 42 | 223 ± 55 |
| 25° C. | 177 ± 34 | 24 ± 3 | 285 ± 45 | 831 ± 44 | 419 ± 99 |
| 37° C. | 268 ± 45 | 45 ± 6 | 884 ± 140 | 1123 ± 130 | 3787 ± 1700 |

Example 9

Cap-Binding Activity of Wild-Type and Mutant Polymerase Complexes

To investigate the relevance of the cap-binding site for the biological activity of influenza RNPs we introduced the same mutations into full-length PB2 of influenza A/Victoria/3/75 and tested the activity of the resultant trimeric polymerase or recombinant RNPs. None of the mutations altered the accumulation of PB2 when expressed in the context of the polymerase complex, nor changed the capacity of PB2 to form trimeric polymerase complexes (Table 4).

For cap-binding of trimeric polymerase, HEK293T cells were co-transfected with plasmids pCMVPB1 encoding the PB1 subunit, pCMVPB2His encoding the PB2 wild-type subunit or mutants thereof, and pCMVPA encoding the PA subunit of the influenza virus RNA polymerase and cell extracts were prepared 24 h post-transfection. The extracts were prepared in a buffer containing 50 mM Tris-HCl, 100 mM NaCl, 5 mM EDTA, 1 mM DTT, 0.2% NP40, protein inhibitors (Roche, Complete cocktail) at pH 7.5 and incubated with $m^7$GTP-Sepharose (GE Healthcare) for 3 h at 4° C. After washing with 100 volumes of the same buffer, the protein retained was eluted with the same buffer containing 1 mM $m^7GTP$ and was analysed by Western blot using PA-specific antibodies (FIG. 13). Under these conditions wild-type polymerase was not retained on a control Sepharose resin. Mutant H357W behaved as wild-type, whereas all other mutations abolished binding, except F325A that still bound, mirroring the results the results obtained for the isolated domain.

Example 10

Replication and Transcription Activities of Wild-Type and Mutant Recombinant Mini-RNPs The replication activity of the wild-type or mutant polymerases was tested by measuring the accumulation of RNPs in a recombinant system in vivo (Ortega et al., 2000; Martin-Benito et al., 2001). For RNP reconstitution, HEK293T cells were co-transfected with plasmids pCMVPB1, pCMVPB2His, pCMVPA, pCMVNP and pHHclone23 using a calcium-phosphate precipitation protocol. At 24 h post-transfection, extracts were prepared and RNPs were purified by chromatography over $Ni^{2+}$-NTA-agarose resin as described (Area et al., 2004). Western-blotting was carried out using antibodies specific for PA and NP. Progeny RNPs were extracted, purified and their accumulation monitored using anti-PA and anti-NP antibodies. Most mutations did not alter substantially the replication activity of the RNPs (FIG. 14 and Table 4). Only mutations F325A and K376A reduced partially the accumulation of RNPs.

The transcription activity of purified wild-type or mutant RNPs was tested in vitro using either ApG or β-globin mRNA as primers, to reveal cap-independent or cap-dependent transcription, respectively. For in vitro RNA synthesis, equal amounts of purified RNPs, as determined by Western blot were incubated in 20 μl reaction mixtures containing 50 mM Tris-HCl (pH 8.0), 2 mM $MgCl_2$, 100 mM KCl, 1 mM dithiothreitol, 0.5 mM each ATP, CTP, and UTP, 10 μM α-$^{32}$P-GTP (0.5 μCi/nmol), 10 μg/ml actinomycin D, 1 U/ml of human placental RNase inhibitor and either 100 μM ApG or 10 μg/ml β-globin mRNA, for 60 min at 30° C. The synthesized RNA was TCA-precipitated and recovered by filtration in a dot-blot apparatus. Incorporation was quantified with a phosphorimager. Most mutant RNPs were fully active when primed with ApG (FIG. 15 and Table 4): Mutations H357A and F404A led to RNPs transcriptionally more efficient than wild-type and only mutant F325A showed a strong deficiency.

In contrast, β-globin mRNA dependent transcription was severely affected for most of the mutants, except mutations H357W and H357A that were fully and partially active, respectively (FIG. 16 and Table 4). The ratio of β-globin versus ApG-primed transcription activity (FIG. 17 and Table 4) shows that all mutants except H357W were strongly affected in their ability to use β-globin mRNA as primer for transcription.

Figure 13:
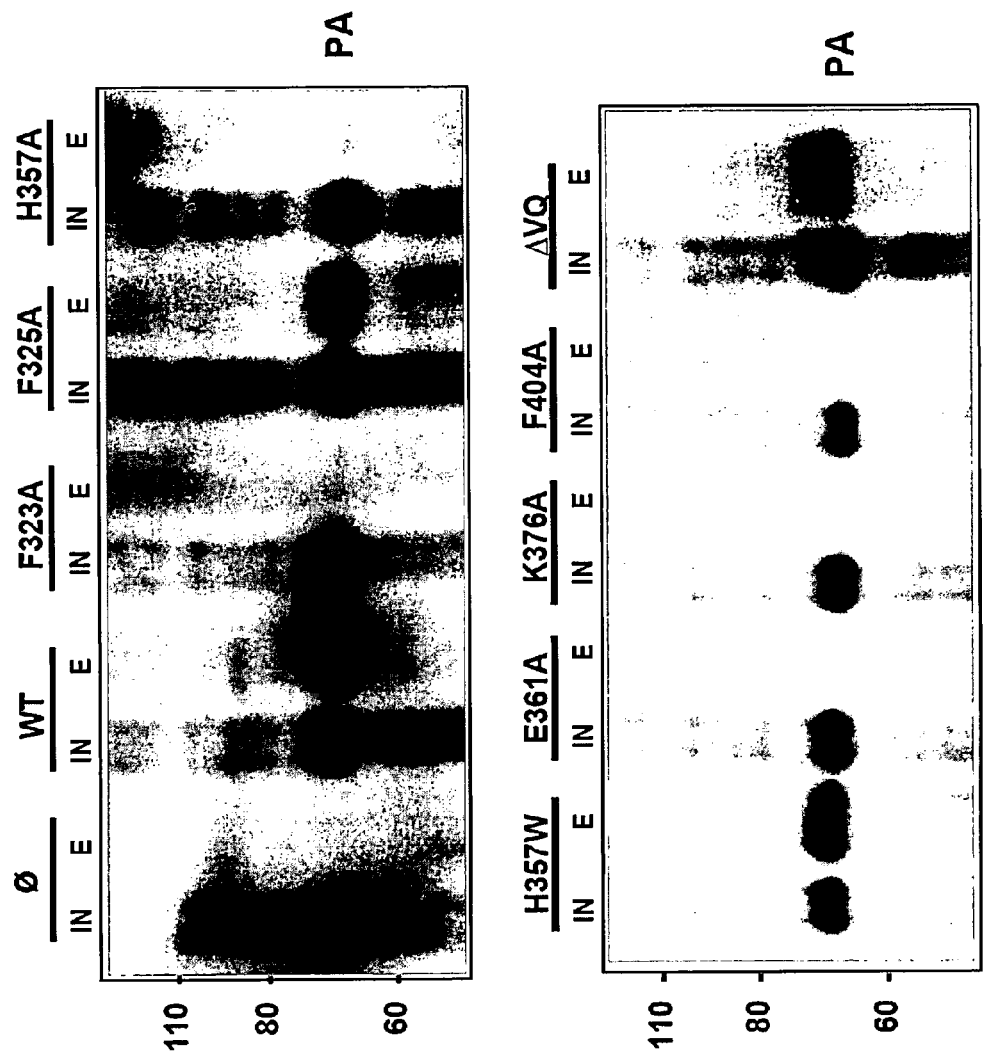

All but one of the mutations designed to reduce cap-binding activity abolished interaction with m$^7$GTP-Sepharose, both as protein domains and as mutant polymerase complexes (Table 4, FIGS. 12 and 13). The exception, F325A, was poorly expressed in the domain context and severely affected in most of the functional assays at the polymerase or RNP level at 37° C. (Table 4). However it retained reasonable cap-binding affinity at 4° C. (FIGS. 12 and 13) suggesting a possible temperature sensitive phenotype.

Table 4: Summary of biochemical and biological activity of PB2 cap-binding site mutants

|  | Solubility of domain | Cap-binding to domain at 4° C. | Cap-binding to polymerase at 4° C. | RNP accumulation | ApG-dependent transcription | β-globin-dependent transcription | Ratio β-globin/ApG transcription |
|---|---|---|---|---|---|---|---|
| Wild-type | +++ | +++ | +++ | +++ | +++ | +++ | +++ |
| F323A | ++ | + | − | +++ | + | − | − |
| F325A | +/− | ++ | ++ | ++ | − | − | − |
| H357A | +++ | − | − | ++++ | ++++ | + | − |
| H357W | +++ | ++++ | +++ | ++ | +++ | ++++ | +++ |
| E361A | ++ | − | − | +++ | +++ | − | − |
| F363A | − | nd | nd | nd | nd | nd | nd |
| K376A | +++ | − | − | + | +++ | − | − |
| F404A | +++ | − | − | ++++ | ++++ | − | − |
| ΔVQ | +++ | +++ | + | +++ | ++ | − | − | nd: not determined

Example 11

Cap-Dependent Transcription Requires Integrity of the 424-Loop

Figure 14:
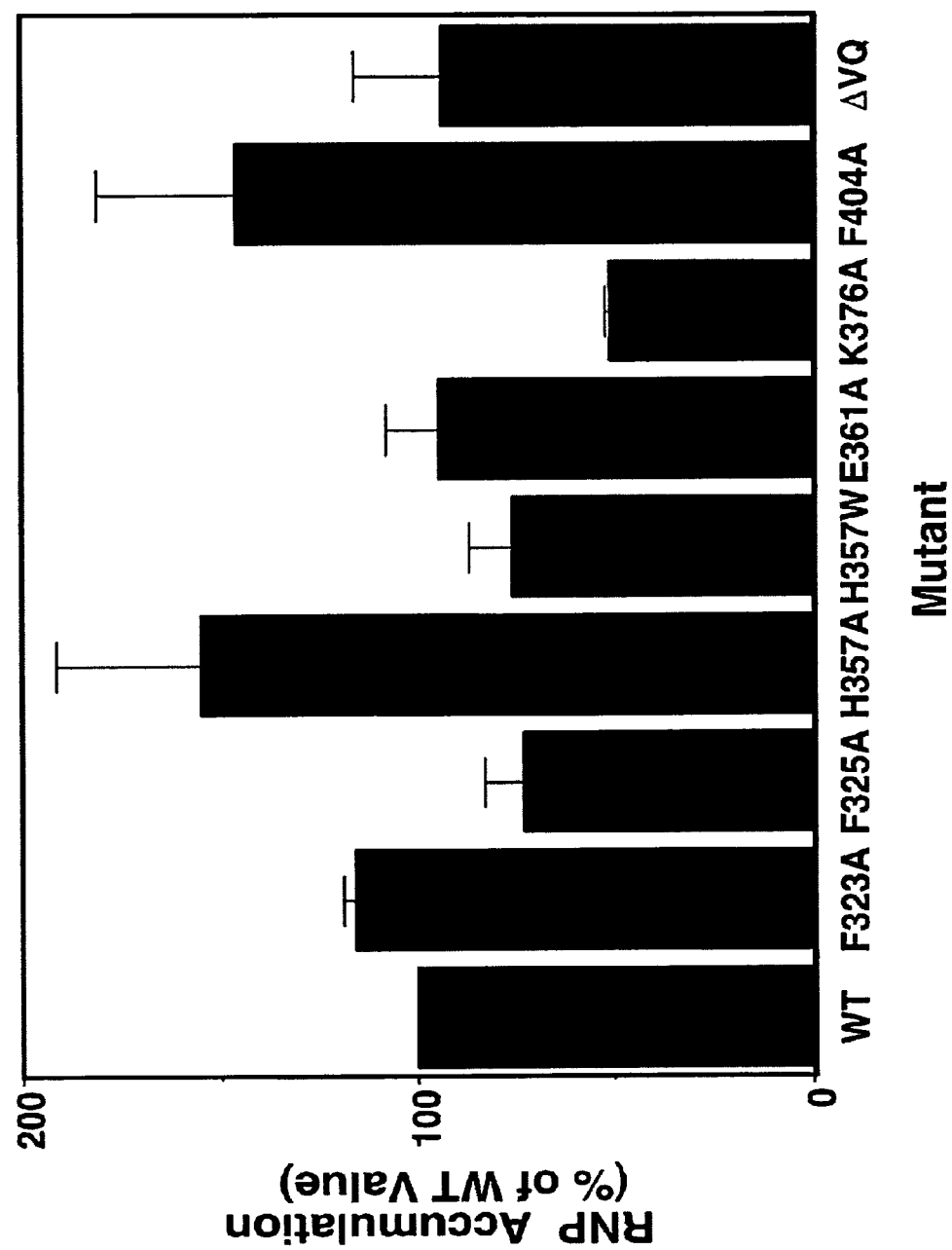
Figure 15:
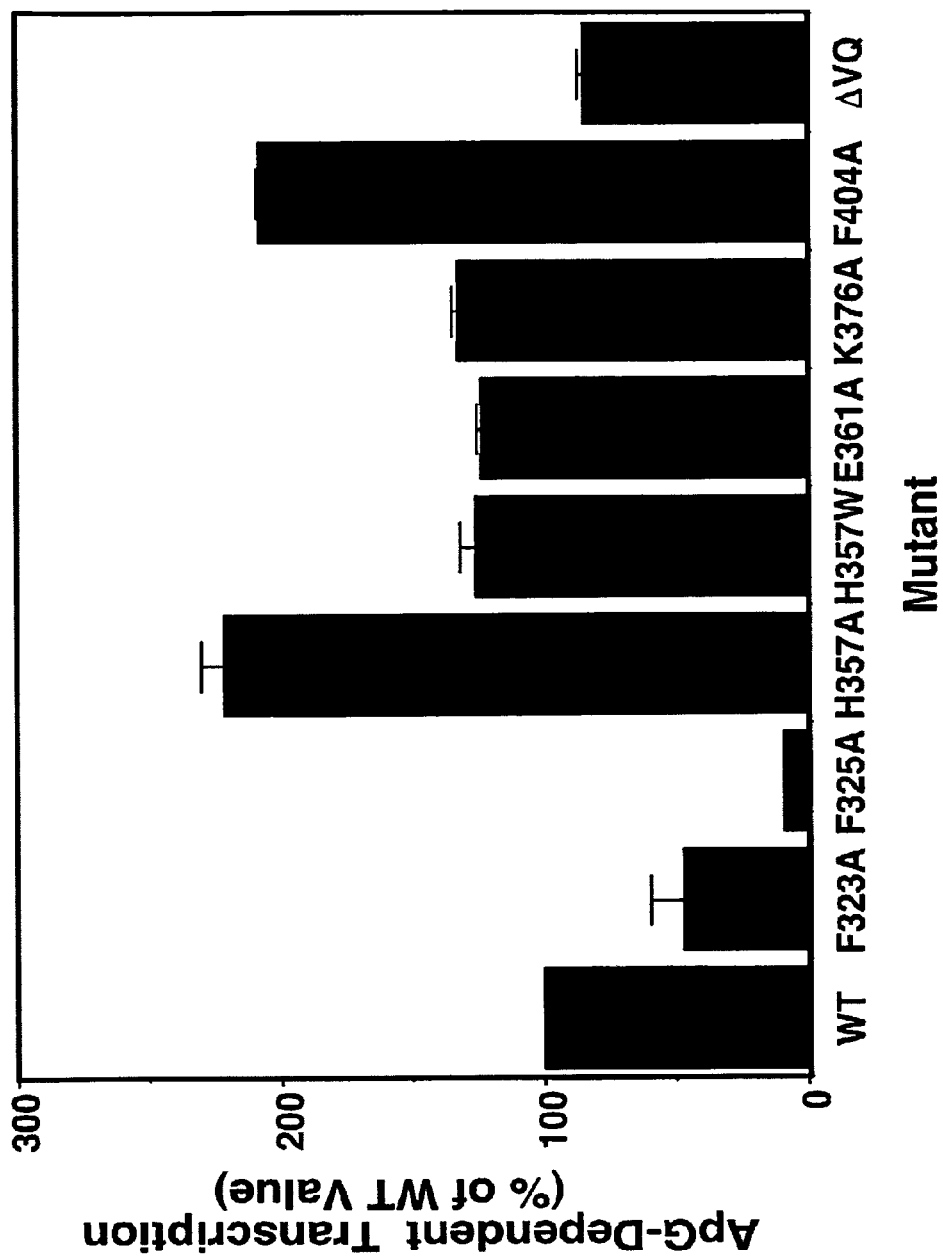

We were intrigued by the conspicuously exposed 420-loop (FIGS. 5 and 6), whose sequence is relatively well conserved between influenza A and B (FIG. 9). To investigate the possible function of this loop, we shortened it by replacing residues Val421-Gln426 by three glycines (mutant ΔVQ). The isolated cap-binding domain bearing this mutation behaved as wild-type with respect to m$^7$GTP-Sepharose binding activity (FIG. 12) and apparent $K_D$ (data not shown). In the context of the trimeric polymerase and recombinant RNPs, this mutant retained the ability to bind to cap-analogue resins, albeit to a reduced extent, and yielded wild-type levels of replication and ApG primed transcription activity (FIGS. 14 and 15). In contrast, the mutant was unable to perform β-globin-dependent transcription in vitro (FIGS. 16, 17, and Table 4). The ΔVQ mutant thus is defective in cap-dependent transcription but not cap-binding. We speculate that this loop may play an allosteric role in regulating the activity of the PB1 subunit.

REFERENCES CITED

Area, E. et al., (2004), "3D structure of influenza virus polymerase complex: localization of subunit domains", PNAS USA, 101, pp. 308-313

Balbes, L. M. et al., (1994), "A Perspective in Modern Methods in Computer-Aided Drug Design", Reviews in Computational Chemistry, Vol. 5, K. B. Lipkowitz and D. B. Boyd, Eds., VCH, New York, pp. 37-380

Bartlett, P. A. et al., (1989), "CAVEAT: A Program to Facilitate the Structure-Derived Design of Biologically Active Molecules", in Molecular Recognition in Chemical and Biological Problems", Special Publication, Royal Chem. Soc., 78, pp. 182-196

Berge, S. M. et al., (1977), "Pharmaceutical Salts", J. Pharm. Sci., 66, pp. 1-19

Blundell, T. L. and Johnson, L. N., (1976), "Protein Crystallography", Academic Press, New York Bohm, H.-J., (1992), "The Computer Program LUDI: A New Method for the De Novo Design of Enzyme Inhibitors", J. Comp. Aid. Mol. Des., 6, pp. 61-78

Cianci, C. et al., (1995), "Differential activation of the influenza virus polymerase via template RNA binding", J. Virol., 69, pp. 3995-3999.

Cohen, N. C. et al., (1990), "Molecular Modeling Software and Methods for Medicinal Chemistry", J. Med. Chem., 33, pp. 883-894

Drenth, J., "Principles of protein X-ray crystallography", 2$^{nd}$ Ed., Springer Advanced Texts in Chemistry, New York (1999)

Eisen, M. B. et al., (1994), "HOOK: A Program for Finding Novel Molecular Architectures that Satisfy the Chemical and Steric Requirements of a Macromolecule Binding Site", Proteins: Struct., Funct., Genet., 19, pp. 199-221

Eriksson, B. et al., (1977), Inhibition of Influenza virus ribonucleic acid polymerase by ribavirin triphosphate. Antimicrob. Agents Chemother., 11, pp. 946-951

Fechter, P. et al., (2003), "Two aromatic residues in the PB2 subunit of influenza A RNA polymerase are crucial for cap binding", J. Biol. Chem., 278, pp. 20381-20388

Furuta, Y. et al., (2005), "Mechanism of action of T-705 against influenza virus", Antimicrob. Agents Chemother., 49, pp. 981-986

Ghanem, A. et al., (2007), "Peptide-mediated interference with influenza A virus polymerase". J. Virol., 81, pp. 7801-7804

Gillet, V. et al., (1993), "SPROUT: A Program for Structure Generation", J. Comp. Aid. Mol. Des., 7, pp. 127-153

Goodman, L. S. et al., Eds., (1985), "Goodman and Gilman's The Pharmacological Basis of Therapeutics", 8th Edition, Pergamon Press Goodsell, D. S. et al., (1990), "Automated Docking of Substrates to Proteins by Simulated Annealing", Proteins: Struct., Funct., Genet., 8, pp. 195-202

Guida, W. C., (1994), "Software for Structure-Based Drug Design", Curr. Opin. Struct. Biol., 4, pp. 777-781

Harlow, E. and Lane, D., Eds., (1990), "Antibodies: A Laboratory Manual", Cold Spring Harbor Laboratory Press, Cold Spring Harbor, N.Y.

Holm, L. and Sander, C., (1993), "Protein structure comparison by alignment of distance matrices", J. Mol. Biol., 233, pp. 123-138.

Honda, A. et al., (1999), "Two separate sequences of PB2 subunit constitute the RNA cap-binding site of influenza virus RNA polymerase", Genes to Cells, 4, pp. 475-485

Hooker, L. et al., (2003), "Quantitative analysis of the influenza virus RNP interaction with RNA cap structures and comparison to human cap binding protein eIF4E", Biochemistry, 42, pp. 6234-6240

Jorgensen, W. L., (1998), "OPLS Force Fields", Encyclopedia of Computational Chemistry, Schleyer, Ed., Wiley, New York, Vol. 3, pp. 1986-1989

Kukkonen, S. K. et al (2005), "L protein, the RNA-dependent RNA polymerase of hantaviruses", Arch. Virol., 150, pp. 533-556

Kuntz, I. D. et al., (1982), "A Geometric Approach to Macromolecule-Ligand Interactions", J. Mol. Biol., 161, pp. 269-288

Lauri, G. and Bartlett, P. A., (1994), "CAVEAT: A Program to Facilitate the Design of Organic Molecules", J. Comp. Aid. Mol. Des., 8, pp. 51-66

Leahy, M. B. et al, (2005), "In Vitro Polymerase Activity of Thogoto Virus: Evidence for a Unique Cap-Snatching Mechanism in a Tick-Borne Orthomyxovirus", J. Virol., 71, pp. 8347-8351

Leuenberger, H. G. W. et al., Eds., (1995), "A Multilingual Glossary of Biotechnological Terms: IUPAC Recommendations", Helvetica Chimica Acta, CH-4010 Basel, Switzerland, Li, M.-L. et al., (2001), "The active site of the influenza cap-dependent endonuclease are on different polymerase subunits", EMBO J., 20, pp. 2078-2086

Lipinski, C. A. et al., (1997), "Experimental and computational approaches to estimate solubility and permeability in drug discovery and development settings", Adv. Drug Deliv. Rev., 23, pp. 3-25

Lovell, S. C. et al., (2003), "Structure validation by Calpha geometry: phi, psi and Cbeta deviation", Proteins, 50, pp. 437-450.

Magden, J. et al., (2005), "Inhibitors of virus replication: recent developments and prospects", Appl. Microbiol. Biotechnol., 66, pp. 612-621

Martin, Y. C., (1992), "3D Database Searching in Drug Design", J. Med. Chem., 35, pp. 2145-2154

Martin-Benito, J et al., (2001), "Three-dimensional reconstruction of a recombinant influenza virus ribonucleoprotein particle", EMBO Rep., 2, pp. 313-317

Meng, E. C. et al., (1992), "Automated Docking with Grid-Based Energy Evaluation", J. Comp. Chem., 13, pp. 505-524

Moon, J. B. and Howe, W. J., (1991), "Computer Design of Bioactive Molecules: A Method for Receptor-Based De Novo Ligand Design", Proteins, 11, pp. 314-328

Murshudov, G. N., (1997), "Refinement of macromolecular structures by the maximum-likelihood method", Acta Crystallogr. D. Biol. Crystallogr. 53, pp. 240-255.

Natarajan, A. et al., (2004), Synthesis of fluorescein labeled 7-methylguanosinemono-phosphate. Bioorg. Med. Chem. Lett., 14, pp. 2657-2660

Navia, M. A. and Murcko, M. A., (1992), "The Use of Structural Information in Drug Design", Curr. Opin. Struct. Biol., 2, pp. 202-210

Nishibata, Y. and Itai, A., (1991), "Automatic creation of drug candidate structures based on receptor structure. Starting point for artificial lead generation", Tetrahedron, 47, pp. 8985-8990

Noah, D. L. and Krug, R. M., (2005), "Influenza virus virulence and its molecular determinants", Adv. Virus Res., 65, pp. 121-145

Ortega, J. et al., (2000), "Ultrastructural and functional analyses of recombinant influenza virus ribonucleoproteins suggest dimerization of nucleoprotein during virus amplification", J. Virol., 74, pp. 156-163

Perrakis A. et al., (1999), "Automated protein model building combined with iterative structure refinement", Nat. Struct. Biol., 6, pp. 458-63

Plotch, S. J. et al., (1981), "A unique cap(m7 GpppXm)-dependent influenza virion endonuclease cleaves capped RNAs to generate the primers that initiate viral RNA transcription", Cell, 23, pp. 847-858

Ren, J. et al., (1996), "Synthesis of a fluorescent 7-methylguanosine analog and a fluorescence spectroscopic study of its reaction with wheat germ cap binding proteins", Nucleic Acids Res., 15, pp. 3629-3634

Rotstein, S. H. and Murcko, M. A., (1993), "GroupBuild: A Fragment-Based Method for De Novo Drug Design", J. Med. Chem., 36, pp. 1700-1710

Ryder, S. P. and Strobel, S. A., (1999), "Nucleotide analog interference mapping", Methods, 18, pp. 38-50

Sali, A. and Blundell, T. L., (1993), "Comparative protein modelling by satisfaction of spatial restraints", J. Mol. Biol., 234, pp. 779-815

Sambrook, J. et al., Eds., (1989), "Molecular Cloning: A Laboratory Manual", Cold Spring Harbor Laboratory Press, Cold Spring Harbor, N.Y.

Schneider T. R. and Sheldrick G. M., (2002), "Substructure solution with SHELXD", Acta Crystallogr. D. Biol. Crystallogr. (Pt 10 Pt 2), pp. 1772-1779

Schulz, G. E. and Schirmer, R. H., (1985), "Principles of Protein Structure", Springer Verlag, New York Tarendeau, F. et al., (2007), "Structure and nuclear import function of the C-terminal domain of influenza virus polymerase PB2 subunit", Nat. Struct. Mol. Biol., 14, pp. 229-233

Terwilliger, T. C., (2000), "Maximum likelihood density modification," Acta Cryst. D. Biol. Crystallogr., 56, pp. 965-972

Tisdale, M. et al., (1995), "Inhibition of influenza virus transcription by 2'-deoxy-2'-fluoroguanosine", Antimicrob. Agents Chemother., 39, pp. 2454-2458

Tomassini, J. et al., (1994), "Inhibition of cap ($m^7$ GpppXm)-dependent endonuclease of influenza virus by 4-substituted 2,4-diocobutanic acid compounds", Antimicrob. Agents Chemother., 38, pp. 2827-2837

Tomassini, J. et al., (1996), "A novel antiviral agent which inhibits the endonuclease of influenza viruses", Antimicrob. Agents Chemother., 40, pp. 1189-1193

Van Duyne, G. D. et al., (1993), "Atomic structures of the human immunophilin FKBP-12 complexes with FK506 and rapamycin", J. Mol. Biol., 229, pp. 105-124

Von Itzstein, M. et al., (1993), "Rational design of potent sialidase-based inhibitors of influenza virus replication", Nature, 363, pp. 418-423

Vonrhein C. et al., (2006), "Automated Structure Solution With autoSHARP", Methods Mol. Biol., 364, pp. 215-30

Wallace, A. C. et al., (1995). "LIGPLOT: A program to generate schematic diagrams of protein-ligand interactions", Prot. Eng., 8, pp. 127-134.

What is claimed is:

1. A complex comprising a soluble polypeptide fragment of Influenza virus RNA-dependent RNA polymerase subunit PB2 and an RNA cap analog, wherein said soluble polypeptide fragment is capable of binding to a RNA cap or analog thereof and remains in the supernatant after centrifugation for 30 min at 100,000×g in an aqueous buffer under physiologically isotonic conditions at a protein concentration of 5 mg/ml in the absence of denaturants in effective concentrations and is selected from the group consisting of (i) a polypeptide fragment between residues 220 and 510 of SEQ ID NO: 1;

(ii) a polypeptide fragment between residues 222 and 511 of SEQ ID NO: 2;

(iii) a polypeptide fragment between residues 227 and 528 of SEQ ID NO: 3; and (iv) variants thereof having at least 80% sequence identity to polypeptide fragment according to (i), (ii) or (iii); and wherein the RNA cap analog is selected from the group consisting of $m^7G$, $m^7GMP$, $m^7GTP$, $m^7$ GpppG, $m^7$ GpppGm, $m^7$ GpppA, $m^7$ GpppAm, $m^7$ GpppC, $m^7$ GpppCm, $m^7$ GpppU, and $m^7$ GpppUm.

2. The complex of claim 1, wherein said soluble polypeptide fragment is purified to a purity of at least 95%.

3. The complex of claim 1, wherein the Influenza virus RNA-dependent RNA polymerase subunit PB2 is from an Influenza A, B, or C virus.

4. The complex of claim 1, wherein said soluble polypeptide fragment consisting of an amino acid sequence selected from the group consisting of amino acid sequences according to SEQ ID NO: 4 to 13 and variant thereof having at least 90% sequence identity to an amino acid sequence according to SEQ ID NO: 4 to 13.

5. A crystal of the complex of claim 1, wherein said soluble polypeptide fragment consists of the amino acid sequence according to SEQ ID NO: 11 and said RNA cap analog is m⁷GTP, and wherein said crystal has a space group C222₁, and unit cell dimensions of a=92 Å, b=94 Å; c=220 Å(±3 Å).

6. The crystal of claim 5, wherein the crystal diffracts X-rays to a resolution of 3.0 Å or a higher resolution.

7. The crystal of claim 5, wherein the crystal diffracts X-rays to a resolution of 2.4 Å or a higher resolution.

8. A method for identifying compounds which associate with the RNA cap binding pocket of influenza virus RNA dependent RNA polymerase subunit PB2, comprising the steps of (i) contacting a soluble polypeptide fragment of Influenza virus RNA-dependent RNA polymerase subunit PB2 in solution with a test compound and (ii) determining the ability of said test compound to bind to the polypeptide fragment PB2, wherein said soluble polypeptide fragment is capable of binding to an RNA cap or analog thereof and remains in the supernatant after centrifugation for 30 min at 100,000×g in an aqueous buffer under physiologically isotonic conditions at a protein concentration of 5 mg/ml in the absence of denaturants in effective concentrations and is selected from the group consisting of
  (i) a polypeptide fragment between residues 220 and 510 of SEQ ID NO: 1;
  (ii) a polypeptide fragment between residues 222 and 511 of SEQ ID NO: 2;
  (iii) a polypeptide fragment between residues 227 and 528 of SEQ ID NO: 3; and
  (iv) variants thereof having at least 80% sequence identity to the polypeptide fragment according to (i), (ii) or (iii); and
wherein the RNA cap analog is selected from the group consisting of m⁷G, m⁷GMP, m⁷GTP, m⁷GpppG, m⁷GpppGm, m⁷GpppA, m⁷GpppAm, m⁷GpppC, m⁷GpppCm, m⁷GpppU, and m⁷GpppUm.

9. The method of claim 8, comprising the further step of adding an RNA cap or analog thereof, wherein the RNA cap analog is selected from the group consisting of m⁷G, m⁷GMP, m⁷GTP, m⁷GpppG, m⁷GpppGm, m⁷GpppA, m⁷GpppAm, m⁷GpppC, m⁷GpppCm, m⁷GpppU, and m⁷GpppUm.

10. The method of claim 9, wherein the ability of said test compound to bind to PB2 in presence of said RNA cap or analog thereof or the ability of said test compound to inhibit binding of said RNA cap or analog thereof to PB2 is analyzed.

11. The method of claim 9, wherein said RNA cap or analog thereof is added prior, concomitantly, or after addition of said test compound.

12. The method of 8, being a high-throughput method.

13. The method of claim 8, wherein said test compound is a small molecule having a molecular weight between 50 and about 2500 Daltons.

14. The method of claim 8, wherein said test compound is a peptide or protein.

\* \* \* \* \*

SEQUENCE LISTING

```
<160> NUMBER OF SEQ ID NOS: 27

<210> SEQ ID NO 1
<211> LENGTH: 759
<212> TYPE: PRT
<213> ORGANISM: Influenza A virus
<220> FEATURE:
<221> NAME/KEY: CHAIN
<222> LOCATION: (1)..(759)
<223> OTHER INFORMATION: PB2

<400> SEQUENCE: 1

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Ser Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300
```

```
Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Ile Lys Arg Glu Glu Val Leu Thr Gly Asn Leu Gln Thr Leu
        340                 345                 350

Lys Ile Arg Val His Glu Gly Tyr Glu Glu Phe Thr Met Val Gly Lys
            355                 360                 365

Arg Ala Thr Ala Ile Leu Arg Lys Ala Thr Arg Arg Leu Val Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
            405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Val Gly Val Leu
450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
            485                 490                 495

Ser Ile Asp Arg Phe Leu Arg Val Arg Asp Gln Arg Gly Asn Val Leu
        500                 505                 510

Leu Ser Pro Glu Glu Val Ser Glu Thr His Gly Thr Glu Arg Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
            565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
            645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
```

```
                    725                 730                 735
Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 2
<211> LENGTH: 770
<212> TYPE: PRT
<213> ORGANISM: Influenza B virus
<220> FEATURE:
<221> NAME/KEY: CHAIN
<222> LOCATION: (1)..(770)
<223> OTHER INFORMATION: PB2

<400> SEQUENCE: 2

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320
```

-continued

```
Ile Arg Gln Arg Gln Arg Phe Gly Arg Leu Glu Leu Lys Arg Ile Ser
                325                 330                 335
Gly Arg Gly Phe Lys Asn Asp Glu Glu Ile Leu Ile Gly Asn Gly Thr
            340                 345                 350
Ile Gln Lys Ile Gly Ile Trp Asp Gly Glu Glu Phe His Val Arg
        355                 360                 365
Cys Gly Glu Cys Arg Gly Ile Leu Lys Lys Ser Lys Met Arg Met Glu
    370                 375                 380
Lys Leu Leu Ile Asn Ser Ala Lys Glu Asp Met Lys Asp Leu Ile
385                 390                 395                 400
Ile Leu Cys Met Val Phe Ser Gln Asp Thr Arg Met Phe Gln Gly Val
                405                 410                 415
Arg Gly Glu Ile Asn Phe Leu Asn Arg Ala Gly Gln Leu Leu Ser Pro
            420                 425                 430
Met Tyr Gln Leu Gln Arg Tyr Phe Leu Asn Arg Ser Asn Asp Leu Phe
        435                 440                 445
Asp Gln Trp Gly Tyr Glu Glu Ser Pro Lys Ala Ser Glu Leu His Gly
    450                 455                 460
Ile Asn Glu Leu Met Asn Ala Ser Asp Tyr Thr Leu Lys Gly Val Val
465                 470                 475                 480
Val Thr Lys Asn Val Ile Asp Asp Phe Ser Ser Thr Glu Thr Glu Lys
                485                 490                 495
Val Ser Ile Thr Lys Asn Leu Ser Leu Ile Lys Arg Thr Gly Glu Val
            500                 505                 510
Ile Met Gly Ala Asn Asp Val Ser Glu Leu Glu Ser Gln Ala Gln Leu
        515                 520                 525
Met Ile Thr Tyr Asp Thr Pro Lys Met Trp Glu Met Gly Thr Thr Lys
    530                 535                 540
Glu Leu Val Gln Asn Thr Tyr Gln Trp Val Leu Lys Asn Leu Val Thr
545                 550                 555                 560
Leu Lys Ala Gln Phe Leu Leu Gly Lys Glu Asp Met Phe Gln Trp Asp
                565                 570                 575
Ala Phe Glu Ala Phe Glu Ser Ile Ile Pro Gln Lys Met Ala Gly Gln
            580                 585                 590
Tyr Ser Gly Phe Ala Arg Ala Val Leu Lys Gln Met Arg Asp Gln Glu
        595                 600                 605
Val Met Lys Thr Asp Gln Phe Ile Lys Leu Leu Pro Phe Cys Phe Ser
    610                 615                 620
Pro Pro Lys Leu Arg Ser Asn Gly Glu Pro Tyr Gln Phe Leu Arg Leu
625                 630                 635                 640
Val Leu Lys Gly Gly Glu Asn Phe Ile Glu Val Arg Lys Gly Ser
                645                 650                 655
Pro Leu Phe Ser Tyr Asn Pro Gln Thr Glu Val Leu Thr Ile Cys Gly
            660                 665                 670
Arg Met Met Ser Leu Lys Gly Lys Ile Glu Asp Glu Arg Asn Arg
        675                 680                 685
Ser Met Gly Asn Ala Val Leu Ala Gly Phe Leu Val Ser Gly Lys Tyr
    690                 695                 700
Asp Pro Asp Leu Gly Asp Phe Lys Thr Ile Glu Glu Leu Glu Lys Leu
705                 710                 715                 720
Lys Pro Gly Glu Lys Ala Asn Ile Leu Leu Tyr Gln Gly Lys Pro Val
                725                 730                 735
```

-continued

Lys Val Val Lys Arg Lys Arg Tyr Ser Ala Leu Ser Asn Asp Ile Ser
                740                 745                 750

Gln Gly Ile Lys Arg Gln Arg Met Thr Val Glu Ser Met Gly Trp Ala
        755                 760                 765

Leu Ser
    770

<210> SEQ ID NO 3
<211> LENGTH: 774
<212> TYPE: PRT
<213> ORGANISM: Influenza C virus
<220> FEATURE:
<221> NAME/KEY: CHAIN
<222> LOCATION: (1)..(774)
<223> OTHER INFORMATION: PB2

<400> SEQUENCE: 3

Met Ser Phe Leu Leu Thr Ile Ala Lys Glu Tyr Lys Arg Leu Cys Gln
1               5                   10                  15

Asp Ala Lys Ala Ala Gln Met Met Thr Val Gly Thr Val Ser Asn Tyr
            20                  25                  30

Thr Thr Phe Lys Lys Trp Thr Thr Ser Arg Lys Glu Lys Asn Pro Ser
        35                  40                  45

Leu Arg Met Arg Trp Ala Met Ser Ser Lys Phe Pro Ile Ile Ala Asn
    50                  55                  60

Lys Arg Met Leu Glu Glu Ala Gln Ile Pro Lys Glu His Asn Asn Val
65                  70                  75                  80

Ala Leu Trp Glu Asp Thr Glu Asp Val Ser Lys Arg Asp His Val Leu
                85                  90                  95

Ala Ser Ala Ser Cys Ile Asn Tyr Trp Asn Phe Cys Gly Pro Cys Val
            100                 105                 110

Asn Asn Ser Glu Val Ile Lys Glu Val Tyr Lys Ser Arg Phe Gly Arg
        115                 120                 125

Leu Glu Arg Arg Lys Glu Ile Met Trp Lys Glu Leu Arg Phe Thr Leu
    130                 135                 140

Val Asp Arg Gln Arg Arg Arg Val Asp Thr Gln Pro Val Glu Gln Arg
145                 150                 155                 160

Leu Arg Thr Gly Glu Ile Lys Asp Leu Gln Met Trp Thr Leu Phe Glu
                165                 170                 175

Asp Glu Ala Pro Leu Ala Ser Lys Phe Ile Leu Asp Asn Tyr Gly Leu
            180                 185                 190

Val Lys Glu Met Arg Ser Lys Phe Ala Asn Lys Pro Leu Asn Lys Glu
        195                 200                 205

Val Val Ala His Met Leu Glu Lys Gln Phe Asn Pro Glu Ser Arg Phe
    210                 215                 220

Leu Pro Val Phe Gly Ala Ile Arg Pro Glu Arg Met Glu Leu Ile His
225                 230                 235                 240

Ala Leu Gly Gly Glu Thr Trp Ile Gln Glu Ala Asn Thr Ala Gly Ile
                245                 250                 255

Ser Asn Val Asp Gln Arg Lys Asn Asp Met Arg Ala Val Cys Arg Lys
            260                 265                 270

Val Cys Leu Ala Ala Asn Ala Ser Ile Met Asn Ala Lys Ser Lys Leu
        275                 280                 285

Val Glu Tyr Ile Lys Ser Thr Ser Met Arg Ile Gly Glu Thr Glu Arg
    290                 295                 300

Lys Leu Glu Glu Leu Ile Leu Glu Thr Asp Asp Val Ser Pro Glu Val

```
            305                 310                 315                 320
        Thr Leu Cys Lys Ser Ala Leu Gly Gly Pro Leu Gly Lys Thr Leu Ser
                        325                 330                 335
        Phe Gly Pro Met Leu Leu Lys Lys Ile Ser Gly Ser Gly Val Lys Val
                        340                 345                 350
        Lys Asp Thr Val Tyr Ile Gln Gly Val Arg Ala Val Gln Phe Glu Tyr
                        355                 360                 365
        Trp Ser Glu Gln Glu Glu Phe Tyr Gly Glu Tyr Lys Ser Ala Thr Ala
                370                 375                 380
        Leu Phe Ser Arg Lys Glu Arg Ser Leu Glu Trp Ile Thr Ile Gly Gly
        385                 390                 395                 400
        Gly Ile Asn Glu Asp Arg Lys Arg Leu Leu Ala Met Cys Met Ile Phe
                        405                 410                 415
        Cys Arg Asp Gly Asp Tyr Phe Lys Asp Ala Pro Ala Thr Ile Thr Met
                        420                 425                 430
        Ala Asp Leu Ser Thr Lys Leu Gly Arg Glu Ile Pro Tyr Gln Tyr Val
                        435                 440                 445
        Met Met Asn Trp Ile Gln Lys Ser Glu Asp Asn Leu Glu Ala Leu Leu
                450                 455                 460
        Tyr Ser Arg Gly Ile Val Glu Thr Asn Pro Gly Lys Met Gly Ser Ser
        465                 470                 475                 480
        Met Gly Ile Asp Gly Ser Lys Arg Ala Ile Lys Ser Leu Arg Ala Val
                        485                 490                 495
        Thr Ile Gln Ser Gly Lys Ile Asp Met Pro Glu Ser Lys Glu Lys Ile
                        500                 505                 510
        His Leu Glu Leu Ser Asp Asn Leu Glu Ala Phe Asp Ser Ser Gly Arg
                        515                 520                 525
        Ile Val Ala Thr Ile Leu Asp Leu Pro Ser Asp Lys Lys Val Thr Phe
                        530                 535                 540
        Gln Asp Val Ser Phe Gln His Pro Asp Leu Ala Val Leu Arg Asp Glu
        545                 550                 555                 560
        Lys Thr Ala Ile Thr Lys Gly Tyr Glu Ala Leu Ile Lys Arg Leu Gly
                        565                 570                 575
        Thr Gly Asp Asn Asp Ile Pro Ser Leu Ile Ala Lys Lys Asp Tyr Leu
                        580                 585                 590
        Ser Leu Tyr Asn Leu Pro Glu Val Lys Leu Met Ala Pro Leu Ile Arg
                        595                 600                 605
        Pro Asn Arg Lys Gly Val Tyr Ser Arg Val Ala Arg Lys Leu Val Ser
                        610                 615                 620
        Thr Gln Val Thr Thr Gly His Tyr Ser Leu His Glu Leu Ile Lys Val
        625                 630                 635                 640
        Leu Pro Phe Thr Tyr Phe Ala Pro Lys Gln Gly Met Phe Glu Gly Arg
                        645                 650                 655
        Leu Phe Phe Ser Asn Asp Ser Phe Val Glu Pro Gly Val Asn Asn Asn
                        660                 665                 670
        Val Phe Ser Trp Ser Lys Ala Asp Ser Ser Lys Ile Tyr Cys His Gly
                        675                 680                 685
        Ile Ala Ile Arg Val Pro Leu Val Val Gly Asp Glu His Met Asp Thr
                        690                 695                 700
        Ser Leu Ala Leu Leu Glu Gly Phe Ser Val Cys Glu Asn Asp Pro Arg
        705                 710                 715                 720
        Ala Pro Met Val Thr Arg Gln Asp Leu Ile Asp Val Gly Phe Gly Gln
                        725                 730                 735
```

```
Lys Val Arg Leu Phe Val Gly Gln Gly Ser Val Arg Thr Phe Lys Arg
                740                 745                 750

Thr Ala Ser Gln Arg Ala Ala Ser Asp Val Asn Lys Asn Val Lys
            755                 760                 765

Lys Ile Lys Met Ser Asn
    770

<210> SEQ ID NO 4
<211> LENGTH: 262
<212> TYPE: PRT
<213> ORGANISM: Influenza A virus
<220> FEATURE:
<221> NAME/KEY: CHAIN
<222> LOCATION: (1)..(262)
<223> OTHER INFORMATION: PB2 235 to 496

<400> SEQUENCE: 4

Thr Gln Gly Thr Cys Trp Glu Gln Met Tyr Thr Pro Gly Gly Glu Val
1               5                   10                  15

Arg Asn Asp Asp Ile Asp Gln Ser Leu Ile Ile Ala Ala Arg Asn Ile
            20                  25                  30

Val Arg Arg Ala Ser Val Ser Ala Asp Pro Leu Ala Ser Leu Leu Glu
        35                  40                  45

Met Cys His Ser Thr Gln Ile Gly Gly Thr Arg Met Val Asp Ile Leu
    50                  55                  60

Arg Gln Asn Pro Thr Glu Glu Gln Ala Val Asp Ile Cys Lys Ala Ala
65                  70                  75                  80

Met Gly Leu Arg Ile Ser Ser Phe Ser Phe Gly Gly Phe Thr Phe
                85                  90                  95

Lys Arg Thr Ser Gly Ser Ser Ile Lys Arg Glu Glu Val Leu Thr
            100                 105                 110

Gly Asn Leu Gln Thr Leu Lys Ile Arg Val His Glu Gly Tyr Glu Glu
            115                 120                 125

Phe Thr Met Val Gly Lys Arg Ala Thr Ala Ile Leu Arg Lys Ala Thr
    130                 135                 140

Arg Arg Leu Val Gln Leu Ile Val Ser Gly Arg Asp Glu Gln Ser Ile
145                 150                 155                 160

Ala Glu Ala Ile Ile Val Ala Met Val Phe Ser Gln Glu Asp Cys Met
                165                 170                 175

Ile Lys Ala Val Arg Gly Asp Leu Asn Phe Val Asn Arg Ala Asn Gln
            180                 185                 190

Arg Leu Asn Pro Met His Gln Leu Leu Arg His Phe Gln Lys Asp Ala
        195                 200                 205

Lys Val Leu Phe Gln Asn Trp Gly Ile Glu His Ile Asp Asn Val Met
    210                 215                 220

Gly Met Val Gly Val Leu Pro Asp Met Thr Pro Ser Thr Glu Met Ser
225                 230                 235                 240

Met Arg Gly Ile Arg Val Ser Lys Met Gly Val Asp Glu Tyr Ser Ser
                245                 250                 255

Thr Glu Arg Val Val Val
            260

<210> SEQ ID NO 5
<211> LENGTH: 243
<212> TYPE: PRT
<213> ORGANISM: Influenza A virus
<220> FEATURE:
```

```
<221> NAME/KEY: CHAIN
<222> LOCATION: (1)..(243)
<223> OTHER INFORMATION: PB2 241 to 483

<400> SEQUENCE: 5

Glu Gln Met Tyr Thr Pro Gly Gly Glu Val Arg Asn Asp Asp Ile Asp
1               5                   10                  15

Gln Ser Leu Ile Ile Ala Ala Arg Asn Ile Val Arg Arg Ala Ser Val
            20                  25                  30

Ser Ala Asp Pro Leu Ala Ser Leu Leu Glu Met Cys His Ser Thr Gln
        35                  40                  45

Ile Gly Gly Thr Arg Met Val Asp Ile Leu Arg Gln Asn Pro Thr Glu
50                  55                  60

Glu Gln Ala Val Asp Ile Cys Lys Ala Ala Met Gly Leu Arg Ile Ser
65                  70                  75                  80

Ser Ser Phe Ser Phe Gly Gly Phe Thr Phe Lys Arg Thr Ser Gly Ser
                85                  90                  95

Ser Ile Lys Arg Glu Glu Val Leu Thr Gly Asn Leu Gln Thr Leu
            100                 105                 110

Lys Ile Arg Val His Glu Gly Tyr Glu Glu Phe Thr Met Val Gly Lys
            115                 120                 125

Arg Ala Thr Ala Ile Leu Arg Lys Ala Thr Arg Arg Leu Val Gln Leu
130                 135                 140

Ile Val Ser Gly Arg Asp Glu Gln Ser Ile Ala Glu Ala Ile Ile Val
145                 150                 155                 160

Ala Met Val Phe Ser Gln Glu Asp Cys Met Ile Lys Ala Val Arg Gly
                165                 170                 175

Asp Leu Asn Phe Val Asn Arg Ala Asn Gln Arg Leu Asn Pro Met His
            180                 185                 190

Gln Leu Leu Arg His Phe Gln Lys Asp Ala Lys Val Leu Phe Gln Asn
            195                 200                 205

Trp Gly Ile Glu His Ile Asp Asn Val Met Gly Met Val Gly Val Leu
        210                 215                 220

Pro Asp Met Thr Pro Ser Thr Glu Met Ser Met Arg Gly Ile Arg Val
225                 230                 235                 240

Ser Lys Met

<210> SEQ ID NO 6
<211> LENGTH: 216
<212> TYPE: PRT
<213> ORGANISM: Influenza A virus
<220> FEATURE:
<221> NAME/KEY: CHAIN
<222> LOCATION: (1)..(216)
<223> OTHER INFORMATION: PB2 268 to 483

<400> SEQUENCE: 6

Arg Arg Ala Ser Val Ser Ala Asp Pro Leu Ala Ser Leu Leu Glu Met
1               5                   10                  15

Cys His Ser Thr Gln Ile Gly Gly Thr Arg Met Val Asp Ile Leu Arg
            20                  25                  30

Gln Asn Pro Thr Glu Glu Gln Ala Val Asp Ile Cys Lys Ala Ala Met
        35                  40                  45

Gly Leu Arg Ile Ser Ser Ser Phe Ser Phe Gly Gly Phe Thr Phe Lys
50                  55                  60

Arg Thr Ser Gly Ser Ser Ile Lys Arg Glu Glu Val Leu Thr Gly
65                  70                  75                  80
```

-continued

```
Asn Leu Gln Thr Leu Lys Ile Arg Val His Glu Gly Tyr Glu Glu Phe
                85                  90                  95
Thr Met Val Gly Lys Arg Ala Thr Ala Ile Leu Arg Lys Ala Thr Arg
            100                 105                 110
Arg Leu Val Gln Leu Ile Val Ser Gly Arg Asp Glu Gln Ser Ile Ala
        115                 120                 125
Glu Ala Ile Ile Val Ala Met Val Phe Ser Gln Glu Asp Cys Met Ile
    130                 135                 140
Lys Ala Val Arg Gly Asp Leu Asn Phe Val Asn Arg Ala Asn Gln Arg
145                 150                 155                 160
Leu Asn Pro Met His Gln Leu Leu Arg His Phe Gln Lys Asp Ala Lys
                165                 170                 175
Val Leu Phe Gln Asn Trp Gly Ile Glu His Ile Asp Asn Val Met Gly
            180                 185                 190
Met Val Gly Val Leu Pro Asp Met Thr Pro Ser Thr Glu Met Ser Met
        195                 200                 205
Arg Gly Ile Arg Val Ser Lys Met
    210                 215

<210> SEQ ID NO 7
<211> LENGTH: 204
<212> TYPE: PRT
<213> ORGANISM: Influenza A virus
<220> FEATURE:
<221> NAME/KEY: CHAIN
<222> LOCATION: (1)..(204)
<223> OTHER INFORMATION: PB2 277 to 480

<400> SEQUENCE: 7

Leu Ala Ser Leu Leu Glu Met Cys His Ser Thr Gln Ile Gly Gly Thr
1               5                   10                  15
Arg Met Val Asp Ile Leu Arg Gln Asn Pro Thr Glu Glu Gln Ala Val
            20                  25                  30
Asp Ile Cys Lys Ala Ala Met Gly Leu Arg Ile Ser Ser Ser Phe Ser
        35                  40                  45
Phe Gly Gly Phe Thr Phe Lys Arg Thr Ser Gly Ser Ser Ile Lys Arg
    50                  55                  60
Glu Glu Glu Val Leu Thr Gly Asn Leu Gln Thr Leu Lys Ile Arg Val
65                  70                  75                  80
His Glu Gly Tyr Glu Glu Phe Thr Met Val Gly Lys Arg Ala Thr Ala
                85                  90                  95
Ile Leu Arg Lys Ala Thr Arg Arg Leu Val Gln Leu Ile Val Ser Gly
            100                 105                 110
Arg Asp Glu Gln Ser Ile Ala Glu Ala Ile Ile Val Ala Met Val Phe
        115                 120                 125
Ser Gln Glu Asp Cys Met Ile Lys Ala Val Arg Gly Asp Leu Asn Phe
    130                 135                 140
Val Asn Arg Ala Asn Gln Arg Leu Asn Pro Met His Gln Leu Leu Arg
145                 150                 155                 160
His Phe Gln Lys Asp Ala Lys Val Leu Phe Gln Asn Trp Gly Ile Glu
                165                 170                 175
His Ile Asp Asn Val Met Gly Met Val Gly Val Leu Pro Asp Met Thr
            180                 185                 190
Pro Ser Thr Glu Met Ser Met Arg Gly Ile Arg Val
        195                 200
```

<210> SEQ ID NO 8
<211> LENGTH: 202
<212> TYPE: PRT
<213> ORGANISM: Influenza A virus
<220> FEATURE:
<221> NAME/KEY: CHAIN
<222> LOCATION: (1)..(202)
<223> OTHER INFORMATION: PB2 281 to 482

<400> SEQUENCE: 8

Leu Glu Met Cys His Ser Thr Gln Ile Gly Gly Thr Arg Met Val Asp
1               5                   10                  15

Ile Leu Arg Gln Asn Pro Thr Glu Glu Gln Ala Val Asp Ile Cys Lys
            20                  25                  30

Ala Ala Met Gly Leu Arg Ile Ser Ser Phe Ser Phe Gly Gly Phe
        35                  40                  45

Thr Phe Lys Arg Thr Ser Gly Ser Ser Ile Lys Arg Glu Glu Glu Val
    50                  55                  60

Leu Thr Gly Asn Leu Gln Thr Leu Lys Ile Arg Val His Glu Gly Tyr
65                  70                  75                  80

Glu Glu Phe Thr Met Val Gly Lys Arg Ala Thr Ala Ile Leu Arg Lys
                85                  90                  95

Ala Thr Arg Arg Leu Val Gln Leu Ile Val Ser Gly Arg Asp Glu Gln
            100                 105                 110

Ser Ile Ala Glu Ala Ile Ile Val Ala Met Val Phe Ser Gln Glu Asp
        115                 120                 125

Cys Met Ile Lys Ala Val Arg Gly Asp Leu Asn Phe Val Asn Arg Ala
130                 135                 140

Asn Gln Arg Leu Asn Pro Met His Gln Leu Leu Arg His Phe Gln Lys
145                 150                 155                 160

Asp Ala Lys Val Leu Phe Gln Asn Trp Gly Ile Glu His Ile Asp Asn
                165                 170                 175

Val Met Gly Met Val Gly Val Leu Pro Asp Met Thr Pro Ser Thr Glu
            180                 185                 190

Met Ser Met Arg Gly Ile Arg Val Ser Lys
        195                 200

<210> SEQ ID NO 9
<211> LENGTH: 194
<212> TYPE: PRT
<213> ORGANISM: Influenza A virus
<220> FEATURE:
<221> NAME/KEY: CHAIN
<222> LOCATION: (1)..(194)
<223> OTHER INFORMATION: PB2 290 to 483

<400> SEQUENCE: 9

Gly Gly Thr Arg Met Val Asp Ile Leu Arg Gln Asn Pro Thr Glu Glu
1               5                   10                  15

Gln Ala Val Asp Ile Cys Lys Ala Ala Met Gly Leu Arg Ile Ser Ser
            20                  25                  30

Ser Phe Ser Phe Gly Gly Phe Thr Phe Lys Arg Thr Ser Gly Ser Ser
        35                  40                  45

Ile Lys Arg Glu Glu Glu Val Leu Thr Gly Asn Leu Gln Thr Leu Lys
    50                  55                  60

Ile Arg Val His Glu Gly Tyr Glu Glu Phe Thr Met Val Gly Lys Arg
65                  70                  75                  80

Ala Thr Ala Ile Leu Arg Lys Ala Thr Arg Arg Leu Val Gln Leu Ile

```
                    85                  90                  95
Val Ser Gly Arg Asp Glu Gln Ser Ile Ala Glu Ala Ile Ile Val Ala
                100                 105                 110

Met Val Phe Ser Gln Glu Asp Cys Met Ile Lys Ala Val Arg Gly Asp
                115                 120                 125

Leu Asn Phe Val Asn Arg Ala Asn Gln Arg Leu Asn Pro Met His Gln
            130                 135                 140

Leu Leu Arg His Phe Gln Lys Asp Ala Lys Val Leu Phe Gln Asn Trp
145                 150                 155                 160

Gly Ile Glu His Ile Asp Asn Val Met Gly Met Val Gly Val Leu Pro
                165                 170                 175

Asp Met Thr Pro Ser Thr Glu Met Ser Met Arg Gly Ile Arg Val Ser
                180                 185                 190

Lys Met

<210> SEQ ID NO 10
<211> LENGTH: 188
<212> TYPE: PRT
<213> ORGANISM: Influenza A virus
<220> FEATURE:
<221> NAME/KEY: CHAIN
<222> LOCATION: (1)..(188)
<223> OTHER INFORMATION: PB2 295 to 482

<400> SEQUENCE: 10

Val Asp Ile Leu Arg Gln Asn Pro Thr Glu Glu Gln Ala Val Asp Ile
1               5                   10                  15

Cys Lys Ala Ala Met Gly Leu Arg Ile Ser Ser Ser Phe Ser Phe Gly
                20                  25                  30

Gly Phe Thr Phe Lys Arg Thr Ser Gly Ser Ser Ile Lys Arg Glu Glu
            35                  40                  45

Glu Val Leu Thr Gly Asn Leu Gln Thr Leu Lys Ile Arg Val His Glu
        50                  55                  60

Gly Tyr Glu Glu Phe Thr Met Val Gly Lys Arg Ala Thr Ala Ile Leu
65                  70                  75                  80

Arg Lys Ala Thr Arg Arg Leu Val Gln Leu Ile Val Ser Gly Arg Asp
                85                  90                  95

Glu Gln Ser Ile Ala Glu Ala Ile Ile Val Ala Met Val Phe Ser Gln
                100                 105                 110

Glu Asp Cys Met Ile Lys Ala Val Arg Gly Asp Leu Asn Phe Val Asn
            115                 120                 125

Arg Ala Asn Gln Arg Leu Asn Pro Met His Gln Leu Leu Arg His Phe
        130                 135                 140

Gln Lys Asp Ala Lys Val Leu Phe Gln Asn Trp Gly Ile Glu His Ile
145                 150                 155                 160

Asp Asn Val Met Gly Met Val Gly Val Leu Pro Asp Met Thr Pro Ser
                165                 170                 175

Thr Glu Met Ser Met Arg Gly Ile Arg Val Ser Lys
            180                 185

<210> SEQ ID NO 11
<211> LENGTH: 166
<212> TYPE: PRT
<213> ORGANISM: Influenza A virus
<220> FEATURE:
<221> NAME/KEY: CHAIN
<222> LOCATION: (1)..(166)
<223> OTHER INFORMATION: PB2 318 to 483 R389K
```

-continued

<400> SEQUENCE: 11

Arg Ile Ser Ser Ser Phe Ser Phe Gly Gly Phe Thr Phe Lys Arg Thr
1               5                   10                  15

Ser Gly Ser Ser Ile Lys Arg Glu Glu Glu Val Leu Thr Gly Asn Leu
            20                  25                  30

Gln Thr Leu Lys Ile Arg Val His Glu Gly Tyr Glu Glu Phe Thr Met
        35                  40                  45

Val Gly Lys Arg Ala Thr Ala Ile Leu Arg Lys Ala Thr Arg Arg Leu
    50                  55                  60

Val Gln Leu Ile Val Ser Gly Lys Asp Glu Gln Ser Ile Ala Glu Ala
65                  70                  75                  80

Ile Ile Val Ala Met Val Phe Ser Gln Glu Asp Cys Met Ile Lys Ala
                85                  90                  95

Val Arg Gly Asp Leu Asn Phe Val Asn Arg Ala Asn Gln Arg Leu Asn
            100                 105                 110

Pro Met His Gln Leu Leu Arg His Phe Gln Lys Asp Ala Lys Val Leu
        115                 120                 125

Phe Gln Asn Trp Gly Ile Glu His Ile Asp Asn Val Met Gly Met Val
130                 135                 140

Gly Val Leu Pro Asp Met Thr Pro Ser Thr Glu Met Ser Met Arg Gly
145                 150                 155                 160

Ile Arg Val Ser Lys Met
                165

<210> SEQ ID NO 12
<211> LENGTH: 164
<212> TYPE: PRT
<213> ORGANISM: Influenza A virus
<220> FEATURE:
<221> NAME/KEY: CHAIN
<222> LOCATION: (1)..(164)
<223> OTHER INFORMATION: PB2 320 to 483

<400> SEQUENCE: 12

Ser Ser Ser Phe Ser Phe Gly Gly Phe Thr Phe Lys Arg Thr Ser Gly
1               5                   10                  15

Ser Ser Ile Lys Arg Glu Glu Glu Val Leu Thr Gly Asn Leu Gln Thr
            20                  25                  30

Leu Lys Ile Arg Val His Glu Gly Tyr Glu Glu Phe Thr Met Val Gly
        35                  40                  45

Lys Arg Ala Thr Ala Ile Leu Arg Lys Ala Thr Arg Arg Leu Val Gln
    50                  55                  60

Leu Ile Val Ser Gly Arg Asp Glu Gln Ser Ile Ala Glu Ala Ile Ile
65                  70                  75                  80

Val Ala Met Val Phe Ser Gln Glu Asp Cys Met Ile Lys Ala Val Arg
                85                  90                  95

Gly Asp Leu Asn Phe Val Asn Arg Ala Asn Gln Arg Leu Asn Pro Met
            100                 105                 110

His Gln Leu Leu Arg His Phe Gln Lys Asp Ala Lys Val Leu Phe Gln
        115                 120                 125

Asn Trp Gly Ile Glu His Ile Asp Asn Val Met Gly Met Val Gly Val
130                 135                 140

Leu Pro Asp Met Thr Pro Ser Thr Glu Met Ser Met Arg Gly Ile Arg
145                 150                 155                 160

Val Ser Lys Met

```
<210> SEQ ID NO 13
<211> LENGTH: 82
<212> TYPE: PRT
<213> ORGANISM: Influenza A virus
<220> FEATURE:
<221> NAME/KEY: CHAIN
<222> LOCATION: (1)..(82)
<223> OTHER INFORMATION: PB2 323 to 404

<400> SEQUENCE: 13

Phe Ser Phe Gly Gly Phe Thr Phe Lys Arg Thr Ser Gly Ser Ser Ile
1               5                   10                  15

Lys Arg Glu Glu Glu Val Leu Thr Gly Asn Leu Gln Thr Leu Lys Ile
            20                  25                  30

Arg Val His Glu Gly Tyr Glu Glu Phe Thr Met Val Gly Lys Arg Ala
        35                  40                  45

Thr Ala Ile Leu Arg Lys Ala Thr Arg Arg Leu Val Gln Leu Ile Val
    50                  55                  60

Ser Gly Arg Asp Glu Gln Ser Ile Ala Glu Ala Ile Ile Val Ala Met
65                  70                  75                  80

Val Phe

<210> SEQ ID NO 14
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 320 to 330

<400> SEQUENCE: 14

Ser Ser Ser Phe Ser Phe Gly Gly Phe Thr Phe
1               5                   10

<210> SEQ ID NO 15
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 330 to 340

<400> SEQUENCE: 15

Phe Lys Arg Thr Ser Gly Ser Ser Ile Lys Arg
1               5                   10

<210> SEQ ID NO 16
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 340 to 350

<400> SEQUENCE: 16

Arg Glu Glu Glu Val Leu Thr Gly Asn Leu Gln
1               5                   10

<210> SEQ ID NO 17
<211> LENGTH: 11
<212> TYPE: PRT
```

<213> ORGANISM: Influenza A virus
<220> FEATURE:
<221> NAME/KEY: CHAIN
<222> LOCATION: (1)..(11)
<223> OTHER INFORMATION: PB2 350 to 360

<400> SEQUENCE: 17

Gln Thr Leu Lys Ile Arg Val His Glu Gly Tyr
1               5                   10

<210> SEQ ID NO 18
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 360 to 370

<400> SEQUENCE: 18

Tyr Glu Glu Phe Thr Met Val Gly Lys Arg Ala
1               5                   10

<210> SEQ ID NO 19
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 370 to 380

<400> SEQUENCE: 19

Ala Thr Ala Ile Leu Arg Lys Ala Thr Arg Arg
1               5                   10

<210> SEQ ID NO 20
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 380 to 390

<400> SEQUENCE: 20

Arg Leu Val Gln Leu Ile Val Ser Gly Arg Asp
1               5                   10

<210> SEQ ID NO 21
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: PB2 390 to 400

<400> SEQUENCE: 21

Asp Glu Gln Ser Ile Ala Glu Ala Ile Ile Val
1               5                   10

<210> SEQ ID NO 22
<211> LENGTH: 11
<212> TYPE: PRT
<213> ORGANISM: Influenza A virus
<220> FEATURE:
<221> NAME/KEY: CHAIN
<222> LOCATION: (1)..(11)

<223> OTHER INFORMATION: PB2 400 to 410

<400> SEQUENCE: 22

```
Val Ala Met Val Phe Ser Gln Glu Asp Cys Met
1               5                   10
```

<210> SEQ ID NO 23
<211> LENGTH: 2277
<212> TYPE: DNA
<213> ORGANISM: Influenza A virus
<220> FEATURE:
<221> NAME/KEY: CDS
<222> LOCATION: (1)..(2277)
<223> OTHER INFORMATION: PB2 WT

<400> SEQUENCE: 23

```
atggaaagaa taaaagaact acggaacctg atgtcacagt ctcgcactcg cgagatacta      60
acaaaaacca cagtggacca catggccata attaagaaat acacatcagg gagacaggaa     120
aagaacccgt cacttaggat gaaatggatg atggcaatga aatatccaat tacagctgac     180
aagaggataa cagaaatggt tcctgagaga aatgagcaag gacaaaccct atggagtaaa     240
atgagtgatg ccgggtcaga tcgagtgatg gtatcacctt tggcagtgac atggtggaat     300
agaaatggac cagtgacaag tacggttcat tatccaaaag tctacaagac ttattttgat     360
aaagtcgaaa ggttaaaaca tggaaccttt ggccctgtcc attttagaaa ccaagtcaaa     420
atacgccgaa gagttgacat aaaccctggt catgcagacc tcagtgccaa ggaggcacaa     480
gatgtaatca tggaagttgt tttccccaat gaagtggggg ccaggatact aacgtcggaa     540
tcacaattga caataaccaa agagaaaaaa gaagaactcc aagattgcaa aatttctcct     600
ttgatggttg catacatgtt agagagagaa cttgtccgaa aaacgagatt tctcccagtt     660
gctggtggaa caagcagtgt gtacattgaa gtgttacact tgactcaagg aacgtgttgg     720
gaacagatgt acactccagg tggagaagtg aggaatgacg atattgacca aagcctaatt     780
attgcagcca ggaacatagt gagaagagca tcagtatcag cagatccact agcatcttta     840
ttggagatgt gccacagcac acaaattggc gggacaagga tggtggacat tcttagacag     900
aacccgacgg aagaacaagc tgtggatata tgcaaggctg caatgggact gagaatcagc     960
tcatccttca gttttggtgg gttcacattt aagagaacaa gcgggtcatc aatcaaaaga    1020
gaggaagaag tgcttacggg caatctccaa acattgaaaa taagggtgca tgaagggtac    1080
gaggagttca caatggtggg gaaaagggca acagctatac tcagaaaagc aaccaggaga    1140
ttggttcagc ttatagtgag tggaagggac gagcagtcaa tagccgaagc gataattgta    1200
gccatggtgt tttcacaaga ggattgcatg ataaaagcag ttagaggtga cctgaatttc    1260
gttaacaggg caaatcagcg gttgaatccc atgcaccaac ttttaaggca ttttcagaaa    1320
gatgcgaaag tgctttttca gaattgggga attgaacata ttgacaatgt gatgggaatg    1380
gttggagtat taccagacat gactccaagc acagagatgt caatgagagg aataagagtc    1440
agcaaaatgg gcgtggatga atactccagc acagagaggg tagtggttag cattgatcgg    1500
tttttgagag ttcgagacca acgtgggaat gtattactat ctcctgagga ggtcagtgaa    1560
acacatggga cagagagact gacaataact tactcatcgt caatgatgtg ggagattaat    1620
ggccctgagt cagtgttggt caatacctat caatggatca tcagaaattg ggaaactgtt    1680
aaaattcaat ggtctcagaa tcctacaatg ttgtacaaca aaatggaatt tgagccattt    1740
cagtctttag ttcctaaggc cattagaggc caatacagtg gatttgtcag aactctattc    1800
```

-continued

| | |
|---|---|
| caacaaatga gggatgtact tgggacattt gataccaccc agataataaa gcttctcccc | 1860 |
| tttgcagccg ccccaccaaa gcaaagtaga atgcagttct cttcattgac tgtgaatgtg | 1920 |
| aggggatcag ggatgagaat acttgtaagg ggcaattctc ctgtattcaa ctacaacaag | 1980 |
| accactaaaa gactaacaat tctcggaaaa gatgctggca ctttaattga agacccagat | 2040 |
| gaaagcacat ccggagtgga gtccgctgtt ttgagaggat ttctcattct aggtaaggaa | 2100 |
| gatagaagat acggaccagc attaagcatc aatgaactga gcaaccttgc aaaaggagaa | 2160 |
| aaggctaatg tgctaattgg gcaaggagac gtggtgttgg taatgaaacg aaaacgggac | 2220 |
| tctagcatac ttactgacag ccagacagcg accaaaagaa ttcggatggc catcaat | 2277 |

<210> SEQ ID NO 24
<211> LENGTH: 2277
<212> TYPE: DNA
<213> ORGANISM: Influenza A virus
<220> FEATURE:
<221> NAME/KEY: CDS
<222> LOCATION: (1)..(2277)
<223> OTHER INFORMATION: PB2 Arg389Lys

<400> SEQUENCE: 24

| | |
|---|---|
| atggaaagaa taaagaaact acggaacctg atgtcacagt ctcgcactcg cgagatacta | 60 |
| acaaaaacca cagtggacca catggccata attaagaaat acacatcagg gagacaggaa | 120 |
| aagaacccgt cacttaggat gaaatggatg atggcaatga atatccaat tacagctgac | 180 |
| aagaggataa cagaaatggt tcctgagaga atgagcaag acaaaccct atggagtaaa | 240 |
| atgagtgatg ccgggtcaga tcgagtgatg gtatcacctt tggcagtgac atggtggaat | 300 |
| agaaatggac cagtgacaag tacggttcat tatccaaaag tctacaagac ttattttgat | 360 |
| aaagtcgaaa ggttaaaaca tggaaccttt ggccctgtcc attttagaaa ccaagtcaaa | 420 |
| atacgccgaa gagttgacat aaaccctggt catgcagacc tcagtgccaa ggaggcacaa | 480 |
| gatgtaatca tggaagttgt tttccccaat gaagtggggg ccaggatact aacgtcggaa | 540 |
| tcacaattga caataaccaa agaaaaaaa gaagaactcc aagattgcaa aatttctcct | 600 |
| ttgatggttg catacatgtt agagagagaa cttgtccgaa aaacgagatt tctcccagtt | 660 |
| gctggtggaa caagcagtgt gtacattgaa gtgttacact tgactcaagg aacgtgttgg | 720 |
| gaacagatgt acactccagg tggagaagtg aggaatgacg atattgacca agcctaatt | 780 |
| attgcagcca ggaacatagt gagaagagca tcagtatcag cagatccact agcatcttta | 840 |
| ttggagatgt gccacagcac acaaattggc gggacaagga tggtggacat tcttagacag | 900 |
| aacccgacgg aagaacaagc tgtggatata tgcaaggctg caatgggact gagaatcagc | 960 |
| tcatccttca gttttggtgg gttcacattt aagagaacaa gcgggtcatc aatcaaaaga | 1020 |
| gaggaagaag tgcttacggg caatctccaa acattgaaaa taagggtgca tgaagggtac | 1080 |
| gaggagttca caatggtggg gaaaagggca acagctatac tcagaaaagc aaccaggaga | 1140 |
| ttggttcagc ttatagtgag tggaaaggac gagcagtcaa tagccgaagc gataattgta | 1200 |
| gccatggtgt tttcacaaga ggattgcatg ataaaagcag ttagaggtga cctgaatttc | 1260 |
| gttaacaggg caaatcagcg gttgaatccc atgcaccaac ttttaaggca ttttcagaaa | 1320 |
| gatgcgaaag tgcttttca gaattgggga attgaacata ttgacaatgt gatgggaatg | 1380 |
| gttggagtat taccagacat gactccaagc acagagatgt caatgagagg aataagagtc | 1440 |
| agcaaaatgg gcgtggatga atactccagc acagagaggg tagtggttag cattgatcgg | 1500 |
| ttttttgagag ttcgagacca acgtgggaat gtattactat ctcctgagga ggtcagtgaa | 1560 |

```
acacatggga cagagagact gacaataact tactcatcgt caatgatgtg ggagattaat   1620
ggccctgagt cagtgttggt caatacctat caatggatca tcagaaattg ggaaactgtt   1680
aaaattcaat ggtctcagaa tcctacaatg ttgtacaaca aaatggaatt tgagccattt   1740
cagtctttag ttcctaaggc cattagaggc caatacagtg gatttgtcag aactctattc   1800
caacaaatga gggatgtact tgggacattt gataccaccc agataataaa gcttctcccc   1860
tttgcagccg ccccaccaaa gcaaagtaga atgcagttct cttcattgac tgtgaatgtg   1920
aggggatcag ggatgagaat acttgtaagg ggcaattctc ctgtattcaa ctacaacaag   1980
accactaaaa gactaacaat tctcggaaaa gatgctggca ctttaattga agacccagat   2040
gaaagcacat ccggagtgga gtccgctgtt ttgagaggat ttctcattct aggtaaggaa   2100
gatagaagat acggaccagc attaagcatc aatgaactga gcaaccttgc aaaaggagaa   2160
aaggctaatg tgctaattgg gcaaggagac gtggtgttgg taatgaaacg aaaacgggac   2220
tctagcatac ttactgacag ccagacagcg accaaaagaa ttcggatggc catcaat      2277
```

<210> SEQ ID NO 25
<211> LENGTH: 2277
<212> TYPE: DNA
<213> ORGANISM: Influenza A virus
<220> FEATURE:
<221> NAME/KEY: CDS
<222> LOCATION: (1)..(2274)
<223> OTHER INFORMATION: PB2 synthetic gene, optimized for E.coli codon usage

<400> SEQUENCE: 25

```
atggaacgca ttaaagaact gcgcaacctg atgagccaga gccgtacccg tgaaattctg     60
accaaaacca ccgtggatca catggcgatc atcaaaaaat ataccagcgg ccgtcaggaa    120
aaaaatccga gcctgcgcat gaaatggatg atggcgatga aatatccgat caccgcggat    180
aaacgcatta ccgaaatggt gccggaacgt aatgaacagg gccagaccct gtggagcaaa    240
atgagcgatg cgggtagcga tcgtgttatg gttagcccgc tggcggttac ctggtggaat    300
cgtaatggtc cggttaccag caccgtgcat tatccgaaag tgtacaaaac ctatttcgat    360
aaagtggaac gcctgaaaca tggcaccttt ggcccggtgc attttcgtaa ccaggtgaaa    420
attcgtcgtc gcgtggatat taatccgggt catgcggatc tgagcgcgaa agaagcgcaa    480
gacgttatca tggaagttgt tttcccgaac gaagttggtg cgcgtattct gaccagcgaa    540
agccagctga ccatcaccaa agaaaaaaaa gaagaactgc aggattgcaa aattagcccg    600
ctgatggtgg cgtatatgct ggaacgtgaa ctggttcgta aaacccgttt tctgccggtt    660
gcgggtggca ccagcagcgt gtatattgaa gtgctgcatc tgacccaggg cacctgttgg    720
gaacagatgt ataccccggg tggtgaagtg cgtaacgatg atatcgatca gagcctgatt    780
attgcggcgc gtaacattgt tcgtcgtgcg agcgttagcg cggatccgct ggcgagcctg    840
ctggaaatgt gtcatagcac ccagattggt ggcacccgta tggttgatat tctgcgtcag    900
aacccgaccg aagaacaggc ggtggatatt tgtaaagcgg cgatgggtct gcgtattagc    960
agcagcttta gctttggcgg ctttaccttt aaacgtacca gcggcagcag cattaaacgt   1020
gaagaagaag tgctgaccgg taatctgcag accctgaaaa ttcgtgtgca cgaaggctat   1080
gaagaattca cgatggttgg caaacgtgcg accgcgattc tgcgtaaagc gacccgtcgt   1140
ctggttcagc tgattgtgag cggcaaagat gaacagagca ttgcggaagc gattatcgtt   1200
gcgatggttt tcagccagga agattgcatg attaaagcgg ttcgtggcga tctgaacttt   1260
```

```
gtgaaccgtg cgaaccagcg tctgaatccg atgcaccagc tgctgcgcca ttttcagaaa    1320
gatgcgaaag tgctgtttca gaactggggc atcgaacata tcgataacgt gatgggcatg    1380
gttggtgttc tgccggatat gaccccgagc accgaaatga gcatgcgtgg tattcgtgtg    1440
agcaaaatgg gcgtggatga atacagcagc accgaacgtg tggttgtgag cattgatcgt    1500
tttctgcgtg tgcgtgatca gcgtggtaat gttctgctga gcccggagga ggttagcgaa    1560
acgcacggca ccgaacgtct gaccattacc tatagcagca gcatgatgtg ggagattaac    1620
ggtccggaaa gcgtgctggt gaacacctat cagtggatca ttcgcaactg gaaaccgtg     1680 aaaattcagt ggagccagaa tccgaccatg ctgtacaaca aaatggaatt cgaaccgttt    1740
cagagcctgg ttccgaaagc gattcgtggt cagtatagcg ttttgtgcg taccctgttt     1800 cagcagatgc gtgatgttct gggcaccttt gataccaccc agatcattaa actgctgccg    1860
tttgcggcgg caccgccgaa acagagccgt atgcagttta gcagcctgac cgtgaatgtt    1920
cgtggtagcg gcatgcgtat tctggttcgt ggtaacagcc cggtgttcaa ctataacaaa    1980
accaccaaac gcctgaccat tctgggtaaa gatgcgggca ccctgattga agatccggat    2040
gaaagcacca gcggcgttga aagcgcggtt ctgcgcggtt ttctgattct gggcaaggag    2100
gatcgtcgtt acggtccggc gctgagcatt aacgaactga gcaatctggc gaaaggcgaa    2160
aaagcgaacg ttctgattgg tcagggtgat gtggtgctgg tgatgaaacg taaacgcgat    2220
agcagcattc tgaccgatag ccagaccgcg accaaacgta ttcgtatggc gattaat       2277
```

<210> SEQ ID NO 26
<211> LENGTH: 2313
<212> TYPE: DNA
<213> ORGANISM: Influenza B virus
<220> FEATURE:
<221> NAME/KEY: CDS
<222> LOCATION: (1)..(2313)
<223> OTHER INFORMATION: PB2

<400> SEQUENCE: 26

```
atgacattgg ctaaaattga attgttaaaa caactgttaa gggacaatga agccaaaaca     60
gtattgaaac aaacaacggt agaccaatat aacataataa gaaaattcaa tacatcaaga    120
attgaaaaga acccttcatt aaggatgaag tgggcaatgt gttctaattt tcccttggct    180
ttgaccaagg gtgacatggc aaacagaatc cccttggaat acaagggaat acaacttaaa    240
acaaatgctg aagacatagg aaccaaaggc caaatgtgct caatagcagc agttacctgg    300
tggaatacat atggaccaat aggagatact gaaggtttcg aaaaagtcta cgaaagcttt    360
tttctcagaa agatgagact tgacaatgcc acttggggcc gaataacttt tggcccagtt    420
gaaagagtaa gaaaaagggt actgctaaac cctctcacta aggaaatgcc tccagatgaa    480
gcaagtaatg tgataatgga aatattgttc cctaaggaag caggaatacc aagagaatct    540
acttggatac atagggaact gataaaagaa aaaagagaaa aattgaaagg aacgatgata    600
actcccattg tactggcata catgcttgag agggaattgg ttgccaggag aaggttcctg    660
ccggtggcag gagcaacatc agctgagttc atagaaatgc tacactgctt acaaggtgaa    720
aattggagac aaatatacca cccgggaggg aataaactaa ctgaatctag gtctcaatcg    780
atgattgtgg cttgtagaaa gataatcaga agatcaatag tcgcatcaaa cccattggag    840
ctggctgtag aaattgcaaa caagactgtg atagatactg aacctttaaa atcatgtctg    900
acagccatag acggaggtga tgtcgcctgt gacataataa gagctgcatt aggactaaag    960
```

```
atcagacaaa gacaaagatt tggacgactt gaactaaaaa ggatatcagg aagaggattc      1020
aaaaatgatg aagaaatatt aatcgggaac ggaacaatac agaagattgg aatatgggac      1080
ggagaagagg agttccatgt aagatgtggt gaatgcaggg aatattaaa  aaagagcaaa      1140 atgagaatgg aaaaactact aataaattca gctaaaaagg aagacatgaa agatttaata      1200
atcttgtgca tggtattttc tcaagacact aggatgttcc aaggagtaag gggagaaata      1260
aattttctta atagagcagg ccaacttttta tctccaatgt accaactcca aagatatttt      1320
ttgaatagaa gtaacgatct ctttgatcaa tgggggtatg aggaatcacc caaagcaagt      1380
gagctacatg ggataaatga attaatgaat gcatctgact cactttgaa  aggggttgta      1440 gtaacaaaaa atgtgattga tgattttagt tctactgaaa cagaaaaagt atctataaca      1500
aaaaatctta gtttaataaa agaactgggg aagtcataa  tggggccaa  tgacgtaagt      1560 gaattagaat cacaagctca gctaatgata acatatgata cacctaagat gtgggagatg      1620
ggaacaacca aggaactggt gcaaacacc  tatcaatggg tgctaaaaaa tttggtaaca      1680
ctgaaggctc agtttcttct aggaaaagaa gacatgttcc aatgggatgc atttgaagca      1740
tttgaaagca taatccccca gaagatggct ggccaataca gtggatttgc aagagcagtg      1800
ctcaaacaaa tgagagacca agaggtcatg aaaactgacc agttcataaa gttgttgccc      1860
ttttgtttct caccaccaaa gttaaggagc aatggggagc ttatcagtt  cttgaggctt      1920 gtattgaagg gaggaggaga aaatttcatc gaagtaagga aagggtctcc tctattctct      1980
tacaatccac aaacagaagt cctaactata tgcggcagaa tgatgtcatt aaaagggaaa      2040
attgaagatg aagaaaggaa tagatcaatg gggaatgcag tgttggcggg ttttcttgtt      2100
agtggcaagt atgacccaga tcttggagat ttcaaaacta ttgaagaact tgaaaagcta      2160
aaaccggggg agaaagcaaa catcttactt tatcaaggaa agcccgttaa agtagttaaa      2220
aggaaaagat atagtgctt  tatccaatgac atttcacaag gaattaagag acaagaatg      2280 acagttgagt ccatggggtg ggccttgagc taa                                   2313
```

<210> SEQ ID NO 27
<211> LENGTH: 2325
<212> TYPE: DNA
<213> ORGANISM: Influenza C virus
<220> FEATURE:
<221> NAME/KEY: CDS
<222> LOCATION: (1)..(2325)
<223> OTHER INFORMATION: PB2

<400> SEQUENCE: 27

```
atgtcttttc tattgacaat agcaaaggaa tacaaaagac tatgccaaga tgctaaggca       60
gctcaaatga tgacagtagg aactgtatca aactacacta cgttcaagaa atggactaca      120
tcaaggaagg aaaagaatcc ttcactaaga atgagatggg caatgagcag caaattccca      180
ataatagcta acaagagaat gctggaagaa gctcaaattc ctaaagaaca caacaatgta      240 gcccctttggg aagacacaga agatgtttca aaaagggatc atgttcttgc aagcgcctct      300
tgtataaatt attggaattt ttgtggacct tgtgtcaaca attcagaagt gatcaaagaa      360
gtttataaat ctagatttgg aagattagaa agaggaaag aaataatgtg aaagaacatt       420
agatttacat tagttgatag acaacgaaga gagttgaca  ctcagcctgt agaacaagaa      480
ttgagaactg agaaaattaa agacttgcaa atgtggactt tgttcgaaga tgaagctcct      540
cttgctagca aatttatttt agacaattat ggtctagtca agaaatgag  atcaaagttt      600 gcaaacaaac ctctgaataa agaagtagtt gcacacatgt tagaaaaaca attcaatccg      660
```

-continued

```
gaaagtagat tcttgcctgt tttcggagct ataaggccag aaagaatgga attgatccat    720
gcattaggag gagaaacttg gatacaagaa gctaacactg cagggatttc caatgttgat    780
caaaggaaaa atgatatgag agcagtatgt aggaaagttt gtcttgcagc aaatgcaagt    840
ataatgaacg ccaaaagcaa actggttgag tatataaaaa gtacaagtat gagaattgga    900
gaaacagaaa gaaagcttga agaacttata cttgaaaccg atgatgtctc acctgaagta    960
acattatgta aatctgcttt aggaggacca ttaggaaaaa ctctatcttt tgggcccatg    1020
ctactcaaga aaatttctgg ttccggagta aaagttaaag atacagtata tatccaaggt    1080
gtcagagcag tacaatttga atactggagt gagcaagaag aattctatgg agaatataag    1140
tcagccaccg ctttattcag cagaaaggaa agatcactag aatggattac aataggagga    1200
ggaataaatg aagacagaaa gagacttcta gctatgtgca tgatattttg cagagatgga    1260
gattatttta aagacgcccc tgcaacaata acaatggcag atttaagtac gaagttagga    1320
agagaaattc catatcaata tgtgatgatg aattggacaa aaaaatcaga agataatctc    1380
gaagccttat tatacagtag gggaattgta gaaaccaatc caggaaaaat ggggagctca    1440
atgggaattg atggttccaa aagagcaatt aaatctttaa gggctgtcac aatacaatca    1500
ggaaagattg acatgccaga atcaaaagaa aaaattcacc ttgagctctc tgataatctt    1560
gaagcatttg attcatcagg aagaattgtt gcaacaattt tagaccttcc tagtgacaaa    1620
aaggtaacat ttcaggatgt aagctttcaa catcctgatc tggcagtatt gagagatgag    1680
aaaacggcca taacaaaagg gtatgaagcg ctaatcaaaa ggctaggaac aggggacaat    1740
gatattcctt ccttaattgc aaagaaggat tatttgtctc tttataattt accagaagta    1800
aaattaatgg ctcccttaat cagacccaat agaaaaggag tttattccag agttgctaga    1860
aaattagtgt ctacacaagt tactactgga cattattcat tacatgaatt gataaaggtc    1920
ttacccttta cttatttcgc cccaaaacag ggaatgtttg aaggaaggct tttctttagc    1980
aacgatagct tgttgagcc tggagtaaat aacaatgtat tttcttggag taaggctgac    2040
agttctaaaa tatattgtca tggaatagcg ataagggtac ctttagttgt tggagatgaa    2100
cacatggaca cttcgttagc actattagaa gggtttagtg tttgtgaaaa cgaccccaga    2160
gcaccaatgg taacaagaca agatttaatt gatgtgggat ttgggcaaaa agttagactc    2220
ttcgtaggcc aagggagcgt tagaaccttc aagcgaactg cctcacaaag ggctgcatca    2280
agcgatgtaa ataagaatgt gaaaaagata aagatgtcta actaa                    2325
```